(12) United States Patent
McSwiggen

(10) Patent No.: US 7,022,828 B2
(45) Date of Patent: Apr. 4, 2006

(54) SIRNA TREATMENT OF DISEASES OR CONDITIONS RELATED TO LEVELS OF IKK-GAMMA

(75) Inventor: James A. McSwiggen, Boulder, CO (US)

(73) Assignee: Sirna Theraputics, Inc., Boulder, CO (US)

( * ) Notice: Subject to any disclaimer, the term of this patent is extended or adjusted under 35 U.S.C. 154(b) by 354 days.

(21) Appl. No.: 10/156,306

(22) Filed: May 28, 2002

(65) Prior Publication Data

US 2003/0119017 A1    Jun. 26, 2003

Related U.S. Application Data

(60) Provisional application No. 60/294,412, filed on May 29, 2001.

(51) Int. Cl.
*C07H 21/02* (2006.01)

(52) U.S. Cl. .................. 536/23.1; 536/23.5; 514/44

(58) Field of Classification Search ............. 514/44; 536/23.1, 23.5
See application file for complete search history.

(56) References Cited

U.S. PATENT DOCUMENTS

| | | | |
|---|---|---|---|
| 4,987,071 A | 1/1991 | Cech et al. ............. 435/91.31 |
| 5,334,711 A | 8/1994 | Sproat et al. ............ 536/24.5 |
| 5,589,332 A | 12/1996 | Shih et al. ................. 435/6 |
| 5,624,803 A | 4/1997 | Noonberg et al. ............ 435/6 |
| 5,627,053 A | 5/1997 | Usman et al. ............. 435/91.1 |
| 5,631,359 A | 5/1997 | Chowrira et al. .......... 536/24.5 |
| 5,633,133 A | 5/1997 | Long et al. ................. 435/6 |
| 5,670,633 A | 9/1997 | Cook et al. .............. 536/23.1 |
| 5,672,695 A | 9/1997 | Eckstein et al. .......... 536/24.5 |
| 5,716,824 A | 2/1998 | Beigelman et al. ......... 435/366 |
| 5,741,679 A | 4/1998 | George et al. ........... 435/91.31 |
| 5,792,847 A | 8/1998 | Buhr et al. ............... 536/23.1 |
| 5,801,154 A | 9/1998 | Baracchini et al. .......... 514/44 |
| 5,814,620 A | 9/1998 | Robinson et al. ............ 514/44 |
| 5,834,186 A | 11/1998 | George et al. ............... 435/6 |
| 5,849,902 A | 12/1998 | Arrow et al. ............. 536/24.5 |
| 5,871,914 A | 2/1999 | Nathan ..................... 435/6 |
| 5,898,031 A | 4/1999 | Crooke .................... 435/91.3 |
| 5,989,912 A | 11/1999 | Arrow et al. .............. 435/375 |
| 6,001,311 A | 12/1999 | Brennan et al. ............ 422/131 |
| 6,005,087 A | 12/1999 | Cook et al. .............. 536/23.1 |
| 6,107,094 A | 8/2000 | Crooke .................... 435/455 |
| 6,159,714 A | 12/2000 | Usman et al. ........... 435/91.31 |
| 6,476,205 B1 | 11/2002 | Buhr et al. ............... 536/23.1 |
| 6,506,559 B1 | 1/2003 | Fire et al. ................... 435/6 |
| 2002/0012965 A1 | 1/2002 | Strittmatter ............... 435/69.1 |

FOREIGN PATENT DOCUMENTS

| | | |
|---|---|---|
| CA | 2359180 | 3/2000 |
| EP | 0360257 | 3/1990 |

(Continued)

OTHER PUBLICATIONS

Reynolds et al, Nature Biotechnology 22(3), 326 (2004).*

(Continued)

*Primary Examiner*—James Martinell
(74) *Attorney, Agent, or Firm*—McDonnell Boehnen Hulbert & Berghoff LLP

(57) ABSTRACT

The present invention relates to nucleic acid molecules, including antisense and enzymatic nucleic acid molecules, such as hammerhead ribozymes, DNAzymes, allozymes, aptamers, decoys and siRNA (RNAi), which modulate the expression or function of IKK genes, such as IKK-gamma, IKK-alpha, or IKK-beta, and PKR genes.

16 Claims, 4 Drawing Sheets

*Examples of Nuclease Stable Ribozyme Motifs*

FOREIGN PATENT DOCUMENTS

| | | |
|---|---|---|
| EP | 1325955 | 7/2003 |
| JP | 2000253884 | 9/2000 |
| WO | WO 89/02439 | 3/1989 |
| WO | 90/14090 | 11/1990 |
| WO | WO 91/03162 | 3/1991 |
| WO | WO 92/07065 | 4/1992 |
| WO | WO 93/15187 | 8/1993 |
| WO | WO 93/23057 | 11/1993 |
| WO | WO 93/23569 | 11/1993 |
| WO | 94/01550 | 1/1994 |
| WO | WO 94/02595 | 2/1994 |
| WO | 95/04142 | 2/1995 |
| WO | WO 95/04818 | 2/1995 |
| WO | WO 95/11304 | 4/1995 |
| WO | WO 95/11910 | 4/1995 |
| WO | WO 95/13380 | 5/1995 |
| WO | WO 95/23225 | 8/1995 |
| WO | WO 96/10390 | 4/1996 |
| WO | WO 96/10391 | 4/1996 |
| WO | WO 96/10392 | 4/1996 |
| WO | WO 96/19736 | 6/1996 |
| WO | WO 97/26270 | 7/1997 |
| WO | WO 98/13526 | 4/1998 |
| WO | WO 98/27104 | 6/1998 |
| WO | WO 98/28317 | 7/1998 |
| WO | WO 98/43993 | 10/1998 |
| WO | WO 98/58058 | 12/1998 |
| WO | WO 99/04819 | 2/1999 |
| WO | WO 99/05094 | 2/1999 |
| WO | WO 99/16871 | 4/1999 |
| WO | WO 99/29842 | 6/1999 |
| WO | 99/32619 | 7/1999 |
| WO | 99/49029 | 9/1999 |
| WO | 99/53050 | 10/1999 |
| WO | WO 99/54459 | 10/1999 |
| WO | WO 99/55857 | 11/1999 |
| WO | 99/61631 | 12/1999 |
| WO | WO 00/24931 | 5/2000 |
| WO | WO 00/26226 | 5/2000 |
| WO | 00/44914 | 8/2000 |
| WO | 00/49035 | 8/2000 |
| WO | 00/63364 | 10/2000 |
| WO | 01/36646 | 5/2001 |
| WO | 01/57206 | 8/2001 |
| WO | 01/96584 | 12/2001 |
| WO | 01/097850 | 12/2001 |
| WO | 02/07747 | 1/2002 |
| WO | 02/10378 | 2/2002 |
| WO | 02/22636 | 3/2002 |
| WO | 02/096927 | 12/2002 |
| WO | 03/068797 | 8/2003 |
| WO | 03/070910 | 8/2003 |
| WO | 03/080638 | 10/2003 |
| WO | 04/043977 | 5/2004 |
| WO | 04/072261 | 8/2004 |
| WO | WO 95/06731 | 3/2005 |

OTHER PUBLICATIONS

Abramovitz et al., "Catalytic Role of 2'-Hydroxyl Groups Within a Group II Intron Active Site," *Science* 271:1410-1413 (1996).

Akhtar and Juliano, Cellular Uptake and Intracellular Fate of AntiSense Oligonucleotides, *Trends Cell Biol.* 2:139-144 (1992).

Aldrian-Herrada et al., "A peptide nucleic acid (PNA) is more rapidly internalized in culture neurons when coupled to a *retro-inverso* delivery peptide. The antisense activity depresses the target mRNA and protein in magnocellular oxytocin neurons," *Nucleic Acids Research* 26:4910-4916 (1998).

Banerjee and Turner, "The Time Dependence of Chemical Modification Reveals Slow Steps in the Folding of a Group I Ribozyme," *Biochemistry* 34:6504-6512 (1995).

Bartel and Szostak," Isolation of New Ribozymes from a Large Pool of Random Sequences," *Science* 261:1411-1418 (1993).

Bass, "The short answer," *Nature* 411:428-429 (2001).

Beaudry and Joyce, "Directed Evolution of an RNA Enzyme," *Science* 257:635-641 (1992.

Beigelman et al., "Chemical Modification of Hammerhead Ribozymes," *The Journal of Biological Chemistry* 270: 24702-24708 (1995).

Bellas et al., "Inhibition of NF-$_\kappa$B Activity Induces Apoptosis in Murine Hepatocytes," *American Journal of Pathology* 151:891-896 (1997).

Bellon et al., "Amino-Linked Ribozymes: Post-Synthetic Conjugation of Half-Ribozymes," *Nucleosides & Nucleotides* 16:951-954 (1997).

Bellon et al., "Post-synthetically Ligated Ribozymes: An Alternative Approach to Iterative Solid Phase Synthesis," *Bioconjugate Chem.* 8:204-212 (1997).

Berzal-Herranz et al., "Essential nucleotide sequences and secondary structure elements of the hairpin ribozyme," *EBMO J.* 12:2567-2574 (1993).

Berzal-Herranz et al., "In vitro selection of active hairpin ribozymes by sequential RNA-catalyzed clevage and ligation reactions," *Genes & Development* 6:129-134 (1992).

Bevilacqua et al., "A Mechanistic Framework for the Second Step of Splicing Catalyzed by the *Tetrahymena* Ribozyme," *Biochemistry* 35:648-568 (1996).

Blesch, "Delivery of Neurotrophic Factors to Neuronal Targets: Toward Gene Therapy in the CNS," *Drug News & Perspectives* 13:269-280 (2000).

Boado et al., "Drug Delivery of Antisense Molecules to the Brain for Treatment of Alzheimer's Disease and Cerebral AIDS," *Journal of Pharmaceutical Sciences* 87:1308-1315 (1998).

Boado, "Antisense drug delivery through the blood-brain barrier," *Advanced Drug Delivery Reviews* 15:73-107 (1995).

Breaker and Joyce, "Inventing and improving ribozyme function: rational design versus iterative selection methods," *TIBTECH* 12:268-275 (1994).

Breaker et al., "A DNA enzyme with $Mg^2$-dependent RNA phosphoesterase activity," *Chemistry & Biology* 2(10):655-660 (1995).

Breaker, "Are engineered proteins getting competition from RNA?" *Current Opinion in Biotechnology* 7:442-448 (1996).

Breaker, "Catalytic DNA: in training and seeking employment," *Nature Biotechnology* 17:422-423 (1999).

Brennan et al., "Two-Dimensional Parallel Array Technology as a New Approach to Automated Combinatorial Solid-Phase Organic Synthesis," *Biotechnology and Bioengineering (Combinatorial Chemistry)* 61:33-45 (1998).

Brody and Gold, "Aptamers as therapeutic and diagnostic agents," *Reviews in Molecular Biotechnology* 74:5-13 (2000).

Burgin et al., "Chemically Modified Hammerhead Ribozymes with Improved Catalytic Rates," *Biochemistry* 35:14090-14097 (1996) (vol. No. mistakenly listed as 6).

Burlina et al., "Chemical Engineering of RNase Resistant and Catalytically Active Hammerhead Ribozymes," *Bioorganic & Medicinal Chemistry* 5:1999-2010 (1997).
Caruthers et al., "Chemical Synthesis of Deoxyoligonucleotides and Deoxyoligonucleotide Analogs," *Methods in Enzymology* 211:3-19 (1992).
Cech, "Ribozymes and Their Medical Implications," *JAMA* 260:3030-3034 (1988).
Chartrand et al., "An oligodeoxyribonucleotide that supports catalytic activity in the hammerhead ribozyme domain," *Nucleic Acids Research* 23(20):4092-4096 (1995).
Chen et al., "Multitarget-Ribozyme Directed to Cleave at up to Nine Highly Conserved HIV 1 env RNA Regions Inhibits HIV-1 Replication-Potential Effectiveness Against Most Presently Sequenced HIV-1 Isolates," *Nucleic Acids Research* 20:4581-4589 (1992).
Chowrira et al., "In Vitro and in Vivo Comparison of Hammerhead, Hairpin, and Hepatitis Delta Virus Self-Processing Ribozyme Cassettes," *J. Biol. Chem.* 269:25856-25864 (1994.
Chowrira et al., "Novel guanosine requirement for catalysis by the hairpin ribozyme," *Nature* 354:320-322 (1991).
Christoffersen and Marr, "Riobozymes as Human Therapeutic Agents," *J. Med. Chem.* 38:2023-2037 (1995) (also referred to as Christofferson and Marr).
Christoffersen et al., "Application of computational technologies to ribozyme biotechnology products," *Journal of Molecular Structure (Theochem)* 311:273-284 (1994).
Cload and Schepartz, "Polyther Tethered Oligonucleotide Probes," *J. Am. Chem. Soc.* 113:6324-6326 (1991).
Collins and Olive, "Reaction Conditions and Kinetics of Self-Cleavage of Ribozyme Derived From *Neurospora* VS RNA," *Biochemistry* 32:2795-2799 (1993).
Couture and Stinchcomb, "Anti-gene therapy: the use of ribozymes to inhibit gene function," *Trends In Genetics* 12:510-515 (1996).
Crooke, "Advances in Understanding the Pharmacological Properties of Antisense Oligonucleotides," *Advances in Pharmacology* 40:1-49 (1997).
Crooke, "Antisense Therapeutics," *Biotechnology and Genetic Engineering Reviews* 15:121-157 (1998).
Crooke, "Progress in Antisense Technology: The End of the Beginning," *Methods in Enzymology* 313:3-45 (1999).
Daniels et al., "Two Competing Pathways for Self-splicing by Group II Introns: A Quantitative Analysis of in Vitro Reaction Rates and Products," *J. Mol. Biol.* 256:31-49 (1996).
Delihas et al., "Natural antisense RNA/target RNA interactions: Possible models for antisense oligonucleotide drug design," *Nature Biotechnology* 15:751-753 (1997).
Dreyfus, "Restriction Ribozymes?" *Einstein Quarterly Journal of Biology and Medicine* 6:92-93 (1988).
Dropulic et al., "Functional Characterization of a U5 Ribozyme: Intracellular Suppression o Human Immunodeficiency Virus Type I Expression," *Journal of Virology* 66:1432-1441 (1992).
Durand et al., "Circular Dichroism Studies of an Oligodeoxyribonucleotide Containing a Hairpin Loop Made of a Hexaethylene Glycol Chain: Conformation and Stability," *Nucleic Acids Research* 18:6353-6359 (1990).
Duval-Valentin, "Specific inhibition of transcription by triple helix-forming oligonucleotides," *Proc. Natl. Acad. Sci. USA* 89:504-508 (1992).

Earnshaw et al., "Modified Oligoribonucleotides as Site-Specific Probes of RNA Structure and Function," *Biopolymers* 48:39-55 (1998).
Eck et al., "Inhibition of Phorbol Ester-Induced Cellular Adhesion by Competitive Binding o $NF\text{-}_{\kappa}B$ In Vivo," *Mol. Cell. Biol.* 13:6530-6536 (1993).
Egholm et al., "PNA hybridizes to complementary oligonucleotides obeying the Watson-Crick hydrogen-bonding rules," *Nature* 365:566-568 (1993).
Elbashir et al., "Duplexes of 21-nucleotide RNAs mediate RNA interference in cultured mammalian cells," *Nature* 411: 494-498 (2001).
Elkins and Rossi, "Ch. 2 —Cellular Delivery of Ribozymes," *Delivery Strategies for Antisense Oligonucleotide Therapeutics*, edited by Akhtar, CRC Press, pp. 17-220 (1995).
Elroy-Stein and Moss, "Cytoplasmic Expression System Based on Constitutive Synthesis of Bacteriophage T7 RNA Polymerase in Mammalian Cells," *Proc. Natl. Acad. Sci. USA* 87:6743-6747 (1990).
Emerich et al., "Biocompatability of Poly (DL-Lactide-*co*-Glycolide) Microspheres Implante Into the Brain," *Cell Transplantation* 8:47-58 (1999).
Feldstein et al., "Two sequences participating in the autolytic processing of satellite tobacco ringspot virus complementary RNA," *Gene* 82:53-61 (1989).
Ferentz and Verdine, "Disulfied Cross-Linked Oligonucleotides," *J. Am. Chem. Soc.* 113:4000-4002 (1991).
Forster and Altman, "External Guide Sequences for an RNA Enzyme," *Science* 249:783-786 (1990).
Fox, "Targeting DNA with Triplexes," *Current Medicinal Chemistry* 7:17-37 (2000).
Freier et al., "Improved free-energy parameters for predictions of RNA duplex stability," *Proc. Natl. Acad. Sci. USA* 83:9373-9377 (1986).
Gao and Huang, "Cytoplasmic Expression of a Reporter Gene by Co-Delivery of T7 RNA Polymerase and T7 Promoter Sequence with Cationic Liposomes," *Nucleic Acids Research* 21:2867-2872 (1993).
Gold et al., "Diversity of Oligonecleotide Functions," *Annu. Rev. Biochem.* 64:763-797 (1995).
Gold, "Axonal Regeneration of Sensory Nerves is Delayed by Continuous Intrathecal Infusion of Nerve Growth Factor," *Neuroscience* 76:1153-1158 (1997).
Good et al., "Expression of small, therapuetic RNAs in human nuclei," *Gene Therapy* 4:4554 (1997).
Grasby et al., "Purine Functional Groups in Essential Residues of the Hairpin Ribozyme Required for Catalytic Cleavage of RNA," *Biochemistry* 34:4068-4076 (1995).
Griffin et al., "Group II intron ribozymes that cleave DNA and RNA linkages with similar efficiency, and lack contacts with substrate 2'-hydroxyl groups," *Chemistry & Biology* 2:761-770 (1995).
Groothuis and Levy, "The entry of antiviral and antiretroviral drugs into the central nervous system," *Journal of NeuroVirology* 3:387-400 (1997).
Guerrier-Takada et al., "The RNA Moiety of Ribonuclease P Is the Catalytic Subunit of the Enzyme," *Cell* 35:849-857 (1983).
Guo and Collins, "Efficent *trans*-cleavage of a stem-loop RNA substrate by a ribozyme derived from *Neurospora* VS RNA," *EMBO J.* 14:368-376 (1995).

Hagihara et al., "Widespread gene transfection into the central nervous system of primates," *Gene Therapy* 7:759-763 (2000).

Hammann et al., "Length Variation of Helix III in a Hammerhead Ribozyme and Its Influence on Cleavage Activity," *Antisense & Nucleic Acid Drug Development* 9:25-31 (1999).

Hampel and Tritz, "RNA Catalytic Properties of the Minimum (-)s TRSV Sequence," *Biochemistry* 28:4929-4933 (1989).

Hampel et al., "'Hairpin'Catalytic RNA Model: Evidence for Helices and Sequence Requirement for Substrate RNA," *Nucleic Acids Research* 18:299-304 (1990).

Harris et al., "Identification of phosphates involves in catalysis by the ribozyme RNase P RNA," *RNA* 1:210-218 (1995).

Haseloff and Gerlach, "Sequences required for self-catalysed cleavage of the satellite RNA of tobacco ringspot virus," *Gene* 82:43-52 (1989).

Haseloff and Gerlach, "Simple RNA Enzymes with New and Highly Specific Endoribonuclease," *Nature* 334:585-591 (1988).

Hegg et al., "Kinetics and Thermodynamics of Intermolecular Catalysis by Hairpin Ribozymes," *Biochemistry* 34:15813-15828 (1995).

Hermann and Patel, "Adaptive Recognition by Nucleic Acid Aptamers," *Science* 287:820-825 (2000).

Herrlinger et al., HSV-1 Vectors for Gene Theerapy of Experimental CNS Tumors, *Methods Mol. Med.*, 35, 287-312 (2000).

Herschlag and Cech, "Catalysis of RNA Cleavage by the *Tetrahymena thermophila* Ribozyme 1. Kinetic Description of the Reaction of an RNA Substrate Complementary to the Active Site," *Biochemistry* 29:10159-10171 (1990).

Herschlag and Cech, "Catalysis of RNA Cleavage by the *Tetrahymena thermophila* Ribozyme. 2. Kinetic Description of the Reaction of an RNA Substrate That Forms a Mismatch at the Active Site," *Biochemistry* 29:10172-10180 (1990).

Hertel et al., "A Kinetic Thermodynamic Framework for the Hammerhead Ribozyme Reaction," *Biochemistry* 33:3374-3385 (1994).

Hertel et al., "Numbering System for the Hammerhead," *Nucleic Acids Research* 20:3252 (1992).

Hunziker et al., "Nucleic Acid Analogues: Synthesis and Properties, in Modern Synthetic Methods," *VCH*, 331-417.

Ishiwata et al., "Physical-Chemistry Characteristics and Biodistribution of Poly(ethyleneglycol)-Coated Liposomes Using Poly(oxyethylene) Cholesteryl Ether," *Chem. Pharm. Bul* 43:1005-1011 (1995).

Izant and Weintraub, "Constitutive and Conditional Suppression of Exogenous and Endogeneous Genes by Anti-Sense RNA," *Science* 229:345-352 (1985).

Jaeger et al., "Improved Predictions of Secondary Structures for RNA," *Proc. Natl. Acad. Sci. USA* 86:7706-7710 (1989).

Jarvis et al., "Optimizing the Cell Efficacy of Synthetic Ribozymes," *Journal of Biological Chemistry* 271:29107-29112 (1996).

Jaschke et al., "Automated Incorporation of Polyethylene Glycol into Synthetic Oligonucleotides," *Tetrahedron Letters* 34:301-304 (1993).

Jayasena, "Aptamers: An Emerging Class of Molecules that Rival Antibodies in Diagnostics," *Clinical Chemistry* 45:1628-1650 (1999).

Jeffries and Symons, "A Catalytic 13-mer Ribozyme," *Nucleic Acids Research* 17:1371-1377 (1989).

Jolliet-Riant and Tillement, "Drug transfer across the blood-brain barrier and improvement of brain delivery," *Fudam. Clin. Pharmacol.* 13:16-26 (1999).

Joseph et al., "Substrate selection rules for the hairpin ribozyme determined by in vitro selection, mutation, and analysis of mismatched substrates," *Genes & Development* 7:130-138 (1993).

Joyce et al., "Amplification, mutation and selection of catalytic RNA," *Gene* 82:83-87 (1989).

Joyce, "Directed Molecular Evolution," *Scientific American* 267:90-97 (1992).

Karpeisky et al, "Highly Efficient Synthesis of 2'-O-Amino Nucleosides And Their Incorporation in Hammerhead Ribozymes," *Tetrahedron Letters* 39:1131-1134 (1998).

Kashani-Sabet et al., "Reversal of the Malignant Phenotype by an Anti-*ras* Ribozyme," *Antisense Research & Development* 2:3-15 (1992).

Kim and Cech, "Three-dimensional model of the active site of the self-splicing rRNA precursor of *Tetrahymena*," *Proc. Natl. Acad. Sci. USA* 84:8788-8792 (1987).

Kitajima et al., "Ablation of Tranplanted HTLV-I Tax-Transformed Tumors in Mice by Antisense Inhibition of NF-$_\kappa$B," *Science* 258:1792-1795 (1992).

Knitt et al., "ph Dependencies of the *Tetrahymena* Ribozyme Reveal an Unconvential Origin of an Apparent p$K_a$," *Biochemistry* 35:1560-1570 (1996).

Kore, et al., "Sequence specificity of the hammerhead ribozyme revisistsed; the NIH rule," *Nucleic Acids Research*, 26(18):4116-4120 (1998).

Krappmann et al., The IκB Kinase (IKK) Complex is Tripartite and Contains IKKγ but Not IKAP as a Regular Component J. Biol. Chem. 2000 275:29779-29787.

Kumar and Ellington, "Artificial evolution and natural ribozymes," *FASEB J.* 9:1183-1195 (1995).

Kunsch and Rosen, "NF-$_\kappa$B Subunit-Specific Regulation of the Interleukin-8 Promoter," *Mol. Cell. Biol.* 13:6137-6146 (1993).

Kusser, "Chemically modified nucleic acid aptamers for in vitro selections: evolving evolution," *Reviews in Molecular Biotechnology* 74:27-38 (2000).

Lasic and Needham "The 'Stealth' Lipsome: A Prototypical Biomaterial," *Chemical Reviews* 95:2601-2627 (1995).

Lasic and Papahadjopoulos, "Liposomes Revisited," *Science* 267:1275-1276 (1995).

Lenardo and Baltimore, "NF-$_\kappa$B: A Pleiotropic Mediator of Inducible and Tissue Specific Gene Control," *Cell* 58:227-229 (1989).

Li and Altman, "Cleavage by RNase P of gene N mRNA reduces bacteriophage λ burst size," *Nucleic Acids Research* 24:835-842 (1996).

Li et al., "Thermodynamic and Activation Parameters for Binding of a Pyrene-Labeled Substrate by the *Tetrahymena* Ribozyme: Docking is Not Diffusion-Controlled and is Driven by a Favorable Entropy Change," *Biochemistry* 34:14394-14399 (1995).

Leiber et al., "Stable High-Level Gene Expression in Mammalian Cells by T7 Phage RNA Polymerase," *Methods Enzymol.* 217:47-66 (1993).

Lim et al., "Nuclear Factor-κB Regulats Cyclooxygenase-2 Expression and Cell Proliferation in Human Gastric Cancer Cells," *Laboratory Investigation* 81:349-360 (2001).

Limbach et al., "Summary: the modified nucleosides of RNA," *Nucleic Acids Research* 22(12):2183-2196 (1994).

Lisacek et al., "Automatic Identification of Group I Intron Cores in Genomic DNA Sequences," *J. Mol. Biol.* 235:1206-1217 (1994).

Lisziewicz et al., "Inhbition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000-8004 (1993).

Liu et al., "Cationic Liposome-mediated Intravenous Gene Delivery," *J. Biol. Chem.* 270(42):24864-24870 (1995).

Liu et al., "Specific NF-$_\kappa$B Subunits Act in Concert with Tat To Stimulate Human Immunodeficiency Virus Type 1 Transcription," *J. Virology* 66:3883-3887 (1992).

Ma et al., "Design and Synthesis of RNA Miniduplexes via a Synthetic Linker Approach. 2. Generation of Covalently Closed, Double-Stranded Cyclic HIV-1 TAR RNA Analogs with High Tat-Binding Affinity," *Nucleic Acids Research* 21:2585-2589 (1993).

Ma et al., "Design and Synthesis of RNA Miniduplexes via a Synthetic Linker Approach," *Biochemistry* 32:1751-1758 (1993).

Maher et al., "Kinetic Analysis of Oligodeoxyribonucleotide-Directed Triple-Helix Formation on DNA," *Biochemistry* 29:8820-8826 (1990).

McCurdy et al., "Deoxyoligonucleotides with Inverted Polarity: Synthesis and Use in Triple-Helix Formation" *Nucleosides & Nucleotides* 10:287-290 (1991).

McGarry and Lindquist, "Inhibition of heat shock protein synthesis by heat-inducible antisense RNA," *Proc. Natl. Acad. Sci. USA* 83:399-403 (1986).

McKay, "Structure and function of the hammerhead ribozyme: an unfinished story," *RNA* 2:395-403 (1996).

Mesmaeker et al, "Novel Backbone Replacements for Oligonucleotides," *American Chemical Society*, pp. 24-39 (1994).

Michel and Westhof, "Slippery substratrates," *Nat. Struct. Biol.* 1:5-7 (1994).

Michel et al., "Structure and Activities of a Group II Introns," *Annu. Rev. Biochem.* 64:435-461 (1995).

Michels and Pyle, "Conversion of a Group II Intron into a New Multiple-Turnover Ribozyme that Selectively Cleaves Oligonucleotides: Elucidation of Reaction Mechanism and Structure/Function Relationships," *Biochemistry* 34:2965-2977 (1995).

Milligan and Uhlenbeck, "Synthesis of Small RNAs Using T7 RNA Polymerase," *Methods Enzymol.* 180:51-62 (1989).

Milner et al., "Selecting effective antisense reagents on combinatorial oligonucleotide arrays," *Nature Biotechnology* 15:537-541 (1997).

Moore and Sharp, "Site-Specific Modification of Pre-mRNA: The 2'-Hydroxyl Groups at the Splice Sites," *Science* 256:992-996 (1992).

Mukhopadhyay et al., "Antisense Regulation of Oncogenes in Human Cancer," *Critical Reviews in Oncogenesis* 7:151-190 (1996).

Narayanan et al., "Evidence for Differential Functions of the p50 and p65 Subunits of NF-$_\kappa$B with a Cell Adhesion Model," *Mol. Cell. Biol.* 13:3802-3810 (1993).

Nathans and Smith, "Restriction Endonucleases in the analysis and Restruturing of DNA Molecules," *Ann. Rev. Biochem.* 44:273-293 (1975).

Noonberg et al., In vivo generation of higly abundant sequence-specific oligonucleotides for antisense and triplex gene regulation, *Nucleic Acids Research* 22(14):2830-2836 (1994).

Ohkawa et al., "Activities of HIV-RNA Targeted Ribozymes Transcribed From a 'Shot-Gun Type Ribozyme-trimming Plasmid," *Nucleic Acids Symp. Ser.* 27:15-16 (1992).

Ojwang et al., "Inhibition of Human Immunodeficiency Virus Type 1 Expression by a Hairpin Ribozyme," *Proc. Natl. Acad. Sci. USA* 89:10802-10806(1992).

Oku et al., "Real-time analysis of liposomal trafficking in tumor-bearing mice by use of positron emission tomography," *Biochimica et Biophysica Acta* 1238:86-90 (1995).

Ono et al., "DNA Triplex Formation of Oligonucleotide Analogues Consisting of Linker Groups and Octamer Segments That Have Opposite Sugar-Phosphate Backbone Polarities," *Biochemistry* 30:9914-9921 (1991).

Orgel, "Selection in vitro," *Proc. R. Soc. London B.* 205:435-442 (1979).

Pan et al., "Probing of tertiary interactions in RNA: 2'-Hydroxyl-base contacts between the Rnase P and pre-tRNA," *Proc. Natl. Acad. Sci. USA* 92:12510-12514 (1995).

Pardridge et al., "Vector-mediated delivery of a polyamide ("peptide") nucleic acid analogue through the blood-brain barrier in vivo," *Proc. Natl. Acad. Sci. USA* 92:5592-559 (1995).

Peel and Klein, "Adeno-associated virus vectors: activity and applications in the CNS," *Journal of Neuroscience Methods* 98:95-104 (2000).

Perkins et al., "Distinct combinations of NF-$_\kappa$B subunits determine the specificity of transcriptional activation," *Proc. Natl. Acad. Sci. USA* 89:1529-1533 (1992).

Perreault et al., "Mixed Deoxyribo- and Robo-Oligonucleotides with Catalytic Activity," *Nature* 344:565-567 (1990).

Perrotta and Been, "A pseudoknot-like structure required for efficient self-cleavage of hepatitis delta virus RNA," *Nature* 350:434-436 (1991).

Perrotta and Been, "Cleavage of Oligoribonucleotides by a Ribozyme Derived from the Hepatitis $\delta$ Virus RNA Sequence," *Biochemistry* 31:16-21 (1992).

Peterson et al., "Future Prospects of Gene Therapy for Treating CNS Diseases," *Central Nervous System Diseases* Chapter 24:485-508 (2000).

Pianetti et al., "Her-2/neu overexpression induces NF-κB via a Pl3-kinase/Akt pathway involving calpain-mediated degradation of lκB-α that can be inhibited by the tumor suppressor PTEN," *Oncogene* 20:1287-1299 (2001).

Pieken et al., "Kinetic Characterization of Ribonuclease-Resistant 2'-Modified Hammerhea Ribozymes," *Science* 253:314-317 (1991).

Praseuth et al., "Triple helix formation and the antigene for sequence-specific control of gene expression," *Biochimica et Biophysica Acta* 1489:181-206 (1999).

Puttaraju et al., "A circular trans-acting hepatitis delta virus ribozyme," *Nucleic Acids Research* 21:4253-4258 (1993).

Pyle et al., "Building a Kinetic Framework for Group II Intron Ribozyme Activity: Quantitation of Interdomain Binding and Reaction Rate," *Biochemistry* 33:2716-2725 (1994).

Ray and Prefontaine, "Physical association and functional antagonism between the p65 subunit of transcription factor NF-$_\kappa$B and the glucocorticoid receptor," *Proc. Natl. Acad. Sci. USA* 91:752-756 (1994).

Read et al., "NF-$_\kappa$B and I$_\kappa$B$_\alpha$: An Inducible Regulatory System in Endothelial Activation," *J. Exp. Med.* 179:503-512 (1994).

Richardson and Schepartz, "Tethered Oligonucleotide Probes. A Strategy for the Recognition of Structured RNA," *J. Am. Chem. Soc.* 113:5109-5111 (1991).

Robertson et al., "Purification and Properties of a Specific *Escherichia coli* Riobnuclease which Cleaves a Tyrosine Transfer Ribonucleic Acid Precursor," *J. Biol. Chem.* 247:5243-5251 (1972).

Rossi et al., "Ribozymes as Anti-HIV-1 Therapeutic Agents: Principles, Applications, and Problems," *Aids Research and Human Retroviruses* 8:183-189 (1992).

Santoro and Joyce, "A general purpose RNA-cleaving DNA enzyme," *Proc. Natl. Acad. Sci. USA* 94:4262-4266 (1997).

Santoro et al., "Mechanism and Utility of an RNA-Cleaving DNA Enzyme," *Biochemistry* 37:13330-13342 (1998).

Santoro et al., "RNA Cleavage by a DNA Enzyme with Extended Chemical Functionality," *J. Am. Chem. Soc.* 122:2433-2439 (2000).

Sarver et al., "Ribozymes as Potential Anti-HIV-1 Therapeutic Agents" *Science* 247:1222-1225 (1990).

Savill and Collins, "A Site-Specific Self-Cleavage Reaction Performed by a Novel RNA In Neurospora Mitochondria," *Cell* 61:685-696 (1990).

Saville and Collins, "RNA-Mediated Ligation of Self-Cleavage Products of a *Neurospora* Mitochondria Plasmid Transcript," *Proc. Natl. Acad. Sci. USA* 88:8826-8830 (1991).

Scanlon et al., "Ribozyme-Mediated Cleavage of c-fos mRNA Reduces Gene Expression of DNA Synthesis Enzymes and Metallothionein," *Proc. Natl. Acad. Sci. USA* 88:10591-10595 (1991).

Scaringe et al., "Chemical synthesis of biologically active oligoribonucleotides using β-cyanoethyl protected ribonucleoside phosphoramidites," *Nucl Acids Res.* 18:5433-5441 (1990).

Schmajuk et al., "Antisense Oligonucleotides with Different Backbones," *The Journal of Biological Chemistry* 274:21783-21789 (1999).

Schmidt et al., "Base and sugar requirements for RNA cleavage of essential nucleoside residues in internal loop B of the hairpin ribozyme: implications for secondary structure," *Nucleic Acids Research* 24:573-581 (1996).

Schroeder et al., "Diffusion Enhancement of Drugs by Loaded Nanoparticles in Vitro," *Pro Neuro-Psychopharmacol. & Biol. Psychiat.* 23:941-949 (1999).

Scott et al., "The crystal structure of an All-RNA hammerhead ribozyme: A proposed mechanism for RNA catalytic cleavage," *Cell* 81:991-1002 (1995).

Seela and Kaiser, "Oligodeoxyribonucleotides containing 1,3-propanediol as nucleoside substitute," *Nucleic Acids Research* 15:3113-3129 (1987).

Shabarova et al., "Chemical ligation of DNA: The first non-enyzmatic assembly of a biologically active gene," *Nucleic Acids Research* 19:4247-4251 (1991).

Silverman et al., "Selective RNA Cleavage by Isolated RNase L Activated with 2-5A Antisense Chimeric Oligonucleotides," *Methods in Enzymology* 313:522-533 (1999).

Sovak et al., "Aberrant Nuclear Factor-$_k$B/Rel Expression and the Pathogenesis of Breast Cancer," *J. Clin. Invest.* 100:2952-2960 (1997).

Stein and Cheng, "Antisense Oligonucleotides as Theapeutic Agents —Is the Bullet Really Magical?" *Science* 261:1004-1288 (1993).

Stein et al., "A Specificity Comparison of Four Antisense Types: Morpholino, 2'-O-Methyl RNA, DNA, and Phosphorothioate DNA," *Antisense & Nucleic Acid Drug Development* 7:151-157 (1997).

Strobel and Dervan, "Site-Specific Cleavage of a Yeast Chromosome by Oligonucleotide-Directed Triple-Helix Formation," *Science* 249:73-75 (1990).

Strobel et al., "Exocylic Amine of the Conserved G.U Pair at the Cleavage Site of the *Tetrahymena* Ribozyme Contributes to 5'-Splice Site Selection and Transition State Stabilization," *Biochemistry* 35:1201-1211 (1996).

Strobel et al., "Minor Groove Recognition of the Conserved G.U Pair at the *Tetrahymena* Ribozyme Reaction Site," *Science* 267:675-679 (1995).

Sullenger and Cech, "Ribozyme-mediated repair of defective mRNA by targeted trans-splicing," *Nature* 371:619-622 (1994).

Sullenger and Cech, "Tethering Ribozymes to a Retroviral Packaging Signal for Destruction of Viral RNA," *Science* 262:1566-1569 (1993).

Sullenger et al., "Overexpression of TAR Sequences Renders Cells Resistant to Human Immunodeficiency Virus Replication," *Cell* 63:601-608 (1990).

Sun, "Technology evaluation: SELEX, Giliad Sciences Inc," *Current Opinion in Molecular Therapeutics* 2:100-105 (2000).

Szostak and Ellington, "Ch. 20 —In Vitro Selection of Functional RNA Sequences,"in *The RNA World*, edited by Gesteland and Atkins, Cold Spring Harbor Laboratory Press, pp. 511-533 (1993).

Szostak, In Vitro Genetics, TIBS 17:89-93 (1993).

Taira et al., "Construction of a novel RNA-transcript-trimming plasmid which can be used both in vitro in place of run-off and (G)-free transcriptions and in vivo as multisequences transcription vectors," *Nucleic Acids Research* 19:5125-5130 (1991).

Tang et al., "Examination of the catalytic fitness of the hammerhead ribozyme by in vitro selection," *RNA* 3:914-925 (1997).

Thompson et al., "Improved accumulation and activity of ribozymes expressed from a tRNA-based RNA polymerase III promoter," *Nucleic Acids Research* 23:2259-2268 (1995).

Torrence et al., "Targeting RNA for degradation with a (2'-5') oligoadenylate-antisense chimera," *Proc. Natl. Acad. Sci. USA* 90:1300-1304 (1993).

Turner et al., "Improved Parameters for Prediction of RNA Structure," *Cold Spring Harbor Symposia on Quantitative Biology* vol. LII, pp. 123-133 (1987).

Turner et al., "Free Energy Increments for Hydrogen Bonds in Nucleic Acid Base Pairs," *J. Am. Chem. Soc.* 109:3783-3785 (1987).

Tyler et al., "Peptide nucleic acids targeted to the neurotensin receptor and administered i.p. cross the blood-brain barrier and specifically reduce gene expression," *Proc. Natl. Acad. Sci. USA* 96:7053-7058 (1999).

Tyler et al., "Specific gene blockade shows that peptide nucleic acids readily enter neuronal cells in vivo," *FEBS Letters* 421:280-284 (1998).

Uhlenbeck, "A Small Catalytic Oligoribonucleotide," *Nature* 328:596-600 (1987).

Usman and Cedergren, "Exploiting the chemical synthesis of RNA," *TIBS* 17:334-339 (1992).

Usman and McSwiggen, "Ch. 30 —Catalytic RNA (Ribozymes) as Drugs," *Annual Reports in Medicinal Chemistry* 30:285-294 (1995).

Usman et al., "Automated Chemical Synthesis of Long Oligoribonucleotides Using 2'-O-Silylated Ribonucleoside 3'-O-Phosphoramidites on a Controlled-Pore Glass Support: Synthesis of a 43Nucleotide Sequence Similar to the 3'-Half Molecule of an *Escherichia coli* Formylmethoionine tRNA," *J. Am. Chem. Soc.* 109:7845-7854 (1987).
Usman et al., "Chemical modification of hammerhead ribozymes: activity and nuclease resistance," *Nucleic Acids Symposium Series* 31:163-164 (1994).
Usman et al., "Hammerhead ribozymes engineering," *Current Opinion in Structural Biology* 1:527-533 (1996).
Vaish et al., "Isolation of Hammerhead Ribozymes with Altered Core Sequences by in Vitro Selection," *Biochemistry* 36:6495-6501 (1997).
van de Stolpe et al., "12-O-Tetradecanoylphorbol- 13-acetate- and Tumor Necrosis Factor α-meidated Induction of Intercellular Adhesion Molecule-1 Is Inhibited by Dexamethasone," *J. Biol. Chem.* 269:6185-6192 (1994).
Ventura et al., "Activation of HIV-Specific Ribozyme Activity by Self-Cleavage," *Nucleic Acids Research* 21:3249-3255 (1993).
Verma and Eckstein, "Modified Oligonucleotides: Synthesis and Strategy for Users," *Annu Rev. Biochem.* 67:99-134 (1998).
Warashina, et al., "Extremeley High and Specific Activity of DNA Enzymes in Cells with a Philadelphia Chromosome," *Chemistry & Biology*, 6(4):237-250 (1999).
Werner and Uhlenbeck, "The effect of base mismatches in the substrate recognition helices of hammerhead ribozymes on binding and catalysis," *Nucleic Acids Research* 23:2092-2096 (1995).
Wincott et al., "Synthesis deprotection, analysis and purification of RNA and ribozymes," *Nucleic Acids Research* 23(14):2677-2684 (1995).
Wincott et al., "A Practical Method for the Production of RNA and Ribozymes," *Methods in Molecular Biology* 74: 59-69 (1997).
Woolf et al., "Specificity of Antisense Oligonucleotides in vivo," *Proc. Natl. Acad. Sci. USA* 89:7305-7309 (1992).
Yu et al., "A Hairpin Ribozyme Inhibits Expression of Diverse Strains of Human Immunodeficiency Virus Type 1," *Proc. Natl. Acad. Sci. USA* 90:6340-6344 (1993).
Yuan et al., "Targeted cleavage of mRNA by human RNase P," *Proc. Natl. Acad. Sci. USA* 89:8006-8010 (1992).
Zarrinkar and Williamson, "The P9.1-P9.2 peripheral extension helps guide folding of the *Tetrahymena* ribozyme," *Nucleic Acids Research* 24:854-858 (1996).
Zaug et al., "The *Tetrahymena* Ribozyme Acts Like an RNA Restriction Endonuclease," *Nature* 324:429-433 (1986).
Zhou et al., "Synthesis of Functional mRNA in Mammalian Cells by Bacteriophage T3 RNA Polymerase," *Mol. Cell. Biol.* 10:4529-4537 (1990).
Zimmerly et al., "A Group II Itron RNA is a Catalytic Component of a DNA Endonuclease Involved in Intron Mobility," *Cell* 83:529-538 (1995).
Amitabha et al., "RNA-Dependent Protein Kinase PKR Is Required for Activation of NF-$^K$B by IFN-$^\gamma$ in a STAT 1 Independent Pathway," *I Immunol* 166:6170-6180 (2001).
Fournier et al., "Identification of a receptor mediating Nogo-66 inhibition of axonal regeneration", Nature, 409:341-346 (2001).
Ho and Hartig, "Antisense oligonucleotides for large validation in the CNS," *Current Opinion in Molecular Therapeutics*, 1:336-343 (1999).
International Search Report from PCT/US02/10512.
Ishii et al., "Activation of the I$^{78}$ B$_\alpha$Kinase (IKK) complex by double-stranded RNA-binding defective and catalytic inactive mutants of the interferon-inducible protein kinase PKR," Oncogene, 20, 1900-1912 (2001).
Ng et al.,"Nogos and the Nogo-66 Receptor: Factors Inhibiting CNS Neuron Regeneration," *Journ. of Neurosicence Research* 67:559-565 (2002).
Sun et al., "Catalytic Nucleic Acids: From Lab to Applications," *Pharmacological Reviews* 52:325-347 (2000).
Woolf et al., "It Takes More Than Two to Nogo," Science 297:1132-1134 (2002).
Anderson et al., "Bispecific Short Hairpin siRNA Constructs Targeted to CD4, CXCR4, and CCR5 Confer HIV-1 Resistance," *Oligonucleotides*, 13:303-312 (2003).
Bahramian et al., "Transcriptional and Posttranscriptional Silencing of Rodent α1 (l) Collagen by a Homologous Transcriptionally Self-Silenced Transgene," Molecular and Cellular Biology, 274-283 (1999).
Elbashir et al., "Functional-Anatomy of siRNAs for Mediating Efficient RNAi in *Drosophila Melanogaster* Embryo Lysate," *The EMBO Journal* 20:6877-6888 (2001).
Elbashir et al., "RNA Interference is Mediated by 21- and 22-Nucleotide RNAs," *Genes and Development* 15:188-200 (2001).
Fire et al., "Potent and Specific Genetic Interference by Double-Stranded RNA in *Caenorhabditis Elegans,"  Nature* 391:806-811 (1998).
Fire et al., "Potent and Specific Genetic Interference by Double-Stranded RNA in Caenorhabditis Elegans," Nature 391:806-811 (1998).
Futami et al., "Induction of apoptosis in HeLa cells with siRNA expression vector targeted against bcl-2," Nucleic Acids Research Supplement, 251-252 (2002).
Hamilton, et al., "A Species of Small Antisense RNA in Posttranscriptional Gene Silencing in Plants," Science, 286, 950-952 (1999).
International Search Report for PCT/US03/05028 mailed Oct. 17, 2003.
International Search Report for PCT/US03/05346 mailed Oct. 17, 2003.
International Search Report for PCT/US2004/016390 mailed Mar. 31, 2005.
Leirdal et al., "Gene silencing in mammalian cells by preformed small RNA duplexes," Biochemical and Biophysical Research Communications, 295, 744-748 (2002).
Lin et al., "A Novel mRNA-cRNA Interference Phenomenon for Silencing bcl-2 Expression in Human LNCaP Cells," Biochemical and Biophysical Research Communications, 281, 639-644 (2001).
Lin et al., "Policing rogue genes," Nature, 402, 128-129 (1999).
Parrish, "Functional Anatomy of a dsRNA Trigger: Differential Requirement for the Two Trigger Strands in RNA Interference," *Molecular Cell* 6:1077-1087 (2000).
Partial European Search Report for EP 02 76 3926 dated Jan. 12, 2005.
Sharp et al., "RNAi and double-strand RNA," Genes & Development, 13:139-141 (1999).
Strauss, Evelyn, "Molecular Biology Candidate 'Gene Sliencers' Found," Science vol. 286, No. 5441, p. 886 (1999).
Tuschl et al., "Small Interfering RNAs: A Revolutionary Tool for Analysis of Gene Function and Gene Therapy," Molecular Interventions, 295, 3, 158-167 (2002).

Tuschl et al., "Targeted mRNA Degradation by Double-Stranded RNA In Vitro," *Genes & Development* 13:3191-3197 (1999).

Tuschl, "RNA Interference and Small Interefering RNAs," *Chembiochem* 2:239-245 (2001).

Waterhouse et al., "Virus resistance and gene silencing in plants can be induced by simultaneous expression of sense and antisense RNA, " Proc. Natl. Acad. Sci. USA, 95, 13959-13964 (1998).

L'Huillier, "Efficacy of Hammerhead Ribozymes Targeting α-Lactalbumin Transcripts: Experiments in Cells and Transgenic Mice, " *Nucleic Acids and Molecular Biology*, vol. 10, 283-300, 1996.

Player and Torrence, "The 2-5A System: Modulation of Viral and Cellular Processes Through Acceleration of RNA Degradation, " *Pharmacol Ther.* 78:55-113 (1998).

Weerasinghe et al., "Resistance to Human Immunodeficiency Virus Type 1 (HIV-1) Infection in Human $CD4^+$ Lymphocyte-Derived Cell Lines Conferred by Using Retroviral Vectors Expressing an HIV-1 RNA-Specific Ribozyme," *Journal of Virology* 65:5531-5534 (1994).

* cited by examiner

Figure 1: Examples of Nuclease Stable Ribozyme Motifs

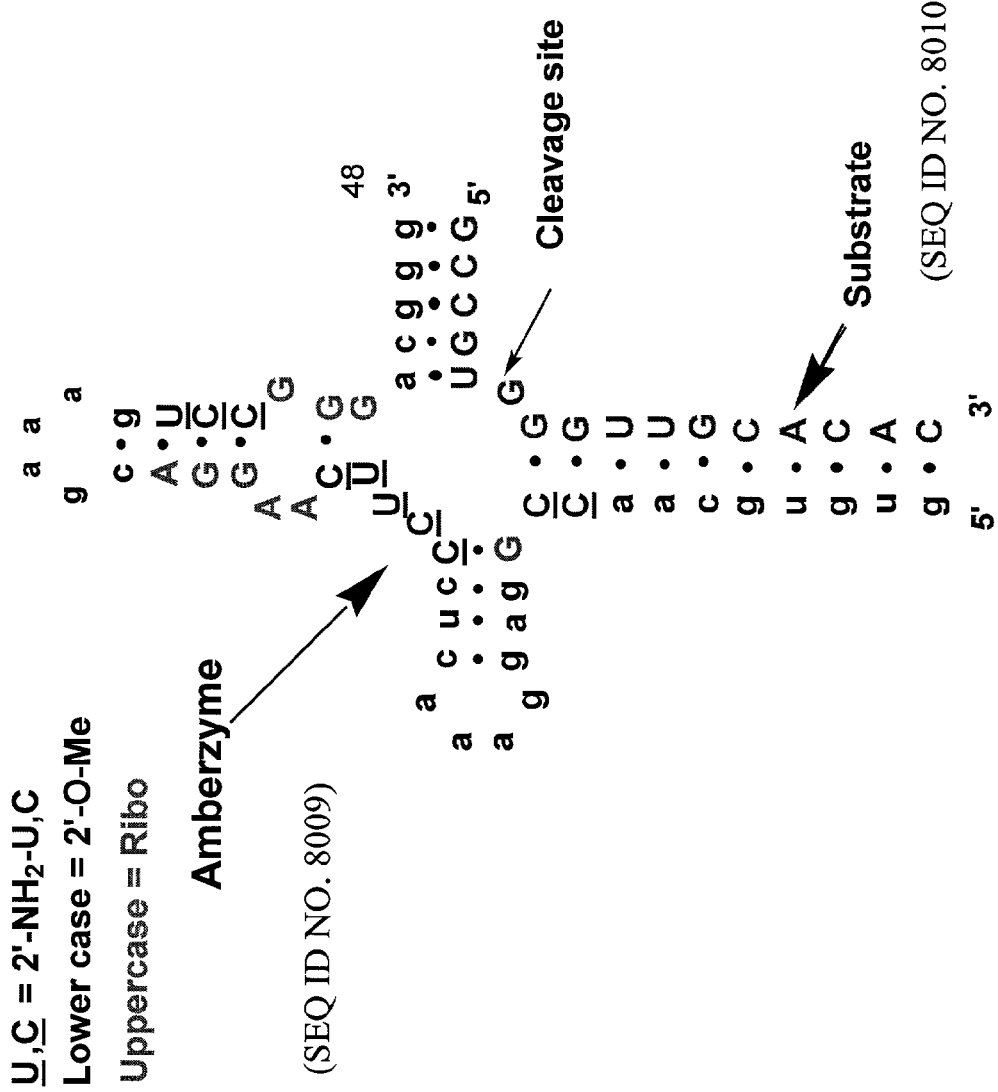

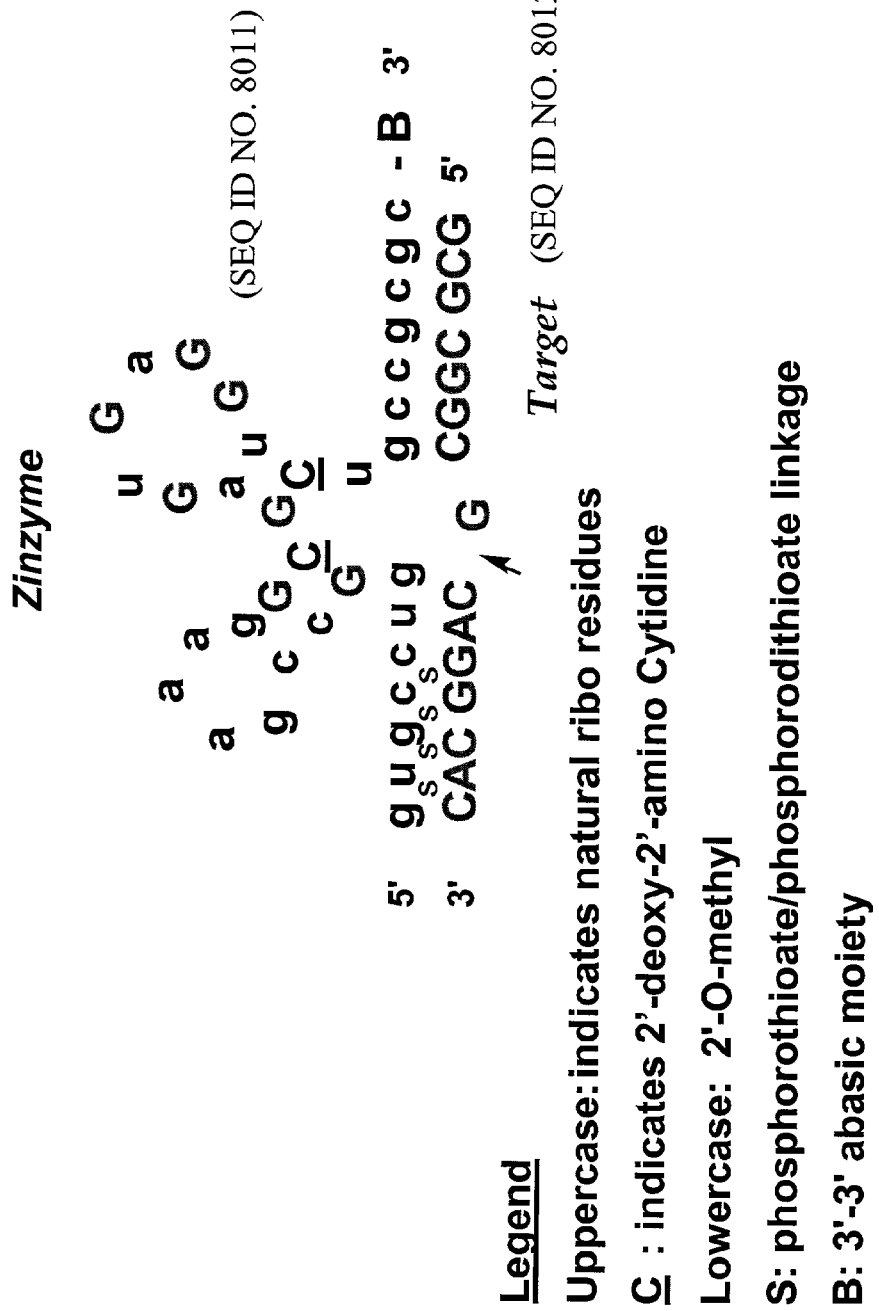
Figure 3: Stabilized Zinzyme Ribozyme Motif

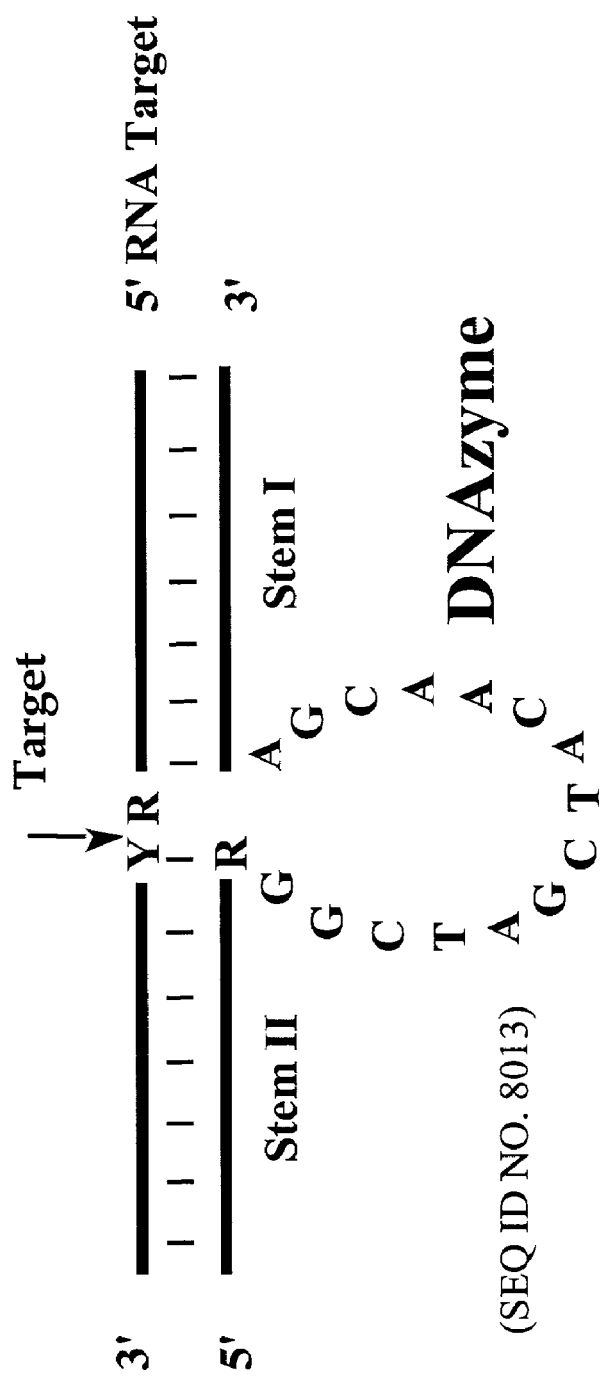
*Figure 4: DNAzyme Motif*
(SEQ ID NO. 8013)
Legend
Y = U or C
R = A or G

SIRNA TREATMENT OF DISEASES OR CONDITIONS RELATED TO LEVELS OF IKK-GAMMA

This patent application claims priority from U.S. Ser. No. 60/294,412, filed May 29, 2001, entitled 'ENZYMATIC NUCLEIC ACID TREATMENT OF DISEASES OR CONDITIONS RELATED TO LEVELS OF IKK-GAMMA AND PKR." This application is hereby incorporated by reference herein in its entirety including the drawings.

INCORPORATION BY REFERENCE

The sequence listing submitted on compact discs, in compliance with 37 C. F. R. § 1.52(e)(5), is incorporated by reference. Two separate compact discs have been submitted, each containing the file "01-664-A_Seq.Listing"which is 1,821,582 bytes in size and was created on May 16, 2005.

FIELD OF THE INVENTION

The present invention relates to therapeutic compositions and methods for the treatment or diagnosis of diseases or conditions related to IKK gamma (IKKG) and PKR levels, such as cancer, inflammatory, and autoimmune diseases and/or disorders.

BACKGROUND OF THE INVENTION

The following is a brief description of the physiological role of nuclear factor kappa B (NFKB), IKK kinases, and protein kinase PKR. The discussion is provided only for understanding the invention that follows. This summary is not an admission that any of the work described below is prior art to the claimed invention.

Nuclear factor kappa B (NFKB) is a multiunit transcription factor which regulates the expression of genes involved in a number of physiologic and pathologic processes. NFKB is a key component of the TNF signaling pathway. These processes include, but are not limited to: apoptosis, immune, inflammatory and acute phase responses. The REL-A gene product (a.k.a. RelA or p65), and p50 subunits of NFKB, have been implicated in the induction of inflammatory responses and cellular transformation. NFKB exists in the cytoplasm as an inactive heterodimer of the p50 and p65 subunits. NFKB is complexed with an inhibitory protein complex, IkappaB (IKK complex), until activated by the appropriate stimuli. NFKB activation can occur following stimulation of a variety of cell types by inflammatory mediators, for example TNF and IL-1, and reactive oxygen intermediates. In response to induction, NFKB can stimulate production of pro-inflammatory cytokines such as TNF-alpha, IL-1-beta, IL-6 and iNOS, thereby perpetuating a positive feedback loop. NFKB appears to play a role in a number of disease processes including: ischemia/reperfusion injury (CNS and myocardial), glomerulonephritis, sepsis, allergic airway inflammation, inflammatory bowel disease, infection, arthritis, and cancer.

The nuclear DNA-binding protein, NFKB, was first identified as a factor that binds and activates the immunoglobulin kappa light chain enhancer in B cells. NFKB now is known to activate transcription of a variety of other cellular genes (e.g., cytokines, adhesion proteins, oncogenes and viral proteins) in response to a variety of stimuli (e.g., phorbol esters, mitogens, cytokines and oxidative stress). In addition, molecular and biochemical characterization of NFKB has shown that the activity is due to a homodimer or heterodimer of a family of DNA binding subunits. Each subunit bears a stretch of 300 amino acids that is homologous to the oncogene, v-rel. The activity first described as NFKB is a heterodimer of p49 or p50 with p65. The p49 and p50 subunits of NFKB (encoded by the NF-kappa B2 or NF kappa B1 genes, respectively) are generated from the precursors NFKB1 (p105) or NFKB2 (p100). The p65 subunit of NFKB (now termed REL-A) is encoded by the rel-A locus.

The roles of each specific transcription-activating complex now are being elucidated in cells (Perkins, et al., 1992, *Proc. Natl. Acad. Sci USA*, 89, 1529–1533). For instance, the heterodimer of NFKB1 and Rel A (p50/p65) activates transcription of the promoter for the adhesion molecule, VCAM-1, while NFKB2/RelA heterodimers (p49/p65) actually inhibit transcription (Shu, et al, 1993, *Mol. Cell. Biol.*, 13, 6283–6289). Conversely, heterodimers of NFKB2/RelA (p49/p65) act with Tat-I to activate transcription of the HIV genome, while NFKB1/RelA (p50/p65) heterodimers have little effect (Liu et al., 1992, *J. Virol.*, 66, 3883–3887). Similarly, blocking rel A gene expression with antisense oligonucleotides specifically blocks embryonic stem cell adhesion; blocking NFKB 1 gene expression with antisense oligonucleotides had no effect on cellular adhesion (Narayanan et al., 1993, *Mol. Cell. Biol.*, 13, 3802–3810). Thus, the promiscuous role initially assigned to NFKB in transcriptional activation (Lenardo, and Baltimore, 1989, *Cell*, 58, 227–229) represents the sum of the activities of the rel family of DNA-binding proteins. This conclusion is supported by recent transgenic "knock-out" mice of individual members of the rel family. Such "knock-outs" show few developmental defects, suggesting that essential transcriptional activation functions can be performed by more than one member of the rel family.

A number of specific inhibitors of NFKB function in cells exist, including treatment with phosphorothioate antisense oliogonucleotide, treatment with double-stranded NFKB binding sites, and over expression of the natural inhibitor MAD-3 (an Ikappa-B family member). These agents have been used to show that NFKB is required for induction of a number of molecules involved in cancer and/or inflammation, as described below.

NFKB is required for phorbol ester-mediated induction of IL-6 (Kitajima, et al., 1992, *Science*, 258, 1792–5) and IL-8 (Kunsch and Rosen, 1993, *Mol. Cell. Biol.*, 13, 6137–46).

NFk is required for induction of the adhesion molecules ICAM-1 (Eck, et al., 1993, *Mol. Cell. Biol.*, 13, 6530–6536), VCAM-1 (Shu et al., supra), and E-selectin (Read, et al., 1994, *J. Exp. Med.*, 179, 503–512) on endothelial cells.

NFKB is involved in the induction of the integrin subunit, CD18, and other adhesive properties of leukocytes (Eck et al., 1993 supra).

HER2/Neu overexpression induces NFKB via a PI3-kinase/Akt pathway involving calpain-mediated degradation of IkB-alpha. Breast cancer has been shown to typify the aberrant expression of NFKB/REL factors (Pianetti et al., 2001, *Oncogene*, 20, 1287–1299; Sovak et al., 1999, *J. Clin. Invest.*, 100, 2952–2960).

Inhibition of NFKB activity has been shown to induce apoptosis in murine hepatocytes (Bellas et al., 1997, *Am. J. Pathol.*, 151,891–896).

NFKB has been shown to regulate cyclooxygenase-2 expression and cell proliferation in human gastric cancer cells (Joo Weon et al., 2001, *Laboratory Investigation*, 81, 349–360).

The above studies suggest that NFKB is integrally involved in the induction of cytokines and adhesion molecules by inflammatory mediators and is involved in the transformation of cancerous cells. Two reported studies point to another connection between NFKB and inflammation: glucocorticoids can exert their anti-inflammatory effects by inhibiting NFKB. The glucocorticoid receptor and p65 both act at NFKB binding sites in the ICAM-1 promoter (van de Stolpe, et al., 1994, *J. Biol. Chem.*, 269, 6185–6192). Glucocorticoid receptor inhibits NFKB-mediated induction of IL-6 (Ray and Prefontaine, 1994 *Proc. Natl. Acad. Sci USA*, 91, 752–756). Conversely, overexpression of p65 inhibits glucocorticoid induction of the mouse mammary tumor virus promoter. Finally, protein cross-linking and co-immunoprecipitation experiments demonstrated direct physical interaction between p65 and the glucocorticoid receptor.

The IKK complex that sequesters NFKB in the cytoplasm comprises IkappaB (IκB) proteins (IκB-alpha, IκB-beta, IκB-epsilon, p105, and p100). The phosphorylation of IκB proteins results in the release of NFKB from the IκB complex which is transported to the nucleus via the unmasking of nuclear translocation signals. Phosphorylation marks IκB proteins for ubiquitination and degradation via the proteosome pathway. Most NFKB inducing stimuli initiate activation of an IκB kinase (IKK) complex that contains two catalytic subunits, IKK-alpha (IKK1) and IKK-beta (IKK2), that phosphorylate IκB-alpha and IκB-beta, with IKK-beta playing a predominant role in pro-inflammatory signaling. In addition to the two kinases, the IKK complex contains regulatory subunits, including IKK-gamma (NEMO/IKKAP1). IKK-gamma is a protein that is critical for the assembly of the IKK complex. IKK-gamma directly binds to IKK-beta and is required for activation of NFKB, for example by TNF-alpha, IL-1-beta, lipopolysaccharide, phorbol 12-myristate 13-acetate, the human T-cell lymphotrophic virus (HTLV-1), or double stranded RNA. Genomic rearrangements in IKK-gamma have been shown to impair NFKB activation and result in incontinentia pigmenti. Additional proteins that associate with the IKK complex include, MEK kinase (MEKK1), NFKB inducing kinase (NIK), receptor interacting protein (RIP), protein kinase CK2, and IKK-associated protein (IKAP), which appears to be associated with the IκB Kinase (IKK) complex, but does not appear to be an integral component of the tripartite IKK complex as does IKK-gamma (Krappmann et al., 2001, *J. Biol. Chem.*, 275, 29779–87).

The RNA-dependent protein kinase PKR is a signal transducer for NFKB and IFN regulatory factor-1. PKR is required for activation of NFKB by IFN-gamma via a STAT-1 independent pathway (Amitabha et al., 2001, *J. Immunol.*, 166, 6170–6180). The induction of NFKB by PKR takes place though phosphorylation of IκB-alpha, and appears not to require the catalytic activity of PKR, thereby proceeding independently of the dsRNA-binding properties of PKR (Ishii et al., 2001, *Oncogene*, 20, 1900–1912). PKR also plays an important role in the regulation of protein synthesis by modulating the activity of eukaryotic initiation factor 2 (eIF-2-alpha) through interferon induction.

Kamiya, JP 2000253884, describes specific antisense oligonucleotides for inhibiting IκB-kinase subunit expression. Krappmann et al, 2001, *J. Biol. Chem.*, describe specific antisense oligonucleotides to IKK-gamma.

SUMMARY OF THE INVENTION

The present invention features a nucleic acid molecule, such as decoy RNA, dsRNA, siRNA, aptamers, antisense nucleic acid molecules, and enzymatic nucleic acid molecule which down regulates expression of a sequence encoding an IkappaB kinase (IKK) subunit. The invention also features an enzymatic nucleic acid molecule which down regulates expression of a sequence encoding protein kinase PKR.

In one embodiment, an enzymatic nucleic acid molecule of the invention comprises a sequence selected from the group consisting of SEQ ID NOs. 632–1261, 1762–2260, 2480–2698, 2904–3485, 3814–4360, 4555–4748, 5253–5756, 6034–6310, 6380–6789, 7142–7770, and 7884–8001.

In another embodiment, an enzymatic nucleic acid molecule of the invention comprises at least one binding arm wherein one or more of said binding arms comprises a sequence complementary to a sequence selected from the group consisting of SEQ ID NOs. 1–631, 1263–1761, 2261–2479, 2699–2903, 3486–3813, 4361–4554, 4749–5252, 5757–6033, 6311–6379, 6790–7141 and 7771–7883.

In another embodiment, an antisense nucleic acid molecule of the invention comprises a sequence complementary to a sequence selected from the group consisting of SEQ ID NOs. 1–631, 1263–1761, 2261–2479, 2699–2903, 3486–3813, 4361–4554, 4749–5252, 5757–6033, 6311–6379, 6790–7141, and 7771–7883.

In another embodiment, a nucleic acid molecule of the invention is adapted to treat cancer. In yet another embodiment, an enzymatic nucleic acid molecule of the invention has an endonuclease activity to cleave RNA having IKK-gamma or PKR nucleic acid sequence.

In one embodiment, an enzymatic nucleic acid molecule of the invention is in an Inozyme, Zinzyme, G-cleaver, Amberzyme, DNAzyme, or Hammerhead configuration.

In another embodiment, an Inozyme of the invention comprises a sequence complementary to a sequence selected from the group consisting of SEQ ID NOs. 1263–1761, 4749–5252, 7781–7787, 7796–7800, 7822–7846, and 7866–7870.

In another embodiment, an Inozyme of the invention comprises a sequence selected from the group consisting of SEQ ID NOs. 1762–2260, 5253–5756, 7894–7900, 7909–7913, 7938–7962, and 7982–7986.

In another embodiment, a Zinzyme of the invention comprises a sequence complementary to a sequence selected from the group consisting of SEQ ID NOs. 2261–2479, 5757–6033, 7788–7790, 7847–7860, and 7871–7895.

In another embodiment, a Zinzyme of the invention comprises a sequence selected from the group consisting of SEQ ID NOs 2480–2698, 6034–6310, 7901–7903, 7963–7976, and 7987–7991.

In another embodiment, an Amberzyme of the invention comprises a sequence selected from the group consisting of SEQ ID NOs 3814–4360, 7142–7770, 7924–7928, and 7997–8001.

In another embodiment, a DNAzyme of the invention comprises a sequence selected from the group consisting of SEQ ID NOs 2904–3485, 6380–6789, 7919–7923, and 7992–7996.

In another embodiment, a Hammerhead of the invention comprises a sequence complementary to a sequence selected from the group consisting of SEQ ID NOs. 1–631, 4361–4554, 7771–7780, 7791–7795, 7813–7821, and 7861–7865.

In another embodiment, a Hammerhead of the invention comprises a sequence selected from the group consisting of SEQ ID NOs 632–1262, 4555–4748, 7884–7894, 7904–7908, 7929–7937, 7977–7981.

In one embodiment, a nucleic acid molecule of the invention comprises between 12 and 100 bases complementary to RNA having an IKK-gamma or PKR nucleic acid sequence. In another embodiment, a nucleic acid molecule of the invention comprises between 14 and 24 bases complementary to RNA having anIKK-gamma or PKR nucleic acid sequence.

In yet another embodiment, a nucleic acid molecule of the invention is chemically synthesized.

In another embodiment, a nucleic acid molecule or antisense nucleic acid molecule of the invention comprises at least one 2'-sugar modification, at least one nucleic acid base modification, or at least one phosphate backbone modification.

In one embodiment, a siRNA molecule of the invention comprises a double stranded RNA wherein one strand of the RNA is complimentary to the RNA of IKK-gamma or PKR gene. In another embodiment, a siRNA molecule of the invention comprises a double stranded RNA wherein one strand of the RNA comprises a portion of a sequence of RNA having IKK-gamma or PKR gene sequence. In yet another embodiment, a siRNA molecule of the invention comprises a double stranded RNA wherein both strands of RNA are connected by a non-nucleotide linker. Alternately, a siRNA molecule of the invention comprises a double stranded RNA wherein both strands of RNA are connected by a nucleotide linker, such as a loop or stem loop structure.

In one embodiment, a single strand component of a siRNA molecule of the invention is from about 14 to about 50 nucleotides in length. In another embodiment, a single strand component of a siRNA molecule of the invention is about 14, 15, 16, 17, 18, 19, 20, 21, 22, 23, 24, 25, 26, 27, or 28 nucleotides in length. In yet another embodiment, a single strand component of a siRNA molecule of the invention is about 23 nucleotides in length. In one embodiment, a siRNA molecule of the invention is from about 28 to about 56 nucleotides in length. In another embodiment, a siRNA molecule of the invention is about 40, 41, 42, 43, 44, 45, 46, 47, 48, 49, 50, 51, or 52 nucleotides in length. In yet another embodiment, a siRNA molecule of the invention is about 46 nucleotides in length.

In another embodiment, an enzymatic nucleic acid molecule, antisense nucleic acid molecule, decoy RNA, dsRNA, siRNA, or aptamer molecules of the invention comprises at least one 2'-sugar modification.

In another embodiment, an enzymatic nucleic acid molecule, antisense nucleic acid molecule, decoy RNA, dsRNA, siRNA, or aptamer, nucleic acids of the invention comprises at least one nucleic acid base modification.

In another embodiment, an enzymatic nucleic acid molecule, antisense nucleic acid molecule, decoy RNA, dsRNA, siRNA, or aptamer, nucleic acids of the invention comprises at least one phosphate backbone modification.

In one embodiment, the invention features a mammalian cell, for example a human cell, including an nucleic acid molecule of the invention.

The present invention features method of down-regulating PKR activity in a cell, comprising contacting the cell with an enzymatic nucleic acid molecule or antisense nucleic acid molecule, or other nucleic acid molecule of the invention, under conditions suitable for down-regulating of PKR activity.

The present invention also features method of treatment of a subject having a condition associated with the level of PKR, comprising contacting cells of the subject with an enzymatic nucleic acid molecule or antisense nucleic acid molecule or other nucleic acid molecule of the invention under conditions suitable for the treatment.

The present invention features method of down-regulating IKK-gamma activity in a cell, comprising contacting the cell with an enzymatic nucleic acid molecule or antisense nucleic acid molecule or other nucleic acid molecule of the invention, under conditions suitable for down-regulating of IKK-gamma activity.

The present invention also features method of treatment of a subject having a condition associated with the level of IKK-gamma, comprising contacting cells of the subject with the enzymatic nucleic acid molecule or antisense nucleic acid molecule or other nucleic acid molecule of the invention, under conditions suitable for the treatment.

In one embodiment, a method of treatment of the invention comprises the use of one or more drug therapies under conditions suitable for said treatment.

The present invention features methods of cleaving RNA comprising a PKR nucleic acid sequence comprising contacting an enzymatic nucleic acid molecule of the invention with the RNA under conditions suitable for the cleavage.

The present invention also features methods of cleaving RNA comprising a IKK-gamma nucleic acid sequence comprising contacting an enzymatic nucleic acid molecule of the invention with the RNA under conditions suitable for the cleavage.

In one embodiment, a method of cleavage of the invention is carried out in the presence of a divalent cation, for example Mg2+.

In another embodiment, an enzymatic nucleic acid or antisense nucleic acid molecule or other nucleic acid molecule of the invention comprises a cap structure, wherein the cap structure is at the 5'-end, or 3'-end, or both the 5'-end and the 3'-end, for example a 3', 3'-linked or 5', 5'-linked deoxyabasic derivative.

The present invention also features an expression vector comprising a nucleic acid sequence encoding at least one enzymatic nucleic acid molecule, antisense, or other nucleic acid molecule of the invention in a manner which allows expression of the nucleic acid molecule.

In one embodiment, the invention features a mammalian cell, for example a human cell, including an expression vector contemplated by the invention.

In another embodiment, an expression vector of the invention further comprises an antisense nucleic acid molecule complementary to RNA of a subunit of IKK-gamma or PKR.

In yet another embodiment, an expression vector of the invention comprises a nucleic acid sequence encoding two or more enzymatic nucleic acid molecules, which can be the same or different.

The present invention also features a method for treatment of cancer, for example breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, lymphoma, glioma, or multidrug resistant cancer, comprising administering to a subject an enzymatic nucleic acid molecule or antisense nucleic acid molecule or other nucleic acid molecule of the invention under conditions suitable for said treatment.

In one embodiment, a nucleic acid molecule of the invention comprises at least five ribose residues, at least ten 2'-O-methyl modifications, and a 3'- end modification such as a 3'-3' inverted abasic moiety, and/or phosphorothioate linkages on at least three of the 5' terminal nucleotides.

In another embodiment, other drug therapies contemplated by the invention include monoclonal antibodies, IKI-gamma or PKR-specific inhibitors, chemotherapy, or radiation therapy.

Specific chemotherapy contemplated by the invention include paclitaxel, docetaxel, cisplatin, methotrexate, cyclophosphamide, 5-fluoro uridine, Leucovorin, Irinotecan (CAMPTOSAR® or CPT-11 or Camptothecin-11 or Campto), Paclitaxel, Carboplatin doxorubin, fluorouracil carboplatin, edatrexate, gemcitabine, or vinorelbine or a combination thereof.

The invention also features a method for treatment of an inflammatory disease, for example rheumatoid arthritis, restenosis, asthma, Crohn's disease, diabetes, obesity, autoimmune disease, lupus, multiple sclerosis, transplant/graft rejection, gene therapy applications, ischemia/reperfusion injury, glomerulonephritis, sepsis, allergic airway inflammation, inflammatory bowel disease, or infection, comprising the step of administering to a subject an enzymatic nucleic acid or antisense nucleic acid molecule of the invention under conditions suitable for the treatment.

The present invention features compositions comprising the enzymatic nucleic acid and/or antisense nucleic acid molecules of the invention in a pharmaceutically acceptable carrier.

The invention also features a method of administering to a cell, such as mammalian cell (e.g. human cell), where the cell can be in culture or in a mammal, such as a human, an enzymatic nucleic acid molecule or antisense molecule of the instant invention, comprising contacting the cell with the enzymatic nucleic acid molecule or antisense molecule or other nucleic acid molecule of the invention under conditions suitable for such administration. The method of administration can be in the presence of a delivery reagent, for example a lipid, cationic lipid, phospholipid, or liposome.

DETAILED DESCRIPTION OF THE INVENTION

First the drawings will be described briefly.

DRAWINGS

FIG. 1 shows examples of chemically stabilized ribozyme motifs. HH Rz, represents hammerhead ribozyme motif (Usman et al., 1996, *Curr. Op. Struct. Bio.*, 1, 527); NCH Rz represents the NCH ribozyme motif (Ludwig & Sproat, International PCT Publication No. WO 98/58058); G-Cleaver, represents G-cleaver ribozyme motif (Kore et al., 1998, *Nucleic Acids Research* 26, 4116–4120, Eckstein et al., International PCT publication No. WO 99/16871). N or n, represent independently a nucleotide which can be same or different and have complementarity to each other; rI, represents ribo-Inosine nucleotide; arrow indicates the site of cleavage within the target. Position 4 of the HH Rz and the NCH Rz is shown as having 2'-C-allyl modification, but those skilled in the art will recognize that this position can be modified with other modifications well known in the art, so long as such modifications do not significantly inhibit the activity of the ribozyme.

FIG. 2 shows an example of the Amberzyme ribozyme motif that is chemically stabilized (see for example Beigelman et al, International PCT publication No. WO 99/55857).

FIG. 3 shows an example of the Zinzyme A ribozyme motif that is chemically stabilized (see for example Beigelman et al., Beigelman et al., International PCT publication No. WO 99/55857).

FIG. 4 shows an example of a DNAzyme motif described by Santoro et al., 1997, *PNAS*, 94, 4262.

The invention features nucleic acid molecules, for example enzymatic nucleic acid molecules, antisense nucleic acid molecules, 2,5-A chimeras, decoys, double stranded RNA, triplex oligonucleotides, and/or aptamers, and methods to modulate gene expression, for example, genes encoding a member of the IκB kinase IKK complex, such as IKK-alpha (IKK1), IKK-beta (IKK2), or IKK-gamma (IKKγ) and/or a protein kinase PKR protein. In particular, the instant invention features nucleic-acid based molecules and methods to modulate the expression of IKK-gamma (IKKγ) and protein kinase PKR.

The invention features one or more enzymatic nucleic acid-based molecules and methods that independently or in combination modulate the expression of gene(s) encoding a member of the IκB kinase IKK complex or PKR. In particular embodiments, the invention features nucleic acid-based molecules and methods that modulate the expression of a member of the IκB kinase IKK complex, for example IKK-alpha (IKK1), IKK-beta (IKK2), or IKK-gamma (IKKγ) and/or a protein kinase PKR protein, such as IKK-alpha (IKK1) gene (Genbank Accession No. NM_001278); IKK-beta (IKK2) gene, for example (Genbank Accession No. AF080158), IKK-ganima (IKKγ) gene, for example (Genbank Accession No. NM_003639) (SEQ ID NO:8014), and protein kinase PKR gene, for example (Genbank Accession No. NM_002759).

The description below of the various aspects and embodiments is provided with reference to the exemplary IKK-gamma and PKR genes. IKK-gamma is also known as NEMO/IKKAP1. However, the various aspects and embodiments are also directed to other genes which encode other subunits of the IKK complex, such as IKK-alpha (IKK1) or IKK-beta (IKK2). Those additional genes can be analyzed for target sites using the methods described for IKK-gamma or PKR. Thus, the inhibition and the effects of such inhibition of the other genes can be performed as described herein.

In one embodiment, the invention features the use of an enzymatic nucleic acid molecule, preferably in the hammerhead, NCH, G-cleaver, amberzyme, zinzyme and/or DNAzyme motif, to down-regulate the expression of IKK-gamma or PKR genes.

By "inhibit" or "down-regulate" it is meant that the expression of the gene, or level of RNAs or equivalent RNAs encoding one or more protein subunits, or activity of one or more protein subunits, such as IKK-gamma or PKR subunit(s), is reduced below that observed in the absence of the nucleic acid molecules of the invention. In one embodiment, inhibition or down-regulation with enzymatic nucleic acid molecule preferably is below that level observed in the presence of an enzymatically inactive or attenuated molecule that is able to bind to the same site on the target RNA, but is unable to cleave that RNA. In another embodiment, inhibition or down-regulation with antisense oligonucleotides is preferably below that level observed in the presence of, for example, an oligonucleotide with scrambled sequence or with mismatches. In another embodiment, inhibition or down-regulation of IKK-gamma or PKR with the nucleic acid molecule of the instant invention is greater in the presence of the nucleic acid molecule than in its absence.

By "up-regulate" is meant that the expression of the gene, or level of RNAs or equivalent RNAs encoding one or more protein subunits, or activity of one or more protein subunits, such as IKK-gamma or PKR subunit(s), is greater than that observed in the absence of the nucleic acid molecules of the invention. For example, the expression of a gene, such as IKK-gamma or PKR gene, can be increased in order to treat, prevent, ameliorate, or modulate a pathological condition caused or exacerbated by an absence or low level of gene expression.

By "modulate" is meant that the expression of the gene, or level of RNAs or equivalent RNAs encoding one or more protein subunits, or activity of one or more protein subunit(s) is up-regulated or down-regulated, such that the expression, level, or activity is greater than or less than that observed in the absence of the nucleic acid molecules of the invention.

By "enzymatic nucleic acid molecule" it is meant a nucleic acid molecule which has complementarity in a substrate binding region to a specified gene target, and also has an enzymatic activity which is active to specifically cleave target RNA. That is, the enzymatic nucleic acid molecule is able to intermolecularly cleave RNA and thereby inactivate a target RNA molecule. These complementary regions allow sufficient hybridization of the enzymatic nucleic acid molecule to the target RNA and thus permit cleavage. One hundred percent complementarity is preferred, but complementarity as low as 50–75% can also be useful in this invention (see for example Werner and Uhlenbeck, 1995, *Nucleic Acids Research*, 23, 2092–2096; Hammann et al., 1999, *Antisense and Nucleic Acid Drug Dev.*, 9, 25–31). The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity. The specific enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving and/or ligation activity to the molecule (Cech et al., U.S. Pat. No. 4,987,071; Cech et al., 1988, 260 *JAMA* 3030).

Several varieties of enzymatic RNAs are known presently. Each can catalyze the hydrolysis of RNA phosphodiester bonds in trans (and thus can cleave other RNA molecules) under physiological conditions. Table I summarizes some of the characteristics of these ribozymes. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets. Thus, a single ribozyme molecule is able to cleave many molecules of target RNA. In addition, the ribozyme is a highly specific inhibitor of gene expression, with the specificity of inhibition depending not only on the base-pairing mechanism of binding to the target RNA, but also on the mechanism of target RNA cleavage. Single mismatches, or base-substitutions, near the site of cleavage can completely eliminate catalytic activity of a ribozyme.

By "nucleic acid molecule" as used herein is meant a molecule having nucleotides. The nucleic acid can be single, double, or multiple stranded and can comprise modified or unmnodified nucleotides or non-nucleotides or various mixtures and combinations thereof.

By "enzymatic portion" or "catalytic domain" is meant that portion/region of the enzymatic nucleic acid molecule essential for cleavage of a nucleic acid substrate (for example see FIGS. 1–4).

By "substrate binding arm" or "substrate binding domain" is meant that portion/region of a enzymatic nucleic acid which is able to interact, for example via complementarity (i.e., able to base-pair with), with a portion of its substrate. Preferably, such complementarity is 100%, but can be less if desired. For example, as few as 10 bases out of 14 can be base-paired (see for example Werner and Uhlenbeck, 1995, *Nucleic Acids Research*, 23, 2092–2096; Hammann et al., 1999, *Antisense and Nucleic Acid Drug Dev.*, 9, 25–31). Examples of such arms are shown generally in FIGS. 1–4. That is, these arms contain sequences within a enzymatic nucleic acid which are intended to bring enzymatic nucleic acid and target RNA together through complementary base-pairing interactions. The enzymatic nucleic acid of the invention can have binding arms that are contiguous or non-contiguous and can be of varying lengths. The length of the binding arm(s) are preferably greater than or equal to three nucleotides and of sufficient length to stably interact with the target RNA; preferably 12–100 nucleotides; more preferably 14–24 nucleotides long (see for example Werner and Uhlenbeck, supra; Hamman et al., supra; Hampel et al., EP0360257; Berzal-Herranz et al., 1993, *EMBO J.*, 12, 2567–73). If two binding arms are chosen, the design is such that the length of the binding arms are symmetrical (i.e., each of the binding arms is of the same length; e.g., five and five nucleotides, or six and six nucleotides, or seven and seven nucleotides long) or asymmetrical (i.e., the binding arms are of different length; e.g., six and three nucleotides; three and six nucleotides long; four and five nucleotides long; four and six nucleotides long; four and seven nucleotides long; and the like).

By "Inozyme" or "NCH" motif or configuration is meant, an enzymatic nucleic acid molecule comprising a motif as is generally described as NCH Rz in FIG. 1. Inozymes possess endonuclease activity to cleave RNA substrates having a cleavage triplet NCH/, where N is a nucleotide, C is cytidine and H is adenosine, uridine or cytidine, and / represents the cleavage site. H is used interchangeably with X. Inozymes can also possess endonuclease activity to cleave RNA substrates having a cleavage triplet NCN/, where N is a nucleotide, C is cytidine, and / represents the cleavage site. "I" in FIG. 1 represents an Inosine nucleotide, preferably a ribo-Inosine or xylo-Inosine nucleoside.

By "G-cleaver" motif or configuration is meant, an enzymatic nucleic acid molecule comprising a motif as is generally described as G-cleaver Rz in FIG. 1. G-cleavers possess endonuclease activity to cleave RNA substrates having a cleavage triplet NYN/, where N is a nucleotide, Y is uridine or cytidine and / represents the cleavage site. G-cleavers can be chemically modified as is generally shown in FIG. 1.

By "amberzyme" motif or configuration is meant, an enzymatic nucleic acid molecule comprising a motif as is generally described in FIG. 2. Amberzymes possess endonuclease activity to cleave RNA substrates having a cleavage triplet NG/N, where N is a nucleotide, G is guanosine, and / represents the cleavage site. Amberzymes can be chemically modified to increase nuclease stability through substitutions as are generally shown in FIG. 2. In addition, differing nucleoside and/or non-nucleoside linkers can be used to substitute the 5'-gaaa-3' loops shown in the figure. Amberzymes represent a non-limiting example of an enzymatic nucleic acid molecule that does not require a ribonucleotide (2'-OH) group within its own nucleic acid sequence for activity.

By "zinzyme" motif or configuration is meant, an enzymatic nucleic acid molecule comprising a motif as is generally described in FIG. 3. Zinzymes possess endonuclease activity to cleave RNA substrates having a cleavage triplet including but not limited to YG/Y, where Y is uridine or cytidine, and G is guanosine and / represents the cleavage site. Zinzymes can be chemically modified to increase nuclease stability through substitutions as are generally shown in FIG. 3, including substituting 2'-O-methyl guanosine nucleotides for guanosine nucleotides. In addition, differing nucleotide and/or non-nucleotide linkers can be used to substitute the 5'-gaaa-2' loop shown in the figure. Zinzymes represent a non-limiting example of an enzymatic nucleic acid molecule that does not require a ribonucleotide (2'-OH) group within its own nucleic acid sequence for activity.

By 'DNAzyme' is meant, an enzymatic nucleic acid molecule that does not require the presence of a 2'-OH group within its own nucleic acid sequence for activity. In particular embodiments the enzymatic nucleic acid molecule can have an attached linker(s) or other attached or associated groups, moieties, or chains containing one or more nucleotides with 2'-OH groups. DNAzymes can be synthesized chemically or expressed endogenously in vivo, by means of a single stranded DNA vector or equivalent thereof. An example of a DNAzyme is shown in FIG. 4 and is generally reviewed in Usman et al., U.S. Pat. No. 6,159,714; Chartrand et al., 1995, *NAR* 23, 4092; Breaker et al., 1995, *Chem. Bio.* 2, 655; Santoro et al., 1997, *PNAS* 94, 4262; Breaker, 1999, *Nature Biotechnology*, 17, 422–423; and Santoro et. al., 2000, *J. Am. Chem. Soc.*, 122, 2433–39. Additional DNAzyme motifs can be selected for using techniques similar to those described in these references, and hence, are within the scope of the present invention.

By "sufficient length" is meant an oligonucleotide of greater than or equal to 3 nucleotides that is of a length great enough to provide the intended function under the expected condition. For example, for binding arms of enzymatic nucleic acid "sufficient length" means that the binding arm sequence is long enough to provide stable binding to a target site under the expected binding conditions. Preferably, the binding arms are not so long as to prevent useful turnover of the nucleic acid molecule.

By "stably interact" is meant interaction of the oligonucleotides with target nucleic acid (e.g., by forming hydrogen bonds with complementary nucleotides in the target under physiological conditions) that is sufficient to the intended purpose (e.g., cleavage of target RNA by an enzyme).

By "equivalent" or "related" RNA to IKK-gamma is meant to include those naturally occurring RNA molecules having homology (partial or complete) to TKK-gamma proteins or encoding for proteins with similar function as IKK-gamma proteins in various organisms, including human, rodent, primate, rabbit, pig, protozoans, flngi, plants, and other microorganisms and parasites. The equivalent RNA sequence also includes in addition to the coding region, regions such as 5'-untranslated region, 3'-untranslated region, introns, intron-exon junction and the like.

By "equivalent" or "related" RNA to PKR is meant to include those naturally occurring -RNA molecules having homology (partial or complete) to PKR proteins or encoding for proteins Awith similar function as PKR proteins in various organisms, including human, rodent, primate, rabbit, pig, protozoans, fungi, plants, and other microorganisms and parasites. The equivalent RNA sequence also includes in addition to the coding region, regions such as 5'-untranslated region, 3'-untranslated region, introns, intron-exon junction and the like.

By "homology" is meant the nucleotide sequence of two or more nucleic acid molecules is partially or completely identical.

By "antisense nucleic acid", it is meant a non-enzymatic nucleic acid molecule that binds to target RNA by means of RNA—RNA or RNA-DNA or RNA-PNA (protein nucleic acid; Egholm et al., 1993 *Nature* 365, 566) interactions and alters the activity of the target RNA (for a review, see Stein and Cheng, 1993 *Science* 261, 1004 and Woolf et al., U.S. Pat. No. 5,849,902). Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both. For a review of current antisense strategies, see Schmajuk et al., 1999, *J. Biol. Chem.*, 274, 21783–21789, Delihas et al., 1997, *Nature*, 15, 751–753, Stein et al., 1997, *Antisense N. A. Drug Dev.*, 7, 151, Crooke, 2000, *Methods Enzymol.*, 313, 3–45; Crooke, 1998, *Biotech. Genet. Eng. Rev.*, 15, 121–157, Crooke, 1997, *Ad. Pharmacol*, 40, 1–49. In addition, antisense DNA can be used to target RNA by means of DNA-RNA interactions, thereby activating RNase H, which digests the target RNA in the duplex. The antisense oligonucleotides can comprise one or more RNAse H activating region, which is capable of activating RNAse H cleavage of a target RNA. Antisense DNA can be synthesized chemically or expressed via the use of a single stranded DNA expression vector or equivalent thereof.

By "RNase H activating region" is meant a region (generally greater than or equal to 4–25 nucleotides in length, preferably from 5–11 nucleotides in length) of a nucleic acid molecule capable of binding to a target RNA to form a non-covalent complex that is recognized by cellular RNase H enzyme (see for example Arrow et al., U.S. Pat. No. 5,849,902; Arrow et al., U.S. Pat. No. 5,989,912). The RNase H enzyme binds to the nucleic acid molecule-target RNA complex and cleaves the target RNA sequence. The RNase H activating region comprises, for example, phosphodiester, phosphorothioate (preferably at least four of the nucleotides are phosphorothiote substitutions; more specifically, 4–11 of the nucleotides are phosphorothiote substitutions); phosphorodithioate, 5'-thiophosphate, or methylphosphonate backbone chemistry or a combination thereof. In addition to one or more backbone chemistries described above, the RNase H activating region can also comprise a variety of sugar chemistries. For example, the RNase H activating region can comprise deoxyribose, arabino, fluoroarabino or a combination thereof, nucleotide sugar chemistry. Those skilled in the art will recognize that the foregoing are non-limiting examples and that any combination of phosphate, sugar and base chemistry of a nucleic acid that supports the activity of RNase H enzyme is within the scope of the definition of the RNase H activating region and the instant invention.

By "2–5A chimera" is meant an oligonucleotide, for example an antisense nucleic acid molecule or enzymatic nucleic acid molecule, containing a 5'-phosphorylated 2'-5'-linked adenylate residue. These chimeras bind to target RNA in a sequence-specific manner and activate a cellular 2–5A-dependent ribonuclease which, in turn, cleaves the target RNA (Torrence et al., 1993 *Proc. Natl. Acad. Sci. USA* 90, 1300; Silverman et al., 2000, *Methods Enzymol.*, 313, 522–533; Player and Torrence, 1998, *Pharmacol. Ther.*, 78, 55–113).

By "triplex forming oligonucleotides" or "triplex oligonucleotide" is meant an oligonucleotide that can bind to a double-stranded DNA in a sequence-specific manner to form a triple-strand helix. Formation of such triple helix structure has been shown to inhibit transcription of the targeted gene (Duval-Valentin et al., 1992 *Proc. Natl. Acad. Sci. USA* 89, 504; Fox, 2000, *Curr. Med. Chem.*, 7, 17–37; Praseuth et. al., 2000, *Biochim. Biophys. Acta*, 1489, 181–206).

By "double stranded RNA" or "dsRNA" is meant a double stranded RNA that matches a predetermined gene sequence that is capable of activating cellular enzymes that degrade the corresponding messenger RNA transcripts of the gene. These dsRNAs are referred to as short intervening RNA (siRNA) and can be used to inhibit gene expression (see for example Elbashir et al., 2001, *Nature*, 411, 494–498; and Bass, 2001, *Nature*, 411, 428–429). The term "double stranded RNA" or "dsRNA" as used herein refers to a double stranded RNA molecule capable of RNA interference "RNAi", including short interfering RNA "siRNA" see for example Bass, 2001, *Nature*, 411, 428–429; Elbashir et al., 2001, *Nature*, 411, 494–498; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914.

By "gene" it is meant a nucleic acid that encodes an RNA, for example, nucleic acid sequences including but not limited to structural genes encoding a polypeptide.

"Complementarity" refers to the ability of a nucleic acid to form hydrogen bond(s) with another RNA sequence by either traditional Watson-Crick or other non-traditional types. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, antisense or triple helix inhibition. Determination of binding free energies for nucleic acid molecules is well known in the art (see, e.g., Turner et al., 1987, *CSH Symp. Quant. Biol.* LII pp. 123–133; Frier et al., 1986, *Proc. Nat. Acad. Sci. USA* 83:9373–9377; Turner et al., 1987, *J. Am. Chem. Soc.* 109:3783–3785). A percent complementarity indicates the percentage of contiguous residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

By "RNA" is meant a molecule comprising at least one ribonucleotide residue. By "ribonucleotide" or "2'-OH" is meant a nucleotide with a hydroxyl group at the 2' position of a β-D-ribo-furanose moiety.

By "decoy" is meant a nucleic acid molecule, for example RNA or DNA, or aptamer that is designed to preferentially bind to a predetermined ligand. Such binding can result in the inhibition or activation of a target molecule. The decoy or aptamer can compete with a naturally occurring binding target for the binding of a specific ligand. For example, it has been shown that over-expression of HIV trans-activation response (TAR) RNA can act as a "decoy" and efficiently binds HIV tat protein, thereby preventing it from binding to TAR sequences encoded in the HIV RNA (Sullenger et al., 1990, Cell, 63, 601–608). This is but a specific example and those in the art will recognize that other embodiments can be readily generated using techniques generally known in the art, see for example Gold et al., 1995, *Annu. Rev. Biochem.*, 64, 763; Brody and Gold, 2000, *J. Biotechnol.*, 74, 5; Sun, 2000, *Curr. Opin. Mol. Ther.*, 2, 100; Kusser, 2000, *J. Biotechnol.*, 74, 27; Hermann and Patel, 2000, *Science*, 287, 820; and Jayasena, 1999, *Clinical Chemistry*, 45, 1628. Similarly, a decoys can be designed to bind to IKK-gamma or PKR and block the binding of IKK-gamma or PKR or a decoy can be designed to bind to IKK-gamma or PKR and prevent interaction with the IKK-garma or PKR protein.

By "aptamer" or "nucleic acid aptamer" as used herein is meant a nucleic acid molecule that binds specifically to a target molecule wherein the nucleic acid molecule has sequence that is distinct from sequence recognized by the target molecule in its natural setting. Alternately, an aptamer can be a nucleic acid molecule that binds to a target molecule where the target molecule does not naturally bind to a nucleic acid. The target molecule can be any molecule of interest. For example, the aptamer can be used to bind to a ligand binding domain of a protein, thereby preventing interaction of the naturally occurring ligand with the protein. Similarly, the nucleic acid molecules of the instant invention can bind to IKK-gamma or PKR to block activity of the respective proteins. This is a non-limiting example and those in the art will recognize that other embodiments can be readily generated using techniques generally known in the art, see for example Gold et al., U.S. Pat. No. 5,475,096 and 5,270,163; Gold et al., 1995, *Annu. Rev. Biochem.*, 64, 763; Brody and Gold, 2000, *J. Biotechnol.*, 74, 5; Sun, 2000, *Curr. Opin. Mol. Ther.*, 2, 100; Kusser, 2000, *J. Biotechnol.*, 74, 27; Hermann and Patel, 2000, *Science*, 287, 820; and Jayasena, 1999, *Clinical Chemistry*, 45, 1628.

The enzymatic nucleic acid molecule, antisense nucleic acid or other nucleic acid molecules of the invention that down regulate IKK-gamma or PKR gene expression represent a therapeutic approach to treat a variety of inflammatory-related diseases and conditions, including but not limited to rheumatoid arthritis, restenosis, asthma, Crohn's disease, incontinentia pigmenti, diabetes, obesity, autoimmune disease, lupus, multiple sclerosis, transplant/graft rejection, gene therapy applications, ischemia/reperfusion injury (CNS and myocardial), glomerulonephritis, sepsis, allergic airway inflammation, inflanmmatory bowel disease, infection, and any other inflammatory disease or condition which respond to the modulation of IKK-gamma or PKR function.

The enzymatic nucleic acid molecule, antisense nucleic acid or other nucleic acid molecules of the invention that down regulate IKK-gamma or PKR gene expression also represent a therapeutic approach to treat a variety of cancers, including but not limited to breast, lung, prostate, colorectal, brain, esophageal, bladder, pancreatic, cervical, head and neck, and ovarian cancer, melanoma, lymphoma, glioma, multidrug resistant cancers, and/or other cancers which respond to the modulation of IKK-gamma or PKR function.

In one embodiment of the inventions described herein, the enzymatic nucleic acid molecule is formed in a hammerhead or hairpin motif, but can also be formed in the motif of a hepatitis delta virus, group I intron, group II intron or RNase P RNA (in association with an RNA guide sequence), Neurospora VS RNA, DNAzymes, NCH cleaving motifs, or G-cleavers. Examples of such hammerhead motifs are described by Dreyfus, supra, Rossi et al., 1992, *AIDS Research and Human Retroviruses* 8, 183; of hairpin motifs by Hampel et al., EP0360257, Hampel and Tritz, 1989 *Biochemistry* 28, 4929, Feldstein et al., 1989, *Gene* 82, 53, Haseloff and Gerlach, 1989, *Gene*, 82, 43, and Hampel et al., 1990 *Nucleic Acids Res.* 18, 299; Chowrira & McSwiggen, U.S. Pat. No. 5,631,359; of the hepatitis delta virus motif is described by Perrotta and Been, 1992 *Biochemistry* 31, 16; of the RNase P motif by Guerrier-Takada et al., 1983 *Cell* 35, 849; Forster and Altman, 1990, *Science* 249, 783; Li and Altman, 1996, *Nucleic Acids Res.* 24, 835; *Neurospora* VS RNA ribozyme motif is described by Collins (Saville and Collins, 1990 *Cell* 61, 685–696; Saville and Collins, 1991 *Proc. Natl. Acad. Sci. USA* 88, 8826–8830; Collins and Olive, 1993 *Biochemistry* 32, 2795–2799; Guo and Collins, 1995, *EMBO. J* 14, 363); Group II introns are described by Griffin et al., 1995, *Chem. Biol.* 2, 761; Michels and Pyle, 1995, *Biochemistry* 34, 2965; Pyle et al., International PCT Publication No. WO 96/22689; of the Group I intron by Cech et al., U.S. Pat. No. 4,987,071 and of DNAzymes by Usman et al., International PCT Publication No. WO 95/11304; Chartrand et al., 1995, *NAR* 23, 4092; Breaker et al., 1995, *Chem. Bio.* 2, 655; Santoro et al., 1997, *PNAS* 94, 4262, and Beigelman et al., International PCT publication No. WO 99/55857. NCH cleaving motifs are described in Ludwig & Sproat, International PCT Publication No. WO 98/58058; and G-cleavers are described in Kore et al., 1998, *Nucleic Acids Research* 26, 4116–4120 and Eckstein et al., International PCT Publication No. WO 99/16871. Additional motifs such as the Aptazyme (Breaker et al., WO 98/43993), Amberzyme (Class I motif; FIG. 2; Beigelman et al., U.S. Ser. No. 09/301,511) and Zinzyme (FIG. 3) (Beigelman et al., U.S. Ser. No. 09/301,511), all included by reference herein including drawings, can also be used in the present invention. These specific motifs or configurations are not limiting in the invention and those skilled in the art will recognize that all that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule (Cech et al., U.S. Pat. No. 4,987,071).

In one embodiment of the present invention, a nucleic acid molecule of the instant invention can be between about 10 and 100 nucleotides in length. Exemplary enzymatic nucleic acid molecules of the invention are shown in Tables III to VII. For example, enzymatic nucleic acid molecules of the invention are preferably between about 15 and 50 nucleotides in length, more preferably between about 25 and 40 nucleotides in length, e.g., 34, 36, or 38 nucleotides in length (for example see Jarvis et al., 1996, *J. Biol. Chem.*, 271, 29107–29112). Exemplary DNAzymes of the invention are preferably between about 15 and 40 nucleotides in length, more preferably between about 25 and 35 nucleotides in length, e.g., 29, 30, 31, or 32 nucleotides in length (see for example Santoro et al., 1998, *Biochemistry*, 37, 13330–13342; Chartrand et al., 1995, *Nucleic Acids Research*, 23, 4092–4096). Exemplary antisense molecules of the invention are preferably between about 15 and 75 nucleotides in length, more preferably between about 20 and 35 nucleotides in length, e.g., 25, 26, 27, or 28 nucleotides in length (see for example Woolf et al., 1992, *PNAS.*, 89, 7305–7309; Milner et al., 1997, *Nature Biotechnology*, 15, 537–541). Exemplary triplex forming oligonucleotide molecules of the invention are preferably between about 10 and 40 nucleotides in length, more preferably between about 12 and 25 nucleotides in length, e.g., 18, 19, 20, or 21 nucleotides in length (see for example Maher et al, 1990, *Biochemistry*, 29, 8820–8826; Strobel and Dervan, 1990, *Science*, 249, 73–75). Those skilled in the art will recognize that all that is required is that the nucleic acid molecule be of sufficient length and suitable conformation for the nucleic acid molecule to interact with its target and/or catalyze a reaction contemplated herein. The length of the nucleic acid molecules of the instant invention are not limiting within the general limits stated.

Preferably, a nucleic acid molecule that modulates, for example, down-regulates IKK-gamma or PKR expression comprises between 12 and 100 bases complementary to a RNA molecule of IKK-gamma or PKR. Even more preferably, a nucleic acid molecule that modulates, for example IKK-gamma or PKR expression comprises between 14 and 24 bases complementary to a RNA molecule of IKK-gamma or PKR.

The invention provides a method for producing a class of nucleic acid-based gene modulating agents which exhibit a high degree of specificity for the RNA of a desired target. For example, the enzymatic nucleic acid molecule is preferably targeted to a highly conserved sequence region of target RNAs encoding IKK-gamma or PKR (specifically IKK-gamma or PKR genes) such that specific treatment of a disease or condition can be provided with either one or several nucleic acid molecules of the invention. Such nucleic acid molecules can be delivered exogenously to specific tissue or cellular targets as required. Alternatively, the nucleic acid molecules (e.g., ribozymes and antisense) can be expressed from DNA and/or RNA vectors that are delivered to specific cells.

As used in herein "cell" is used in its usual biological sense, and does not refer to an entire multicellular organism. The cell can, for example, be in vitro, e.g., in cell culture, or present in a multicellular organism, including, e.g., birds, plants and mammals such as humans, cows, sheep, apes, monkeys, swine, dogs, and cats. The cell can be prokaryotic (e.g., bacterial cell) or eukaryotic (e.g., mammalian or plant cell).

By "IKK-gamma proteins" is meant, a peptide or protein comprising a IKK-gamma or NEMO/IKKAP1 component of the IKK complex, for example a regulatory IKK subunit involved in the assembly of the high molecular weight IKK complex and/or induction of NFKB.

By "PKR proteins" is meant, a peptide or protein comprising a protein kinase PKR activity, for example the activation of NFKB.

By "highly conserved sequence region" is meant, a nucleotide sequence of one or more regions in a target gene does not vary significantly from one generation to the other or from one biological system to the other.

Nucleic acid-based inhibitors of IKK-gamma or PKR function are useful for the prevention and/or treatment of cancers and cancerous conditions such as breast, lung, prostate, colorectal, brain, esophageal, bladder, pancreatic, cervical, head and neck, and ovarian cancer, melanoma, lymphoma, glioma, multidrug resistant cancers, and any other diseases or conditions that are related to or will respond to the levels of IKK-gamma or PKR in a cell or tissue, alone or in combination with other therapies.

Nucleic acid-based inhibitors of IKK-gamma or PKR function are also useful for the prevention and/or treatment of inflammatory related diseases and conditions, including but not limited to rheumatoid arthritis, restenosis, asthma, Crohn's disease, incontinentia pigmenti, diabetes, obesity, autoimmune disease, lupus, multiple sclerosis, transplant/graft rejection, gene therapy applications, ischemia/reperfusion injury (CNS and myocardial), glomerulonephritis, sepsis, allergic airway inflammation, inflammatory bowel disease, infection, and any other inflammatory disease or condition which respond to the modulation of IKK-gamma or PKR function.

The nucleic acid-based inhibitors of the invention are added directly, or can be complexed with cationic lipids, packaged within liposomes, or otherwise delivered to target cells or tissues. The nucleic acid or nucleic acid complexes can be locally administered to relevant tissues ex vivo, or in vivo through injection or infusion pump, with or without their incorporation in biopolymers. In preferred embodiments, the enzymatic nucleic acid inhibitors comprise sequences, which are complementary to the substrate sequences in Tables III to XIII. Examples of such enzymatic nucleic acid molecules also are shown in Tables III to XIII. Examples of such enzymatic nucleic acid molecules consist essentially of sequences defined in these tables.

In another embodiment, the invention features antisense nucleic acid molecules and 2–5A chimera including sequences complementary to the substrate sequences shown in Tables III to XIII. Such nucleic acid molecules can include sequences as shown for the binding arms of the enzymatic nucleic acid molecules in Tables III to XIII. Similarly, triplex molecules can be provided targeted to the corresponding DNA target regions, and containing the DNA equivalent of a target sequence or a sequence complementary to the specified target (substrate) sequence. Typically, antisense molecules are complementary to a target sequence along a single contiguous sequence of the antisense molecule. However, in certain embodiments, an antisense molecule can bind to substrate such that the substrate molecule forms a loop, and/or an antisense molecule can bind such that the antisense molecule forms a loop. Thus, the antisense molecule can be complementary to two (or even more) non-contiguous substrate sequences or two (or even more) non-contiguous sequence portions of an antisense molecule can be complementary to a target sequence or both.

By "consists essentially of" is meant that the active nucleic acid molecule of the invention, for example, an enzymatic nucleic acid molecule, contains an enzymatic center or core equivalent to those in the examples, and binding arms able to bind RNA such that cleavage at the target site occurs. Other sequences can be present which do not interfere with such cleavage. Thus, a core region can, for example, include one or more loop, stem-loop structure, or linker which does not prevent enzymatic activity. Thus, the underlined regions in the sequences in Tables III, IV, VIII, and IX can be such a loop, stem-loop, nucleotide linker, and/or non-nucleotide linker and can be represented generally as sequence "X". For example, a core sequence for a hammerhead enzymatic nucleic acid can comprise a conserved sequence, such as 5'-CUGAUGAG-3' and 5'-CGAA-3' connected by "X", where X is 5'-<u>GCCGUUAGGC</u>-3' (SEQ ID NO 8002), or any other Stem II region known in the art, or a nucleotide and/or non-nucleotide linker. Similarly, for other nucleic acid molecules of the instant invention, such as Inozyme, G-cleaver, amberzyme, zinzyme, DNAzyme, antisense, 2–5A antisense, triplex forming nucleic acid, and decoy nucleic acids, other sequences or non-nucleotide linkers can be present that do not interfere with the function of the nucleic acid molecule.

Sequence X can be a linker of ≧2 nucleotides in length, preferably 3, 4, 5, 6, 7, 8, 9, 10, 15, 20, 26, 30, where the nucleotides can preferably be internally base-paired to form a stem of preferably ≧2 base pairs. In yet another embodiment, the nucleotide linker X can be a nucleic acid aptamer, such as an ATP aptamer, HIV Rev aptamer (RRE), HIV Tat aptamer (TAR) and others (for a review see Gold et al., 1995, *Annu. Rev. Biochem.*, 64, 763; and Szostak & Ellington, 1993, in *The RNA World*, ed. Gesteland and Atkins, pp. 511, CSH Laboratory Press). A "nucleic acid aptamer" as used herein is meant to indicate a nucleic acid sequence capable of interacting with a ligand. The ligand can be any natural or a synthetic molecule, including but not limited to a resin, metabolites, nucleosides, nucleotides, drugs, toxins, transition state analogs, peptides, lipids, proteins, amino acids, nucleic acid molecules, hormones, carbohydrates, receptors, cells, viruses, bacteria and others.

In yet another embodiment, alternatively or in addition, sequence X can be a non-nucleotide linker. Non-nucleotides as can include abasic nucleotide, polyether, polyamine, polyamide, peptide, carbohydrate, lipid, or polyhydrocarbon compounds. Specific examples include those described by Seela and Kaiser, *Nucleic Acids Res.* 1990, 18:6353 and *Nucleic Acids Res.* 1987, 15:3113; Cload and Schepartz, *J. Am. Chem. Soc.* 1991, 113:6324; Richardson and Schepartz, *J. Am. Chem. Soc.* 1991, 113:5109; Ma et al, *Nucleic Acids Res.* 1993, 21:2585 and *Biochemistry* 1993, 32:1751; Durand et al., *Nucleic Acids Res.* 1990, 18:6353; McCurdy et al., *Nucleosides & Nucleotides* 1991, 10:287; Jschke et al., *Tetrahedron Lett.* 1993, 34:301; Ono et al., *Biochemistry* 1991, 30:9914; Arnold et al., International Publication No. WO 89/02439; Usman et al., International Publication No. WO 95/06731; Dudycz et al., International Publication No. WO 95/11910 and Ferentz and Verdine, *J. Am. Chem. Soc.* 1991, 113:4000, all hereby incorporated by reference herein. A "non-nucleotide" further means any group or compound which can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine. Thus, in a preferred embodiment, the invention features an enzymatic nucleic acid molecule having one or more non-nucleotide moieties, and having enzymatic activity to cleave an RNA or DNA molecule.

In another aspect of the invention, enzymatic nucleic acid molecules or antisense molecules that interact with target RNA molecules and down-regulate IKK-gamma or PKR (specifically IKK-gamma or PKR gene) activity are expressed from transcription units inserted into DNA or RNA vectors. The recombinant vectors are preferably DNA plasmids or viral vectors. Enzymatic nucleic acid molecule or antisense expressing viral vectors can be constructed based on, but not limited to, adeno-associated virus, retrovirus, adenovirus, or alphavirus. Preferably, the recombinant vectors capable of expressing the enzymatic nucleic acid molecules or antisense are delivered as described above, and persist in target cells. Alternatively, viral vectors can be used that provide for transient expression of enzymatic nucleic acid molecules or antisense. Such vectors can be repeatedly administered as necessary. Once expressed, the enzymatic nucleic acid molecules or antisense bind to the target RNA and down-regulate its function or expression. Delivery of enzymatic nucleic acid molecule or antisense expressing vectors can be systemic, such as by intravenous or intramuscular administration, by administration to target cells explanted from the patient or subject followed by reintroduction into the patient or subject, or by any other means that would allow for introduction into the desired target cell. Antisense DNA can be expressed via the use of a single stranded DNA intracellular expression vector.

By "vectors" is meant any nucleic acid- and/or viral-based technique used to deliver a desired nucleic acid.

By "subject" is meant an organism, which is a donor or recipient of explanted cells or the cells themselves. "subject" also refers to an organism to which the nucleic acid molecules of the invention can be administered. Preferably, a subject is a mammal or mammalian cells. More preferably, a subject is a human or human cells.

By "enhanced enzymatic activity" is meant to include activity measured in cells and/or in vivo where the activity is a reflection of both the catalytic activity and the stability of the nucleic acid molecules of the invention. In this invention, the product of these properties can be increased in vivo compared to an all RNA enzymatic nucleic acid or all DNA enzyme. In some cases, the activity or stability of the nucleic acid molecule can be decreased (i.e., less than ten-fold), but the overall activity of the nucleic acid molecule is enhanced, in vivo.

The nucleic acid molecules of the instant invention, individually, or in combination or in conjunction with other drugs, can be used to treat diseases or conditions discussed above. For example, to treat a disease or condition associated with the levels of IKK-gamma or PKR, the subject can be treated, or other appropriate cells can be treated, as is evident to those skilled in the art, individually or in combination with one or more drugs under conditions suitable for the treatment.

In a further embodiment, the described nucleic acid molecules, such as antisense or ribozymes, can be used in combination with other known treatments to treat conditions or diseases discussed above. For example, the described molecules can be used in combination with one or more known therapeutic agents to treat breast, lung, prostate, colorectal, brain, esophageal, bladder, pancreatic, cervical, head and neck, and ovarian cancer, melanoma, lymphoma, glioma, multidrug resistant cancers, rheumatoid arthritis, restenosis, asthma, Crohn's disease, diabetes, incontinentia pigmenti, obesity, autoimmune disease, lupus, multiple sclerosis, transplant/graft rejection, gene therapy applications, ischemia/reperfusion injury (CNS and myocardial), glomerulonephritis, sepsis, allergic airway inflammation, inflammatory bowel disease, infection, and any other cancerous disease or inflammatory disease or condition which respond to the modulation of IKK-gamma or PKR expression.

In another embodiment, the invention features nucleic acid-based inhibitors (e.g., enzymatic nucleic acid molecules (eg; ribozymes), antisense nucleic acids, 2–5A antisense chimeras, triplex DNA, dsRNA, antisense nucleic acids containing RNA cleaving chemical groups) and methods for their use to down regulate or inhibit the expression of genes (e.g., IKK-gamma or PKR) capable of progression and/or maintenance of cancer, inflammatory diseases, and/or other disease states which respond to the modulation of IKK-gamma or PKR expression.

By "comprising" is meant including, but not limited to, whatever follows the word "comprising". Thus, use of the term "comprising" indicates that the listed elements are required or mandatory, but that other elements are optional and can or can not be present. By "consisting of" is meant including, and limited to, whatever follows the phrase "consisting of". Thus, the phrase "consisting of" indicates that the listed elements are required or mandatory, and that no other elements can be present.

Other features and advantages of the invention will be apparent from the following description of the preferred embodiments thereof, and from the claims.

Mechanism of Action of Nucleic Acid Molecules of the Invention as Proposed in the Art Antisense: Antisense molecules can be modified or unmodified RNA, DNA, or mixed polymer oligonucleotides and primarily function by specifically binding to matching sequences resulting in inhibition of peptide synthesis (Wu-Pong, November 1994, *BioPharm*, 20–33). The antisense oligonucleotide binds to target RNA by Watson Crick base-pairing and blocks gene expression by preventing ribosomal translation of the bound sequences either by steric blocking or by activating RNase H enzyme. Antisense molecules can also alter protein synthesis by interfering with RNA processing or transport from the nucleus into the cytoplasm (Mukhopadhyay & Roth, 1996, *Crit. Rev. in Oncogenesis* 7, 151–190).

In addition, binding of single stranded DNA to RNA can result in nuclease degradation of the heteroduplex (Wu-Pong, supra; Crooke, supra). To date, the only backbone modified DNA chemistry which act as substrates for RNase H are phosphorothioates, phosphorodithioates, and borontrifluoridates. Recently it has been reported that 2'-arabino and 2'-fluoro arabino-containing oligos can also activate RNase H activity.

A number of antisense molecules have been described that utilize novel configurations of chemically modified nucleotides, secondary structure, and/or RNase H substrate domains (Woolf et al., International PCT Publication No. WO 98/13526; Thompson et al., International PCT Publication No. WO 99/54459; Hartmann et al., U.S. Ser. No. 60/101,174 which was filed on Sep. 21, 1998) all of these are incorporated by reference herein in their entirety.

In addition, antisense deoxyoligoribonucleotides can be used to target RNA by means of DNA-RNA interactions, thereby activating RNase H, which digests the target RNA in the duplex. Antisense DNA can be expressed via the use of a single stranded DNA intracellular expression vector or equivalents and variations thereof.

Enzymatic Nucleic Acid: Several varieties of enzymatic RNAs are presently known. In addition, several in vitro selection (evolution) strategies (Orgel, 1979, *Proc. R. Soc. London*, B 205, 435) have been used to evolve new nucleic acid catalysts capable of catalyzing cleavage and ligation of phosphodiester linkages (Joyce, 1989, *Gene*, 82, 83–87; Beaudry et al., 1992, *Science* 257, 635–641; Joyce, 1992, *Scientific American* 267, 90–97; Breaker et al., 1994, *TIBTECH* 12, 268; Bartel et al.,1993, *Science* 261:1411–1418; Szostak, 1993, *TIBS* 17, 89–93; Kumar et al., 1995, *FASEB J.*, 9, 1183; Breaker, 1996, *Curr. Op. Biotech.*, 7, 442; Santoro et al., 1997, *Proc. Natl. Acad. Sci.*, 94, 4262; Tang et al., 1997, *RNA* 3, 914; Nakacane & Eckstein, 1994, supra; Long & Uhlenbeck, 1994, supra; Ishizaka et al., 1995, supra; Vaish et al., 1997, *Biochemistry*

36, 6495; all of these are incorporated by reference herein). Each can catalyze a series of reactions including the hydrolysis of phosphodiester bonds in trans (and thus can cleave other RNA molecules) under physiological conditions.

Nucleic acid molecules of this invention will block to some extent IKK-gamma or PKR and/or IKK-gamma or PKR protein expression and can be used to treat disease or diagnose disease associated with the levels of IKK-gamma or PKR and/or IKK-gamma or PKR. Enzymatic nucleic acid sequences targeting IKK-gamma or PKR RNA and sequences that can be targeted with nucleic acid molecules of the invention to down-regulate IKK-gamma or PKR expression are shown in Tables III to XIII.

The enzymatic nature of an enzymatic nucleic acid molecule can allow the concentration of enzymatic nucleic acid molecule necessary to affect a therapeutic treatment to be lower. This reflects the ability of the enzymatic nucleic acid molecule to act enzymatically. Thus, a single enzymatic nucleic acid molecule is able to cleave many molecules of target RNA. In addition, the enzymatic nucleic acid molecule is a highly specific inhibitor, with the specificity of inhibition depending not only on the base-pairing mechanism of binding to the target RNA, but also on the mechanism of target RNA cleavage. Single mismatches, or base-substitutions, near the site of cleavage can be chosen to greatly attenuate the catalytic activity of a enzymatic nucleic acid molecule.

Nucleic acid molecules having an endonuclease enzymatic activity are able to repeatedly cleave other separate RNA molecules in a nucleotide base sequence-specific manner. Such enzymatic nucleic acid molecules can be targeted to virtually any RNA transcript, and achieve efficient cleavage in vitro (Zaug et al., 324, *Nature* 429 1986; Uhlenbeck, 1987 *Nature* 328, 596; Kim et al., 84 *Proc. Natl. Acad. Sci. USA* 8788, 1987; Dreyfus, 1988, *Einstein Quart. J. Bio. Med.*, 6, 92; Haseloff and Gerlach, 334 *Nature* 585, 1988; Cech, 260 *JAMA* 3030, 1988; and Jefferies et al., 17 *Nucleic Acids Research* 1371, 1989; Santoro et al., 1997 supra).

Because of their sequence specificity, trans-cleaving enzymatic nucleic acid molecules can be used as therapeutic agents for human disease (Usman & McSwiggen, 1995 *Ann. Rep. Med. Chem.* 30, 285–294; Christoffersen and Marr, 1995 *J. Med. Chem.* 38, 2023–2037). Enzymatic nucleic acid molecules can be designed to cleave specific RNA targets within the background of cellular RNA. Such a cleavage event renders the RNA non-functional and abrogates protein expression from that RNA. In this manner, synthesis of a protein associated with a disease state can be selectively inhibited (Warashina et al., 1999, *Chemistry and Biology*, 6, 237–250).

Enzymatic nucleic acid molecules of the invention that are allosterically regulated ("allozymes") can be used to modulate IKK-gamma or PKR expression. These allosteric enzymatic nucleic acids or allozymes (see for example George et al, U.S. Pat. Nos. 5,834,186 and 5,741,679, Shih et al., U.S. Pat. No. 5,589,332, Nathan et al., U.S. Pat. No. 5,871,914, Nathan and Ellington, International PCT publication No. WO 00/24931, Breaker et al., International PCT Publication Nos. WO 00/26226 and 98/27104, and Sullenger et al., International PCT publication No. WO 99/29842) are designed to respond to a signaling agent, for example, mutant IKK-gamma protein, wild-type IKK-gamma protein, mutant IKK-gamma RNA, wild-type IKK-gainma RNA, other proteins and/or RNAs involved in IKK-gamma activity, compounds, metals, polymers, molecules and/or drugs that are targeted to IKK-gamma or an IKK subunit, such as IKK-alpha or IKK-beta, expressing cells etc., which in turn modulates the activity of the enzymatic nucleic acid molecule. In response to interaction with a predetermined signaling agent, the allosteric enzymatic nucleic acid molecule's activity is activated or inhibited such that the expression of a particular target is selectively down-regulated. The target can comprise wild-type IKK-gamma, mutant IKK-gamma, a component of IKK-gamma, and/or a predetermined cellular component that modulates IKK-gamnma activity. In a specific example, allosteric enzymatic nucleic acid molecules that are activated by interaction with a RNA encoding a mutant IKK-gamma protein are used as therapeutic agents in vivo. The presence of RNA encoding the mutant IKK-gamma activates the allosteric enzymatic nucleic acid molecule that subsequently cleaves the RNA encoding a mutant IKK-gamma protein resulting in the inhibition of mutant IKK-gamma protein expression. In this manner, cells that express the mutant form of the IKK-gamma protein are selectively targeted. Such an approach, can be used to treat, for example, incontinentia pigmenti.

In another non-limiting example, an allozyme can be activated by a IKK-gamma or PKR protein, peptide, or mutant polypeptide that caused the allozyme to inhibit the expression of IKK-gamma or PKR gene, by, for example, cleaving RNA encoded by IKK-gamma or PKR gene. In this non-limiting example, the allozyme acts as a decoy to inhibit the function of IKK-gamma or PKR and also inhibit the expression of IKK-gamma or PKR once activated by the IKK-gamma or PKR protein.

The nucleic acid molecules of the instant invention are also referred to as GeneBloc reagents, which are essentially nucleic acid molecules (eg; ribozymes, antisense) capable of down-regulating gene expression.

Target Sites

Targets for useful enzymatic nucleic acid molecules and antisense nucleic acids can be determined as disclosed in Draper et al., WO 93/23569; Sullivan et al., WO 93/23057; Thompson et al., WO 94/02595; Draper et al., WO 95/04818; McSwiggen et al., U.S. Pat. No. 5,525,468, and hereby incorporated by reference herein in totality. Other examples include the following PCT applications, which concern inactivation of expression of disease-related genes: WO 95/23225, WO 95/13380, WO 94/02595, incorporated by reference herein. Rather than repeat the guidance provided in those documents here, below are provided specific examples of such methods, not limiting to those in the art. Enzymatic nucleic acid molecules and antisense to such targets are designed as described in those applications and synthesized to be tested in vitro and in vivo, as also described. The sequences of human IKK-gamma or PKR RNAs were screened for optimal enzymatic nucleic acid and antisense target sites using a computer-folding algorithm. Antisense, hammerhead, DNAzyme, NCH, amberzyme, zinzyme, or G-Cleaver enzymatic nucleic acid molecule binding/cleavage sites were identified. These sites are shown in Tables III to XIII (all sequences are 5' to 3' in the tables; underlined regions can be any sequence "X" or linker X, the actual sequence is not relevant here). The nucleotide base position is noted in the Tables as that site to be cleaved by the designated type of enzymatic nucleic acid molecule. While human sequences can be screened and enzymatic nucleic acid molecule and/or antisense thereafter designed, as discussed in Stinchcomb et al., WO 95/23225, mouse targeted enzymatic nucleic acid molecules can be useful to test efficacy of action of the enzymatic nucleic acid molecule and/or antisense prior to testing in humans.

Antisense, hammerhead, DNAzyme, NCH, amberzyme, zinzyme or G-Cleaver enzymatic nucleic acid molecule binding/cleavage sites were identified. The nucleic acid molecules are individually analyzed by computer folding (Jaeger et al., 1989 *Proc. Natl. Acad. Sci. USA*, 86, 7706) to assess whether the sequences fold into the appropriate secondary structure. Those nucleic acid molecules with unfavorable intramolecular interactions such as between the binding arms and the catalytic core are eliminated from consideration. Varying binding arm lengths can be chosen to optimize activity.

Antisense, hammerhead, DNAzyme, NCH, amberzyme, zinzyme or G-Cleaver enzymatic nucleic acid molecule binding/cleavage sites were identified and were designed to anneal to various sites in the RNA target. The binding arms are complementary to the target site sequences described above. The nucleic acid molecules were chemically synthesized. The method of synthesis used follows the procedure for normal DNA/RNA synthesis as described below and in Usman et al., 1987 *J. Am. Chem. Soc.*, 109, 7845; Scaringe et al., 1990 *Nucleic Acids Res.*, 18, 5433; and Wincott et al., 1995 *Nucleic Acids Res.* 23, 2677–2684; Caruthers et al., 1992, *Methods in Enzymology* 211,3–19.

Synthesis of Nucleic Acid Molecules

Synthesis of nucleic acids greater than 100 nucleotides in length can be difficult using automated methods, and the therapeutic cost of such molecules can be prohibitive. In this invention, small nucleic acid motifs ("small refers to nucleic acid motifs less than about 100 nucleotides in length, preferably less than about 80 nucleotides in length, and more preferably less than about 50 nucleotides in length; e.g., antisense oligonucleotides, hammerhead or the NCH ribozymes) are preferably used for exogenous delivery. The simple structure of these molecules increases the ability of the nucleic acid to invade targeted regions of RNA structure. Exemplary molecules of the instant invention are chemically synthesized, and others can similarly be synthesized.

Oligonucleotides (eg; antisense, GeneBlocs) are synthesized using protocols known in the art as described in Caruthers et al., 1992, *Methods in Enzymology* 211, 3–19, Thompson et al., International PCT Publication No. WO 99/54459, Wincott et al., 1995, *Nucleic Acids Res.* 23, 2677–2684, Wincott et al., 1997, *Methods Mol. Bio.*, 74, 59, Brennan et al, 1998, *Biotechnol Bioeng.*, 61, 33–45, and Brennan, U.S. Pat. No. 6,001,311. All of these references are incorporated herein by reference. The synthesis of oligonucleotides makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 μmol scale protocol with a 2.5 min coupling step for 2'-O-methylated nucleotides and a 45 sec coupling step for 2'-deoxy nucleotides. Table II outlines the amounts and the contact times of the reagents used in the synthesis cycle. Alternatively, syntheses at the 0.2 μmol scale can be performed on a 96-well plate synthesizer, such as the instrument produced by Protogene (Palo Alto, Calif.) with minimal modification to the cycle. A 33-fold excess (60 μL of 0.11 M=6.6 μmol) of 2'-O-methyl phosphoramidite and a 105-fold excess of S-ethyl tetrazole (60 μL of 0.25 M=15 μmol) can be used in each coupling cycle of 2'-O-methyl residues relative to polymer-bound 5'-hydroxyl. A 22-fold excess (40 μL of 0.11 M=4.4 μmol) of deoxy phosphoramidite and a 70-fold excess of S-ethyl tetrazole (40 μL of 0.25 M=10 μmol) can be used in each coupling cycle of deoxy residues relative to polymer-bound 5'-hydroxyl. Average coupling yields on the 394 Applied Biosystems, Inc. synthesizer, determined by calorimetric quantitation of the trityl fractions, are typically 97.5–99%. Other oligonucleotide synthesis reagents for the 394 Applied Biosystems, Inc. synthesizer include; detritylation solution is 3% TCA in methylene chloride (ABI); capping is performed with 16% N-methylimidazole in THF (ABI) and 10% acetic anhydride/10% 2,6-lutidine in THF (ABI); and oxidation solution is 16.9 mM $I_2$, 49 mM pyridine, 9% water in THF (PERSEPTIVE#). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide, 0.05 M in acetonitrile) is used.

Deprotection of the antisense oligonucleotides is performed as follows: the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder.

The method of synthesis used for RNA and chemically modified RNA including certain enzymatic nucleic acid molecules follows the procedure as described in Usman et al., 1987, *J. Am. Chem. Soc.*, 109, 7845; Scaringe et al., 1990, *Nucleic Acids Res.*, 18, 5433; and Wincott et al, 1995, *Nucleic Acids Res.* 23, 2677–2684 Wincott et al., 1997, *Methods Mol Bio.*, 74, 59, and makes use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 μmol scale protocol with a 7.5 min coupling step for alkylsilyl protected nucleotides and a 2.5 min coupling step for 2'-O-methylated nucleotides. Table II outlines the amounts and the contact times of the reagents used in the synthesis cycle. Alternatively, syntheses at the 0.2 μmol scale can be done on a 96-well plate synthesizer, such as the instrument produced by Protogene (Palo Alto, Calif.) with minimal modification to the cycle. A 33-fold excess (60 μL of 0.11 M=6.6 μmol) of 2'-O-methyl phosphoramidite and a 75-fold excess of S-ethyl tetrazole (60 μL of 0.25 M=15 μmol) can be used in each coupling cycle of 2'-O-methyl residues relative to polymer-bound 5'-hydroxyl. A 66-fold excess (120 μL of 0.11 M=13.2 μmol) of alkylsilyl (ribo) protected phosphoramidite and a 150-fold excess of S-ethyl tetrazole (120 μL of 0.25 M=30 μmol) can be used in each coupling cycle of ribo residues relative to polymer-bound 5'-hydroxyl. Average coupling yields on the 394 Applied Biosystems, Inc. synthesizer, determined by colorimetric quantitation of the trityl fractions, are typically 97.5–99%. Other oligonucleotide synthesis reagents for the 394 Applied Biosystems, Inc. synthesizer include; detritylation solution is 3% TCA in methylene chloride (ABI); capping is performed with 16% N-methylimidazole in THF (ABI) and 10% acetic anhydride/10% 2,6-lutidine in THF (ABI); oxidation solution is 16.9 mM $I_2$, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide 0.05 M in acetonitrile) is used.

Deprotection of the RNA is performed using either a two-pot or one-pot protocol. For the two-pot protocol, the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder. The base deprotected oligoribonucleotide is resuspended in anhydrous TEA/HF/NMP solution (300 μL of a solution of 1.5 mL N-methylpyrrolidinone, 750 μL TEA and 1 mL TEA.3HF to provide a 1.4 M HF concentration) and heated to 65° C. After 1.5 h, the oligomer is quenched with 1.5 M $NH_4HCO_3$.

Alternatively, for the one-pot protocol, the polymer-bound trityl-on oligoribonucleotide is transferred to a 4 mL glass screw top vial and suspended in a solution of 33% ethanolic methylamine/DMSO: 1/1 (0.8 mL) at 65° C. for 15 min. The vial is brought to r.t. TEA.3HF (0.1 mL) is added and the vial is heated at 65° C. for 15 min. The sample is cooled at −20° C. and then quenched with 1.5 M $NH_4HCO_3$.

For purification of the trityl-on oligomers, the quenched $NH_4HCO_3$ solution is loaded onto a C-18 containing cartridge that had been prewashed with acetonitrile followed by 50 mM TEAA. After washing the loaded cartridge with water, the RNA is detritylated with 0.5% TFA for 13 min. The cartridge is then washed again with water, salt exchanged with 1 M NaCl and washed with water again. The oligonucleotide is then eluted with 30% acetonitrile.

Inactive hammerhead ribozymes or binding attenuated control (BAC) oligonucleotides can be synthesized by substituting a U for $G_5$ and a U for $A_{14}$ (numbering from Hertel, K. J., et al., 1992, *Nucleic Acids Res.*, 20, 3252). Similarly, one or more nucleotide substitutions can be introduced in other enzymatic nucleic acid molecules to inactivate the molecule and such molecules can serve as a negative control.

The average stepwise coupling yields are typically >98% (Wincott et al., 1995 *Nucleic Acids Res.* 23, 2677–2684). Those of ordinary skill in the art will recognize that the scale of synthesis can be adapted to be larger or smaller than the example described above including but not limited to 96 well format, with the ratio of chemicals being used in the reaction adjusted accordingly.

Alternatively, the nucleic acid molecules of the present invention can be synthesized separately and joined together post-synthetically, for example by ligation (Moore et al., 1992, *Science* 256, 9923; Draper et al., International PCT publication No. WO 93/23569; Shabarova et al., 1991, *Nucleic Acids Research* 19, 4247; Bellon et al., 1997, *Nucleosides & Nucleotides*, 16, 951; Bellon et al., 1997, *Bioconjugate Chem.* 8, 204).

The nucleic acid molecules of the present invention are modified extensively to enhance stability by modification with nuclease resistant groups, for example, 2'-amino, 2'-C-allyl, 2'-flouro, 2'-O-methyl, 2'-H (for a review see Usman and Cedergren, 1992, *TIBS* 17, 34; Usman et al., 1994, *Nucleic Acids Symp. Ser.* 31, 163). Ribozymes are purified by gel electrophoresis using general methods or are purified by high pressure liquid chromatography (HPLC; See Wincott et al., Supra, the totality of which is hereby incorporated herein by reference) and are re-suspended in water.

The sequences of the nucleic acid molecules, including enzymatic nucleic acid molecules and antisense, that are chemically synthesized, are shown in Table XIII. The sequences of the enzymatic nucleic acid and antisense constructs that are chemically synthesized, are complementary to the Substrate sequences shown in Table XIII. Those in the art will recognize that these sequences are representative only of many more such sequences where the enzymatic portion of the ribozyme (all but the binding arms) is altered to affect activity. The enzymatic nucleic acid and antisense construct sequences listed in Tables III to XIII can be formed of ribonucleotides or other nucleotides or non-nucleotides. Such enzymatic nucleic acid molecules with enzymatic activity are equivalent to the enzymatic nucleic acid molecules described specifically in the Tables.

Optimizing Activity of the Nucleic Acid Molecule of the Invention

Chemically synthesizing nucleic acid molecules with modifications (base, sugar and/or phosphate) that prevent their degradation by serum ribonucleases can increase their potency (see e.g., Eckstein et al., International Publication No. WO 92/07065; Perrault et al., 1990 *Nature* 344, 565; Pieken et al., 1991, *Science* 253, 314; Usman and Cedergren, 1992, *Trends in Biochem. Sci.* 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of the nucleic acid molecules herein). Modifications which enhance their efficacy in cells, and removal of bases from nucleic acid molecules to shorten oligonucleotide synthesis times and reduce chemical requirements are desired. (All these publications are hereby incorporated by reference herein).

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-flouro, 2'-O-methyl, 2'-H, nucleotide base modifications (for a review see Usman and Cedergren, 1992, *TIBS.* 17, 34; Usman et al., 1994, *Nucleic Acids Symp. Ser.* 31, 163; Burgin et al., 1996, *Biochemistry*, 35, 14090). Sugar modification of nucleic acid molecules have been extensively described in the art (see Eckstein et al., International Publication PCT No. WO 92/07065; Perrault et al. *Nature,* 1990, 344, 565–568; Pieken et al. *Science,* 1991, 253, 314–317; Usman and Cedergren, *Trends in Biochem. Sci.* , 1992, 17, 334–339; Usman et al. *International Publication* PCT No. WO 93/15187; Sproat, U.S. Pat. No. 5,334,711 and Beigelman et al., 1995, *J. Biol. Chem.,* 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., U.S. Ser. No. 60/082,404 which was filed on Apr. 20, 1998; Karpeisky et al., 1998, *Tetrahedron Lett.,* 39, 1131; Earnshaw and Gait, 1998, *Biopolymers (Nucleic acid Sciences)*, 48, 39–55; Verma and Eckstein, 1998, *Annu. Rev. Biochem.,* 67, 99–134; and Burlina et al., 1997, *Bioorg. Med. Chem.,* 5, 1999–2010; all of the references are hereby incorporated in their totality by reference herein). Such publications describe general methods and strategies to determine the location of incorporation of sugar, base and/or phosphate modifications and the like into ribozymes without inhibiting catalysis, and are incorporated by reference herein. In view of such teachings, similar modifications can be used as described herein to modify the nucleic acid molecules of the instant invention.

While chemical modification of oligonucleotide internucleotide linkages with phosphorothioate, phosphorothioate, and/or 5'-methylphosphonate linkages improves stability, too many of these modifications can cause some toxicity. Therefore when designing nucleic acid molecules the amount of these internucleotide linkages should be minimized. The reduction in the concentration of these linkages should lower toxicity resulting in increased efficacy and higher specificity of these molecules.

Nucleic acid molecules having chemical modifications that maintain or enhance activity are provided. Such nucleic acid is also generally more resistant to nucleases than unmodified nucleic acid. Thus, in a cell and/or in vivo the activity can not be significantly lowered. Therapeutic nucleic acid molecules delivered exogenously are optimally stable within cells until translation of the target RNA has been inhibited long enough to reduce the levels of the undesirable protein. This period of time varies between hours to days depending upon the disease state. Nucleic acid molecules are preferably resistant to nucleases in order to function as effective intracellular therapeutic agents. Improvements in the chemical synthesis of RNA and DNA (Wincott et al., 1995 *Nucleic Acids Res.* 23, 2677; Caruthers et al., 1992, *Methods in Enzymology* 211,3–19 (incorporated by reference herein) have expanded the ability to modify nucleic acid molecules by introducing nucleotide modifications to enhance their nuclease stability as described above.

Use of the nucleic acid-based molecules of the invention can lead to better treatment of the disease progression by affording the possibility of combination therapies (e.g., multiple antisense or enzymatic nucleic acid molecules targeted to different genes, nucleic acid molecules coupled with known small molecule inhibitors, or intermittent treatment with combinations of molecules (including different motifs) and/or other chemical or biological molecules). The treatment of subjects with nucleic acid molecules can also include combinations of different types of nucleic acid molecules.

Therapeutic nucleic acid molecules (e.g., enzymatic nucleic acid molecules and antisense nucleic acid molecules) delivered exogenously are optimally stable within cells until translation of the target RNA has been inhibited long enough to reduce the levels of the undesirable protein. This period of time varies between hours to days depending upon the disease state. These nucleic acid molecules should be resistant to nucleases in order to function as effective intracellular therapeutic agents. Improvements in the chemical synthesis of nucleic acid molecules described in the instant invention and in the art have expanded the ability to modify nucleic acid molecules by introducing nucleotide modifications to enhance their nuclease stability as described above.

In one embodiment, nucleic acid catalysts having chemical modifications that maintain or enhance enzymatic activity are provided. Such nucleic acids are also generally more resistant to nucleases than unmodified nucleic acid. Thus, in a cell and/or in vivo the activity of the nucleic acid can not be significantly lowered. As exemplified herein such enzymatic nucleic acids are useful in a cell and/or in vivo even if activity over all is reduced about 10 fold (Burgin et al., 1996, *Biochemistry*, 35, 14090). Such enzymatic nucleic acids herein are said to "maintain" the enzymatic activity of an all RNA ribozyme or all DNA DNAzyme.

In another aspect the nucleic acid molecules comprise a 5' and/or a 3'-cap structure.

By "cap structure" is meant chemical modifications, which have been incorporated at either terminus of the oligonucleotide (see for example Wincott et al, WO 97/26270, incorporated by reference herein). These terminal modifications protect the nucleic acid molecule from exonuclease degradation, and can help in delivery and/or localization within a cell. The cap can be present at the 5'-terminus (5'-cap) or at the 3'-terminus (3'-cap) or can be present on both terminus. In non-limiting examples, the 5'-cap includes inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

In another embodiment the 3'-cap includes, for example 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, *Tetrahedron* 49, 1925; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine.

The term "alkyl" as used herein refers to a saturated aliphatic hydrocarbon, including straight-chain, branched-chain "isoalkyl", and cyclic alkyl groups. The term "alkyl" also comprises alkoxy, alkyl-thio, alkyl-thio-alkyl, alkoxyalkyl, alkylamino, alkenyl, alkynyl, alkoxy, cycloalkenyl, cycloalkyl, cycloalkylalkyl, heterocycloalkyl, heteroaryl, C1–C6 hydrocarbyl, aryl or substituted aryl groups. Preferably, the alkyl group has 1 to 12 carbons. More preferably it is a lower alkyl of from about 1 to 7 carbons, more preferably about 1 to 4 carbons. The alkyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1–C6 hydrocarbyl, aryl or substituted aryl groups. The term "alkyl" also includes alkenyl groups containing at least one carbon-carbon double bond, including straight-chain, branched-chain, and cyclic groups. Preferably, the alkenyl group has about 2 to 12 carbons. More preferably it is a lower alkenyl of from about 2 to 7 carbons, more preferably about 2 to 4 carbons. The alkenyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, $C_1$–$C_6$ hydrocarbyl, aryl or substituted aryl groups. The term "alkyl" also includes alkynyl groups containing at least one carbon-carbon triple bond, including straight-chain, branched-chain, and cyclic groups. Preferably, the alkynyl group has about 2 to 12 carbons. More preferably it is a lower alkynyl of from about 2 to 7 carbons, more preferably about 2 to 4 carbons. The alkynyl group can be substituted or unsubstituted. When substituted the substituted group(s) preferably comprise hydroxy, oxy, thio, amino, nitro, cyano, alkoxy, alkyl-thio, alkyl-thio-alkyl, alkoxyalkyl, alkylamino, silyl, alkenyl, alkynyl, alkoxy, cycloalkenyl, cycloalkyl, cycloalkylalkyl, heterocycloalkyl, heteroaryl, C1–C6 hydrocarbyl, aryl or substituted aryl groups. Alkyl groups or moieties of the invention can also include aryl, alkylaryl, carbocyclic aryl, heterocyclic aryl, amide and ester groups. The preferred substituent(s) of aryl groups are halogen, trihalomethyl, hydroxyl, SH, OH, cyano, alkoxy, alkyl, alkenyl, alkynyl, and amino groups. An "alkylaryl" group refers to an alkyl group (as described above) covalently joined to an aryl group (as described above). Carbocyclic aryl groups are groups wherein the ring atoms on the aromatic ring are all carbon atoms. The carbon atoms are optionally substituted. Heterocyclic aryl groups are groups having from about 1 to 3 heteroatoms as ring atoms in the aromatic ring and the remainder of the ring atoms are carbon atoms. Suitable heteroatoms include oxygen, sulfur, and nitrogen, and include furanyl, thienyl, pyridyl, pyrrolyl, N-lower alkyl pyrrolo, pyrimidyl, pyrazinyl, imidazolyl and the like, all optionally substituted. An "amide" refers to an —C(O)—NH—R, where R is either alkyl, aryl, alkylaryl or hydrogen. An "ester" refers to an —C(O)—OR', where R is either alkyl, aryl, alkylaryl or hydrogen.

The term "alkoxyalkyl" as used herein refers to an alkyl-O-alkyl ether, for example methoxyethyl or ethoxymethyl.

The term "alkyl-thio-alkyl" as used herein refers to an alkyl-S-alkyl thioether, for example methylthiomethyl or methylthioethyl.

The term "amino" as used herein refers to a nitrogen containing group as is known in the art derived from ammonia by the replacement of one or more hydrogen radicals by organic radicals. For example, the terms "aminoacyl" and "aminoalkyl" refer to specific N-substituted organic radicals with acyl and alkyl substituent groups respectively.

The term "amination" as used herein refers to a process in which an amino group or substituted amine is introduced into an organic molecule.

The term "exocyclic amine protecting moiety" as used herein refers to a nucleobase amino protecting group compatible with oligonucleotide synthesis, for example an acyl or amide group.

The term "alkenyl" as used herein refers to a straight or branched hydrocarbon of a designed number of carbon atoms containing at least one carbon-carbon double bond. Examples of "alkenyl" include vinyl, allyl, and 2-methyl-3-heptene.

The term "alkoxy" as used herein refers to an alkyl group of indicated number of carbon atoms attached to the parent molecular moiety through an oxygen bridge. Examples of alkoxy groups include, for example, methoxy, ethoxy, propoxy and isopropoxy.

The term "alkynyl" as used herein refers to a straight or branched hydrocarbon of a designed number of carbon atoms containing at least one carbon-carbon triple bond. Examples of "alkynyl" include propargyl, propyne, and 3-hexyne.

The term "aryl" as used herein refers to an aromatic hydrocarbon ring system containing at least one aromatic ring. The aromatic ring can optionally be fused or otherwise attached to other aromatic hydrocarbon rings or non-aromatic hydrocarbon rings. Examples of aryl groups include, for example, phenyl, naphthyl, 1,2,3,4-tetrahydronaphthalene and biphenyl. Preferred examples of aryl groups include phenyl and naphthyl.

The term "cycloalkenyl" as used herein refers to a C3–C8 cyclic hydrocarbon containing at least one carbon-carbon double bond. Examples of cycloalkenyl include cyclopropenyl, cyclobutenyl, cyclopentenyl, cyclopentadiene, cyclohexenyl, 1,3-cyclohexadiene, cycloheptenyl, cycloheptatrienyl, and cyclooctenyl.

The term "cycloalkyl" as used herein refers to a C3–C8 cyclic hydrocarbon. Examples of cycloalkyl include cyclopropyl, cyclobutyl, cyclopentyl, cyclohexyl, cycloheptyl and cyclooctyl.

The term "cycloalkylalkyl," as used herein, refers to a C3–C7 cycloalkyl group attached to the parent molecular moiety through an alkyl group, as defined above. Examples of cycloalkylalkyl groups include cyclopropylmethyl and cyclopentylethyl.

The terms "halogen" or "halo" as used herein refers to indicate fluorine, chlorine, bromine, and iodine.

The term "heterocycloalkyl," as used herein refers to a non-aromatic ring system containing at least one heteroatom selected from nitrogen, oxygen, and sulfur. The heterocycloalkyl ring can be optionally fused to or otherwise attached to other heterocycloalkyl rings and/or non-aromatic hydrocarbon rings. Preferred heterocycloalkyl groups have from 3 to 7 members. Examples of heterocycloalkyl groups include, for example, piperazine, morpholine, piperidine, tetrahydrofuran, pyrrolidine, and pyrazole. Preferred heterocycloalkyl groups include piperidinyl, piperazinyl, morpholinyl, and pyrolidinyl.

The term "heteroaryl" as used herein refers to an aromatic ring system containing at least one heteroatom selected from nitrogen, oxygen, and sulfur. The heteroaryl ring can be filsed or otherwise attached to one or more heteroaryl rings, aromatic or non-aromatic hydrocarbon rings or heterocycloalkyl rings. Examples of heteroaryl groups include, for example, pyridine, furan, thiophene, 5,6,7,8-tetrahydroisoquinoline and pyrimidine. Preferred examples of heteroaryl groups include thienyl, benzothienyl, pyridyl, quinolyl, pyrazinyl, pyrimidyl, imidazolyl, benzimidazolyl, furanyl, benzofuranyl, thiazolyl, benzothiazolyl, isoxazolyl, oxadiazolyl, isothiazolyl, benzisothiazolyl, triazolyl, tetrazolyl, pyrrolyl, indolyl, pyrazolyl, and benzopyrazolyl.

The term "C1–C6 hydrocarbyl" as used herein refers to straight, branched, or cyclic alkyl groups having 1–6 carbon atoms, optionally containing one or more carbon-carbon double or triple bonds. Examples of hydrocarbyl groups include, for example, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, vinyl, 2-pentene, cyclopropylmethyl, cyclopropyl, cyclohexylmethyl, cyclohexyl and propargyl. When reference is made herein to C1–C6 hydrocarbyl containing one or two double or triple bonds it is understood that at least two carbons are present in the alkyl for one double or triple bond, and at least four carbons for two double or triple bonds.

By "nucleotide" is meant a heterocyclic nitrogenous base in N-glycosidic linkage with a phosphorylated sugar. Nucleotides are recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see for example, Usman and McSwiggen, supra; Eckstein et al., International PCT Publication No. WO 92/07065; Usman et al., International PCT Publication No. WO 93/15187; Uhlman & Peyman, supra all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, for example, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonyhnethyluridine, 5-methyloxyuridine, 5-methyl-2-thiouridine, 2-methylthio-N6-isopentenyladenosine, beta-D-mannosylqueosine, uridine-5-oxyacetic acid, 2-thiocytidine, threonine derivatives and others (Burgin et al., 1996, Biochemistry, 35, 14090; Uhlman & Peyman, supra). By "modified bases" in this aspect is meant nucleotide bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

By "nucleoside" is meant a heterocyclic nitrogenous base in N-glycosidic linkage with a sugar. Nucleosides are recognized in the art to include natural bases (standard), and modified bases well known in the art. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, modified nucleosides, non-natural nucleosides, non-standard nucleosides and other; see for example, Usman and McSwiggen, supra; Eckstein et al., International PCT Publication No. WO 92/07065; Usman et al, International PCT Publication No. WO 93/15187; Uhl-man & Peyman, supra all are hereby incorporated by reference herein). There are several examples of modified nucleic acid bases known in the art as summarized by Limbach et al., 1994, Nucleic Acids Res. 22, 2183. Some of the non-limiting examples of chemically modified and other natural nucleic acid bases that can be introduced into nucleic acids include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, quesosine, 2-thiouridine, 4-thiouridine, wybutosine, wybutoxosine, 4-acetylcytidine, 5-(carboxyhydroxymethyl)uridine, 5'-carboxymethylaminomethyl-2-thiouridine, 5-carboxymethylaminomethyluridine, beta-D-galactosylqueosine, 1-methyladenosine, 1-methylinosine, 2,2-dimethylguanosine, 3-methylcytidine, 2-methyladenosine, 2-methylguanosine, N6-methyladenosine, 7-methylguanosine, 5-methoxyaminomethyl-2-thiouridine, 5-methylaminomethyluridine, 5-methylcarbonylmethyluridine, 5-methyloxyuridine, 5-methyl-2-thiouridine, 2-methylthio-N6-isopentenyladenosine, beta-D-mannosylqueosine, uridine-5-oxyacetic acid, 2-thiocytidine, threonine derivatives and others (Burgin et al, 1996, Biochemistry, 35, 14090; Uhlman & Peyman, supra). By "modified bases" in this aspect is meant nucleoside bases other than adenine, guanine, cytosine and uracil at 1' position or their equivalents; such bases can be used at any position, for example, within the catalytic core of an enzymatic nucleic acid molecule and/or in the substrate-binding regions of the nucleic acid molecule.

In one embodiment, the invention features modified enzymatic nucleic acid molecules with phosphate backbone modifications comprising one or more phosphorothioate, phosphorodithioate, methylphosphonate, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications see Hunziker and Leumann, 1995, *Nucleic Acid Analogues: Synthesis and Properties*, in *Modern Synthetic Methods*, VCH, 331–417, and Mesmaeker et al., 1994, *Novel Backbone Replacements for Oligonucleotides*, in *Carbohydrate Modifications in Antisense Research*, ACS, 24–39. These references are hereby incorporated by reference herein.

By "abasic" is meant sugar moieties lacking a base or having other chemical groups in place of a base at the 1' position, for example a 3',3'-linked or 5',5'-linked deoxyabasic ribose derivative (for more details see Wincott et al., International PCT publication No. WO 97/26270).

By "unmodified nucleoside" is meant one of the bases adenine, cytosine, guanine, thymine, uracil joined to the 1' carbon of β-D-ribo-furanose.

By "modified nucleoside" is meant any nucleotide base which contains a modification in the chemical structure of an unmodified nucleotide base, sugar and/or phosphate.

In connection with 2'-modified nucleotides as described for the present invention, by "amino" is meant 2'-NH$_2$ or 2'-O—NH$_2$, which can be modified or unmodified. Such modified groups are described, for example, in Eckstein et al., U.S. Pat. No. 5,672,695 and Matulic-Adamic et al, WO 98/28317, respectively, which are both incorporated by reference in their entireties.

Various modifications to nucleic acid (e.g., antisense and ribozyme) structure can be made to enhance the utility of these molecules. For example, such modifications can enhance shelf-life, half-life in vitro, stability, and ease of introduction of such oligonucleotides to the target site, including e.g., enhancing penetration of cellular membranes and conferring the ability to recognize and bind to targeted cells.

Use of these molecules can lead to better treatment of the disease progression by affording the possibility of combination therapies (e.g., multiple enzymatic nucleic acid molecules targeted to different genes, enzymatic nucleic acid molecules coupled with known small molecule inhibitors, or intermittent treatment with combinations of enzymatic nucleic acid molecules (including different enzymatic nucleic acid molecule motifs) and/or other chemical or biological molecules). The treatment of subjects with nucleic acid molecules can also include combinations of different types of nucleic acid molecules. Therapies can be devised which include a mixture of enzymatic nucleic acid molecules (including different enzymatic nucleic acid molecule motifs), antisense and/or 2–5A chimera molecules to one or more targets to alleviate symptoms of a disease.

Administration of Nucleic Acid Molecules

Methods for the delivery of nucleic acid molecules are described in Akhtar et al., 1992, *Trends Cell Bio.*, 2, 139; and *Delivery Strategies for Antisense Oligonucleotide Therapeutics*, ed. Akhtar, 1995 which are both incorporated herein by reference. Sullivan et al., PCT WO 94/02595, further describes the general methods for delivery of enzymatic RNA molecules. These protocols can be utilized for the delivery of virtually any nucleic acid molecule. Nucleic acid molecules can be administered to cells by a variety of methods known to those familiar to the art, including, but not restricted to, encapsulation in liposomes, by iontophoresis, or by a incorporation into other vehicles, such as hydrogels, cyclodextrins, biodegradable nanocapsules, and bioadhesive microspheres. Alternatively, the nucleic acid/vehicle combination is locally delivered by direct injection or by use of an infusion pump. Other routes of delivery include, but are not limited to oral (tablet or pill form) and/or intrathecal delivery (Gold, 1997, *Neuroscience*, 76, 1153–1158). Other approaches include the use of various transport and carrier systems, for example, through the use of conjugates and biodegradable polymers. For a comprehensive review on drug delivery strategies including CNS delivery, see Ho et al., 1999, *Curr. Opin. Mol. Ther.*, 1, 336–343 and Jain, *Drug Delivery Systems: Technologies and Commercial Opportunities*, Decision Resources, 1998 and Groothuis et al., 1997, *J. NeuroVirol.*, 3, 387–400. More detailed descriptions of nucleic acid delivery and administration are provided in Sullivan et al., supra, Draper et al., PCT WO93/23569, Beigelman et al., PCT WO99/05094, and Klimuk et al., PCT WO99/04819 all of which have been incorporated by reference herein.

The molecules of the instant invention can be used as pharmaceutical agents. Pharmaceutical agents prevent, inhibit the occurrence, or treat (alleviate a symptom to some extent, preferably all of the symptoms) of a disease state in a subject.

The negatively charged polynucleotides of the invention can be administered (e.g., RNA, DNA or protein) and introduced into a subject by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration; suppositories for rectal administration; sterile solutions; suspensions for injectable administration; and the other compositions known in the art.

The present invention also includes pharmaceutically acceptable formulations of the compounds described. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or subject, preferably a human. Suitable forms, in part, depend upon the use or the route of entry, for example oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

By "systemic administration" is meant in vivo systemic absorption or accumulation of drugs in the blood stream followed by distribution throughout the entire body. Administration routes which lead to systemic absorption include, without limitations: intravenous, subcutaneous, intraperitoneal, inhalation, oral, intrapulmonary and intramuscular. Each of these administration routes expose the desired negatively charged polymers, e.g., nucleic acids, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as cancer cells.

By pharmaceutically acceptable formulation is meant, a composition or formulation that allows for the effective distribution of the nucleic acid molecules of the instant invention in the physical location most suitable for their desired activity. Non-limiting examples of agents suitable for formulation with the nucleic acid molecules of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, for example the CNS (Jolliet-Riant and Tillement, 1999, *Fundam. Clin. Pharmacol.*, 13, 16–26); biodegradable polymers, such as poly (DL-lactide-coglycolide) microspheres for sustained release delivery after implantation (Emerich, DF et al, 1999, *Cell Transplant*, 8, 47–58) Alkermes, Inc. Cambridge, Mass.; and loaded nanoparticles, such as those made of polybutylcyanoacrylate, which can deliver drugs across the blood brain barrier and can alter neuronal uptake mechanisms (*Prog Neuropsychopharmacol Biol Psychiatry*, 23, 941–949, 1999). Other non-limiting examples of delivery strategies, including CNS delivery of the nucleic acid molecules of the instant invention include material described in Boado et al., 1998, *J. Pharm. Sci.*, 87, 1308–1315; Tyler et al, 1999, *FEBS Lett.*, 421, 280–284; Pardridge et al., 1995, *PNAS*

USA., 92, 5592–5596; Boado, 1995, *Adv. Drug Delivery Rev.*, 15, 73–107; Aldrian-Herrada et al., 1998, *Nucleic Acids Res.*, 26, 4910–4916; and Tyler et al., 1999, *PNAS USA.*, 96, 7053–7058. All these references are hereby incorporated herein by reference.

The invention also features the use of the composition comprising surface-modified liposomes containing poly (ethylene glycol) lipids (PEG-modified, or long-circulating liposomes or stealth liposomes). Nucleic acid molecules of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601–2627; Ishiwata et al., *Chem. Pharm. Bull.* 1995, 43, 1005–1011). Such liposomes have been shown to accumulate selectively in tumors, presumably by extravasation and capture in the neovascularized target tissues (Lasic et al., *Science* 1995, 267, 1275–1276; Oku et al., 1995, *Biochim. Biophys. Acta*, 1238, 86–90). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 1995, 42, 24864–24870; Choi et al., International PCT Publication No. WO 96/10391; Ansell et al., International PCT Publication No. WO 96/10390; Holland et al., International PCT Publication No. WO 96/10392; all of which are incorporated by reference herein). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985) hereby incorporated by reference herein. For example, preservatives, stabilizers, dyes and flavoring agents can be provided. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the negatively charged polymer.

The nucleic acid molecules of the invention and formulations thereof can be administered orally, topically, parenterally, by inhalation or spray or rectally in dosage unit formulations containing conventional non-toxic pharmaceutically acceptable carriers, adjuvants and vehicles. The term parenteral as used herein includes percutaneous, subcutaneous, intravascular (e.g., intravenous), intramuscular, or intrathecal injection or infusion techniques and the like. In addition, there is provided a pharmaceutical formulation comprising a nucleic acid molecule of the invention and a pharmaceutically acceptable carrier. One or more nucleic acid molecules of the invention can be present in association with one or more non-toxic pharmaceutically acceptable carriers and/or diluents and/or adjuvants, and if desired other active ingredients. The pharmaceutical compositions containing nucleic acid molecules of the invention can be in a form suitable for oral use, for example, as tablets, troches, lozenges, aqueous or oily suspensions, dispersible powders or granules, emulsion, hard or soft capsules, or syrups or elixirs.

Compositions intended for oral use can be prepared according to any method known to the art for the manufacture of pharmaceutical compositions and such compositions can contain one or more such sweetening agents, flavoring agents, coloring agents or preservative agents in order to provide pharmaceutically elegant and palatable preparations. Tablets contain the active ingredient in admixture with non-toxic pharmaceutically acceptable excipients that are suitable for the manufacture of tablets. These excipients can be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets can be uncoated or they can be coated by known techniques. In some cases such coatings can be prepared by known techniques to delay disintegration and absorption in the gastrointestinal tract and thereby provide a sustained action over a longer period. For example, a time delay material such as glyceryl monosterate or glyceryl distearate can be employed.

Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

Syrups and elixirs can be formulated with sweetening agents, for example glycerol, propylene glycol, sorbitol, glucose or sucrose. Such formulations can also contain a demulcent, a preservative and flavoring and coloring agents. The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose any bland fixed oil can be employed including synthetic mono-or diglycerides. In addition, fatty acids such as oleic acid find use in the preparation of injectables.

The nucleic acid molecules of the invention can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

Nucleic acid molecules of the invention can be administered parenterally in a sterile medium. The drug, depending on the vehicle and concentration used, can either be suspended or dissolved in the vehicle. Advantageously, adjuvants such as local anesthetics, preservatives and buffering agents can be dissolved in the vehicle.

Dosage levels of the order of from about 0.1 mg to about 140 mg per kilogram of body weight per day are useful in the treatment of the above-indicated conditions (about 0.5 mg to about 7 g per patient or subject per day). The amount of active ingredient that can be combined with the carrier materials to produce a single dosage form varies depending upon the host treated and the particular mode of administration. Dosage unit forms generally contain between from about 1 mg to about 500 mg of an active ingredient.

It is understood that the specific dose level for any particular patient or subject depends upon a variety of factors including the activity of the specific compound employed, the age, body weight, general health, sex, diet, time of administration, route of administration, and rate of excretion, drug combination and the severity of the particular disease undergoing therapy.

For administration to non-human animals, the composition can also be added to the animal feed or drinking water. It can be convenient to formulate the animal feed and drinking water compositions so that the animal takes in a therapeutically appropriate quantity of the composition along with its diet. It can also be convenient to present the composition as a premix for addition to the feed or drinking water.

The nucleic acid molecules of the present invention can also be administered to a subject in combination with other therapeutic compounds to increase the overall therapeutic effect. The use of multiple compounds to treat an indication can increase the beneficial effects while reducing the presence of side effects.

Alternatively, certain of the nucleic acid molecules of the instant invention can be expressed within cells from eukaryotic promoters (e.g., Izant and Weintraub, 1985, *Science*, 229, 345; McGarry and Lindquist, 1986, *Proc. Natl. Acad. Sci., USA* 83, 399; Scanlon et al., 1991, *Proc. Natl. Acad. Sci. USA*, 88, 10591–5; Kashani-Sabet et al., 1992, *Antisense Res. Dev.*, 2, 3–15; Dropulic et al., 1992, *J. Virol.*, 66, 1432–41; Weerasinghe et al., 1991, *J. Virol.*, 65, 5531–4; Ojwang et al., 1992, *Proc. Natl. Acad. Sci. USA*, 89, 10802–6; Chen et al., 1992, *Nucleic Acids Res.*, 20, 4581–9; Sarver et al., 1990 *Science*, 247, 1222–1225; Thompson et al, 1995, *Nucleic Acids Res.*, 23, 2259; Good et al., 1997, *Gene Therapy*, 4, 45; all of these references are hereby incorporated in their totalities by reference herein). Those skilled in the art realize that any nucleic acid can be expressed in eukaryotic cells from the appropriate DNA/RNA vector. The activity of such nucleic acids can be augmented by their release from the primary transcript by a enzymatic nucleic acid (Draper et al., PCT WO 93/23569, and Sullivan et al., PCT WO 94/02595; Ohkawa et al., 1992, *Nucleic Acids Symp. Ser.*, 27, 15–6; Taira et al., 1991, *Nucleic Acids Res.*, 19, 5125–30; Ventura et al., 1993, *Nucleic Acids Res.*, 21, 3249–55; Chowrira et al., 1994, *J. Biol. Chem.*, 269, 25856; all of these references are hereby incorporated in their totalities by reference herein). Gene therapy approaches specific to the CNS are described by Blesch et al., 2000, *Drug News Perspect.*, 13, 269–280; Peterson et al., 2000, *Cent. Nerv. Syst. Dis.*, 485–508; Peel and Klein, 2000, *J. Neurosci. Methods*, 98, 95–104; Hagihara et al., 2000, *Gene Ther.*, 7, 759–763; and Herrlinger et al., 2000, *Methods Mol. Med.*, 35, 287–312. AAV-mediated delivery of nucleic acid to cells of the nervous system is further described by Kaplitt et al., U.S. Pat. No. 6,180,613.

In another aspect of the invention, RNA molecules of the present invention are preferably expressed from transcription units (see for example Couture et al., 1996, *TIG.*, 12, 510) inserted into DNA or RNA vectors. The recombinant vectors are preferably DNA plasmids or viral vectors. Ribozyme expressing viral vectors can be constructed based on, but not limited to, adeno-associated virus, retrovirus, adenovirus, or alphavirus. Preferably, the recombinant vectors capable of expressing the nucleic acid molecules are delivered as described above, and persist in target cells. Alternatively, viral vectors can be used that provide for transient expression of nucleic acid molecules. Such vectors can be repeatedly administered as necessary. Once expressed, the nucleic acid molecule binds to the target mRNA. Delivery of nucleic acid molecule expressing vectors can be systemic, such as by intravenous or intramuscular administration, by administration to target cells explanted from the patient or subject followed by reintroduction into the patient or subject, or by any other means that would allow for introduction into the desired target cell (for a review see Couture et al., 1996, *TIG.*, 12, 510).

In one aspect the invention features an expression vector comprising a nucleic acid sequence encoding at least one of the nucleic acid molecules of the instant invention is disclosed. The nucleic acid sequence encoding the nucleic acid molecule of the instant invention is operably linked in a manner which allows expression of that nucleic acid molecule.

In another aspect the invention features an expression vector comprising: a) a transcription initiation region (e.g., eukaryotic pol I, II or III initiation region); b) a transcription termination region (e.g., eukaryotic pol I, II or III termination region); c) a nucleic acid sequence encoding at least one of the nucleic acid catalyst of the instant invention; and wherein said sequence is operably linked to said initiation region and said termination region, in a manner which allows expression and/or delivery of said nucleic acid molecule. The vector can optionally include an open reading frame (ORF) for a protein operably linked on the 5' side or the 3'-side of the sequence encoding the nucleic acid catalyst of the invention; and/or an intron (intervening sequences).

Transcription of the nucleic acid molecule sequences are driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990, *Proc. Natl. Acad. Sci. USA*, 87, 6743–7; Gao and Huang 1993, *Nucleic Acids Res.*, 21, 2867–72; Lieber et al., 1993, *Methods Enzymol.*, 217, 47–66; Zhou et al., 1990, *Mol. Cell. Biol.*, 10, 4529–37). All of these references are incorporated by reference herein. Several investigators have demonstrated that nucleic acid molecules, such as ribozymes expressed from such promoters can function in mammalian cells (e.g. Kashani-Sabet et al., 1992, *Antisense Res. Dev.*, 2, 3–15; Ojwang et al., 1992, *Proc. Natl. Acad. Sci. USA*, 89, 10802–6; Chen et al, 1992, *Nucleic Acids Res.*, 20, 4581–9; Yu et al., 1993, *Proc. Natl. Acad. Sci. USA*, 90, 6340–4; L'Huillier et al., 1992, *EMBO J.*, 11, 4411–8; Lisziewicz et al., 1993, *Proc. Natl. Acad. Sci. U.S.A*, 90, 8000–4; Thompson et al., 1995, *Nucleic Acids Res.*, 23, 2259; Sullenger & Cech, 1993, *Science*, 262, 1566). More specifically, transcription units such as the ones derived from genes encoding U6 small nuclear (snRNA), transfer RNA (tRNA) and adenovirus VA RNA are useful in generating high concentrations of desired RNA molecules such as ribozymes in cells (Thompson et al., supra; Couture and Stinchcomb, 1996, supra; Noonberg et al., 1994, *Nucleic Acid Res.*, 22, 2830; Noonberg et al., U.S. Pat. No. 5,624,803; Good et al., 1997, *Gene Ther.*, 4, 45; Beigelman et al., International PCT Publication No. WO 96/18736; all of these publications are incorporated by reference herein. The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

In another aspect the invention features an expression vector comprising nucleic acid sequence encoding at least one of the nucleic acid molecules of the invention, in a manner which allows expression of that nucleic acid molecule. The expression vector comprises in one embodiment; a) a transcription initiation region; b) a transcription termination region; c) a nucleic acid sequence encoding at least one said nucleic acid molecule; and wherein said sequence is operably linked to said initiation region and said termination region, in a manner which allows expression and/or delivery of said nucleic acid molecule.

In another embodiment the expression vector comprises: a) a transcription initiation region; b) a transcription termination region; c) an open reading frame; d) a nucleic acid sequence encoding at least one said nucleic acid molecule, wherein said sequence is operably linked to the 3'-end of said open reading frame; and wherein said sequence is operably linked to said initiation region, said open reading frame and said termination region, in a manner which allows expression and/or delivery of said nucleic acid molecule. In yet another embodiment the expression vector comprises: a) a transcription initiation region; b) a transcription termination region; c) an intron; d) a nucleic acid sequence encoding at least one said nucleic acid molecule; and wherein said sequence is operably linked to said initiation region, said intron and said termination region, in a manner which allows expression and/or delivery of said nucleic acid molecule.

In another embodiment, the expression vector comprises: a) a transcription initiation region; b) a transcription termination region; c) an intron; d) an open reading frame; e) a nucleic acid sequence encoding at least one said nucleic acid molecule, wherein said sequence is operably linked to the 3'-end of said open reading frame; and wherein said sequence is operably linked to said initiation region, said intron, said open reading frame and said termination region, in a manner which allows expression and/or delivery of said nucleic acid molecule.

EXAMPLES

The following are non-limiting examples showing the selection, isolation, synthesis and activity of nucleic acids of the instant invention.

The following examples demonstrate the selection and design of Antisense, hammerhead, DNAzyme, NCH, Amberzyme, Zinzyme, or G-Cleaver ribozyme molecules and binding/cleavage sites within IKK-gamma or PKR RNA.

Example 1

Identification of Potential Target Sites in Human IKK-Gamma and PKR RNA

The sequence of human IKK-gamma or PKR genes are screened for accessible sites using a computer-folding algorithm. Regions of the RNA that do not form secondary folding structures and contained potential enzymatic nucleic acid molecule and/or antisense binding/cleavage sites are identified. The sequences of these binding/cleavage sites are shown in Tables III–XIII.

Example 2

Selection of Enzymatic Nucleic Acid Cleavage Sites in Human IKK-Gamma and PKR RNA Enzymatic nucleic acid molecule target sites are chosen by analyzing sequences of Human IKK-gamma (Genbank accession No: NM_003639) (SEQ ID NO:8014) and PKR (Genbank accession No: NM_002759) and prioritizing the sites on the basis of folding. Enzymatic nucleic acid molecules are designed that can bind each target and are individually analyzed by computer folding (Christoffersen et al., 19941 Mol. Struc. Theochern, 311, 273; Jaeger et al., 1989, Proc. Natl. Acad. Sci. USA, 86, 7706) to assess whether the enzymatic nucleic acid molecule sequences fold into the appropriate secondary structure. Those enzymatic nucleic acid molecules with unfavorable intramolecular interactions between the binding arms and the catalytic core were eliminated from consideration. As noted below, varying binding arm lengths can be chosen to optimize activity. Generally, at least 5 bases on each arm are able to bind to, or otherwise interact with, the target RNA.

Example 3

Chemical Synthesis and Purification of Ribozymes and Antisense for Efficient Cleavage and/or Blocking of IKK-Gamma and PKR RNA Enzymatic nucleic acid molecules and antisense constructs are designed to anneal to various sites in the RNA message. The binding arms of the enzymatic nucleic acid molecules are complementary to the target site sequences described above, while the antisense constructs are fully complementary to the target site sequences described above. The enzymatic nucleic acid molecules and antisense constructs were chemically synthesized. The method of synthesis used followed the procedure for normal RNA synthesis as described above and in Usman et al., (1987 J. Am. Chem. Soc., 109, 7845), Scaringe et al., (1990 Nucleic Acids Res., 18, 5433) and Wincott et al., supra, and made use of common nucleic acid protecting and coupling groups, such as dimetboxytrityl at the 5'-end, and phosphoramidites at the 3'-end. The average stepwise coupling yields were typically >98%.

Enzymatic nucleic acid molecules and antisense constructs are also synthesized from DNA templates using bacteriophage T7 RNA polymerase (Milligan and Uhlenbeck, 1989, Methods Enzymol. 180, 51). Enzymatic nucleic acid molecules and antisense constructs are purified by gel electrophoresis using general methods or are purified by high pressure liquid chromatography (HPLC; See Wincott et al., supra; the totality of which is hereby incorporated herein by reference) and are resuspended in water. The sequences of the chemically synthesized enzymatic nucleic acid molecules used in this study are shown below in Table XIII. The sequences of the chemically synthesized antisense constructs used in this study are complementary sequences to the Substrate sequences shown below as in Tables III to XIII.

Example 4

Enzymatic Nucleic Acid Molecule Cleavage of IKK-Gamma and PKR RNA Target In Vitro Enzymatic nucleic acid molecules targeted to the human IKK-gamma or PKR RNA are designed and synthesized as described above. These enzymatic nucleic acid molecules can be tested for cleavage activity in vitro, for example, using the following procedure. The target sequences and the nucleotide location within the IKK-gamma or PKR RNA are given in Tables III–XIII.

Cleavage Reactions: Full-length or partially full-length, internally-labeled target RNA for enzymatic nucleic acid molecule cleavage assay is prepared by in vitro transcription in the presence of [a-$^{32}$P] CTP, passed over a G 50 Sephadex column by spin chromatography and used as substrate RNA without further purification. Alternately, substrates are 5'-$^{32}$P-end labeled using T4 polynucleotide kinase enzyme. Assays are performed by pre-warming a 2× concentration of purified enzymatic nucleic acid molecule in enzymatic nucleic acid molecule cleavage buffer (50 mM Tris-HCl, pH 7.5 at 37° C., 10 mM MgCl$_2$) and the cleavage reaction was initiated by adding the 2× enzymatic nucleic acid molecule mix to an equal volume of substrate RNA (maximum of 1–5 nM) that was also pre-warmed in cleavage buffer. As an initial screen, assays are carried out for 1 hour at 37° C. using a final concentration of either 40 nM or 1 mM enzymatic nucleic acid molecule, i.e., enzymatic nucleic acid molecule excess. The reaction is quenched by the addition of an equal volume of 95% formamide, 20 mM EDTA, 0.05% bromophenol blue and 0.05% xylene cyanol after which the sample is heated to 95° C. for 2 minutes, quick chilled and loaded onto a denaturing polyacrylamide gel. Substrate RNA and the specific RNA cleavage products generated by enzymatic nucleic acid molecule cleavage are visualized on an autoradiograph of the gel. The percentage of cleavage is determined by Phosphor Imager® quantitation of bands representing the intact substrate and the cleavage products.

Example 5

Nucleic Acid Down-Regulation of IKK-Gamma and PKR Target RNA In Vivo

Nucleic acid molecules targeted to the human IKK-gamma or PKR RNA are designed and synthesized as described above. These nucleic acid molecules can be tested for cleavage activity in vivo, for example using the procedures described below. The target sequences and the nucleotide location within the IKK-gamma or PKR RNA are given in Tables III–XIII.

Example 6

In Vivo Models Used to Evaluate the Down-Regulation of IKK-Gamma or PKR Gene Expression A variety of endpoints have been used in cell culture models to evaluate IKK-gamma or PKR-mediated effects after treatment with anti-IKK-gamma or PKR agents. Phenotypic endpoints include inhibition of cell proliferation, apoptosis assays and reduction of IKK-gamma or PKR protein expression, or a decrease in NFKB expression. Since IKK-gamma and PKR are both involved in the induction of NFKB, NFKB can be used as a surrogate marker in cell culture, animal, and clinical studies. Because overexpression of NFKB is directly associated with increased proliferation of tumor cells, a proliferation endpoint for cell culture assays is preferably used as a primary screen. There are several methods by which this endpoint can be measured. Following treatment of cells with nucleic acid molecules, cells are allowed to grow (typically 5 days) after which either the cell viability, the incorporation of [$^3$H] thymidine into cellular DNA and/or the cell density can be measured. The assay of cell density is very straightforward and can be performed in a 96-well format using commercially available fluorescent nucleic acid stains (such as Syto® 13 or CyQuant®). An assay using CyQuant® is described herein.

As a secondary, confirmatory endpoint a nucleic acid-mediated decrease in the level of IKK-gamma or PKR RNA and/or IKK-gamma or PKR protein expression can be evaluated. Alternately, a decrease in the level of NFKB RNA can be evaluated.

Cell Culture

Cell types that express/over-express NFKB include HeLa, macrophages, peripheral blood lymphocytes, hepatocytes, fibroblasts, endothelial cells and epithelial cells. In culture, these cells can be stimulated to express/over-express NFKB by addition of TNF-alpha PMA or IL-1-beta to the culture medium. Some of these cell types also can respond with a similar activation of NFKB following LPS treatment. Activation of NFKB in cultured cells can be evaluated by electrophoretic mobility shift assay (EMSA). Delineation of alterations in the subunits can be determined by Western blot.

Primary Screen

A useful cell culture system in evaluating NFKB modulation is human colonic epithelial cells. One suitable cell line is SW620 colon carcinoma cells (CCL227). These cells respond to stimulation with TNF-alpha, LPS and/or IL-1-beta with an increase in NFKB activation. SW620 cells are grown in MEM supplemented with 10% heat-inactivated FBS and glutamine (2 mmol/L).

TNF-alpha dose-response curves in these cells are determined by incubating cells with various concentrations of recombinant human TNF-alpha (Sigma Chemical Co.). Maximal DNA binding activity induction can occur with 150 U/ml TNF-alpha in the culture medium. Induction is typically evident within 10 minutes of treatment with TNF-alpha reaches a peak at one hour post-treatment and persists for up to 4 hours post-treatment. The primary readout can be NFKB DNA activity in nuclear extracts of SW620 cells as determined by electrophoretic mobility shift assays (EMSA). Once the appropriate TNF-alpha dose/response profile has been determined, inhibition of IKK-gamma, PKR, or NFKB activation is evaluated using specific and non-specific inhibitors of activation, sulfasalazine and steroids, respectively. Cells are incubated with inhibitors or control media for 30 minutes prior to stimulation with TNF-alpha Nuclear extracts are prepared and evaluated for DNA binding activity by EMSA. Once the activity of positive controls has been established, enzymatic nucleic acids targeting the IKK-gamma or PKR are evaluated in this system. Supershift assays using polyclonal antibodies against the NFKB or PKR protein subunits can be performed to confirm down-regulation of NFKB.

Secondary Screens

SW620 cells can be transfected with the 3×Ig-kappa-B-Luc reporter construct 18 hours before challenge with TNF-alpha, LPS or PMA. The readout for this assay is luciferase activity. Test compounds are applied 17.5 hours after transfection (30 minutes before challenge). Cells are harvested 24 hours after challenge and relative changes in luciferase activity is used as the endpoint. Lastly, the activation of NFKB can be visualized fluorescently. Inactive NFKB heterodimers are held in the cytoplasm by inhibitory proteins. Once activated, the free heterodimers translocate to the nucleus. Thus, the relative change in cytoplasmic versus nuclear fluorescence can indicate the degree of NFKB activation. Cells can be grown on chamber slides, treated with TNF-alpha with and without test compounds), and the location of the NFKB subunit can be determined by immunofluorescence using a FITC-labeled antibody to NFKB.

Animal Models

Evaluating the efficacy of anti-IKK-gamma or PKR agents in animal models is an important prerequisite to human clinical trials. Studies have shown that human breast carcinoma cell lines express high levels of NFKB (Sovak et al., 1997, *J. Clin. Invest.*, 100, 2952–2960). High levels of NFKB have also been observed in carcinogen-induced primary rat mammary tumors and in human breast cancer specimins. Additionally, HER2/neu overexpression has been shown to activate NFKB (Pianetti et al., 2001, *Oncogene*, 20, 1287–1299). As such, xenografts of cell lines that over-express NFKB can be used in animal models of tumorigenesis and/or inflammation to study the inhibition of NFKB.

Oncology Animal Model Development

Tumor cell lines are characterized to establish their growth curves in mice. These cell lines are implanted into both nude and SCID mice and primary tumor volumes are measured 3 times per week. Growth characteristics of these tumor lines using a Matrigel implantation format can also be established. The use of other cell lines that have been engineered to express high levels of NFKB can also be used in the described studies. The tumor cell line(s) and implantation method that supports the most consistent and reliable tumor growth is used in animal studies testing the lead IKK-gamma or PKR nucleic acid(s). Nucleic acids are administered by daily subcutaneous injection or by continuous subcutaneous infusion from Alzet mini osmotic pumps beginning 3 days after tumor implantation and continuing for the duration of the study. Group sizes of at least 10 animals are employed. Efficacy is determined by statistical comparison of tumor volume of nucleic acid-treated animals to a control group of animals treated with saline alone. Because the growth of these tumors is generally slow (45–60 days), an initial endpoint is the time in days it takes to establish an easily measurable primary tumor (i.e. 50–100 mm$^3$) in the presence or absence of nucleic acid treatment.

Inflammation Animal Model Development

Chronic, sublethal administration of indomethacin to outbred rats produces an enteropathy characterized by thickening of the small intestine and mesentery, ulcerations, granulomatous inflammation, crypt abcesses and adhesions. These lesions are similar to those that are characteristic findings in human patients with Crohn's disease (CD). Thus, any beneficial therapeutic effects revealed using this model can be extrapolated to potential benefit for patients with CD.

Male Sprague-Dawley rats (200–275 g) are utilized for these studies. Chronic intestinal inflammation is induced by two subcutaneous injections of indomethacin (7.5 mg/kg in 5% NaHCO3) administered on subsequent days (Day-0 and Day-1). Animals are followed for four days following the first indomethacin injection. The mortality rate associated with this model is typically less than 10%. On the last day of the study, animals are euthanized by CO$_2$ asphyxiation, small intestines excised and gross pathologic findings ranked according to the following criteria: 0, normal ; 1, minimal abnormalities, slight thickening of the small intestine, no adhesions; 2, obvious thickening of small intestine with 1 adhesion; 3, obvious thickening of small intestine with 2 or 3 adhesions; 4, massive adhesions to the extent that the intestine cannot be separated, contents primarily fluid; 5, severe peritonitis resulting in death. A 10-cm portion of the most affected region of the small intestine is weighed, placed in 10% neutral buffered formalin and submitted for histopathologic evaluation.

The 10 cm portion of gut from each animal is cut into five equal sections. Transverse and longitudinal sections of each portion are cut and stained with hematoxylin and eosin. All slides are read in a blinded fashion and each section is scored for necrosis (% area of involvement) and inflammatory response according to the following scale:

Necrosis—1, 10%; 2, 10–25%; 3, 25–50%; 4, 50–75%; 5, 75–100%;

Inflammation—
1=minimal in mesentery and muscle or lesion
2=mild in mesentery and muscle or lesion
3=moderate in mesentery and muscle or lesion
4=marked in lesion
5=severe in lesion The scores for each of the five sections are averaged for necrosis and for inflammation.

NFKB Levels for Patient Screening and as a Potential Endpoint

Because elevated NFKB levels can be detected in cancers, cancer patients can be pre-screened for elevated NFKB prior to admission to initial clinical trials testing an anti-IKK-gamma or PKR nucleic acid. Initial NFKB levels can be determined (by ELISA) from tumor biopsies or resected tumor samples. During clinical trials, it can be possible to monitor circulating NFKB protein by ELISA. Evaluation of serial blood/serum samples over the course of the anti-IKK-gamma or PKR nucleic acid treatment period could be useful in determining early indications of efficacy.

Example 7

Activity of Nucleic Acid Molecules Used to Down-Regulate IKK-Gamma and PKR Gene Expression Several nucleic acid molecules targeted against IKK-gamma or PKR RNA have been designed and synthesized. These nucleic acid molecules can be tested in cell proliferation and RNA reduction assays described herein.

Proliferation Assay

The model proliferation assay used in the study requires a cell-plating density of 2,000–10,000 cells/well in 96-well plates and at least 2 cell doublings over a 5-day treatment period. Cells used in proliferation studies were either lung or ovarian cancer cells (A549 and SKOV-3 cells respectively). To calculate cell density for proliferation assays, the FIPS (fluoro-imaging processing system) method known in the art was used. This method allows for cell density measurements after nucleic acids are stained with CyQuant® dye, and has the advantage of accurately measuring cell densities over a very wide range 1,000–100,000 cells/well in 96-well format. Enzymatic nucleic acid molecules (50–200 nM) are delivered in the presence of cationic lipid at 2.5–5.0 µg/nL and inhibition of proliferation was determined on day 5 post-treatment.

RNA Assay

RNA is harvested 24 hours post-treatment using the Qiagen RNeasy® 96 procedure. Real time RT-PCR (Taq-Man® assay) is performed on purified RNA samples using separate primer/probe sets specific for target IKK-gamma or PKR RNA.

Indications

Particular degenerative and disease states that can be associated with IKK-gamma or PKR expression modulation include but are not limited to cancerous and/or inflammatory diseases and conditions such as breast, lung, prostate, colorectal, brain, esophageal, bladder, pancreatic, cervical, head and neck, and ovarian cancer, melanoma, lymphoma, glioma, multidrug resistant cancers, rheumatoid arthritis, restenosis, asthma, Crohn's disease, diabetes, obesity, autoimmune disease, lupus, multiple sclerosis, transplant/graft rejection, gene therapy applications, ischemia/reperfusion injury (CNS and myocardial), glomerulonephritis, sepsis, allergic airway inflammation, inflammatory bowel disease, infection, incontinentia pigmenti and any other diseases or conditions that are related to or respond to the levels of IKK-gamma or PKR in a cell or tissue. The present body of knowledge in IKI-gamma and PKR research indicates the need for methods to assay IKK-gamma and PKR activity and for compounds that can regulate IKK-gamma and PKR expression for research, diagnostic, and therapeutic use.

The use of monoclonal antibodies, chemotherapy, radiation therapy, analgesics, and/or anti-inflammatory compounds, are all non-limiting examples of a methods that can be combined with or used in conjunction with the nucleic acid molecules (e.g. ribozymes and antisense molecules) of the instant invention. Common chemotherapies that can be combined with nucleic acid molecules of the instant invention include various combinations of cytotoxic drugs to kill cancer cells. These drugs include but are not limited to paclitaxel (Taxol), docetaxel, cisplatin, methotrexate, cyclophosphamide, doxorubin, fluorouracil carboplatin, edatrexate, gemcitabine, vinorelbine etc. Those skilled in the art will recognize that other drug compounds and therapies can be similarly be readily combined with the nucleic acid molecules of the instant invention (e.g. ribozymes and antisense molecules) are hence within the scope of the instant invention.

Diagnostic Uses

The nucleic acid molecules of this invention (e.g., enzymatic nucleic acid molecules) can be used as diagnostic tools to examine genetic drift and mutations within diseased cells or to detect the presence of IKK-gamma or PKR RNA in a cell. The close relationship between enzymatic nucleic acid molecule activity and the structure of the target RNA allows the detection of mutations in any region of the molecule which alters the base-pairing and three-dimensional structure of the target RNA. By using multiple enzymatic nucleic acid molecules described in this invention, one can map nucleotide changes which are important to RNA structure and function in vitro, as well as in cells and tissues. Cleavage of target RNAs with enzymatic nucleic acid molecules can be used to inhibit gene expression and define the role (essentially) of specified gene products in the progression of disease. In this manner, other genetic targets can be defined as important mediators of the disease. These experiments can lead to better treatment of the disease progression by affording the possibility of combinational therapies (e.g., multiple enzymatic nucleic acid molecules targeted to different genes, enzymatic nucleic acid molecules coupled with known small molecule inhibitors, or intermittent treatment with combinations of enzymatic nucleic acid molecules and/or other chemical or biological molecules).

Other in vitro uses of enzymatic nucleic acid molecules of this invention are well known in the art, and include detection of the presence of mRNAs associated with IKK-gamma or PKR-related condition. Such RNA is detected by determining the presence of a cleavage product after treatment with an enzymatic nucleic acid molecule using standard methodology.

In a specific example, enzymatic nucleic acid molecules which cleave only wild-type or mutant forms of the target RNA are used for the assay. The first enzymatic nucleic acid molecule is used to identify wild-type RNA present in the sample and the second enzymatic nucleic acid molecule is used to identify mutant RNA in the sample. As reaction controls, synthetic substrates of both wild-type and mutant RNA are cleaved by both enzymatic nucleic acid molecules to demonstrate the relative enzymatic nucleic acid molecule efficiencies in the reactions and the absence of cleavage of the "non-targeted" RNA species. The cleavage products from the synthetic substrates also serve to generate size markers for the analysis of wild-type and mutant RNAs in the sample population. Thus each analysis requires two enzymatic nucleic acid molecules, two substrates and one unknown sample which is combined into six reactions. The presence of cleavage products is determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype (i.e., IKK-gamma or PKR) is adequate to establish risk. If probes of comparable specific activity are used for both transcripts, then a qualitative comparison of RNA levels will be adequate and will decrease the cost of the initial diagnosis. Higher mutant form to wild-type ratios are correlated with higher risk whether RNA levels are compared qualitatively or quantitatively. The use of enzymatic nucleic acid molecules in diagnostic applications contemplated by the instant invention is more fully described in George et al., U.S. Pat. Nos. 5,834,186 and 5,741,679, Shih et al., U.S. Pat. No. 5,589,332, Nathan et al., U.S. Pat. No. 5,871,914, Nathan and Ellington, International PCT publication No. WO 00/24931, Breaker et al., International PCT Publication Nos. WO 00/26226 and 98/27104, and Sullenger et al., International PCT publication No. WO 99/29842.

Additional Uses

Potential uses of sequence-specific enzymatic nucleic acid molecules of the instant invention can have many of the same applications for the study of RNA that DNA restriction endonucleases have for the study of DNA (Nathans et al., 1975 *Ann. Rev. Biochem.* 44:273). For example, the pattern of restriction fragments can be used to establish sequence relationships between two related RNAs, and large RNAs can be specifically cleaved to fragments of a size more useful for study. The ability to engineer sequence specificity of the enzymatic nucleic acid molecule is ideal for cleavage of RNAs of unknown sequence. Applicant has described the use of nucleic acid molecules to down-regulate gene expression of target genes in bacterial, microbial, fungal, viral, and eukaryotic systems including plant, or mammalian cells.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications can be made to the invention disclosed herein without departing from the scope and spirit of the invention. Thus, such additional embodiments are within the scope of the present invention and the following claims.

The invention illustratively described herein suitably can be practiced in the absence of any element or elements, limitation or limitations which is not specifically disclosed herein. Thus, for example, in each instance herein any of the terms "comprising", "consisting essentially of" and "consisting of" can be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed can be restored to by tose skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group1

Other embodiments are within the claims that follow.

TABLE I

Characteristics of naturally occurring ribozymes

Group I Introns

Size: ~150 to >1000 nucleotides.
Requires a U in the target sequence immediately 5' of the cleavage site.
Binds 4–6 nucleotides at the 5'-side of the cleavage site.
Reaction mechanism: attack by the 3'-OH of guanosine to generate cleavage products with 3'-OH and 5'-guanosine.

TABLE I-continued

Characteristics of naturally occurring ribozymes

Additional protein cofactors required in some cases to help folding and maintenance of the active structure.
Over 300 known members of this class. Found as an intervening sequence in *Tetrahymena thermophila* rRNA, fungal mitochondria, chloroplasts, phage T4, blue-green algae, and others.
Major structural features largely established through phylogenetic comparisons, mutagenesis, and biochemical studies [i,ii].
Complete kinetic framework established for one ribozyme [iii,iv,v,vi].
Studies of ribozyme folding and substrate docking underway [vii,viii,ix].
Chemical modification investigation of important residues well established [x,xi].
The small (4–6 nt) binding site can make this ribozyme too non-specific for targeted RNA cleavage, however, the Tetrahymena group I intron has been used to repair a "defective" β-galactosidase message by the ligation of new β-galactosidase sequences onto the defective message [xii].

RNAse P RNA (M1 RNA)

Size: ~290 to 400 nucleotides.
RNA portion of a ubiquitous ribonucleoprotein enzyme.
Cleaves tRNA precursors to form mature tRNA [xiii].
Reaction mechanism: possible attack by $M^{2+}$-OH to generate cleavage products with 3'-OH and 5'-phosphate.
RNAse P is found throughout the prokaryotes and eukaryotes. The RNA subunit has been sequenced from bacteria, yeast, rodents, and primates.
Recruitment of endogenous RNAse P for therapeutic applications is possible through hybridization of an External Guide Sequence (EGS) to the target RNA [xiv,xv]
Important phosphate and 2' OH contacts recently identified [xvi,xvii]

Group II Introns

Size: >1000 nucleotides.
Trans cleavage of target RNAs recently demonstrated [xviii,xix].
Sequence requirements not fully determined.
Reaction mechanism: 2'-OH of an internal adenosine generates cleavage products with 3'-OH and a "lariat" RNA containing a 3'-5' and a 2'-5' branch point.
Only natural ribozyme with demonstrated participation in DNA cleavage [xx,xxi] in addition to RNA cleavage and ligation.
Major structural features largely established through phylogenetic comparisons [xxii].
Important 2'OH contacts beginning to be identified [xxiii]
Kinetic framework under development [xxiv]

Neurospora VS RNA

Size: ~144 nucleotides.
Trans cleavage of hairpin target RNAs recently demonstrated [xxv].
Sequence requirements not fully determined.
Reaction mechanism: attack by 2'-OH 5' to the scissile bond to generate cleavage products with 2',3'-cyclic phosphate and 5'-OH ends.
Binding sites and structural requirements not fully determined.
Only 1 known member of this class. Found in Neurospora VS RNA.

Hammerhead Ribozyme
(see text for references)

Size: ~13 to 40 nucleotides.
Requires the target sequence UH immediately 5' of the cleavage site.
Binds a variable number nucleotides on both sides of the cleavage site.
Reaction mechanism: attack by 2'-OH 5' to the scissile bond to generate cleavage products with 2',3'-cyclic phosphate and 5'-OH ends.
14 known members of this class. Found in a number of plant pathogens (virusoids) that use RNA as the infectious agent.
Essential structural features largely defined, including 2 crystal structures [xxvi,xxvii]
Minimal ligation activity demonstrated (for engineering through in vitro selection) [xxviii]
Complete kinetic framework established for two or more ribozymes [xxix].
Chemical modification investigation of important residues well established [xxx].

Hairpin Ribozyme

Size: ~50 nucleotides.
Requires the target sequence GUC immediately 3' of the cleavage site.
Binds 4–6 nucleotides at the 5'-side of the cleavage site and a variable number to the 3'-side of the cleavage site.
Reaction mechanism: attack by 2'-OH 5' to the scissile bond to generate cleavage products with 2',3'-cyclic phosphate and 5'-OH ends.
3 known members of this class. Found in three plant pathogen (satellite RNAs of the tobacco ringspot virus, arabis mosaic virus and chicory yellow mottle virus) which uses RNA as the infectious agent.
Essential structural features largely defined [xxxi,xxxii,xxxiii,xxxiv]
Ligation activity (in addition to cleavage activity) makes ribozyme amenable to

TABLE I-continued

Characteristics of naturally occurring ribozymes engineering through in vitro selection [xxxv]
Complete kinetic framework established for one ribozyme [xxxvi].
Chemical modification investigation of important residues begun [xxxvii,xxxviii].
Hepatitis Delta Virus (HDV) Ribozyme Size: ~60 nucleotides.
Trans cleavage of target RNAs demonstrated [xxxix].
Binding sites and structural requirements not fully determined, although no sequences 5' of cleavage site are required. Folded ribozyme contains a pseudoknot structure [xl].
Reaction mechanism: attack by 2'-OH 5' to the scissile bond to generate cleavage products with 2',3'-cyclic phosphate and 5'-OH ends.
Only 2 known members of this class. Found in human HDV.
Circular form of HDV is active and shows increased nuclease stability [xli]

---

[i]. Michel, Francois; Westhof, Eric. Slippery substrates. Nat. Struct. Biol. (1994), 1(1), 5–7.

[ii]. Lisacek, Frederique; Diaz, Yolande; Michel, Francois. Automatic identification of group I intron cores in genomic DNA sequences. J. Mol. Biol. (1994), 235(4), 1206–17.

[iii]. Herschlag, Daniel; Cech, Thomas R.. Catalysis of RNA cleavage by the *Tetrahymena thermophila* ribozyme. 1. Kinetic description of the reaction of an RNA substrate complementary to the active site. Biochemistry (1990), 29(44), 10159–71.

[iv]. Herschlag, Daniel; Cech, Thomas R.. Catalysis of RNA cleavage by the *Tetrahymena thermophila* ribozyme. 2. Kinetic description of the reaction of an RNA substrate that forms a mismatch at the active site. Biochemistry (1990), 29(44), 10172–80.

[v]. Knitt, Deborah S.; Herschlag, Daniel. pH Dependencies of the Tetrahymena Ribozyme Reveal an Unconventional Origin of an Apparent pKa. Biochemistry (1996), 35(5), 1560–70.

[vi]. Bevilacqua, Philip C.; Sugimoto, Naoki; Turner, Douglas H.. A mechanistic framework for the second step of splicing catalyzed by the Tetrahymena ribozyme. Biochemistry (1996), 35(2), 648–58.

[vii]. Li, Yi; Bevilacqua, Philip C.; Mathews, David; Turner, Douglas H.. Thermodynamic and activation parameters for binding of a pyrene-labeled substrate by the Tetrahymena ribozyme: docking is not diffusion-controlled and is driven by a favorable entropy change. Biochemistry (1995), 34(44), 14394–9.

[viii]. Banerjee, Aloke Raj; Turner, Douglas H.. The time dependence of chemical modification reveals slow steps in the folding of a group I ribozyme. Biochemistry (1995), 34(19), 6504–12.

[ix]. Zarrinkar, Patrick P.; Williamson, James R.. The P9.1–P9.2 peripheral extension helps guide folding of the Tetrahymena ribozyme. Nucleic Acids Res. (1996), 24(5), 854–8.

[x]. Strobel, Scott A.; Cech, Thomas R.. Minor groove recognition of the conserved G.cntdot.U pair at the Tetrahymena ribozyme reaction site. Science (Washington, D. C.) (1995), 267(5198), 675–9.

[xi]. Strobel, Scott A.; Cech, Thomas R.. Exocyclic Amine of the Conserved G.cntdot.U Pair at the Cleavage Site of the Tetrahymena Ribozyme Contributes to 5'-Splice Site Selection and Transition State Stabilization. Biochemistry (1996), 35(4), 1201–11.

[xii]. Sullenger, Bruce A.; Cech, Thomas R.. Ribozyme-mediated repair of defective mRNA by targeted trans-splicing. Nature (London) (1994), 371(6498), 619–22.

[xiii]. Robertson, H. D.; Altman, S.; Smith, J. D. J. Biol. Chem., 247, 5243–5251 (1972).

[xiv]. Forster, Anthony C.; Altman, Sidney. External guide sequences for an RNA enzyme. Science (Washington, D. C., 1883–) (1990), 249(4970), 783–6.

[xv]. Yuan, Y.; Hwang, E. S.; Altman, S. Targeted cleavage of mRNA by human RNase P. Proc. Natl. Acad. Sci. USA (1992) 89, 8006–10.

[xvi]. Harris, Michael E.; Pace, Norman R.. Identification of phosphates involved in catalysis by the ribozyme RNase P RNA. RNA (1995), 1(2), 210–18.

[xvii]. Pan, Tao; Loria, Andrew; Zhong, Kun. Probing of tertiary interactions in RNA: 2'-hydroxyl-base contacts between the RNase P RNA and pre-tRNA. Proc. Natl. Acad. Sci. U.S.A. (1995), 92(26), 12510–14.

[xviii]. Pyle, Anna Marie; Green, Justin B.. Building a Kinetic Framework for Group II Intron Ribozyme Activity: Quantitation of Interdomain Binding and Reaction Rate. Biochemistry (1994), 33(9), 2716–25.

[xix]. Michels, William J. Jr.; Pyle, Anna Marie. Conversion of a Group II Intron into a New Multiple-Turnover Ribozyme that Selectively Cleaves Oligonucleotides: Elucidation of Reaction Mechanism and Structure/Function Relationships. Biochemistry (1995), 34(9), 2965–77.

[xx]. Zimmerly, Steven; Guo, Huatao; Eskes, Robert; Yang, Jian; Perlman, Philip S.; Lambowitz, Alan M.. A group II intron RNA is a catalytic component of a DNA endonuclease involved in intron mobility. Cell (Cambridge, Mass.) (1995), 83(4), 529–38.

[xxi]. Griffin, Edmund A., Jr.; Qin, Zhifeng; Michels, Williams J., Jr.; Pyle, Anna Marie. Group II intron ribozymes that cleave DNA and RNA linkages with similar efficiency, and lack contacts with substrate 2'-hydroxyl groups. Chem. Biol. (1995), 2(11), 761–70.

[xxii]. Michel, Francois; Ferat, Jean Luc. Structure and activities of group II introns. Annu. Rev. Biochem. (1995), 64, 435–61.

[xxiii]. Abramovitz, Dana L.; Friedman, Richard A.; Pyle, Anna Marie. Catalytic role of 2'-hydroxyl groups within a group II intron active site. Science (Washington, D. C.) (1996), 271(5254), 1410–13.

[xxiv]. Daniels, Danette L.; Michels, William J., Jr.; Pyle, Anna Marie. Two competing pathways for self-splicing by group II introns: a quantitative analysis of in vitro reaction rates and products. J. Mol. Biol. (1996), 256(1), 31–49.

TABLE I-continued

Characteristics of naturally occurring ribozymes

[xxv]. Guo, Hans C. T.; Collins, Richard A.. Efficient trans-cleavage of a stem-loop RNA substrate by a ribozyme derived from Neurospora VS RNA. EMBO J. (1995), 14(2), 368–76.
[xxvi]. Scott, W. G., Finch, J. T., Aaron, K. The crystal structure of an all RNA hammerhead ribozyme: Aproposed mechanism for RNA catalytic cleavage. Cell, (1995), 81, 991–1002.
[xxvii]. McKay, Structure and function of the hammerhead ribozyme: an unfinished story. RNA, (1996), 2, 395–403.
[xxviii]. Long, D., Uhlenbeck, O., Hertel, K. Ligation with hammerhead ribozymes. U.S. Pat. No. 5,633,133.
[xxix]. Hertel, K. J., Herschlag, D., Uhlenbeck, O. A kinetic and thermodynamic framework for the hammerhead ribozyme reaction. Biochemistry, (1994) 33, 3374–3385. Beigelman, L., et al., Chemical modifications of hammerhead ribozymes. J. Biol. Chem., (1995) 270, 25702–25708.
[xxx]. Beigelman, L., et al., Chemical modifications of hammerhead ribozymes. J. Biol. Chem., (1995) 270, 25702–25708.
[xxxi]. Hampel, Arnold; Tritz, Richard; Hicks, Margaret; Cruz, Phillip. 'Hairpin' catalytic RNA model: evidence for helixes and sequence requirement for substrate RNA. Nucleic Acids Res. (1990), 18(2), 299–304.
[xxxii]. Chowrira, Bharat M.; Berzal-Herranz, Alfredo; Burke, John M.. Novel guanosine requirement for catalysis by the hairpin ribozyme. Nature (London) (1991), 354(6351), 320–2.
[xxxiii]. Berzal-Herranz, Alfredo; Joseph, Simpson; Chowrira, Bharat M.; Butcher, Samuel E.; Burke, John M.. Essential nucleotide sequences and secondary structure elements of the hairpin ribozyme. EMBO J. (1993), 12(6), 2567–73.
[xxxiv]. Joseph, Simpson; Berzal-Herranz, Alfredo; Chowrira, Bharat M.; Butcher, Samuel E.. Substrate selection rules for the hairpin ribozyme determined by in vitro selection, mutation, and analysis of mismatched substrates. Genes Dev. (1993), 7(1), 130–8.
[xxxv]. Berzal-Herranz, Alfredo; Joseph, Simpson; Burke, John M.. In vitro selection of active hairpin ribozymes by sequential RNA-catalyzed cleavage and ligation reactions. Genes Dev. (1992), 6(1), 129–34.
[xxxvi]. Hegg, Lisa A.; Fedor, Martha J.. Kinetics and Thermodynamics of Intermolecular Catalysis by Hairpin Ribozymes. Biochemistry (1995), 34(48), 15813–28.
[xxxvii]. Grasby, Jane A.; Mersmann, Karin; Singh, Mohinder; Gait, Michael J.. Purine Functional Groups in Essential Residues of the Hairpin Ribozyme Required for Catalytic Cleavage of RNA. Biochemistry (1995), 34(12), 4068–76.
[xxxviii]. Schmidt, Sabine; Beigelman, Leonid; Karpeisky, Alexander; Usman, Nassim; Sorensen, Ulrik S.; Gait, Michael J.. Base and sugar requirements for RNA cleavage of essential nucleoside residues in internal loop B of the hairpin ribozyme: implications for secondary structure. Nucleic Acids Res. (1996), 24(4), 573–81.
[xxxix]. Perrotta, Anne T.; Been, Michael D.. Cleavage of oligoribonucleotides by a ribozyme derived from the hepatitis .delta. virus RNA sequence. Biochemistry (1992), 31(1), 16–21.
[xl]. Perrotta, Anne T.; Been, Michael D.. A pseudoknot-like structure required for efficient self-cleavage of hepatitis delta virus RNA. Nature (London) (1991), 350(6317), 434–6.
[xli]. Puttaraju, M.; Perrotta, Anne T.; Been, Michael D.. A circular trans-acting hepatitis delta virus ribozyme. Nucleic Acids Res. (1993), 21(18), 4253–8.

TABLE II

| A. 2.5 µmol Synthesis Cycle ABI 394 Instrument | | | | | |
|---|---|---|---|---|---|
| Reagent | Equivalents | Amount | Wait Time* DNA | Wait Time* 2'-O-methyl | Wait Time*RNA |
| Phosphoramidites | 6.5 | 163 µL | 45 sec | 2.5 min | 7.5 min |
| S-Ethyl Tetrazole | 23.8 | 238 µL | 45 sec | 2.5 min | 7.5 min |
| Acetic Anhydride | 100 | 233 µL | 5 sec | 5 sec | 5 sec |
| N-Methyl Imidazole | 186 | 233 µL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 µL | 100 sec | 300 sec | 300 sec |
| Acetonitrile | NA | 6.67 mL | NA | NA | NA |

| B. 0.2 µmol Synthesis Cycle ABI 394 Instrument | | | | | |
|---|---|---|---|---|---|
| Reagent | Equivalents | Amount | Wait Time* DNA | Wait Time* 2'-O-methyl | Wait Time*RNA |
| Phosphoramidites | 15 | 31 µL | 45 sec | 233 sec | 465 sec |
| S-Ethyl Tetrazole | 38.7 | 31 µL | 45 sec | 233 min | 465 sec |
| Acetic Anhydride | 655 | 124 µL | 5 sec | 5 sec | 5 sec |
| N-Methyl Imidazole | 1245 | 124 µL | 5 sec | 5 sec | 5 sec |
| TCA | 700 | 732 µL | 10 sec | 10 sec | 10 sec |
| Iodine | 20.6 | 244 µL | 15 sec | 15 sec | 15 sec |
| Beaucage | 7.7 | 232 µL | 100 sec | 300 sec | 300 sec |
| Acetonitrile | NA | 2.64 mL | NA | NA | NA |

TABLE II-continued

C. 0.2 μmol Synthesis Cycle 96 well Instrument

| Reagent | Equivalents:DNA/ 2'-O-methyl/Ribo | Amount: DNA/2'-O-methyl/Ribo | Wait Time* DNA | Wait Time* 2'-O-methyl | Wait Time* Ribo |
|---|---|---|---|---|---|
| Phosphoramidites | 22/33/66 | 40/60/120 μL | 60 sec | 180 sec | 360 sec |
| S-Ethyl Tetrazole | 70/105/210 | 40/60/120 μL | 60 sec | 180 min | 360 sec |
| Acetic Anhydride | 265/265/265 | 50/50/50 μL | 10 sec | 10 sec | 10 sec |
| N-Methyl Imidazole | 502/502/502 | 50/50/50 μL | 10 sec | 10 sec | 10 sec |
| TCA | 238/475/475 | 250/500/500 μL | 15 sec | 15 sec | 15 sec |
| Iodine | 6.8/6.8/6.8 | 80/80/80 μL | 30 sec | 30 sec | 30 sec |
| Beaucage | 34/51/51 | 80/120/120 | 100 sec | 200 sec | 200 sec |
| Acetonitrile | NA | 1150/1150/1150 μL | NA | NA | NA |

*Wait time does not include contact time during delivery.

TABLE III

Human IKK-gamma Hammerhead and Substrate Sequence

| Pos | Substrate | Seq ID | Hammerhead | Seq ID |
|---|---|---|---|---|
| 18 | AUGGCCCU U GUGAUCCA | 4361 | UGGAUCAC CUGAUGAGGCCGUUAGGCCGAA AGGGCCAU | 4555 |
| 24 | CUUGUGAU C CAGGUGGG | 4362 | CCCACCUG CUGAUGAGGCCGUUAGGCCGAA AUCACAAG | 4556 |
| 39 | GGGAAACU A AGGCCCAG | 4363 | CUGGGCCU CUGAUGAGGCCGUUAGGCCGAA AGUUUCCC | 4557 |
| 70 | CGCAGACU A UCAAUCCC | 4364 | GGGAUUGA CUGAUGAGGCCGUUAGGCCGAA AGUCUGCG | 4558 |
| 72 | CAGACUAU C AAUCCCAG | 4365 | CUGGGAUU CUGAUGAGGCCGUUAGGCCGAA AUAGUCUG | 4559 |
| 76 | CUAUCAAU C CCAGUCUC | 4366 | GAGACUGG CUGAUGAGGCCGUUAGGCCGAA AUUGAUAG | 4560 |
| 82 | AUCCCAGU C UCUUCCCC | 4367 | GGGGAAGA CUGAUGAGGCCGUUAGGCCGAA ACUGGGAU | 4561 |
| 84 | CCCAGUCU C UUCCCCUC | 4368 | GAGGGGAA CUGAUGAGGCCGUUAGGCCGAA AGACUGGG | 4562 |
| 86 | CAGUCUCU U CCCCUCAC | 4369 | GUGAGGGG CUGAUGAGGCCGUUAGGCCGAA AGAGACUG | 4563 |
| 87 | AGUCUCUU C CCCUCACU | 4370 | AGUGAGGG CUGAUGAGGCCGUUAGGCCGAA AAGAGACU | 4564 |
| 92 | CUUCCCCU C ACUCCCUG | 4371 | CAGGGAGU CUGAUGAGGCCGUUAGGCCGAA AGGGGAAG | 4565 |
| 96 | CCCUCACU C CCUGUGAA | 4372 | UUCACAGG CUGAUGAGGCCGUUAGGCCGAA AGUGAGGG | 4566 |
| 108 | GUGAAGCU C UCCAGCAU | 4373 | AUGCUGGA CUGAUGAGGCCGUUAGGCCGAA AGCUUCAC | 4567 |
| 110 | GAAGCUCU C CAGCAUCA | 4374 | UGAUGCUG CUGAUGAGGCCGUUAGGCCGAA AGAGCUUC | 4568 |
| 117 | UCCAGCAU C AUCGAGGU | 4375 | ACCUCGAU CUGAUGAGGCCGUUAGGCCGAA AUGCUGGA | 4569 |
| 120 | AGCAUCAU C GAGGUCCC | 4376 | GGGACCUC CUGAUGAGGCCGUUAGGCCGAA AUGAUGCU | 4570 |
| 126 | AUCGAGGU C CAUCAGC | 4377 | GCUGAUGG CUGAUGAGGCCGUUAGGCCGAA ACCUCGAU | 4571 |
| 131 | GGUCCCAU C AGCCCUUG | 4378 | CAAGGGCU CUGAUGAGGCCGUUAGGCCGAA AUGGGACC | 4572 |
| 138 | UCAGCCCU U GCCCUGUU | 4379 | AACAGGGC CUGAUGAGGCCGUUAGGCCGAA AGGGCUGA | 4573 |
| 146 | UGCCCUGU U GGAUGAAU | 4380 | AUUCAUCC CUGAUGAGGCCGUUAGGCCGAA ACAGGGCA | 4574 |
| 155 | GGAUGAAU A GCACCUC | 4381 | GAGGUGCC CUGAUGAGGCCGUUAGGCCGAA AUUCAUCC | 4575 |
| 163 | AGGCACCU C UGGAAGAG | 4382 | CUCUUCCA CUGAUGAGGCCGUUAGGCCGAA AGGUGCCU | 4576 |
| 218 | CAGCAGAU C AGGACGUA | 4383 | UACGUCCU CUGAUGAGGCCGUUAGGCCGAA AUCUGCUG | 4577 |
| 226 | CAGGACGU A CUGGGCGA | 4384 | UCGCCCAG CUGAUGAGGCCGUUAGGCCGAA ACGUCCUG | 4578 |
| 240 | CGAAGAGU C UCCUCUGG | 4385 | CCAGAGGA CUGAUGAGGCCGUUAGGCCGAA ACUCUUCG | 4579 |
| 242 | AAGAGUCU C CUCUGGGG | 4386 | CCCCAGAG CUGAUGAGGCCGUUAGGCCGAA AGACUCUU | 4580 |
| 245 | AGUCUCCU C UGGGGAAG | 4387 | CUUCCCCA CUGAUGAGGCCGUUAGGCCGAA AGGAGACU | 4581 |
| 275 | ACCUGCCU U CAGAACAG | 4388 | CUGUUCUG CUGAUGAGGCCGUUAGGCCGAA AGGCAGGU | 4582 |
| 276 | CCUGCCUU C AGAACAGG | 4389 | CCUGUUCU CUGAUGAGGCCGUUAGGCCGAA AAGGCAGG | 4583 |
| 290 | AGGGCGCU C CUGAGACC | 4390 | GGUCUCAG CUGAUGAGGCCGUUAGGCCGAA AGCGCCCU | 4584 |
| 301 | GAGACCCU C CAGCGCUG | 4391 | CAGCGCUG CUGAUGAGGCCGUUAGGCCGAA AGGGUCUC | 4585 |
| 323 | AGGAGAAU A AGAGCUC | 4392 | GAGCUCUU CUGAUGAGGCCGUUAGGCCGAA AUUCUCCU | 4586 |
| 331 | CAAGAGCU C CGAGAUGC | 4393 | GCAUCUCG CUGAUGAGGCCGUUAGGCCGAA AGCUCUUG | 4587 |
| 343 | GAUGCCAU C CGGCAGAG | 4394 | CUCUGCCG CUGAUGAGGCCGUUAGGCCGAA AUGGCAUC | 4588 |
| 361 | AACCAGAU U CUGCGGGA | 4395 | UCCCGCAG CUGAUGAGGCCGUUAGGCCGAA AUCUGGUU | 4589 |
| 362 | ACCAGAUU C UGCGGGAG | 4396 | CUCCCGCA CUGAUGAGGCCGUUAGGCCGAA AAUCUGGU | 4590 |
| 385 | GAGGAGCU U CUGCAUUU | 4397 | AAAUGCAG CUGAUGAGGCCGUUAGGCCGAA AGCUCCUC | 4591 |
| 386 | AGGAGCUU C UGCAUUUC | 4398 | GAAAUGCA CUGAUGAGGCCGUUAGGCCGAA AAGCUCCU | 4592 |
| 392 | UUCUGCAU U UCCAAGCC | 4399 | GGCUUGGA CUGAUGAGGCCGUUAGGCCGAA AUGCAGAA | 4593 |
| 393 | UCUGCAUU U CCAAGCCA | 4400 | UGGCUUGG CUGAUGAGGCCGUUAGGCCGAA AAUGCAGA | 4594 |
| 394 | CUGCAUUU C CAAGCAG | 4401 | CUGGCUUG CUGAUGAGGCCGUUAGGCCGAA AAAUGCAG | 4595 |
| 423 | GAAGGAGU U CCUCAUGU | 4402 | ACAUGAGG CUGAUGAGGCCGUUAGGCCGAA ACUCCUUC | 4596 |
| 424 | AAGGAGUU C CUCAUGUG | 4403 | CACAUGAG CUGAUGAGGCCGUUAGGCCGAA AACUCCUU | 4597 |
| 427 | GAGUUCCU C AUGUGCAA | 4404 | UUGCACAU CUGAUGAGGCCGUUAGGCCGAA AGGAACUC | 4598 |
| 438 | GUGCAAGU U CCAGGAGG | 4405 | CCUCCUGG CUGAUGAGGCCGUUAGGCCGAA ACUUGCAC | 4599 |
| 439 | UGCAAGUU C CAGGAGGC | 4406 | GCCUCCUG CUGAUGAGGCCGUUAGGCCGAA AACUUGCA | 4600 |
| 469 | GAGAGACU C GGCUGGA | 4407 | UCCAGGCC CUGAUGAGGCCGUUAGGCCGAA AGUCUCUC | 4601 |
| 484 | GAGAACGU C GAUCUGAA | 4408 | UUCAGAUC CUGAUGAGGCCGUUAGGCCGAA AGUCUUCU | 4602 |
| 488 | AGCUCGAU C UGAAGAGG | 4409 | CCUCUUCA CUGAUGAGGCCGUUAGGCCGAA AUCGAGCU | 4603 |
| 512 | AGCAGGCU C UGCGGGAG | 4410 | CUCCCGCA CUGAUGAGGCCGUUAGGCCGAA AGCCUGCU | 4604 |
| 570 | CAAGGCCU C UGUGAAAG | 4411 | CUUUCACA CUGAUGAGGCCGUUAGGCCGAA AGGCCUUG | 4605 |
| 591 | GGUGACGU C CUUGCUCG | 4412 | CGAGCAAG CUGAUGAGGCCGUUAGGCCGAA ACGUCACC | 4606 |
| 594 | GACGUCCU U GCUCGGGG | 4413 | CCCCGAGC CUGAUGAGGCCGUUAGGCCGAA AGGACGUC | 4607 |

TABLE III-continued

Human IKK-gamma Hammerhead and Substrate Sequence

| Pos | Substrate | Seq ID | Hammerhead | Seq ID |
|---|---|---|---|---|
| 598 | UCCUUGCU C GGGGAGCU | 4414 | AGCUCCCC CUGAUGAGGCCGUUAGGCCGAA AGCAAGGA | 4608 |
| 623 | GCCAGAGU C GCUUGGAG | 4415 | CUCCAAGC CUGAUGAGGCCGUUAGGCCGAA ACUCUGGC | 4609 |
| 627 | GAGUCGCU U GGAGGCUG | 4416 | CAGCCUCC CUGAUGAGGCCGUUAGGCCGAA AGCGACUC | 4610 |
| 641 | CUGCCACU A AGGAAUGC | 4417 | GCAUUCCU CUGAUGAGGCCGUUAGGCCGAA AGUGGCAG | 4611 |
| 656 | GCCAGGCU C UGGAGGGU | 4418 | ACCCUCCA CUGAUGAGGCCGUUAGGCCGAA AGCCUGGC | 4612 |
| 665 | UGGAGGGU C GGGCCCGG | 4419 | CCGGGCCC CUGAUGAGGCCGUUAGGCCGAA ACCCUCCA | 4613 |
| 787 | GCCGCGCU C CGCAUGGA | 4420 | UCCAUGCG CUGAUGAGGCCGUUAGGCCGAA AGCGCGGC | 4614 |
| 810 | GGCCGCCU C GGAGGAGA | 4421 | UCUCCUCC CUGAUGAGGCCGUUAGGCCGAA AGGCGGCC | 4615 |
| 837 | GGCCCAGU U GCAGGUGG | 4422 | CCACCUGC CUGAUGAGGCCGUUAGGCCGAA ACUGGGCC | 4616 |
| 849 | GGUGGCCU A UCACCAGC | 4423 | GCUGGUGA CUGAUGAGGCCGUUAGGCCGAA AGGCCACC | 4617 |
| 851 | UGGCCUAU C ACCAGCUC | 4424 | GAGCUGGU CUGAUGAGGCCGUUAGGCCGAA AUAGGCCA | 4618 |
| 859 | CACCAGCU C UUCCAAGA | 4425 | UCUUGGAA CUGAUGAGGCCGUUAGGCCGAA AGCUGGUG | 4619 |
| 861 | CCAGCUCU U CCAAGAAU | 4426 | AUUCUUGG CUGAUGAGGCCGUUAGGCCGAA AGAGCUGG | 4620 |
| 862 | CAGCUCUU C CAAGAAUA | 4427 | UAUUCUUG CUGAUGAGGCCGUUAGGCCGAA AAGAGCUG | 4621 |
| 870 | CCAAGAAU A CGACAACC | 4428 | GGUUGUCG CUGAUGAGGCCGUUAGGCCGAA AUUCUUGG | 4622 |
| 883 | AACCACAU C AAGAGCAG | 4429 | CUGCUCUU CUGAUGAGGCCGUUAGGCCGAA AUGUGGUU | 4623 |
| 935 | UGGAAGAU C UCAAACAG | 4430 | CUGUUUGA CUGAUGAGGCCGUUAGGCCGAA AUCUUCCA | 4624 |
| 937 | GAAGAUCU C AAACAGCA | 4431 | UGCUGUUU CUGAUGAGGCCGUUAGGCCGAA AGAUCUUC | 4625 |
| 949 | CAGCAGCU C CAGCAGGC | 4432 | GCCUGCUG CUGAUGAGGCCGUUAGGCCGAA AGCUGCUG | 4626 |
| 991 | GAGGUGAU C GAUAAGCU | 4433 | AGCUUAUC CUGAUGAGGCCGUUAGGCCGAA AUCACCUC | 4627 |
| 995 | UGAUCGAU A AGCUGAAG | 4434 | CUUCAGCU CUGAUGAGGCCGUUAGGCCGAA AUCGAUCA | 4628 |
| 1027 | CACAAGAU U GUGAUGGA | 4435 | UCCAUCAC CUGAUGAGGCCGUUAGGCCGAA AUCUUGUG | 4629 |
| 1042 | GAGACCGU U CCGGUGCU | 4436 | AGCACCGG CUGAUGAGGCCGUUAGGCCGAA ACGGUCUC | 4630 |
| 1043 | AGACCGUU C CGGUGCUG | 4437 | CAGCACCG CUGAUGAGGCCGUUAGGCCGAA AACGGUCU | 4631 |
| 1067 | AGGCGGAU A UCUACAAG | 4438 | CUUGUAGA CUGAUGAGGCCGUUAGGCCGAA AUCCGCCU | 4632 |
| 1069 | GCGGAUAU C UACAAGGC | 4439 | GCCUUGUA CUGAUGAGGCCGUUAGGCCGAA AUAUCCGC | 4633 |
| 1071 | GGAUAUCU A CAAGGCGG | 4440 | CCGCCUUG CUGAUGAGGCCGUUAGGCCGAA AGAUAUCC | 4634 |
| 1083 | GGCGGACU U CCAGGCUG | 4441 | CAGCCUGG CUGAUGAGGCCGUUAGGCCGAA AGUCCGCC | 4635 |
| 1084 | GCGGACUU C CAGGCUGA | 4442 | UCAGCCUG CUGAUGAGGCCGUUAGGCCGAA AAGUCCGC | 4636 |
| 1132 | AAGGAGCU C CUGCAGGA | 4443 | UCCUGCAG CUGAUGAGGCCGUUAGGCCGAA AGCUCCUU | 4637 |
| 1167 | GAGGGAGU A CAGCAAAC | 4444 | GUUUGCUG CUGAUGAGGCCGUUAGGCCGAA ACUCCCUC | 4638 |
| 1190 | CCAGCUGU C AGGAGUCG | 4445 | CGACUCCU CUGAUGAGGCCGUUAGGCCGAA ACAGCUGG | 4639 |
| 1197 | UCAGGAGU C GGCCAGGA | 4446 | UCCUGGCC CUGAUGAGGCCGUUAGGCCGAA ACUCCUGA | 4640 |
| 1207 | GCCAGGAU C GAGGACAU | 4447 | AUGUCCUC CUGAUGAGGCCGUUAGGCCGAA AUCCUGGC | 4641 |
| 1231 | CGGCAUGU C GAGGUCUC | 4448 | GAGACCUC CUGAUGAGGCCGUUAGGCCGAA ACAUGCCG | 4642 |
| 1237 | GUCGAGGU C UCCCAGGC | 4449 | GCCUGGGA CUGAUGAGGCCGUUAGGCCGAA ACCUCGAC | 4643 |
| 1239 | CGAGGUCU C CCAGGCCC | 4450 | GGGCCUGG CUGAUGAGGCCGUUAGGCCGAA AGACCUCG | 4644 |
| 1251 | GGCCCCCU U GCCCCCCG | 4451 | CGGGGGGC CUGAUGAGGCCGUUAGGCCGAA AGGGGGCC | 4645 |
| 1269 | CCCUGCCU A CCUCUCCU | 4452 | AGGAGAGG CUGAUGAGGCCGUUAGGCCGAA AGGCAGGG | 4646 |
| 1273 | GCCUACCU C UCCUCUCC | 4453 | GGAGAGGA CUGAUGAGGCCGUUAGGCCGAA AGGUAGGC | 4647 |
| 1275 | CUACCUCU C CUCUCCCC | 4454 | GGGGAGAG CUGAUGAGGCCGUUAGGCCGAA AGAGGUAG | 4648 |
| 1278 | CCUCUCCU C UCCCCUGG | 4455 | CCAGGGGA CUGAUGAGGCCGUUAGGCCGAA AGGAGAGG | 4649 |
| 1280 | UCUCCUCU C CCCUGGCC | 4456 | GGCCAGGG CUGAUGAGGCCGUUAGGCCGAA AGAGGAGA | 4650 |
| 1332 | ACCUGACU C UGCUGUC | 4457 | GACAGCAG CUGAUGAGGCCGUUAGGCCGAA AGUCAGGU | 4651 |
| 1333 | CCUGACUU C UGCUGUCC | 4458 | GGACAGCA CUGAUGAGGCCGUUAGGCCGAA AAGUCAGG | 4652 |
| 1340 | UCUGCUGU C CAAGUGC | 4459 | GCACUUGG CUGAUGAGGCCGUUAGGCCGAA ACAGCAGA | 4653 |
| 1353 | GUGCCAGU A UCAGGCCC | 4460 | GGGCCUGA CUGAUGAGGCCGUUAGGCCGAA ACUGGCAC | 4654 |
| 1355 | GCCAGUAU C AGGCCCCU | 4461 | AGGGGCCU CUGAUGAGGCCGUUAGGCCGAA AUACUGGC | 4655 |
| 1367 | CCCCUGAU A UGGACACC | 4462 | GGUGUCCA CUGAUGAGGCCGUUAGGCCGAA AUCAGGGG | 4656 |
| 1384 | CUGCAGAU A CAUGUCAU | 4463 | AUGACAUG CUGAUGAGGCCGUUAGGCCGAA AUCUGCAG | 4657 |
| 1390 | AUACAUGU C AUGGAGUG | 4464 | CACUCCAU CUGAUGAGGCCGUUAGGCCGAA ACAUGUAU | 4658 |
| 1402 | GAGUGCAU U GAGUAGGG | 4465 | CCCUACUC CUGAUGAGGCCGUUAGGCCGAA AUGCACUC | 4659 |
| 1407 | CAUUGAGU A GGGCCGGC | 4466 | GCCGGCCC CUGAUGAGGCCGUUAGGCCGAA ACUCAAUG | 4660 |
| 1464 | CGUGCAGU C UGCGCUUU | 4467 | AAAGCGCA CUGAUGAGGCCGUUAGGCCGAA ACUGCACG | 4661 |
| 1471 | UCUGCGCU U UCCUCUCC | 4468 | GGAGAGGA CUGAUGAGGCCGUUAGGCCGAA AGCGCAGA | 4662 |
| 1472 | CUGCGCUU U CCUCUCCC | 4469 | GGGAGAGG CUGAUGAGGCCGUUAGGCCGAA AAGCGCAG | 4663 |
| 1473 | UGCGCUUU C CUCUCCCG | 4470 | CGGGAGAG CUGAUGAGGCCGUUAGGCCGAA AAAGCGCA | 4664 |
| 1476 | GCUUUCCU C UCCCGCCU | 4471 | AGGCGGGA CUGAUGAGGCCGUUAGGCCGAA AGGAAAGC | 4665 |
| 1478 | UUUCCUCU C CCGCCUGC | 4472 | GCAGGCGG CUGAUGAGGCCGUUAGGCCGAA AGAGGAAA | 4666 |
| 1489 | GCCUGCCU A GCCCAGGA | 4473 | UCCUGGGC CUGAUGAGGCCGUUAGGCCGAA AGGCAGGC | 4667 |
| 1565 | CGGCACCU U ACGCUUCA | 4474 | UGAAGCGU CUGAUGAGGCCGUUAGGCCGAA AGGUGCCG | 4668 |
| 1566 | GGCACCUU A CGCUUCAG | 4475 | CUGAAGCG CUGAUGAGGCCGUUAGGCCGAA AAGGUGCC | 4669 |
| 1571 | CUUACGCU U CAGCUGUU | 4476 | AACAGCUG CUGAUGAGGCCGUUAGGCCGAA AGCGUAAG | 4670 |
| 1572 | UUACGCUU C AGCUGUUG | 4477 | CAACAGCU CUGAUGAGGCCGUUAGGCCGAA AAGCGUAA | 4671 |
| 1579 | UCAGCUGU U GAUCCGCU | 4478 | AGCGGAUC CUGAUGAGGCCGUUAGGCCGAA ACAGCUGA | 4672 |
| 1583 | CUGUUGAU C CGCUGGUC | 4479 | GACCAGCG CUGAUGAGGCCGUUAGGCCGAA AUCAACAG | 4673 |
| 1591 | CCGCUGGU C CCCUCUUU | 4480 | AAAGAGGG CUGAUGAGGCCGUUAGGCCGAA ACCAGCGG | 4674 |
| 1596 | GGUCCCCU C UUUGGGG | 4481 | CCCCAAAA CUGAUGAGGCCGUUAGGCCGAA AGGGGACC | 4675 |
| 1598 | UCCCCUCU U UGGGGUA | 4482 | UACCCCAA CUGAUGAGGCCGUUAGGCCGAA AGAGGGGA | 4676 |
| 1599 | CCCCUCUU U UGGGGUAG | 4483 | CUACCCCA CUGAUGAGGCCGUUAGGCCGAA AAGAGGGG | 4677 |
| 1600 | CCCUCUUU U GGGGUAGA | 4484 | UCUACCCC CUGAUGAGGCCGUUAGGCCGAA AAAGAGGG | 4678 |
| 1606 | UUUGGGGU A GAUGCGGC | 4485 | GCCGCAUC CUGAUGAGGCCGUUAGGCCGAA ACCCCAAA | 4679 |
| 1621 | GCCCCGAU C AGGCCUGA | 4486 | UCAGGCCU CUGAUGAGGCCGUUAGGCCGAA AUCGGGGC | 4680 |
| 1632 | GCCUGACU C GCUGCUCU | 4487 | AGAGCAGC CUGAUGAGGCCGUUAGGCCGAA AGUCAGGC | 4681 |

TABLE III-continued

Human IKK-gamma Hammerhead and Substrate Sequence

| Pos | Substrate | Seq ID | Hammerhead | Seq ID |
|---|---|---|---|---|
| 1639 | UCGCUGCU C UUUUUGUU | 4488 | AACAAAAA CUGAUGAGGCCGUUAGGCCGAA AGCAGCGA | 4682 |
| 1641 | GCUGCUCU U UUUGUUCC | 4489 | GGAACAAA CUGAUGAGGCCGUUAGGCCGAA AGAGCAGC | 4683 |
| 1642 | CUGCUCUU U UUGUUCCC | 4490 | GGGAACAA CUGAUGAGGCCGUUAGGCCGAA AAGAGCAG | 4684 |
| 1643 | UGCUCUUU U UGUUCCCU | 4491 | AGGGAACA CUGAUGAGGCCGUUAGGCCGAA AAAAGCA | 4685 |
| 1644 | GCUCUUUU U GUUCCCUU | 4492 | AAGGGAAC CUGAUGAGGCCGUUAGGCCGAA AAAAGAGC | 4686 |
| 1647 | CUUUUUGU U CCCUUCUG | 4493 | CAGAAGGG CUGAUGAGGCCGUUAGGCCGAA ACAAAAAG | 4687 |
| 1648 | UUUUUGUU C CCUUCUGU | 4494 | ACAGAAGG CUGAUGAGGCCGUUAGGCCGAA AACAAAAA | 4688 |
| 1652 | UGUUCCCU U CUGUCUGC | 4495 | GCAGACAG CUGAUGAGGCCGUUAGGCCGAA AGGGAACA | 4689 |
| 1653 | GUUCCCUU C UGUCUGCU | 4496 | AGCAGACA CUGAUGAGGCCGUUAGGCCGAA AAGGGAAC | 4690 |
| 1657 | CCUUCUGU C UGCUCGAA | 4497 | UUCGAGCA CUGAUGAGGCCGUUAGGCCGAA ACAGAAGG | 4691 |
| 1662 | UGUCUGCU C GAACCACU | 4498 | AGUGGUUC CUGAUGAGGCCGUUAGGCCGAA AGCAGACA | 4692 |
| 1671 | GAACCACU U GCCUCGGG | 4499 | CCCGAGGC CUGAUGAGGCCGUUAGGCCGAA AGUGGUUC | 4693 |
| 1676 | ACUUGCCU C GGGCUAAU | 4500 | AUUAGCCC CUGAUGAGGCCGUUAGGCCGAA AGGCAAGU | 4694 |
| 1682 | CUCGGGCU A AUCCCUCC | 4501 | GGAGGGAU CUGAUGAGGCCGUUAGGCCGAA AGCCCGAG | 4695 |
| 1685 | GGGCUAAU C CCUCCCUC | 4502 | GAGGGAGG CUGAUGAGGCCGUUAGGCCGAA AUUAGCCC | 4696 |
| 1689 | UAAUCCCU C CCUCUUCC | 4503 | GGAAGAGG CUGAUGAGGCCGUUAGGCCGAA AGGGAUUA | 4697 |
| 1693 | CCCUCCCU C UUCCUCCA | 4504 | UGGAGGAA CUGAUGAGGCCGUUAGGCCGAA AGGGAGGG | 4698 |
| 1695 | CUCCCUCU U CCUCCACC | 4505 | GGUGGAGG CUGAUGAGGCCGUUAGGCCGAA AGAGGGAG | 4699 |
| 1696 | UCCCUCUU C CUCCACCC | 4506 | GGGUGGAG CUGAUGAGGCCGUUAGGCCGAA AAGAGGGA | 4700 |
| 1699 | CUCUUCCU C CACCCGGC | 4507 | GCCGGGUG CUGAUGAGGCCGUUAGGCCGAA AGGAAGAG | 4701 |
| 1719 | GGGGAAGU C AAGAAUGG | 4508 | CCAUUCUU CUGAUGAGGCCGUUAGGCCGAA ACUUCCCC | 4702 |
| 1739 | CUGGGCCU C UCAGGGAG | 4509 | CUCCCUGA CUGAUGAGGCCGUUAGGCCGAA AGCCCCAG | 4703 |
| 1741 | GGGCUCUC C AGGGAGAA | 4510 | UUCUCCCU CUGAUGAGGCCGUUAGGCCGAA AGAGCCCC | 4704 |
| 1755 | GAACUGCU U CCCCUGGC | 4511 | GCCAGGGG CUGAUGAGGCCGUUAGGCCGAA AGCAGUUC | 4705 |
| 1756 | AACUGCUU C CCCUGGCA | 4512 | UGCCAGGG CUGAUGAGGCCGUUAGGCCGAA AAGCAGUU | 4706 |
| 1781 | UGGCAGCU C UUCCUCCC | 4513 | GGGAGGAA CUGAUGAGGCCGUUAGGCCGAA AGCUGCCA | 4707 |
| 1783 | GCAGCUCU U CCUCCCAC | 4514 | GUGGGAGG CUGAUGAGGCCGUUAGGCCGAA AGAGCUGC | 4708 |
| 1784 | CAGCUCUU C CUCCCACC | 4515 | GGUGGGAG CUGAUGAGGCCGUUAGGCCGAA AAGAGCUG | 4709 |
| 1787 | CUCUUCCU C CACCGGA | 4516 | UCCGGUGG CUGAUGAGGCCGUUAGGCCGAA AGGAAGAG | 4710 |
| 1836 | GCUGCCCU C UUACCAUG | 4517 | CAUGGUAA CUGAUGAGGCCGUUAGGCCGAA AGGGCAGC | 4711 |
| 1838 | UGCCCUCU U ACCAUGCA | 4518 | UGCAUGGU CUGAUGAGGCCGUUAGGCCGAA AGAGGGCA | 4712 |
| 1839 | GCCCUCUU A CCAUGCAC | 4519 | GUGCAUGG CUGAUGAGGCCGUUAGGCCGAA AAGAGGGC | 4713 |
| 1857 | CGGGUGCU C UCCUUUUG | 4520 | CAAAAGGA CUGAUGAGGCCGUUAGGCCGAA AGCACCCG | 4714 |
| 1859 | GGUGCUCU C CUUUUGGG | 4521 | CCCAAAAG CUGAUGAGGCCGUUAGGCCGAA AGAGCACC | 4715 |
| 1862 | GCUCUCCU U UGGGCUG | 4522 | CAGCCCAA CUGAUGAGGCCGUUAGGCCGAA AGGAGAGC | 4716 |
| 1863 | CUCUCCUU U UGGGCUGC | 4523 | GCAGCCCA CUGAUGAGGCCGUUAGGCCGAA AAGGAGAG | 4717 |
| 1864 | UCUCCUUU U GGGCUGCA | 4524 | UGCAGCCC CUGAUGAGGCCGUUAGGCCGAA AAAGGAGA | 4718 |
| 1877 | UGCAUGCU A UUCCAUUU | 4525 | AAAUGGAA CUGAUGAGGCCGUUAGGCCGAA AGCAUGCA | 4719 |
| 1879 | CAUGCUAU U CCAUUUG | 4526 | CAAAAUGG CUGAUGAGGCCGUUAGGCCGAA AUAGCAUG | 4720 |
| 1880 | AUGCUAUU C CAUUUGC | 4527 | GCAAAAUG CUGAUGAGGCCGUUAGGCCGAA AAUAGCAU | 4721 |
| 1884 | UAUUCCAU U UUCCAGCC | 4528 | GGCUGCAA CUGAUGAGGCCGUUAGGCCGAA AUGGAAUA | 4722 |
| 1885 | AUUCCAUU U UGCAGCCA | 4529 | UGGCUGCA CUGAUGAGGCCGUUAGGCCGAA AAUGGAAU | 4723 |
| 1886 | UUCCAUUU U GCAGCCAG | 4530 | CUGGCUGC CUGAUGAGGCCGUUAGGCCGAA AAAUGGAA | 4724 |
| 1905 | CGAUGUGU A UUUAACCA | 4531 | UGGUUAAA CUGAUGAGGCCGUUAGGCCGAA ACACAUCG | 4725 |
| 1907 | AUGUGUAU U UAACCAGU | 4532 | ACUGGUUA CUGAUGAGGCCGUUAGGCCGAA AUACACAU | 4726 |
| 1908 | UGUGUAUU U AACCAGUC | 4533 | GACUGGUU CUGAUGAGGCCGUUAGGCCGAA AAUACACA | 4727 |
| 1909 | GUGUAUUU A ACCAGUCA | 4534 | UGACUGGU CUGAUGAGGCCGUUAGGCCGAA AAAUACAC | 4728 |
| 1916 | UAACCAGU C ACUAUUGA | 4535 | UCAAUAGU CUGAUGAGGCCGUUAGGCCGAA ACUGGUUA | 4729 |
| 1920 | CAGUCACU A UUGAUGGA | 4536 | UCCAUCAA CUGAUGAGGCCGUUAGGCCGAA AGUGACUG | 4730 |
| 1922 | GUCACUAU U GAUGGACA | 4537 | UGUCCAUC CUGAUGAGGCCGUUAGGCCGAA AUAGUGAC | 4731 |
| 1932 | AUGGACAU U UGGGUUGU | 4538 | ACAACCCA CUGAUGAGGCCGUUAGGCCGAA AUGUCCAU | 4732 |
| 1933 | UGGACAUU U GGGUUGUU | 4539 | AACAACCC CUGAUGAGGCCGUUAGGCCGAA AAUGUCCA | 4733 |
| 1938 | AUUUGGGU U GUUUCCCA | 4540 | UGGGAAAC CUGAUGAGGCCGUUAGGCCGAA ACCCAAAU | 4734 |
| 1941 | UGGGUUGU U UCCAUCU | 4541 | AGAUGGGA CUGAUGAGGCCGUUAGGCCGAA ACAACCCA | 4735 |
| 1942 | GGGUUGUU C CCAUCUU | 4542 | AAGAUGGG CUGAUGAGGCCGUUAGGCCGAA AACAACCC | 4736 |
| 1943 | GGUUGUUU C CAUCUUU | 4543 | AAAGAUGG CUGAUGAGGCCGUUAGGCCGAA AAACAACC | 4737 |
| 1948 | UUUCCCAU C UUUUGUU | 4544 | AACAAAAA CUGAUGAGGCCGUUAGGCCGAA AUGGGAAA | 4738 |
| 1950 | UCCCAUCU U UUUGUUAC | 4545 | GUAACAAA CUGAUGAGGCCGUUAGGCCGAA AGAUGGGA | 4739 |
| 1951 | CCCAUCUU U UUGUUACC | 4546 | GGUAACAA CUGAUGAGGCCGUUAGGCCGAA AAGAUGGG | 4740 |
| 1952 | CCAUCUUU U UGUUACCA | 4547 | UGGUAACA CUGAUGAGGCCGUUAGGCCGAA AAAGAUGG | 4741 |
| 1953 | CAUCUUUU U GUUACCAU | 4548 | AUGGUAAC CUGAUGAGGCCGUUAGGCCGAA AAAAGAUG | 4742 |
| 1956 | CUUUUUGU U ACCAUAAA | 4549 | UUUAUGGU CUGAUGAGGCCGUUAGGCCGAA ACAAAAAG | 4743 |
| 1957 | UUUUUGUU A CCAUAAAU | 4550 | AUUUAUGG CUGAUGAGGCCGUUAGGCCGAA AACAAAAA | 4744 |
| 1962 | GUUACCAU A AAUAAUGG | 4551 | CCAUUAUU CUGAUGAGGCCGUUAGGCCGAA AUGGUAAC | 4745 |
| 1966 | CCAUAAAU A AUGGCAUA | 4552 | UAUGCCAU CUGAUGAGGCCGUUAGGCCGAA AUUUAUGG | 4746 |
| 1974 | AAUGGCAU A GUAAAAAA | 4553 | UUUUUUAC CUGAUGAGGCCGUUAGGCCGAA AUGCCAUU | 4747 |
| 1977 | GGCAUAGU A AAAAAAAA | 4554 | UUUUUUUU CUGAUGAGGCCGUUAGGCCGAA ACUAUGCC | 4748 |

Input Sequence = NM_003639. Cut Site = UH/.
Arm Length = 8. Core Sequence = CUGAUGAG GCCGUUAGGC CGAA
NM_003639 (*Homo sapiens* inhibitor of kappa light polypeptide gene enhancer in B-cells, kinase gamma (IKBKG), mRNA.; 1994 bp)

Underlined region can be any X sequence or linker, as described herein.

TABLE IV

Human IKK-gamma Inozyme and Substrate Sequence

| Pos | Substrate | Seq ID | Inozyme | Seq ID |
|---|---|---|---|---|
| 10 | GCACGAGC A UGGCCCUU | 4749 | AAGGGCCA CUGAUGAGGCCGUUAGGCCGAA ICUCGUGC | 5253 |
| 15 | AGCAUGGC C CUUGUGAU | 4750 | AUCACAAG CUGAUGAGGCCGUUAGGCCGAA ICCAUGCU | 5254 |
| 16 | GCAUGGCC C UUGUGAUC | 4751 | GAUCACAA CUGAUGAGGCCGUUAGGCCGAA IGCCAUGC | 5255 |
| 17 | CAUGGCCC U UGUGAUCC | 4752 | GGAUCACA CUGAUGAGGCCGUUAGGCCGAA IGGCCAUG | 5256 |
| 25 | UUGUGAUC C AGGUGGGG | 4753 | CCCCACCU CUGAUGAGGCCGUUAGGCCGAA IAUCACAA | 5257 |
| 26 | UGUGAUCC A GGUGGGGA | 4754 | UCCCCACC CUGAUGAGGCCGUUAGGCCGAA IGAUCACA | 5258 |
| 38 | GGGGAAAC U AAGGCCCA | 4755 | UGGGCCUU CUGAUGAGGCCGUUAGGCCGAA IUUUCCCC | 5259 |
| 44 | ACUAAGGC C CAGAGAAG | 4756 | CUUCUCUG CUGAUGAGGCCGUUAGGCCGAA ICCUUAGU | 5260 |
| 45 | CUAAGGCC C AGAGAAGU | 4757 | ACUUCUCU CUGAUGAGGCCGUUAGGCCGAA IGCCUUAG | 5261 |
| 46 | UAAGGCCC A GAGAAGUG | 4758 | CACUUCUC CUGAUGAGGCCGUUAGGCCGAA IGGCCUUA | 5262 |
| 60 | GUGAGGAC C CCGCAGAC | 4759 | GUCUGCGG CUGAUGAGGCCGUUAGGCCGAA IUCCUCAC | 5263 |
| 61 | UGAGGACC C CGCAGACU | 4760 | AGUCUGCG CUGAUGAGGCCGUUAGGCCGAA IGUCCUCA | 5264 |
| 62 | GAGGACCC C GCAGACUA | 4761 | UAGUCUGC CUGAUGAGGCCGUUAGGCCGAA IGGUCCUC | 5265 |
| 65 | GACCCCGC A GACUAUCA | 4762 | UGAUAGUC CUGAUGAGGCCGUUAGGCCGAA ICGGGGUC | 5266 |
| 69 | CCGCAGAC U AUCAAUCC | 4763 | GGAUUGAU CUGAUGAGGCCGUUAGGCCGAA IUCUGCGG | 5267 |
| 73 | AGACUAUC A AUCCCAGU | 4764 | ACUGGGAU CUGAUGAGGCCGUUAGGCCGAA IAUAGUCU | 5268 |
| 77 | UAUCAAUC C CAGUCUCU | 4765 | AGAGACUG CUGAUGAGGCCGUUAGGCCGAA IAUUGAUA | 5269 |
| 78 | AUCAAUCC C AGUCUCUU | 4766 | AAGAGACU CUGAUGAGGCCGUUAGGCCGAA IGAUUGAU | 5270 |
| 79 | UCAAUCCC A GUCUCUUC | 4767 | GAAGAGAC CUGAUGAGGCCGUUAGGCCGAA IGGAUUGA | 5271 |
| 83 | UCCCAGUC U CUUCCCU | 4768 | AGGGGAAG CUGAUGAGGCCGUUAGGCCGAA IACUGGGA | 5272 |
| 85 | CCAGUCUC U UCCCCUCA | 4769 | UGAGGGGA CUGAUGAGGCCGUUAGGCCGAA IAGACUGG | 5273 |
| 88 | GUCUCUUC C CCUCACUC | 4770 | GAGUGAGG CUGAUGAGGCCGUUAGGCCGAA IAAGAGAC | 5274 |
| 89 | UCUCUUCC C CUCACUCC | 4771 | GGAGUGAG CUGAUGAGGCCGUUAGGCCGAA IGAAGAGA | 5275 |
| 90 | CUCUUCCC C UCACUCCC | 4772 | GGGAGUGA CUGAUGAGGCCGUUAGGCCGAA IGGAAGAG | 5276 |
| 91 | UCUUCCCC U CACUCCCU | 4773 | AGGGAGUG CUGAUGAGGCCGUUAGGCCGAA IGGGAAGA | 5277 |
| 93 | UUCCCCUC A CUCCCUGU | 4774 | ACAGGGAG CUGAUGAGGCCGUUAGGCCGAA IAGGGGAA | 5278 |
| 95 | CCCCUCAC U CCCUGUGA | 4775 | UCACAGGG CUGAUGAGGCCGUUAGGCCGAA IUGAGGGG | 5279 |
| 97 | CCUCACUC C CUGUGAAG | 4776 | CUUCACAG CUGAUGAGGCCGUUAGGCCGAA IAGUGAGG | 5280 |
| 98 | CUCACUCC C UGUGAAGC | 4777 | GCUUCACA CUGAUGAGGCCGUUAGGCCGAA IGAGUGAG | 5281 |
| 99 | UCACUCCC U GUGAAGCU | 4778 | AGCUUCAC CUGAUGAGGCCGUUAGGCCGAA IGGAGUGA | 5282 |
| 107 | UGUGAAGC U CUCCAGCA | 4779 | UGCUGGAG CUGAUGAGGCCGUUAGGCCGAA ICUUCACA | 5283 |
| 109 | UGAAGCUC U CCAGCAUC | 4780 | GAUGCUGG CUGAUGAGGCCGUUAGGCCGAA IAGCUUCA | 5284 |
| 111 | AAGCUCUC C AGCAUCAU | 4781 | AUGAUGCU CUGAUGAGGCCGUUAGGCCGAA IAGAGCUU | 5285 |
| 112 | AGCUCUCC A GCAUCAUC | 4782 | GAUGAUGC CUGAUGAGGCCGUUAGGCCGAA IGAGAGCU | 5286 |
| 115 | UCUCCAGC A UCAUCGAG | 4783 | CUCGAUGA CUGAUGAGGCCGUUAGGCCGAA ICUGGAGA | 5287 |
| 118 | CCAGCAUC A UCGAGGUC | 4784 | GACCUCGA CUGAUGAGGCCGUUAGGCCGAA IAUGCUGG | 5288 |
| 127 | UCGAGGUC C CAUCAGCC | 4785 | GGCUGAUG CUGAUGAGGCCGUUAGGCCGAA IACCUCGA | 5289 |
| 128 | CGAGGUCC C AUCAGCCC | 4786 | GGGCUGAU CUGAUGAGGCCGUUAGGCCGAA IGACCUCG | 5290 |
| 129 | GAGGUCCC A UCAGCCCU | 4787 | AGGGCUGA CUGAUGAGGCCGUUAGGCCGAA IGGACCUC | 5291 |
| 132 | GUCCCAUC A GCCCUUGC | 4788 | GCAAGGGC CUGAUGAGGCCGUUAGGCCGAA IAUGGGAC | 5292 |
| 135 | CCAUCAGC C CUUGCCCU | 4789 | AGGGCAAG CUGAUGAGGCCGUUAGGCCGAA ICUGAUGG | 5293 |
| 136 | CAUCAGCC C UUGCCCUG | 4790 | CAGGGCAA CUGAUGAGGCCGUUAGGCCGAA IGCUGAUG | 5294 |
| 137 | AUCAGCCC U UGCCCUGU | 4791 | ACAGGGCA CUGAUGAGGCCGUUAGGCCGAA IGGCUGAU | 5295 |
| 141 | GCCCUUGC C CUGUUGGA | 4792 | UCCAACAG CUGAUGAGGCCGUUAGGCCGAA ICAAGGGC | 5296 |
| 142 | CCCUUGCC C UGUUGGAU | 4793 | AUCCAACA CUGAUGAGGCCGUUAGGCCGAA IGCAAGGG | 5297 |
| 143 | CCUUGCCC U GUUGGAUG | 4794 | CAUCCAAC CUGAUGAGGCCGUUAGGCCGAA IGGCAAGG | 5298 |
| 159 | GAAUAGGC A CCUCUGGA | 4795 | UCCAGAGG CUGAUGAGGCCGUUAGGCCGAA ICCUAUUC | 5299 |
| 161 | AUAGGCAC C UCUGGAAG | 4796 | CUUCCAGA CUGAUGAGGCCGUUAGGCCGAA IUGCCUAU | 5300 |
| 162 | UAGGCACC U CUGGAAGA | 4797 | UCUUCCAG CUGAUGAGGCCGUUAGGCCGAA IGUGCCUA | 5301 |
| 164 | GGCACCUC U GGAAGAGC | 4798 | GCUCUUCC CUGAUGAGGCCGUUAGGCCGAA IAGGUGCC | 5302 |
| 173 | GGAAGAGC C AACUGUGU | 4799 | ACACAGUU CUGAUGAGGCCGUUAGGCCGAA ICUCUUCC | 5303 |
| 174 | GAAGAGCC A ACUGUGUG | 4800 | CACACAGU CUGAUGAGGCCGUUAGGCCGAA IGCUCUUC | 5304 |
| 177 | GAGCCAAC U GUGUGAGA | 4801 | UCUCACAC CUGAUGAGGCCGUUAGGCCGAA IUUGGCUC | 5305 |
| 192 | GAUGGUGC A GCCCAGUG | 4802 | CACUGGGC CUGAUGAGGCCGUUAGGCCGAA ICACCAUC | 5306 |
| 195 | GGUGCAGC C CAGUGGUG | 4803 | CACCACUG CUGAUGAGGCCGUUAGGCCGAA ICUGCACC | 5307 |
| 196 | GUGCAGCC C AGUGGUGG | 4804 | CCACCACU CUGAUGAGGCCGUUAGGCCGAA IGCUGCAC | 5308 |
| 197 | UGCAGCCC A GUGGUGGC | 4805 | GCCACCAC CUGAUGAGGCCGUUAGGCCGAA IGGCUGCA | 5309 |
| 206 | GUGGUGGC C CGGCAGCA | 4806 | UGCUGCCG CUGAUGAGGCCGUUAGGCCGAA ICCACCAC | 5310 |
| 207 | UGGUGGCC C GGCAGCAG | 4807 | CUGCUGCC CUGAUGAGGCCGUUAGGCCGAA IGCCACCA | 5311 |
| 211 | GGCCCGGC A GCAGAUCA | 4808 | UGAUCUGC CUGAUGAGGCCGUUAGGCCGAA ICCGGGCC | 5312 |
| 214 | CCGGCAGC A GAUCAGGA | 4809 | UCCUGAUC CUGAUGAGGCCGUUAGGCCGAA ICUGCCGG | 5313 |
| 219 | AGCAGAUC A GGACGUAC | 4810 | GUACGUCC CUGAUGAGGCCGUUAGGCCGAA IAUCUGCU | 5314 |
| 228 | GGACGUAC U GGGCGAAG | 4811 | CUUCGCCC CUGAUGAGGCCGUUAGGCCGAA IUACGUCC | 5315 |
| 241 | GAAGAGUC U CCUCUGGG | 4812 | CCCAGAGG CUGAUGAGGCCGUUAGGCCGAA IACUCUUC | 5316 |
| 243 | AGAGUCUC C UCUGGGGA | 4813 | UCCCCAGA CUGAUGAGGCCGUUAGGCCGAA IAGACUCU | 5317 |
| 244 | GAGUCUCC U CUGGGGAA | 4814 | UUCCCCAG CUGAUGAGGCCGUUAGGCCGAA IGAGACUC | 5318 |
| 246 | GUCUCCUC U GGGGAAGC | 4815 | GCUUCCCC CUGAUGAGGCCGUUAGGCCGAA IAGGAGAC | 5319 |
| 255 | GGGGAAGC C AGCCAUGC | 4816 | GCAUGGCU CUGAUGAGGCCGUUAGGCCGAA ICUUCCCC | 5320 |
| 256 | GGGAAGCC A GCCAUGCU | 4817 | AGCAUGGC CUGAUGAGGCCGUUAGGCCGAA IGCUUCCC | 5321 |
| 259 | AAGCCAGC C AUGCUGCA | 4818 | UGCAGCAU CUGAUGAGGCCGUUAGGCCGAA ICUGGCUU | 5322 |

TABLE IV-continued

Human IKK-gamma Inozyme and Substrate Sequence

| Pos | Substrate | Seq ID | Inozyme | Seq ID |
|---|---|---|---|---|
| 260 | AGCCAGCC A UGCUGCAC | 4819 | GUGCAGCA CUGAUGAGGCCGUUAGGCCGAA IGCUGGCU | 5323 |
| 264 | AGCCAUGC U GCACCUGC | 4820 | GCAGGUGC CUGAUGAGGCCGUUAGGCCGAA ICAUGGCU | 5324 |
| 267 | CAUGCUGC A CCUGCCUU | 4821 | AAGGCAGG CUGAUGAGGCCGUUAGGCCGAA ICAGCAUG | 5325 |
| 269 | UGCUGCAC C UGCCUUCA | 4822 | UGAAGGCA CUGAUGAGGCCGUUAGGCCGAA IUGCAGCA | 5326 |
| 270 | GCUGCACC U GCCUUCAG | 4823 | CUGAAGGC CUGAUGAGGCCGUUAGGCCGAA IGUGCAGC | 5327 |
| 273 | GCACCUGC C UUCAGAAC | 4824 | GUUCUGAA CUGAUGAGGCCGUUAGGCCGAA ICAGGUGC | 5328 |
| 274 | CACCUGCC U UCAGAACA | 4825 | UGUUCUGA CUGAUGAGGCCGUUAGGCCGAA IGCAGGUG | 5329 |
| 277 | CUGCCUUC A GAACAGGG | 4826 | CCCUGUUC CUGAUGAGGCCGUUAGGCCGAA IAAGGCAG | 5330 |
| 282 | UUCAGAAC A GGGCGCUC | 4827 | GAGCGCCC CUGAUGAGGCCGUUAGGCCGAA IUUCUGAA | 5331 |
| 289 | CAGGGCGC U CCUGAGAC | 4828 | GUCUCAGG CUGAUGAGGCCGUUAGGCCGAA ICGCCCUG | 5332 |
| 291 | GGGCGCUC C UGAGACCC | 4829 | GGGUCUCA CUGAUGAGGCCGUUAGGCCGAA IAGCGCCC | 5333 |
| 292 | GGCGCUCC U GAGACCCU | 4830 | AGGGUCUC CUGAUGAGGCCGUUAGGCCGAA IGAGCGCC | 5334 |
| 298 | CCUGAGAC C UCCAGCG | 4831 | CGCUGGAG CUGAUGAGGCCGUUAGGCCGAA IUCUCAGG | 5335 |
| 299 | CUGAGACC C UCCAGCGC | 4832 | GCGCUGGA CUGAUGAGGCCGUUAGGCCGAA IGUCUCAG | 5336 |
| 300 | UGAGACCC U CCAGCGCU | 4833 | AGCGCUGG CUGAUGAGGCCGUUAGGCCGAA IGGUCUCA | 5337 |
| 302 | AGACCCUC C AGCGCUGC | 4834 | GCAGCGCU CUGAUGAGGCCGUUAGGCCGAA IAGGGUCU | 5338 |
| 303 | GACCCUCC A GCGCUGCC | 4835 | GGCAGCGC CUGAUGAGGCCGUUAGGCCGAA IGAGGGUC | 5339 |
| 308 | UCCAGCGC U GCCUGGAG | 4836 | CUCCAGGC CUGAUGAGGCCGUUAGGCCGAA ICGCUGGA | 5340 |
| 311 | AGCGCUGC C UGGAGGAG | 4837 | CUCCUCCA CUGAUGAGGCCGUUAGGCCGAA ICAGCGCU | 5341 |
| 312 | GCGCUGCC U GGAGGAGA | 4838 | UCUCCUCC CUGAUGAGGCCGUUAGGCCGAA IGCAGCGC | 5342 |
| 324 | GGAGAAUC A AGAGCUCC | 4839 | GGAGCUCU CUGAUGAGGCCGUUAGGCCGAA IAUUCUCC | 5343 |
| 330 | UCAAGAGC U CCGAGAUG | 4840 | CAUCUCGG CUGAUGAGGCCGUUAGGCCGAA ICUCUUGA | 5344 |
| 332 | AAGAGCUC C GAGAUGCC | 4841 | GGCAUCUC CUGAUGAGGCCGUUAGGCCGAA IAGCUCUU | 5345 |
| 340 | CGAGAUGC C AUCCGGCA | 4842 | UGCCGGAU CUGAUGAGGCCGUUAGGCCGAA ICAUCUCG | 5346 |
| 341 | GAGAUGCC A UCCGGCAG | 4843 | CUGCCGGA CUGAUGAGGCCGUUAGGCCGAA IGCAUCUC | 5347 |
| 344 | AUGCCAUC C GGCAGAGC | 4844 | GCUCUGCC CUGAUGAGGCCGUUAGGCCGAA IAUGGCAU | 5348 |
| 348 | CAUCCGGC A GAGCAACC | 4845 | GGUUGCUC CUGAUGAGGCCGUUAGGCCGAA ICCGGAUG | 5349 |
| 353 | GGCAGAGC A ACCAGAUU | 4846 | AAUCUGGU CUGAUGAGGCCGUUAGGCCGAA ICUCUGCC | 5350 |
| 356 | AGAGCAAC C AGAUUCUG | 4847 | CAGAAUCU CUGAUGAGGCCGUUAGGCCGAA IUUGCUCU | 5351 |
| 357 | GAGCAACC A GAUUCUGC | 4848 | GCAGAAUC CUGAUGAGGCCGUUAGGCCGAA IGUUGCUC | 5352 |
| 363 | CCAGAUUC U GCGGGAGC | 4849 | GCUCCCGC CUGAUGAGGCCGUUAGGCCGAA IAAUCUGG | 5353 |
| 374 | GGGAGCGC U GCGAGGAG | 4850 | CUCCUCGC CUGAUGAGGCCGUUAGGCCGAA ICGCUCCC | 5354 |
| 384 | CGAGGAGC U UCUGCAUU | 4851 | AAUGCAGA CUGAUGAGGCCGUUAGGCCGAA ICUCCUCG | 5355 |
| 387 | GGAGCUUC U GCAUUCC | 4852 | GGAAAUGC CUGAUGAGGCCGUUAGGCCGAA IAAGCUCC | 5356 |
| 390 | GCUUCUGC A UUUCCAAG | 4853 | CUUGGAAA CUGAUGAGGCCGUUAGGCCGAA ICAGAAGC | 5357 |
| 395 | UGCAUUUC C AAGCCAGC | 4854 | GCUGGCUU CUGAUGAGGCCGUUAGGCCGAA IAAAUGCA | 5358 |
| 396 | GCAUUUCC A AGCCAGCC | 4855 | GGCUGGCU CUGAUGAGGCCGUUAGGCCGAA IGAAAUGC | 5359 |
| 400 | UUCCAAGC C AGCCAGAG | 4856 | CUCUGGCU CUGAUGAGGCCGUUAGGCCGAA ICUUGGAA | 5360 |
| 401 | UCCAAGCC A GCCAGAGG | 4857 | CCUCUGGC CUGAUGAGGCCGUUAGGCCGAA IGCUUGGA | 5361 |
| 404 | AAGCCAGC C AGAGGGAG | 4858 | CUCCCUCU CUGAUGAGGCCGUUAGGCCGAA ICUGGCUU | 5362 |
| 405 | AGCCAGCC A GAGGGAGG | 4859 | CCUCCCUC CUGAUGAGGCCGUUAGGCCGAA IGCUGGCU | 5363 |
| 425 | AGGAGUUC C UCAUGUGC | 4860 | GCACAUGA CUGAUGAGGCCGUUAGGCCGAA IAACUCCU | 5364 |
| 426 | GGAGUUCC U CAUGUGCA | 4861 | UGCACAUG CUGAUGAGGCCGUUAGGCCGAA IGAACUCC | 5365 |
| 428 | AGUUCCUC A UGUGCAAG | 4862 | CUUGCACA CUGAUGAGGCCGUUAGGCCGAA IAGGAACU | 5366 |
| 434 | UCAUGUGC A AGUUCCAG | 4863 | CUGGAACU CUGAUGAGGCCGUUAGGCCGAA ICACAUGA | 5367 |
| 440 | GCAAGUUC C AGGAGGCC | 4864 | GGCCUCCU CUGAUGAGGCCGUUAGGCCGAA IAACUUGC | 5368 |
| 441 | CAAGUUCC A GGAGGCCA | 4865 | UGGCCUCC CUGAUGAGGCCGUUAGGCCGAA IGAACUUG | 5369 |
| 448 | CAGGAGGC C AGGAAACU | 4866 | AGUUUCCU CUGAUGAGGCCGUUAGGCCGAA ICCUCCUG | 5370 |
| 449 | AGGAGGCC A GGAAACUG | 4867 | CAGUUUCC CUGAUGAGGCCGUUAGGCCGAA IGCCUCCU | 5371 |
| 456 | CAGGAAAC U GGUGGAGA | 4868 | UCUCCACC CUGAUGAGGCCGUUAGGCCGAA IUUUCCUG | 5372 |
| 468 | GGAGAGAC U CGGCCUGG | 4869 | CCAGGCCG CUGAUGAGGCCGUUAGGCCGAA IUCUCUCC | 5373 |
| 473 | GACUCGGC C UGGAGAAG | 4870 | CUUCUCCA CUGAUGAGGCCGUUAGGCCGAA ICCGAGUC | 5374 |
| 474 | ACUCGGCC U GGAGAAGC | 4871 | GCUUCUCC CUGAUGAGGCCGUUAGGCCGAA IGCCGAGU | 5375 |
| 483 | GGAGAAGC U CGAUCUGA | 4872 | UCAGAUCG CUGAUGAGGCCGUUAGGCCGAA ICUUCUCC | 5376 |
| 489 | GCUCGAUC U GAAGAGGC | 4873 | GCCUCUUC CUGAUGAGGCCGUUAGGCCGAA IAUCGAGC | 5377 |
| 498 | GAAGAGGC A GAAGGAGC | 4874 | GCUCCUUC CUGAUGAGGCCGUUAGGCCGAA ICCUCUUC | 5378 |
| 507 | GAAGGAGC A GGCUCUGC | 4875 | GCAGAGCC CUGAUGAGGCCGUUAGGCCGAA ICUCCUUC | 5379 |
| 511 | GAGCAGGC U CUGCGGGA | 4876 | UCCCGCAG CUGAUGAGGCCGUUAGGCCGAA ICCUGCUC | 5380 |
| 513 | GCAGGCUC U GCGGGAGG | 4877 | CCUCCCGC CUGAUGAGGCCGUUAGGCCGAA IAGCCUGC | 5381 |
| 528 | GGUGGAGC A CCUGAAGA | 4878 | UCUUCAGG CUGAUGAGGCCGUUAGGCCGAA ICUCCACC | 5382 |
| 530 | UGGAGCAC C UGAAGAGA | 4879 | UCUCUUCA CUGAUGAGGCCGUUAGGCCGAA IUGCUCCA | 5383 |
| 531 | GGAGCACC U GAAGAGAU | 4880 | AUCUCUUC CUGAUGAGGCCGUUAGGCCGAA IGUGCUCC | 5384 |
| 542 | AGAGAUGC C AGCAGCAG | 4881 | CUGCUGCU CUGAUGAGGCCGUUAGGCCGAA ICAUCUCU | 5385 |
| 543 | GAGAUGCC A GCAGCAGA | 4882 | UCUGCUGC CUGAUGAGGCCGUUAGGCCGAA IGCAUCUC | 5386 |
| 546 | AUGCCAGC A GCAGAUGG | 4883 | CCAUCUGC CUGAUGAGGCCGUUAGGCCGAA ICUGGCAU | 5387 |
| 549 | CCAGCAGC A GAUGGCUG | 4884 | CAGCCAUC CUGAUGAGGCCGUUAGGCCGAA ICUGCUGG | 5388 |
| 556 | CAGAUGGC U GAGGACAA | 4885 | UUGUCCUC CUGAUGAGGCCGUUAGGCCGAA ICCAUCUG | 5389 |
| 563 | CUGAGGAC A AGGCCUCU | 4886 | AGAGGCCU CUGAUGAGGCCGUUAGGCCGAA IUCCUCAG | 5390 |
| 568 | GACAAGGC C UCUGUGAA | 4887 | UUCACAGA CUGAUGAGGCCGUUAGGCCGAA ICCUUGUC | 5391 |
| 569 | ACAAGGCC U CUGUGAAA | 4888 | UUUCACAG CUGAUGAGGCCGUUAGGCCGAA IGCCUUGU | 5392 |
| 571 | AAGGCCUC U GUGAAAGC | 4889 | GCUUUCAC CUGAUGAGGCCGUUAGGCCGAA IAGGCCUU | 5393 |
| 580 | GUGAAAGC C CAGGUGAC | 4890 | GUCACCUG CUGAUGAGGCCGUUAGGCCGAA ICUUUCAC | 5394 |
| 581 | UGAAAGCC C AGGUGACG | 4891 | CGUCACCU CUGAUGAGGCCGUUAGGCCGAA IGCUUUCA | 5395 |
| 582 | GAAAGCCC A GGUGACGU | 4892 | ACGUCACC CUGAUGAGGCCGUUAGGCCGAA IGGCUUUC | 5396 |

TABLE IV-continued

Human IKK-gamma Inozyme and Substrate Sequence

| Pos | Substrate | Seq ID | Inozyme | Seq ID |
|---|---|---|---|---|
| 592 | GUGACGUC C UUGCUCGG | 4893 | CCGAGCAA CUGAUGAGGCCGUUAGGCCGAA IACGUCAC | 5397 |
| 593 | UGACGUCC U UGCUCGGG | 4894 | CCCGAGCA CUGAUGAGGCCGUUAGGCCGAA IGACGUCA | 5398 |
| 597 | GUCCUUGC U CGGGGAGC | 4895 | GCUCCCCG CUGAUGAGGCCGUUAGGCCGAA ICAAGGAC | 5399 |
| 606 | CGGGGAGC U GCAGGAGA | 4896 | UCUCCUGC CUGAUGAGGCCGUUAGGCCGAA ICUCCCCG | 5400 |
| 609 | GGAGCUGC A GGAGAGCC | 4897 | GGCUCUCC CUGAUGAGGCCGUUAGGCCGAA ICAGCUCC | 5401 |
| 617 | AGGAGAGC C AGAGUCGC | 4898 | GCGACUCU CUGAUGAGGCCGUUAGGCCGAA ICUCUCCU | 5402 |
| 618 | GGAGAGCC A GAGUCGCU | 4899 | AGCGACUC CUGAUGAGGCCGUUAGGCCGAA IGCUCUCC | 5403 |
| 626 | AGAGUCGC U UGGAGGCU | 4900 | AGCCUCCA CUGAUGAGGCCGUUAGGCCGAA ICGACUCU | 5404 |
| 634 | UUGGAGGC U GCCACUAA | 4901 | UUAGUGGC CUGAUGAGGCCGUUAGGCCGAA ICCUCCAA | 5405 |
| 637 | GAGGCUGC C ACUAAGGA | 4902 | UCCUUAGU CUGAUGAGGCCGUUAGGCCGAA ICAGCCUC | 5406 |
| 638 | AGGCUGCC A CUAAGGAA | 4903 | UUCCUUAG CUGAUGAGGCCGUUAGGCCGAA IGCAGCCU | 5407 |
| 640 | GCUGCCAC U AAGGAAUG | 4904 | CAUUCCUU CUGAUGAGGCCGUUAGGCCGAA IUGGCAGC | 5408 |
| 650 | AGGAAUGC C AGGCUCUG | 4905 | CAGAGCCU CUGAUGAGGCCGUUAGGCCGAA ICAUUCCU | 5409 |
| 651 | GGAAUCCC A GGCUCUGG | 4906 | CCAGAGCC CUGAUGAGGCCGUUAGGCCGAA IGCAUUCC | 5410 |
| 655 | UGCCAGGC U CGGAGGGG | 4907 | CCCUCCAG CUGAUGAGGCCGUUAGGCCGAA ICCUGGCA | 5411 |
| 657 | CCAGGCUC U GGAGGGUC | 4908 | GACCCUCC CUGAUGAGGCCGUUAGGCCGAA IAGCCUGG | 5412 |
| 670 | GGUCGGGC C CGGGCGGC | 4909 | GCCGCCCG CUGAUGAGGCCGUUAGGCCGAA ICCCGACC | 5413 |
| 671 | GUCGGGCC C GGGCGGCC | 4910 | GGCCGCCC CUGAUGAGGCCGUUAGGCCGAA IGCCCGAC | 5414 |
| 679 | CGGGCGGC C AGCGAGCA | 4911 | UGCUCGCU CUGAUGAGGCCGUUAGGCCGAA ICCGCCCG | 5415 |
| 680 | GGGCGGCC A GCGAGCAG | 4912 | CUGCUCGC CUGAUGAGGCCGUUAGGCCGAA IGCCGCCC | 5416 |
| 687 | CAGCGAGC A GGCGCGGC | 4913 | GCCGCGCC CUGAUGAGGCCGUUAGGCCGAA ICUCGCUG | 5417 |
| 696 | GGCGCGGC A GCUGGAGA | 4914 | UCUCCAGC CUGAUGAGGCCGUUAGGCCGAA ICCGCGCC | 5418 |
| 699 | GCGGCAGC U GGAGAGUG | 4915 | CACUCUCC CUGAUGAGGCCGUUAGGCCGAA ICUGCCGC | 5419 |
| 720 | CGAGGCGC U GCAGCAGC | 4916 | GCUGCUGC CUGAUGAGGCCGUUAGGCCGAA ICGCCUCG | 5420 |
| 723 | GGCGCUGC A GCAGCAGC | 4917 | GCUGCUGC CUGAUGAGGCCGUUAGGCCGAA ICAGCGCC | 5421 |
| 726 | GCUGCAGC A GCAGCACA | 4918 | UGUGCUGC CUGAUGAGGCCGUUAGGCCGAA ICUGCAGC | 5422 |
| 729 | GCAGCAGC A GCACAGCG | 4919 | CGCUGUGC CUGAUGAGGCCGUUAGGCCGAA ICUGCUGC | 5423 |
| 732 | GCAGCAGC A CAGCGUGC | 4920 | GCACGCUG CUGAUGAGGCCGUUAGGCCGAA ICUGCUGC | 5424 |
| 734 | AGCAGCAC A GCGUGCAG | 4921 | CUGCACGC CUGAUGAGGCCGUUAGGCCGAA IUGCUGCU | 5425 |
| 741 | CAGCGUGC A GGUGGACC | 4922 | GGUCCACC CUGAUGAGGCCGUUAGGCCGAA ICACGCUG | 5426 |
| 749 | AGGUGGAC C AGCUGCGC | 4923 | GCGCAGCU CUGAUGAGGCCGUUAGGCCGAA ICCACCU | 5427 |
| 750 | GGUGGACC A GCUGCGCA | 4924 | UGCGCAGC CUGAUGAGGCCGUUAGGCCGAA IGUCCACC | 5428 |
| 753 | GGACCAGC U GCGCAUGC | 4925 | GCAUGCGC CUGAUGAGGCCGUUAGGCCGAA ICUGGUCC | 5429 |
| 758 | AGCUGCGC A UGCAGGGC | 4926 | GCCCUGCA CUGAUGAGGCCGUUAGGCCGAA ICGCAGCU | 5430 |
| 762 | GCGCAUGC A GGGCCAGA | 4927 | UCUGGCCC CUGAUGAGGCCGUUAGGCCGAA ICAUGCGC | 5431 |
| 767 | UGCAGGGC C AGAGCGUG | 4928 | CACGCUCU CUGAUGAGGCCGUUAGGCCGAA ICCCUGCA | 5432 |
| 768 | GCAGGGCC A GAGCGUGG | 4929 | CCACGCUC CUGAUGAGGCCGUUAGGCCGAA IGCCCUGC | 5433 |
| 781 | GUGGAGGC C GCGCUCCG | 4930 | CGGAGCGC CUGAUGAGGCCGUUAGGCCGAA ICCUCCAC | 5434 |
| 786 | GGCCGCGC U CCGCAUGG | 4931 | CCAUGCGG CUGAUGAGGCCGUUAGGCCGAA ICGCGGCC | 5435 |
| 788 | CCGCGCUC C GCAUGGAG | 4932 | CUCCAUGC CUGAUGAGGCCGUUAGGCCGAA IAGCGCGG | 5436 |
| 791 | CGCUCCGC A UGGAGCGC | 4933 | GCGCUCCA CUGAUGAGGCCGUUAGGCCGAA ICGGAGCG | 5437 |
| 800 | UGGAGCGC C AGGCCGCC | 4934 | GGCGGCCU CUGAUGAGGCCGUUAGGCCGAA ICGCUCCA | 5438 |
| 801 | GGAGCGCC A GGCCGCCU | 4935 | AGGCGGCC CUGAUGAGGCCGUUAGGCCGAA IGCGCUCC | 5439 |
| 805 | CGCCAGGC C GCCUCGGA | 4936 | UCCGAGGC CUGAUGAGGCCGUUAGGCCGAA ICCUGGCG | 5440 |
| 808 | CAGGCCGC C UCGGAGGA | 4937 | UCCUCCGA CUGAUGAGGCCGUUAGGCCGAA ICGGCCUG | 5441 |
| 809 | AGGCCGCC U CGGAGGAG | 4938 | CUCCUCCG CUGAUGAGGCCGUUAGGCCGAA IGCGGCCU | 5442 |
| 828 | GAGGAAGC U GGCCCAGU | 4939 | ACUGGGCC CUGAUGAGGCCGUUAGGCCGAA ICUUCCUC | 5443 |
| 832 | AAGCUGGC C CAGUUGCA | 4940 | UGCAACUG CUGAUGAGGCCGUUAGGCCGAA ICCAGCUU | 5444 |
| 833 | AGCUGGCC C AGUUGCAG | 4941 | CUGCAACU CUGAUGAGGCCGUUAGGCCGAA IGCCAGCU | 5445 |
| 834 | GCUGGCCC A GUUGCAGG | 4942 | CCUGCAAC CUGAUGAGGCCGUUAGGCCGAA IGGCCAGC | 5446 |
| 840 | CCAGUUGC A GGUGGCCU | 4943 | AGGCCACC CUGAUGAGGCCGUUAGGCCGAA ICAACUGG | 5447 |
| 847 | CAGGUGGC C UAUCACCA | 4944 | UGGUGAUA CUGAUGAGGCCGUUAGGCCGAA ICCACCUG | 5448 |
| 848 | AGGUGGCC U AUCACCAG | 4945 | CUGGUGAU CUGAUGAGGCCGUUAGGCCGAA IGCCACCU | 5449 |
| 852 | GGCCUAUC A CCAGCUCU | 4946 | AGAGCUGG CUGAUGAGGCCGUUAGGCCGAA IAUAGGCC | 5450 |
| 854 | CCUAUCAC C AGCUCUUC | 4947 | GAAGAGCU CUGAUGAGGCCGUUAGGCCGAA IUGAUAGG | 5451 |
| 855 | CUAUCACC A GCUCUUCC | 4948 | GGAAGAGC CUGAUGAGGCCGUUAGGCCGAA IGUGAUAG | 5452 |
| 858 | UCACCAGC U CUUCCAAG | 4949 | CUUGGAAG CUGAUGAGGCCGUUAGGCCGAA ICUGGUGA | 5453 |
| 860 | ACCAGCUC U UCCAAGAA | 4950 | UUCUUGGA CUGAUGAGGCCGUUAGGCCGAA IAGCUGGU | 5454 |
| 863 | AGCUCUUC C AAGAAUAC | 4951 | GUAUUCUU CUGAUGAGGCCGUUAGGCCGAA IAAGAGCU | 5455 |
| 864 | GCUCUUCC A AGAAUACG | 4952 | CGUAUUCU CUGAUGAGGCCGUUAGGCCGAA IGAAGAGC | 5456 |
| 875 | AAUACGAC A ACCACAUC | 4953 | GAUGUGGU CUGAUGAGGCCGUUAGGCCGAA IUCGUAUU | 5457 |
| 878 | ACGACAAC C ACAUCAAG | 4954 | CUUGAUGU CUGAUGAGGCCGUUAGGCCGAA IUUGUCGU | 5458 |
| 879 | CGACAACC A CAUCAAGA | 4955 | UCUUGAUG CUGAUGAGGCCGUUAGGCCGAA IGUUGUCG | 5459 |
| 881 | ACAACCAC A UCAAGAGC | 4956 | GCUCUUGA CUGAUGAGGCCGUUAGGCCGAA IUGGUUGU | 5460 |
| 884 | ACCACAUC A AGAGCAGC | 4957 | GCUGCUCU CUGAUGAGGCCGUUAGGCCGAA IAUGUGGU | 5461 |
| 890 | UCAAGAGC A GCGUGGUG | 4958 | CACCACGC CUGAUGAGGCCGUUAGGCCGAA ICUCUUGA | 5462 |
| 902 | UGGUGGGC A GUGAGCGG | 4959 | CCGCUCAC CUGAUGAGGCCGUUAGGCCGAA ICCCACCA | 5463 |
| 924 | AGGAAUGC A GCUGGAAG | 4960 | CUUCCAGC CUGAUGAGGCCGUUAGGCCGAA ICAUUCCU | 5464 |
| 927 | AAUGCAGC U GGAAGAUC | 4961 | GAUCUUCC CUGAUGAGGCCGUUAGGCCGAA ICUGCAUU | 5465 |
| 936 | GGAAGAUC U CAAACAGC | 4962 | GCUGUUUG CUGAUGAGGCCGUUAGGCCGAA IAUCUUCC | 5466 |
| 938 | AAGAUCUC A AACAGCAG | 4963 | CUGCUGUU CUGAUGAGGCCGUUAGGCCGAA IAGAUCUU | 5467 |
| 942 | UCUCAAAC A GCAGCUCC | 4964 | GGAGCUGC CUGAUGAGGCCGUUAGGCCGAA IUUUGAGA | 5468 |
| 945 | CAAACAGC A GCUCCAGC | 4965 | GCUGGAGC CUGAUGAGGCCGUUAGGCCGAA ICUGUUUG | 5469 |
| 948 | ACAGCAGC U CCAGCAGG | 4966 | CCUGCUGG CUGAUGAGGCCGUUAGGCCGAA ICUGCUGU | 5470 |

TABLE IV-continued

Human IKK-gamma Inozyme and Substrate Sequence

| Pos | Substrate | Seq ID | Inozyme | Seq ID |
|---|---|---|---|---|
| 950 | AGCAGCUC C AGCAGGCC | 4967 | GGCCUGCU CUGAUGAGGCCGUUAGGCCGAA IAGCUGCU | 5471 |
| 951 | GCAGCUCC A GCAGGCCG | 4968 | CGGCCUGC CUGAUGAGGCCGUUAGGCCGAA IGAGCUGC | 5472 |
| 954 | GCUCCAGC A GGCCGAGG | 4969 | CCUCGGCC CUGAUGAGGCCGUUAGGCCGAA ICUGGAGC | 5473 |
| 958 | CAGCAGGC C GAGGAGGC | 4970 | GCCUCCUC CUGAUGAGGCCGUUAGGCCGAA ICCUGCUG | 5474 |
| 967 | GAGGAGGC C CUGGUGGC | 4971 | GCCACCAG CUGAUGAGGCCGUUAGGCCGAA ICCUCCUC | 5475 |
| 968 | AGGAGGCC C UGGUGGCC | 4972 | GGCCACCA CUGAUGAGGCCGUUAGGCCGAA IGCCUCCU | 5476 |
| 969 | GGAGGCCC U GGUGGCCA | 4973 | UGGCCACC CUGAUGAGGCCGUUAGGCCGAA IGGCCUCC | 5477 |
| 976 | CUGGUGGC C AAACAGGA | 4974 | UCCUGUUU CUGAUGAGGCCGUUAGGCCGAA ICCACCAG | 5478 |
| 977 | UGGUGGCC A AACAGGAG | 4975 | CUCCUGUU CUGAUGAGGCCGUUAGGCCGAA IGCCACCA | 5479 |
| 981 | GGCCAAAC A GGAGGUGA | 4976 | UCACCUCC CUGAUGAGGCCGUUAGGCCGAA IUUUGGCC | 5480 |
| 999 | CGAUAAGC U GAAGGAGG | 4977 | CCUCCUUC CUGAUGAGGCCGUUAGGCCGAA ICUUAUCG | 5481 |
| 1012 | GAGGAGGC C GAGCAGCA | 4978 | UGCUGCUC CUGAUGAGGCCGUUAGGCCGAA ICCUCCUC | 5482 |
| 1017 | GGCCGAGC A GCACAAGA | 4979 | UCUUGUGC CUGAUGAGGCCGUUAGGCCGAA ICUCGGCC | 5483 |
| 1020 | CGAGCAGC A CAAGAUGG | 4980 | CAAUCUUG CUGAUGAGGCCGUUAGGCCGAA ICUGCUCG | 5484 |
| 1022 | AGCAGCAC A AGAUUGUG | 4981 | CACAAUCU CUGAUGAGGCCGUUAGGCCGAA IUGCUGCU | 5485 |
| 1039 | AUGGAGAC C GUUCCGGU | 4982 | ACCGGAAC CUGAUGAGGCCGUUAGGCCGAA IUCUCCAU | 5486 |
| 1044 | GACCGUUC C GGUGCUGA | 4983 | UCAGCACC CUGAUGAGGCCGUUAGGCCGAA IAACGGUC | 5487 |
| 1050 | UCCGGUGC U GAAGGCCC | 4984 | GGGCCUUC CUGAUGAGGCCGUUAGGCCGAA ICACCGGA | 5488 |
| 1057 | CUGAAGGC C CAGGCGGA | 4985 | UCCGCCUG CUGAUGAGGCCGUUAGGCCGAA ICCUUCAG | 5489 |
| 1058 | UGAAGGCC C AGGCGGAU | 4986 | AUCCGCCU CUGAUGAGGCCGUUAGGCCGAA IGCCUUCA | 5490 |
| 1059 | GAAGGCCC A GGCGGAUA | 4987 | UAUCCGCC CUGAUGAGGCCGUUAGGCCGAA IGGCCUUC | 5491 |
| 1070 | CGGAUAUC U ACAAGGCG | 4988 | CGCCUUGU CUGAUGAGGCCGUUAGGCCGAA IAUAUCCG | 5492 |
| 1073 | AUAUCUAC A AGGCGGAC | 4989 | GUCCGCCU CUGAUGAGGCCGUUAGGCCGAA IUAGAUAU | 5493 |
| 1082 | AGGCGGAC U UCCAGGCU | 4990 | AGCCUGGA CUGAUGAGGCCGUUAGGCCGAA IUCCGCCU | 5494 |
| 1085 | CGGACUUC C AGGCUGAG | 4991 | CUCAGCCU CUGAUGAGGCCGUUAGGCCGAA IAAGUCCG | 5495 |
| 1086 | GGACUUCC A GGCUGAGA | 4992 | UCUCAGCC CUGAUGAGGCCGUUAGGCCGAA IGAAGUCC | 5496 |
| 1090 | UUCCAGGC U GAGAGGCA | 4993 | UGCCUCUC CUGAUGAGGCCGUUAGGCCGAA ICCUGGAA | 5497 |
| 1098 | UGAGAGGC A GGCCCGGG | 4994 | CCCGGGCC CUGAUGAGGCCGUUAGGCCGAA ICCUCUCA | 5498 |
| 1102 | AGGCAGGC C CGGGAGAA | 4995 | UUCUCCCG CUGAUGAGGCCGUUAGGCCGAA ICCUGCCU | 5499 |
| 1103 | GGCAGGCC C GGGAGAAG | 4996 | CUUCUCCC CUGAUGAGGCCGUUAGGCCGAA IGCCUGCC | 5500 |
| 1113 | GGAGAAGC U GGCCGAGA | 4997 | UCUCGGCC CUGAUGAGGCCGUUAGGCCGAA ICUUCUCC | 5501 |
| 1117 | AAGCUGGC C GAGAAGAA | 4998 | UUCUUCUC CUGAUGAGGCCGUUAGGCCGAA ICCAGCUU | 5502 |
| 1131 | GAAGGAGC U CCUGCAGG | 4999 | CCUGCAGG CUGAUGAGGCCGUUAGGCCGAA ICUCCUUC | 5503 |
| 1133 | AGGAGCUC C UGCAGGAG | 5000 | CUCCUGCA CUGAUGAGGCCGUUAGGCCGAA IAGCUCCU | 5504 |
| 1134 | GGAGCUCC U GCAGGAGC | 5001 | GCUCCUGC CUGAUGAGGCCGUUAGGCCGAA IGAGCUCC | 5505 |
| 1137 | GCUCCUGC A GGAGCAGC | 5002 | GCUGCUCC CUGAUGAGGCCGUUAGGCCGAA ICAGGAGC | 5506 |
| 1143 | GCAGGAGC A GCUGGAGC | 5003 | GCUCCAGC CUGAUGAGGCCGUUAGGCCGAA ICUCCUGC | 5507 |
| 1146 | GGAGCAGC U GGAGCAGC | 5004 | GCUGCUCC CUGAUGAGGCCGUUAGGCCGAA ICUGCUCC | 5508 |
| 1152 | GCUGGAGC A GCUGCAGA | 5005 | UCUGCAGC CUGAUGAGGCCGUUAGGCCGAA ICUCCAGC | 5509 |
| 1155 | GGAGCAGC U GCAGAGGG | 5006 | CCCUCUGC CUGAUGAGGCCGUUAGGCCGAA ICUGCUCC | 5510 |
| 1158 | GCAGCUGC A GAGGGAGU | 5007 | ACUCCCUC CUGAUGAGGCCGUUAGGCCGAA ICAGCUGC | 5511 |
| 1169 | GGGAGUAC A GCAAACUG | 5008 | CAGUUUGC CUGAUGAGGCCGUUAGGCCGAA IUACUCCC | 5512 |
| 1172 | AGUACAGC A AACUGAAG | 5009 | CUUCAGUU CUGAUGAGGCCGUUAGGCCGAA ICUGUACU | 5513 |
| 1176 | CAGCAAAC U GAAGGCCA | 5010 | UGGCCUUC CUGAUGAGGCCGUUAGGCCGAA IUUUGCUG | 5514 |
| 1183 | CUGAAGGC C AGCUGUCA | 5011 | UGACAGCU CUGAUGAGGCCGUUAGGCCGAA ICCUUCAG | 5515 |
| 1184 | UGAAGGCC A GCUGUCAG | 5012 | CUGACAGC CUGAUGAGGCCGUUAGGCCGAA IGCCUUCA | 5516 |
| 1187 | AGGCCAGC U GUCAGGAG | 5013 | CUCCUGAC CUGAUGAGGCCGUUAGGCCGAA ICUGGCCU | 5517 |
| 1191 | CAGCUGUC A GGAGUCGG | 5014 | CCGACUCC CUGAUGAGGCCGUUAGGCCGAA IACAGCUG | 5518 |
| 1201 | GAGUCGGC C GGAUCGAG | 5015 | UCGAUCCU CUGAUGAGGCCGUUAGGCCGAA ICCGACUC | 5519 |
| 1202 | AGUCGGCC A GGAUCGAG | 5016 | CUCGAUCC CUGAUGAGGCCGUUAGGCCGAA IGCCGACU | 5520 |
| 1214 | UCGAGGAC A UGAGGAAG | 5017 | CUUCCUCA CUGAUGAGGCCGUUAGGCCGAA IUCCUCGA | 5521 |
| 1227 | GAAGCGGA A UGUCGAGG | 5018 | CCUCGACA CUGAUGAGGCCGUUAGGCCGAA ICCGCUUC | 5522 |
| 1238 | UCGAGGUC U CCCAGGCC | 5019 | GGCCUGGG CUGAUGAGGCCGUUAGGCCGAA IACCUCGA | 5523 |
| 1240 | GAGGUCUC C CAGGCCCC | 5020 | GGGGCCUG CUGAUGAGGCCGUUAGGCCGAA IAGACCUC | 5524 |
| 1241 | AGGUCUCC C AGGCCCCU | 5021 | GGGGGCCU CUGAUGAGGCCGUUAGGCCGAA IGAGACCU | 5525 |
| 1242 | GGUCUCCC A GGCCCCUU | 5022 | AGGGGGCC CUGAUGAGGCCGUUAGGCCGAA IGGAGACC | 5526 |
| 1246 | UCCCAGGC C CCUUGCCC | 5023 | GGCAAGGG CUGAUGAGGCCGUUAGGCCGAA ICCUGGGA | 5527 |
| 1247 | CCCAGGCC C CUUGCCCC | 5024 | GGGCAAGG CUGAUGAGGCCGUUAGGCCGAA IGCCUGGG | 5528 |
| 1248 | CCAGGCCC C UUGCCCCC | 5025 | GGGGCAAG CUGAUGAGGCCGUUAGGCCGAA IGGCCUGG | 5529 |
| 1249 | CAGGCCCC U UGCCCCCU | 5026 | GGGGGCAA CUGAUGAGGCCGUUAGGCCGAA IGGGCCUG | 5530 |
| 1250 | AGGCCCCU U GCCCCCGC | 5027 | GGGGGGCA CUGAUGAGGCCGUUAGGCCGAA IGGGGCCU | 5531 |
| 1254 | CCCCUUGC C CCCGCCCC | 5028 | GGGCGGGG CUGAUGAGGCCGUUAGGCCGAA ICAAGGGG | 5532 |
| 1255 | CCCUUGCC C CCGCCCCC | 5029 | GGGGCGGG CUGAUGAGGCCGUUAGGCCGAA IGCAAGGG | 5533 |
| 1256 | CCUUGCCC C CGCCCCCU | 5030 | AGGGGCGG CUGAUGAGGCCGUUAGGCCGAA IGGCAAGG | 5534 |
| 1257 | CUUGCCCC C CGCCCCUG | 5031 | CAGGGGCG CUGAUGAGGCCGUUAGGCCGAA IGGGCAAG | 5535 |
| 1258 | UUGCCCCC C GCCCCUGC | 5032 | GCAGGGGC CUGAUGAGGCCGUUAGGCCGAA IGGGGCAA | 5536 |
| 1261 | CCCCCCGC C CCUGCCUA | 5033 | UAGGCAGG CUGAUGAGGCCGUUAGGCCGAA ICGGGGGG | 5537 |
| 1262 | CCCCCGCC C CUGCCUAC | 5034 | GUAGGCAG CUGAUGAGGCCGUUAGGCCGAA IGCGGGGG | 5538 |
| 1263 | CCCCGCCC C UGCCUACC | 5035 | GGUAGGCA CUGAUGAGGCCGUUAGGCCGAA IGGCGGGG | 5539 |
| 1264 | CCCGCCCC U GCCUACCU | 5036 | AGGUAGGC CUGAUGAGGCCGUUAGGCCGAA IGGGCGGG | 5540 |
| 2267 | GCCCCUGC C UACUCUC | 5037 | GAGAGGUA CUGAUGAGGCCGUUAGGCCGAA ICAGGGGC | 5541 |
| 1268 | CCCCUGCC U ACCUCCC | 5038 | GGAGAGGU CUGAUGAGGCCGUUAGGCCGAA IGCAGGGG | 5542 |
| 1271 | CUGCCUAC C UCUCCUCU | 5039 | AGAGGAGA CUGAUGAGGCCGUUAGGCCGAA IUAGGCAG | 5543 |
| 1272 | UGCCUACC U CUCCUCUC | 5040 | GAGAGGAG CUGAUGAGGCCGUUAGGCCGAA IGUAGGCA | 5544 |

TABLE IV-continued

Human IKK-gamma Inozyme and Substrate Sequence

| Pos | Substrate | Seq ID | Inozyme | Seq ID |
|---|---|---|---|---|
| 1274 | CCUACCUC U CCUCUCCC | 5041 | GGGAGAGG CUGAUGAGgccGUUAGGCCGAA IAGGUAGG | 5545 |
| 1276 | UACCUCUC C UCUCCCCU | 5042 | AGGGGAGA CUGAUGAGgccGUUAGGCCGAA IAGAGGUA | 5546 |
| 1277 | ACCUCUCC U CUCCCCUG | 5043 | CAGGGGAG CUGAUGAGgccGUUAGGCCGAA IAGAGGGU | 5547 |
| 1279 | CUCUCCUC U CCCCUGGC | 5044 | GCCAGGGG CUGAUGAGgccGUUAGGCCGAA IAGGAGAG | 5548 |
| 1281 | CUCCCUCU C CCUGGCCC | 5045 | GGGCCAGG CUGAUGAGgccGUUAGGCCGAA IAGAGGAG | 5549 |
| 1282 | UCCUCUCC C CUGGCCCU | 5046 | AGGGCCAG CUGAUGAGgccGUUAGGCCGAA IAGAGGGA | 5550 |
| 1283 | CCUCUCCC C UGGCCCUG | 5047 | CAGGGCCA CUGAUGAGgccGUUAGGCCGAA IGGAGAGG | 5551 |
| 1284 | CUCUCCCC U GGCCCUGC | 5048 | GCAGGGCC CUGAUGAGgccGUUAGGCCGAA IGGGAGAG | 5552 |
| 1288 | CCCCUGGC C CUGCCCAG | 5049 | CUGGGCAG CUGAUGAGgccGUUAGGCCGAA ICCAGGGG | 5553 |
| 1289 | CCCUGGCC C UGCCCAGC | 5050 | GCUGGGCA CUGAUGAGgccGUUAGGCCGAA IGCCAGGG | 5554 |
| 1290 | CCUGGCCC U GCCCAGCC | 5051 | GGCUGGGC CUGAUGAGgccGUUAGGCCGAA IGGCCAGG | 5555 |
| 1293 | GGCCCUGC C CAGCCAGA | 5052 | UCUGGCUG CUGAUGAGgccGUUAGGCCGAA ICAGGGCC | 5556 |
| 1294 | GCCCUGCC C AGCCAGAG | 5053 | CUCUGGCU CUGAUGAGgccGUUAGGCCGAA IGCAGGGC | 5557 |
| 1295 | CCCUGCCC A GCCAGAGG | 5054 | CCUCUGGC CUGAUGAGgccGUUAGGCCGAA IGGCAGGG | 5558 |
| 1298 | UGCCCAGC C AGAGGAGG | 5055 | CCUCCUCU CUGAUGAGgccGUUAGGCCGAA ICUGGGCA | 5559 |
| 1299 | GCCCAGCC A GAGGAGGA | 5056 | UCCUCCUC CUGAUGAGgccGUUAGGCCGAA IGCUGGGC | 5560 |
| 1310 | GGAGGAGC C CCCCGAG | 5057 | CUCGGGGG CUGAUGAGgccGUUAGGCCGAA ICUCCUCC | 5561 |
| 1311 | GAGGAGCC C CCCGAGG | 5058 | CCUCGGGG CUGAUGAGgccGUUAGGCCGAA IGCUCCUC | 5562 |
| 1312 | AGGAGCCC C CCGAGGA | 5059 | UCCUCGGG CUGAUGAGgccGUUAGGCCGAA IGGCUCCU | 5563 |
| 1313 | GGAGCCCC C CGAGGAG | 5060 | CUCCUCGG CUGAUGAGgccGUUAGGCCGAA IGGGCUCC | 5564 |
| 1314 | GAGCCCCC C GAGGAGC | 5061 | GCUCCUCG CUGAUGAGgccGUUAGGCCGAA IGGGGCUC | 5565 |
| 1315 | AGCCCCCC C GAGGAGCC | 5062 | GGCUCCUC CUGAUGAGgccGUUAGGCCGAA IGGGGGCU | 5566 |
| 1323 | CGAGGAGC C ACCUGACU | 5063 | AGUCAGGU CUGAUGAGgccGUUAGGCCGAA ICUCCUCG | 5567 |
| 1324 | GAGGAGCC A CCUGACUU | 5064 | AAGUCAGG CUGAUGAGgccGUUAGGCCGAA IGCUCCUC | 5568 |
| 1326 | GGAGCCAC C UGACUUCU | 5065 | AGAAGUCA CUGAUGAGgccGUUAGGCCGAA IUGGCUCC | 5569 |
| 1327 | GAGCCACC U GACUUCUG | 5066 | CAGAAGUC CUGAUGAGgccGUUAGGCCGAA IGUGGCUC | 5570 |
| 1331 | CACCGAC U UCUGCUGU | 5067 | ACAGCAGA CUGAUGAGgccGUUAGGCCGAA IUCAGGUG | 5571 |
| 1334 | CUGACUUC U GCUGUCCC | 5068 | GGGACAGC CUGAUGAGgccGUUAGGCCGAA IAAGUCAG | 5572 |
| 1337 | ACUUCUGC U GUCCCAAG | 5069 | CUUGGGAC CUGAUGAGgccGUUAGGCCGAA ICAGAAGU | 5573 |
| 1341 | CUGCUGUC C CAAGUGCC | 5070 | GGCACUUG CUGAUGAGgccGUUAGGCCGAA IACAGCAG | 5574 |
| 1342 | UGCUGUCC C AAGUGCCA | 5071 | UGGCACUU CUGAUGAGgccGUUAGGCCGAA IGACAGCA | 5575 |
| 1343 | GCUGUCCC A AGUGCCAG | 5072 | CUGGCACU CUGAUGAGgccGUUAGGCCGAA IGGACAGC | 5576 |
| 1349 | CCAAGUGC C AGUAUCAG | 5073 | CUGAUACU CUGAUGAGgccGUUAGGCCGAA ICACUUGG | 5577 |
| 1350 | CAAGUGCC A GUAUCAGG | 5074 | CCUGAUAC CUGAUGAGgccGUUAGGCCGAA IGCACUUG | 5578 |
| 1356 | CCAGUAUC A GGCCCUG | 5075 | CAGGGCC CUGAUGAGgccGUUAGGCCGAA IAUACUGG | 5579 |
| 1360 | UAUCAGGC C CCUGAUAU | 5076 | AUAUCAGG CUGAUGAGgccGUUAGGCCGAA ICCUGAUA | 5580 |
| 1361 | AUCAGGCC C UGAUAUG | 5077 | CAUAUCAG CUGAUGAGgccGUUAGGCCGAA IGCCUGAU | 5581 |
| 1362 | UCAGGCCC U GAUAUGG | 5078 | CCAUAUCA CUGAUGAGgccGUUAGGCCGAA IGGCCUGA | 5582 |
| 1363 | CAGGCCCU U GAUAUGGA | 5079 | UCCAUAUC CUGAUGAGgccGUUAGGCCGAA IGGGCCUG | 5583 |
| 1373 | AUAUGGAC A CCCUGCAG | 5080 | CUGCAGGG CUGAUGAGgccGUUAGGCCGAA IUCCAUAU | 5584 |
| 1375 | AUGGACAC C CUGCAGAU | 5081 | AUCUGCAG CUGAUGAGgccGUUAGGCCGAA IUGUCCAU | 5585 |
| 1376 | UGGACACC C UGCAGAUA | 5082 | UAUCUGCA CUGAUGAGgccGUUAGGCCGAA IGUGUCCA | 5586 |
| 1377 | GGACACCU U GCAGAUAC | 5083 | GUAUCUGC CUGAUGAGgccGUUAGGCCGAA IGGUGUCC | 5587 |
| 1380 | CACCCUGC A GAUACAUG | 5084 | CAUGUAUC CUGAUGAGgccGUUAGGCCGAA ICAGGGUG | 5588 |
| 1386 | GCAGAUAC A UGUCAUGG | 5085 | CCAUGACA CUGAUGAGgccGUUAGGCCGAA IUAUCUGC | 5589 |
| 1391 | UACAUGUC A UGGAGUGC | 5086 | GCACUCCA CUGAUGAGgccGUUAGGCCGAA IACAUGUA | 5590 |
| 1400 | UGGAGUGC A UUGAGUAG | 5087 | CUACUCAA CUGAUGAGgccGUUAGGCCGAA ICACUCCA | 5591 |
| 1412 | AGUAGGGC C GGCCAGUG | 5088 | CACUGGCC CUGAUGAGgccGUUAGGCCGAA ICCCUACU | 5592 |
| 1416 | GGGCCGGC C AGUGCAAG | 5089 | CUUGCACU CUGAUGAGgccGUUAGGCCGAA ICCGGCCC | 5593 |
| 1417 | GGCCGGCC A GUGCAAGG | 5090 | CCUUGCAC CUGAUGAGgccGUUAGGCCGAA IGCCGGCC | 5594 |
| 1422 | GCCAGUGC A AGGCCACU | 5091 | AGUGGCCU CUGAUGAGgccGUUAGGCCGAA ICACUGGC | 5595 |
| 1427 | UGCAAGGC C ACUGCCUG | 5092 | CAGGCAGU CUGAUGAGgccGUUAGGCCGAA ICCUUGCA | 5596 |
| 1428 | GCAAGGCC A CUGCCUGC | 5093 | GCAGGCAG CUGAUGAGgccGUUAGGCCGAA IGCCUUGC | 5597 |
| 1430 | AAGGCCAC U GCCUGCCC | 5094 | GGGCAGGC CUGAUGAGgccGUUAGGCCGAA IUGGCCUU | 5598 |
| 1433 | GCCACUGC C UGCCCGAG | 5095 | CUCGGGCA CUGAUGAGgccGUUAGGCCGAA ICAGUGGC | 5599 |
| 1434 | CCACUGCU U GCCCGAGG | 5096 | CCUCGGGC CUGAUGAGgccGUUAGGCCGAA IGCAGUGG | 5600 |
| 1437 | CUGCCUGC C CGAGGACG | 5097 | CGUCCUCG CUGAUGAGgccGUUAGGCCGAA ICAGGCAG | 5601 |
| 1438 | UGCCUGCC C GAGGACGU | 5098 | ACGUCCUC CUGAUGAGgccGUUAGGCCGAA IGCAGGCA | 5602 |
| 1449 | GGACGUGC C CGGGACCG | 5099 | CGGUCCCG CUGAUGAGgccGUUAGGCCGAA ICACGUCC | 5603 |
| 1450 | GACGUGCC C GGGACCGU | 5100 | ACGGUCCC CUGAUGAGgccGUUAGGCCGAA IGCACGUC | 5604 |
| 1456 | CCCGGGAC C GUGCAGUC | 5101 | GACUGCAC CUGAUGAGgccGUUAGGCCGAA IUCCCGGG | 5605 |
| 1461 | GACCGUGC A GUCUGCGC | 5102 | GCGCAGAC CUGAUGAGgccGUUAGGCCGAA ICACGGUC | 5606 |
| 1465 | GUGCAGUC U GCGCUUUC | 5103 | GAAAGCGC CUGAUGAGgccGUUAGGCCGAA IACUGCAC | 5607 |
| 1470 | GUCUGCGC U UUCCUCUC | 5104 | GAGAGGAA CUGAUGAGgccGUUAGGCCGAA ICGCAGAC | 5608 |
| 1474 | GCGCUUUC C UCUCCGC | 5105 | GCGGGAGA CUGAUGAGgccGUUAGGCCGAA IAAAGCGC | 5609 |
| 1475 | CGCUUUCC U CUCCCGCC | 5106 | GGCGGGAG CUGAUGAGgccGUUAGGCCGAA IGAAAGCG | 5610 |
| 1477 | CUUUCCUC U CCCGCCUG | 5107 | CAGGCGGG CUGAUGAGgccGUUAGGCCGAA IAGGAAAG | 5611 |
| 1479 | UUCCUCUC C CGCUGCC | 5108 | GGCAGGCG CUGAUGAGgccGUUAGGCCGAA IAGAGGAA | 5612 |
| 1480 | UCCUCUCC C GCCUGCCU | 5109 | AGGCAGGC CUGAUGAGgccGUUAGGCCGAA IGAGAGGA | 5613 |
| 1483 | UCUCCCGC C UGCCUAGCC | 5110 | GCUAGGCA CUGAUGAGgccGUUAGGCCGAA ICGGGAGA | 5614 |
| 1484 | CUCCCGCC U GCCUAGCC | 5111 | GGCUAGGC CUGAUGAGgccGUUAGGCCGAA IGCGGGAG | 5615 |
| 1487 | CCGCCUGC C UAGCCCAG | 5112 | CUGGGCUA CUGAUGAGgccGUUAGGCCGAA ICAGGCGG | 5616 |
| 1488 | CGCCUGCU U AGCCCAGG | 5113 | CCUGGGCU CUGAUGAGgccGUUAGGCCGAA IGCAGGCG | 5617 |
| 1492 | UGCCUAGC C CAGGAUGA | 5114 | UCAUCCUG CUGAUGAGgccGUUAGGCCGAA ICUAGGCA | 5618 |

TABLE IV-continued

Human IKK-gamma Inozyme and Substrate Sequence

| Pos | Substrate | Seq ID | Inozyme | Seq ID |
|---|---|---|---|---|
| 1493 | GCCUAGCC C AGGAUGAA | 5115 | UUCAUCCU CUGAUGAGGCCGUUAGGCCGAA IGCUAGGC | 5619 |
| 1494 | CCUAGCCC A GGAUGAAG | 5116 | CUUCAUCC CUGAUGAGGCCGUUAGGCCGAA IGGCUAGG | 5620 |
| 1506 | UGAAGGGC U GGGUGGCC | 5117 | GGCCACCC CUGAUGAGGCCGUUAGGCCGAA ICCCUUCA | 5621 |
| 1514 | UGGGUGGC C ACAACUGG | 5118 | CCAGUUGU CUGAUGAGGCCGUUAGGCCGAA ICCACCCA | 5622 |
| 1515 | GGGUGGCC A CAACUGGG | 5119 | CCCAGUUG CUGAUGAGGCCGUUAGGCCGAA IGCCACCC | 5623 |
| 1517 | GUGGCCAC A ACUGGGAU | 5120 | AUCCCAGU CUGAUGAGGCCGUUAGGCCGAA IUGGCCAC | 5624 |
| 1520 | GCCACAAC U GGGAUGCC | 5121 | GGCAUCCC CUGAUGAGGCCGUUAGGCCGAA IUUGUGGC | 5625 |
| 1528 | UGGGAUGC C ACCUGGAG | 5122 | CUCCAGGU CUGAUGAGGCCGUUAGGCCGAA ICAUCCCA | 5626 |
| 1529 | GGGAUGCC A CCUGGAGC | 5123 | GCUCCAGG CUGAUGAGGCCGUUAGGCCGAA IGCAUCCC | 5627 |
| 1531 | GAUGCCAC C UGGAGCCC | 5124 | GGGCUCCA CUGAUGAGGCCGUUAGGCCGAA IUGGCAUC | 5628 |
| 1532 | AUGCCACC U GGAGCCCC | 5125 | GGGGCUCC CUGAUGAGGCCGUUAGGCCGAA IGUGGCAU | 5629 |
| 1538 | CCUGGAGC C CACCCAG | 5126 | CUGGGUGG CUGAUGAGGCCGUUAGGCCGAA ICUCCAGG | 5630 |
| 1539 | CUGGAGCC C ACCCAGG | 5127 | CCUGGGUG CUGAUGAGGCCGUUAGGCCGAA IGCUCCAG | 5631 |
| 1540 | UGGAGCCC C ACCCAGGA | 5128 | UCCUGGGU CUGAUGAGGCCGUUAGGCCGAA IGGCUCCA | 5632 |
| 1541 | GGAGCCCC A CCCAGGAG | 5129 | CUCCUGGG CUGAUGAGGCCGUUAGGCCGAA IGGGCUCC | 5633 |
| 1543 | AGCCCCAC C CAGGAGCU | 5130 | AGCUCCUG CUGAUGAGGCCGUUAGGCCGAA IUGGGGCU | 5634 |
| 1544 | GCCCCACC C AGGAGCUG | 5131 | CAGCUCCU CUGAUGAGGCCGUUAGGCCGAA IGUGGGGC | 5635 |
| 1545 | CCCCACCC A GGAGCUGG | 5132 | CCAGCUCC CUGAUGAGGCCGUUAGGCCGAA IGGUGGGG | 5636 |
| 1551 | CCAGGAGC U GGCCGCGG | 5133 | CCGCGGCC CUGAUGAGGCCGUUAGGCCGAA ICUCCUGG | 5637 |
| 1555 | GAGCUGGC C GCGGCACC | 5134 | GGUGCCGC CUGAUGAGGCCGUUAGGCCGAA ICCAGCUC | 5638 |
| 1561 | GCCGCGGC A CCUUACGC | 5135 | GCGUAAGG CUGAUGAGGCCGUUAGGCCGAA ICCGCGGC | 5639 |
| 1563 | CGCGGCAC C UUACGCUU | 5136 | AAGCGUAA CUGAUGAGGCCGUUAGGCCGAA IUGCCGCG | 5640 |
| 1564 | GCGGCACC U UACGCUUC | 5137 | GAAGCGUA CUGAUGAGGCCGUUAGGCCGAA IGUGCCGC | 5641 |
| 1570 | CCUUACGC U UCAGCUUG | 5138 | ACAGCUGA CUGAUGAGGCCGUUAGGCCGAA ICGUAAGG | 5642 |
| 1573 | UACGCUUC A GCUUGA | 5139 | UCAACAGC CUGAUGAGGCCGUUAGGCCGAA IAAGCGUA | 5643 |
| 1576 | GCUUCAGC U UGAUCC | 5140 | GGAUCAAC CUGAUGAGGCCGUUAGGCCGAA ICUGAAGC | 5644 |
| 1584 | UGUUGAUC C GCUGGUCC | 5141 | GGACCAGC CUGAUGAGGCCGUUAGGCCGAA IAUCAACA | 5645 |
| 1587 | UGAUCCGC U GGUCCCU | 5142 | AGGGGACC CUGAUGAGGCCGUUAGGCCGAA ICGGAUCA | 5646 |
| 1592 | CGCUGGUC C CCUCUUUU | 5143 | AAAAGAGG CUGAUGAGGCCGUUAGGCCGAA IACCAGCG | 5647 |
| 1593 | GCUGGUCC C CUCUUUUG | 5144 | CAAAAGAG CUGAUGAGGCCGUUAGGCCGAA IGACCAGC | 5648 |
| 1594 | CUGGUCCC C UCUUUUGG | 5145 | CCAAAAGA CUGAUGAGGCCGUUAGGCCGAA IGGACCAG | 5649 |
| 1595 | UGGUCCCC U CUUUUGGG | 5146 | CCCAAAAG CUGAUGAGGCCGUUAGGCCGAA IGGGACCA | 5650 |
| 1597 | GUCCCCUC U UUUGGGU | 5147 | ACCCCAAA CUGAUGAGGCCGUUAGGCCGAA IAGGGGAC | 5651 |
| 1615 | GAUGCGGC C CGAUCAG | 5148 | CUGAUCGG CUGAUGAGGCCGUUAGGCCGAA ICCGCAUC | 5652 |
| 1616 | AUGCGGCC C CGAUCAGG | 5149 | CCUGAUCG CUGAUGAGGCCGUUAGGCCGAA IGCCGCAU | 5653 |
| 1617 | UGCGGCCC C GAUCAGGC | 5150 | GCCUGAUC CUGAUGAGGCCGUUAGGCCGAA IGGCCGCA | 5654 |
| 1622 | CCCCGAUC A GGCCUGAC | 5151 | GUCAGGCC CUGAUGAGGCCGUUAGGCCGAA IAUCGGGG | 5655 |
| 1626 | GAUCAGGC C UGAUCGC | 5152 | GCGAGUCA CUGAUGAGGCCGUUAGGCCGAA ICCUGAUC | 5656 |
| 1627 | AUCAGGCC U GACUCGCU | 5153 | AGCGAGUC CUGAUGAGGCCGUUAGGCCGAA IGCCUGAU | 5657 |
| 1631 | GGCCUGAC U CGCUGCUC | 5154 | GAGCAGCG CUGAUGAGGCCGUUAGGCCGAA IUCAGGCC | 5658 |
| 1635 | UGACUCGC U GCUCUUUU | 5155 | AAAAGAGC CUGAUGAGGCCGUUAGGCCGAA ICGAGUCA | 5659 |
| 1638 | CUCGCUGC U CUUUUGU | 5156 | ACAAAAAG CUGAUGAGGCCGUUAGGCCGAA ICAGCGAG | 5660 |
| 1640 | CGCUGCUC U UUUGUUC | 5157 | GAACAAAA CUGAUGAGGCCGUUAGGCCGAA IAGCAGCG | 5661 |
| 1649 | UUUUGUUC C CUUCUGUC | 5158 | GACAGAAG CUGAUGAGGCCGUUAGGCCGAA IAACAAAA | 5662 |
| 1650 | UUUGUUCC C UUCUGUCU | 5159 | AGACAGAA CUGAUGAGGCCGUUAGGCCGAA IGAACAAA | 5663 |
| 1651 | UUGUUCCC U UCUGUCUG | 5160 | CAGACAGA CUGAUGAGGCCGUUAGGCCGAA IGGAACAA | 5664 |
| 1654 | UUCCCUUC U GUCUGCUC | 5161 | GAGCAGAC CUGAUGAGGCCGUUAGGCCGAA IAAGGGAA | 5665 |
| 1658 | CUUCUGUC U GCUCGAAC | 5162 | GUUCGAGC CUGAUGAGGCCGUUAGGCCGAA IACAGAAG | 5666 |
| 1661 | CUGUCUGC U CGAACCAC | 5163 | GUGGUUCG CUGAUGAGGCCGUUAGGCCGAA ICAGACAG | 5667 |
| 1667 | GCUCGAAC C ACUUGCCU | 5164 | AGGCAAGU CUGAUGAGGCCGUUAGGCCGAA IUUCGAGC | 5668 |
| 1668 | CUCGAACC A CUUGCCUC | 5165 | GAGGCAAG CUGAUGAGGCCGUUAGGCCGAA IGUUCGAG | 5669 |
| 1670 | CGAACCAC U UGCCUCGG | 5166 | CCGAGGCA CUGAUGAGGCCGUUAGGCCGAA IUGGUUCG | 5670 |
| 1674 | CCACUUGC C UCGGCUA | 5167 | UAGCCCGA CUGAUGAGGCCGUUAGGCCGAA ICAAGUGG | 5671 |
| 1675 | CACUUGCC U CGGCUAA | 5168 | UUAGCCCG CUGAUGAGGCCGUUAGGCCGAA IGCAAGUG | 5672 |
| 1681 | CCUCGGGC U AAUCCCUC | 5169 | GAGGGAUU CUGAUGAGGCCGUUAGGCCGAA ICCCGAGG | 5673 |
| 1686 | GGCUAAUC C CUCCCUCU | 5170 | AGAGGGAG CUGAUGAGGCCGUUAGGCCGAA IAUUAGCC | 5674 |
| 1687 | GCUAAUCC C UCCCUCUU | 5171 | AAGAGGGA CUGAUGAGGCCGUUAGGCCGAA IGAUUAGC | 5675 |
| 1688 | CUAAUCCC U CCCUCUUC | 5172 | GAAGAGGG CUGAUGAGGCCGUUAGGCCGAA IGGAUUAG | 5676 |
| 1690 | AAUCCCUC C UCUUCCU | 5173 | AGGAAGAG CUGAUGAGGCCGUUAGGCCGAA IAGGGAUU | 5677 |
| 1691 | AUCCCUCC U CUUCCUC | 5174 | GAGGAAGA CUGAUGAGGCCGUUAGGCCGAA IGAGGGAU | 5678 |
| 1692 | UCCCUCCU C UUCCUCC | 5175 | GGAGGAAG CUGAUGAGGCCGUUAGGCCGAA IGGAGGGA | 5679 |
| 1694 | CCUCCUCU U UCCUCCAC | 5176 | GUGGAGGA CUGAUGAGGCCGUUAGGCCGAA IAGGGAGG | 5680 |
| 1697 | CCCUCUUC U UCCACCCG | 5177 | CGGGUGGA CUGAUGAGGCCGUUAGGCCGAA IAAGAGGG | 5681 |
| 1698 | CCUCUUCU U CCACCCGG | 5178 | CCGGGUGG CUGAUGAGGCCGUUAGGCCGAA IGAAGAGG | 5682 |
| 1700 | UCUUCCUC C ACCCGGCA | 5179 | UGCCGGGU CUGAUGAGGCCGUUAGGCCGAA IAGGAAGA | 5683 |
| 1701 | CUUCCUCC A CCCGGCAC | 5180 | GUGCCGGG CUGAUGAGGCCGUUAGGCCGAA IGAGGAAG | 5684 |
| 1703 | UCCUCCAC C CGGCACUG | 5181 | CAGUGCCG CUGAUGAGGCCGUUAGGCCGAA IUGGAGGA | 5685 |
| 1704 | CCUCCACC C GGCACUGG | 5182 | CCAGUGCC CUGAUGAGGCCGUUAGGCCGAA IGUGGAGG | 5686 |
| 1708 | CACCCGGC A CUGGGAA | 5183 | UUCCCAGU CUGAUGAGGCCGUUAGGCCGAA ICCGGGUG | 5687 |
| 1710 | CCCGGCAC U GGGAAGU | 5184 | ACUUCCCC CUGAUGAGGCCGUUAGGCCGAA IUGCCGGG | 5688 |
| 1720 | GGGAAGUC A AGAAUGGG | 5185 | CCCAUUCU CUGAUGAGGCCGUUAGGCCGAA IACUUCCC | 5689 |
| 1731 | AAUGGGGC C UGGGGCUC | 5186 | GAGCCCCA CUGAUGAGGCCGUUAGGCCGAA ICCCCAUU | 5690 |
| 1732 | AUGGGGCC U GGGGCUCU | 5187 | AGAGCCCC CUGAUGAGGCCGUUAGGCCGAA ICCCCCAU | 5691 |
| 1738 | CCUGGGGC U CUCAGGGA | 5188 | UCCCUGAG CUGAUGAGGCCGUUAGGCCGAA ICCCCAGG | 5692 |

TABLE IV-continued

Human IKK-gamma Inozyme and Substrate Sequence

| Pos | Substrate | Seq ID | Inozyme | Seq ID |
|---|---|---|---|---|
| 1740 | UGGGGCUC U CAGGGAGA | 5189 | UCUCCCUG CUGAUGAGGCCGUUAGGCCGAA IAGCCCCA | 5693 |
| 1742 | GGGCUCUC A GGGAGAAC | 5190 | GUUCUCCC CUGAUGAGGCCGUUAGGCCGAA IAGAGCCC | 5694 |
| 1751 | GGGAGAAC U GCUUCCCC | 5191 | GGGGAAGC CUGAUGAGGCCGUUAGGCCGAA IUUCUCCC | 5695 |
| 1754 | AGAACUGC U UCCCCUGG | 5192 | CCAGGGGA CUGAUGAGGCCGUUAGGCCGAA ICAGUUCU | 5696 |
| 1757 | ACUGCUUC C CCUGGCAG | 5193 | CUGCCAGG CUGAUGAGGCCGUUAGGCCGAA IAAGCAGU | 5697 |
| 1758 | CUGCUUCC C CUGGCAGA | 5194 | UCUGCCAG CUGAUGAGGCCGUUAGGCCGAA IGAAGCAG | 5698 |
| 1759 | UGCUUCCC C UGGCAGAG | 5195 | CUCUGCCA CUGAUGAGGCCGUUAGGCCGAA IGGAAGCA | 5699 |
| 1760 | GCUUCCCC U GGCAGAGC | 5196 | GCUCUGCC CUGAUGAGGCCGUUAGGCCGAA IGGGAAGC | 5700 |
| 1764 | CCCCUGGC A GAGCUGGG | 5197 | CCCAGCUC CUGAUGAGGCCGUUAGGCCGAA ICCAGGGG | 5701 |
| 1769 | GGCAGAGC U GGGUGGCA | 5198 | UGCCACCC CUGAUGAGGCCGUUAGGCCGAA ICUCUGCC | 5702 |
| 1777 | UGGGUGGC A GCUCUUCC | 5199 | GGAAGAGC CUGAUGAGGCCGUUAGGCCGAA ICCACCCA | 5703 |
| 1780 | GUGGCAGC U CUUCCUCC | 5200 | GGAGGAAG CUGAUGAGGCCGUUAGGCCGAA ICUGCCAC | 5704 |
| 1782 | GGCAGCUC U CCUCCCA | 5201 | UGGGAGGA CUGAUGAGGCCGUUAGGCCGAA IAGCUGCC | 5705 |
| 1785 | AGCUCUUC C UCCCACCG | 5202 | CGGUGGGA CUGAUGAGGCCGUUAGGCCGAA IAAGAGCU | 5706 |
| 1786 | GCUCUUCC U CCCACCGG | 5203 | CCGGUGGG CUGAUGAGGCCGUUAGGCCGAA IGAAGAGC | 5707 |
| 1788 | UCUUCCUC C CACCGGAC | 5204 | GUCCGGUG CUGAUGAGGCCGUUAGGCCGAA IAGGAAGA | 5708 |
| 1789 | CUUCCUCC C ACCGGACA | 5205 | UGUCCGGU CUGAUGAGGCCGUUAGGCCGAA IGAGGAAG | 5709 |
| 1790 | UUCCUCCC A CCGGACAC | 5206 | GUGUCCGG CUGAUGAGGCCGUUAGGCCGAA IGGACGAA | 5710 |
| 1792 | CCUCCCAC C GGACACCG | 5207 | CGGUGUCC CUGAUGAGGCCGUUAGGCCGAA IUGGGAGG | 5711 |
| 1797 | CACCGGAC A CCGACCCG | 5208 | CGGGUCGG CUGAUGAGGCCGUUAGGCCGAA IUCCGGUG | 5712 |
| 1799 | CCGGACAC C GACCCGCC | 5209 | GGCGGGUC CUGAUGAGGCCGUUAGGCCGAA IUGUCCGG | 5713 |
| 1803 | ACACCGAC C CGCCCGCC | 5210 | GGCGGGCG CUGAUGAGGCCGUUAGGCCGAA IUCGGUGU | 5714 |
| 1804 | CACCGACC C GCCCGCCG | 5211 | CGGCGGGC CUGAUGAGGCCGUUAGGCCGAA IGUCGGUG | 5715 |
| 1807 | CGACCCGC C CGCCGCUG | 5212 | CAGCGGCG CUGAUGAGGCCGUUAGGCCGAA ICGGGUCG | 5716 |
| 1808 | GACCCGCC C GCCGCUGU | 5213 | ACAGCGGC CUGAUGAGGCCGUUAGGCCGAA IGCGGGUC | 5717 |
| 1811 | CCGCCCGC C GCUGUGCC | 5214 | GGCACAGC CUGAUGAGGCCGUUAGGCCGAA ICGGGCGG | 5718 |
| 1814 | CCCGCCGC U GUGCCCUG | 5215 | CAGGGCAC CUGAUGAGGCCGUUAGGCCGAA ICGGCGGG | 5719 |
| 1819 | CGCUGUGC C CUGGGAGU | 5216 | ACUCCCAG CUGAUGAGGCCGUUAGGCCGAA ICACAGCG | 5720 |
| 1820 | GCUGUGCC C UGGGAGUG | 5217 | CACUCCCA CUGAUGAGGCCGUUAGGCCGAA IGCACAGC | 5721 |
| 1821 | CUGUGCCC U GGGAGUGC | 5218 | GCACUCCC CUGAUGAGGCCGUUAGGCCGAA IGGCACAG | 5722 |
| 1830 | GGGAGUGC U GCCCUCUU | 5219 | AAGAGGGC CUGAUGAGGCCGUUAGGCCGAA ICACUCCC | 5723 |
| 1833 | AGUGCUGC C CUCUUACC | 5220 | GGUAAGAG CUGAUGAGGCCGUUAGGCCGAA ICAGCACU | 5724 |
| 1834 | GUGCUGCC C UCUUACCA | 5221 | UGGUAAGA CUGAUGAGGCCGUUAGGCCGAA IGCAGCAC | 5725 |
| 1835 | UGCUGCCC U CUUACCAU | 5222 | AUGGUAAG CUGAUGAGGCCGUUAGGCCGAA IGGCAGCA | 5726 |
| 1837 | CUGCCCUC U UACCAUGC | 5223 | GCAUGGUA CUGAUGAGGCCGUUAGGCCGAA IAGGGCAG | 5727 |
| 1841 | CCUCUUAC C AUGCACAC | 5224 | GUGUGCAU CUGAUGAGGCCGUUAGGCCGAA IUAAGAGG | 5728 |
| 1842 | CUCUUACC A UGCACACG | 5225 | CGUGUGCA CUGAUGAGGCCGUUAGGCCGAA IGUAAGAG | 5729 |
| 1846 | UACCAUGC A CACGGGUG | 5226 | CACCCGUG CUGAUGAGGCCGUUAGGCCGAA ICAUGGUA | 5730 |
| 1848 | CCAUGCAC A CGGGUGCU | 5227 | AGCACCCG CUGAUGAGGCCGUUAGGCCGAA IUGCAUGG | 5731 |
| 1856 | ACGGGUGC U CUCCUUUU | 5228 | AAAAGGAG CUGAUGAGGCCGUUAGGCCGAA ICACCCGU | 5732 |
| 1858 | GGGUGCUC U CCUUUUGG | 5229 | CCAAAAGG CUGAUGAGGCCGUUAGGCCGAA IAGCACCC | 5733 |
| 1860 | GUGCUCUC C UUUUGGGC | 5230 | GCCCAAAA CUGAUGAGGCCGUUAGGCCGAA IAGAGCAC | 5734 |
| 1861 | UGCUCUCC U UUUGGGCU | 5231 | AGCCCAAA CUGAUGAGGCCGUUAGGCCGAA IGAGAGCA | 5735 |
| 1869 | UUUUGGGC U GCAUGCUA | 5232 | UAGCAUGC CUGAUGAGGCCGUUAGGCCGAA ICCCAAAA | 5736 |
| 1872 | UGGGCUGC A UGCUAUUC | 5233 | GAAUAGCA CUGAUGAGGCCGUUAGGCCGAA ICAGCCCA | 5737 |
| 1876 | CUGCAUGC U AUUCCAUU | 5234 | AAUGGAAU CUGAUGAGGCCGUUAGGCCGAA ICAUGCAG | 5738 |
| 1881 | UGCUAUUC C AUUUGCA | 5235 | UGCAAAAU CUGAUGAGGCCGUUAGGCCGAA IAAUAGCA | 5739 |
| 1882 | GCUAUUCC A UUUGCAG | 5236 | CUGCAAAA CUGAUGAGGCCGUUAGGCCGAA IGAAUAGC | 5740 |
| 1889 | CAUUUGC A GCCAGACC | 5237 | GGUCUGGC CUGAUGAGGCCGUUAGGCCGAA ICAAAAUG | 5741 |
| 1892 | UUUGCAGC C AGACCGAU | 5238 | AUCGGUCU CUGAUGAGGCCGUUAGGCCGAA ICUGCAAA | 5742 |
| 1893 | UUGCAGCC A GACCGAUG | 5239 | CAUCGGUC CUGAUGAGGCCGUUAGGCCGAA IGCUGCAA | 5743 |
| 1897 | AGCCAGAC C GAUGUGUA | 5240 | UACACAUC CUGAUGAGGCCGUUAGGCCGAA IUCUGGCU | 5744 |
| 1912 | UAUUUAAC C AGUCACUA | 5241 | UAGUCACU CUGAUGAGGCCGUUAGGCCGAA IUUAAAUA | 5745 |
| 1913 | AUUUAACC A GUCACUAU | 5242 | AUAGUGAC CUGAUGAGGCCGUUAGGCCGAA IGUUAAAU | 5746 |
| 1917 | AACCAGUC A CUAUUGAU | 5243 | AUCAAUAG CUGAUGAGGCCGUUAGGCCGAA IACUGGUU | 5747 |
| 1919 | CCAGUCAC U AUUGAUGG | 5244 | CCAUCAAU CUGAUGAGGCCGUUAGGCCGAA IUGACUGG | 5748 |
| 1930 | UGAUGGAC A UUUGGGUU | 5245 | AACCCAAA CUGAUGAGGCCGUUAGGCCGAA IUCCAUCA | 5749 |
| 1944 | GUUGUUUC C CAUCUUUU | 5246 | AAAAGAUG CUGAUGAGGCCGUUAGGCCGAA IAAACAAC | 5750 |
| 1945 | UUGUUUCC C AUCUUUUU | 5247 | AAAAAGAU CUGAUGAGGCCGUUAGGCCGAA IGAAACAA | 5751 |
| 1946 | UGUUUCCC A UCUUUUUG | 5248 | CAAAAAGA CUGAUGAGGCCGUUAGGCCGAA IGGAAACA | 5752 |
| 1949 | UUCCCAUC U UUUUGUUA | 5249 | UAACAAAA CUGAUGAGGCCGUUAGGCCGAA IAUGGGAA | 5753 |
| 1959 | UUUGUUAC C AUAAAUAA | 5250 | UUAUUUAU CUGAUGAGGCCGUUAGGCCGAA IUAACAAA | 5754 |
| 1960 | UUGUUACC A UAAAUAAU | 5251 | AUUAUUUA CUGAUGAGGCCGUUAGGCCGAA IGUAACAA | 5755 |
| 1972 | AUAAUGGC A UAGUAAAA | 5252 | UUUUACUA CUGAUGAGGCCGUUAGGCCGAA ICCAUUAU | 5756 |

Input Sequence NM_003639. Cut Site = CH/.
Arm Length = 8. Core Sequence CUGAUGAG GCCGUUAGGC CGAA
NM_003639 (*Homo sapiens* inhibitor of kappa light polypeptide gene enhancer in B-cells, kinase gamma (IKBKG), mRNA.; 1994 bp)

Underlined region can be any X sequence or linker, as described herein. "I" stands for Inosine.

TABLE V

Human IKK-gamma Zinzyme and Substrate Sequence

| Pos | Substrate | Seq ID | Zinzyme | Seq ID |
|---|---|---|---|---|
| 13 | CGAGCAUG G CCCUUGUG | 5757 | CACAAGGG GCCGAAAGGCGAGUGAGGUCU CAUGCUCG | 6034 |
| 19 | UGGCCCUU G UGAUCCAG | 5758 | CUGGAUCA GCCGAAAGGCGAGUGAGGUCU AAGGGCCA | 6035 |
| 28 | UGAUCCAG G UGGGGAAA | 5759 | UUUCCCCA GCCGAAAGGCGAGUGAGGUCU CUGGAUCA | 6036 |
| 42 | AAACUAAG G CCCAGAGA | 5760 | UCUCUGGG GCCGAAAGGCGAGUGAGGUCU CUUAGUUU | 6037 |
| 52 | CCAGAGAA G UGAGGACC | 5761 | GGUCCUCA GCCGAAAGGCGAGUGAGGUCU UUCUCUGG | 6038 |
| 63 | AGGACCCC G CAGACUAU | 5762 | AUAGUCUG GCCGAAAGGCGAGUGAGGUCU GGGGUCCU | 6039 |
| 80 | CAAUCCCA G UCUCUUCC | 5763 | GGAAGAGA GCCGAAAGGCGAGUGAGGUCU UGGGAUUG | 6040 |
| 100 | CACUCCCU G UGAAGCUC | 5764 | GAGCUUCA GCCGAAAGGCGAGUGAGGUCU AGGGAGUG | 6041 |
| 105 | CCUGUGAA G CUCUCCAG | 5765 | CUGGAGAG GCCGAAAGGCGAGUGAGGUCU UUCACAGG | 6042 |
| 113 | GCUCUCCA G CAUCAUCG | 5766 | CGAUGAUG GCCGAAAGGCGAGUGAGGUCU UGGAGAGC | 6043 |
| 124 | UCAUCGAG G UCCCAUCA | 5767 | UGAUGGGA GCCGAAAGGCGAGUGAGGUCU CUCGAUGA | 6044 |
| 133 | UCCCAUCA G CCCUUGCC | 5768 | GGCAAGGG GCCGAAAGGCGAGUGAGGUCU UGAUGGGA | 6045 |
| 139 | CAGCCCUU G CCCUGUUG | 5769 | CAACAGGG GCCGAAAGGCGAGUGAGGUCU AAGGGCUG | 6046 |
| 144 | CUUGCCCU G UUGGAUGA | 5770 | UCAUCCAA GCCGAAAGGCGAGUGAGGUCU AGGGCAAG | 6047 |
| 157 | AUGAAUAG G CACCUCUG | 5771 | CAGAGGUG GCCGAAAGGCGAGUGAGGUCU CUAUUCAU | 6048 |
| 171 | CUGGAAGA G CCAACUGU | 5772 | ACAGUUGG GCCGAAAGGCGAGUGAGGUCU UCUUCCAG | 6049 |
| 178 | AGCCAACU G UGUGAGAU | 5773 | AUCUCACA GCCGAAAGGCGAGUGAGGUCU AGUUGGCU | 6050 |
| 180 | CCAACUGU G UGAGAUGG | 5774 | CCAUCUCA GCCGAAAGGCGAGUGAGGUCU ACAGUUGG | 6051 |
| 188 | GUGAGAUG G UGCAGCCC | 5775 | GGGCUGCA GCCGAAAGGCGAGUGAGGUCU CAUCUCAC | 6052 |
| 190 | GAGAUGGU G CAGCCCAG | 5776 | CUGGGCUG GCCGAAAGGCGAGUGAGGUCU ACCAUCUC | 6053 |
| 193 | AUGGUGCA G CCCAGUGG | 5777 | CCACUGGG GCCGAAAGGCGAGUGAGGUCU UGCACCAU | 6054 |
| 198 | GCAGCCCA G UGGUGGCC | 5778 | GGCCACCA GCCGAAAGGCGAGUGAGGUCU UGGGCUGC | 6055 |
| 201 | GCCCAGUG G UGGCCCGG | 5779 | CCGGGCCA GCCGAAAGGCGAGUGAGGUCU CACUGGGC | 6056 |
| 204 | CAGUGGUG G CCCGGCAG | 5780 | CUGCCGGG GCCGAAAGGCGAGUGAGGUCU CACCACUG | 6057 |
| 209 | GUGGCCCG G CAGCAGAU | 5781 | AUCUGCUG GCCGAAAGGCGAGUGAGGUCU CGGGCCAC | 6058 |
| 212 | GCCCGGCA G CAGAUCAG | 5782 | CUGAUCUG GCCGAAAGGCGAGUGAGGUCU UGCCGGGC | 6059 |
| 224 | AUCAGGAC G UACUGGGC | 5783 | GCCCAGUA GCCGAAAGGCGAGUGAGGUCU GUCCUGAU | 6060 |
| 231 | CGUACUGG G CGAAGAGU | 5784 | ACUCUUCG GCCGAAAGGCGAGUGAGGUCU CCAGUACG | 6061 |
| 238 | GGCGAAGA G UCUCCUCU | 5785 | AGAGGAGA GCCGAAAGGCGAGUGAGGUCU UCUUCGCC | 6062 |
| 253 | CUGGGGAA G CCAGCCAU | 5786 | AUGGCUGG GCCGAAAGGCGAGUGAGGUCU UUCCCCAG | 6063 |
| 257 | GGAAGCCA G CCAUGCUG | 5787 | CAGCAUGG GCCGAAAGGCGAGUGAGGUCU UGGCUUCC | 6064 |
| 262 | CCAGCCAU G CUGCACCU | 5788 | AGGUGCAG GCCGAAAGGCGAGUGAGGUCU AUGGCUGG | 6065 |
| 265 | GCCAUGCU G CACCGCC | 5789 | GGCAGGUG GCCGAAAGGCGAGUGAGGUCU AGCAUGGC | 6066 |
| 271 | CUGCACCU G CCUUCAGA | 5790 | UCUGAAGG GCCGAAAGGCGAGUGAGGUCU AGGUGCAG | 6067 |
| 285 | AGAACAGG G CGCUCCUG | 5791 | CAGGAGCG GCCGAAAGGCGAGUGAGGUCU CCUGUUCU | 6068 |
| 287 | AACAGGGC G CUCCUGAG | 5792 | CUCAGGAG GCCGAAAGGCGAGUGAGGUCU GCCCGUU | 6069 |
| 304 | ACCCUCCA G CGCUGCCU | 5793 | AGGCAGCG GCCGAAAGGCGAGUGAGGUCU UGGAGGGU | 6070 |
| 306 | CCUCCAGC G CUGCCUGG | 5794 | CCAGGCAG GCCGAAAGGCGAGUGAGGUCU GCUGGAGG | 6071 |
| 309 | CCAGCGCU G CCUGGAGG | 5795 | CCUCCAGG GCCGAAAGGCGAGUGAGGUCU AGCGCUGG | 6072 |
| 328 | AAUCAAGA G CUCCGAGA | 5796 | UCUCGGAG GCCGAAAGGCGAGUGAGGUCU UCUUGAUU | 6073 |
| 338 | UCCGAGAU G CCAUCCGG | 5797 | CCGGAUGG GCCGAAAGGCGAGUGAGGUCU AUCUCGGA | 6074 |
| 346 | GCCAUCCG G CAGAGCAA | 5798 | UUGCUCUG GCCGAAAGGCGAGUGAGGUCU CGGAUGGC | 6075 |
| 351 | CCGGCAGA G CAACCAGA | 5799 | UCUGGUUG GCCGAAAGGCGAGUGAGGUCU UCUGCCGG | 6076 |
| 364 | CAGAUUCU G CGGGAGCG | 5800 | CGCUCCCG GCCGAAAGGCGAGUGAGGUCU AGAAUCUG | 6077 |
| 370 | CUGCGGGA G CGCUGCGA | 5801 | UCGCAGCG GCCGAAAGGCGAGUGAGGUCU UCCCGCAG | 6078 |
| 372 | GCGGGAGC G CUGCGAGG | 5802 | CCUCGCAG GCCGAAAGGCGAGUGAGGUCU GCUCCCGC | 6079 |
| 375 | GGAGCGCU G CGAGGAGC | 5803 | GCUCCUCG GCCGAAAGGCGAGUGAGGUCU AGCGCUCC | 6080 |
| 382 | UGCGAGGA G CUUCUGCA | 5804 | UGCAGAAG GCCGAAAGGCGAGUGAGGUCU UCCUCGCA | 6081 |
| 388 | GAGCUUCU G CAUUUCCA | 5805 | UGGAAAUG GCCGAAAGGCGAGUGAGGUCU AGAAGCUC | 6082 |
| 398 | AUUUCCAA G CCAGCCAG | 5806 | CUGGCUGG GCCGAAAGGCGAGUGAGGUCU UUGGAAAU | 6083 |
| 402 | CCAAGCCA G CCAGAGGG | 5807 | CCCUCUGG GCCGAAAGGCGAGUGAGGUCU UGGCUUGG | 6084 |
| 421 | GAGAAGGA G UUCCUCAU | 5808 | AUGAGGAA GCCGAAAGGCGAGUGAGGUCU UCCUUCUC | 6085 |
| 430 | UUCCUCAU G UGCAAGUU | 5809 | AACUUGCA GCCGAAAGGCGAGUGAGGUCU AUGAGGAA | 6086 |
| 432 | CCUCAUGU G CAAGUUCC | 5810 | GGAACUUG GCCGAAAGGCGAGUGAGGUCU ACAUGAGG | 6087 |
| 436 | AUGUGCAA G UUCAGGA | 5811 | UCCUGGAA GCCGAAAGGCGAGUGAGGUCU UUGCACAU | 6088 |
| 446 | UCCAGGAG G CCAGGAAA | 5812 | UUUCCUGG GCCGAAAGGCGAGUGAGGUCU CUCCUGGA | 6089 |
| 458 | GGAAACUG G UGGAGAGA | 5813 | UCUCUCCA GCCGAAAGGCGAGUGAGGUCU CAGUUUCC | 6090 |
| 471 | GAGACUCG G CCUGGAGA | 5814 | UCUCCAGG GCCGAAAGGCGAGUGAGGUCU CGAGUCUC | 6091 |
| 481 | CUGGAGAA G CUCGAUCU | 5815 | AGAUCGAG GCCGAAAGGCGAGUGAGGUCU UUCUCCAG | 6092 |
| 496 | CUGAGAG G CAGAAGGA | 5816 | UCCUUCUG GCCGAAAGGCGAGUGAGGUCU CUCUUCAG | 6093 |
| 505 | CAGAAGGA G CAGGCUCU | 5817 | AGAGCCUG GCCGAAAGGCGAGUGAGGUCU UCCUUCUG | 6094 |
| 509 | AGGAGCAG G CUCUGCGG | 5818 | CCGCAGAG GCCGAAAGGCGAGUGAGGUCU CUGCUCCU | 6095 |
| 514 | CAGGCUCU G CGGGAGGU | 5819 | ACCUCCCG GCCGAAAGGCGAGUGAGGUCU AGAUCCUG | 6096 |
| 521 | UGCGGGAG G UGGAUCAC | 5820 | GUGCUCCA GCCGAAAGGCGAGUGAGGUCU CUCCCGCA | 6097 |
| 526 | GAGGUGGA G CACCUGAA | 5821 | UUCAGGUG GCCGAAAGGCGAGUGAGGUCU UCCACCUC | 6098 |
| 540 | GAAGAGAU G CCAGCAGC | 5822 | GCUGCUGG GCCGAAAGGCGAGUGAGGUCU AUCUCUUC | 6099 |
| 544 | AGAUGCCA G CAGCAGAU | 5823 | AUCUGCUG GCCGAAAGGCGAGUGAGGUCU UGGCAUCU | 6100 |
| 547 | UGCCAGCA G CAGAUGGC | 5824 | GCCAUCUG GCCGAAAGGCGAGUGAGGUCU UGCUGGCA | 6101 |
| 554 | AUCAGAUG G CUGAGGAC | 5825 | GUCCUCAG GCCGAAAGGCGAGUGAGGUCU CAUCUGCU | 6102 |
| 566 | AGGACAAG G CCUCUGUG | 5826 | CACAGAGG GCCGAAAGGCGAGUGAGGUCU CUUGUCCU | 6103 |
| 572 | AGGCCUCU G UGAAAGCC | 5827 | GGCUUUCA GCCGAAAGGCGAGUGAGGUCU AGAGGCCU | 6104 |
| 578 | CUGUGAAA G CCCAGGUG | 5828 | CACCUGGG GCCGAAAGGCGAGUGAGGUCU UUUCACAG | 6105 |
| 584 | AAGCCCAG G UGACGUCC | 5829 | GGACGUCA GCCGAAAGGCGAGUGAGGUCU CUGGGCUU | 6106 |
| 589 | CAGGUGAC G UCCUUGCU | 5830 | AGCAAGGA GCCGAAAGGCGAGUGAGGUCU GUCACCUG | 6107 |

TABLE V-continued

Human IKK-gamma Zinzyme and Substrate Sequence

| Pos | Substrate | Seq ID | Zinzyme | Seq ID |
|-----|-----------|--------|---------|--------|
| 595 | ACGUCCUU G CUCGGGGA | 5831 | UCCCCGAG GCCGAAAGGCGAGUGAGGUCU AAGGACGU | 6108 |
| 604 | CUCGGGGA G CUGCAGGA | 5832 | UCCUGCAG GCCGAAAGGCGAGUGAGGUCU UCCCCGAG | 6109 |
| 607 | GGGGAGCU G CAGGAGAG | 5833 | CUCUCCUG GCCGAAAGGCGAGUGAGGUCU AGCUCCCC | 6110 |
| 615 | GCAGGAGA G CCAGAGUC | 5834 | GACUCUGG GCCGAAAGGCGAGUGAGGUCU UCUCCUGC | 6111 |
| 621 | GAGCCAGA G UCGCUUGG | 5835 | CCAAGCGA GCCGAAAGGCGAGUGAGGUCU UCUGUCUC | 6112 |
| 624 | CCAGAGUC G CUUGGAGG | 5836 | CCUCCAAG GCCGAAAGGCGAGUGAGGUCU GACUCUGG | 6113 |
| 632 | GCUUGGAG G CUGCCACU | 5837 | AGUGUCAG GCCGAAAGGCGAGUGAGGUCU CUCCAAGC | 6114 |
| 635 | UGGAGGCU G CCACUAAG | 5838 | CUUAGUGG GCCGAAAGGCGAGUGAGGUCU AGCCUCCA | 6115 |
| 648 | UAAGGAAU G CCAGGCUC | 5839 | GAGCCUGG GCCGAAAGGCGAGUGAGGUCU AUUCCUUA | 6116 |
| 653 | AAUGCCAG G CUCUGGAG | 5840 | CUCCAGAG GCCGAAAGGCGAGUGAGGUCU CUGGCAUU | 6117 |
| 663 | UCUGGAGG G UCGGGCCC | 5841 | GGGCCCGA GCCGAAAGGCGAGUGAGGUCU CCUCCAGA | 6118 |
| 668 | AGGGUCGG G CCCGGGCG | 5842 | CGCCCGGG GCCGAAAGGCGAGUGAGGUCU CCGACCCU | 6119 |
| 674 | GGGCCCGG G CGGCCAGC | 5843 | GCUGGCCG GCCGAAAGGCGAGUGAGGUCU CCGGGCCC | 6120 |
| 677 | CCCGGGCG G CCACGCAG | 5844 | CUCGCUGG GCCGAAAGGCGAGUGAGGUCU CGCCCGGG | 6121 |
| 681 | GGCGGCCA G CGAGCAGG | 5845 | CCUGCUCG GCCGAAAGGCGAGUGAGGUCU UGGCCGCC | 6122 |
| 685 | GCCAGCGA G CAGGCGCG | 5846 | CGCGCCUG GCCGAAAGGCGAGUGAGGUCU UCGCUGGC | 6123 |
| 689 | GCGAGCAG G CGCGGCAG | 5847 | CUGCCGCG GCCGAAAGGCGAGUGAGGUCU CUGCUCGC | 6124 |
| 691 | GAGCAGGC G CGGCAGCU | 5848 | AGCUGCCG GCCGAAAGGCGAGUGAGGUCU GCCUGCUC | 6125 |
| 694 | CAGGCGCG G CAGCUGGA | 5849 | UCCAGCUG GCCGAAAGGCGAGUGAGGUCU CGCGCCUG | 6126 |
| 697 | GCGCGGCA G CUGGAGAG | 5850 | CUCUCCAG GCCGAAAGGCGAGUGAGGUCU UGCCGCUG | 6127 |
| 705 | GCUGGAGA G UGAGCGCG | 5851 | CGCGCUCA GCCGAAAGGCGAGUGAGGUCU UCUCCAGC | 6128 |
| 709 | GAGAGUGA G CGCGAGGC | 5852 | GCCUCGCG GCCGAAAGGCGAGUGAGGUCU UCACUCUC | 6129 |
| 711 | GAGUGAGC G CGAGGCGC | 5853 | GCGCCUCG GCCGAAAGGCGAGUGAGGUCU GCUCACUC | 6130 |
| 716 | AGCGCGAG G CGCUGCAG | 5854 | CUGCAGCG GCCGAAAGGCGAGUGAGGUCU CUCGCGCU | 6131 |
| 718 | CGCGAGGC G CUGCAGCA | 5855 | UGCUGCAG GCCGAAAGGCGAGUGAGGUCU GCCUCGCG | 6132 |
| 721 | GAGGCGCU G CAGCAGCA | 5856 | UGCUGCUG GCCGAAAGGCGAGUGAGGUCU AGCGCCUC | 6133 |
| 724 | GCGCUGCA G CAGCAGCA | 5857 | UGCUGCUG GCCGAAAGGCGAGUGAGGUCU UGCAGCGC | 6134 |
| 727 | CUGCAGCA G CAGCACAG | 5858 | CUGUGCUG GCCGAAAGGCGAGUGAGGUCU UGCUGCAG | 6135 |
| 730 | CAGCAGCA G CACAGCGU | 5859 | ACGCUGUG GCCGAAAGGCGAGUGAGGUCU UGCUGCUG | 6136 |
| 735 | GCAGCACA G CGUGCAGG | 5860 | CCUGCACG GCCGAAAGGCGAGUGAGGUCU UGUGCUGC | 6137 |
| 737 | AGCACAGC G UGCAGGUG | 5861 | CACCUGCA GCCGAAAGGCGAGUGAGGUCU GCUGUGCU | 6138 |
| 739 | CACAGCGU G CAGGUGGA | 5862 | UCCACCUG GCCGAAAGGCGAGUGAGGUCU ACGCUGUG | 6139 |
| 743 | GCGUGCAG G UGGACCAG | 5863 | CUGGUCCA GCCGAAAGGCGAGUGAGGUCU CUGCACGC | 6140 |
| 751 | GUGGACCA G CUGCGCAU | 5864 | AUGCGCAG GCCGAAAGGCGAGUGAGGUCU UGGUCCAC | 6141 |
| 754 | GACCAGCU G CGCAUGCA | 5865 | UGCAUGCG GCCGAAAGGCGAGUGAGGUCU AGCUGGUC | 6142 |
| 756 | CCAGCUGC G CAUGCAGG | 5866 | CCUGCAUG GCCGAAAGGCGAGUGAGGUCU GCAGCUGG | 6143 |
| 760 | CUGCGCAU G CAGGGCCA | 5867 | UGGCCCUG GCCGAAAGGCGAGUGAGGUCU AUGCGCAG | 6144 |
| 765 | CAUGCAGG G CCAGAGCG | 5868 | CGCUCUGG GCCGAAAGGCGAGUGAGGUCU CCUGCAUG | 6145 |
| 771 | GGGCCAGA G CGUGGAGG | 5869 | CCUCCACG GCCGAAAGGCGAGUGAGGUCU UCUGGCCC | 6146 |
| 773 | GCCAGAGC G UGGAGGCC | 5870 | GGCCUCCA GCCGAAAGGCGAGUGAGGUCU GCUCUGGC | 6147 |
| 779 | GCGUGGAG G CCGCGCUC | 5871 | GAGCGCGG GCCGAAAGGCGAGUGAGGUCU CUCCACGC | 6148 |
| 782 | UGGAGGCC G CGCUCCGC | 5872 | GCGGAGCG GCCGAAAGGCGAGUGAGGUCU GGCCUCCA | 6149 |
| 784 | GACGCCGC G CUCCGCAU | 5873 | AUGCGGAG GCCGAAAGGCGAGUGAGGUCU GCGGCCUC | 6150 |
| 789 | CGCGCUCC G CAUGGAGC | 5874 | GCUCCAUG GCCGAAAGGCGAGUGAGGUCU GGACCGCG | 6151 |
| 796 | CGCAUGGA G CGCCAGGC | 5875 | GCCUGGCG GCCGAAAGGCGAGUGAGGUCU UCCAUCCG | 6152 |
| 798 | CAUGGAGC G CCAGCCCG | 5876 | CGGGCUGG GCCGAAAGGCGAGUGAGGUCU GCUCCAUG | 6153 |
| 803 | AGCGCCAC G CCGCCUCG | 5877 | CGAGCCGG GCCGAAAGGCGAGUGAGGUCU CUGGCGCU | 6154 |
| 806 | GCCCAGGC G CCUCGGAG | 5878 | CUCCGAGG GCCGAAAGGCGAGUGAGGUCU GCCCUGGC | 6155 |
| 826 | AAGAGGAA G CUGGCCAG | 5879 | UGGGCCAG GCCGAAAGGCGAGUGAGGUCU UUCCUCUU | 6156 |
| 830 | GGAAGCUG G CCCAGUUG | 5880 | CAACUGGG GCCGAAAGGCGAGUGAGGUCU CAGCUUCC | 6157 |
| 835 | CUGGCCCA G UUGCAGGU | 5881 | ACCUGCAA GCCGAAAGGCGAGUGAGGUCU UGGGCCAG | 6158 |
| 838 | GCCCAGUU G CAGGUGGC | 5882 | GCCACCUG GCCGAAAGGCGAGUGAGGUCU AACUGGGC | 6159 |
| 842 | AGUUGCAG G UGGCCUAU | 5883 | AUAGGCCA GCCGAAAGGCGAGUGAGGUCU CUGCAACU | 6160 |
| 845 | UGCAGGUG G CCUAUCAC | 5884 | GUGAUAGG GCCGAAAGGCGAGUGAGGUCU CACCUGCA | 6161 |
| 856 | UAUCACCA G CUCUUCCA | 5885 | UGGAAGAG GCCGAAAGGCGAGUGAGGUCU UGGUGAUA | 6162 |
| 888 | CAUCAAGA G CAGCGUGG | 5886 | CCACCCUG GCCGAAAGGCGAGUGAGGUCU UCUUGAUG | 6163 |
| 891 | CAAGAGCA G CGUGCUGG | 5887 | CCACCACG GCCGAAAGGCGAGUGAGGUCU UGCUCUUG | 6164 |
| 893 | AGACCAGC G UGGUGCCC | 5888 | GCCCACCA GCCGAAAGGCGAGUGAGGUCU GCUGCUCU | 6165 |
| 896 | GCACCGUG G UGGGCAGU | 5889 | ACUGCCCA GCCGAAAGGCGAGUGAGGUCU CACGCUGC | 6166 |
| 900 | CGUGGUCG G CAGUGAGC | 5890 | GCUCACUG GCCGAAAGGCGAGUGAGGUCU CCACCACG | 6167 |
| 903 | GGUGGGCA G UCAGCGGA | 5891 | UCCGCUCA GCCGAAAGGCGAGUGAGGUCU UGCCCACC | 6168 |
| 907 | GGCAGUGA G CGGAAGCG | 5892 | CGCUUCCG GCCGAAAGGCGAGUGAGGUCU UCACUGCC | 6169 |
| 913 | GAGCGGAA G CGAGGAAU | 5893 | AUUCCUCG GCCGAAAGGCGAGUGAGGUCU UUCCGCUC | 6170 |
| 922 | CGAGGAAU G CAGCUGGA | 5894 | UCCAGCUG GCCGAAAGGCGAGUGAGGUCU AUUCCUCG | 6171 |
| 925 | GGAAUGCA G CUGGAAGA | 5895 | UCUUCCAG GCCGAAAGGCGAGUGAGGUCU UGCAUUCC | 6172 |
| 943 | CUCAAACA G CAGCUCCA | 5896 | UGGAGCUG GCCGAAAGGCGAGUGAGGUCU UGUUUGAC | 6173 |
| 946 | AAACAGCA G CUCCAGCA | 5897 | UGCUGGAC GCCGAAAGGCGAGUGAGGUCU UGCUGUUU | 6174 |
| 952 | CAGCUCCA G CAGCCCGA | 5898 | UCGGCCUG GCCGAAAGGCGAGUGAGGUCU UGGAGCUG | 6175 |
| 956 | UCCAGCAC G CCGAGGAG | 5899 | CUCCUCGG GCCGAAAGGCGAGUGAGGUCU CUGCUGGA | 6176 |
| 965 | CCGAGGAG G CCCUGGUG | 5900 | CACCAGGG GCCGAAAGGCGAGUGAGGUCU CUCCUCGG | 6177 |
| 971 | AGGCCCUG G UGGCCAAA | 5901 | UUUGGCCA GCCGAAAGGCGAGUGAGGUCU CAGGGCCU | 6178 |
| 974 | CCCUGGUG G CCAAACAG | 5902 | CUGUUUGG GCCGAAAGGCGAGUGAGGUCU CACCAGGG | 6179 |
| 986 | AACAGGAG G UGAUCGAU | 5903 | AUCGAUCA GCCGAAAGGCGAGUGAGGUCU CUCCUGUU | 6180 |
| 997 | AUCGAUAA G CUGAAGGA | 5904 | UCCUUCAG GCCGAAAGGCGAGUGAGGUCU UUAUCGAU | 6181 |

TABLE V-continued

Human IKK-gamma Zinzyme and Substrate Sequence

| Pos | Substrate | Seq ID | Zinzyme | Seq ID |
|---|---|---|---|---|
| 1010 | AGGAGGAG G CCGAGCAG | 5905 | CUGCUCGG GCCGAAAGGCGAGUGAGGUCU CUCCUCCU | 6182 |
| 1015 | GAGGCCGA G CAGCACAA | 5906 | UUGUGCUG GCCGAAAGGCGAGUGAGGUCU UCGGCCUC | 6183 |
| 1018 | GCCGAGCA G CACAAGAU | 5907 | AUCUUGUG GCCGAAAGGCGAGUGAGGUCU UGCUCGGC | 6184 |
| 1028 | ACAAGAUU G UGAUGGAG | 5908 | CUCCAUCA GCCGAAAGGCGAGUGAGGUCU AAUCUUGU | 6185 |
| 1040 | UGGAGACC G UUCCGGUG | 5909 | CACCGGAA GCCGAAAGGCGAGUGAGGUCU GGUCUCCA | 6186 |
| 1046 | CCGUUCCG G UGCUGAAG | 5910 | CUUCAGCA GCCGAAAGGCGAGUGAGGUCU CGGAACGG | 6187 |
| 1048 | GUUCCGGU G CUGAAGGC | 5911 | GCCUUCAG GCCGAAAGGCGAGUGAGGUCU ACCGGAAC | 6188 |
| 1055 | UGCUGAAG G CCCAGGCG | 5912 | CGCCUGGG GCCGAAAGGCGAGUGAGGUCU CUUCAGCA | 6189 |
| 1061 | AGGCCCAG G CGGAUAUC | 5913 | GAUAUCCG GCCGAAAGGCGAGUGAGGUCU CUGGGCCU | 6190 |
| 1076 | UCUACAAG G CGGACUUC | 5914 | GAAGUCCG GCCGAAAGGCGAGUGAGGUCU CUUGUAGA | 6191 |
| 1088 | ACUUCCAG G CUGAGAGG | 5915 | CCUCUCAG GCCGAAAGGCGAGUGAGGUCU CUGGAAGU | 6192 |
| 1096 | GCUGAGAG G CAGGCCCG | 5916 | CGGGCCUG GCCGAAAGGCGAGUGAGGUCU CUCUCAGC | 6193 |
| 1100 | AGAGGCAG G CCCGGGAG | 5917 | CUCCCGGG GCCGAAAGGCGAGUGAGGUCU CUGCCUCU | 6194 |
| 1111 | CGGGAGAA G CUGGCCGA | 5918 | UCGGCCAG GCCGAAAGGCGAGUGAGGUCU UUCUCCCG | 6195 |
| 1115 | AGAAGCUG G CCGAGAAG | 5919 | CUUCUCGG GCCGAAAGGCGAGUGAGGUCU CAGCUUCU | 6196 |
| 1129 | AAGAAGGA G CUCCUGCA | 5920 | UGCAGGAG GCCGAAAGGCGAGUGAGGUCU UCCUUCUU | 6197 |
| 1135 | GAGCUCCU G CAGGAGCA | 5921 | UGCUCCUG GCCGAAAGGCGAGUGAGGUCU AGGAGCUC | 6198 |
| 1141 | CUGCAGGA G CAGCUGGA | 5922 | UCCAGCUG GCCGAAAGGCGAGUGAGGUCU UCCUGCAG | 6199 |
| 1144 | CAGGACCA G CUGGAGCA | 5923 | UGCUCCAG GCCGAAAGGCGAGUGAGGUCU UGCUCCUG | 6200 |
| 1150 | CAGCUGGA G CAGCUGCA | 5924 | UGCAGCUG GCCGAAAGGCGAGUGAGGUCU UCCAGCUG | 6201 |
| 1153 | CUGGAGCA G CUGCAGAG | 5925 | CUCUGCAG GCCGAAAGGCGAGUGAGGUCU UGCUCCAG | 6202 |
| 1156 | GAGCAGCU G CAGAGGGA | 5926 | UCCCUCUG GCCGAAAGGCGAGUGAGGUCU AGCUGCUC | 6203 |
| 1165 | CAGAGGGA G UACAGCAA | 5927 | UUGCUGUA GCCGAAAGGCGAGUGAGGUCU UCCCUCUG | 6204 |
| 1170 | GGAGUACA G CAAACUGU | 5928 | UCAGUUUG GCCGAAAGGCGAGUGAGGUCU UGUACUCC | 6205 |
| 1181 | AACUGAAG G CCAGCUGU | 5929 | ACAGCUGG GCCGAAAGGCGAGUGAGGUCU CUUCAGUU | 6206 |
| 1185 | GAAGGCCA G CUGUCAGG | 5930 | CCUGACAG GCCGAAAGGCGAGUGAGGUCU UGGCCUUC | 6207 |
| 1188 | GGCCAGCU G UCAGGAGU | 5931 | ACUCCUGA GCCGAAAGGCGAGUGAGGUCU AGCUGGCC | 6208 |
| 1195 | UGUCAGGA G UCGGCCAG | 5932 | CUGGCCGA GCCGAAAGGCGAGUGAGGUCU UCCUGACA | 6209 |
| 1199 | AGGAGUCG G CCAGGAUC | 5933 | GAUCCUGG GCCGAAAGGCGAGUGAGGUCU CGACUCCU | 6210 |
| 1222 | AUGAGGAA G CGGCAUGU | 5934 | ACAUGCCG GCCGAAAGGCGAGUGAGGUCU UUCCUCAU | 6211 |
| 1225 | AGGAAGCG G CAUGUCGA | 5935 | UCGACAUG GCCGAAAGGCGAGUGAGGUCU CGCUUCCU | 6212 |
| 1229 | AGCGGCAU G UCGAGGUC | 5936 | GACCUCGA GCCGAAAGGCGAGUGAGGUCU AUGCCGCU | 6213 |
| 1235 | AUGUCGAG G UCUCCCAG | 5937 | CUGGGAGA GCCGAAAGGCGAGUGAGGUCU CUCGACAU | 6214 |
| 1244 | UCUCCCAG G CCCCCUUG | 5938 | CAAGGGGG GCCGAAAGGCGAGUGAGGUCU CUGGGAGA | 6215 |
| 1252 | GCCCCCUU G CCCCCCGC | 5939 | GCGGGGGG GCCGAAAGGCGAGUGAGGUCU AAGGGGGC | 6216 |
| 1259 | UGCCCCCC G CCCCUGCC | 5940 | GGCAGGGG GCCGAAAGGCGAGUGAGGUCU GGGGGGCA | 6217 |
| 1265 | CCGCCCCU G CCUACCUC | 5941 | GAGGUAGG GCCGAAAGGCGAGUGAGGUCU AGGGGCGG | 6218 |
| 1286 | CUCCCCUG G CCCUGCCC | 5942 | GGGCAGGG GCCGAAAGGCGAGUGAGGUCU CAGGGGAG | 6219 |
| 1291 | CUGGCCCU G CCCAGCCA | 5943 | UGGCUGGG GCCGAAAGGCGAGUGAGGUCU AGGGCCAG | 6220 |
| 1296 | CCUGCCCA G CCAGAGGA | 5944 | UCCUCUGG GCCGAAAGGCGAGUGAGGUCU UGGGCAGG | 6221 |
| 1308 | GAGGAGGA G CCCCCCCG | 5945 | CGGGGGGG GCCGAAAGGCGAGUGAGGUCU UCCUCCUC | 6222 |
| 1321 | CCCGAGGA G CCACCUGA | 5946 | UCAGGUGG GCCGAAAGGCGAGUGAGGUCU UCCUCGGG | 6223 |
| 1335 | UGACUUCU G CUGUCCCA | 5947 | UGGGACAG GCCGAAAGGCGAGUGAGGUCU AGAAGUCA | 6224 |
| 1338 | CUUCUGCU G UCCCAAGU | 5948 | ACUUGGGA GCCGAAAGGCGAGUGAGGUCU AGCAGAAG | 6225 |
| 1345 | UGUCCCAA G UGCCAGUA | 5949 | UACUGGCA GCCGAAAGGCGAGUGAGGUCU UUGGGACA | 6226 |
| 1347 | UCCCAAGU G CCAGUAUC | 5950 | GAUACUGG GCCGAAAGGCGAGUGAGGUCU ACUUGGGA | 6227 |
| 1351 | AAGUGCCA G UAUCAGGC | 5951 | GCCUGAUA GCCGAAAGGCGAGUGAGGUCU UGGCACUU | 6228 |
| 1358 | AGUAUCAG G CCCCUGAU | 5952 | AUCAGGGG GCCGAAAGGCGAGUGAGGUCU CUGAUACU | 6229 |
| 1378 | GACACCCU G CAGAUACA | 5953 | UGUAUCUG GCCGAAAGGCGAGUGAGGUCU AGGGUGUC | 6230 |
| 1388 | AGAUACAU G UCAUGGAG | 5954 | CUCCAUGA GCCGAAAGGCGAGUGAGGUCU AUGUAUCU | 6231 |
| 1396 | GUCAUGGA G UGCAUUGA | 5955 | UCAAUGCA GCCGAAAGGCGAGUGAGGUCU UCCAUGAC | 6232 |
| 1398 | CAUGGAGU G CAUUGAGU | 5956 | ACUCAAUG GCCGAAAGGCGAGUGAGGUCU ACUCCAUG | 6233 |
| 1405 | UGCAUUGA G UAGGGCCG | 5957 | CGGCCCUA GCCGAAAGGCGAGUGAGGUCU UCAAUGCA | 6234 |
| 1410 | UUGAGUAGG G CCGGCCAG | 5958 | CUGGCCGG GCCGAAAGGCGAGUGAGGUCU CCUACUCA | 6235 |
| 1414 | GUAGGGCCG G CCAGUGCA | 5959 | UGCACUGG GCCGAAAGGCGAGUGAGGUCU CGGCCCUA | 6236 |
| 1418 | GCCGGCCA G UGCAAGGC | 5960 | GCCUUGCA GCCGAAAGGCGAGUGAGGUCU UGGCCGGC | 6237 |
| 1420 | CGGCCAGU G CAAGGCCA | 5961 | UGGCCUUG GCCGAAAGGCGAGUGAGGUCU ACUGGCCG | 6238 |
| 1425 | AGUGCAAG G CCACUGCC | 5962 | GGCAGUGG GCCGAAAGGCGAGUGAGGUCU CUUGCACU | 6239 |
| 1431 | AGGCCACU G CCUGCCCG | 5963 | CGGGCAGG GCCGAAAGGCGAGUGAGGUCU AGUGGCCU | 6240 |
| 1435 | CACUGCCU G CCCGAGGA | 5964 | UCCUCGGG GCCGAAAGGCGAGUGAGGUCU AGGCAGUG | 6241 |
| 1445 | CCGAGGAC G UGCCCGGG | 5965 | CCCGGGCA GCCGAAAGGCGAGUGAGGUCU GUCCUCGG | 6242 |
| 1447 | GAGGACGU G CCCGGGAC | 5966 | GUCCCGGG GCCGAAAGGCGAGUGAGGUCU ACGUCCUC | 6243 |
| 1457 | CCGGGACC G UGCAGUCU | 5967 | AGACUGCA GCCGAAAGGCGAGUGAGGUCU GGUCCCGG | 6244 |
| 1459 | GGGACCGU G CAGUCGC | 5968 | GCAGACUG GCCGAAAGGCGAGUGAGGUCU ACGGUCCC | 6245 |
| 1462 | ACCGUGCA G UCUGCGCU | 5969 | AGCGCAGA GCCGAAAGGCGAGUGAGGUCU UGCACGGU | 6246 |
| 1466 | UGCAGUCU G CGCUUUCC | 5970 | GGAAAGCG GCCGAAAGGCGAGUGAGGUCU AGACUGCA | 6247 |
| 1468 | CAGUCUGC G CUUUCCUC | 5971 | GAGGAAAG GCCGAAAGGCGAGUGAGGUCU GCAGACUG | 6248 |
| 1481 | CCUCUCCC G CCUGCCUA | 5972 | UAGGCAGG GCCGAAAGGCGAGUGAGGUCU GGGAGAGG | 6249 |
| 1485 | UCCCGCCU G CCUAGCCC | 5973 | GGGCUAGG GCCGAAAGGCGAGUGAGGUCU AGGCGGGA | 6250 |
| 1490 | CCUGCCUA G CCCAGGAU | 5974 | AUCCUGGG GCCGAAAGGCGAGUGAGGUCU UAGGCAGG | 6251 |
| 1504 | GAUGAAGG G CUGGGUGG | 5975 | CCACCCAG GCCGAAAGGCGAGUGAGGUCU CCUUCAUC | 6252 |
| 1509 | AGGGCUGG G UGGCCACA | 5976 | UGUGCCCA GCCGAAAGGCGAGUGAGGUCU CCAGCCCU | 6253 |
| 1512 | GCUGGGUG G CCACAACU | 5977 | AGUUGUGG GCCGAAAGGCGAGUGAGGUCU CACCCAGC | 6254 |
| 1526 | ACUGGGAU G CCACCUGG | 5978 | CCAGGUGG GCCGAAAGGCGAGUGAGGUCU AUCCCAGU | 6255 |

TABLE V-continued

Human IKK-gamma Zinzyme and Substrate Sequence

| Pos | Substrate | Seq ID | Zinzyme | Seq ID |
|---|---|---|---|---|
| 1536 | CACCUGGA G CCCCACCC | 5979 | GGGUGGGG GCCGAAAGGCGAGUGAGGUCU UCCAGGUG | 6256 |
| 1549 | ACCCAGGA G CUGGCCGC | 5980 | GCGGCCAG GCCGAAAGGCGAGUGAGGUCU UCCUGGGU | 6257 |
| 1553 | AGGAGCUG G CCGCGGCA | 5981 | UGCCGCGG GCCGAAAGGCGAGUGAGGUCU CAGCUCCU | 6258 |
| 1556 | AGCUGGCC G CGGCACCU | 5982 | AGGUGCCG GCCGAAAGGCGAGUGAGGUCU GGCCAGCU | 6259 |
| 1559 | UGGCCGCG G CACCUUAC | 5983 | GUAAGGUG GCCGAAAGGCGAGUGAGGUCU CGCGGCCA | 6260 |
| 1568 | CACCUUAC G CUUCAGCU | 5984 | AGCUGAAG GCCGAAAGGCGAGUGAGGUCU GUAAGGUG | 6261 |
| 1574 | ACGCUUCA G CUGUUGAU | 5985 | AUCAACAG GCCGAAAGGCGAGUGAGGUCU UGAAGCGU | 6262 |
| 1577 | CUUCAGCU G UUGAUCCG | 5986 | CGGAUCAA GCCGAAAGGCGAGUGAGGUCU AGCUGAAG | 6263 |
| 1585 | GUUGAUCC G CUGGUCCC | 5987 | GGGACCAG GCCGAAAGGCGAGUGAGGUCU GGAUCAAC | 6264 |
| 1589 | AUCCGCUG G UCCCCUCU | 5988 | AGAGGGGA GCCGAAAGGCGAGUGAGGUCU CAGCGGAU | 6265 |
| 1604 | CUUUUGGG G UAGAUGCG | 5989 | CGCAUCUA GCCGAAAGGCGAGUGAGGUCU CCCAAAAG | 6266 |
| 1610 | GGGUAGAU G CGGCCCCG | 5990 | CGGGGCCG GCCGAAAGGCGAGUGAGGUCU AUCUACCC | 6267 |
| 1613 | UAGAUGCG G CCCCGAUC | 5991 | GAUCGGGG GCCGAAAGGCGAGUGAGGUCU CGCAUCUA | 6268 |
| 1624 | CCGAUCAG G CCUGACUC | 5992 | GAGUCAGG GCCGAAAGGCGAGUGAGGUCU CUGAUCGG | 6269 |
| 1633 | CCUGACUC G CUGCUCUU | 5993 | AAGAGCAG GCCGAAAGGCGAGUGAGGUCU GAGUCAGG | 6270 |
| 1636 | GACUCGCU G CUCUUUUU | 5994 | AAAAAGAG GCCGAAAGGCGAGUGAGGUCU AGCGAGUC | 6271 |
| 1645 | CUCUUUUU G UUCCCUUC | 5995 | GAAGGGAA GCCGAAAGGCGAGUGAGGUCU AAAAAGAG | 6272 |
| 1655 | UCCCUUCU G UCUGCUCG | 5996 | CGAGCAGA GCCGAAAGGCGAGUGAGGUCU AGAAGGGA | 6273 |
| 1659 | UUCUGUCU G CUCGAACC | 5997 | GGUUCGAG GCCGAAAGGCGAGUGAGGUCU AGACAGAA | 6274 |
| 1672 | AACCACUU G CCUCGGGC | 5998 | GCCCGAGG GCCGAAAGGCGAGUGAGGUCU AAGUGGUU | 6275 |
| 1679 | UGCCUCGG G CUAAUCCC | 5999 | GGGAUUAG GCCGAAAGGCGAGUGAGGUCU CCGAGGCA | 6276 |
| 1706 | UCCACCCG G CACUGGGG | 6000 | CCCCAGUG GCCGAAAGGCGAGUGAGGUCU CGGGUGGA | 6277 |
| 1717 | CUGGGGAA G UCAAOAAU | 6001 | AUUCUUGA GCCGAAAGGCGAGUGAGGUCU UUCCCCAG | 6278 |
| 1729 | AGAAUGGG G CCUGGGGC | 6002 | GCCCCAGG GCCGAAAGGCGAGUGAGGUCU CCCAUUCU | 6279 |
| 1736 | GGCCUGGG G CUCUCAGG | 6003 | CCUGAGAG GCCGAAAGGCGAGUGAGGUCU CCCAGGCC | 6280 |
| 1752 | GGAGAACU G CUUCCCCU | 6004 | AGGGGAAG GCCGAAAGGCGAGUGAGGUCU AGUUUCUC | 6281 |
| 1762 | UUCCCCUG G CAGAGCUG | 6005 | CAGCUCUG GCCGAAAGGCGAGUGAGGUCU CAGGGGAA | 6282 |
| 1767 | CUGGCAGA G CUGGGUGG | 6006 | CCACCCAG GCCGAAAGGCGAGUGAGGUCU UCUGCCAG | 6283 |
| 1772 | AGAGCUGG G UGGCAGCU | 6007 | AGCUGCCA GCCGAAAGGCGAGUGAGGUCU CCAGCUCU | 6284 |
| 1775 | GCUGGGUG G CAGCUCUU | 6008 | AAGAGCUG GCCGAAAGGCGAGUGAGGUCU CACCCAGC | 6285 |
| 1778 | GGGUGGCA G CUCUUCCU | 6009 | AGGAAGAG GCCGAAAGGCGAGUGAGGUCU UGCCACCC | 6286 |
| 1805 | ACCGACCC G CCCGCCGC | 6010 | GCGGCGGG GCCGAAAGGCGAGUGAGGUCU GGGUCGGU | 6287 |
| 1809 | ACCCGCCC G CCGCUGUG | 6011 | CACAGCGG GCCGAAAGGCGAGUGAGGUCU GGGCGGGU | 6288 |
| 1812 | CGCCCGCC G CUGUGCCC | 6012 | CGGCACAG GCCGAAAGGCGAGUGAGGUCU CGCGCGCG | 6289 |
| 1815 | CCGCCGCU G UGCCCUGG | 6013 | CCACGGCA GCCGAAAGGCGAGUGAGGUCU AGCGGCCG | 6290 |
| 1817 | GCCGCUGU G CCCUGGGA | 6014 | UCCCAGGG GCCGAAAGGCGAGUGAGGUCU ACAGCGGC | 6291 |
| 1826 | CCCUGGGA G UGCUGCCC | 6015 | GGGCAGCA GCCGAAAGGCGAGUGAGGUCU UCCCAGGC | 6292 |
| 1828 | CUGGGAGU G CUGCCCUC | 6016 | GAGCGCAG GCCGAAAGGCGAGUGAGGUCU ACUCCCAG | 6293 |
| 1831 | GGAGUGCU G CCCUCUUA | 6017 | UAACAGGG GCCGAAAGGCGAGUGAGGUCU AGCACUCC | 6294 |
| 1844 | CUUACCAU G CACACGGG | 6018 | CCCGUGUG GCCGAAAGGCGAGUGAGGUCU AUGGUAAG | 6295 |
| 1852 | GCACACGG G UGCUCUCC | 6019 | GGAGAGCA GCCGAAAGGCGAGUGAGGUCU CCGUGUGC | 6296 |
| 1854 | ACACGGGU G CUCUCCUU | 6020 | AAGCAGAG GCCGAAAGGCGAGUGAGGUCU ACCCGUGU | 6297 |
| 1867 | CCUUUUGG G CUGCAUGC | 6021 | GCAUGCAC GCCGAAAGGCGAGUGAGGUCU CCAAAACG | 6298 |
| 1870 | UUUGGGCU G CAUGCUAU | 6022 | AUAGCAUG GCCGAAAGGCGAGUGAGGUCU AGCCCAAA | 6299 |
| 1874 | GGCUGCAU G CUAUUCCA | 6023 | UGGAAUAG GCCGAAAGGCGAGUGAGGUCU AUGCAGCC | 6300 |
| 1887 | UCCAUUUU G CAGCCAGA | 6024 | UCUGGCUG GCCGAAAGGCGAGUGAGGUCU AAAAUGGA | 6301 |
| 1890 | AUUUUGCA G CCAGACCG | 6025 | CGGUCUGC GCCGAAAGGCGAGUGAGGUCU UGCAAAAU | 6302 |
| 1901 | AGACCGAU G UGUAUUUA | 6026 | UAAAUACA GCCGAAAGGCGAGUGAGGUCU AUCGGUCU | 6303 |
| 1903 | ACCGAUGU G UAUUUAAC | 6027 | GUUAAAUA GCCGAAAGGCGAGUGAGGUCU ACAUCGGU | 6304 |
| 1914 | UUUAACCA G UCACUAUU | 6028 | AAUAGUCA GCCGAAAGGCGAGUGAGGUCU UGGUUAAA | 6305 |
| 1936 | ACAUUUGG G UUGUUUCC | 6029 | GGAAACAA GCCGAAAGGCGAGUGAGGUCU CCAAAUGU | 6306 |
| 1939 | UUUGGGUU G UUUCCCAU | 6030 | AUGGGAAA GCCGAAAGGCGAGUGAGGUCU AACCCAAA | 6307 |
| 1954 | AUCUUUUU G UUACCAUA | 6031 | UAUGGUAA GCCGAAAGGCGAGUGAGGUCU AAAAAGAU | 6308 |
| 1970 | AAAUAAUG G CAUAGUAA | 6032 | UUACUAUG GCCGAAAGGCGAGUGAGGUCU CAUUAUUU | 6309 |
| 1975 | AUGCCAUA G UAAAAAAA | 6033 | UUUUUUUA GCCGAAAGGCGAGUGAGGUCU UAUGCCAU | 6310 |

Input Sequence = NM_003639. Cut Site = G/Y
Arm Length = 8. Core Sequence GCcgaaagGCGaGuCaaGGuCu
NM_003639 (*Homo sapiens* inhibitor of kappa light polypeptide gene enhancer in B-cells, kinase gamma (IKBKG), mRNA.; 1994 bp)

TABLE VI

Human IKK-gamma DNAzyme and Substrate Sequence

| Pos | Substrate | Seq ID | DNAzyme | Seq ID |
|---|---|---|---|---|
| 10 | GCACGAGC A UGGCCCUU | 4749 | AAGGGCCA GGCTAGCTACAACGA GCTCGTGC | 6380 |
| 13 | CGAGCAUG G CCUUGUG | 5757 | CACAAGGG GGCTAGCTACAACGA CATGCTCG | 6381 |
| 19 | UGGCCCUU G UGAUCCAG | 5758 | CTGGATCA GGCTAGCTACAACGA AAGGGCCA | 6382 |
| 22 | CCCUUGUG A UCCAGGUG | 6311 | CACCTGGA GGCTAGCTACAACGA CACAAGGG | 6383 |

TABLE VI-continued

Human IKK-gamma DNAzyme and Substrate Sequence

| Pos | Substrate | Seq ID | DNAzyme | Seq ID |
|---|---|---|---|---|
| 28 | UGAUCCAG G UGGGGAAA | 5759 | TTTCCCCA GGCTAGCTACAACGA CTGGATCA | 6384 |
| 36 | GUGGGGAA A CUAAGGCC | 6312 | GGCCTTAG GGCTAGCTACAACGA TTCCCCAC | 6385 |
| 42 | AAACUAAG G CCCAGAGA | 5760 | TCTCTGGG GGCTAGCTACAACGA CTTAGTTT | 6386 |
| 52 | CCAGAGAA G UGAGGACC | 5761 | GGTCCTCA GGCTAGCTACAACGA TTCTCTGG | 6387 |
| 58 | AAGUGAGG A CCCCGCAG | 6313 | CTGCGGGG GGCTAGCTACAACGA CCTCACTT | 6388 |
| 63 | AGGACCCC G CAGACUAU | 5762 | ATAGTCTG GGCTAGCTACAACGA GGGGTCCT | 6389 |
| 67 | CCCCGCAG A CUAUCAAU | 6314 | ATTGATAG GGCTAGCTACAACGA CTGCGGGG | 6390 |
| 70 | CGCAGACU A UCAAUCCC | 4364 | GGGATTGA GGCTAGCTACAACGA AGTCTGCG | 6391 |
| 74 | GACUAUCA A UCCCAGUC | 6315 | GACTGGGA GGCTAGCTACAACGA TGATAGTC | 6392 |
| 80 | CAAUCCCA G UCUCUUCC | 5763 | GGAAGAGA GGCTAGCTACAACGA TGGGATTG | 6393 |
| 93 | UUCCCCUC A CUCCCUGU | 4774 | ACAGGGAG GGCTAGCTACAACGA GAGGGGAA | 6394 |
| 100 | CACUCCCU G UGAAGCUC | 5764 | GAGCTTCA GGCTAGCTACAACGA AGGGAGTG | 6395 |
| 105 | CCUGUGAA G CUCUCCAG | 5765 | CTGGAGAG GGCTAGCTACAACGA TTCACAGG | 6396 |
| 113 | GCUCUCCA G CAUCAUCG | 5766 | CGATGATG GGCTAGCTACAACGA TGGAGAGC | 6397 |
| 115 | UCUCCAGC A UCAUCGGA | 4783 | CTCGATGA GGCTAGCTACAACGA GCTGGAGA | 6398 |
| 118 | CCAGCAUC A UCGAGGUC | 4784 | GACCTCGA GGCTAGCTACAACGA GATGCTGG | 6399 |
| 124 | UCAUCGAG G UCCCAUCA | 5767 | TGATGGGA GGCTAGCTACAACGA CTCGATGA | 6400 |
| 129 | GAGGUCCC A UCAGCCCU | 4787 | AGGGCTGA GGCTAGCTACAACGA GGGACCTC | 6401 |
| 133 | UCCCAUCA G CCCUUGCC | 5768 | GGCAAGGG GGCTAGCTACAACGA TGATGGGA | 6402 |
| 139 | CAGCCCUU G CCCUGUUG | 5769 | CAACAGGG GGCTAGCTACAACGA AAGGGCTG | 6403 |
| 144 | CUUGCCCU G UUGGAUGA | 5770 | TCATCCAA GGCTAGCTACAACGA AGGGCAAG | 6404 |
| 149 | CCUGUUGG A UGAAUAGG | 6316 | CCTATTCA GGCTAGCTACAACGA CCAACAGG | 6405 |
| 153 | UUGGAUGA A UAGGCACC | 6317 | GGTGCCTA GGCTAGCTACAACGA TCATCCAA | 6406 |
| 157 | AUGAAUAG G CACCCUG | 5771 | CAGAGGTG GGCTAGCTACAACGA CTATTCAT | 6407 |
| 159 | GAAUAGGC A CCCUCUGGA | 4795 | TCCAGAGG GGCTAGCTACAACGA GCCTATTC | 6408 |
| 171 | CUGGAAGA G CCAACUGU | 5772 | ACAGTTGG GGCTAGCTACAACGA TCTTCCAG | 6409 |
| 175 | AAGAGCCA A CUGUGUGA | 6318 | TCACACAG GGCTAGCTACAACGA TGGCTCTT | 6410 |
| 178 | AGCCAACU G UGUGAGAU | 5773 | ATCTCACA GGCTAGCTACAACGA AGTTGGCT | 6411 |
| 180 | CCAACUGU G UGAGAUGG | 5774 | CCATCTCA GGCTAGCTACAACGA ACAGTTGG | 6412 |
| 185 | UGUGUGAG A UGGUCCAG | 6319 | CTGCACCA GGCTAGCTACAACGA CTCACACA | 6413 |
| 188 | GUGAGAUG G UGCAGCCC | 5775 | GGGCTGCA GGCTAGCTACAACGA CATCTCAC | 6414 |
| 190 | GAGAUGGU G CAGCCCAG | 5776 | CTGGGCTG GGCTAGCTACAACGA ACCATCTC | 6415 |
| 193 | AUGGUGCA G CCCAGUGG | 5777 | CCACTGGG GGCTAGCTACAACGA TGCACCAT | 6416 |
| 198 | GCAGCCCA G UGGUGGCC | 5778 | GGCCACCA GGCTAGCTACAACGA TGGGCTGC | 6417 |
| 201 | GCCCAGUG G UGGCCCGG | 5779 | CCGGGCCA GGCTAGCTACAACGA CACTGGGC | 6418 |
| 204 | CAGUGGUG G CCCGGCAG | 5780 | CTGCCGGG GGCTAGCTACAACGA CACCACTG | 6419 |
| 209 | GUGGCCCG G CAGCAGAU | 5781 | ATCTGCTG GGCTAGCTACAACGA CGGGCCAC | 6420 |
| 212 | GCCCGGCA G CAGAUCAG | 5782 | CTGATCTG GGCTAGCTACAACGA TGCCGGGC | 6421 |
| 216 | GGCAGCAG A UCAGGACG | 6320 | CGTCCTGA GGCTAGCTACAACGA CTGCTGCC | 6422 |
| 222 | AGAUCAGG A CGUACGG | 6321 | CCAGTACG GGCTAGCTACAACGA CCTGATCT | 6423 |
| 224 | AUCAGGAC G UACUGGGC | 5783 | GCCCAGTA GGCTAGCTACAACGA GTCCTGAT | 6424 |
| 226 | CAGGACGU A CUGGGCGA | 4384 | TCGCCCAG GGCTAGCTACAACGA ACGTCCTG | 6425 |
| 231 | CGUACUGG G CGAAGAGU | 5784 | ACTCTTCG GGCTAGCTACAACGA CCAGTACG | 6426 |
| 238 | GGCGAAGA G UCUCCUCU | 5785 | AGAGGAGA GGCTAGCTACAACGA TCTTCGCC | 6427 |
| 253 | CUGGGGAA G CCAGCCAU | 5786 | ATGGCTGG GGCTAGCTACAACGA TTCCCCAG | 6428 |
| 257 | GGAAGCCA G CCAUGCUG | 5787 | CAGCATGG GGCTAGCTACAACGA TGGCTTCC | 6429 |
| 260 | AGCCAGCC A UGCUGCAC | 4819 | GTGCAGCA GGCTAGCTACAACGA GGCTGGCT | 6430 |
| 262 | CCAGCCAU G CUGCACCU | 5788 | AGGTGCAG GGCTAGCTACAACGA ATGCTGG | 6431 |
| 265 | GCCAUGCU G CACCUGCC | 5789 | GGCAGGTG GGCTAGCTACAACGA AGCATGGC | 6432 |
| 267 | CAUGCUGC A CCUGCCUU | 4821 | AAGGCAGG GGCTAGCTACAACGA GCAGCATG | 6433 |
| 271 | CUGCACCU G CCUUCAGA | 5790 | TCTGAAGG GGCTAGCTACAACGA AGGTGCAG | 6434 |
| 280 | CCUUCAGA A CAGGGCGC | 6322 | GCGCCCTG GGCTAGCTACAACGA TCTGAAGG | 6435 |
| 285 | AGAACAGG G CGCUCCUG | 5791 | CAGGAGCG GGCTAGCTACAACGA CCTGTTCT | 6436 |
| 287 | AACACGGC G CUCCUGAG | 5792 | CTCAGGAG GGCTAGCTACAACGA GCCCTGTT | 6437 |
| 296 | CUCCUGAG A CCCUCCAG | 6323 | CTGGAGGG GGCTAGCTACAACGA CTCAGGAG | 6438 |
| 304 | ACCCUCCA G CGCUGCCU | 5793 | AGGCAGCG GGCTAGCTACAACGA TGGAGGGT | 6439 |
| 306 | CCUCCAGC G CUGCCUGG | 5794 | CCAGGCAG GGCTAGCTACAACGA GCTGGAGG | 6440 |
| 309 | CCAGCGCU G CCUGGAGG | 5795 | CCTCCAGG GGCTAGCTACAACGA AGCGCTGG | 6441 |
| 321 | GGAGGAGA A UCAAGAGC | 6324 | GCTCTTGA GGCTAGCTACAACGA TCTCCTCC | 6442 |
| 328 | AAUCAAGA G CUCCGAGA | 5796 | TCTCGGAG GGCTAGCTACAACGA TCTTGATT | 6443 |
| 336 | GCUCCGAG A UGCCAUCC | 6325 | GGATGGCA GGCTAGCTACAACGA CTCGGAGC | 6444 |
| 338 | UCCGAGAU G CCAUCCGG | 5797 | CCGGATGG GGCTAGCTACAACGA ATCTCGGA | 6445 |
| 341 | GAGAUGCC A UCCGGCAG | 4843 | CTGCCGGA GGCTAGCTACAACGA GGCATCTC | 6446 |
| 346 | GCCAUCCG G CAGAGCAA | 5798 | TTGCTCTG GGCTAGCTACAACGA CGGATGGC | 6447 |
| 351 | CCGGCAGA G CAACCAGA | 5799 | TCTGGTTG GGCTAGCTACAACGA TCTGCCGG | 6448 |
| 354 | GCAGAGCA A CCAGAUUC | 6326 | GAATCTGG GGCTAGCTACAACGA TGCTCTGC | 6449 |
| 359 | GCAACCAG A UUCUGCGG | 6327 | CCGCAGAA GGCTAGCTACAACGA CTGGTTGC | 6450 |
| 364 | CAGAUUCU G CGGGAGCG | 5800 | CGCTCCCG GGCTAGCTACAACGA AGAATCTG | 6451 |
| 370 | CUGCGGGA G CGCUGCGA | 5801 | TCGCAGCG GGCTAGCTACAACGA TCCCGCAG | 6452 |
| 372 | GCGGGAGC G CUGCGAGG | 5802 | CCTCGCAC GGCTAGCTACAACGA GCTCCCGC | 6453 |
| 375 | GGAGCGCU G CGAGGAGC | 5803 | GCTCCTCG GGCTAGCTACAACGA AGCGCTCC | 6454 |
| 382 | UGCGAGGA G CUUCUGCA | 5804 | TGCAGAAG GGCTAGCTACAACGA TCCTCGCA | 6455 |
| 388 | GAGCUUCU G CAUUUCCA | 5805 | TGGAAATG GGCTAGCTACAACGA AGAAGCTC | 6456 |
| 390 | GCUUCUGC A UUUCCAAG | 4853 | CTTGGAAA GGCTAGCTACAACGA GCAGAAGC | 6457 |

TABLE VI-continued

Human IKK-gamma DNAzyme and Substrate Sequence

| Pos | Substrate | Seq ID | DNAzyme | Seq ID |
|-----|-----------|--------|---------|--------|
| 398 | AUUUCCAA G CCAGCCAG | 5806 | CTGGCTGG GGCTAGCTACAACGA TTGGAAAT | 6458 |
| 402 | CCAAGCCA G CCAGAGGG | 5807 | CCCTCTGG GGCTAGCTACAACGA TGGCTTGG | 6459 |
| 421 | GAGAAGGA G UUCCUCAU | 5808 | ATGAGGAA GGCTAGCTACAACGA TCCTTCTC | 6460 |
| 428 | AGUUCCUC A UGUGCAAC | 4862 | CTTGCACA GGCTAGCTACAACGA GAGGAACT | 6461 |
| 430 | UUCCUCAU G UGCAAGUU | 5809 | AACTTGCA GGCTAGCTACAACGA ATGAGCAA | 6462 |
| 432 | CCUCAUGU G CAAGUUCC | 5810 | CGAACTTG GGCTAGCTACAACGA ACATGAGG | 6463 |
| 436 | AUGUGCAA G UUCCAGGA | 5811 | TCCTGGAA GGCTAGCTACAACGA TTGCACAT | 6464 |
| 446 | UCCAGGAG G CCAGCAAA | 5812 | TTTCCTGG GGCTAGCTACAACGA CTCCTGGA | 6465 |
| 454 | GCCAGGAA A CUGGUGGA | 6328 | TCCACCAG GGCTAGCTACAACGA TTCCTGGC | 6466 |
| 458 | GGAAACUG G UGGAGAGA | 5813 | TCTCTCCA GGCTAGCTACAACGA CAGTTTCC | 6467 |
| 466 | GUGGAGAG A CUCGCCCU | 6329 | AGGGCGAG GGCTAGCTACAACGA CTCTCCAC | 6468 |
| 471 | GAGACUCG G CCUGGAGA | 5814 | TCTCCAGG GGCTAGCTACAACGA CGACTCTC | 6469 |
| 481 | CUGGAGAA G CUCGAUCU | 5815 | AGATCGAC GGCTAGCTACAACGA TTCTCCAG | 6470 |
| 486 | GAACCUCG A UCUGAAGA | 6330 | TCTTCAGA GGCTAGCTACAACGA CCAGCTTC | 6471 |
| 496 | CUGAAGAG G CAGAAGGA | 5816 | TCCTTCTG GGCTAGCTACAACGA CTCTTCAG | 6472 |
| 505 | CAGAAGCA G CACGCUCU | 5817 | AGAGCCTG GGCTAGCTACAACGA TCCTTCTG | 6473 |
| 509 | AGGAGCAG G CUCUCCGG | 5818 | CCCCAGAC GGCTAGCTACAACGA CTGCTCCT | 6474 |
| 514 | CAGCCUCU C GCGAGCU | 5819 | ACCTCCCG GGCTAGCTACAACGA AGAGCCTG | 6475 |
| 521 | UGCGGGAG G UGGAGCAC | 5820 | GTGCTCCA GGCTAGCTACAACGA CTCCCGCA | 6476 |
| 526 | GAGGUGGA G CACCUGAA | 5821 | TTCAGGTG GGCTAGCTACAACGA TCCACCTC | 6477 |
| 528 | GGUGGAGC A CCUGAAGA | 4878 | TCTTCAGG GGCTAGCTACAACGA GCTCCACC | 6478 |
| 538 | CUGAAGAG A UGCCAGCA | 6331 | TGCTGGCA GGCTAGCTACAACGA CTCTTCAG | 6479 |
| 540 | GAAGAGAU G CCAGCAGC | 5822 | GCTGCTGG GGCTAGCTACAACGA ATCTCTTC | 6480 |
| 544 | AGAUGCCA G CAGCAGAU | 5823 | ATCTGCTG GGCTAGCTACAACGA TGGCATCT | 6481 |
| 547 | UGCCAGCA G CAGAUGGC | 5824 | GCCATCTG GGCTAGCTACAACGA TGCTGGCA | 6482 |
| 551 | AGCAGCAG A UGGCUGAG | 6332 | CTCAGCCA GGCTAGCTACAACGA CTGCTGCT | 6483 |
| 554 | AGCAGAUG G CUGAGGAC | 5825 | GTCCTCAG GGCTAGCTACAACGA CATCTGCT | 6484 |
| 561 | GCUGAGG A CAAGGCCU | 6333 | AGGCCTTG GGCTAGCTACAACGA CCTCAGCC | 6485 |
| 566 | AGGACAAG G CCUCUGUG | 5826 | CACAGAGG GGCTAGCTACAACGA CTTGTCCT | 6486 |
| 572 | AGGCCUCU G UGAAAGCC | 5827 | GGCTTTCA GGCTAGCTACAACGA AGAGGCCT | 6487 |
| 578 | CUGUGAAA G CCCAGGUG | 5828 | CACCTGGG GGCTAGCTACAACGA TTTCACAG | 6488 |
| 584 | AAGCCCAG G UGACGUCC | 5829 | GGACGTCA GGCTAGCTACAACGA CTGGGCTT | 6489 |
| 587 | CCCAGGUG A CGUCCUUG | 6334 | CAAGGACG GGCTAGCTACAACGA CACCTGGG | 6490 |
| 589 | CAGGUGAC G UCCUUGCU | 5830 | AGCAAGGA GGCTAGCTACAACGA GTCACCTG | 6491 |
| 595 | ACGUCCUU G CUCGGGGA | 5831 | TCCCCGAG GGCTAGCTACAACGA AAGGACGT | 6492 |
| 604 | CUCGGGGA G CUGCAGGA | 5832 | TCCTGCAG GGCTAGCTACAACGA TCCCCGAG | 6493 |
| 607 | GGGGAGCU G CAGGAGAG | 5833 | CTCTCCTG GGCTAGCTACAACGA AGCTCCCC | 6494 |
| 615 | GCAGGAGA G CCAGAGUC | 5834 | GACTCTGG GGCTAGCTACAACGA TCTCCTGC | 6495 |
| 621 | GAGCCAGA G UCGCUUGG | 5835 | CCAAGCGA GGCTAGCTACAACGA TCTGGCTC | 6496 |
| 624 | CCAGAGUC G CUUGGAGG | 5836 | CCTCCAAG GGCTAGCTACAACGA GACTCTGG | 6497 |
| 632 | GCUUGGAG G CUGCCACU | 5837 | AGTGGCAG GGCTAGCTACAACGA CTCCAAGC | 6498 |
| 635 | UGGAGGCU G CCACUAAG | 5838 | CTTAGTGG GGCTAGCTACAACGA AGCCTCCA | 6499 |
| 638 | AGGCUGCC A CUAAGGAA | 4903 | TTCCTTAG GGCTAGCTACAACGA GGCAGCCT | 6500 |
| 646 | ACUAAGGA A UGCCAGGC | 6335 | GCCTGGCA GGCTAGCTACAACGA TCCTTAGT | 6501 |
| 648 | UAAGGAAU G CCAGGCUC | 5839 | GAGCCTGG GGCTAGCTACAACGA ATTCCTTA | 6502 |
| 653 | AAUGCCAG G CUCUGGAG | 5840 | CTCCAGAG GGCTAGCTACAACGA CTGGCATT | 6503 |
| 663 | UCUGGAGG G UCGGGCCC | 5841 | GGGCCCGA GGCTAGCTACAACGA CCTCCAGA | 6504 |
| 668 | AGGGUCGG G CCCGGGCG | 5842 | CGCCCGGG GGCTAGCTACAACGA CCGACCCT | 6505 |
| 674 | GGGCCCGG G CGGCCAGC | 5843 | GCTGGCCG GGCTAGCTACAACGA CCGGGCCC | 6506 |
| 677 | CCCGGGCG G CCAGCGAG | 5844 | CTCGCTGG GGCTAGCTACAACGA CGCCCGGG | 6507 |
| 681 | GGCGGCCA G CGAGCAGG | 5845 | CCTGCTCG GGCTAGCTACAACGA TGGCCGCC | 6508 |
| 685 | GCCAGCGA G CAGGCGCG | 5846 | CGCGCCTG GGCTAGCTACAACGA TCGCTGGC | 6509 |
| 689 | GCGAGCAG G CGCGGCAG | 5847 | CTGCCGCG GGCTAGCTACAACGA CTGCTCGC | 6510 |
| 691 | GAGCAGGC G CGGCAGCU | 5848 | AGCTGCCG GGCTAGCTACAACGA GCCTGCTC | 6511 |
| 694 | CAGGCGCG G CAGCUGGA | 5849 | TCCAGCTG GGCTAGCTACAACGA CGCGCCTG | 6512 |
| 697 | GCGCGGCA G CUGGAGAG | 5850 | CTCTCCAG GGCTAGCTACAACGA TGCCGCGC | 6513 |
| 705 | GCUGGAGA G UGAGCGGC | 5851 | CGCGCTCA GGCTAGCTACAACGA TCTCCAGC | 6514 |
| 709 | GAGAGUGA G CGCGAGGC | 5852 | GCCTCGCG GGCTAGCTACAACGA TCACTCTC | 6515 |
| 711 | GAGUGAGC G CGAGCCGC | 5853 | GCGCCTCG GGCTAGCTACAACGA GCTCACTC | 6516 |
| 716 | AGCGCGAG G CGCUGCAG | 5854 | CTGCAGCG GGCTAGCTACAACGA CTCGCGCT | 6517 |
| 718 | CGCGAGGC G CUGCAGCA | 5855 | TGCTGCAG GGCTAGCTACAACGA GCCTCGCG | 6518 |
| 721 | GAGGCGCU G CAGCAGCA | 5856 | TGCTGCTG GGCTAGCTACAACGA AGCGCCTC | 6519 |
| 724 | GCGCUGCA G CAGCAGCA | 5857 | TGCTGCTG GGCTAGCTACAACGA TGCAGCGC | 6520 |
| 727 | CUGCAGCA G CAGCACAG | 5858 | CTGTGCTG GGCTAGCTACAACGA TGCTGCAG | 6521 |
| 730 | CAGCAGCA G CACAGCGU | 5859 | ACGCTGTG GGCTAGCTACAACGA TGCTGCTG | 6522 |
| 732 | GCAGCAGC A CAGCGUGC | 4920 | GCACGCTG GGCTAGCTACAACGA GCTGCTGC | 6523 |
| 735 | GCAGCACA G CGUGCAGG | 5860 | CCTGCACG GGCTAGCTACAACGA TGTGCTGC | 6524 |
| 737 | AGCACAGC G UGCAGGUG | 5861 | CACCTGCA GGCTAGCTACAACGA GCTGTGCT | 6525 |
| 739 | CACAGCGU G CAGGUGGA | 5862 | TCCACCTG GGCTAGCTACAACGA ACGCTGTG | 6526 |
| 743 | GCGUGCAG G UGGACCAG | 5863 | CTGGTCCA GGCTAGCTACAACGA CTGCACGC | 6527 |
| 747 | GCAGGUGG A CCAGCUGC | 6336 | GCAGCTGG GGCTAGCTACAACGA CCACCTGC | 6528 |
| 751 | GUGGACCA G CUGCGCAU | 5864 | ATGCGCAG GGCTAGCTACAACGA TGGTCCAC | 6529 |
| 754 | GACCAGCU G CGCAUGCA | 5865 | TGCATGCG GGCTAGCTACAACGA AGCTGGTC | 6530 |
| 756 | CCAGCUGC G CAUGCAGG | 5866 | CCTGCATG GGCTAGCTACAACGA GCAGCTGG | 6531 |

TABLE VI-continued

Human IKK-gamma DNAzyme and Substrate Sequence

| Pos | Substrate | Seq ID | DNAzyme | Seq ID |
|---|---|---|---|---|
| 758 | AGCUGCGC A UGCAGGGC | 4926 | GCCCTGCA GGCTAGCTACAACGA GCGCAGCT | 6532 |
| 760 | CUGCGCAU G CAGGGCCA | 5867 | TGGCCCTG GGCTAGCTACAACGA ATGCGCAG | 6533 |
| 765 | CAUGCAGG G CCAGAGCG | 5868 | CGCTCTGG GGCTAGCTACAACGA CCTGCATG | 6534 |
| 771 | GGGCCAGA G CGUGGAGG | 5869 | CCTCCACG GGCTAGCTACAACGA TCTGGCCC | 6535 |
| 773 | GCCAGAGC G UGGAGGCC | 5870 | GGCCTCCA GGCTAGCTACAACGA GCTCTGGC | 6536 |
| 779 | GCGUGGAG G CCGCGCUC | 5871 | GAGCGCGG GGCTAGCTACAACGA CTCCACGC | 6537 |
| 782 | UGGAGGCC G CGCUCCGC | 5872 | GCGGAGCG GGCTAGCTACAACGA GGCCTCCA | 6538 |
| 784 | GAGGCCGC G CUCCGCAU | 5873 | ATGCGGAG GGCTAGCTACAACGA GCGGCCTC | 6539 |
| 789 | CGCGCUCC G CAUGGAGC | 5874 | GCTCCATG GGCTAGCTACAACGA GGAGCGCG | 6540 |
| 791 | CGCUCCGC A UGGAGCGC | 4933 | GCGCTCCA GGCTAGCTACAACGA GCGGAGCG | 6541 |
| 796 | CGCAUGGA G CGCCAGGC | 5875 | GCCTGGCG GGCTAGCTACAACGA TCCATGCG | 6542 |
| 798 | CAUGGAGC G CCAGGCCG | 5876 | CGGCCTGG GGCTAGCTACAACGA GCTCCATG | 6543 |
| 803 | AGCGCCAG G CCGCCUCG | 5877 | CGAGGCGG GGCTAGCTACAACGA CTGGCGCT | 6544 |
| 806 | GCCAGGCC G CCUCGGAG | 5878 | CTCCGAGG GGCTAGCTACAACGA GGCCTGGC | 6545 |
| 826 | AAGAGGAA G CUGGCCCA | 5879 | TGGGCCAG GGCTAGCTACAACGA TTCCTCTT | 6546 |
| 830 | GGAAGCUG G CCCAGUUG | 5880 | CAACTGGG GGCTAGCTACAACGA CAGCTTCC | 6547 |
| 835 | CUGGCCCA G UUGCAGGU | 5881 | ACCTGCAA GGCTAGCTACAACGA TGGGCCAG | 6548 |
| 838 | GCCCAGUU G CAGGUGGC | 5882 | GCCACCTG GGCTAGCTACAACGA AACTGGGC | 6549 |
| 842 | AGUUGCAG G UGGCCUAU | 5883 | ATAGGCCA GGCTAGCTACAACGA CTGCAACT | 6550 |
| 845 | UGCAGGUG G CCUAUCAC | 5884 | GTGATAGG GGCTAGCTACAACGA CACCTGCA | 6551 |
| 849 | GGUGGCCU A UCACCAGC | 4423 | GCTGGTGA GGCTAGCTACAACGA AGGCCACC | 6552 |
| 852 | GGCCUAUC A CCAGCUCU | 4946 | AGAGCTGG GGCTAGCTACAACGA GATAGGCC | 6553 |
| 856 | UAUCACCA G CUCUUCCA | 5885 | TGGAAGAG GGCTAGCTACAACGA TGGTGATA | 6554 |
| 868 | UUCCAAGA A UACGACAA | 6337 | TTGTCGTA GGCTAGCTACAACGA TCTTGGAA | 6555 |
| 870 | CCAAGAAU A CGACAACC | 4428 | GGTTGTCG GGCTAGCTACAACGA ATTCTTGG | 6556 |
| 873 | AGAAUACG A CAACCACA | 6338 | TGTGGTTG GGCTAGCTACAACGA CGTATTCT | 6557 |
| 876 | AUACGACA A CCACAUCA | 6339 | TGATGTGG GGCTAGCTACAACGA TGTCGTAT | 6558 |
| 879 | CGACAACC A CAUCAAGA | 4955 | TCTTGATG GGCTAGCTACAACGA GGTTGTCG | 6559 |
| 881 | ACAACCAC A UCAAGAGC | 4956 | GCTCTTGA GGCTAGCTACAACGA GTGGTTGT | 6560 |
| 888 | CAUCAAGA G CAGCGUGG | 5886 | CCACGCTG GGCTAGCTACAACGA TCTTGATG | 6561 |
| 891 | CAAGAGCA G CGUGGUGG | 5887 | CCACCACG GGCTAGCTACAACGA TGCTCTTG | 6562 |
| 893 | AGAGCAGC G UGGUGGCC | 5888 | GCCCACCA GGCTAGCTACAACGA GCTGCTCT | 6563 |
| 896 | GCAGCGUG G UGGGCAGU | 5889 | ACTGCCCA GGCTAGCTACAACGA CACGCTGC | 6564 |
| 900 | CGUGGUGG G CAGUGAGC | 5890 | GCTCACTG GGCTAGCTACAACGA CCACCACG | 6565 |
| 903 | GGUGGGCA G UGAGCGGA | 5891 | TCCGCTCA GGCTAGCTACAACGA TGCCCACC | 6566 |
| 907 | GGCAGUGA G CGGAAGCG | 5892 | CGCTTCCG GGCTAGCTACAACGA TCACTGCC | 6567 |
| 913 | GAGCGGAA G CGAGGAAU | 5893 | ATTCCTCG GGCTAGCTACAACGA TTCCGCTC | 6568 |
| 920 | AGCGAGGA A UGCAGCUG | 6340 | CAGCTGCA GGCTAGCTACAACGA TCCTCGCT | 6569 |
| 922 | CGAGGAAU G CACCUGGA | 5894 | TCCAGGTG GGCTAGCTACAACGA ATTCCTCG | 6570 |
| 925 | GGAAUGCA G CUGGAAGA | 5895 | TCTTCCAG GGCTAGCTACAACGA TGCATTCC | 6571 |
| 933 | GCUGGAAG A UCUCAAAC | 6341 | GTTTGAGA GGCTAGCTACAACGA CTTCCAGC | 6572 |
| 940 | GAUCUCAA A CAGCAGCU | 6342 | AGCTGCTG GGCTAGCTACAACGA TTGAGATC | 6573 |
| 943 | CUCAAACA G CAGCUCCA | 5896 | TGGAGCTG GGCTAGCTACAACGA TGTTTGAG | 6574 |
| 946 | AAACAGCA G CUCCAGCA | 5897 | TGCTGGAG GGCTAGCTACAACGA TGCTGTTT | 6575 |
| 952 | CAGCUCCA G CAGGCCGA | 5898 | TCGGCCTG GGCTAGCTACAACGA TGGAGCTG | 6576 |
| 956 | UCCAGCAG G CCGAGGAG | 5899 | CTCCTCGG GGCTAGCTACAACGA CTGCTGGA | 6577 |
| 965 | CCGAGGAG G CCCUGGUG | 5900 | CACCAGGG GGCTAGCTACAACGA CTCCTCGG | 6578 |
| 971 | AGGCCCUG G UGGCCAAA | 5901 | TTTGGCCA GGCTAGCTACAACGA CAGGGCCT | 6579 |
| 974 | CCCUGGUG G CCAAACAG | 5902 | CTGTTTGG GGCTAGCTACAACGA CACCAGGG | 6580 |
| 979 | GUGGCCAA A CAGGAGGU | 6343 | ACCTCCTG GGCTAGCTACAACGA TTGGCCAC | 6581 |
| 986 | AACAGGAG G UGAUCGAU | 5903 | ATCGATCA GGCTAGCTACAACGA CTCCTGTT | 6582 |
| 989 | AGGAGGUG A UCGAUAAG | 6344 | CTTATCGA GGCTAGCTACAACGA CACCTCCT | 6583 |
| 993 | GGUGAUCG A UAAGCUGA | 6345 | TCAGCTTA GGCTAGCTACAACGA CGATCACC | 6584 |
| 997 | AUCGAUAA G CUGAAGGA | 5904 | TCCTTCAG GGCTAGCTACAACGA TTATCGAT | 6585 |
| 1010 | AGGAGGAG G CCGAGCAG | 5905 | CTGCTCGG GGCTAGCTACAACGA CTCCTCCT | 6586 |
| 1015 | GAGGCCGA G CAGCACAA | 5906 | TTGTGCTG GGCTAGCTACAACGA TCGGCCTC | 6587 |
| 1018 | GCCGAGCA G CACAAGAU | 5907 | ATCTTGTG GGCTAGCTACAACGA TGCTGGGC | 6588 |
| 1020 | CGAGCAGC A CAAGAUUG | 4980 | CAATCTTG GGCTAGCTACAACGA GCTGCTCG | 6589 |
| 1025 | AGCACAAG A UUGUGAUG | 6346 | CATCACAA GGCTAGCTACAACGA CTTGTGCT | 6590 |
| 1028 | ACAAGAUU G UGAUGGAG | 5908 | CTCCATCA GGCTAGCTACAACGA AATCTTGT | 6591 |
| 1031 | AGAUUGUG A UGGAGACA | 6347 | GGTCTCCA GGCTAGCTACAACGA CACAATCT | 6592 |
| 1037 | UGAUGGAG A CCGUUCCG | 6348 | CGGAACGG GGCTAGCTACAACGA CTCCATCA | 6593 |
| 1040 | UGGAGACC G UUCCGGUG | 5909 | CACCGGAA GGCTAGCTACAACGA GGTCTCCA | 6594 |
| 1046 | CCGUUCCG G UGCUGAAG | 5910 | CTTCAGCA GGCTAGCTACAACGA CGGAACGG | 6595 |
| 1048 | GUUCCGGU G CUGAAGGC | 5911 | GCCTTCAG GGCTAGCTACAACGA ACCGGAAC | 6596 |
| 1055 | UGCUGAAG G CCCAGGCG | 5912 | CGCCTGGG GGCTAGCTACAACGA CTTCAGCA | 6597 |
| 1061 | AGGCCCAG G CGGAUAUC | 5913 | GATATCCG GGCTAGCTACAACGA CTGGGCCT | 6598 |
| 1065 | CCAGGCGG A UAUCUACA | 6349 | TGTAGATA GGCTAGCTACAACGA CCGCCTGG | 6599 |
| 1067 | AGGCGGAU A UCUACAAG | 4438 | CTTGTAGA GGCTAGCTACAACGA ATCGCCT | 6600 |
| 1071 | GGAUAUCU A CAAGGCGG | 4440 | CCGCCTTG GGCTAGCTACAACGA AGATATCC | 6601 |
| 1076 | UCUACAAG G CGGACUUC | 5914 | GAAGTCCG GGCTAGCTACAACGA CTTGTAGA | 6602 |
| 1080 | CAAGGCGG A CUUCCAGG | 6350 | CCTGGAAG GGCTAGCTACAACGA CCGCCTTG | 6603 |
| 1088 | ACUUCCAG G CUGAGAGG | 5915 | CCTCTCAG GGCTAGCTACAACGA CTGGAAGT | 6604 |
| 1096 | GCUGAGAG G CAGGCCCG | 5916 | CGGGCCTG GGCTAGCTACAACGA CTCTCAGC | 6605 |

TABLE VI-continued

Human IKK-gamma DNAzyme and Substrate Sequence

| Pos | Substrate | Seq ID | DNAzyme | Seq ID |
|---|---|---|---|---|
| 1100 | AGAGGCAG G CCCGGGAG | 5917 | CTCCCGGG GGCTAGCTACAACGA CTGCCTCT | 6606 |
| 1111 | CGGGAGAA G CUGGCCGA | 5918 | TCGGCCAG GGCTAGCTACAACGA TTCTCCCG | 6607 |
| 1115 | AGAAGCUG G CCGAGAAG | 5919 | CTTCTCGG GGCTAGCTACAACGA CAGCTTCT | 6608 |
| 1129 | AAGAAGGA G CUCCUGCA | 5920 | TGCAGGAG GGCTAGCTACAACGA TCCTTCTT | 6609 |
| 1135 | GAGCUCCU G CAGGAGCA | 5921 | TGCTCCTG GGCTAGCTACAACGA AGGAGCTC | 6610 |
| 1141 | CUGCAGGA G CAGCUGGA | 5922 | TCCAGCTG GGCTAGCTACAACGA TCCTGCAG | 6611 |
| 1144 | CAGGAGCA G CUGGAGCA | 5923 | TGCTCCAG GGCTAGCTACAACGA TGCTCCTG | 6612 |
| 1150 | CAGCUGGA G CAGCUGCA | 5924 | TGCAGCTG GGCTAGCTACAACGA TCCAGCTG | 6613 |
| 1153 | CUGGAGCA G CUGCAGAG | 5925 | CTCTGCAG GGCTAGCTACAACGA TGCTCCAG | 6614 |
| 1156 | GAGCAGCU G CAGAGGGA | 5926 | TCCCTCTG GGCTAGCTACAACGA AGCTGCTC | 6615 |
| 1165 | CAGAGGGA G UACAGCAA | 5927 | TTGCTGTA GGCTAGCTACAACGA TCCCTCTG | 6616 |
| 1167 | GAGGGAGU A CAGCAAAC | 4444 | GTTTGCTG GGCTAGCTACAACGA ACTCCCTC | 6617 |
| 1170 | GGAGUACA G CAAACUGA | 5928 | TCAGTTTG GGCTAGCTACAACGA TGTACTCC | 6618 |
| 1174 | UACAGCAA A CUGAAGGC | 6351 | GCCTTCAG GGCTAGCTACAACGA TTGCTGTA | 6619 |
| 1181 | AACUGAAG G CCAGCUGU | 5929 | ACAGCTGG GGCTAGCTACAACGA CTTCAGTT | 6620 |
| 1185 | GAAGGCCA G CUGUCAGG | 5930 | CCTGACAG GGCTAGCTACAACGA TGGCCTTC | 6621 |
| 1188 | GGCCAGCU G UCAGGAGU | 5931 | ACTCCTGA GGCTAGCTACAACGA AGCTGGCC | 6622 |
| 1195 | UGUCAGGA G UCGGCCAG | 5932 | CTGGCCGA GGCTAGCTACAACGA TCCTGACA | 6623 |
| 1199 | AGGAGUCG G CCAGGAUC | 5933 | GATCCTGG GGCTAGCTACAACGA CGACTCCT | 6624 |
| 1205 | CGGCCAGG A UCGAGGAC | 6352 | GTCCTCGA GGCTAGCTACAACGA CCTGGCCG | 6625 |
| 1212 | GAUCGAGG A CAUGAGGA | 6353 | TCCTCATG GGCTAGCTACAACGA CCTCGATC | 6626 |
| 1214 | UCGAGGAC A UGAGGAAG | 5017 | CTTCCTCA GGCTAGCTACAACGA GTCCTCGA | 6627 |
| 1222 | AUGAGGAA G CGGCAUGU | 5934 | ACATGCCG GGCTAGCTACAACGA TTCCTCAT | 6628 |
| 1225 | AGGAAGCG G CAUGCGA | 5935 | TCGACATG GGCTAGCTACAACGA CGCTTCCT | 6629 |
| 1227 | GAAGCGGC A UGUCGAGG | 5018 | CCTCGACA GGCTAGCTACAACGA GCCGCTTC | 6630 |
| 1229 | AGCGGCAU G UCGAGGUC | 5936 | GACCTCGA GGCTAGCTACAACGA ATGCCGCT | 6631 |
| 1235 | AUGUCGAG G UCUCCCAG | 5937 | CTGGGAGA GGCTAGCTACAACGA CTCGACAT | 6632 |
| 1244 | UCUCCCAG G CCCCCUUG | 5938 | CAAGGGGG GGCTAGCTACAACGA CTGGGAGA | 6633 |
| 1252 | GCCCCCUU G CCCCCCGC | 5939 | GCGGGGGG GGCTAGCTACAACGA AAGGGGGC | 6634 |
| 1259 | UGCCCCCC G CCUACCUC | 5940 | GGCAGGGG GGCTAGCTACAACGA GGGGGGCA | 6635 |
| 1265 | CCGCCCCU G CCUACCUC | 5941 | GAGGTAGG GGCTAGCTACAACGA AGGGGCGG | 6636 |
| 1269 | CCCUGCCU A CCUCUCCU | 4452 | AGGAGAGG GGCTAGCTACAACGA AGGCAGGG | 6637 |
| 1286 | CUCCCCUG G CCCUGCCC | 5942 | GGGCAGGG GGCTAGCTACAACGA CAGGGGAG | 6638 |
| 1291 | CUGGCCCU G CCCAGCCA | 5943 | TGGCTGGG GGCTAGCTACAACGA AGGGCCAG | 6639 |
| 1296 | CCUGCCCA G CCAGAGGA | 5944 | TCCTCTGG GGCTAGCTACAACGA TGGGCAGG | 6640 |
| 1308 | GAGGAGGA G CCCCCCCG | 5945 | CGGGGGGG GGCTAGCTACAACGA TCCTCCTC | 6641 |
| 1321 | CCCGAGGA G CCACCUGA | 5946 | TCAGGTGG GGCTAGCTACAACGA TCCTCGGG | 6642 |
| 1324 | GAGGAGCC A CCUGACUU | 5064 | AAGTCAGG GGCTAGCTACAACGA GGCTCCTC | 6643 |
| 1329 | GCCACCUG A CUUCUGCU | 6354 | AGCAGAAG GGCTAGCTACAACGA CAGGTGGC | 6644 |
| 1335 | UGACUUUU G CUGUCCCA | 5947 | TGGGACAG GGCTAGCTACAACGA AGAAGTCA | 6645 |
| 1338 | CUUCUGCU G UCCAAGU | 5948 | ACTTGGGA GGCTAGCTACAACGA AGCAGAAG | 6646 |
| 1345 | UGUCCCAA G UGCCAGUA | 5949 | TACTGGCA GGCTAGCTACAACGA TTGGGACA | 6647 |
| 1347 | UCCCAAGU G CCAGUAUC | 5950 | GATACTGG GGCTAGCTACAACGA ACTTGGGA | 6648 |
| 1351 | AAGUGCCA G UAUCAGGC | 5951 | GCCTGATA GGCTAGCTACAACGA TGGCAGTT | 6649 |
| 1353 | GUGCCAGU A UCAGGCCC | 4460 | GGGCCTGA GGCTAGCTACAACGA ACTGGCAC | 6650 |
| 1358 | AGUAUCAG G CCCCUGAU | 5952 | ATCAGGGG GGCTAGCTACAACGA CTGATACT | 6651 |
| 1365 | GGCCCCUG A UAUGGACA | 6355 | TGTCCATA GGCTAGCTACAACGA CAGGGGCC | 6652 |
| 1367 | CCCCUGAU A UGGACACC | 4462 | GGTGTCCA GGCTAGCTACAACGA ATCAGGGG | 6653 |
| 1371 | UGAUAUGG A CACCCUGC | 6356 | GCAGGGTG GGCTAGCTACAACGA CCATATCA | 6654 |
| 1373 | AUAUGGAC A CCCUGCAG | 5080 | CTGCAGGG GGCTAGCTACAACGA GTCCATAT | 6655 |
| 1378 | GACACCCU G CAGAUACA | 5953 | TGTATCTG GGCTAGCTACAACGA AGGGTGTC | 6656 |
| 1382 | CCCUGCAG A UACAUGUC | 6357 | GACATGTA GGCTAGCTACAACGA CTGCAGGG | 6657 |
| 1384 | CUGCAGAU A CAUGUCAU | 4463 | ATGACATG GGCTAGCTACAACGA ATCTGCAG | 6658 |
| 1386 | GCAGAUAC A UGUCAUGG | 5085 | CCATGACA GGCTAGCTACAACGA GTATCTGC | 6659 |
| 1388 | AGAUACAU G UCAUGGAG | 5954 | CTCCATGA GGCTAGCTACAACGA ATGTATCT | 6660 |
| 1391 | UACAUGUC A UGGAGUGC | 5086 | GCACTCCA GGCTAGCTACAACGA GACATGTA | 6661 |
| 1396 | GUCAUGGA G UGCAUUGA | 5955 | TCAATGCA GGCTAGCTACAACGA TCCATGAC | 6662 |
| 1398 | CAUGGAGU G CAUUGAGU | 5956 | ACTCAATG GGCTAGCTACAACGA ACTCCATG | 6663 |
| 1400 | UGGAGUGC A UUGAGUAG | 5087 | CTACTCAA GGCTAGCTACAACGA GCACTCCA | 6664 |
| 1405 | UGCAUUGA G UAGGGCCG | 5957 | CGGCCCTA GGCTAGCTACAACGA TCAATGCA | 6665 |
| 1410 | UGAGUAGG G CCGGCCAG | 5958 | CTGGCCGG GGCTAGCTACAACGA CCTACTCA | 6666 |
| 1414 | UAGGGCCG G CCAGUGCA | 5959 | TGCACTGG GGCTAGCTACAACGA CGGCCCTA | 6667 |
| 1418 | GCCGGCCA G UGCAAGGC | 5960 | GCCTTGCA GGCTAGCTACAACGA TGGCCGGC | 6668 |
| 1420 | CGGCCAGU G CAAGGCCA | 5961 | TGGCCTTG GGCTAGCTACAACGA ACTGGCCG | 6669 |
| 1425 | AGUGCAAG G CCACUGCC | 5962 | GGCAGTGG GGCTAGCTACAACGA CTTGCACT | 6670 |
| 1428 | GCAAGGCC A CUGCCUGC | 5093 | GCAGGCAG GGCTAGCTACAACGA GGCCTTGC | 6671 |
| 1431 | AGGCCACU G CCUGCCCG | 5963 | CGGGCAGG GGCTAGCTACAACGA AGTGGCCT | 6672 |
| 1435 | CACUGCCU G CCCGAGGA | 5964 | TCCTCGGG GGCTAGCTACAACGA AGGCAGTG | 6673 |
| 1443 | GCCCGAGG A CGUGCCCG | 6358 | CGGGCACG GGCTAGCTACAACGA CCTCGGGC | 6674 |
| 1445 | CCGAGGAC G UGCCCGGG | 5965 | CCCGGGCA GGCTAGCTACAACGA GTCCTCGG | 6675 |
| 1447 | GAGGACGU G CCCGGGAC | 5966 | GTCCCGGG GGCTAGCTACAACGA ACGTCCTC | 6676 |
| 1454 | UGCCCGGG A CCGUGCAG | 6359 | CTGCACGG GGCTAGCTACAACGA CCCGGGCA | 6677 |
| 1457 | CCGGGACC G UGCAGUCU | 5967 | AGACTGCA GGCTAGCTACAACGA GGTCCCGG | 6678 |
| 1459 | GGGACCGU G CAGUCUGC | 5968 | GCAGACTG GGCTAGCTACAACGA ACGGTCCC | 6679 |

TABLE VI-continued

Human IKK-gamma DNAzyme and Substrate Sequence

| Pos | Substrate | Seq ID | DNAzyme | Seq ID |
|---|---|---|---|---|
| 1462 | ACCGUGCA G UCUGCGCU | 5969 | AGCGCAGA GGCTAGCTACAACGA TGCACGGT | 6680 |
| 1466 | UGCAGUCU G CGCUUUCC | 5970 | GGAAAGCG GGCTAGCTACAACGA AGACTGCA | 6681 |
| 1468 | CAGUCUGC G CUUUCCUC | 5971 | GAGGAAAG GGCTAGCTACAACGA GCAGACTG | 6682 |
| 1481 | CCUCUCCC G CCUGCCUA | 5972 | TAGGCAGG GGCTAGCTACAACGA GGGAGAGG | 6683 |
| 1485 | UCCCGCCU G CCUACCCC | 5973 | GGGCTAGG GGCTAGCTACAACGA AGCCGGGA | 6684 |
| 1490 | CCUGCCUA G CCCAGGAU | 5974 | ATCCTGGG GGCTAGCTACAACGA TACGCAGG | 6685 |
| 1497 | AGCCCAGG A UGAAGGGC | 6360 | GCCCTTCA GGCTAGCTACAACGA CCTCGGCT | 6686 |
| 1504 | GAUGAAGG G CUGGGUGG | 5975 | CCACCCAG GGCTAGCTACAACGA CCTTCATC | 6687 |
| 1509 | AGGGCUGG G UGCCCACA | 5976 | TCTGGCCA GGCTAGCTACAACGA CCAGCCCT | 6688 |
| 1512 | GCUGGGUG G CCACAACU | 5977 | AGTTGTGG GGCTAGCTACAACGA CACCCACC | 6689 |
| 1515 | GGGUGCCC A CAACUGGC | 5119 | CCCAGTTG GGCTAGCTACAACGA GGGCACCC | 6690 |
| 1518 | UGGCCACA A CUGGGAUC | 6361 | CATCCCAG GGCTAGCTACAACGA TGTCCCCA | 6691 |
| 1524 | CAACUGGG A UGCCACCU | 6362 | AGCTGGCA GGCTAGCTACAACGA CCCAGTTG | 6692 |
| 1526 | ACUGGGAU G CCACCUGG | 5978 | CCAGGTGG GGCTAGCTACAACGA ATCCCAGT | 6693 |
| 1529 | GGGAUGCC A CCUGGAGC | 5123 | GCTCCAGG GGCTAGCTACAACGA GGCATCCC | 6694 |
| 1536 | CACCUGGA G CCCCACCC | 5979 | GGGTGGGG GGCTAGCTACAACGA TCCAGGTG | 6695 |
| 1541 | GGACCCCC A CCCAGGAG | 5129 | CTCCTGGG GGCTAGCTACAACGA GGGGCTCC | 6696 |
| 1549 | ACCCAGGA G CUGGCCGC | 5980 | CCGGCCAG GGCTAGCTACAACGA TCCTGGGT | 6697 |
| 1553 | AGGAGCUG G CCGCGGCA | 5981 | TGCCGCGG GGCTAGCTACAACGA CAGCTCCT | 6698 |
| 1556 | AGCUGGCC G CGGCACCU | 5982 | AGGTGCCG GGCTAGCTACAACGA GGCCAGCT | 6699 |
| 1559 | UGGCCGCC G CACCUUAC | 5983 | GTAAGGTC GGCTAGCTACAACGA CGCCCCCA | 6700 |
| 1561 | GCCGCGCC A CCUUACGC | 5135 | GCGTAAGG GGCTAGCTACAACGA GCCGCGGC | 6701 |
| 1566 | GGCACCUU A CGCUUCAG | 4475 | CTGAAGCG GGCTAGCTACAACGA AAGGTGCC | 6702 |
| 1568 | CACCUUAC G CUUCACCU | 5984 | ACCTGAAG GGCTAGCTACAACGA GTAAGGTG | 6703 |
| 1574 | ACGCUUCA G CUGUUGAU | 5985 | ATCAACAG GGCTAGCTACAACGA TGAAGCGT | 6704 |
| 1577 | CUUCAGCU G UUGAUCCG | 5986 | CGGATCAA GGCTAGCTACAACGA AGCTGAAG | 6705 |
| 1581 | AGCUGUUG A UCCGCUGG | 6363 | CCAGCGGA GGCTAGCTACAACGA CAACAGCT | 6706 |
| 1585 | GUUGAUCC G CUGGUCAC | 5987 | GGGACCAG GGCTAGCTACAACGA GGATCAAC | 6707 |
| 1589 | AUCCGCUG G UCCCCUCU | 5988 | AGAGGGGA GGCTAGCTACAACGA CAGCGGAT | 6708 |
| 1604 | CUUUGGG G UAGAUGCG | 5989 | CGCATCTA GGCTAGCTACAACGA CCCAAAAG | 6709 |
| 1608 | UGGGGUAG A UGCGGCCC | 6364 | GGGCCGCA GGCTAGCTACAACGA CTACCCCA | 6710 |
| 1610 | GGGUAGAU G CGGCCCCG | 5990 | CGGGGCCG GGCTAGCTACAACGA ATCTACCC | 6711 |
| 1613 | UAGAUGCG G CCCCGAUC | 5991 | GATCGGGG GGCTAGCTACAACGA CGCATCTA | 6712 |
| 1619 | CGGCCCCG A UCAGGCCU | 6365 | AGGCCTGA GGCTAGCTACAACGA CGGGGCCG | 6713 |
| 1624 | CCGAUCAG G CCUGACUC | 5992 | GAGTCAGG GGCTAGCTACAACGA CTGATCGG | 6714 |
| 1629 | CAGGCCUG A CUCGCUGC | 6366 | GCAGCGAC GGCTAGCTACAACGA CAGGCCTG | 6715 |
| 1633 | CCUGACUC G CUGCUCUU | 5993 | AAGAGCAG GGCTAGCTACAACGA GAGTCAGG | 6716 |
| 1636 | GACUCGCU G CUCUUUUU | 5994 | AAAAAGAG GGCTAGCTACAACGA AGCGAGTC | 6717 |
| 1645 | CUCUUUUU G UUCCCUUC | 5995 | GAAGGGAA GGCTAGCTACAACGA AAAAAGAG | 6718 |
| 1655 | UCCCUUCU G UCUGCUCG | 5996 | CGAGCAGA GGCTAGCTACAACGA AGAAGGGA | 6719 |
| 1659 | UUCUGUCU G CUCGAACC | 5997 | GGTTCGAC GGCTAGCTACAACGA AGACACAA | 6720 |
| 1665 | CUGCUCGA A CCACUUGC | 6367 | GCAAGTGG GGCTAGCTACAACGA TCGAGCAG | 6721 |
| 1668 | CUCGAACC A CUUGCCUC | 5165 | GAGGCAAG GGCTAGCTACAACGA GGTTCGAG | 6722 |
| 1672 | AACCACUU G CCUCGGGC | 5998 | GCCGCAGG GGCTAGCTACAACGA AAGTGGTT | 6723 |
| 1679 | UGCCUCGG G CUAAUCCC | 5999 | GGGATTAG GGCTAGCTACAACGA CCGAGGCA | 6724 |
| 1683 | UCGGGCUA A UCCCUCCC | 6368 | GGGAGGGA GGCTAGCTACAACGA TAGCCCGA | 6725 |
| 1701 | CUUCCUCC A CCCGGCAC | 5180 | GTGCCGGG GGCTAGCTACAACGA GGAGGAAG | 6726 |
| 1706 | UCCACCCG G CACUGGGG | 6000 | CCCCAGTG GGCTAGCTACAACGA CGGGTGGA | 6727 |
| 1708 | CACCCGGC A CUGGGGAA | 5183 | TTCCCCAG GGCTAGCTACAACGA GCCGGGTG | 6728 |
| 1717 | CUGGGGAA G UCAAGAAU | 6001 | ATTCTTGA GGCTAGCTACAACGA TTCCCCAG | 6729 |
| 1724 | AGUCAAGA A UGGGGCCU | 6369 | AGGCCCCA GGCTAGCTACAACGA TCTTGACT | 6730 |
| 1729 | AGAAUGGG G CCUGGGGC | 6002 | GCCCCAGG GGCTAGCTACAACGA CCCATTCT | 6731 |
| 1736 | GGCCUGGG G CUCUCAGG | 6003 | CCTGAGAG GGCTAGCTACAACGA CCCAGGCC | 6732 |
| 1749 | CAGGGAGA A CUGCUUCC | 6370 | GGAAGCAG GGCTAGCTACAACGA TCTCCCTG | 6733 |
| 1752 | GGAGAACU G CUUCCCCU | 6004 | AGGGGAAG GGCTAGCTACAACGA AGTTCTCC | 6734 |
| 1762 | UUCCCCUG G CAGAGCUG | 6005 | CAGCTCTG GGCTAGCTACAACGA CAGGGGAA | 6735 |
| 1767 | CUGGCAGA G CUGGGUGG | 6006 | CCACCCAG GGCTAGCTACAACGA TCTGCCAG | 6736 |
| 1772 | AGAGCUGG G UGGCAGCU | 6007 | AGCTGCCA GGCTAGCTACAACGA CCAGCTCT | 6737 |
| 1775 | GCUGGGUG G CAGCUCUU | 6008 | AAGAGCTG GGCTAGCTACAACGA CACCCAGC | 6738 |
| 1778 | GGGUGGCA G CUCUUCCU | 6009 | AGGAAGAG GGCTAGCTACAACGA TGCCACCC | 6739 |
| 1790 | UUCCUCCC A CCGGACAC | 5206 | GTGTCCGG GGCTAGCTACAACGA GGGAGGAA | 6740 |
| 1795 | CCCACCGG A CACCGACC | 6371 | GGTCGGTG GGCTAGCTACAACGA CCGGTGGG | 6741 |
| 1797 | CACCGGAC A CCGACCCG | 5208 | CGGGTCGG GGCTAGCTACAACGA GTCCGGTG | 6742 |
| 1801 | GGACACCG A CCCGCCCG | 6372 | CGGGCGGG GGCTAGCTACAACGA CGGTGTCC | 6743 |
| 1805 | ACCGACCC G CCCGCCGC | 6010 | GCGGCGGG GGCTAGCTACAACGA GGGTCGGT | 6744 |
| 1809 | ACCCGCCC G CCGCUGUG | 6011 | CACAGCGG GGCTAGCTACAACGA GGGCGGGT | 6745 |
| 1812 | CGCCCGCC G CUGUGCCC | 6012 | GGGCACAG GGCTAGCTACAACGA GGCGGGCG | 6746 |
| 1815 | CCGCCGCU G UGCCCUGG | 6013 | CCAGGGCA GGCTAGCTACAACGA AGCGGCGG | 6747 |
| 1817 | GCCGCUGU G CCCUGGGA | 6014 | TCCCAGGG GGCTAGCTACAACGA ACAGCGGC | 6748 |
| 1826 | CCCUGGGA G UGCUGCCC | 6015 | GGGCAGCA GGCTAGCTACAACGA TCCCAGGG | 6749 |
| 1828 | CUGGGAGU G CUGCCCUC | 6016 | GAGGGCAG GGCTAGCTACAACGA ACTCCCAG | 6750 |
| 1831 | GGAGUGCU G CCCUCUUA | 6017 | TAAGAGGG GGCTAGCTACAACGA AGCACTCC | 6751 |
| 1839 | GCCCUCUU A CCAUGCAC | 4519 | GTGCATGG GGCTAGCTACAACGA AAGAGGGC | 6752 |
| 1842 | CUCUUACC A UGCACACG | 5225 | CGTGTGCA GGCTAGCTACAACGA GGTAAGAG | 6753 |

TABLE VI-continued

Human IKK-gamma DNAzyme and Substrate Sequence

| Pos | Substrate | Seq ID | DNAzyme | Seq ID |
|---|---|---|---|---|
| 1844 | CUUACCAU G CACACGGG | 6018 | CCCGTGTG GGCTAGCTACAACGA ATGGTAAG | 6754 |
| 1846 | UACCAUGC A CACGGGUG | 5226 | CACCCGTG GGCTAGCTACAACGA GCATGGTA | 6755 |
| 1848 | CCAUGCAC A CGGGUGCU | 5227 | AGCACCCG GGCTAGCTACAACGA GTGCATGG | 6756 |
| 1852 | GCACACGG G UGCUCUCC | 6019 | GGAGAGCA GGCTAGCTACAACGA CCGTGTGC | 6757 |
| 1854 | ACACGGGU G CUCUCCUU | 6020 | AAGGAGAG GGCTAGCTACAACGA ACCCGTGT | 6758 |
| 1867 | CCUUUUGG G CUGCAUGC | 6021 | GCATGCAG GGCTAGCTACAACGA CCAAAAGG | 6759 |
| 1870 | UUUGGGCU G CAUGCUAU | 6022 | ATAGCATG GGCTAGCTACAACGA AGCCCAAA | 6760 |
| 1872 | UGGGCUGC A UGCUAUUC | 5233 | GAATAGCA GGCTAGCTACAACGA GCAGCCCA | 6761 |
| 1874 | GGCUGCAU G CUAUUCCA | 6023 | TGGAATAG GGCTAGCTACAACGA ATGCAGCC | 6762 |
| 1877 | UGCAUGCU A UUCCAUUU | 4525 | AAATGGAA GGCTAGCTACAACGA AGCATGCA | 6763 |
| 1882 | GCUAUUCC A UUUUGCAC | 5236 | CTGCAAAA GGCTAGCTACAACGA GGAATAGC | 6764 |
| 1887 | UCCAUUUU G CAGCCAGA | 6024 | TCTGGCTG GGCTAGCTACAACGA AAAATGGA | 6765 |
| 1890 | AUUUUGCA G CCAGACCG | 6025 | CGGTCTGG GGCTAGCTACAACGA TGCAAAAT | 6766 |
| 1895 | GCAGCCAG A CCGAUGUG | 6373 | CACATCGG GGCTAGCTACAACGA CTGGCTGC | 6767 |
| 1899 | CCAGACCG A UGUAUUU | 6374 | AATACACA GGCTAGCTACAACGA CGGTCTGG | 6768 |
| 1901 | AGACCGAU G UGUAUUUA | 6026 | TAAATACA GGCTAGCTACAACGA ATCGGTCT | 6769 |
| 1903 | ACCGAUGU G UAUUUAAC | 6027 | GTTAAATA GGCTAGCTACAACGA ACATCGGT | 6770 |
| 1905 | CGAUGUGU A UUUAACCA | 4531 | TGGTTAAA GGCTAGCTACAACGA ACACATCG | 6771 |
| 1910 | UGUAUUUA A CCAGUCAC | 6375 | GTGACTGG GGCTAGCTACAACGA TAAATACA | 6772 |
| 1914 | UUUAACCA G UCACUAUU | 6028 | AATAGTGA GGCTAGCTACAACGA TGGTTAAA | 6773 |
| 1917 | AACCAGUC A CUAUUGAU | 5243 | ATCAATAG GGCTAGCTACAACGA GACTGGTT | 6774 |
| 1920 | CAGUCACU A UUGAUGGA | 4536 | TCCATCAA GGCTAGCTACAACGA AGTGACTG | 6775 |
| 1924 | CACUAUUG A UGGACAUU | 6376 | AATGTCCA GGCTAGCTACAACGA CAATAGTG | 6776 |
| 1928 | AUUGAUGG A CAUUUGGG | 6377 | CCCAAATG GGCTAGCTACAACGA CCATCAAT | 6777 |
| 1930 | UGAUGGAC A UUUGGGUU | 5245 | AACCCAAA GGCTAGCTACAACGA GTCCATCA | 6778 |
| 1936 | ACAUUUGG G UUGUUUCC | 6029 | GGAAACAA GGCTAGCTACAACGA CCAAATGT | 6779 |
| 1939 | UUUGGGUU G UUUCCCAU | 6030 | ATGGGAAA GGCTAGCTACAACGA AACCCAAA | 6780 |
| 1946 | UGUUUCCC A UCUUUUUG | 5248 | CAAAAAGA GGCTAGCTACAACGA GGGAAACA | 6781 |
| 1954 | AUCUUUUU G UUACCAUA | 6031 | TATGGTAA GGCTAGCTACAACGA AAAAAGAT | 6782 |
| 1957 | UUUUUGUU A CCAUAAAU | 4550 | ATTTATGG GGCTAGCTACAACGA AACAAAAA | 6783 |
| 1960 | UUGUUACC A UAAAUAAU | 5251 | ATTATTTA GGCTAGCTACAACGA GGTAACAA | 6784 |
| 1964 | UACCAUAA A UAAUGGCA | 6378 | TGCCATTA GGCTAGCTACAACGA TTATGGTA | 6785 |
| 1967 | CAUAAAUA A UGGCAUAG | 6379 | CTATGCCA GGCTAGCTACAACGA TATTTATG | 6786 |
| 1970 | AAAUAAUG G CAUAGUAA | 6032 | TTACTATG GGCTAGCTACAACGA CATTATTT | 6787 |
| 1972 | AUAAUGGC A UAGUAAAA | 5252 | TTTTACTA GGCTAGCTACAACGA GCCATTAT | 6788 |
| 1975 | AUGGCAUA G UAAAAAAA | 6033 | TTTTTTTA GGCTAGCTACAACGA TATGCCAT | 6789 |

Input Sequence = NM_003639. Cut Site = R/Y
Arm Length = 8. Core Sequence = GGCTAGCTACAACGA
NM_003639 (*Homo Sapiens* inhibitor of kappa light polypeptide gene enhancer in B-cells, kinase gamma (IKBKG), mRNA.; 1994 bp)

TABLE VII

Human IKK-gamma Amberzyme and Substrate Sequence

| Pos | Substrate | Seq ID | Amberzyme | Seq ID |
|---|---|---|---|---|
| 12 | ACGAGCAU G GCCCUUGU | 6790 | ACAAGGGC GGAGGAAACUCC CU UCAAGGACAUCGUCCGGG AUGCUCGU | 7142 |
| 13 | CGAGCAUG G CCCUUGUG | 5757 | CACAAGGG GGAGGAAACUCC CU UCAAGGACAUCGUCCGGG CAUGCUCG | 7143 |
| 19 | UGGCCCUU G UGAUCCAG | 5758 | CUGGAUCA GGAGGAAACUCC CU UCAAGGACAUCGUCCGGG AAGGGCCA | 7144 |
| 21 | GCCCUUGU G AUCCAGGU | 6791 | ACCUGGAU GGAGGAAACUCC CU UCAAGGACAUCGUCCGGG ACAAGGGC | 7145 |
| 27 | GUGAUCCA G GUGGGGAA | 6792 | UUCCCCAC GGAGGAAACUCC CU UCAAGGACAUCGUCCGGG UGGAUCAC | 7146 |
| 28 | UGAUCCAG G UGGGGAAA | 5759 | UUUCCCCA GGAGGAAACUCC CU UCAAGGACAUCGUCCGGG CUGGAUCA | 7147 |
| 30 | AUCCAGGU G GGGAAACU | 6793 | AGUUUCCC GGAGGAAACUCC CU UCAAGGACAUCGUCCGGG ACCUGGAU | 7148 |
| 31 | UCCAGGUG G GGAAACUA | 6794 | UAGUUUCC GGAGGAAACUCC CU UCAAGGACAUCGUCCGGG CACCUGGA | 7149 |
| 32 | CCAGGUGG G GAAACUAA | 6795 | UUAGUUUC GGAGGAAACUCC CU UCAAGGACAUCGUCCGGG CCACCUGG | 7150 |
| 33 | CAGGUGGG G AAACUAAG | 6796 | CUUAGUUU GGAGGAAACUCC CU UCAAGGACAUCGUCCGGG CCCACCUG | 7151 |
| 41 | GAAACUAA G GCCCAGAG | 6797 | CUCUGGGC GGAGGAAACUCC CU UCAAGGACAUCGUCCGGG UUAGUUUC | 7152 |
| 42 | AAACUAAG G CCCAGAGA | 5760 | UCUCUGGG GGAGGAAACUCC CU UCAAGGACAUCGUCCGGG CUUAGUUU | 7153 |
| 47 | AAGGCCCA G AGAAGUGA | 6798 | UCACUUCU GGAGGAAACUCC CU UCAAGGACAUCGUCCGGG UGGGCCUU | 7154 |
| 49 | GGCCCAGA G AAGUGAGG | 6799 | CCUCACUU GGAGGAAACUCC CU UCAAGGACAUCGUCCGGG UCUGGGCC | 7155 |
| 52 | CCAGAGAA G UGAGGACC | 5761 | GGUCCUCA GGAGGAAACUCC CU UCAAGGACAUCGUCCGGG UUCUCUGG | 7156 |
| 54 | AGAGAAGU G AGGACCCC | 6800 | GGGGUCCU GGAGGAAACUCC CU UCAAGGACAUCGUCCGGG ACUUCUCU | 7157 |
| 56 | AGAAGUGA G GACCCCGC | 6801 | GCGGGGUC GGAGGAAACUCC CU UCAAGGACAUCGUCCGGG UCACUUCU | 7158 |
| 57 | GAAGUGAG G ACCCCGCA | 6802 | UGCGGGGU GGAGGAAACUCC CU UCAAGGACAUCGUCCGGG CUCACUUC | 7159 |
| 63 | AGGACCCC G CAGACAUG | 5762 | AUAGUCUG GGAGGAAACUCC CU UCAAGGACAUCGUCCGGG GGGGUCCU | 7160 |
| 66 | ACCCCGCA G ACUAUCAA | 6803 | UUGAUAGU GGAGGAAACUCC CU UCAAGGACAUCGUCCGGG UGCGGGGU | 7161 |
| 80 | CAAUCCCA G UCUCUUCC | 5763 | GGAAGAGA GGAGGAAACUCC CU UCAAGGACAUCGUCCGGG UGGGAUUG | 7162 |
| 100 | CACUCCCU G UGAAGCUC | 5764 | GAGCUUCA GGAGGAAACUCC CU UCAAGGACAUCGUCCGGG AGGGAGUG | 7163 |
| 102 | CUCCCUGU G AAGCUCUC | 6804 | GAGAGCUU GGAGGAAACUCC CU UCAAGGACAUCGUCCGGG ACAGGGAG | 7164 |
| 105 | CCUGUGAA G CUCUCCAG | 5765 | CUGGAGAG GGAGGAAACUCC CU UCAAGGACAUCGUCCGGG UUCACAGG | 7165 |

TABLE VII-continued

Human IKK-gamma Amberzyme and Substrate Sequence

| Pos | Substrate | | | Seq ID | Amberzyme | | | | Seq ID |
|---|---|---|---|---|---|---|---|---|---|
| 113 | GCUCUCCA | G | CAUCAUCG | 5766 | CGAUGAUG | GGAGGAAACUCC | CU | UCAAGGACAUCGUCCGGG | UGGAGAGC | 7166 |
| 121 | GCAUCAUC | G | AGGUCCCA | 6805 | UGGGACCU | GGAGGAAACUCC | CU | UCAAGGACAUCGUCCGGG | GAUGAUGC | 7167 |
| 123 | AUCAUCGA | G | GUCCCAUC | 6806 | GAUGGGAC | GGAGGAAACUCC | CU | UCAAGGACAUCGUCCGGG | UCGAUGAU | 7168 |
| 124 | UCAUCGAG | G | UCCCAUCA | 5767 | UGAUGGGA | GGAGGAAACUCC | CU | UCAAGGACAUCGUCCGGG | CUCGAUGA | 7169 |
| 133 | UCCCAUCA | G | CCCUUGCC | 5768 | GGCAAGGG | GGAGGAAACUCC | CU | UCAAGGACAUCGUCCGGG | UGAUGGGA | 7170 |
| 139 | CAGCCCUU | G | CCCUGUUG | 5769 | CAACAGGG | GGAGGAAACUCC | CU | UCAAGGACAUCGUCCGGG | AAGGGCUG | 7171 |
| 144 | CUUGCCCU | G | UUGGAUGA | 5770 | UCAUCCAA | GGAGGAAACUCC | CU | UCAAGGACAUCGUCCGGG | AGGGCAAG | 7172 |
| 147 | GCCCUGUU | G | GAUGAAUA | 6807 | UAUUCAUC | GGAGGAAACUCC | CU | UCAAGGACAUCGUCCGGG | AACAGGGC | 7173 |
| 148 | CCCUGUUG | G | AUGAAUAG | 6808 | CUAUUCAU | GGAGGAAACUCC | CU | UCAAGGACAUCGUCCGGG | CAACAGGG | 7174 |
| 151 | UGUUGGAU | G | AAUAGGCA | 6809 | UGCCUAUU | GGAGGAAACUCC | CU | UCAAGGACAUCGUCCGGG | AUCCAACA | 7175 |
| 156 | GAUGAAUA | G | GCACCUCU | 6810 | AGAGGUGC | GGAGGAAACUCC | CU | UCAAGGACAUCGUCCGGG | UAUUCAUC | 7176 |
| 157 | AUGAAUAG | G | CACCUCUG | 5771 | CAGAGGUG | GGAGGAAACUCC | CU | UCAAGGACAUCGUCCGGG | CUAUUCAU | 7177 |
| 165 | GCACCUCU | G | GAAGAGCC | 6811 | GGCUCUUC | GGAGGAAACUCC | CU | UCAAGGACAUCGUCCGGG | AGAGGUGC | 7178 |
| 166 | CACCUCUG | G | AAGAGCCA | 6812 | UGGCUCUU | GGAGGAAACUCC | CU | UCAAGGACAUCGUCCGGG | CAGAGGUG | 7179 |
| 169 | CUCUGGAA | G | AGCCAACU | 6813 | AGUUGGCU | GGAGGAAACUCC | CU | UCAAGGACAUCGUCCGGG | UUCCAGAG | 7180 |
| 171 | CUGGAAGA | G | CCAACUGU | 5772 | ACAGUUGG | GGAGGAAACUCC | CU | UCAAGGACAUCGUCCGGG | UCUUCCAG | 7181 |
| 178 | AGCCAACU | G | UGUGAGAU | 5773 | AUCUCACA | GGAGGAAACUCC | CU | UCAAGGACAUCGUCCGGG | AGUUGGCU | 7182 |
| 180 | CCAACUGU | G | UGAGAUGG | 5774 | CCAUCUCA | GGAGGAAACUCC | CU | UCAAGGACAUCGUCCGGG | ACAGUUGG | 7183 |
| 182 | AACUGUGU | G | AGAUGGUG | 6814 | CACCAUCU | GGAGGAAACUCC | CU | UCAAGGACAUCGUCCGGG | ACACAGUU | 7184 |
| 184 | CUGUGUGA | G | AUGGUGCA | 6815 | UGCACCAU | GGAGGAAACUCC | CU | UCAAGGACAUCGUCCGGG | UCACACAG | 7185 |
| 187 | UGUGAGAU | G | GUGCAGCC | 6816 | GGCUGCAC | GGAGGAAACUCC | CU | UCAAGGACAUCGUCCGGG | AUCUCACA | 7186 |
| 188 | GUGAGAUG | G | UGCAGCCC | 5775 | GGGCUGCA | GGAGGAAACUCC | CU | UCAAGGACAUCGUCCGGG | CAUCUCAC | 7187 |
| 190 | GAGAUGGU | G | CAGCCCAG | 5776 | CUGGGCUG | GGAGGAAACUCC | CU | UCAAGGACAUCGUCCGGG | ACCAUCUC | 7188 |
| 193 | AUGGUGCA | G | CCCAGUGG | 5777 | CCACUGGG | GGAGGAAACUCC | CU | UCAAGGACAUCGUCCGGG | UGCACCAU | 7189 |
| 198 | GCAGCCCA | G | UGGCCCGG | 5778 | GGCCACCA | GGAGGAAACUCC | CU | UCAAGGACAUCGUCCGGG | UGGGCUGC | 7190 |
| 200 | AGCCCAGU | G | GUGGCCCG | 6817 | CGGGCCAC | GGAGGAAACUCC | CU | UCAAGGACAUCGUCCGGG | ACUGGGCU | 7191 |
| 201 | GCCCAGUG | G | UGGCCCGG | 5779 | CCGGGCCA | GGAGGAAACUCC | CU | UCAAGGACAUCGUCCGGG | CACUGGGC | 7192 |
| 203 | CCAGUGGU | G | GCCCGGCA | 6818 | UGCCGGGC | GGAGGAAACUCC | CU | UCAAGGACAUCGUCCGGG | ACCACUGG | 7193 |
| 204 | CAGUGGUG | G | CCCGGCAG | 5780 | CUGCCGGG | GGAGGAAACUCC | CU | UCAAGGACAUCGUCCGGG | CACCACUG | 7194 |
| 208 | GGUGGCCC | G | GCAGCAGA | 6819 | UCUGCUGC | GGAGGAAACUCC | CU | UCAAGGACAUCGUCCGGG | GGGCCACC | 7195 |
| 209 | GUGGCCCG | G | CAGCAGAU | 5781 | AUCUGCUG | GGAGGAAACUCC | CU | UCAAGGACAUCGUCCGGG | CGGGCCAC | 7196 |
| 212 | GCCCGGCA | G | CAGAUCAG | 5782 | CUGAUCUG | GGAGGAAACUCC | CU | UCAAGGACAUCGUCCGGG | UGCCGGGC | 7197 |
| 215 | CGGCAGCA | G | AUCAGGAC | 6820 | GUCCUGAU | GGAGGAAACUCC | CU | UCAAGGACAUCGUCCGGG | UGCUGCCG | 7198 |
| 220 | GCAGAUCA | G | GACGUACU | 6821 | AGUACCUC | GGAGGAAACUCC | CU | UCAAGGACAUCGUCCGGG | UGAUCUGC | 7199 |
| 221 | CAGAUCAG | G | ACGUACUG | 6822 | CAGUACGU | GGAGGAAACUCC | CU | UCAAGGACAUCGUCCGGG | CUGAUCUG | 7200 |
| 224 | AUCAGGAC | G | UACUGGGC | 5783 | GCCCAGUA | GGAGGAAACUCC | CU | UCAAGGACAUCGUCCGGG | GUCCUGAU | 7201 |
| 229 | GACGUACU | G | GGCGAAGA | 6823 | UCUUCGCC | GGAGGAAACUCC | CU | UCAAGGACAUCGUCCGGG | AGUACGUC | 7202 |
| 230 | ACGUACUG | G | GCGAAGAG | 6824 | CUCUUCGC | GGAGGAAACUCC | CU | UCAAGGACAUCGUCCGGG | CAGUACGU | 7203 |
| 231 | CGUACUGG | G | CGAAGAGU | 5784 | ACUCUUCG | GGAGGAAACUCC | CU | UCAAGGACAUCGUCCGGG | CCAGUACG | 7204 |
| 233 | UACUGGGC | G | AAGAGUCU | 6825 | AGACUCUU | GGAGGAAACUCC | CU | UCAAGGACAUCGUCCGGG | GCCCAGUA | 7205 |
| 236 | UGGGCGAA | G | AGUCUCU | 6826 | AGGAGACU | GGAGGAAACUCC | CU | UCAAGGACAUCGUCCGGG | UUCGCCCA | 7206 |
| 238 | GGCGAAGA | G | UCCCUCU | 5785 | AGAGGAGA | GGAGGAAACUCC | CU | UCAAGGACAUCGUCCGGG | UCUUCGCC | 7207 |
| 247 | UCUCCUCU | G | GGGAAGCC | 6827 | GGCUUCCC | GGAGGAAACUCC | CU | UCAAGGACAUCGUCCGGG | AGAGGAGA | 7208 |
| 248 | CUCCUCUG | G | GAAGCCA | 6828 | UGGCUUCC | GGAGGAAACUCC | CU | UCAAGGACAUCGUCCGGG | CAGAGGAG | 7209 |
| 249 | UCCUCUGG | G | AAGCCAG | 6829 | CUGGCUUC | GGAGGAAACUCC | CU | UCAAGGACAUCGUCCGGG | CCAGAGGA | 7210 |
| 250 | CCUCUGGG | A | AGCCAGC | 6830 | GCUGGCUU | GGAGGAAACUCC | CU | UCAAGGACAUCGUCCGGG | CCCAGAGG | 7211 |
| 253 | CUGGGAA | G | CCAGCAU | 5786 | AUGGCUGG | GGAGGAAACUCC | CU | UCAAGGACAUCGUCCGGG | UUCCCCAG | 7212 |
| 257 | GGAAGCCA | G | CCAUGCUG | 5787 | CAGCAUGG | GGAGGAAACUCC | CU | UCAAGGACAUCGUCCGGG | UGGCUUCC | 7213 |
| 262 | CCAGCCAU | G | CUGCACCU | 5788 | AGGUCCAG | GGAGGAAACUCC | CU | UCAAGGACAUCGUCCGGG | AUGGCUGG | 7214 |
| 265 | GCCAUGCU | G | CACCUGCC | 5789 | GGCAGGUG | GGAGGAAACUCC | CU | UCAAGGACAUCGUCCGGG | AGCAUGGC | 7215 |
| 271 | CUGCACCU | G | CCUUCAGA | 5790 | UCUGAAGG | GGAGGAAACUCC | CU | UCAAGGACAUCGUCCGGG | AGGUCCAG | 7216 |
| 278 | UGCCUUCA | G | AACAGGGC | 6831 | GCCCUGUU | GGAGGAAACUCC | CU | UCAAGGACAUCGUCCGGG | UGAAGGCA | 7217 |
| 283 | UCAGAACA | G | GGCGCUCC | 6832 | CCACCCCC | GGAGGAAACUCC | CU | UCAAGGACAUCGUCCGGG | UGUUCUCA | 7218 |
| 284 | CAGAACAG | G | CCCCUCCU | 6833 | AGGAGCCC | GGAGGAAACUCC | CU | UCAAGGACAUCGUCCGGG | CUGUUCUG | 7219 |
| 285 | AGAACAGG | G | CGCUCCUC | 5791 | CACCAGCG | GGAGGAAACUCC | CU | UCAAGGACAUCGUCCGGG | CCUGUUCU | 7220 |
| 287 | AACAGGGC | G | CUCCUCAC | 5792 | CUCAGGAG | GGAGGAAACUCC | CU | UCAAGGACAUCGUCCGGG | GCCCUGUU | 7221 |
| 293 | GCGCUCCU | C | AGACCCUC | 6834 | GAGGGUCU | GGAGGAAACUCC | CU | UCAAGGACAUCGUCCGGG | AGGACCCC | 7222 |
| 295 | GCUCCUGA | G | ACCCUCCA | 6835 | UCGAGGGU | GGAGGAAACUCC | CU | UCAAGGACAUCGUCCGGG | UCAGGAGC | 7223 |
| 304 | ACCCUCCA | G | CGCUCCCU | 5793 | ACGCAGCG | GGAGGAAACUCC | CU | UCAAGGACAUCGUCCGGG | UCCAGGGU | 7224 |
| 306 | CCUCCAGC | G | CUCCCUGG | 5794 | CCAGGCAC | GGAGGAAACUCC | CU | UCAAGGACAUCGUCCGGG | CCUGGACC | 7225 |
| 309 | CCACCGCU | C | CCUGGAGG | 5795 | CCUCCACC | GGAGGAAACUCC | CU | UCAAGGACAUCGUCCGGG | AGCGCUGG | 7226 |
| 313 | CGCUCCCU | G | GAGGAGAU | 6836 | UUCUCCUC | GGAGGAAACUCC | CU | UCAAGGACAUCGUCCGGG | AGCCAGCC | 7227 |
| 314 | GCUGCCUC | G | AGGAGAAU | 6837 | AUUCUCCU | GGAGGAAACUCC | CU | UCAAGGACAUCGUCCGGG | CAGCCAGC | 7228 |
| 316 | UGCCUGCA | G | GAGAAUCA | 6838 | UCAUUCUC | GGAGGAAACUCC | CU | UCAAGGACAUCGUCCGGG | UCCACCCA | 7229 |
| 317 | CCCUCCAC | G | AGAAUCAA | 6839 | UUCAUUCU | GGAGGAAACUCC | CU | UCAAGGACAUCGUCCGGG | CUCCACCC | 7230 |
| 319 | CUGGACCA | G | AAUCAAGA | 6840 | UCUUGAUU | GGAGGAAACUCC | CU | UCAAGGACAUCGUCCGGG | UCCUCCAG | 7231 |
| 326 | AGAAUCAA | G | ACCUCCCA | 6841 | UCCCACCU | GGAGGAAACUCC | CU | UCAAGGACAUCGUCCGGG | UUGAUUCU | 7232 |
| 328 | AAUCAAGA | G | CUCCCACA | 5796 | UCUCCCAC | GGAGGAAACUCC | CU | UCAAGGACAUCGUCCGGG | UCUUGAUU | 7233 |
| 333 | ACACCUCC | G | ACAUGCCA | 6842 | UCCCAUCU | GGAGGAAACUCC | CU | UCAAGGACAUCGUCCGGG | CGACCUCU | 7234 |
| 335 | ACCUCCCA | G | AUCCCAUC | 6843 | CAUCCCAU | GGAGGAAACUCC | CU | UCAAGGACAUCGUCCGGG | UCCCACCU | 7235 |
| 338 | UCCCACAU | G | CCAUCCCC | 5797 | CCCCAUCC | GGAGGAAACUCC | CU | UCAAGGACAUCGUCCGGG | AUCUCGGA | 7236 |
| 345 | UGCCAUCC | G | GCAGAGCA | 6844 | UGCUCUGC | GGAGGAAACUCC | CU | UCAAGGACAUCGUCCGGG | GGAUGGCA | 7237 |
| 346 | GCCAUCCG | G | CAGAGCAA | 5798 | UUGCUCUG | GGAGGAAACUCC | CU | UCAAGGACAUCGUCCGGG | CGGAUGGC | 7238 |
| 349 | AUCCGGCA | G | AGCAACCA | 6845 | UGGUUGCU | GGAGGAAACUCC | CU | UCAAGGACAUCGUCCGGG | UGCCGGAU | 7239 |
| 351 | CCGGCAGA | G | CAACCAGA | 5799 | UCUGGUUG | GGAGGAAACUCC | CU | UCAAGGACAUCGUCCGGG | UCUGCCGG | 7240 |

TABLE VII-continued

Human IKK-gamma Amberzyme and Substrate Sequence

| Pos | Substrate | Seq ID | Amberzyme | Seq ID |
|---|---|---|---|---|
| 358 | AGCAACCA G AUUCUGCG | 6846 | CGCAGAAU GGAGGAAACUCC CU UCAAGGACAUCGUCCGGG UGGUUGCU | 7241 |
| 364 | CAGAUUCU G CGGGAGCG | 5800 | CGCUCCCG GGAGGAAACUCC CU UCAAGGACAUCGUCCGGG AGAAUCUG | 7242 |
| 366 | GAUUCUGC G GGAGCGCU | 6847 | AGCGCUCC GGAGGAAACUCC CU UCAAGGACAUCGUCCGGG GCAGAAUC | 7243 |
| 367 | AUUCUGCG G GAGCGCUG | 6848 | CAGCGCUC GGAGGAAACUCC CU UCAAGGACAUCGUCCGGG CGCAGAAU | 7244 |
| 368 | UUCUGCGG G AGCGCUGC | 6849 | GCAGCGCU GGAGGAAACUCC CU UCAAGGACAUCGUCCGGG CCGCAGAA | 7245 |
| 370 | CUGCGGGA G CGCUGCGA | 5801 | UCGCAGCG GGAGGAAACUCC CU UCAAGGACAUCGUCCGGG UCCCGCAG | 7246 |
| 372 | GCGGGAGC G CUGCGAGG | 5802 | CCUCGCAG GGAGGAAACUCC CU UCAAGGACAUCGUCCGGG GCUCCCGC | 7247 |
| 375 | GGAGCGCU G CGAGGAGC | 5803 | GCUCCUCG GGAGGAAACUCC CU UCAAGGACAUCGUCCGGG AGCGCUCC | 7248 |
| 377 | AGCGCUGC G AGGAGCUU | 6850 | AAGCUCCU GGAGGAAACUCC CU UCAAGGACAUCGUCCGGG GCAGCGCU | 7249 |
| 379 | CGCUGCGA G GAGCUUCU | 6851 | AGAAGCUC GGAGGAAACUCC CU UCAAGGACAUCGUCCGGG UCGCAGCG | 7250 |
| 380 | GCUGCGAG G AGCUUCUG | 6852 | CAGAAGCU GGAGGAAACUCC CU UCAAGGACAUCGUCCGGG CUCGCAGC | 7251 |
| 382 | UGCGAGGA G CUUCUGCA | 5804 | UGCAGAAG GGAGGAAACUCC CU UCAAGGACAUCGUCCGGG UCCUCGCA | 7252 |
| 388 | GAGCUUCU G CAUUUCCA | 5805 | UGGAAAUG GGAGGAAACUCC CU UCAAGGACAUCGUCCGGG AGAAGCUC | 7253 |
| 398 | AUUUCCAA G CCAGCCAG | 5806 | CUGGCUGG GGAGGAAACUCC CU UCAAGGACAUCGUCCGGG UUGGAAAU | 7254 |
| 402 | CCAAGCCA G CCAGAGGG | 5807 | CCCUCUGG GGAGGAAACUCC CU UCAAGGACAUCGUCCGGG UGGCUUGG | 7255 |
| 406 | GCCAGCCA G AGGGAGGA | 6853 | UCCUCCCU GGAGGAAACUCC CU UCAAGGACAUCGUCCGGG UGGCUGGC | 7256 |
| 408 | CAGCCAGA G GGAGGAGA | 6854 | UCUCCUCC GGAGGAAACUCC CU UCAAGGACAUCGUCCGGG UCUGGCUG | 7257 |
| 409 | AGCCAGAG G GAGGAGAA | 6855 | UUCUCCUC GGAGGAAACUCC CU UCAAGGACAUCGUCCGGG CUCUGGCU | 7258 |
| 410 | GCCAGAGG G AGGAGAAG | 6856 | CUUCUCCU GGAGGAAACUCC CU UCAAGGACAUCGUCCGGG CCUCUGGC | 7259 |
| 412 | CAGAGGGA G GAGAAGGA | 6857 | UCCUUCUC GGAGGAAACUCC CU UCAAGGACAUCGUCCGGG UCCCUCUG | 7260 |
| 413 | AGAGGGAG G AGAAGGAG | 6858 | CUCCUUCU GGAGGAAACUCC CU UCAAGGACAUCGUCCGGG CUCCCUCU | 7261 |
| 415 | AGGGAGGA G AAGGAGUU | 6859 | AACUCCUU GGAGGAAACUCC CU UCAAGGACAUCGUCCGGG UCCUCCCU | 7262 |
| 418 | GAGGAGAA G GAGUUCCU | 6860 | AGGAACUC GGAGGAAACUCC CU UCAAGGACAUCGUCCGGG UUCUCCUC | 7263 |
| 419 | AGGAGAAG G AGUUCCUC | 6861 | GAGGAACU GGAGGAAACUCC CU UCAAGGACAUCGUCCGGG CUUCUCCU | 7264 |
| 421 | GAGAAGGA G UUCCUCAU | 5808 | AUGAGGAA GGAGGAAACUCC CU UCAAGGACAUCGUCCGGG UCCUUCUC | 7265 |
| 430 | UUCCUCAU G UGCAAGUU | 5809 | AACUUGCA GGAGGAAACUCC CU UCAAGGACAUCGUCCGGG AUGAGGAA | 7266 |
| 432 | CCUCAUGU G CAAGUUCC | 5810 | GGAACUUG GGAGGAAACUCC CU UCAAGGACAUCGUCCGGG ACAUGAGG | 7267 |
| 436 | AUGUGCAA G UUCCAGGA | 5811 | UCCUGGAA GGAGGAAACUCC CU UCAAGGACAUCGUCCGGG UUGCACAU | 7268 |
| 442 | AAGUUCCA G AGGCCAG | 6862 | CUGGCCUC GGAGGAAACUCC CU UCAAGGACAUCGUCCGGG UGGAACUU | 7269 |
| 443 | AGUUCCAG G AGGCCAGG | 6863 | CCUGGCCU GGAGGAAACUCC CU UCAAGGACAUCGUCCGGG CUGGAACU | 7270 |
| 445 | UUCCAGGA G GCCAGGAA | 6864 | UUCCUGGC GGAGGAAACUCC CU UCAAGGACAUCGUCCGGG UCCUGGAA | 7271 |
| 446 | UCCAGGAG G CCAGGAAA | 5812 | UUUCCUGG GGAGGAAACUCC CU UCAAGGACAUCGUCCGGG CUCCUGGA | 7272 |
| 450 | GGAGGCCA G GAAACUGG | 6865 | CCAGUUUC GGAGGAAACUCC CU UCAAGGACAUCGUCCGGG UGGCCUCC | 7273 |
| 451 | GAGGCCAG G AAACUGGU | 6866 | ACCAGUUU GGAGGAAACUCC CU UCAAGGACAUCGUCCGGG CUGGCCUC | 7274 |
| 457 | AGGAAACU G UGGAGAG | 6867 | CUCUCCAC GGAGGAAACUCC CU UCAAGGACAUCGUCCGGG AGUUUCCU | 7275 |
| 458 | GGAAACUG G UGGAGAGA | 5813 | UCUCUCCA GGAGGAAACUCC CU UCAAGGACAUCGUCCGGG CAGUUUCC | 7276 |
| 460 | AAACUGGU G AGAGACU | 6868 | AGUCUCUC GGAGGAAACUCC CU UCAAGGACAUCGUCCGGG ACCAGUUU | 7277 |
| 461 | AACUGGUG G AGACUCG | 6869 | GAGUCUCU GGAGGAAACUCC CU UCAAGGACAUCGUCCGGG CACCAGUU | 7278 |
| 463 | CUGGUGGA G AGACUCGG | 6870 | CCGAGUCU GGAGGAAACUCC CU UCAAGGACAUCGUCCGGG UCCACCAG | 7279 |
| 465 | GGUGGAGA G ACUCGGCC | 6871 | GGCCGAGU GGAGGAAACUCC CU UCAAGGACAUCGUCCGGG UCUCCACC | 7280 |
| 470 | AGAGACUC G GCCUGGAG | 6872 | CUCCAGGC GGAGGAAACUCC CU UCAAGGACAUCGUCCGGG GAGUCUCU | 7281 |
| 471 | GAGACUCG G CCUGGAGA | 5814 | UCUCCAGG GGAGGAAACUCC CU UCAAGGACAUCGUCCGGG CGAGUCUC | 7282 |
| 475 | CUCGGCCU G GAGAAGCU | 6873 | AGCUUCUC GGAGGAAACUCC CU UCAAGGACAUCGUCCGGG AGGCCGAG | 7283 |
| 476 | UCGGCCUG G AGAAGCUC | 6874 | GAGCUUCU GGAGGAAACUCC CU UCAAGGACAUCGUCCGGG CAGGCCGA | 7284 |
| 478 | GGCCUGGA G AAGCUCGA | 6875 | UCGAGCUU GGAGGAAACUCC CU UCAAGGACAUCGUCCGGG UCCAGGCC | 7285 |
| 481 | CUGGAGAA G CUCGAUCU | 5815 | AGAUCGAG GGAGGAAACUCC CU UCAAGGACAUCGUCCGGG UUCUCCAG | 7286 |
| 485 | AGAAGCUC G AUCUGAAG | 6876 | CUUCAGAU GGAGGAAACUCC CU UCAAGGACAUCGUCCGGG GAGCUUCU | 7287 |
| 490 | CUCGAUCU G AAGAGGCA | 6877 | UGCCUCUU GGAGGAAACUCC CU UCAAGGACAUCGUCCGGG AGAUGGAG | 7288 |
| 493 | CAUCUGAA G AGGCAGAA | 6878 | UUCUGCCU GGAGGAAACUCC CU UCAAGGACAUCGUCCGGG UUCAGAUC | 7289 |
| 495 | UCUGAAGA G GCAGAAGG | 6879 | CCUUCUGC GGAGGAAACUCC CU UCAAGGACAUCGUCCGGG UCUUCAGA | 7290 |
| 496 | CUGAAGAG G CAGAAGGA | 5816 | UCCUUCUG GGAGGAAACUCC CU UCAAGGACAUCGUCCGGG CUCUUCAG | 7291 |
| 499 | AAGAGGCA G AAGGAGCA | 6880 | UGCUCCUU GGAGGAAACUCC CU UCAAGGACAUCGUCCGGG UGCCUCUU | 7292 |
| 502 | AGGCAGAA G GAGCAGGC | 6881 | GCCUGCUC GGAGGAAACUCC CU UCAAGGACAUCGUCCGGG UUCUGCCU | 7293 |
| 503 | GGCAGAAG G AGCAGGCU | 6882 | AGCCUGCU GGAGGAAACUCC CU UCAAGGACAUCGUCCGGG CUUCUGCC | 7294 |
| 505 | CAGAAGGA G CAGGCUCU | 5817 | AGAGCCUG GGAGGAAACUCC CU UCAAGGACAUCGUCCGGG UCCUUCUG | 7295 |
| 508 | AAGGAGCA G CUCUGCG | 6883 | CGCAGAGC GGAGGAAACUCC CU UCAAGGACAUCGUCCGGG UGCUCCUU | 7296 |
| 509 | AGGAGCAG G CUCUGCGG | 5818 | CCGCAGAG GGAGGAAACUCC CU UCAAGGACAUCGUCCGGG CUGCUCCU | 7297 |
| 514 | CAGGCUCU G CGGGAGGU | 5819 | ACCUCCCG GGAGGAAACUCC CU UCAAGGACAUCGUCCGGG AGAGCCUG | 7298 |
| 516 | GGCUCUGC G GGAGGUGG | 6884 | CCACCUCC GGAGGAAACUCC CU UCAAGGACAUCGUCCGGG GCAGAGCC | 7299 |
| 517 | GCUCUGCG G GAGGUGGA | 6885 | UCCACCUC GGAGGAAACUCC CU UCAAGGACAUCGUCCGGG CGCAGAGC | 7300 |
| 518 | CUCUGCGG G AGGUGGAG | 6886 | CUCCACCU GGAGGAAACUCC CU UCAAGGACAUCGUCCGGG CCGCAGAG | 7301 |
| 520 | CUGCGGGA G GUGGAGCA | 6887 | UGCUCCAC GGAGGAAACUCC CU UCAAGGACAUCGUCCGGG UCCCGCAG | 7302 |
| 521 | UGCGGGAG G UGGAGCAC | 5820 | GUGCUCCA GGAGGAAACUCC CU UCAAGGACAUCGUCCGGG CUCCCGCA | 7303 |
| 523 | CGGGAGGU G AGCACCU | 6888 | AGGUCCUC GGAGGAAACUCC CU UCAAGGACAUCGUCCGGG ACCUCCCG | 7304 |
| 524 | GGGAGGUG G AGCACCUG | 6889 | CAGGUGCU GGAGGAAACUCC CU UCAAGGACAUCGUCCGGG CACCUCCC | 7305 |
| 526 | GAGGUGGA G CACCUGAA | 5821 | UUCAGGUG GGAGGAAACUCC CU UCAAGGACAUCGUCCGGG UCCACCUC | 7306 |
| 532 | GAGCACCU G AAGAGAUG | 6890 | CAUCUCUU GGAGGAAACUCC CU UCAAGGACAUCGUCCGGG AGGUCCUC | 7307 |
| 535 | CACCUGAA G AGAUGCCA | 6891 | UGGCAUCU GGAGGAAACUCC CU UCAAGGACAUCGUCCGGG UUCAGGUG | 7308 |
| 537 | CCUGAAGA G AUGCCAGC | 6892 | GCUGGCAU GGAGGAAACUCC CU UCAAGGACAUCGUCCGGG UCUUCAGG | 7309 |
| 540 | GAAGAGAU G CCAGCAGC | 5822 | GCUGCUGG GGAGGAAACUCC CU UCAAGGACAUCGUCCGGG AUCUCUUC | 7310 |
| 544 | AGAUGCCA G CAGCAGAU | 5823 | AUCUGCUG GGAGGAAACUCC CU UCAAGGACAUCGUCCGGG UGGCAUCU | 7311 |
| 547 | UGCCAGCA G CAGAUGGC | 5824 | GCCAUCUG GGAGGAAACUCC CU UCAAGGACAUCGUCCGGG UGCUGGCA | 7312 |
| 550 | CAGCAGCA G AUGGCUGA | 6893 | UCAGCCAU GGAGGAAACUCC CU UCAAGGACAUCGUCCGGG UGCUGCUG | 7313 |
| 553 | CAGCAGAU G GCUGAGGA | 6894 | UCCUCAGC GGAGGAAACUCC CU UCAAGGACAUCGUCCGGG AUCUGCUG | 7314 |
| 554 | AGCAGAUG G CUGAGGAC | 5825 | GUCCUCAG GGAGGAAACUCC CU UCAAGGACAUCGUCCGGG CAUCUGCU | 7315 |

TABLE VII-continued

Human IKK-gamma Amberzyme and Substrate Sequence

| Pos | Substrate | Seq ID | Amberzyme | Seq ID |
|---|---|---|---|---|
| 557 | AGAUGGCU G AGGACAAG | 6895 | CUUGUCCU GGAGGAAACUCC CU UCAAGGACAUCGUCCGGG AGCCAUCU | 7316 |
| 559 | AUGGCUGA G GACAAGGC | 6896 | GCCUUGUC GGAGGAAACUCC CU UCAAGGACAUCGUCCGGG UCAGCCAU | 7317 |
| 560 | UGGCUGAG G ACAAGGCC | 6897 | GGCCUUGU GGAGGAAACUCC CU UCAAGGACAUCGUCCGGG CUCAGCCA | 7318 |
| 565 | GAGGACAA G CCCUCUCU | 6898 | ACAGAGGC GGAGGAAACUCC CU UCAAGGACAUCGUCCGGG UUGUCCUC | 7319 |
| 566 | AGGACAAG G CCUCUCUC | 5826 | CACAGAGG GGAGGAAACUCC CU UCAAGGACAUCGUCCGGG CUUGUCCU | 7320 |
| 572 | AGGCCUCU G UGAAACCC | 5827 | GGCUUUCA GGAGGAAACUCC CU UCAAGGACAUCGUCCGGG AGAGGCCU | 7321 |
| 574 | GCCUCUGU G AAACCCA | 6899 | UGGGCUUU GGAGGAAACUCC CU UCAAGGACAUCGUCCGGG ACAGAGGC | 7322 |
| 578 | CUGUGAAA G CCCACCUC | 5828 | CACCUGGG GGAGGAAACUCC CU UCAAGGACAUCGUCCGGG UUUCACAG | 7323 |
| 583 | AAAGCCCA G CUCACCUC | 6900 | GACGUCAC GGAGGAAACUCC CU UCAAGGACAUCGUCCGGG UGGGCUUU | 7324 |
| 584 | AAGCCCAG G UCACCUCC | 5829 | GGACGUCA GGAGGAAACUCC CU UCAAGGACAUCGUCCGGG CUGGGCUU | 7325 |
| 586 | GCCCAGGU G ACCUCCUU | 6901 | AAGGACGU GGAGGAAACUCC CU UCAAGGACAUCGUCCGGG ACCUGGGC | 7326 |
| 589 | CAGGUGAC G UCCUUCCU | 5830 | AGCAAGGA GGAGGAAACUCC CU UCAAGGACAUCGUCCGGG GUCACCUG | 7327 |
| 595 | ACGUCCUU G CUCCCGCA | 5831 | UCCCCGAG GGAGGAAACUCC CU UCAAGGACAUCGUCCGGG AAGGACGU | 7328 |
| 599 | CCUUGCUC G CCCACCUC | 6902 | CAGCUCCC GGAGGAAACUCC CU UCAAGGACAUCGUCCGGG GAGCAAGG | 7329 |
| 600 | CUUGCUCG G CCACCGCC | 6903 | GCAGCUCC GGAGGAAACUCC CU UCAAGGACAUCGUCCGGG CGAGCAAG | 7330 |
| 601 | UUGCUCGG G CACCUCCA | 6904 | UGCAGCUC GGAGGAAACUCC CU UCAAGGACAUCGUCCGGG CCGAGCAA | 7331 |
| 602 | UGCUCGGG G ACCUCCAC | 6905 | CUGCAGCU GGAGGAAACUCC CU UCAAGGACAUCGUCCGGG CCCGAGCA | 7332 |
| 604 | CUCGGGGA G CUCCACCA | 5832 | UCCUGCAG GGAGGAAACUCC CU UCAAGGACAUCGUCCGGG UCCCCGAG | 7333 |
| 607 | GGGGAGCU G CACCACAC | 5833 | CUCUCCUG GGAGGAAACUCC CU UCAAGGACAUCGUCCGGG AGCUCCCC | 7334 |
| 610 | GAGCUGCA G CACACCCA | 6906 | UGGCUCUC GGAGGAAACUCC CU UCAAGGACAUCGUCCGGG UGCAGCUC | 7335 |
| 611 | AGCUGCAG G ACACCCAC | 6907 | CUGGCUCU GGAGGAAACUCC CU UCAAGGACAUCGUCCGGG CUGCAGCU | 7336 |
| 613 | CUGCAGGA G AGCCAGAG | 6908 | CUCUGGCU GGAGGAAACUCC CU UCAAGGACAUCGUCCGGG UCCUGCAG | 7337 |
| 615 | GCAGGAGA G CCAGAGUC | 5834 | GACUCUGG GGAGGAAACUCC CU UCAAGGACAUCGUCCGGG UCUCCUGC | 7338 |
| 619 | GAGAGCCA G AGUCGCUU | 6909 | AAGCGACU GGAGGAAACUCC CU UCAAGGACAUCGUCCGGG UGGCUCUC | 7339 |
| 621 | GAGCCAGA G UCGCUUGG | 5835 | CCAAGCGA GGAGGAAACUCC CU UCAAGGACAUCGUCCGGG UCUGGCUC | 7340 |
| 624 | CCAGAGUC G CUUGGAGG | 5836 | CCUCCAAG GGAGGAAACUCC CU UCAAGGACAUCGUCCGGG GACUCUGG | 7341 |
| 628 | ACUCGCUU G CAGGCUGC | 6910 | GCAGCCUC GGAGGAAACUCC CU UCAAGGACAUCGUCCGGG AAGCGACU | 7342 |
| 629 | CUCGCUUG G AGGCUGCC | 6911 | GGCAGCCU GGAGGAAACUCC CU UCAAGGACAUCGUCCGGG CAAGCGAC | 7343 |
| 631 | CGCUUGGA G GCUGCCU | 6912 | GUGGCAGC GGAGGAAACUCC CU UCAAGGACAUCGUCCGGG UCCAAGCG | 7344 |
| 632 | GCUUGGAC G CUGCCACU | 5837 | AGUGGCAC GGAGGAAACUCC CU UCAAGGACAUCGUCCGGG CUCCAAGC | 7345 |
| 635 | UGGAGGCU G CCACUAAG | 5838 | CUUAGUGG GGAGGAAACUCC CU UCAAGGACAUCGUCCGGG AGCCUCCA | 7346 |
| 643 | CCCACUAA G GAAUGCCA | 6913 | UGGCAUUC GGAGGAAACUCC CU UCAAGGACAUCGUCCGGG UUAGUGGC | 7347 |
| 644 | CCACUAAG G AAUGCCAC | 6914 | CUGGCAUU GGAGGAAACUCC CU UCAAGGACAUCGUCCGGG CUUAGUGG | 7348 |
| 648 | UAAGGAAU G CCAGGCUC | 5839 | GAGCCUCG GGAGGAAACUCC CU UCAAGGACAUCGUCCGGG AUUCCUUA | 7349 |
| 652 | CAAUGCCA G CCUCUCCA | 6915 | UCCACAGC GGAGGAAACUCC CU UCAAGGACAUCGUCCGGG UGGCAUUC | 7350 |
| 653 | AAUGCCAG G CUCUGGAG | 5840 | CUCCAGAG GGAGGAAACUCC CU UCAAGGACAUCGUCCGGG CUGGCAUU | 7351 |
| 658 | CACGCUCU G CAGGGUCG | 6916 | CGACCCUG GGAGGAAACUCC CU UCAAGGACAUCGUCCGGG AGAGCCUG | 7352 |
| 659 | ACGCUCUG G AGGCUCGC | 6917 | CCCACCCU GGAGGAAACUCC CU UCAAGGACAUCGUCCGGG CAGAGCCU | 7353 |
| 661 | GCUCUGGA G CGUCGGGC | 6918 | GCCCGACC GGAGGAAACUCC CU UCAAGGACAUCGUCCGGG UCCAGAGC | 7354 |
| 662 | CUCUGGAG G UCGCGCC | 6919 | GGCCCAC GGAGGAAACUCC CU UCAAGGACAUCGUCCGGG CUCCAGAG | 7355 |
| 663 | UCUGGAGG G UCGCGGCC | 5841 | GGGCCCGA GGAGGAAACUCC CU UCAAGGACAUCGUCCGGG CCUCCAGA | 7356 |
| 666 | GGAGGCUC G GGCCCGGG | 6920 | CCCGGGCC GGAGGAAACUCC CU UCAAGGACAUCGUCCGGG GACCCUCC | 7357 |
| 667 | GACGUCG G CCCGGGC | 6921 | GCCCGGGC GGAGGAAACUCC CU UCAAGGACAUCGUCCGGG CGACCCUC | 7358 |
| 668 | ACGGUCGG G CCCGCGCG | 5842 | CGCCCGGG GGAGGAAACUCC CU UCAAGGACAUCGUCCGGG CCGACCCU | 7359 |
| 672 | UCGGGCCC G GGCCCCA | 6922 | UGGCCGCC GGAGGAAACUCC CU UCAAGGACAUCGUCCGGG GGGCCCGA | 7360 |
| 673 | CGCCCCCG G CGCCCAG | 6923 | CUGGCCGC GGAGGAAACUCC CU UCAAGGACAUCGUCCGGG CGGGCCCG | 7361 |
| 674 | GGGCCCGG G CCCCAGC | 5843 | GCUGGCCG GGAGGAAACUCC CU UCAAGGACAUCGUCCGGG CCGGGCCC | 7362 |
| 676 | GCCCGGGC G CCAGCCA | 6924 | UCGCUGGC GGAGGAAACUCC CU UCAAGGACAUCGUCCGGG GCCCGGGC | 7363 |
| 677 | CCCGGGCG G CCAGCCAC | 5844 | CUCGCUGG GGAGGAAACUCC CU UCAAGGACAUCGUCCGGG CGCCCGGG | 7364 |
| 681 | GGCGGCCA G CGAGCAGG | 5845 | CCUGCUCG GGAGGAAACUCC CU UCAAGGACAUCGUCCGGG UGGCCGCC | 7365 |
| 683 | CGGCCAGC G AGCAGGCG | 6925 | CGCCUCCU GGAGGAAACUCC CU UCAAGGACAUCGUCCGGG GCUGGCCG | 7366 |
| 685 | GCCAGCGA G CAGGCGCG | 5846 | CGCGCCUG GGAGGAAACUCC CU UCAAGGACAUCGUCCGGG UCGCUGGC | 7367 |
| 688 | AGCGAGCA G GCGCGGCA | 6926 | UGCCGCGC GGAGGAAACUCC CU UCAAGGACAUCGUCCGGG UGCUCGCU | 7368 |
| 689 | GCGAGCAG G CGCGGCAG | 5847 | CUGCCGCG GGAGGAAACUCC CU UCAAGGACAUCGUCCGGG CUGCUCGC | 7369 |
| 691 | GAGCAGGC G CGGCAGCU | 5848 | AGCUGCCG GGAGGAAACUCC CU UCAAGGACAUCGUCCGGG GCGUCCUC | 7370 |
| 693 | GCAGGCGC G CAGCUGG | 6927 | CCAGCUGC GGAGGAAACUCC CU UCAAGGACAUCGUCCGGG CGCGCUGC | 7371 |
| 694 | CAGGCGCG G CAGCUGGA | 5849 | UCCAGCUG GGAGGAAACUCC CU UCAAGGACAUCGUCCGGG CGCGCCUG | 7372 |
| 697 | GCGCGGCA G CUGGAGAG | 5850 | CUCUCCAG GGAGGAAACUCC CU UCAAGGACAUCGUCCGGG UGCCGCGC | 7373 |
| 700 | CGGCAGCU G GAGAGUGA | 6928 | UCACUCUC GGAGGAAACUCC CU UCAAGGACAUCGUCCGGG AGCUGCCG | 7374 |
| 701 | GGCAGCUG G AGAGUGAG | 6929 | CUCACUCU GGAGGAAACUCC CU UCAAGGACAUCGUCCGGG CAGCUGCC | 7375 |
| 703 | CAGCUGGA G AGUGAGCG | 6930 | CGCUCACU GGAGGAAACUCC CU UCAAGGACAUCGUCCGGG UCCAGCUC | 7376 |
| 705 | GCUGGAGA G UGAGCGCG | 5851 | CGCGCUCA GGAGGAAACUCC CU UCAAGGACAUCGUCCGGG UCUCCAGC | 7377 |
| 707 | UGGAGAGU G AGCGCGAG | 6931 | CUCGCGCU GGAGGAAACUCC CU UCAAGGACAUCGUCCGGG ACUCUCCA | 7378 |
| 709 | GAGAGUGA G CGCGAGGC | 5852 | GCCUCGCG GGAGGAAACUCC CU UCAAGGACAUCGUCCGGG UCACUCUC | 7379 |
| 711 | GAGUGAGC G CGAGGCGC | 5853 | GCGCCUCG GGAGGAAACUCC CU UCAAGGACAUCGUCCGGG GCUCACUC | 7380 |
| 713 | GUGAGCGC G AGGCUG | 6932 | CAGCGCCU GGAGGAAACUCC CU UCAAGGACAUCGUCCGGG GCGCACAC | 7381 |
| 715 | GAGCGCGA G GCGCUGCA | 6933 | UGCAGCGC GGAGGAAACUCC CU UCAAGGACAUCGUCCGGG UCGCGCUC | 7382 |
| 716 | AGCGCGAG G CGCUGCAG | 5854 | CUGCAGCG GGAGGAAACUCC CU UCAAGGACAUCGUCCGGG CUCGCGCU | 7383 |
| 718 | CGCGAGGC G CUGCAGCA | 5855 | UGCUGCAG GGAGGAAACUCC CU UCAAGGACAUCGUCCGGG GCCUCGCG | 7384 |
| 721 | GAGGCGCU G CAGCAGCA | 5856 | UGCUGCUG GGAGGAAACUCC CU UCAAGGACAUCGUCCGGG AGCGCCUC | 7385 |
| 724 | GCGCUGCA G CAGCAGCA | 5857 | UGCUGCUG GGAGGAAACUCC CU UCAAGGACAUCGUCCGGG UGCAGCGC | 7386 |
| 727 | CUGCAGCA G CAGCACAG | 5858 | CUGUGCUG GGAGGAAACUCC CU UCAAGGACAUCGUCCGGG UGGUGGAG | 7387 |
| 730 | CAGCAGCA G CACAGCGU | 5859 | ACGCUGUG GGAGGAAACUCC CU UCAAGGACAUCGUCCGGG UGCUGCUG | 7388 |
| 735 | GCAGCACA G CGUGCAGG | 5860 | CCUGCACG GGAGGAAACUCC CU UCAAGGACAUCGUCCGGG UGUGCUGC | 7389 |
| 737 | AGCACAGC G UGCAGGUG | 5861 | CACCUGCA GGAGGAAACUCC CU UCAAGGACAUCGUCCGGG GCUGUGCU | 7390 |

TABLE VII-continued

Human IKK-gamma Amberzyme and Substrate Sequence

| Pos | Substrate | Seq ID | Amberzyme | Seq ID |
|-----|-----------|--------|-----------|--------|
| 739 | CACAGCGU G CAGGUGGA | 5862 | UCCACCUG GGAGGAAACUCC CU UCAAGGACAUCGUCCGGG ACGCUGUG | 7391 |
| 742 | AGCGUGCA G GUGGACCA | 6934 | UGGUCCAC GGAGGAAACUCC CU UCAAGGACAUCGUCCGGG UGCACGCU | 7392 |
| 743 | GCGUGCAG G UGGACCAG | 5863 | CUGGUCCA GGAGGAAACUCC CU UCAAGGACAUCGUCCGGG CUGCACGC | 7393 |
| 745 | GUGCAGGU G GACCAGCU | 6935 | AGCUGGUC GGAGGAAACUCC CU UCAAGGACAUCGUCCGGG ACCUGCAC | 7394 |
| 746 | UGCAGGUG G ACCAGCUG | 6936 | CAGCUGGU GGAGGAAACUCC CU UCAAGGACAUCGUCCGGG CACCUGCA | 7395 |
| 751 | GUGGACCA G CUGCGCAU | 5864 | AUGCGCAG GGAGGAAACUCC CU UCAAGGACAUCGUCCGGG UGGUCCAC | 7396 |
| 754 | GACCAGCU G CGCAUGCA | 5865 | UGCAUGCG GGAGGAAACUCC CU UCAAGGACAUCGUCCGGG AGCUGGUC | 7397 |
| 756 | CCAGCUGC G CAUGCAGG | 5866 | CCUGCAUG GGAGGAAACUCC CU UCAAGGACAUCGUCCGGG GCAGCUGG | 7398 |
| 760 | CUGCGCAU G CAGGGCCA | 5867 | UGGCCCUG GGAGGAAACUCC CU UCAAGGACAUCGUCCGGG AUGCGCAG | 7399 |
| 763 | CGCAUGCA G GGCCAGAG | 6937 | CUCUGGCC GGAGGAAACUCC CU UCAAGGACAUCGUCCGGG UGCAUGCG | 7400 |
| 764 | GCAUGCAG G GCCAGAGC | 6938 | GCUCUGGC GGAGGAAACUCC CU UCAAGGACAUCGUCCGGG CUGCAUGC | 7401 |
| 765 | CAUGCAGG G CCAGAGCG | 5868 | CGCUCUGG GGAGGAAACUCC CU UCAAGGACAUCGUCCGGG CCUGCAUG | 7402 |
| 769 | CAGGGCCA G AGCGUGGA | 6939 | UCCACGCU GGAGGAAACUCC CU UCAAGGACAUCGUCCGGG UGGCCCUG | 7403 |
| 771 | GGGCCAGA G CGUGGAGG | 5869 | CCUCCACG GGAGGAAACUCC CU UCAAGGACAUCGUCCGGG UCUGGCCC | 7404 |
| 773 | GCCAGAGC G UGGAGGCC | 5870 | GGCCUCCA GGAGGAAACUCC CU UCAAGGACAUCGUCCGGG GCUCUGGC | 7405 |
| 775 | CAGAGCGU G GAGGCCGC | 6940 | GCGGCCUC GGAGGAAACUCC CU UCAAGGACAUCGUCCGGG ACGCUCUG | 7406 |
| 776 | AGAGCGUG G AGGCCGCG | 6941 | CGCGGCCU GGAGGAAACUCC CU UCAAGGACAUCGUCCGGG CACGCUCU | 7407 |
| 778 | AGCGUGGA G GCCGCGCU | 6942 | AGCGCGGC GGAGGAAACUCC CU UCAAGGACAUCGUCCGGG UCCACGCU | 7408 |
| 779 | GCGUGGAG G CCGCGCUC | 5871 | GAGCGCGG GGAGGAAACUCC CU UCAAGGACAUCGUCCGGG CUCCACGC | 7409 |
| 782 | UGGAGGCC G CGCUCCGC | 5872 | GCGGAGCG GGAGGAAACUCC CU UCAAGGACAUCGUCCGGG GGCCUCCA | 7410 |
| 784 | GAGGCCGC G CUCCGCAU | 5873 | AUGCGGAG GGAGGAAACUCC CU UCAAGGACAUCGUCCGGG GCGGCCUC | 7411 |
| 789 | CGCGCUCC G CAUGGAGC | 5874 | GCUCCAUG GGAGGAAACUCC CU UCAAGGACAUCGUCCGGG GGAGCGCG | 7412 |
| 793 | CUCCGCAU G GAGCGCCA | 6943 | UGGCGCUC GGAGGAAACUCC CU UCAAGGACAUCGUCCGGG AUGCGGAG | 7413 |
| 794 | UCCGCAUG G AGCGCCAG | 6944 | CUGGCGCU GGAGGAAACUCC CU UCAAGGACAUCGUCCGGG CAUGCGGA | 7414 |
| 796 | CGCAUGGA G CGCCAGCG | 5875 | GCCUGGCG GGAGGAAACUCC CU UCAAGGACAUCGUCCGGG UCCAUGCG | 7415 |
| 798 | CAUGGAGC G CCAGGCCG | 5876 | CGGCCUGG GGAGGAAACUCC CU UCAAGGACAUCGUCCGGG GCUCCAUG | 7416 |
| 802 | GAGCGCCA G GCCGCCUC | 6945 | GAGGCGGC GGAGGAAACUCC CU UCAAGGACAUCGUCCGGG UGGCGCUC | 7417 |
| 803 | AGCGCCAG G CCGCCUCG | 5877 | CGAGGCGG GGAGGAAACUCC CU UCAAGGACAUCGUCCGGG CUGGCGCU | 7418 |
| 806 | GCCAGGCC G CCUCGGAG | 5878 | CUCCGAGG GGAGGAAACUCC CU UCAAGGACAUCGUCCGGG GGCCUGGC | 7419 |
| 811 | GCCGCCUC G GAGGAGAA | 6946 | UUCUCCUC GGAGGAAACUCC CU UCAAGGACAUCGUCCGGG GAGGCGGC | 7420 |
| 812 | CCGCCUCG G AGGAGAAG | 6947 | CUUCUCCU GGAGGAAACUCC CU UCAAGGACAUCGUCCGGG CGAGGCGG | 7421 |
| 814 | GCCUCGGA G GAGAAGAG | 6948 | CUCUUCUC GGAGGAAACUCC CU UCAAGGACAUCGUCCGGG UCCGAGGC | 7422 |
| 815 | CCUCGGAG G AGAAGAGG | 6949 | CCUCUUCU GGAGGAAACUCC CU UCAAGGACAUCGUCCGGG CUCCGAGG | 7423 |
| 817 | UCGGAGGA G AAGAGGAA | 6950 | UUCCUCUU GGAGGAAACUCC CU UCAAGGACAUCGUCCGGG UCCUCCGA | 7424 |
| 820 | GAGGAGAA G AGGAAGCU | 6951 | AGCUUCCU GGAGGAAACUCC CU UCAAGGACAUCGUCCGGG UUCUCCUC | 7425 |
| 822 | GGAGAAGA G GAAGCUGG | 6952 | CCAGCUUC GGAGGAAACUCC CU UCAAGGACAUCGUCCGGG UCUUCUCC | 7426 |
| 823 | GAGAAGAG G AAGCUGGC | 6953 | GCCAGCUU GGAGGAAACUCC CU UCAAGGACAUCGUCCGGG CUCUUCUC | 7427 |
| 826 | AAGAGGAA G CUGGCCCA | 5879 | UGGGCCAG GGAGGAAACUCC CU UCAAGGACAUCGUCCGGG UUCCUCUU | 7428 |
| 829 | AGGAAGCU G GCCCAGUU | 6954 | AACUGGGC GGAGGAAACUCC CU UCAAGGACAUCGUCCGGG AGCUUCCU | 7429 |
| 830 | GGAAGCUG G CCCAGUUG | 5880 | CAACUGGG GGAGGAAACUCC CU UCAAGGACAUCGUCCGGG CAGCUUCC | 7430 |
| 835 | CUGGCCCA G UUGCAGGU | 5881 | ACCUGCAA GGAGGAAACUCC CU UCAAGGACAUCGUCCGGG UGGGCCAG | 7431 |
| 838 | GCCCAGUU G CAGGUGGC | 5882 | GCCACCUG GGAGGAAACUCC CU UCAAGGACAUCGUCCGGG AACUGGGC | 7432 |
| 841 | CAGUUGCA G GUGGCCUA | 6955 | UAGGCCAC GGAGGAAACUCC CU UCAAGGACAUCGUCCGGG UGCAACUG | 7433 |
| 842 | AGUUGCAG G UGGCCUAU | 5883 | AUAGGCCA GGAGGAAACUCC CU UCAAGGACAUCGUCCGGG CUGCAACU | 7434 |
| 844 | UUGCAGGU G GCCUAUCA | 6956 | UGAUAGGC GGAGGAAACUCC CU UCAAGGACAUCGUCCGGG ACCUGCAA | 7435 |
| 845 | UGCAGGUG G CCUAUCAC | 5884 | GUGAUAGG GGAGGAAACUCC CU UCAAGGACAUCGUCCGGG CACCUGCA | 7436 |
| 856 | UAUCACCA G CUCUUCCA | 5885 | UGGAAGAG GGAGGAAACUCC CU UCAAGGACAUCGUCCGGG UGGUGAUA | 7437 |
| 866 | UCUUCCAA G AAUACGAC | 6957 | GUCGUAUU GGAGGAAACUCC CU UCAAGGACAUCGUCCGGG UUGGAAGA | 7438 |
| 872 | AAGAAUAC G ACAACCAC | 6958 | GUGGUUGU GGAGGAAACUCC CU UCAAGGACAUCGUCCGGG GUAUUCUU | 7439 |
| 886 | CACAUCAA G AGCAGCGU | 6959 | ACGCUGCU GGAGGAAACUCC CU UCAAGGACAUCGUCCGGG UUGAUGUG | 7440 |
| 888 | CAUCAAGA G CAGCGUGG | 5886 | CCACGCUG GGAGGAAACUCC CU UCAAGGACAUCGUCCGGG UCUUGAUG | 7441 |
| 891 | CAAGAGCA G CGUGGUGG | 5887 | CCACCACG GGAGGAAACUCC CU UCAAGGACAUCGUCCGGG UGCUCUUG | 7442 |
| 893 | AGAGCAGC G UGGUGGGC | 5888 | GCCCACCA GGAGGAAACUCC CU UCAAGGACAUCGUCCGGG GCUGCUCU | 7443 |
| 895 | AGCAGCGU G GUGGGCAG | 6960 | CUGCCCAC GGAGGAAACUCC CU UCAAGGACAUCGUCCGGG ACGCUGCU | 7444 |
| 896 | GCAGCGUG G UGGGCAGU | 5889 | ACUAGCCA GGAGGAAACUCC CU UCAAGGACAUCGUCCGGG CACGCUGC | 7445 |
| 898 | AGCGUGGU G GCAGUGA | 6961 | UCACUGCC GGAGGAAACUCC CU UCAAGGACAUCGUCCGGG ACCACGCU | 7446 |
| 899 | GCGUGGUG G GCAGUGAG | 5962 | CUCACUGC GGAGGAAACUCC CU UCAAGGACAUCGUCCGGG CACCACGC | 7447 |
| 900 | CGUGGUGG G CAGUGAGC | 5890 | GCUCACUG GGAGGAAACUCC CU UCAAGGACAUCGUCCGGG CCACCACG | 7448 |
| 903 | GGUGGGCA G UGAGCGGA | 5891 | UCCGCUCA GGAGGAAACUCC CU UCAAGGACAUCGUCCGGG UGCCCACC | 7449 |
| 905 | UGGGCAGU G AGCGGAAG | 6963 | CUUCCGCU GGAGGAAACUCC CU UCAAGGACAUCGUCCGGG ACUGCCCA | 7450 |
| 907 | GGCAGUGA G CGGAAGCG | 5892 | CGCUUCCG GGAGGAAACUCC CU UCAAGGACAUCGUCCGGG UCACUGCC | 7451 |
| 909 | CAGUGAGC G GAAGCAG | 6964 | CUCGCUUC GGAGGAAACUCC CU UCAAGGACAUCGUCCGGG GCUCACUG | 7452 |
| 910 | AGUGAGCG G AAGCGAGG | 6965 | CCUCGCUU GGAGGAAACUCC CU UCAAGGACAUCGUCCGGG CGCUCACU | 7453 |
| 913 | GAGCGGAA G CGAGGAAU | 5893 | AUUCCUCG GGAGGAAACUCC CU UCAAGGACAUCGUCCGGG UUCCGCUC | 7454 |
| 915 | GCGGAAGC G AGGAAUGC | 6966 | GCAUUCCU GGAGGAAACUCC CU UCAAGGACAUCGUCCGGG GCUUCCGC | 7455 |
| 917 | GGAAGCGA G GAAUGCAG | 6967 | CUGCAUUC GGAGGAAACUCC CU UCAAGGACAUCGUCCGGG UCGCUUCC | 7456 |
| 918 | GAAGCGAG G AAUGCAGC | 6968 | GCUGCAUU GGAGGAAACUCC CU UCAAGGACAUCGUCCGGG CUCGCUUC | 7457 |
| 922 | CGAGGAAU G CAGCUGGA | 5894 | UCCAGCUG GGAGGAAACUCC CU UCAAGGACAUCGUCCGGG AUUCCUCG | 7458 |
| 925 | GGAAUGCA G CUGGAAGA | 5895 | UCUUCCAG GGAGGAAACUCC CU UCAAGGACAUCGUCCGGG UGCAUUCC | 7459 |
| 928 | AUGCAGCU G GAAGAUCU | 6969 | ACAUCUUC GGAGGAAACUCC CU UCAAGGACAUCGUCCGGG AGCUGCAU | 7460 |
| 929 | UGCAGCUG G AAGAUCUC | 6970 | GAGAUCUU GGAGGAAACUCC CU UCAAGGACAUCGUCCGGG CAGCUGCA | 7461 |
| 932 | AGCUGGAA G AUCUCAAA | 6971 | UUUGAGAU GGAGGAAACUCC CU UCAAGGACAUCGUCCGGG UUCCAGCU | 7462 |
| 943 | CUCAAACA G CAGCUCCA | 5896 | UGGAGCUG GGAGGAAACUCC CU UCAAGGACAUCGUCCGGG UGUUUGAG | 7463 |
| 946 | AAACAGCA G CUCCAGCA | 5897 | UCCUGGAG GGAGGAAACUCC CU UCAAGGACAUCGUCCGGG UGCUGUUU | 7464 |
| 952 | CAGCUCCA G CAGGCCGA | 5898 | UCGGCCUG GGAGGAAACUCC CU UCAAGGACAUCGUCCGGG UGGAGCUG | 7465 |

TABLE VII-continued

Human IKK-gamma Amberzyme and Substrate Sequence

| Pos | Substrate | Seq ID | Amberzyme | Seq ID |
|---|---|---|---|---|
| 955 | CUCCAGCA G CCCGAGGA | 6972 | UCCUCGGC GGAGGAAACUCC CU UCAAGGACAUCGUCCGGG UGCUGGAG | 7466 |
| 956 | UCCAGCAG G CCGAGGAG | 5899 | CUCCUCGG GGAGGAAACUCC CU UCAAGGACAUCGUCCGGG CUGCUGGA | 7467 |
| 959 | AGCAGGCC G AGGAGGCC | 6973 | GGCCUCCU GGAGGAAACUCC CU UCAAGGACAUCGUCCGGG GGCCUCCU | 7468 |
| 961 | CAGGCCGA G GAGGCCCU | 6974 | AGGGCCUC GGAGGAAACUCC CU UCAAGGACAUCGUCCGGG UCGGCCUC | 7469 |
| 962 | AGGCCGAG G AGGCCCUG | 6975 | CAGGGCCU GGAGGAAACUCC CU UCAAGGACAUCGUCCGGG CUCGGCCU | 7470 |
| 964 | GCCGAGGA G GCCCUGGU | 6976 | ACCAGGGC GGAGGAAACUCC CU UCAAGGACAUCGUCCGGG UCCUCGGC | 7471 |
| 965 | CCGAGGAG G CCCUGGUG | 5900 | CACCAGGG GGAGGAAACUCC CU UCAAGGACAUCGUCCGGG CUCCUCGG | 7472 |
| 970 | GAGGCCCU G GUGGCCAA | 6977 | UUGGCCAC GGAGGAAACUCC CU UCAAGGACAUCGUCCGGG AGGGCCUC | 7473 |
| 971 | AGGCCCUG G UGGCCAAA | 5901 | UUUGGCCA GGAGGAAACUCC CU UCAAGGACAUCGUCCGGG CAGGGCCU | 7474 |
| 973 | GCCCUGGU G GCCAAACA | 6978 | UGUUUGGC GGAGGAAACUCC CU UCAAGGACAUCGUCCGGG ACCAGGGC | 7475 |
| 974 | CCCUGGUC C CAAACAG | 5902 | CUGUUUGG GGAGGAAACUCC CU UCAAGGACAUCGUCCGGG CACCAGGG | 7476 |
| 982 | GCCAAACA G GAGGUGAU | 6979 | AUCACCUC GGAGGAAACUCC CU UCAAGGACAUCGUCCGGG UGUUUGGC | 7477 |
| 983 | CCAAACAG G AGGUGAUC | 6980 | GAUCACCU GGAGGAAACUCC CU UCAAGGACAUCGUCCGGG CUGUUUGG | 7478 |
| 985 | AAACAGGA G GUGAUCGA | 6981 | UCGAUCAC GGAGGAAACUCC CU UCAAGGACAUCGUCCGGG UCCUGUUU | 7479 |
| 986 | AACAGGAG G UGAUCGAU | 5903 | AUCGAUCA GGAGGAAACUCC CU UCAAGGACAUCGUCCGGG CUCCUGUU | 7480 |
| 988 | CAGGAGGU G AUCGAUAA | 6982 | UUAUCGAU GGAGGAAACUCC CU UCAAGGACAUCGUCCGGG ACCUCCUG | 7481 |
| 992 | AGGUGAUC G AUAAGCUG | 6983 | CAGCUUAU GGAGGAAACUCC CU UCAAGGACAUCGUCCGGG GAUCACCU | 7482 |
| 997 | AUCGAUAA G CUGAAGGA | 5904 | UCCUUCAG GGAGGAAACUCC CU UCAAGGACAUCGUCCGGG UUAUCGAU | 7483 |
| 1000 | GAUAAGCU G AAGGAGGA | 6984 | UCCUCCUU GGAGGAAACUCC CU UCAAGGACAUCGUCCGGG AGCUUAUC | 7484 |
| 1003 | AAGCUGAA G GAGGAGGC | 6985 | GCCUCCUC GGAGGAAACUCC CU UCAAGGACAUCGUCCGGG UUCAGCUU | 7485 |
| 1004 | AGCUGAAG G AGGAGGCC | 6986 | GGCCUCCU GGAGGAAACUCC CU UCAAGGACAUCGUCCGGG CUUCAGCU | 7486 |
| 1006 | CUGAAGGA G GAGGCCCA | 6987 | UCGGCCUC GGAGGAAACUCC CU UCAAGGACAUCGUCCGGG UCCUUCAG | 7487 |
| 1007 | UGAAGGAG G AGGCCGAG | 6988 | CUCGGCCU GGAGGAAACUCC CU UCAAGGACAUCGUCCGGG CUCCUUCA | 7488 |
| 1009 | AAGGAGGA G GCCGAGCA | 6989 | UGCUCGGC GGAGGAAACUCC CU UCAAGGACAUCGUCCGGG UCCUCCUU | 7489 |
| 1010 | AGGAGGAG G CCGAGCAG | 5905 | CUGCUCGG GGAGGAAACUCC CU UCAAGGACAUCGUCCGGG CUCCUCCU | 7490 |
| 1013 | AGGAGGCC G AGCAGCAC | 6990 | GUGCUGCU GGAGGAAACUCC CU UCAAGGACAUCGUCCGGG GGCCUCCU | 7491 |
| 1015 | GAGGCCGA G CAGCACAA | 5906 | UUGUGCUG GGAGGAAACUCC CU UCAAGGACAUCGUCCGGG UCGGCCUC | 7492 |
| 1018 | GCCGAGCA G CACAAGAU | 5907 | AUCUUGUG GGAGGAAACUCC CU UCAAGGACAUCGUCCGGG UGCUCGGC | 7493 |
| 1024 | CAGCACAA G AUUGUGAU | 6991 | AUCACAAU GGAGGAAACUCC CU UCAAGGACAUCGUCCGGG UUGUGCUG | 7494 |
| 1028 | ACAAGAUU G UGAUGGAG | 5908 | CUCCAUCA GGAGGAAACUCC CU UCAAGGACAUCGUCCGGG AAUCUUGU | 7495 |
| 1030 | AAGAUUGU G AUGGAGAC | 6992 | GUCUCCAU GGAGGAAACUCC CU UCAAGGACAUCGUCCGGG ACAAUCUU | 7496 |
| 1033 | AUUGUGAU G GAGACCGU | 6993 | ACGGUCUC GGAGGAAACUCC CU UCAAGGACAUCGUCCGGG AUCACAAU | 7497 |
| 1034 | UUGUGAUG G AGACCGUU | 6994 | AACGGUCU GGAGGAAACUCC CU UCAAGGACAUCGUCCGGG CAUCACAA | 7498 |
| 1036 | GUGAUGGA G ACCGUUCC | 6995 | GGAACGGU GGAGGAAACUCC CU UCAAGGACAUCGUCCGGG UCCAUCAC | 7499 |
| 1040 | UGGAGACC G UUCCGGUG | 5909 | CACCGGAA GGAGGAAACUCC CU UCAAGGACAUCGUCCGGG GGUCUCCA | 7500 |
| 1045 | ACCGUUCC G GUGCUGAA | 6996 | UUCAGCAC GGAGGAAACUCC CU UCAAGGACAUCGUCCGGG GGAACGGU | 7501 |
| 1046 | CCGUUCCG G UGCUGAAG | 5910 | CUUCAGCA GGAGGAAACUCC CU UCAAGGACAUCGUCCGGG CGGAACGG | 7502 |
| 1048 | GUUCCGGU G CUGAAGGC | 5911 | GCCUUCAG GGAGGAAACUCC CU UCAAGGACAUCGUCCGGG ACCGGAAC | 7503 |
| 1051 | CCGGUGCU G AAGGCCCA | 6997 | UGGGCCUU GGAGGAAACUCC CU UCAAGGACAUCGUCCGGG AGCACCGG | 7504 |
| 1054 | GUGCUGAA G GCCCAGGC | 6998 | GCCUGGGC GGAGGAAACUCC CU UCAAGGACAUCGUCCGGG UUCAGCAC | 7505 |
| 1055 | UGCUGAAG G CCCAGGCG | 5912 | CGCCUGGG GGAGGAAACUCC CU UCAAGGACAUCGUCCGGG CUUCAGCA | 7506 |
| 1060 | AAGGCCCA G GCGGAUAU | 6999 | AUAUCCGC GGAGGAAACUCC CU UCAAGGACAUCGUCCGGG UGGGCCUU | 7507 |
| 1061 | AGGCCCAG G CGGAUAUC | 5913 | GAUAUCCG GGAGGAAACUCC CU UCAAGGACAUCGUCCGGG CUGGGCCU | 7508 |
| 1063 | GCCCAGGC G GAUAUCUA | 7000 | UAGAUAUC GGAGGAAACUCC CU UCAAGGACAUCGUCCGGG GCCUGGGC | 7509 |
| 1064 | CCCAGGCG G AUAUCUAC | 7001 | GUAGAUAU GGAGGAAACUCC CU UCAAGGACAUCGUCCGGG CGCCUGGG | 7510 |
| 1075 | AUCUACAA G CGGACUUC | 7002 | AAGUCCGC GGAGGAAACUCC CU UCAAGGACAUCGUCCGGG UUGUAGAU | 7511 |
| 1076 | UCUACAAG G CGGACUUCA | 5914 | GAAGUCCG GGAGGAAACUCC CU UCAAGGACAUCGUCCGGG CUUGUAGA | 7512 |
| 1078 | UACAAGGC G GACUUCCA | 7003 | UGGAAGUC GGAGGAAACUCC CU UCAAGGACAUCGUCCGGG GCCUUGUA | 7513 |
| 1079 | ACAAGGCG G ACUUCCAG | 7004 | CUGGAAGU GGAGGAAACUCC CU UCAAGGACAUCGUCCGGG CGCCUUGU | 7514 |
| 1087 | GACUUCCA G CUGAGAGG | 7005 | CUCUCAGC GGAGGAAACUCC CU UCAAGGACAUCGUCCGGG UGGAAGUC | 7515 |
| 1088 | ACUUCCAG G CUGAGAGG | 5915 | CCUCUCAG GGAGGAAACUCC CU UCAAGGACAUCGUCCGGG CUGGAAGU | 7516 |
| 1091 | UCCAGGCU G AGAGGCAG | 7006 | CUGCCUCU GGAGGAAACUCC CU UCAAGGACAUCGUCCGGG AGCCUGGA | 7517 |
| 1093 | CAGGCUGA G AGGCAGGC | 7007 | GCCUGCCU GGAGGAAACUCC CU UCAAGGACAUCGUCCGGG UCAGCCUG | 7518 |
| 1095 | GGCUGAGA G GCAGGCCG | 7008 | GGGCCUGC GGAGGAAACUCC CU UCAAGGACAUCGUCCGGG UCUCAGCC | 7519 |
| 1096 | GCUGAGAG G CAGGCCCG | 5916 | CGGGCCUG GGAGGAAACUCC CU UCAAGGACAUCGUCCGGG CUCUCAGC | 7520 |
| 1099 | GAGAGGCA G GCCCGGGA | 7009 | UCCCGGGC GGAGGAAACUCC CU UCAAGGACAUCGUCCGGG UGCCUCUC | 7521 |
| 1100 | AGAGGCAG G CCCGGGAG | 5917 | CUCCCGGG GGAGGAAACUCC CU UCAAGGACAUCGUCCGGG CUGCCUCU | 7522 |
| 1104 | GCAGGCCC G GAGAAGC | 7010 | GCUUCUCC GGAGGAAACUCC CU UCAAGGACAUCGUCCGGG GGGCCUGC | 7523 |
| 1105 | CAGGCCCG G AGAAGCU | 7011 | AGCUUCUC GGAGGAAACUCC CU UCAAGGACAUCGUCCGGG CGGGCCUG | 7524 |
| 1106 | AGGCCCGG G AGAAGCUG | 7012 | CAGCUUCU GGAGGAAACUCC CU UCAAGGACAUCGUCCGGG CCGGGCCU | 7525 |
| 1108 | GCCCGGGA G AAGCUGGC | 7013 | GCCAGCUU GGAGGAAACUCC CU UCAAGGACAUCGUCCGGG UCCCGGGC | 7526 |
| 1111 | CGGGAGAA G CUGGCCGA | 5918 | UCGGCCAG GGAGGAAACUCC CU UCAAGGACAUCGUCCGGG UUCUCCCG | 7527 |
| 1114 | GAGAAGCU G GCCGAGAA | 7014 | UUCUCGGC GGAGGAAACUCC CU UCAAGGACAUCGUCCGGG AGCUUCUC | 7528 |
| 1115 | AGAAGCUG G CCGAGAAG | 5919 | CUUCUCGG GGAGGAAACUCC CU UCAAGGACAUCGUCCGGG CAGCUUCU | 7529 |
| 1118 | AGCUGGCC G AGAAGAAG | 7015 | CUUCUUCU GGAGGAAACUCC CU UCAAGGACAUCGUCCGGG GGCCAGCU | 7530 |
| 1120 | CUGGCCGA G AAGAAGGA | 7016 | UCCUUCUU GGAGGAAACUCC CU UCAAGGACAUCGUCCGGG UCGGCCAG | 7531 |
| 1123 | GCCGAGAA G AAGGAGCU | 7017 | AGCCUCCUU GGAGGAAACUCC CU UCAAGGACAUCGUCCGGG UUCUCGGC | 7532 |
| 1126 | GAGAAGAA G GAGCUCCU | 7018 | AGGAGCUC GGAGGAAACUCC CU UCAAGGACAUCGUCCGGG UUCUUCUC | 7533 |
| 1127 | AGAAGAAG G AGCUCCUG | 7019 | CAGGAGCU GGAGGAAACUCC CU UCAAGGACAUCGUCCGGG CUUCUUCU | 7534 |
| 1129 | AAGAAGGA G CUCCUGCA | 5920 | UGCAGGAG GGAGGAAACUCC CU UCAAGGACAUCGUCCGGG UCCUUCUU | 7535 |
| 1135 | GAGCUCCU G CAGGAGCA | 5921 | UGCUCCUG GGAGGAAACUCC CU UCAAGGACAUCGUCCGGG AGGAGCUC | 7536 |
| 1138 | CUCCUGCA G GAGCAGCU | 7020 | AGCUGCUC GGAGGAAACUCC CU UCAAGGACAUCGUCCGGG UGCAGGAG | 7537 |
| 1139 | UCCUGCAG G AGCAGCUG | 7021 | CAGCUGCU GGAGGAAACUCC CU UCAAGGACAUCGUCCGGG CUGCAGGA | 7538 |
| 1141 | CUGCAGGA G CAGCUGGA | 5922 | UCCAGCUG GGAGGAAACUCC CU UCAAGGACAUCGUCCGGG UCCUGCAG | 7539 |
| 1144 | CAGGAGCA G CUGGAGCA | 5923 | UGCUCCAG GGAGGAAACUCC CU UCAAGGACAUCGUCCGGG UGCUCCUG | 7540 |

TABLE VII-continued

Human IKK-gamma Amberzyme and Substrate Sequence

| Pos | Substrate | Seq ID | Amberzyme | Seq ID |
|---|---|---|---|---|
| 1147 | GACCAGCU G GAGCACCU | 7022 | ACCUCCUC GGAGGAAACUCC CU UCAAGGACAUCGUCCGGG ACCUCCUC | 7541 |
| 1148 | AGCAGCUG G AGCAGCUG | 7023 | CAGCUGCU GGAGGAAACUCC CU UCAAGGACAUCGUCCGGG CAGCUGCU | 7542 |
| 1150 | CACCUGGA G CACCUCCA | 5924 | UGCAGCUG GGAGGAAACUCC CU UCAAGGACAUCGUCCGGG UCCACCUG | 7543 |
| 1153 | CUGGAGCA G CUGCAGAG | 5925 | CUCUGCAG GGAGGAAACUCC CU UCAAGGACAUCGUCCGGG UGCUCCAG | 7544 |
| 1156 | GAGCAGCU G CAGAGGGA | 5926 | UCCCUCUG GGAGGAAACUCC CU UCAAGGACAUCGUCCGGG AGCUGCUC | 7545 |
| 1159 | CAGCUGCA G AGGGAGUA | 7024 | UACUCCCU GGAGGAAACUCC CU UCAAGGACAUCGUCCGGG UGCAGCUG | 7546 |
| 1161 | GCUGCAGA G GGAGUACA | 7025 | UGUACUCC GGAGGAAACUCC CU UCAAGGACAUCGUCCGGG UCUGCAGC | 7547 |
| 1162 | CUGCAGAG G GAGUACAG | 7026 | CUGUACUC GGAGGAAACUCC CU UCAAGGACAUCGUCCGGG CUCUCCAG | 7548 |
| 1163 | UGCAGAGG G AGUACAGC | 7027 | GCUGUACU GGAGGAAACUCC CU UCAAGGACAUCGUCCGGG CCUCUGCA | 7549 |
| 1165 | CAGAGGGA G UACAGCAA | 5927 | UUGCUGUA GGAGGAAACUCC CU UCAAGGACAUCGUCCGGG UCCCUCUG | 7550 |
| 1170 | GGAGUACA G CAAACUGA | 5928 | UCAGUUUG GGAGGAAACUCC CU UCAAGGACAUCGUCCGGG UGUACUCC | 7551 |
| 1177 | AGCAAACU G AAGGCCAG | 7028 | CUGGCCUU GGAGGAAACUCC CU UCAAGGACAUCGUCCGGG AGUUUGCU | 7552 |
| 1180 | AAACUGAA G GCCAGCUG | 7029 | CAGCUGGC GGAGGAAACUCC CU UCAAGGACAUCGUCCGGG UUCAGUUU | 7553 |
| 1181 | AACUGAAG G CCAGCUGU | 5929 | ACAGCUGG GGAGGAAACUCC CU UCAAGGACAUCGUCCGGG CUUCAGUU | 7554 |
| 1185 | GAAGGCCA G CUGUCAGG | 5930 | CCUGACAG GGAGGAAACUCC CU UCAAGGACAUCGUCCGGG UGGCCUUC | 7555 |
| 1188 | GGCCAGCU G UCAGGAGU | 5931 | ACUCCUGA GGAGGAAACUCC CU UCAAGGACAUCGUCCGGG AGCUGGCC | 7556 |
| 1192 | AGCUGUCA G GAGUCGGC | 7030 | GCCGACUC GGAGGAAACUCC CU UCAAGGACAUCGUCCGGG UGACAGCU | 7557 |
| 1193 | GCUGUCAG G AGUCGGCC | 7031 | GGCCGACU GGAGGAAACUCC CU UCAAGGACAUCGUCCGGG CUGACAGC | 7558 |
| 1195 | UGUCAGGA G UCGCCAG | 5932 | CUGGCCGA GGAGGAAACUCC CU UCAAGGACAUCGUCCGGG UCCUGACA | 7559 |
| 1198 | CAGGAGUC G GCCAGGAU | 7032 | AUCCUGGC GGAGGAAACUCC CU UCAAGGACAUCGUCCGGG GACUCCUG | 7560 |
| 1199 | AGGAGUCG G CCAGGAUC | 5933 | GAUCCUGG GGAGGAAACUCC CU UCAAGGACAUCGUCCGGG CGACUCCU | 7561 |
| 1203 | GUCGGCCA G GAUCGAGG | 7033 | CCUCGAUC GGAGGAAACUCC CU UCAAGGACAUCGUCCGGG UGGCCGAC | 7562 |
| 1204 | UCGGCCAG G AUCCAGGA | 7034 | UCCUCGAU GGAGGAAACUCC CU UCAAGGACAUCGUCCGGG CUGGCCGA | 7563 |
| 1208 | CCAGGAUC G AGGACAUC | 7035 | CAUGUCCU GGAGGAAACUCC CU UCAAGGACAUCGUCCGGG GAUCCUGC | 7564 |
| 1210 | AGGAUCGA G GACAUGAG | 7036 | CUCAUGUC GGAGGAAACUCC CU UCAAGGACAUCGUCCGGG UCGAUCCU | 7565 |
| 1211 | GGAUCGAG G ACAUGAGG | 7037 | CCUCAUGU GGAGGAAACUCC CU UCAAGGACAUCGUCCGGG CUCGAUCC | 7566 |
| 1216 | GAGGACAU G AGGAAGCG | 7038 | CGCUUCCU GGAGGAAACUCC CU UCAAGGACAUCGUCCGGG AUGUCCUC | 7567 |
| 1218 | GGACAUGA G GAAGCGGC | 7039 | GCCGCUUC GGAGGAAACUCC CU UCAAGGACAUCGUCCGGG UCAUGUCC | 7568 |
| 1219 | GACAUGAG G AAGCGGCA | 7040 | UGCCGCUU GGAGGAAACUCC CU UCAAGGACAUCGUCCGGG CUCAUGUC | 7569 |
| 1222 | AUGAGGAA G CGGCAUGU | 5934 | ACAUGCCG GGAGGAAACUCC CU UCAAGGACAUCGUCCGGG UUCCUCAU | 7570 |
| 1224 | GAGGAAGC G GCAUGUCG | 7041 | CGACAUGC GGAGGAAACUCC CU UCAAGGACAUCGUCCGGG GCUUCCUC | 7571 |
| 1225 | AGGAAGCG G CAUGUCGA | 5935 | UCGACAUG GGAGGAAACUCC CU UCAAGGACAUCGUCCGGG CGCUUCCU | 7572 |
| 1229 | AGCGGCAU G UCGAGGUC | 5936 | GACCUCGA GGAGGAAACUCC CU UCAAGGACAUCGUCCGGG AUGCCGCU | 7573 |
| 1232 | GCCAUGUC G AGGUCUCC | 7042 | GGAGACCU GGAGGAAACUCC CU UCAAGGACAUCGUCCGGG GACAUGCC | 7574 |
| 1234 | CAUGUCCA G GUCUCCCA | 7043 | UGGGAGAC GGAGGAAACUCC CU UCAAGGACAUCGUCCGGG UCGACAUG | 7575 |
| 1235 | AUGUCGAC G UCUCCCAG | 5937 | CUGGGAGA GGAGGAAACUCC CU UCAAGGACAUCGUCCGGG CUCGACAU | 7576 |
| 1243 | GUCUCCCA G GCCCCUU | 7044 | AAGGGGGC GGAGGAAACUCC CU UCAAGGACAUCGUCCGGG UGGGAGAC | 7577 |
| 1244 | UCUCCCAG G CCCCCUUG | 5938 | CAAGGGGG GGAGGAAACUCC CU UCAAGGACAUCGUCCGGG CUGGGAGA | 7578 |
| 1252 | GCCCCCUU G CCCCCCGC | 5939 | GCGGGGGG GGAGGAAACUCC CU UCAAGGACAUCGUCCGGG AAGGGGGC | 7579 |
| 1259 | UGCCCCCC G CCCCUGCC | 5940 | GGCAGGGG GGAGGAAACUCC CU UCAAGGACAUCGUCCGGG GGGGGGCA | 7580 |
| 1265 | CCCCCCU G CCUACCUC | 5941 | GAGGUAGG GGAGGAAACUCC CU UCAAGGACAUCGUCCGGG AGGGGCGG | 7581 |
| 1285 | UCUCCCCU G GCCCUGCC | 7045 | GGCAGGGC GGAGGAAACUCC CU UCAAGGACAUCGUCCGGG AGGGGAGA | 7582 |
| 1286 | CUCCCCUC G CCCUGCCC | 5942 | GGGCAGGG GGAGGAAACUCC CU UCAAGGACAUCGUCCGGG CAGGGGAG | 7583 |
| 1291 | CUGCCCCU G CCCAGCCA | 5943 | UGGCUGGG GGAGGAAACUCC CU UCAAGGACAUCGUCCGGG AGGGCCAG | 7584 |
| 1296 | CCUGCCCA G CCAGAGGA | 5944 | UCCUCUGG GGAGGAAACUCC CU UCAAGGACAUCGUCCGGG UGGGCAGG | 7585 |
| 1300 | CCCAGCCA G AGGAGGAG | 7046 | CUCCUCCU GGAGGAAACUCC CU UCAAGGACAUCGUCCGGG UGGCUGGG | 7586 |
| 1302 | CAGCCAGA G GAGGAGCC | 7047 | GGCUCCUC GGAGGAAACUCC CU UCAAGGACAUCGUCCGGG UCUGGCUG | 7587 |
| 1303 | AGCCAGAG G AGGAGCCC | 7048 | GGGCUCCU GGAGGAAACUCC CU UCAAGGACAUCGUCCGGG CUCUGGCU | 7588 |
| 1305 | CCAGAGGA G GAGCCCCC | 7049 | GGGGGCUC GGAGGAAACUCC CU UCAAGGACAUCGUCCGGG UCCUCUGG | 7589 |
| 1306 | CAGAGGAG G AGCCCCCC | 7050 | GGGGGGCU GGAGGAAACUCC CU UCAAGGACAUCGUCCGGG CUCCUCUG | 7590 |
| 1308 | GAGGAGGA G CCCCCCCG | 5945 | CGGGGGGG GGAGGAAACUCC CU UCAAGGACAUCGUCCGGG UCCUCCUC | 7591 |
| 1316 | GCCCCCCC G AGGAGCCA | 7051 | UGGCUCCU GGAGGAAACUCC CU UCAAGGACAUCGUCCGGG GGGGGGGC | 7592 |
| 1318 | CCCCCCGA G GAGCCACC | 7052 | GGUGGCUC GGAGGAAACUCC CU UCAAGGACAUCGUCCGGG UCGGGGGG | 7593 |
| 1319 | CCCCCGAG G AGCCACCU | 7053 | AGGUGGCU GGAGGAAACUCC CU UCAAGGACAUCGUCCGGG CUCGGGGG | 7594 |
| 1321 | CCCGAGGA G CCACCUGA | 5946 | UCAGGUGG GGAGGAAACUCC CU UCAAGGACAUCGUCCGGG UCCUCGGG | 7595 |
| 1328 | AGCCACCU G ACUUCUGC | 7054 | GCAGAAGU GGAGGAAACUCC CU UCAAGGACAUCGUCCGGG AGGUGGCU | 7596 |
| 1335 | UGACUUCU G CUGUCCCA | 5947 | UGGGACAG GGAGGAAACUCC CU UCAAGGACAUCGUCCGGG AGAAGUCA | 7597 |
| 1338 | CUUCUGCU G UCCCAAGU | 5948 | ACUUGGGA GGAGGAAACUCC CU UCAAGGACAUCGUCCGGG AGCAGAAG | 7598 |
| 1345 | UGUCCCAA G UGCAGUA | 5949 | UACUGGCA GGAGGAAACUCC CU UCAAGGACAUCGUCCGGG UUGGGACA | 7599 |
| 1347 | UCCCAAGU G CCAGUAUC | 5950 | GAUACUGG GGAGGAAACUCC CU UCAAGGACAUCGUCCGGG ACUUGGGA | 7600 |
| 1351 | AAGUGCCA G UAUCAGGC | 5951 | GCCUGAUA GGAGGAAACUCC CU UCAAGGACAUCGUCCGGG UGGCACUU | 7601 |
| 1357 | CAGUAUCA G GCCCCUGA | 7055 | UCAGGGGC GGAGGAAACUCC CU UCAAGGACAUCGUCCGGG UGAUACUG | 7602 |
| 1358 | AGUAUCAG G CCCCUGAU | 5952 | AUCAGGGG GGAGGAAACUCC CU UCAAGGACAUCGUCCGGG CUGAUACU | 7603 |
| 1364 | AGGCCCCU G AUAUGGAC | 7056 | GUCCAUAU GGAGGAAACUCC CU UCAAGGACAUCGUCCGGG AGGGGCCU | 7604 |
| 1369 | CCUGAUAU G GACACCCU | 7057 | AGGGUGUC GGAGGAAACUCC CU UCAAGGACAUCGUCCGGG AUAUCAGG | 7605 |
| 1370 | CUGAUAUG G ACACCCUG | 7058 | CAGGGUGU GGAGGAAACUCC CU UCAAGGACAUCGUCCGGG CAUAUCAG | 7606 |
| 1378 | GACACCCU G CAGAUACA | 5953 | UGUAUCUG GGAGGAAACUCC CU UCAAGGACAUCGUCCGGG AGGGUGUC | 7607 |
| 1381 | ACCCUGCA G AUACAUGU | 7059 | ACAUGUAU GGAGGAAACUCC CU UCAAGGACAUCGUCCGGG UGCAGGGU | 7608 |
| 1388 | AGAUACAU G UCAUGGAG | 5954 | CUCCAUGA GGAGGAAACUCC CU UCAAGGACAUCGUCCGGG AUGUAUCU | 7609 |
| 1393 | CAUGUCAU G GAGUGCAU | 7060 | AUGCACUC GGAGGAAACUCC CU UCAAGGACAUCGUCCGGG AUGACAUG | 7610 |
| 1394 | AUGUCAUG G AGUGCAUU | 7061 | AAUGCACU GGAGGAAACUCC CU UCAAGGACAUCGUCCGGG CAUGACAU | 7611 |
| 1396 | GUCAUGGA G UGCAUUGA | 5955 | UCAAUGCA GGAGGAAACUCC CU UCAAGGACAUCGUCCGGG UCCAUGAC | 7612 |
| 1398 | CAUGGAGU G CAUUGAGU | 5956 | ACUCAAUG GGAGGAAACUCC CU UCAAGGACAUCGUCCGGG ACUCCAUG | 7613 |
| 1403 | AGUGCAUU G AGUAGGGC | 7062 | GCCCUACU GGAGGAAACUCC CU UCAAGGACAUCGUCCGGG AAUGCACU | 7614 |
| 1405 | UGCAUUGA G UAGGGCCG | 5957 | CGGCCCUA GGAGGAAACUCC CU UCAAGGACAUCGUCCGGG UCAAUGCA | 7615 |

TABLE VII-continued

Human IKK-gamma Amberzyme and Substrate Sequence

| Pos | Substrate | Seq ID | Amberzyme | Seq ID |
|---|---|---|---|---|
| 1408 | AUUGAGUA G GGCCGGCC | 7063 | GGCCGGCC GGAGGAAACUCC CU UCAAGGACAUCGUCCGGG UACUCAAU | 7616 |
| 1409 | UUGAGUAG G GCCGGCCA | 7064 | UGGCCGGC GGAGGAAACUCC CU UCAAGGACAUCGUCCGGG CUACUCAA | 7617 |
| 1410 | UGAGUAGG G CCGGCCAG | 5958 | CUGGCCGG GGAGGAAACUCC CU UCAAGGACAUCGUCCGGG CCUACUCA | 7618 |
| 1413 | GUAGGGCC G GCCAGUGC | 7065 | GCACUGGC GGAGGAAACUCC CU UCAAGGACAUCGUCCGGG GGCCCUAC | 7619 |
| 1414 | UAGGGCCG G CCAGUGCA | 5959 | UGCACUGG GGAGGAAACUCC CU UCAAGGACAUCGUCCGGG CGGCCCUA | 7620 |
| 1418 | GCCGCCCA G UGCAAGGC | 5960 | GCCUUGCA GGAGGAAACUCC CU UCAAGGACAUCGUCCGGG UGGCCGGC | 7621 |
| 1420 | CGGCCAGU G CAAGGCCA | 5961 | UGGCCUUG GGAGGAAACUCC CU UCAAGGACAUCGUCCGGG ACUGGCCG | 7622 |
| 1424 | CAGUGCAA G GCCACUGC | 7066 | GCAGUGGC GGAGGAAACUCC CU UCAAGGACAUCGUCCGGG UUGCACUG | 7623 |
| 1425 | AGUGCAAG G CCACUGCC | 5962 | GGCAGUGG GGAGGAAACUCC CU UCAAGGACAUCGUCCGGG CUUGCACU | 7624 |
| 1431 | AGGCCACU G CCUGCCCG | 5963 | CGGGCAGG GGAGGAAACUCC CU UCAAGGACAUCGUCCGGG AGUGGCCU | 7625 |
| 1435 | CACUGCCU G CCCGAGGA | 5964 | UCCUCGGG GGAGGAAACUCC CU UCAAGGACAUCGUCCGGG AGGCAGUG | 7626 |
| 1439 | GCCUGCCC G AGGACGUG | 7067 | CACGUCCU GGAGGAAACUCC CU UCAAGGACAUCGUCCGGG GGGCAGGC | 7627 |
| 1441 | CUGCCCGA G GACGUGCC | 7068 | GGCACGUC GGAGGAAACUCC CU UCAAGGACAUCGUCCGGG UCGGGCAG | 7628 |
| 1442 | UGCCCGAG G ACGUGCCC | 7069 | GGGCACGU GGAGGAAACUCC CU UCAAGGACAUCGUCCGGG CUCGGGCA | 7629 |
| 1445 | CCGAGGAC G UGCCCGGG | 5965 | CCCGGGCA GGAGGAAACUCC CU UCAAGGACAUCGUCCGGG GUCCUCGG | 7630 |
| 1447 | GAGGACGU G CCCGGGAC | 5966 | GUCCCGGG GGAGGAAACUCC CU UCAAGGACAUCGUCCGGG ACGUCCUC | 7631 |
| 1451 | ACGUGCCC G GGACCGUG | 7070 | CACGGUCC GGAGGAAACUCC CU UCAAGGACAUCGUCCGGG GGGCACGU | 7632 |
| 1452 | CGUGCCCG G GACCGUGC | 7071 | GCACGGUC GGAGGAAACUCC CU UCAAGGACAUCGUCCGGG CGGGCACG | 7633 |
| 1453 | GUGCCCGG G ACCGUGCA | 7072 | UGCACGGU GGAGGAAACUCC CU UCAAGGACAUCGUCCGGG CCGGGCAC | 7634 |
| 1457 | CCGGGACC G UGCAGUCU | 5967 | AGACUGCA GGAGGAAACUCC CU UCAAGGACAUCGUCCGGG GGUCCCGG | 7635 |
| 1459 | GGGACCGU G CAGUCUGC | 5968 | GCAGACUG GGAGGAAACUCC CU UCAAGGACAUCGUCCGGG ACGGUCCC | 7636 |
| 1462 | ACCGUGCA G UCUGCGCU | 5969 | AGCGCAGA GGAGGAAACUCC CU UCAAGGACAUCGUCCGGG UGCACGGU | 7637 |
| 1466 | UGCAGUCU G CGCUUUCC | 5970 | GGAAAGCG GGAGGAAACUCC CU UCAAGGACAUCGUCCGGG AGACUGCA | 7638 |
| 1468 | CAGUCUGC G CUUUCCUC | 5971 | GAGGAAAG GGAGGAAACUCC CU UCAAGGACAUCGUCCGGG GCAGACUG | 7639 |
| 1481 | CCUCUCCG G CCUGCCUA | 5972 | UAGGCAGG GGAGGAAACUCC CU UCAAGGACAUCGUCCGGG GGGAGAGG | 7640 |
| 1485 | UCCGCCUG G CCUAGCCC | 5973 | GGGCUAGG GGAGGAAACUCC CU UCAAGGACAUCGUCCGGG AGGCGGGA | 7641 |
| 1490 | CCUGCCUA G CCCAGGAU | 5974 | AUCCUGGG GGAGGAAACUCC CU UCAAGGACAUCGUCCGGG UAGGCAGG | 7642 |
| 1495 | CUAGCCCA G GAUGAAGG | 7073 | CCUUCAUC GGAGGAAACUCC CU UCAAGGACAUCGUCCGGG UGGGCUAG | 7643 |
| 1496 | UAGCCCAG G AUGAAGGG | 7074 | CCCUUCAU GGAGGAAACUCC CU UCAAGGACAUCGUCCGGG CUGGGCUA | 7644 |
| 1499 | CCCAGGAU G AAGGGCUG | 7075 | CAGCCCUU GGAGGAAACUCC CU UCAAGGACAUCGUCCGGG AUCCUGGG | 7645 |
| 1502 | AGGAUGAA G GGCUGGGU | 7076 | ACCCAGCC GGAGGAAACUCC CU UCAAGGACAUCGUCCGGG UUCAUCCU | 7646 |
| 1503 | GGAUGAAG G GCUGGGUG | 7077 | CACCCAGC GGAGGAAACUCC CU UCAAGGACAUCGUCCGGG CUUCAUCC | 7647 |
| 1504 | GAUGAAGG G CUGGGUGG | 5975 | CCACCCAG GGAGGAAACUCC CU UCAAGGACAUCGUCCGGG CCUUCAUC | 7648 |
| 1507 | GAAGGGCU G GGUGGCCA | 7078 | UGGCCACC GGAGGAAACUCC CU UCAAGGACAUCGUCCGGG AGCCCUUC | 7649 |
| 1508 | AAGGGCUG G GUGGCCAC | 7079 | GUGGCCAC GGAGGAAACUCC CU UCAAGGACAUCGUCCGGG CAGCCCUU | 7650 |
| 1509 | AGGGCUGG G UGGCCACA | 5976 | UGUGGCCA GGAGGAAACUCC CU UCAAGGACAUCGUCCGGG CCAGCCCU | 7651 |
| 1511 | GGCUGGGU G GCCACAAC | 7080 | GUUGUGGC GGAGGAAACUCC CU UCAAGGACAUCGUCCGGG ACCCAGCC | 7652 |
| 1512 | GCUGGGUG G CCACAACU | 5977 | AGUUGUGG GGAGGAAACUCC CU UCAAGGACAUCGUCCGGG CACCCAGC | 7653 |
| 1521 | CCACAACU G GAUGCCA | 7081 | UGGCAUCC GGAGGAAACUCC CU UCAAGGACAUCGUCCGGG AGUUGUGG | 7654 |
| 1522 | CACAACUG G AUGCCAC | 7082 | GUGGCAUC GGAGGAAACUCC CU UCAAGGACAUCGUCCGGG CAGUUGUG | 7655 |
| 1523 | ACAACUGG A UGCCACC | 7083 | GGUGGCAU GGAGGAAACUCC CU UCAAGGACAUCGUCCGGG CCAGUUGU | 7656 |
| 1526 | ACUCGGAU G CCACCUGG | 5978 | CCAGGUGG GGAGGAAACUCC CU UCAAGGACAUCGUCCGGG AUCCGAGU | 7657 |
| 1533 | UGCCACCU G GAGCCCCA | 7084 | UGGGGCUC GGAGGAAACUCC CU UCAAGGACAUCGUCCGGG AGGUGGCA | 7658 |
| 1534 | GCCACCUG G AGCCCCAC | 7085 | GUGGGGCU GGAGGAAACUCC CU UCAAGGACAUCGUCCGGG CAGGUGGC | 7659 |
| 1536 | CACCUGGA G CCCCACCC | 5979 | GGGUGGGG GGAGGAAACUCC CU UCAAGGACAUCGUCCGGG UCCAGGUG | 7660 |
| 1546 | CCCACCCA G AGCUGGCC | 7086 | GCCAGCUC GGAGGAAACUCC CU UCAAGGACAUCGUCCGGG UGGGUGGG | 7661 |
| 1547 | CCACCCAG A GCUGGCCG | 7087 | GGCCAGCU GGAGGAAACUCC CU UCAAGGACAUCGUCCGGG CUGGGUGG | 7662 |
| 1549 | ACCCAGGA G CUGGCCGC | 5980 | GCGGCCAG GGAGGAAACUCC CU UCAAGGACAUCGUCCGGG UCCUGGGU | 7663 |
| 1552 | CAGGAGCU G GCCGCGGC | 7088 | GCCGCGGC GGAGGAAACUCC CU UCAAGGACAUCGUCCGGG AGCUCCUG | 7664 |
| 1553 | AGGAGCUG G CCGCGGCA | 5981 | UGCCGCGG GGAGGAAACUCC CU UCAAGGACAUCGUCCGGG CAGCUCCU | 7665 |
| 1556 | AGCUGGCC G CGGCACCU | 5982 | AGGUGCCG GGAGGAAACUCC CU UCAAGGACAUCGUCCGGG GGCCAGCU | 7666 |
| 1558 | CUGGCCGC G GCACCUUA | 7089 | UAAGGUGC GGAGGAAACUCC CU UCAAGGACAUCGUCCGGG GCGGCCAG | 7667 |
| 1559 | UGGCCGCG G CACCUUAC | 5983 | GUAAGGUG GGAGGAAACUCC CU UCAAGGACAUCGUCCGGG CGCGGCCA | 7668 |
| 1568 | CACCUUAC G CUUCAGCU | 5984 | AGCUGAAG GGAGGAAACUCC CU UCAAGGACAUCGUCCGGG GUAAGGUG | 7669 |
| 1574 | ACGCUUCA G CUGUUGAU | 5985 | AUCAACAG GGAGGAAACUCC CU UCAAGGACAUCGUCCGGG UGAAGCGU | 7670 |
| 1577 | CUUCAGCU G UUGAUCCG | 5986 | CGGAUCAA GGAGGAAACUCC CU UCAAGGACAUCGUCCGGG AGCUGAAG | 7671 |
| 1580 | CAGCUGUU G AUCCGCUG | 7090 | CAGCGGAU GGAGGAAACUCC CU UCAAGGACAUCGUCCGGG AACAGCUG | 7672 |
| 1585 | GUUGAUCC G CUGGUCCC | 5987 | GGGACCAG GGAGGAAACUCC CU UCAAGGACAUCGUCCGGG GGAUCAAC | 7673 |
| 1588 | GAUCCGCU G GUCCCCUC | 7091 | CAGGGGAC GGAGGAAACUCC CU UCAAGGACAUCGUCCGGG AGCGGAUC | 7674 |
| 1589 | AUCCGCUG G UCCCCUCU | 5988 | AGAGGGGA GGAGGAAACUCC CU UCAAGGACAUCGUCCGGG CAGCGGAU | 7675 |
| 1601 | CCUCUUUU G GGUAGAU | 7092 | AUCUACCC GGAGGAAACUCC CU UCAAGGACAUCGUCCGGG AAAAGAGG | 7676 |
| 1602 | CUCUUUUG G GUAGAUG | 7093 | CAUCUACC GGAGGAAACUCC CU UCAAGGACAUCGUCCGGG CAAAAGAG | 7677 |
| 1603 | UCUUUUGG G UAGAUGC | 7094 | GCAUCUAC GGAGGAAACUCC CU UCAAGGACAUCGUCCGGG CCAAAAGA | 7678 |
| 1604 | CUUUUGGG U AGAUGCG | 5989 | CGCAUCUA GGAGGAAACUCC CU UCAAGGACAUCGUCCGGG CCCAAAAG | 7679 |
| 1607 | UUGGGUA G AUGCGGCC | 7095 | GGCCGCAU GGAGGAAACUCC CU UCAAGGACAUCGUCCGGG UACCCCAA | 7680 |
| 1610 | GGGUAGAU G CGGCCCCG | 5990 | CGGGGCCG GGAGGAAACUCC CU UCAAGGACAUCGUCCGGG AUCUACCC | 7681 |
| 1612 | GUAGAUGC G GCCCCGAU | 7096 | AUCGGGGC GGAGGAAACUCC CU UCAAGGACAUCGUCCGGG GCAUCUAC | 7682 |
| 1613 | UAGAUGCG G CCCCGAUC | 5991 | CAUCGGGG GGAGGAAACUCC CU UCAAGGACAUCGUCCGGG CGCAUCUA | 7683 |
| 1618 | GCGGCCCC G AUCAGGCC | 7097 | GGCCUGAU GGAGGAAACUCC CU UCAAGGACAUCGUCCGGG GGGGCCGC | 7684 |
| 1623 | CCCGAUCA G GCCUGACU | 7098 | AGUCAGGC GGAGGAAACUCC CU UCAAGGACAUCGUCCGGG UGAUCGGG | 7685 |
| 1624 | CCGAUCAG G CCUGACUC | 5992 | GAGUCAGG GGAGGAAACUCC CU UCAAGGACAUCGUCCGGG CUGAUCGG | 7686 |
| 1628 | UCAGGCCU G ACUCGCUG | 7099 | CAGCGAGU GGAGGAAACUCC CU UCAAGGACAUCGUCCGGG AGGCCUGA | 7687 |
| 1633 | CCUGACUC G CUGCUCUU | 5993 | AAGAGCAG GGAGGAAACUCC CU UCAAGGACAUCGUCCGGG GAGUCAGC | 7688 |
| 1636 | GACUCGCU G CUCUUUUU | 5994 | AAAAAGAG GGAGGAAACUCC CU UCAAGGACAUCGUCCGGG AGCGAGUC | 7689 |
| 1645 | CUCUUUUU G UUCCCUUC | 5995 | GAAGGGAA GGAGGAAACUCC CU UCAAGGACAUCGUCCGGG AAAAAGAG | 7690 |

TABLE VII-continued

Human IKK-gamma Amberzyme and Substrate Sequence

| Pos | Substrate | Seq ID | Amberzyme | Seq ID |
|---|---|---|---|---|
| 1655 | UCCCUUCU G UCUGCUCG | 5996 | CGAGCAGA GGAGGAAACUCC CU UCAAGGACAUCGUCCGGG AGAAGGGA | 7691 |
| 1659 | UUCUGUCU G CUCGAACC | 5997 | GGUUCGAG GGAGGAAACUCC CU UCAAGGACAUCGUCCGGG AGACAGAA | 7692 |
| 1663 | GUCUGCUC G AACCACUU | 7100 | AAGUGGUU GGAGGAAACUCC CU UCAAGGACAUCGUCCGGG GACCAGAC | 7693 |
| 1672 | AACCACUU G CCUCGGGC | 5998 | GCCCGAGG GGAGGAAACUCC CU UCAAGGACAUCGUCCGGG AAGUGGUU | 7694 |
| 1677 | CUUGCCUC G GGCUAAUC | 7101 | GAUUAGCC GGAGGAAACUCC CU UCAAGGACAUCGUCCGGG GAGGCAAG | 7695 |
| 1678 | UUGCCUCG G GCUAAUCC | 7102 | GGAUUAGC GGAGGAAACUCC CU UCAAGGACAUCGUCCGGG CGAGGCAA | 7696 |
| 1679 | UGCCUCGG G CUAAUCCC | 5999 | GGGAUUAG GGAGGAAACUCC CU UCAAGGACAUCGUCCGGG CCGAGGCA | 7697 |
| 1705 | CUCCACCC G GCACUGGG | 7103 | CCCAGUGC GGAGGAAACUCC CU UCAAGGACAUCGUCCGGG GGGUGGAG | 7698 |
| 1706 | UCCACCCG G CACUGGGG | 6000 | CCCCAGUG GGAGGAAACUCC CU UCAAGGACAUCGUCCGGG CGGUGGA | 7699 |
| 1711 | CCGGCACU G GGAAGUC | 7104 | GACUUCCC GGAGGAAACUCC CU UCAAGGACAUCGUCCGGG AGUGCCGG | 7700 |
| 1712 | CGGCACUG G GGAAGUCA | 7105 | UGACUUCC GGAGGAAACUCC CU UCAAGGACAUCGUCCGGG CAGUGCCG | 7701 |
| 1713 | GGCACUGG G AAGUCAA | 7106 | UUGACUUC GGAGGAAACUCC CU UCAAGGACAUCGUCCGGG CCAGUGCC | 7702 |
| 1714 | GCACUGGG G AAGUCAAG | 7107 | CUUGACUU GGAGGAAACUCC CU UCAAGGACAUCGUCCGGG CCCAGUGC | 7703 |
| 1717 | CUGGGGAA G UCAAGAAU | 6001 | AUUCUUGA GGAGGAAACUCC CU UCAAGGACAUCGUCCGGG UUCCCCAG | 7704 |
| 1722 | GAAGUCAA G AAUGGGGC | 7108 | GCCCCAUU GGAGGAAACUCC CU UCAAGGACAUCGUCCGGG UUGACUUC | 7705 |
| 1726 | UCAAGAAU G CGGCCUGG | 7109 | CCAGGCCC GGAGGAAACUCC CU UCAAGGACAUCGUCCGGG AUUCUUGA | 7706 |
| 1727 | CAAGAAUG G GGCCUGGG | 7110 | CCCACGCC GGAGGAAACUCC CU UCAAGGACAUCGUCCGGG CAUUCUUG | 7707 |
| 1728 | AAGAAUGG G GCCUGGGG | 7111 | CCCCAGGC GGAGGAAACUCC CU UCAAGGACAUCGUCCGGG CCAUUCUU | 7708 |
| 1729 | AGAAUGGG G CCUGGGGC | 6002 | GCCCCAGG GGAGGAAACUCC CU UCAAGGACAUCGUCCGGG CCCAUUCU | 7709 |
| 1733 | UGGGGCCU G GGGCUCUC | 7112 | GAGAGCCC GGAGGAAACUCC CU UCAAGGACAUCGUCCGGG AGGCCCCA | 7710 |
| 1734 | GGGGCCUG G GGCUCUCA | 7113 | UGAGAGCC GGAGGAAACUCC CU UCAAGGACAUCGUCCGGG CAGGCCCC | 7711 |
| 1735 | GGGCCUGG G GCUCUCAG | 7114 | CUGAGAGC GGAGGAAACUCC CU UCAAGGACAUCGUCCGGG CCAGGCCC | 7712 |
| 1736 | GGCCUGGG G CUCUCAGG | 6003 | CCUGAGAG GGAGGAAACUCC CU UCAAGGACAUCGUCCGGG CCCAGGCC | 7713 |
| 1743 | GGCUCUCA G GAGAACU | 7115 | AGUUCUCC GGAGGAAACUCC CU UCAAGGACAUCGUCCGGG UGAGAGCC | 7714 |
| 1744 | GCUCUCAG G AGAACGC | 7116 | CAGUUCUC GGAGGAAACUCC CU UCAAGGACAUCGUCCGGG CUGAGAGC | 7715 |
| 1745 | CUCUCAGG G AGAACGC | 7117 | GCAGUUCU GGAGGAAACUCC CU UCAAGGACAUCGUCCGGG CCUGAGAC | 7716 |
| 1747 | CUCAGGGA G AACUGCUU | 7118 | AAGCAGUU GGAGGAAACUCC CU UCAAGGACAUCGUCCGGG UCCCUGAG | 7717 |
| 1752 | GGAGAACU G CUUCCCU | 6004 | AGGGGAAG GGAGGAAACUCC CU UCAAGGACAUCGUCCGGG AGUUCUCC | 7718 |
| 1761 | CUUCCCCU G GCAGAGCU | 7119 | AGCUCUGC GGAGGAAACUCC CU UCAAGGACAUCGUCCGGG AGGGGAAG | 7719 |
| 1762 | UUCCCCUG G CAGAGCUG | 6005 | CAGCUCUG GGAGGAAACUCC CU UCAAGGACAUCGUCCGGG CAGGGGAA | 7720 |
| 1765 | CCCUGGCA G AGCUGGGU | 7120 | ACCCAGCU GGAGGAAACUCC CU UCAAGGACAUCGUCCGGG UGCCAGGG | 7721 |
| 1767 | CUGGCAGA G CUGGGUGG | 6006 | CCACCCAG GGAGGAAACUCC CU UCAAGGACAUCGUCCGGG UCUGCCAG | 7722 |
| 1770 | GCAGAGCU G GUGGCAGC | 7121 | CUGCCACC GGAGGAAACUCC CU UCAAGGACAUCGUCCGGG AGCUCUGC | 7723 |
| 1771 | CAGAGCUG G UGGCAGCU | 7122 | GCUGCCAC GGAGGAAACUCC CU UCAAGGACAUCGUCCGGG CAGCUCUG | 7724 |
| 1772 | AGAGCUGG G UGGCAGCU | 6007 | AGCUGCCA GGAGGAAACUCC CU UCAAGGACAUCGUCCGGG CCAGCUCU | 7725 |
| 1774 | AGCUGGGU G GCAGCUCU | 7123 | AGAGCUGC GGAGGAAACUCC CU UCAAGGACAUCGUCCGGG ACCCAGCU | 7726 |
| 1775 | GCUGGGUG G CAGCUCUU | 6008 | AAGAGCUG GGAGGAAACUCC CU UCAAGGACAUCGUCCGGG CACCCAGC | 7727 |
| 1778 | CGCUGGCA G CUCUUCCU | 6009 | AGGAAGAG GGAGGAAACUCC CU UCAAGGACAUCGUCCGGG UGCCACCC | 7728 |
| 1793 | CUCCCACC G GACACCGA | 7124 | UCGGUGUC GGAGGAAACUCC CU UCAAGGACAUCGUCCGGG GGUGGGAC | 7729 |
| 1794 | UCCCACCG G ACACCGAC | 7125 | GUCGGUGU GGAGGAAACUCC CU UCAAGGACAUCGUCCGGG CGGUGGGA | 7730 |
| 1800 | CGGACACC G ACCCGCCC | 7126 | GGGCGGGU GGAGGAAACUCC CU UCAAGGACAUCGUCCGGG GGUGUCCG | 7731 |
| 1805 | ACCGACCC G CCCGCCGC | 6010 | GCGGCGGG GGAGGAAACUCC CU UCAAGGACAUCGUCCGGG GGGUCGGU | 7732 |
| 1809 | ACCCGCCC G CCGCUGUG | 6011 | CACAGCGG GGAGGAAACUCC CU UCAAGGACAUCGUCCGGG GGGCGGGU | 7733 |
| 1812 | CGCCCGCC G CUGUGCCC | 6012 | GGGCACAG GGAGGAAACUCC CU UCAAGGACAUCGUCCGGG GGCGGGCG | 7734 |
| 1815 | CCGCCGCU G UGCCCUGG | 6013 | CCAGGGCA GGAGGAAACUCC CU UCAAGGACAUCGUCCGGG AGCGGCGG | 7735 |
| 1817 | GCCGCUGU G CCCUGGGA | 6014 | UCCCAGGG GGAGGAAACUCC CU UCAAGGACAUCGUCCGGG ACAGCGGC | 7736 |
| 1822 | UGUGCCCU G GAGUGCU | 7127 | AGCACUCC GGAGGAAACUCC CU UCAAGGACAUCGUCCGGG AGGGCACA | 7737 |
| 1823 | GUGCCCUG G AGUGCUG | 7128 | CAGCACUC GGAGGAAACUCC CU UCAAGGACAUCGUCCGGG CAGGGCAC | 7738 |
| 1824 | UGCCCUGG G AGUGCUGC | 7129 | GCAGCACU GGAGGAAACUCC CU UCAAGGACAUCGUCCGGG CCAGGGCA | 7739 |
| 1826 | CCCUGGGA G UGCUGCGC | 6015 | GGGCAGCA GGAGGAAACUCC CU UCAAGGACAUCGUCCGGG UCCCAGGG | 7740 |
| 1828 | CUGGGAGU G CUGCCUC | 6016 | GAGGGCAG GGAGGAAACUCC CU UCAAGGACAUCGUCCGGG ACUCCCAG | 7741 |
| 1831 | GGAGUGCU G CCCUCUUA | 6017 | UAAGAGGG GGAGGAAACUCC CU UCAAGGACAUCGUCCGGG AGCACUCC | 7742 |
| 1844 | CUUACCAU G CACACGGG | 6018 | CCCGUGUG GGAGGAAACUCC CU UCAAGGACAUCGUCCGGG AUGGUAAG | 7743 |
| 1850 | AUGCACAC G GGUGCUCU | 7130 | AGAGCACC GGAGGAAACUCC CU UCAAGGACAUCGUCCGGG GUGUGCAU | 7744 |
| 1851 | UGCACACG G GUGCUCUC | 7131 | GAGAGCAC GGAGGAAACUCC CU UCAAGGACAUCGUCCGGG CGUGUGCA | 7745 |
| 1852 | GCACACGG G UGCUCUCC | 6019 | GGAGAGCA GGAGGAAACUCC CU UCAAGGACAUCGUCCGGG CCGUGUGC | 7746 |
| 1854 | ACACGGGU G CUCUCCUU | 6020 | AAGGAGAG GGAGGAAACUCC CU UCAAGGACAUCGUCCGGG ACCCGUGU | 7747 |
| 1865 | CUCCUUUU G GCUGCAU | 7132 | AUGCAGCC GGAGGAAACUCC CU UCAAGGACAUCGUCCGGG AAAAGGAG | 7748 |
| 1866 | UCCUUUUG G CUGCAUG | 7133 | CAUGCAGC GGAGGAAACUCC CU UCAAGGACAUCGUCCGGG CAAAAGGA | 7749 |
| 1867 | CCUUUUGG G CUGCAUGC | 6021 | GCAUGCAG GGAGGAAACUCC CU UCAAGGACAUCGUCCGGG CCAAAAGG | 7750 |
| 1870 | UUGGGCU G CAUGCUAU | 6022 | AUAGCAUG GGAGGAAACUCC CU UCAAGGACAUCGUCCGGG AGCCCAAA | 7751 |
| 1874 | GGCUGCAU G CUAUUCCA | 6023 | UGGAAUAG GGAGGAAACUCC CU UCAAGGACAUCGUCCGGG AUGCAGCC | 7752 |
| 1887 | UCCAUUUU G CAGCCAGA | 6024 | UCUGGCUG GGAGGAAACUCC CU UCAAGGACAUCGUCCGGG AAAAUGGA | 7753 |
| 1890 | AUUUUGCA G CCAGACCG | 6025 | CGGUCUGG GGAGGAAACUCC CU UCAAGGACAUCGUCCGGG UGCAAAAU | 7754 |
| 1894 | UGCAGCCA G ACCGAUGU | 7134 | ACAUCGGU GGAGGAAACUCC CU UCAAGGACAUCGUCCGGG UGGCUGCA | 7755 |
| 1898 | GCCAGACC G AUGUAUU | 7135 | AUACACAU GGAGGAAACUCC CU UCAAGGACAUCGUCCGGG GGUCUGGC | 7756 |
| 1901 | AGACCGAU G UAUUUA | 6026 | UAAAUACA GGAGGAAACUCC CU UCAAGGACAUCGUCCGGG AUCGGUCU | 7757 |
| 1903 | ACCGAUGU G UAUUUAAC | 6027 | GUUAAAUA GGAGGAAACUCC CU UCAAGGACAUCGUCCGGG ACAUCGGU | 7758 |
| 1914 | UUUAACCA G UCACUAUU | 6028 | AAUAGUGA GGAGGAAACUCC CU UCAAGGACAUCGUCCGGG UGGUUAAA | 7759 |
| 1923 | UCACUAUU G AUGGACAU | 7136 | AUGUCCAU GGAGGAAACUCC CU UCAAGGACAUCGUCCGGG AAUAGUGA | 7760 |
| 1926 | CUAUUGAU G GACAUUUG | 7137 | CAAAUGUC GGAGGAAACUCC CU UCAAGGACAUCGUCCGGG AUCAAUAG | 7761 |
| 1927 | UAUUGAUG G ACAUUUGG | 7138 | CCAAAUGU GGAGGAAACUCC CU UCAAGGACAUCGUCCGGG CAUCAAUA | 7762 |
| 1934 | GGACAUUU G GUUGUUU | 7139 | AAACAACC GGAGGAAACUCC CU UCAAGGACAUCGUCCGGG AAAUGUCC | 7763 |
| 1935 | GACAUUUG G UUGUUUC | 7140 | GAAACAAC GGAGGAAACUCC CU UCAAGGACAUCGUCCGGG CAAAUGUC | 7764 |
| 1936 | ACAUUUGG G UUGUUUCC | 6029 | GGAAACAA GGAGGAAACUCC CU UCAAGGACAUCGUCCGGG CCAAAUGU | 7765 |

TABLE VII-continued

Human IKK-gamma Amberzyme and Substrate Sequence

| Pos | Substrate | Seq ID | Amberzyme | Seq ID |
|-----|-----------|--------|-----------|--------|
| 1939 | UUUGGGUU G UUUCCCAU | 6030 | AUGGGAAA GGAGGAAACUCC CU UCAAGGACAUCGUCCGGG AACCCAAA | 7766 |
| 1954 | AUCUUUUU G UUACCAUA | 6031 | UAUGGUAA GGAGGAAACUCC CU UCAAGGACAUCGUCCGGG AAAAAGAU | 7767 |
| 1969 | UAAAUAAU G GCAUAGUA | 7141 | UACUAUGC GGAGGAAACUCC CU UCAAGGACAUCGUCCGGG AUUAUUUA | 7768 |
| 1970 | AAAUAAUG G CAUAGUAA | 6032 | UUACUAUG GGAGGAAACUCC CU UCAAGGACAUCGUCCGGG CAUUAUUU | 7769 |
| 1975 | AUGGCAUA G UAAAAAAA | 6033 | UUUUUUUA GGAGGAAACUCC CU UCAAGGACAUCGUCCGGG UAUGCCAU | 7770 |

Input Sequence = NM_003639. Cut Site = G/.
Arm Length = 8. Core Sequence = GGAGGAAACUCC CU UCAAGGACAUCGUCCGGG NM_003639 (*Homo sapiens* inhibitor of kappa light polypeptide gene enhancer in B-cells, kin (IKBKG), mRNA.; 1994 bp)

TABLE VIII

Human PKR Hammerhead and Substrate Sequence

| Pos | Substrate | Seq ID | Hammerhead | Seq ID |
|-----|-----------|--------|------------|--------|
| 20 | GGCGCAGU U UGCUCAUA | 1 | UAUGAGCA CUGAUGAGGCCGUUAGGCCGAA ACUGCGCC | 632 |
| 21 | GCGCAGUU U GCUCAUAC | 2 | GUAUGAGC CUGAUGAGGCCGUUAGGCCGAA AACUGCGC | 633 |
| 25 | AGUUUGCU C AUACUUUG | 3 | CAAAGUAU CUGAUGAGGCCGUUAGGCCGAA AGCAAACU | 634 |
| 28 | UUGCUCAU A CUUUGUGA | 4 | UCACAAAG CUGAUGAGGCCGUUAGGCCGAA AUGAGCAA | 635 |
| 31 | CUCAUACU U UGUGACUU | 5 | AAGUCACA CUGAUGAGGCCGUUAGGCCGAA AGUAUGAG | 636 |
| 32 | UCAUACUU U GUGACUUG | 6 | CAAGUCAC CUGAUGAGGCCGUUAGGCCGAA AAGUAUGA | 637 |
| 39 | UUGUGACU U GCGGUCAC | 7 | GUGACCGC CUGAUGAGGCCGUUAGGCCGAA AGUCACAA | 638 |
| 45 | CUUGCGGU C ACAGUGGC | 8 | GCCACUGU CUGAUGAGGCCGUUAGGCCGAA ACCGCAAG | 639 |
| 56 | AGUGGCAU U CAGCUCCA | 9 | UGGAGCUG CUGAUGAGGCCGUUAGGCCGAA AUGCCACU | 640 |
| 57 | GUGGCAUU C AGCUCCAC | 10 | GUGGAGCU CUGAUGAGGCCGUUAGGCCGAA AAUGCCAC | 641 |
| 62 | AUUCAGCU C CACACUUG | 11 | CAAGUGUG CUGAUGAGGCCGUUAGGCCGAA AGCUGAAU | 642 |
| 69 | UCCACACU U GGUAGAAC | 12 | GUUCUACC CUGAUGAGGCCGUUAGGCCGAA AGUGUGGA | 643 |
| 73 | CACUUGGU A GAACCACA | 13 | UGUGGUUC CUGAUGAGGCCGUUAGGCCGAA ACCAAGUG | 644 |
| 96 | ACAAGCAU A GAAACAUC | 14 | GAUGUUUC CUGAUGAGGCCGUUAGGCCGAA AUGCUUGU | 645 |
| 104 | AGAAACAU C CUAAACAA | 15 | UUGUUUAG CUGAUGAGGCCGUUAGGCCGAA AUGUUUCU | 646 |
| 107 | AACAUCCU A AACAAUCU | 16 | AGAUUGUU CUGAUGAGGCCGUUAGGCCGAA AGGAUGUU | 647 |
| 114 | UAAACAAU C UUCAUCGA | 17 | UCGAUGAA CUGAUGAGGCCGUUAGGCCGAA AUUGUUUA | 648 |
| 116 | AACAAUCU U CAUCGAGG | 18 | CCUCGAUG CUGAUGAGGCCGUUAGGCCGAA AGAUUGUU | 649 |
| 117 | ACAAUCUU C AUCGAGGC | 19 | GCCUCGAU CUGAUGAGGCCGUUAGGCCGAA AAGAUUGU | 650 |
| 120 | AUCUUCAU C GAGGCAUC | 20 | GAUGCCUC CUGAUGAGGCCGUUAGGCCGAA AUGAAGAU | 651 |
| 128 | CGAGGCAU C GAGGUCCA | 21 | UGGACCUC CUGAUGAGGCCGUUAGGCCGAA AUGCCUCG | 652 |
| 134 | AUCGAGGU C CAUCCCAA | 22 | UUGGGAUG CUGAUGAGGCCGUUAGGCCGAA ACCUCGAU | 653 |
| 138 | AGGUCCAU C CCAAUAAA | 23 | UUUAUUGG CUGAUGAGGCCGUUAGGCCGAA AUGGACCU | 654 |
| 144 | AUCCCAAU A AAAUCAG | 24 | CUGAUUUU CUGAUGAGGCCGUUAGGCCGAA AUUGGGAU | 655 |
| 150 | AUAAAAAU C AGGAGACC | 25 | GGUCUCCU CUGAUGAGGCCGUUAGGCCGAA AUUUUUAU | 656 |
| 165 | CCCUGGCU A UCAUAGAC | 26 | GUCUAUGA CUGAUGAGGCCGUUAGGCCGAA AGCCAGGG | 657 |
| 167 | CUGGCUAU C AUAGACCU | 27 | AGGUCUAU CUGAUGAGGCCGUUAGGCCGAA AUAGCCAG | 658 |
| 170 | GCUAUCAU A GACCUUAG | 28 | CUAAGGUC CUGAUGAGGCCGUUAGGCCGAA AUGAUAGC | 659 |
| 176 | AUAGACCU U AGUCUUCG | 29 | CGAAGACU CUGAUGAGGCCGUUAGGCCGAA AGGUCUAU | 660 |
| 177 | UAGACCUU A GUCUUCGC | 30 | GCGAAGAC CUGAUGAGGCCGUUAGGCCGAA AAGGUCUA | 661 |
| 180 | ACCUUAGU C UUCGCUGG | 31 | CCAGCGAA CUGAUGAGGCCGUUAGGCCGAA ACUAAGGU | 662 |
| 182 | CUUAGUCU U CGCUGGUA | 32 | UACCAGCG CUGAUGAGGCCGUUAGGCCGAA AGACUAAG | 663 |
| 183 | UUAGUCUU C GCUGGUAU | 33 | AUACCAGC CUGAUGAGGCCGUUAGGCCGAA AAGACUAA | 664 |
| 190 | UCGCUGGU A UACUCGCU | 34 | AGCGAGUA CUGAUGAGGCCGUUAGGCCGAA ACCAGCGA | 665 |
| 192 | GCUGGUAU A CUCGCUGU | 35 | ACAGCGAG CUGAUGAGGCCGUUAGGCCGAA AUACCAGC | 666 |
| 195 | GGUAUACU C GCUGCUG | 36 | CAGACAGC CUGAUGAGGCCGUUAGGCCGAA AGUAUACC | 667 |
| 201 | CUCGCUGU C UGUCAACC | 37 | GGUUGACA CUGAUGAGGCCGUUAGGCCGAA ACAGCGAG | 668 |
| 205 | CUGUCUGU C AACCAGCG | 38 | CGCUGGUU CUGAUGAGGCCGUUAGGCCGAA ACAGACAG | 669 |
| 216 | CCAGCGGU U GACUUUUU | 39 | AAAAAGUC CUGAUGAGGCCGUUAGGCCGAA ACCGCUGG | 670 |
| 221 | GGUUGACU U UUUUAAG | 40 | CUUAAAAA CUGAUGAGGCCGUUAGGCCGAA AGUCAACC | 671 |
| 222 | GUUGACUU U UUUAAGC | 41 | GCUUAAAA CUGAUGAGGCCGUUAGGCCGAA AAGUCAAC | 672 |
| 223 | UUGACUUU U UUAAGCC | 42 | GGCUUAAA CUGAUGAGGCCGUUAGGCCGAA AAAGUCAA | 673 |
| 224 | UGACUUUU U UAAGCCU | 43 | AGGCUUAA CUGAUGAGGCCGUUAGGCCGAA AAAAGUCA | 674 |
| 225 | GACUUUUU U AAGCCUU | 44 | AAGGCUUA CUGAUGAGGCCGUUAGGCCGAA AAAAAGUC | 675 |
| 226 | ACUUUUUU U AAGCCUUC | 45 | GAAGGCUU CUGAUGAGGCCGUUAGGCCGAA AAAAAAGU | 676 |
| 227 | CUUUUUUU A AGCCUUCU | 46 | AGAAGGCU CUGAUGAGGCCGUUAGGCCGAA AAAAAAAG | 677 |
| 233 | UUAAGCCU U CUUUUUUC | 47 | GAAAAAAG CUGAUGAGGCCGUUAGGCCGAA AGGCUUAA | 678 |
| 234 | UAAGCCUU C UUUUUUCU | 48 | AGAAAAAA CUGAUGAGGCCGUUAGGCCGAA AAGGCUUA | 679 |
| 236 | AGCCUUCU U UUUUCUCU | 49 | AGAGAAAA CUGAUGAGGCCGUUAGGCCGAA AGAAc3GCU | 680 |
| 237 | GCCUUCUU U UUUCUCUU | 50 | AAGAGAAA CUGAUGAGGCCGUUAGGCCGAA AAGAAGGC | 681 |
| 238 | CCUUCUUU U UUCUCUUU | 51 | AAAGAGAA CUGAUGAGGCCGUUAGGCCGAA AAAGAAGG | 682 |
| 239 | CUUCUUUU U UCUCUUUU | 52 | AAAAGAGA CUGAUGAGGCCGUUAGGCCGAA AAAAGAAG | 683 |
| 240 | UUCUUUUU U CUCUUUUA | 53 | UAAAAGAG CUGAUGAGGCCGUUAGGCCGAA AAAAAGAA | 684 |
| 241 | UCUUUUUU C UCUUUUAC | 54 | GUAAAAGA CUGAUGAGGCCGUUAGGCCGAA AAAAAGAA | 685 |
| 243 | UUUUUUCU C UUUUACCA | 55 | UGGUAAAA CUGAUGAGGCCGUUAGGCCGAA AGAAAAAA | 686 |
| 245 | UUUUCUCU U UUACCAGU | 56 | ACUGGUAA CUGAUGAGGCCGUUAGGCCGAA AGAGAAAA | 687 |
| 246 | UUUCUCUU U UACCAGUU | 57 | AACUGGUA CUGAUGAGGCCGUUAGGCCGAA AAGAGAAA | 688 |

TABLE VIII-continued

Human PKR Hammerhead and Substrate Sequence

| Pos | Substrate | Seq ID | Hammerhead | Seq ID |
|---|---|---|---|---|
| 247 | UUCUCUUU U ACCAGUUU | 58 | AAACUGGU CUGAUGAGGCCGUUAGGCCGAA AAAGAGAA | 689 |
| 248 | UCUCUUUU A CCAGUUUC | 59 | GAAACUGG CUGAUGAGGCCGUUAGGCCGAA AAAAGAGA | 690 |
| 254 | UUACCAGU U UCUGGAGC | 60 | GCUCCAGA CUGAUGAGGCCGUUAGGCCGAA ACUGGUAA | 691 |
| 255 | UACCAGUU C CUGGAGCA | 61 | UGCUCCAG CUGAUGAGGCCGUUAGGCCGAA AACUGGUA | 692 |
| 256 | ACCAGUUU C UGGAGCAA | 62 | UUGCUCCA CUGAUGAGGCCGUUAGGCCGAA AAACUGGU | 693 |
| 267 | GAGCAAAU U CAGUUUGC | 63 | GCAAACUG CUGAUGAGGCCGUUAGGCCGAA AUUUGCUC | 694 |
| 268 | AGCAAAUU C AGUUUGCC | 64 | GGCAAACU CUGAUGAGGCCGUUAGGCCGAA AAUUUGCU | 695 |
| 272 | AAUUCAGU U UGCCUUCC | 65 | GGAAGGCA CUGAUGAGGCCGUUAGGCCGAA ACUGAAUU | 696 |
| 273 | AUUCAGUU U GCCUUCCU | 66 | AGGAAGGC CUGAUGAGGCCGUUAGGCCGAA AACUGAAU | 697 |
| 278 | GUUUGCCU U CCUGGAUU | 67 | AAUCCAGG CUGAUGAGGCCGUUAGGCCGAA AGGCAAAC | 698 |
| 279 | UUUGCCUU C CUGGAUUU | 68 | AAAUCCAG CUGAUGAGGCCGUUAGGCCGAA AAGGCAAA | 699 |
| 286 | UCCUGGAU U UGUAAAUU | 69 | AAUUUACA CUGAUGAGGCCGUUAGGCCGAA AUCCAGGA | 700 |
| 287 | CCUGGAUU U GUAAAUUG | 70 | CAAUUUAC CUGAUGAGGCCGUUAGGCCGAA AAUCCAGG | 701 |
| 290 | GGAUUUGU A AAUUGUAA | 71 | UUACAAUU CUGAUGAGGCCGUUAGGCCGAA ACAAAUCC | 702 |
| 294 | UUGUAAAU U GUAAUGAC | 72 | GUCAUUAC CUGAUGAGGCCGUUAGGCCGAA AUUUACAA | 703 |
| 297 | UAAAUUGU A AUGACCUC | 73 | GAGGUCAU CUGAUGAGGCCGUUAGGCCGAA ACAAUUUA | 704 |
| 305 | AAUGACCU C AAAACUUU | 74 | AAAGUUUU CUGAUGAGGCCGUUAGGCCGAA AGGUCAUU | 705 |
| 312 | UCAAAACU U UAGCAGUU | 75 | AACUGCUA CUGAUGAGGCCGUUAGGCCGAA AGUUUUGA | 706 |
| 313 | CAAAACUU U AGCAGUUC | 76 | GAACUGCU CUGAUGAGGCCGUUAGGCCGAA AAGUUUUG | 707 |
| 314 | AAAACUUU A GCAGUUCU | 77 | AGAACUGC CUGAUGAGGCCGUUAGGCCGAA AAAGUUUU | 708 |
| 320 | UUAGCAGU U CUUCCAUC | 78 | GAUGGAAG CUGAUGAGGCCGUUAGGCCGAA ACUGCUAA | 709 |
| 321 | UAGCAGUU C UUCCAUCU | 79 | AGAUGGAA CUGAUGAGGCCGUUAGGCCGAA AACUGCUA | 710 |
| 323 | GCAGUUCU U CCAUCUGA | 80 | UCAGAUGG CUGAUGAGGCCGUUAGGCCGAA AGAACUGC | 711 |
| 324 | CAGUUCUU C CAUCUGAC | 81 | GUCAGAUG CUGAUGAGGCCGUUAGGCCGAA AAGAACUG | 712 |
| 328 | UCUUCCAU C UGACUCUG | 82 | CUGAGUCA CUGAUGAGGCCGUUAGGCCGAA AUGGAAGA | 713 |
| 334 | AUCUGACU C AGGUUUGC | 83 | GCAAACCU CUGAUGAGGCCGUUAGGCCGAA AGUCAGAU | 714 |
| 339 | ACUCAGGU U UGCUUCUC | 84 | GAGAAGCA CUGAUGAGGCCGUUAGGCCGAA ACCUGAGU | 715 |
| 340 | CUCAGGUU U GCUUCUCU | 85 | AGAGAAGC CUGAUGAGGCCGUUAGGCCGAA AACCUGAG | 716 |
| 344 | GGUUUGCU U CUCUGGCG | 86 | CGCCAGAG CUGAUGAGGCCGUUAGGCCGAA AGCAAACC | 717 |
| 345 | GUUUGCUU C UCUGGCGG | 87 | CCGCCAGA CUGAUGAGGCCGUUAGGCCGAA AAGCAAAC | 718 |
| 347 | UUGCUUCU C UGGCGGUC | 88 | GACCGCCA CUGAUGAGGCCGUUAGGCCGAA AGAAGCAA | 719 |
| 355 | CUGGCGGU C UUCAGAAU | 89 | AUUCUGAA CUGAUGAGGCCGUUAGGCCGAA ACCGCCAG | 720 |
| 357 | GGCGGUCU U CAGAAUCA | 90 | UGAUUCUG CUGAUGAGGCCGUUAGGCCGAA AGACCGCC | 721 |
| 358 | GCGGUCUU C AGAAUCAA | 91 | UUGAUUCU CUGAUGAGGCCGUUAGGCCGAA AAGACCGC | 722 |
| 364 | UUCAGAAU C AACAUCCA | 92 | UGGAUGUU CUGAUGAGGCCGUUAGGCCGAA AUUCUGAA | 723 |
| 370 | AUCAACAU C CACACUUC | 93 | GAAGUGUG CUGAUGAGGCCGUUAGGCCGAA AUGUUGAU | 724 |
| 377 | UCCACACU U CCGUGAUU | 94 | AAUCACGG CUGAUGAGGCCGUUAGGCCGAA AGUGUGGA | 725 |
| 378 | CCACACUU C CGUGAUUA | 95 | UAAUCACG CUGAUGAGGCCGUUAGGCCGAA AAGUGUGG | 726 |
| 385 | UCCGUGAU U AUCUGCGU | 96 | ACGCAGAU CUGAUGAGGCCGUUAGGCCGAA AUCACGGA | 727 |
| 386 | CCGUGAUU A UCUGCGUG | 97 | CACGCAGA CUGAUGAGGCCGUUAGGCCGAA AAUCACGG | 728 |
| 388 | GUGAUUAU C UGCGUGCA | 98 | UGCACGCA CUGAUGAGGCCGUUAGGCCGAA AUAAUCAC | 729 |
| 398 | GCGUGCAU U UGGACAAA | 99 | UUUGUCCA CUGAUGAGGCCGUUAGGCCGAA AUGCACGC | 730 |
| 399 | CGUGCAUU U GGACAAAG | 100 | UUUUGUCC CUGAUGAGGCCGUUAGGCCGAA AAUGCACG | 731 |
| 400 | GUGCAUUU U GGACAAAG | 101 | CUUUGUCC CUGAUGAGGCCGUUAGGCCGAA AAAAUGCAC | 732 |
| 411 | ACAAAGCU U CCAACCAG | 102 | CUGGUUGG CUGAUGAGGCCGUUAGGCCGAA AGCUUUGU | 733 |
| 412 | CAAAGCUU C CAACCAGG | 103 | CCUGGUUG CUGAUGAGGCCGUUAGGCCGAA AAGCUUUG | 734 |
| 423 | ACCAGGAU A CGGAAGAA | 104 | UCUUCCCG CUGAUGAGGCCGUUAGGCCGAA AUCCUGGU | 735 |
| 448 | CUGGUGAU C UUUCAGCA | 105 | UGCUGAAA CUGAUGAGGCCGUUAGGCCGAA AUCACCAG | 736 |
| 450 | GGUGAUCU U UCAGCAGG | 106 | CCUGCUGA CUGAUGAGGCCGUUAGGCCGAA AGAUCACC | 737 |
| 451 | GUGAUCUU U CAGCAGGU | 107 | ACCUGCUG CUGAUGAGGCCGUUAGGCCGAA AAGAUCAC | 738 |
| 452 | UGAUCUUU C AGCAGGUU | 108 | AACCUGCU CUGAUGAGGCCGUUAGGCCGAA AAAGAUCA | 739 |
| 460 | CAGCAGGU U UCUUCAUG | 109 | CAUGAAGA CUGAUGAGGCCGUUAGGCCGAA ACCUGCUG | 740 |
| 461 | AGCAGGUU U CUUCAUGG | 110 | CCAUGAAG CUGAUGAGGCCGUUAGGCCGAA AACCUGCU | 741 |
| 462 | GCAGGUUU C UUCAUGGA | 111 | UCCAUGAA CUGAUGAGGCCGUUAGGCCGAA AAACCUGC | 742 |
| 464 | AGGUUUCU U CAUGGAGG | 112 | CCUCCAUG CUGAUGAGGCCGUUAGGCCGAA AGAAACCU | 743 |
| 465 | GGUUUCUU C AUGGAGGA | 113 | UCCUCCAU CUGAUGAGGCCGUUAGGCCGAA AAGAAACC | 744 |
| 477 | GAGGAACU U AAUACAUA | 114 | UAUGUAUU CUGAUGAGGCCGUUAGGCCGAA AGUUCCUC | 745 |
| 478 | AGGAACUU A AUACAUAC | 115 | GUAUGUAU CUGAUGAGGCCGUUAGGCCGAA AAGUUCCU | 746 |
| 481 | AACUUAAU A CAUACCGU | 116 | ACGGUAUG CUGAUGAGGCCGUUAGGCCGAA AUUAAGUU | 747 |
| 485 | UAAUACAU A CCGUCAGA | 117 | UCUGACGG CUGAUGAGGCCGUUAGGCCGAA AUGUAUUA | 748 |
| 490 | CAUACCGU C AGAAGCAG | 118 | CUGCUUCU CUGAUGAGGCCGUUAGGCCGAA ACGCUAUG | 749 |
| 504 | CAGGGAGU A GUCUUAA | 119 | UUAAGUAC CUGAUGAGGCCGUUAGGCCGAA ACUCCCUG | 750 |
| 507 | GGAGUAGU A CUUAAAUA | 120 | UAUUUAAG CUGAUGAGGCCGUUAGGCCGAA ACUACUCC | 751 |
| 510 | GUAGUACU U AAAUAUCA | 121 | UGAUAUUU CUGAUGAGGCCGUUAGGCCGAA AGUACUAC | 752 |
| 511 | UAGUACUU A AAUAUCAA | 122 | UUGAUAUU CUGAUGAGGCCGUUAGGCCGAA AAGUACUA | 753 |
| 515 | ACUUAAAU A UCAAGAAC | 123 | GUUCUUGA CUGAUGAGGCCGUUAGGCCGAA AUUUAAGU | 754 |
| 517 | UUAAAUAU C AAGAACUG | 124 | CAGUUCUU CUGAUGAGGCCGUUAGGCCGAA AUAUUUAA | 755 |
| 529 | AACUGCCU A AUUCAGGA | 125 | UCCUGAAU CUGAUGAGGCCGUUAGGCCGAA AGGCAGUU | 756 |
| 532 | UGCCUAAU U CAGGACCU | 126 | AGGUCCUG CUGAUGAGGCCGUUAGGCCGAA AUUAGGCA | 757 |
| 533 | GCCUAAUU C AGGACCUC | 127 | GAGGUCCU CUGAUGAGGCCGUUAGGCCGAA AAUUAGGC | 758 |
| 541 | CAGGACCU C CACAUGAU | 128 | AUCAUGUG CUGAUGAGGCCGUUAGGCCGAA AGGUCCUG | 759 |
| 550 | CACAUGAU A GGAGGUUU | 129 | AAACCUCC CUGAUGAGGCCGUUAGGCCGAA AUCAUGUG | 760 |
| 557 | UAGGAGGU U UACAUUUC | 130 | GAAAUGUA CUGAUGAGGCCGUUAGGCCGAA ACCUCCUA | 761 |
| 558 | AGGAGGUU U ACAUUUCA | 131 | UGAAAUGU CUGAUGAGGCCGUUAGGCCGAA AACCUCCU | 762 |
| 559 | GGAGGUUU A CAUUUCAA | 132 | UUGAAAUG CUGAUGAGGCCGUUAGGCCGAA AAACCUCC | 763 |

TABLE VIII-continued

Human PKR Hammerhead and Substrate Sequence

| Pos | Substrate | Seq ID | Hammerhead | Seq ID |
|---|---|---|---|---|
| 563 | GUUUACAU U UCAAGUUA | 133 | UAACUUGA CUGAUGAGGCCGUUAGGCCGAA AUGUAAAC | 764 |
| 564 | UUUACAUU U CAAGUUAU | 134 | AUAACUUG CUGAUGAGGCCGUUAGGCCGAA AAUGUAAA | 765 |
| 565 | UUACAUUU C AAGUUAUA | 135 | UAUAACUU CUGAUGAGGCCGUUAGGCCGAA AAAUGUAA | 766 |
| 570 | UUUCAAGU U AUAAUAGA | 136 | UCUAUUAU CUGAUGAGGCCGUUAGGCCGAA ACUUGAAA | 767 |
| 571 | UUCAAGUU A UAAUAGAU | 137 | AUCUAUUA CUGAUGAGGCCGUUAGGCCGAA AACUUGAA | 768 |
| 573 | CAAGUUAU A AUAGAUGG | 138 | CCAUCUAU CUGAUGAGGCCGUUAGGCCGAA AUAACUUG | 769 |
| 576 | GUUAUAAU A GAUGGAAG | 139 | CUUCCAUC CUGAUGAGGCCGUUAGGCCGAA AUUAUAAC | 770 |
| 590 | AAGAGAAU U UCCAGAAG | 140 | CUUCUGGA CUGAUGAGGCCGUUAGGCCGAA AUUCUCUU | 771 |
| 591 | AGAGAAUU U CCAGAAGG | 141 | CCUUCUGG CUGAUGAGGCCGUUAGGCCGAA AAUUCUCU | 772 |
| 592 | GAGAAUUU C CAGAAGGU | 142 | ACCUUCUG CUGAUGAGGCCGUUAGGCCGAA AAAUUCUC | 773 |
| 607 | GUGAAGGU A GAUCAAAG | 143 | CUUUGAUC CUGAUGAGGCCGUUAGGCCGAA ACCUUCAC | 774 |
| 611 | AGGUAGAU C AAAGAAGG | 144 | CCUUCUUU CUGAUGAGGCCGUUAGGCCGAA AUCUACCU | 775 |
| 644 | AGCCAAAU U AGCUGUUG | 145 | CAACAGCU CUGAUGAGGCCGUUAGGCCGAA AUUUGGCU | 776 |
| 645 | GCCAAAUU A GCUGUUGA | 146 | UCAACAGC CUGAUGAGGCCGUUAGGCCGAA AAUUUGGC | 777 |
| 651 | UUAGCUGU U GAGAUACU | 147 | AGUAUCUC CUGAUGAGGCCGUUAGGCCGAA ACAGCUAA | 778 |
| 657 | GUUGAGAU A CUUAAUAA | 148 | UUAUUAAG CUGAUGAGGCCGUUAGGCCGAA AUCUCAAC | 779 |
| 660 | GAGAUACU U AAUAAGGA | 149 | UCCUUAUU CUGAUGAGGCCGUUAGGCCGAA AGUAUCUC | 780 |
| 661 | AGAUACUU A AUAAGGAA | 150 | UUCCUUAU CUGAUGAGGCCGUUAGGCCGAA AAGUAUCU | 781 |
| 664 | UACUUAAU A AGGAAAAG | 151 | CUUUUCCU CUGAUGAGGCCGUUAGGCCGAA AUUAAGUA | 782 |
| 681 | AAGGCAGU U AGUCCUUU | 152 | AAAGGACU CUGAUGAGGCCGUUAGGCCGAA ACUGCCUU | 783 |
| 682 | AGGCAGUU A GUCCUUUA | 153 | UAAAGGAC CUGAUGAGGCCGUUAGGCCGAA AACUGCCU | 784 |
| 685 | CAGUUAGU C CUUUAUUA | 154 | UAAUAAAG CUGAUGAGGCCGUUAGGCCGAA ACUAACUG | 785 |
| 688 | UUAGUCCU U UAUUAUUG | 155 | CAAUAAUA CUGAUGAGGCCGUUAGGCCGAA AGGACUAA | 786 |
| 689 | UAGUCCUU U AUUAUUGA | 156 | UCAAUAAU CUGAUGAGGCCGUUAGGCCGAA AAGGACUA | 787 |
| 690 | AGUCCUUU A UUAUUGAC | 157 | GUCAAUAA CUGAUGAGGCCGUUAGGCCGAA AAAGGACU | 788 |
| 692 | UCCUUUAU U AUUGACAA | 158 | UUGUCAAU CUGAUGAGGCCGUUAGGCCGAA AUAAAGGA | 789 |
| 693 | CCUUUAUU A UUGACAAC | 159 | GUUGUCAA CUGAUGAGGCCGUUAGGCCGAA AAUAAAGG | 790 |
| 695 | UUUAUUAU U GACAACAA | 160 | UUGUUGUC CUGAUGAGGCCGUUAGGCCGAA AUAAUAAA | 791 |
| 709 | CAACGAUU C UUCAGAA | 161 | UUCUGAAG CUGAUGAGGCCGUUAGGCCGAA AUUCGUUG | 792 |
| 710 | AACGAUUC U UCAGAAG | 162 | CUUCUGAA CUGAUGAGGCCGUUAGGCCGAA AAUUCGUU | 793 |
| 712 | CGAUUCU U CAGAAGGA | 163 | UCCUUCUG CUGAUGAGGCCGUUAGGCCGAA AGAAUUCG | 794 |
| 713 | GAAUUCUC C AGAAGGAU | 164 | AUCCUUCU CUGAUGAGGCCGUUAGGCCGAA AAGAAUUC | 795 |
| 722 | AGAAGGAU U AUCCAUGG | 165 | CCAUGGAU CUGAUGAGGCCGUUAGGCCGAA AUCCUUCU | 796 |
| 723 | GAAGGAUU A UCCAUGGG | 166 | CCCAUGGA CUGAUGAGGCCGUUAGGCCGAA AAUCCUUC | 797 |
| 725 | AGGAUUAU C CAUGGGA | 167 | UCCCCAUG CUGAUGAGGCCGUUAGGCCGAA AUAAUCCU | 798 |
| 736 | UGGGGAAU U ACAUAGUC | 168 | GCCAUGU CUGAUGAGGCCGUUAGGCCGAA AUUCCCCA | 799 |
| 737 | GGGGAAUU A CAUAGGCC | 169 | GGCCUAUG CUGAUGAGGCCGUUAGGCCGAA AAUUCCCC | 800 |
| 741 | AAUUACAU A GGCCUUAU | 170 | AUAAGGCC CUGAUGAGGCCGUUAGGCCGAA AUGUAAUU | 801 |
| 747 | AUAGGCCU U AUCAAUAG | 171 | CUAUUGAU CUGAUGAGGCCGUUAGGCCGAA AGGCCUAU | 802 |
| 748 | UAGGCCUU A UCAAUAGA | 172 | UCUAUUGA CUGAUGAGGCCGUUAGGCCGAA AAGGCCUA | 803 |
| 750 | GGCCUUAU C AAUAGAAU | 173 | AUUCUAUU CUGAUGAGGCCGUUAGGCCGAA AUAAGGCC | 804 |
| 754 | UUAUCAAU A GAAUUGCC | 174 | GGCAAUUC CUGAUGAGGCCGUUAGGCCGAA AUUGAUAA | 805 |
| 759 | AAUAGAAU U GCCAGAA | 175 | UUCUGGGC CUGAUGAGGCCGUUAGGCCGAA AUUCUAUU | 806 |
| 777 | AAAAGACU A ACUGUAAA | 176 | UUUACAGU CUGAUGAGGCCGUUAGGCCGAA AGUCUUUU | 807 |
| 783 | CUAACUGU A AAUAUGA | 177 | UCAUAAUU CUGAUGAGGCCGUUAGGCCGAA ACAGUUAG | 808 |
| 787 | CUGUAAAU U AUGAACAG | 178 | CUGUUCAU CUGAUGAGGCCGUUAGGCCGAA AUUUACAG | 809 |
| 788 | UGUAAAUU A UGAACAGU | 179 | ACUGUUCA CUGAUGAGGCCGUUAGGCCGAA AAUUUACA | 810 |
| 803 | GUGUGCAU C GGGGGUGC | 180 | GCACCCCC CUGAUGAGGCCGUUAGGCCGAA AUGCACAC | 811 |
| 827 | AGAAGGAU U UCAUUAUA | 181 | UAUAAUGA CUGAUGAGGCCGUUAGGCCGAA AUCCUUCU | 812 |
| 828 | GAAGGAUU U CAUUAUAA | 182 | UUAUAAUG CUGAUGAGGCCGUUAGGCCGAA AAUCCUUC | 813 |
| 829 | AAGGAUUU C AUUAUAAA | 183 | UUUAUAAU CUGAUGAGGCCGUUAGGCCGAA AAAUCCUU | 814 |
| 832 | GAUUUCAU U AUAAAUGC | 184 | GCAUUUAU CUGAUGAGGCCGUUAGGCCGAA AUGAAAUC | 815 |
| 833 | AUUUCAUU A UAAAUGCA | 185 | UGCAUUUA CUGAUGAGGCCGUUAGGCCGAA AAUGAAAU | 816 |
| 835 | UUCAUUAU A AAUGCAAA | 186 | UUUGCAUU CUGAUGAGGCCGUUAGGCCGAA AUAAUGAA | 817 |
| 860 | GAAAGAAU A UAGUAUUG | 187 | CAAUACUA CUGAUGAGGCCGUUAGGCCGAA AUUCUUUC | 818 |
| 862 | AAGAGAUA U AGUAUUGGU | 188 | ACCAAUAC CUGAUGAGGCCGUUAGGCCGAA AUAUUCUU | 819 |
| 865 | AAUAUAGU A UUGGUACA | 189 | UGUACCAA CUGAUGAGGCCGUUAGGCCGAA ACUAUAUU | 820 |
| 867 | UAUAGUAU U GGUACAGG | 190 | CCUGUACC CUGAUGAGGCCGUUAGGCCGAA AUACUAUA | 821 |
| 871 | GUAUUGGU A CAGGUUCU | 191 | AGAACCUG CUGAUGAGGCCGUUAGGCCGAA ACCAAUAC | 822 |
| 877 | GUACAGGU U CUACUAAA | 192 | UUUAGUAG CUGAUGAGGCCGUUAGGCCGAA ACCUGUAC | 823 |
| 878 | UACAGGUU C UACUAAAC | 193 | GUUUAGUA CUGAUGAGGCCGUUAGGCCGAA AACCUGUA | 824 |
| 880 | CAGGUUCU A CUAAACAG | 194 | CUGUUUAG CUGAUGAGGCCGUUAGGCCGAA AGAACCUG | 825 |
| 883 | GUUCUACU A AACAGGAA | 195 | UUCCUGUU CUGAUGAGGCCGUUAGGCCGAA AGUAGAAC | 826 |
| 902 | AAAACGCU U GGCCGCUA | 196 | UAGCGGCC CUGAUGAGGCCGUUAGGCCGAA AUUGUUUU | 827 |
| 910 | UGGCCGCU A AACUUGCA | 197 | UGCAAGUU CUGAUGAGGCCGUUAGGCCGAA AGCGGCCA | 828 |
| 915 | GCUAAACU U GCAUAUCU | 198 | AGAUAUGC CUGAUGAGGCCGUUAGGCCGAA AGUUUAGC | 829 |
| 920 | ACUUGCAU A UCUUCAGA | 199 | UCUGAAGA CUGAUGAGGCCGUUAGGCCGAA AUGCAAGU | 830 |
| 922 | UUGCAUAU C UUCAGAUA | 200 | UAUCUGAA CUGAUGAGGCCGUUAGGCCGAA AUAUGCAA | 831 |
| 924 | GCAUAUCU U CAGAUAUU | 201 | AAUAUCUG CUGAUGAGGCCGUUAGGCCGAA AGAUAUGC | 832 |
| 925 | CAUAUCUU C AGAUAUUA | 202 | UAAUAUCU CUGAUGAGGCCGUUAGGCCGAA AAGAUAUG | 833 |
| 930 | CUUCAGAU A UUAUCAGA | 203 | UCUGAUAA CUGAUGAGGCCGUUAGGCCGAA AUCUGAAG | 834 |
| 932 | UCAGAUAU U AUCAGAAG | 204 | CUUCUGAU CUGAUGAGGCCGUUAGGCCGAA AUAUCUGA | 835 |
| 933 | CAGAUAUU A UCAGAAGA | 205 | UCUUCUGA CUGAUGAGGCCGUUAGGCCGAA AAUAUCUG | 836 |
| 935 | GAUAUUAU C AGAAGAAA | 206 | UUUCUUCU CUGAUGAGGCCGUUAGGCCGAA AUAAUAUC | 837 |
| 947 | AGAAACCU C AGUGAAAU | 207 | AUUUCACU CUGAUGAGGCCGUUAGGCCGAA AGGUUUCU | 838 |

TABLE VIII-continued

Human PKR Hammerhead and Substrate Sequence

| Pos | Substrate | Seq ID | Hammerhead | Seq ID |
|---|---|---|---|---|
| 956 | AGUGAAAU C UGACUACC | 208 | GGUAGUCA CUGAUGAGGCCGUUAGGCCGAA AUUUCACU | 839 |
| 962 | AUCUGACU A CCUGUCCU | 209 | AGGACAGG CUGAUGAGGCCGUUAGGCCGAA AGUCAGAU | 840 |
| 968 | CUACCUGU C CUCUGGUU | 210 | AACCAGAG CUGAUGAGGCCGUUAGGCCGAA ACAGGUAG | 841 |
| 971 | CCUGUCCU C UGGUUCUU | 211 | AAGAACCA CUGAUGAGGCCGUUAGGCCGAA AGGACAGG | 842 |
| 976 | CCUCUGGU U CUUUUGCU | 212 | AGCAAAAG CUGAUGAGGCCGUUAGGCCGAA ACCAGAGG | 843 |
| 977 | CUCUGGUU C UUUUGCUA | 213 | UAGCAAAA CUGAUGAGGCCGUUAGGCCGAA AACCAGAG | 844 |
| 979 | CUGGUUCU U UUGCUACU | 214 | AGUAGCAA CUGAUGAGGCCGUUAGGCCGAA AGAACCAG | 845 |
| 980 | UGGUUCUU U UGCUACUA | 215 | UAGUAGCA CUGAUGAGGCCGUUAGGCCGAA AAGAACCA | 846 |
| 981 | GGUUCUUU U GCUACUAC | 216 | GUAGUAGC CUGAUGAGGCCGUUAGGCCGAA AAAGAACC | 847 |
| 985 | CUUUUGCU A CUACGUGU | 217 | ACACGUAG CUGAUGAGGCCGUUAGGCCGAA AGCAAAAG | 848 |
| 988 | UUGCUACU A CGUGUGAG | 218 | CUCACACG CUGAUGAGGCCGUUAGGCCGAA AGUAGCAA | 849 |
| 998 | GUGUGAGU C CCAAAGCA | 219 | UGCUUUGG CUGAUGAGGCCGUUAGGCCGAA ACUCACAC | 850 |
| 1010 | AAGCAACU C UUUAGUGA | 220 | UCACUAAA CUGAUGAGGCCGUUAGGCCGAA AGUUGCUU | 851 |
| 1012 | GCAACUCU U UAGUGACC | 221 | GGUCACUA CUGAUGAGGCCGUUAGGCCGAA AGAGUUGC | 852 |
| 1013 | CAACUCUU U AGUGACCA | 222 | UGGUCACU CUGAUGAGGCCGUUAGGCCGAA AAGAGUUG | 853 |
| 1014 | AACUCUUU A GUGACCAG | 223 | CUGGUCAC CUGAUGAGGCCGUUAGGCCGAA AAAGAGUU | 854 |
| 1029 | AGCACACU C GCUUCUGA | 224 | UCAGAAGC CUGAUGAGGCCGUUAGGCCGAA AGUGUGCU | 855 |
| 1033 | CACUCGCU U CUGAAUCA | 225 | UGAUUCAG CUGAUGAGGCCGUUAGGCCGAA AGCGAGUG | 856 |
| 1034 | ACUCGCUU C UGAAUCAU | 226 | AUGAUUCA CUGAUGAGGCCGUUAGGCCGAA AAGCGAGU | 857 |
| 1040 | UUCUGAAU C AUCAUCUG | 227 | CAGAUGAU CUGAUGAGGCCGUUAGGCCGAA AUUCAGAA | 858 |
| 1043 | UGAAUCAU C AUCUGAAG | 228 | CUUCAGAU CUGAUGAGGCCGUUAGGCCGAA AUGAUUCA | 859 |
| 1046 | AUCAUCAU C UGAGGUG | 229 | CACCUUCA CUGAUGAGGCCGUUAGGCCGAA AUGAUGAU | 860 |
| 1058 | AGGUGACU U CUCAGCAG | 230 | CUGCUGAG CUGAUGAGGCCGUUAGGCCGAA AGUCACCU | 861 |
| 1059 | GGUGACUU C UCAGCAGA | 231 | UCUGCUGA CUGAUGAGGCCGUUAGGCCGAA AAGUCACC | 862 |
| 1061 | UGACUUCU C AGCAGAUA | 232 | UAUCUGCU CUGAUGAGGCCGUUAGGCCGAA AGAAGUCA | 863 |
| 1069 | CAGCAGAU A CAUCAGAG | 233 | CUCUGAUG CUGAUGAGGCCGUUAGGCCGAA AUCUGCUG | 864 |
| 1073 | AGAUACAU C AGAGAUAA | 234 | UUAUCUCU CUGAUGAGGCCGUUAGGCCGAA AUGUAUCU | 865 |
| 1080 | UCAGAGAU A AAUUCUAA | 235 | UUAGAAUU CUGAUGAGGCCGUUAGGCCGAA AUCUCUGA | 866 |
| 1084 | AGAUAAAU U CUAACAGU | 236 | ACUGUUAG CUGAUGAGGCCGUUAGGCCGAA AUUUAUCU | 867 |
| 1085 | GAUAAAUU C UAACAGUG | 237 | CACUGUUA CUGAUGAGGCCGUUAGGCCGAA AAUUUAUC | 868 |
| 1087 | UAAAUUCU A ACAGUGAC | 238 | GUCACUGU CUGAUGAGGCCGUUAGGCCGAA AGAAUUUA | 869 |
| 1099 | GUGACAGU U UAAACAGU | 239 | ACUGUUUA CUGAUGAGGCCGUUAGGCCGAA ACUGUCAC | 870 |
| 1100 | UGACAGUU U AAACAGUU | 240 | AACUGUUU CUGAUGAGGCCGUUAGGCCGAA AACUGUCA | 871 |
| 1101 | GACAGUUU A AACAGUUC | 241 | GAACUGUU CUGAUGAGGCCGUUAGGCCGAA AAACUGUC | 872 |
| 1108 | UAAACAGU U CUUCGUUG | 242 | CAACGAAG CUGAUGAGGCCGUUAGGCCGAA ACUGUUUA | 873 |
| 1109 | AAACAGUU C UUCGUUGC | 243 | GCAACGAA CUGAUGAGGCCGUUAGGCCGAA AACUGUUU | 874 |
| 1111 | ACAGUUCU U CGUUGCUU | 244 | AAGCAACG CUGAUGAGGCCGUUAGGCCGAA AGAACUGU | 875 |
| 1112 | CAGUUCUU C GUUGCUUA | 245 | UAAGCAAC CUGAUGAGGCCGUUAGGCCGAA AAGAACUG | 876 |
| 1115 | UUCUUCGU U GCUUAUGA | 246 | UCAUAAGC CUGAUGAGGCCGUUAGGCCGAA ACGAAGAA | 877 |
| 1119 | UCGUUGCU U AUGAAUGG | 247 | CCAUUCAU CUGAUGAGGCCGUUAGGCCGAA AGCAACGA | 878 |
| 1120 | CGUUGCUU A UGAAUGGU | 248 | ACCAUUCA CUGAUGAGGCCGUUAGGCCGAA AAGCAACG | 879 |
| 1129 | UGAAUGGU C UCAGAAAU | 249 | AUUUCUGA CUGAUGAGGCCGUUAGGCCGAA ACCAUUCA | 880 |
| 1131 | AAUGGUCU C AGAAAUAA | 250 | UUAUUUCU CUGAUGAGGCCGUUAGGCCGAA AGACCAUU | 881 |
| 1138 | UCAGAAAU A AUCAAAGG | 251 | CCUUUGAU CUGAUGAGGCCGUUAGGCCGAA AUUUCUGA | 882 |
| 1141 | GAAAUAAU C AAAGGAAG | 252 | CUUCCUUU CUGAUGAGGCCGUUAGGCCGAA AUUAUUUC | 883 |
| 1160 | AAAAAGAU C UUUGGCAC | 253 | GUGCCAAA CUGAUGAGGCCGUUAGGCCGAA AUCUUUUU | 884 |
| 1162 | AAAGAUCU U UGGCACCC | 254 | GGGUGCCA CUGAUGAGGCCGUUAGGCCGAA AGAUCUUU | 885 |
| 1163 | AAGAUCUU U GGCACCCA | 255 | UGGGUGCC CUGAUGAGGCCGUUAGGCCGAA AAGAUCUU | 886 |
| 1175 | ACCCAGAU U UGACCUUC | 256 | GAAGGUCA CUGAUGAGGCCGUUAGGCCGAA AUCUGGGU | 887 |
| 1176 | CCCAGAUU U GACCUUCC | 257 | GGAAGGUC CUGAUGAGGCCGUUAGGCCGAA AAUCUGGG | 888 |
| 1182 | UUUGACCU U CCUGACAU | 258 | AUGUCAGG CUGAUGAGGCCGUUAGGCCGAA AGGUCAAA | 889 |
| 1183 | UUGACCUU C CUGACAUG | 259 | CAUGUCAG CUGAUGAGGCCGUUAGGCCGAA AAGGUCAA | 890 |
| 1205 | AACAAGU A UACUGUGG | 260 | CCACAGUA CUGAUGAGGCCGUUAGGCCGAA ACUUGUU | 891 |
| 1207 | CAAAGUAU A CUGUGGAC | 261 | GUCCACAG CUGAUGAGGCCGUUAGGCCGAA AUACUUUG | 892 |
| 1223 | CAAGAGGU U UGGCAUGG | 262 | CCAUGCCA CUGAUGAGGCCGUUAGGCCGAA ACCUCUUG | 893 |
| 1224 | AAGAGGUU U GGCAUGGA | 263 | UCCAUGCC CUGAUGAGGCCGUUAGGCCGAA AACCUCUU | 894 |
| 1234 | GCAUGGAU U UUAAAGAA | 264 | UUCUUUAA CUGAUGAGGCCGUUAGGCCGAA AUCCAUGC | 895 |
| 1235 | CAUGGAUU U UAAAGAAA | 265 | UUUCUUUA CUGAUGAGGCCGUUAGGCCGAA AAUCCAUG | 896 |
| 1236 | AUGGAUUU U AAAGAAAU | 266 | AUUUCUUU CUGAUGAGGCCGUUAGGCCGAA AAAUCCAU | 897 |
| 1237 | UGGAUUUU A AAGAAAUA | 267 | UAUUUCUU CUGAUGAGGCCGUUAGGCCGAA AAAAUCCA | 898 |
| 1245 | AAAGAAAU A GAAUUAAU | 268 | AUUAAUUC CUGAUGAGGCCGUUAGGCCGAA AUUUCUUU | 899 |
| 1250 | AAUAGAAU U AAUGGCU | 269 | AGCCAAUU CUGAUGAGGCCGUUAGGCCGAA AUUCUAUU | 900 |
| 1251 | AUAGAAUU A AUUGGCUC | 270 | GAGCCAAU CUGAUGAGGCCGUUAGGCCGAA AAUUCUAU | 901 |
| 1254 | GAAUUAAU U GGCUCAGG | 271 | CCUGAGCC CUGAUGAGGCCGUUAGGCCGAA AUUAAUUC | 902 |
| 1259 | AAUUGGCU C AGGUGGAU | 272 | AUCCACCU CUGAUGAGGCCGUUAGGCCGAA AGCCAAUU | 903 |
| 1268 | AGGUGGAU U UGGCCAAG | 273 | CUUGGCCA CUGAUGAGGCCGUUAGGCCGAA AUCCACCU | 904 |
| 1269 | GGUGGAUU U GGCCAAGU | 274 | ACUUGGCC CUGAUGAGGCCGUUAGGCCGAA AAUCCACC | 905 |
| 1278 | GGCCAAGU U UCAAAGC | 275 | GCUUUGAA CUGAUGAGGCCGUUAGGCCGAA ACUUGGCC | 906 |
| 1279 | GCCAAGUU U CAAAGCA | 276 | UGCUUUGA CUGAUGAGGCCGUUAGGCCGAA AACUUGGC | 907 |
| 1280 | CCAAGUUU U CAAAGCAA | 277 | UUGCUUUG CUGAUGAGGCCGUUAGGCCGAA AAACUUGG | 908 |
| 1281 | CAAGUUUU C AAAGCAAA | 278 | UUUGCUUU CUGAUGAGGCCGUUAGGCCGAA AAAACUUG | 909 |
| 1299 | CACAGAAU U GACGGAAA | 279 | UUUCCGUC CUGAUGAGGCCGUUAGGCCGAA AUUCUGUG | 910 |
| 1312 | GAAAGACU U ACGUUAUU | 280 | AAUAACGU CUGAUGAGGCCGUUAGGCCGAA AGUCUUUC | 911 |
| 1313 | AAAGACUU A CGUUAUUA | 281 | UAAUAACG CUGAUGAGGCCGUUAGGCCGAA AAGUCUUU | 912 |
| 1317 | ACUUACGU U AUUAAACG | 282 | CGUUUAAU CUGAUGAGGCCGUUAGGCCGAA ACGUAAGU | 913 |

TABLE VIII-continued

Human PKR Hammerhead and Substrate Sequence

| Pos | Substrate | Seq ID | Hammerhead | Seq ID |
|---|---|---|---|---|
| 1318 | CUUACGUU A UUAAACGU | 283 | ACGUUUAA CUGAUGAGGCCGUUAGGCCGAA AACGUAAG | 914 |
| 1320 | UACGUUAU U AAACGUGU | 284 | ACACGUUU CUGAUGAGGCCGUUAGGCCGAA AUAACGUA | 915 |
| 1321 | ACGUUAUU A AACGUGUU | 285 | AACACGUU CUGAUGAGGCCGUUAGGCCGAA AAUAACGU | 916 |
| 1329 | AAACGUGU U AAAUAUAA | 286 | UUAUAUUU CUGAUGAGGCCGUUAGGCCGAA ACACGUUU | 917 |
| 1330 | AACGUGUU A AAUAUAAU | 287 | AUUAUAUU CUGAUGAGGCCGUUAGGCCGAA AACACGUU | 918 |
| 1334 | UGUUAAAU A UAAUAACG | 288 | CGUUAUUA CUGAUGAGGCCGUUAGGCCGAA AUUUAACA | 919 |
| 1336 | UUAAAUAU A AUAACGAG | 289 | CUCGUUAU CUGAUGAGGCCGUUAGGCCGAA AUAUUUAA | 920 |
| 1339 | AAUAUAAU A ACGAGAAG | 290 | CUUCUCGU CUGAUGAGGCCGUUAGGCCGAA AUUAUAUU | 921 |
| 1362 | CGUGAAGU A AAAGCAUU | 291 | AAUGCUUU CUGAUGAGGCCGUUAGGCCGAA ACUUCACG | 922 |
| 1370 | AAAAGCAU U GGCAAAAC | 292 | GUUUUGCC CUGAUGAGGCCGUUAGGCCGAA AUGCUUUU | 923 |
| 1380 | GCAAAACU U GAUCAUGU | 293 | ACAUGAUC CUGAUGAGGCCGUUAGGCCGAA AGUUUUGC | 924 |
| 1384 | AACUUGAU C AUGUAAAU | 294 | AUUUACAU CUGAUGAGGCCGUUAGGCCGAA AUCAAGUU | 925 |
| 1389 | GAUCAUGU A AAUAUUGU | 295 | ACAAUAUU CUGAUGAGGCCGUUAGGCCGAA ACAUGAUC | 926 |
| 1393 | AUGUAAAU A UUGUUCAC | 296 | GUGAACAA CUGAUGAGGCCGUUAGGCCGAA AUUUACAU | 927 |
| 1395 | GUAAAUAU U GUUCACUA | 297 | UAGUGAAC CUGAUGAGGCCGUUAGGCCGAA AUAUUUAC | 928 |
| 1398 | AAUAUUGU U CACUACAA | 298 | UUGUAGUG CUGAUGAGGCCGUUAGGCCGAA ACAAUAUU | 929 |
| 1399 | AUAUUGUU C ACUACAAU | 299 | AUUGUAGU CUGAUGAGGCCGUUAGGCCGAA AACAAUAU | 930 |
| 1403 | UGUUCACU A CAAUGGCU | 300 | AGCCAUUG CUGAUGAGGCCGUUAGGCCGAA AGUGAACA | 931 |
| 1414 | AUGGCUGU U GGGAUGGA | 301 | UCCAUCCC CUGAUGAGGCCGUUAGGCCGAA ACAGCCAU | 932 |
| 1424 | GGAUGGAU U UGAUUAUG | 302 | CAUAAUCA CUGAUGAGGCCGUUAGGCCGAA AUCCAUCC | 933 |
| 1425 | GAUGGAUU U GAUUAUGA | 303 | UCAUAAUC CUGAUGAGGCCGUUAGGCCGAA AAUCCAUC | 934 |
| 1429 | GAUUUGAU U AUGAUCCU | 304 | AGGAUCAU CUGAUGAGGCCGUUAGGCCGAA AUCAAAUC | 935 |
| 1430 | AUUUGAUU A UGAUCCUG | 305 | CAGGAUCA CUGAUGAGGCCGUUAGGCCGAA AAUCAAAU | 936 |
| 1435 | AUUAUGAU C CUGAGACC | 306 | GGUCUCAG CUGAUGAGGCCGUUAGGCCGAA AUCAUAAU | 937 |
| 1453 | GUGAUGAU U CUCUUGAG | 307 | CUCAAGAG CUGAUGAGGCCGUUAGGCCGAA AUCAUCAC | 938 |
| 1454 | UGAUGAUU C UCUUGAGA | 308 | UCUCAAGA CUGAUGAGGCCGUUAGGCCGAA AAUCAUCA | 939 |
| 1456 | AUGAUUCU C UUGAGAGC | 309 | GCUCUCAA CUGAUGAGGCCGUUAGGCCGAA AGAAUCAU | 940 |
| 1458 | GAUUCUCU U GAGAGCAG | 310 | CUGCUCUC CUGAUGAGGCCGUUAGGCCGAA AGAGAAUC | 941 |
| 1471 | GCAGUGAU A UGAUCCU | 311 | AGGAUCAU CUGAUGAGGCCGUUAGGCCGAA AUCACUGC | 942 |
| 1472 | CAGUGAUU A UGAUCCUG | 312 | CAGGAUCA CUGAUGAGGCCGUUAGGCCGAA AAUCACUG | 943 |
| 1477 | AUUAUGAU C UGAGAAC | 313 | GUUCUCAG CUGAUGAGGCCGUUAGGCCGAA AUCAUAAU | 944 |
| 1495 | GCAAAAAU A GUUCAAGG | 314 | CCUUGAAC CUGAUGAGGCCGUUAGGCCGAA AUUUUUGC | 945 |
| 1498 | AAAAUAGU U CAAGGUCA | 315 | UGACCUUG CUGAUGAGGCCGUUAGGCCGAA ACUAUUUU | 946 |
| 1499 | AAAUAGUU C AAGGUCAA | 316 | UUGACCUU CUGAUGAGGCCGUUAGGCCGAA AACUAUUU | 947 |
| 1505 | UUCAAGGU C AAAGACUA | 317 | UAGUCUUU CUGAUGAGGCCGUUAGGCCGAA ACCUUGAA | 948 |
| 1513 | CAAAGACU A AGUGCCUU | 318 | AAGGCACU CUGAUGAGGCCGUUAGGCCGAA AGUCUUUG | 949 |
| 1521 | AAGUGCCU U UUCAUCCA | 319 | UGGAUGAA CUGAUGAGGCCGUUAGGCCGAA AGGCACUU | 950 |
| 1522 | AGUGCCUU U UCAUCCAA | 320 | UUGGAUGA CUGAUGAGGCCGUUAGGCCGAA AAGGCACU | 951 |
| 1523 | GUGCCUUU U CAUCCAAA | 321 | UUUGGAUG CUGAUGAGGCCGUUAGGCCGAA AAAGGCAC | 952 |
| 1524 | UGCCUUUU C AUCCAAAU | 322 | AUUUGGAU CUGAUGAGGCCGUUAGGCCGAA AAAAGGCA | 953 |
| 1527 | CUUUUCAU C CAAAUGGA | 323 | UCCAUUUG CUGAUGAGGCCGUUAGGCCGAA AUGAAAAG | 954 |
| 1538 | AAUGGAAU U CUGUGAUA | 324 | UAUCACAG CUGAUGAGGCCGUUAGGCCGAA AUUCCAUU | 955 |
| 1539 | AUGGAAUU C UGUGAUAA | 325 | UUAUCACA CUGAUGAGGCCGUUAGGCCGAA AAUUCCAU | 956 |
| 1546 | UCUGUGAU A AGGGACC | 326 | GGUCCCUU CUGAUGAGGCCGUUAGGCCGAA AUCACAGA | 957 |
| 1556 | AGGGACCU U GGAACAAU | 327 | AUUGUUCC CUGAUGAGGCCGUUAGGCCGAA AGGUCCCU | 958 |
| 1569 | CAAUGGAU U GAAAAAAG | 328 | CUUUUUUC CUGAUGAGGCCGUUAGGCCGAA AUCCAUUG | 959 |
| 1593 | GAGAAACU A GACAAAGU | 329 | ACUUUGUC CUGAUGAGGCCGUUAGGCCGAA AGUUUCUC | 960 |
| 1602 | GACAAAGU U UGGCUUUU | 330 | AAAGCCAA CUGAUGAGGCCGUUAGGCCGAA ACUUUGUC | 961 |
| 1603 | ACAAAGUU U GGCUUUGG | 331 | CAAAGCCA CUGAUGAGGCCGUUAGGCCGAA AACUUUGU | 962 |
| 1604 | CAAAGUUU U GGCUUUGG | 332 | CCAAAGCC CUGAUGAGGCCGUUAGGCCGAA AAACUUUG | 963 |
| 1609 | UUUUGGCU U UGGAACUC | 333 | GAGUUCCA CUGAUGAGGCCGUUAGGCCGAA AGCCAAAA | 964 |
| 1610 | UUUGGCUU U GGAACUCU | 334 | AGAGUUCC CUGAUGAGGCCGUUAGGCCGAA AAGCCAAA | 965 |
| 1617 | UUGGAACU C UUUGAACA | 335 | UGUUCAAA CUGAUGAGGCCGUUAGGCCGAA AGUUCCAA | 966 |
| 1619 | GGAACUCU U UGAACAAA | 336 | UUUGUUCA CUGAUGAGGCCGUUAGGCCGAA AGAGUUCC | 967 |
| 1620 | GAACUCUU U GAACAAAU | 337 | AUUUGUUC CUGAUGAGGCCGUUAGGCCGAA AAGAGUUC | 968 |
| 1629 | GAACAAAU A ACAAAAGG | 338 | CCUUUUGU CUGAUGAGGCCGUUAGGCCGAA AUUUGUUC | 969 |
| 1645 | GGGUGGAU U AUAUACAU | 339 | AUGUAUAU CUGAUGAGGCCGUUAGGCCGAA AUCCACCC | 970 |
| 1646 | GGUGGAUU A UAUACAUU | 340 | AAUGUAUA CUGAUGAGGCCGUUAGGCCGAA AAUCCACC | 971 |
| 1648 | UGGAUUAU A UACAUUCA | 341 | UGAAUGUA CUGAUGAGGCCGUUAGGCCGAA AUAAUCCA | 972 |
| 1650 | GAUUAUAU A CAUUCAAA | 342 | UUUGAAUG CUGAUGAGGCCGUUAGGCCGAA AUAUAAUC | 973 |
| 1654 | AUAUACAU U CAAAAAAA | 343 | UUUUUUUG CUGAUGAGGCCGUUAGGCCGAA AUGUAUAU | 974 |
| 1655 | UAUACAUU C AAAAAAAU | 344 | AUUUUUUU CUGAUGAGGCCGUUAGGCCGAA AAUGUAUA | 975 |
| 1664 | AAAAAAAU U AAUUCAUA | 345 | UAUGAAUU CUGAUGAGGCCGUUAGGCCGAA AUUUUUUU | 976 |
| 1665 | AAAAAAUU A AUUCAUAG | 346 | CUAUGAAU CUGAUGAGGCCGUUAGGCCGAA AAUUUUUU | 977 |
| 1668 | AAAUUAAU U CAUAGAGA | 347 | UCUCUAUG CUGAUGAGGCCGUUAGGCCGAA AUUAAUUU | 978 |
| 1669 | AAUUAAUU C AUAGAGAU | 348 | AUCUCUAU CUGAUGAGGCCGUUAGGCCGAA AAUUAAUU | 979 |
| 1672 | UAAUUCAU A GAGAUCUU | 349 | AAGAUCUC CUGAUGAGGCCGUUAGGCCGAA AUGAAUUA | 980 |
| 1678 | AUAGAGAU C UUAGCCA | 350 | UGGCUUAA CUGAUGAGGCCGUUAGGCCGAA AUCUCUAU | 981 |
| 1680 | AGAGAUCU U AAGCCAAG | 351 | CUUGGCUU CUGAUGAGGCCGUUAGGCCGAA AGAUCUCU | 982 |
| 1681 | GAGAUCUU A AGCCAAGU | 352 | ACUUGGCU CUGAUGAGGCCGUUAGGCCGAA AAGAUCUC | 983 |
| 1690 | AGCCAAGU A AUAUAUUC | 353 | GAAUAUAU CUGAUGAGGCCGUUAGGCCGAA ACUUGGCU | 984 |
| 1693 | CAAGUAAU A UAUUCUUA | 354 | UAAGAAUA CUGAUGAGGCCGUUAGGCCGAA AUUACUUG | 985 |
| 1695 | AGUAAUAU A UUCUUACU | 355 | ACUAAGAA CUGAUGAGGCCGUUAGGCCGAA AUAUUACU | 986 |
| 1697 | UAAUAUAU U CUUAGUAG | 356 | CUACUAAG CUGAUGAGGCCGUUAGGCCGAA AUAUAUUA | 987 |
| 1698 | AAUAUAUU C UUAGUAGA | 357 | UCUACUAA CUGAUGAGGCCGUUAGGCCGAA AAUAUAUU | 988 |

TABLE VIII-continued

Human PKR Hammerhead and Substrate Sequence

| Pos | Substrate | Seq ID | Hammerhead | Seq ID |
|---|---|---|---|---|
| 1700 | UAUAUUCU U AGUAGAUA | 358 | UAUCUACU CUGAUGAGGCCGUUAGGCCGAA AGAAUAUA | 989 |
| 1701 | AUAUUCUU A GUAGAUAC | 359 | GUAUCUAC CUGAUGAGGCCGUUAGGCCGAA AAGAAUAU | 990 |
| 1704 | UUCUAGU A GAUACAAA | 360 | UUUGUAUC CUGAUGAGGCCGUUAGGCCGAA ACUAAGAA | 991 |
| 1708 | UAGUAGAU A CAAAACAA | 361 | UUGUUUUG CUGAUGAGGCCGUUAGGCCGAA AUCUACUA | 992 |
| 1719 | AAACAAGU A AAGAUUGG | 362 | CCAAUCUU CUGAUGAGGCCGUUAGGCCGAA ACUUGUUU | 993 |
| 1725 | GUAAAGU U GGACACUU | 363 | AAGUCUCC CUGAUGAGGCCGUUAGGCCGAA AUCUUUAC | 994 |
| 1733 | UGGACACU U UGGACUUG | 364 | CAAGUCCA CUGAUGAGGCCGUUAGGCCGAA AGUCUCCA | 995 |
| 1734 | GGAGACUU U GGACUUGU | 365 | ACAAGUCC CUGAUGAGGCCGUUAGGCCGAA AAGUCUCC | 996 |
| 1740 | UUUGGACU U GUAACAUC | 366 | GAUGUUAC CUGAUGAGGCCGUUAGGCCGAA AGUCCAAA | 997 |
| 1743 | GGACUUGU A ACAUCUCU | 367 | AGAGAUGU CUGAUGAGGCCGUUAGGCCGAA ACAAGUCC | 998 |
| 1748 | UGUAACAU C UCUGAAAA | 368 | UUUUCAGA CUGAUGAGGCCGUUAGGCCGAA AUGUUACA | 999 |
| 1750 | UAACAUCU C UGAAAAAU | 369 | AUUUUUCA CUGAUGAGGCCGUUAGGCCGAA AGAUGUUA | 1000 |
| 1780 | CAAGGAGU A AGGGAACU | 370 | AGUUCCCU CUGAUGAGGCCGUUAGGCCGAA ACUCCUUG | 1001 |
| 1789 | AGGGAACU U UGCGAUAC | 371 | GUAUCGCA CUGAUGAGGCCGUUAGGCCGAA AGUUCCCU | 1002 |
| 1790 | GGGAACUU U GCGAUACA | 372 | UGUAUCGC CUGAUGAGGCCGUUAGGCCGAA AAGUUCCC | 1003 |
| 1796 | UUUGCGAU A CAUGAGCC | 373 | GGCUCAUG CUGAUGAGGCCGUUAGGCCGAA AUCGCAAA | 1004 |
| 1815 | GAACAGAU U UCUUCGCA | 374 | UGCGAAGA CUGAUGAGGCCGUUAGGCCGAA AUCUGUUC | 1005 |
| 1816 | AACAGAUU U CUUCGCAA | 375 | UUGCGAAG CUGAUGAGGCCGUUAGGCCGAA AAUCUGUU | 1006 |
| 1817 | ACAGAUUU C UUCGCAAG | 376 | CUUGCGAA CUGAUGAGGCCGUUAGGCCGAA AAAUCUGU | 1007 |
| 1819 | AGAUUUCU U CGCAAGAC | 377 | GUCUUGCG CUGAUGAGGCCGUUAGGCCGAA AGAAAUCU | 1008 |
| 1820 | GAUUUCUU C GCAAGACU | 378 | AGUCUUGC CUGAUGAGGCCGUUAGGCCGAA AAGAAAUC | 1009 |
| 1829 | GCAAGACU A UGGAAAGG | 379 | CCUUUCCA CUGAUGAGGCCGUUAGGCCGAA AGUCUUGC | 1010 |
| 1848 | GUGGACCU C UACGCUUU | 380 | AAAGCGUA CUGAUGAGGCCGUUAGGCCGAA AGGUCCAC | 1011 |
| 1850 | GGACCUCU A CGCUUUGG | 381 | CCAAAGCG CUGAUGAGGCCGUUAGGCCGAA AGAGGUCC | 1012 |
| 1855 | UCUACGCU U UGGGCUA | 382 | UAGCCCCA CUGAUGAGGCCGUUAGGCCGAA AGCGUAGA | 1013 |
| 1856 | CUACGCUU U GGGGCUAA | 383 | UUAGCCCC CUGAUGAGGCCGUUAGGCCGAA AAGCGUAG | 1014 |
| 1863 | UUGGGCU A AUUCUUGC | 384 | GCAAGAAU CUGAUGAGGCCGUUAGGCCGAA AGCCCCAA | 1015 |
| 1866 | GGGCUAAU U CUUGCUGA | 385 | UCAGCAAG CUGAUGAGGCCGUUAGGCCGAA AUUAGCCC | 1016 |
| 1867 | GGCUAAUU C UUGCUGAA | 386 | UUCAGCAA CUGAUGAGGCCGUUAGGCCGAA AAUUAGCC | 1017 |
| 1869 | CUAAUUCU U GCUGAACU | 387 | AGUUCAGC CUGAUGAGGCCGUUAGGCCGAA AGAAUUAG | 1018 |
| 1878 | GCUGAACU U CUUCAUGU | 388 | ACAUGAAG CUGAUGAGGCCGUUAGGCCGAA AGUUCAGC | 1019 |
| 1879 | CUGAACUU C UUCAUGUA | 389 | UACAUGAA CUGAUGAGGCCGUUAGGCCGAA AAGUUCAG | 1020 |
| 1881 | GAACUUCU U CAUGUAUG | 390 | CAUACAUG CUGAUGAGGCCGUUAGGCCGAA AGAAGUUC | 1021 |
| 1882 | AACUUCUU C AUGUAUGU | 391 | ACAUACAU CUGAUGAGGCCGUUAGGCCGAA AAGAAGUU | 1022 |
| 1887 | CUUCAUGU A UGUGACAC | 392 | GUGUCACA CUGAUGAGGCCGUUAGGCCGAA ACAUGAAG | 1023 |
| 1900 | ACACGCU U UUGAAACA | 393 | UGUUUCAA CUGAUGAGGCCGUUAGGCCGAA AGCAGUGU | 1024 |
| 1901 | CACUGCUU U UGAAACAU | 394 | AUGUUUCA CUGAUGAGGCCGUUAGGCCGAA AAGCAGUG | 1025 |
| 1902 | ACUGCUUU U GAAACAUC | 395 | GAUGUUUC CUGAUGAGGCCGUUAGGCCGAA AAAGCAGU | 1026 |
| 1910 | UGAAACAU C AAAGUUUU | 396 | AAAACUUU CUGAUGAGGCCGUUAGGCCGAA AUGUUUCA | 1027 |
| 1916 | AUCAAAGU U UUUCACAG | 397 | CUGUGAAA CUGAUGAGGCCGUUAGGCCGAA ACUUUGAU | 1028 |
| 1917 | UCAAAGUU U UUCACAGA | 398 | UCUGUGAA CUGAUGAGGCCGUUAGGCCGAA AACUUUGA | 1029 |
| 1918 | CAAAGUUU U UCACAGAC | 399 | GUCUGUGA CUGAUGAGGCCGUUAGGCCGAA AAACUUUG | 1030 |
| 1919 | AAAGUUUU U CACAGACC | 400 | GGUCUGUG CUGAUGAGGCCGUUAGGCCGAA AAAACUUU | 1031 |
| 1920 | AAGUUUUU C ACAGACCU | 401 | AGGUCUGU CUGAUGAGGCCGUUAGGCCGAA AAAAACUU | 1032 |
| 1929 | ACAGACCU A CGGGAUGG | 402 | CCAUCCCG CUGAUGAGGCCGUUAGGCCGAA AGGUCUGU | 1033 |
| 1941 | GAUGGCAU C AUCUCAGA | 403 | UCUGAGAU CUGAUGAGGCCGUUAGGCCGAA AUGCCAUC | 1034 |
| 1944 | GGCAUCAU C UCAGAUAU | 404 | AUAUCUGA CUGAUGAGGCCGUUAGGCCGAA AUGAUGCC | 1035 |
| 1946 | CAUCUCU C AGAUAUAU | 405 | AUAUAUCU CUGAUGAGGCCGUUAGGCCGAA AGAUGAUG | 1036 |
| 1951 | UCUCAGAU A UAUUUGAU | 406 | AUCAAAUA CUGAUGAGGCCGUUAGGCCGAA AUCUGAGA | 1037 |
| 1953 | UCAGAUAU A UUUGAUAA | 407 | UUAUCAAA CUGAUGAGGCCGUUAGGCCGAA AUAUCUGA | 1038 |
| 1955 | AGAUAUAU U UGAUAAAA | 408 | UUUUAUCA CUGAUGAGGCCGUUAGGCCGAA AUAUAUCU | 1039 |
| 1956 | GAUAUAUU U GAUAAAAA | 409 | UUUUUAUC CUGAUGAGGCCGUUAGGCCGAA AAUAUAUC | 1040 |
| 1960 | UAUUUGAU A AAAAGAA | 410 | UUCUUUUU CUGAUGAGGCCGUUAGGCCGAA AUCAAAUA | 1041 |
| 1975 | AAAAACU U UCUACAG | 411 | CUGUAGAA CUGAUGAGGCCGUUAGGCCGAA AGUUUUUU | 1042 |
| 1977 | AAACUCU U CUACAGAA | 412 | UUCUGUAG CUGAUGAGGCCGUUAGGCCGAA AGAGUUUU | 1043 |
| 1978 | AAACUCUU C UACAGAAA | 413 | UUUCUGUA CUGAUGAGGCCGUUAGGCCGAA AAGAGUUU | 1044 |
| 1980 | ACUCUUCU A CAGAAAUU | 414 | AAUUUCUG CUGAUGAGGCCGUUAGGCCGAA AGAAGAGU | 1045 |
| 1988 | ACAGAAU U ACUCUCAA | 415 | UUGAGAGU CUGAUGAGGCCGUUAGGCCGAA AUUUCUGU | 1046 |
| 1989 | CAGAAAUU A CUCUCAAA | 416 | UUUGAGAG CUGAUGAGGCCGUUAGGCCGAA AAUUUCUG | 1047 |
| 1992 | AAAUUACU C UCAAGAA | 417 | UUCUUGA CUGAUGAGGCCGUUAGGCCGAA AGUAAUUU | 1048 |
| 1994 | AUUACUCU C AAAGAAAC | 418 | GUUUCUUU CUGAUGAGGCCGUUAGGCCGAA AGAGUAAU | 1049 |
| 2011 | CUGAGGAU C GACCUAAC | 419 | GUUAGGUC CUGAUGAGGCCGUUAGGCCGAA AUCCUCAG | 1050 |
| 2017 | AUCGACCU A ACACAUCU | 420 | AGAUGUGU CUGAUGAGGCCGUUAGGCCGAA AGGUCGAU | 1051 |
| 2024 | UAACACAU C UGAAUAC | 421 | GUAUUCA CUGAUGAGGCCGUUAGGCCGAA AUGUGUUA | 1052 |
| 2031 | UCUGAAAU A CUAGGAC | 422 | GUCCUUAG CUGAUGAGGCCGUUAGGCCGAA AUUUCAGA | 1053 |
| 2034 | GAAAUACU A AGGACCUU | 423 | AAGGUCCU CUGAUGAGGCCGUUAGGCCGAA AGUAUUUC | 1054 |
| 2042 | AAGGACCU U GACUGUGU | 424 | ACACAGUC CUGAUGAGGCCGUUAGGCCGAA AGGUCCUU | 1055 |
| 2089 | ACACAUGU U AGAGCCCU | 425 | AGGGCUCU CUGAUGAGGCCGUUAGGCCGAA ACAUGUGU | 1056 |
| 2090 | CACAUGUU A GAGCCCUU | 426 | AAGGGCUC CUGAUGAGGCCGUUAGGCCGAA AACAUGUG | 1057 |
| 2098 | AGAGCCCU U CUGAAAAA | 427 | UUUUUCAG CUGAUGAGGCCGUUAGGCCGAA AGGGCUCU | 1058 |
| 2099 | GAGCCCUU C UGAAAAAG | 428 | CUUUUUCA CUGAUGAGGCCGUUAGGCCGAA AAGGGCUC | 1059 |
| 2109 | GAAAAAGU A UCCUGCUU | 429 | AAGCAGGA CUGAUGAGGCCGUUAGGCCGAA ACUUUUUC | 1060 |
| 2111 | AAAAGUAU C CUGCUUCU | 430 | AGAAGCAG CUGAUGAGGCCGUUAGGCCGAA AUACUUUU | 1061 |
| 2117 | AUCCUGCU U CUGAUAUG | 431 | CAUAUCAG CUGAUGAGGCCGUUAGGCCGAA AGCAGGAU | 1062 |
| 2118 | UCCUGCUU C UGAUAUGC | 432 | GCAUAUCA CUGAUGAGGCCGUUAGGCCGAA AAGCAGGA | 1063 |

TABLE VIII-continued

Human PKR Hammerhead and Substrate Sequence

| Pos | Substrate | Seq ID | Hammerhead | Seq ID |
|---|---|---|---|---|
| 2123 | CUUCUGAU A UGCAGUUU | 433 | AAACUGCA CUGAUGAGGCCGUUAGGCCGAA AUCAGAAG | 1064 |
| 2130 | UAUGCAGU U UUCCUUAA | 434 | UUAAGGAA CUGAUGAGGCCGUUAGGCCGAA ACUGCAUA | 1065 |
| 2131 | AUGCAGUU U UCCUUAAA | 435 | UUUAAGGA CUGAUGAGGCCGUUAGGCCGAA AACUGCAU | 1066 |
| 2132 | UGCAGUUU U CCUUAAAU | 436 | AUUUAAGG CUGAUGAGGCCGUUAGGCCGAA AAACUGCA | 1067 |
| 2133 | GCAGUUUU C CUUAAAUU | 437 | AAUUUAAG CUGAUGAGGCCGUUAGGCCGAA AAAACUGC | 1068 |
| 2136 | GUUUUCCU U AAAUUAUC | 438 | GAUAAUUU CUGAUGAGGCCGUUAGGCCGAA AGGAAAAC | 1069 |
| 2137 | UUUUCCUU A AAUUAUCU | 439 | AGAUAAUU CUGAUGAGGCCGUUAGGCCGAA AAGGAAAA | 1070 |
| 2141 | CCUUAAAU U AUCAAAA | 440 | UUUUAGAU CUGAUGAGGCCGUUAGGCCGAA AUUUAAGG | 1071 |
| 2142 | CUUAAAUU A UCAAAAU | 441 | AUUUUAGA CUGAUGAGGCCGUUAGGCCGAA AAUUUAAG | 1072 |
| 2144 | UAAAAUAU C UAAAAUCU | 442 | AGAUUUUA CUGAUGAGGCCGUUAGGCCGAA AUAAUUUA | 1073 |
| 2146 | AAUUAUCU A AAAUCUGC | 443 | GCAGAUUU CUGAUGAGGCCGUUAGGCCGAA AGAUAAUU | 1074 |
| 2151 | UCUAAAAU C UGCUAGGG | 444 | CCCUAGCA CUGAUGAGGCCGUUAGGCCGAA AUUUUAGA | 1075 |
| 2156 | AAUCUGCU A GGGAAUAU | 445 | AUAUUCCC CUGAUGAGGCCGUUAGGCCGAA AGCAGAUU | 1076 |
| 2163 | UAGGGAAU A UCAAUAGA | 446 | UCUAUUGA CUGAUGAGGCCGUUAGGCCGAA AUUCCCUA | 1077 |
| 2165 | GGGAAUAU C AAUAGAUA | 447 | UAUCUAUU CUGAUGAGGCCGUUAGGCCGAA AUAUUCCC | 1078 |
| 2169 | AUAUCAAU A GAUAUUUA | 448 | UAAAUAUC CUGAUGAGGCCGUUAGGCCGAA AUUGAUAU | 1079 |
| 2173 | CAAUAGAU A UUUACCUU | 449 | AAGGUAAA CUGAUGAGGCCGUUAGGCCGAA AUCUAUUG | 1080 |
| 2175 | AUAGAUAU U UACCUUUU | 450 | AAAAGGUA CUGAUGAGGCCGUUAGGCCGAA AUAUCUAU | 1081 |
| 2176 | UAGAUAUU U ACCUUUUA | 451 | UAAAAGGU CUGAUGAGGCCGUUAGGCCGAA AAUAUCUA | 1082 |
| 2177 | AGAUAUUU A CCUUUUAU | 452 | AUAAAAGG CUGAUGAGGCCGUUAGGCCGAA AAAUAUCU | 1083 |
| 2181 | AUUUACCU U UUAUUUUA | 453 | UAAAAUAA CUGAUGAGGCCGUUAGGCCGAA AGGUAAAU | 1084 |
| 2182 | UUUACCUU U UAUUUUAA | 454 | UUAAAAUA CUGAUGAGGCCGUUAGGCCGAA AAGGUAAA | 1085 |
| 2183 | UUACCUUU U AUUUUAAU | 455 | AUUAAAAU CUGAUGAGGCCGUUAGGCCGAA AAACGUAA | 1086 |
| 2184 | UACCUUUU A UUUUAAUG | 456 | CAUUAAAA CUGAUGAGGCCGUUAGGCCGAA AAAAGGUA | 1087 |
| 2186 | CCUUUUAU U UUAAUGUU | 457 | AACAUUAA CUGAUGAGGCCGUUAGGCCGAA AUAAAAGG | 1088 |
| 2187 | CUUUUAUU U UAAUGUUU | 458 | AAACAUUA CUGAUGAGGCCGUUAGGCCGAA AAUAAAAG | 1089 |
| 2188 | UUUUAUUU U AAUGUUUC | 459 | GAAACAUU CUGAUGAGGCCGUUAGGCCGAA AAAUAAAA | 1090 |
| 2189 | UUUAUUUU A AUGUUUCC | 460 | GGAAACAU CUGAUGAGGCCGUUAGGCCGAA AAAAUAAA | 1091 |
| 2194 | UUUAAUGU U UCCUUUAA | 461 | UUAAAGGA CUGAUGAGGCCGUUAGGCCGAA ACAUUAAA | 1092 |
| 2195 | UUAAUGUU U CCUUUAAU | 462 | AUUAAAGG CUGAUGAGGCCGUUAGGCCGAA AACAUUAA | 1093 |
| 2196 | UAAUGUUU C CUUUAAUU | 463 | AAUUAAAG CUGAUGAGGCCGUUAGGCCGAA AAACAUUA | 1094 |
| 2199 | UGUUUCCU U UAAUUUUU | 464 | AAAAAUUA CUGAUGAGGCCGUUAGGCCGAA AGGAAACA | 1095 |
| 2200 | GUUUCCUU U AAUUUUUU | 465 | AAAAAAUU CUGAUGAGGCCGUUAGGCCGAA AAGGAAAC | 1096 |
| 2201 | UUUCCUUU A AUUUUUUA | 466 | UAAAAAAU CUGAUGAGGCCGUUAGGCCGAA AAAGGAAA | 1097 |
| 2204 | CCUUUAAU U UUUUACUA | 467 | UAGUAAAA CUGAUGAGGCCGUUAGGCCGAA AUUAAAGG | 1098 |
| 2205 | CUUUAAUU U UUUACUAU | 468 | AUAGUAAA CUGAUGAGGCCGUUAGGCCGAA AAUUAAAG | 1099 |
| 2206 | UUUAAUUU U UUACUAUU | 469 | AAUAGUAA CUGAUGAGGCCGUUAGGCCGAA AAAUUAAA | 1100 |
| 2207 | UUAAUUUU U UACUAUUU | 470 | AAAUAGUA CUGAUGAGGCCGUUAGGCCGAA AAAAUUAA | 1101 |
| 2208 | UAAUUUUU U ACUAUUUU | 471 | AAAAUAGU CUGAUGAGGCCGUUAGGCCGAA AAAAAUUA | 1102 |
| 2209 | AAUUUUUU A CUAUUUUU | 472 | AAAAAUAG CUGAUGAGGCCGUUAGGCCGAA AAAAAAUU | 1103 |
| 2212 | UUUUUACU A UUUUACU | 473 | AGUAAAAA CUGAUGAGGCCGUUAGGCCGAA AGUAAAAA | 1104 |
| 2214 | UUUACUAU U UUUACUAA | 474 | UUAGUAAA CUGAUGAGGCCGUUAGGCCGAA AUAGUAAA | 1105 |
| 2215 | UUACUAUU U UUACUAAU | 475 | AUUAGUAA CUGAUGAGGCCGUUAGGCCGAA AAUAGUAA | 1106 |
| 2216 | UACUAUUU U UACUAAUC | 476 | GAUUAGUA CUGAUGAGGCCGUUAGGCCGAA AAAUAGUA | 1107 |
| 2217 | ACUAUUUU U ACUAAUCU | 477 | AGAUUAGU CUGAUGAGGCCGUUAGGCCGAA AAAAUAGU | 1108 |
| 2218 | CUAUUUUU A CUAACUU | 478 | AAGAUUAG CUGAUGAGGCCGUUAGGCCGAA AAAAAUAG | 1109 |
| 2221 | UUUUUACU A AUCUUUCU | 479 | AGAAAGAU CUGAUGAGGCCGUUAGGCCGAA AGUAAAAA | 1110 |
| 2224 | UUACUAAU C UUUCUGCA | 480 | UGCAGAAA CUGAUGAGGCCGUUAGGCCGAA AUUAGUAA | 1111 |
| 2226 | ACUAAUCU U UCUGCAGA | 481 | UCUGCAGA CUGAUGAGGCCGUUAGGCCGAA AGAUUAGU | 1112 |
| 2227 | CUAAUCUU U CUGCAGAA | 482 | UUCUGCAG CUGAUGAGGCCGUUAGGCCGAA AAGAUUAG | 1113 |
| 2228 | UAAUCUUU C UGCAGAAA | 483 | UUUCUGCA CUGAUGAGGCCGUUAGGCCGAA AAAGAUUA | 1114 |
| 2246 | AGAAGGU U UUCUUCUU | 484 | AAGAAGAA CUGAUGAGGCCGUUAGGCCGAA ACCUUUCU | 1115 |
| 2247 | GAAAGGU U UCUUCUUU | 485 | AAAGAAGA CUGAUGAGGCCGUUAGGCCGAA AACCUUUC | 1116 |
| 2248 | AAAGGUUU U CUUCUUUU | 486 | AAAAGAAG CUGAUGAGGCCGUUAGGCCGAA AAACCUUU | 1117 |
| 2249 | AAGGUUUU C UUCUUUUU | 487 | AAAAAGAA CUGAUGAGGCCGUUAGGCCGAA AAAACCUU | 1118 |
| 2251 | GGUUUUCU U CUUUUUGC | 488 | GCAAAAAG CUGAUGAGGCCGUUAGGCCGAA AGAAACCC | 1119 |
| 2252 | GUUUUCUU C UUUUUGCU | 489 | AGCAAAAA CUGAUGAGGCCGUUAGGCCGAA AAGAAAAC | 1120 |
| 2254 | UUUCUUCU U UUUGCUUC | 490 | GAAGCAAA CUGAUGAGGCCGUUAGGCCGAA AGAAGAAA | 1121 |
| 2255 | UUCUUCUU U UUGCUUCA | 491 | UGAAGCAA CUGAUGAGGCCGUUAGGCCGAA AAGAAGAA | 1122 |
| 2256 | UCUUCUUU U UGCUUCAA | 492 | UUGAAGCA CUGAUGAGGCCGUUAGGCCGAA AAAGAAGA | 1123 |
| 2257 | CUUCUUUU U GCUUCAAA | 493 | UUUGAAGC CUGAUGAGGCCGUUAGGCCGAA AAAAGAAG | 1124 |
| 2261 | UUUUGCU U CAAAACA | 494 | UGUUUUUG CUGAUGAGGCCGUUAGGCCGAA AGCAAAAA | 1125 |
| 2262 | UUUUGCUU C AAAACAU | 495 | AUGUUUUU CUGAUGAGGCCGUUAGGCCGAA AAGCAAAA | 1126 |
| 2271 | AAAAACAU U CUUACAUU | 496 | AAUGUAAG CUGAUGAGGCCGUUAGGCCGAA AUGUUUUU | 1127 |
| 2272 | AAAACAUU C UUACAUUU | 497 | AAAUGUAA CUGAUGAGGCCGUUAGGCCGAA AAUGUUUU | 1128 |
| 2274 | AACAUUCU U ACAUUUUA | 498 | UAAAAUGU CUGAUGAGGCCGUUAGGCCGAA AGAAUGUU | 1129 |
| 2275 | ACAUUCUU A CAUUUUAC | 499 | GUAAAAUG CUGAUGAGGCCGUUAGGCCGAA AGAAUGU | 1130 |
| 2279 | UCUUACAU U UACUUUUU | 500 | AAAAGUAA CUGAUGAGGCCGUUAGGCCGAA AUGUAAGA | 1131 |
| 2280 | CUUACAUU U UACUUUUU | 501 | AAAAAGUA CUGAUGAGGCCGUUAGGCCGAA AAUGUAAG | 1132 |
| 2281 | UUACAUUU U ACUUUUCC | 502 | GAAAAGU CUGAUGAGGCCGUUAGGCCGAA AAAUGUAA | 1133 |
| 2282 | UACAUUUU A CUUUUCCU | 503 | GGAAAAG CUGAUGAGGCCGUUAGGCCGAA AAAAUGUA | 1134 |
| 2285 | AUUUUACU U UUCCUGG | 504 | CCAGGAA CUGAUGAGGCCGUUAGGCCGAA AGUAAAAU | 1135 |
| 2286 | UUUUACUU U UCCUGGC | 505 | GCCAGGAA CUGAUGAGGCCGUUAGGCCGAA AAGUAAAA | 1136 |
| 2287 | UUUACUUU U CCUGGCU | 506 | AGCCAGGA CUGAUGAGGCCGUUAGGCCGAA AAAGUAAA | 1137 |
| 2288 | UUACUUUU U CCUGGCUC | 507 | GAGCCAGG CUGAUGAGGCCGUUAGGCCGAA AAAAGUAA | 1138 |

TABLE VIII-continued

Human PKR Hammerhead and Substrate Sequence

| Pos | Substrate | Seq ID | Hammerhead | Seq ID |
|---|---|---|---|---|
| 2289 | UACUUUUU C CUGGCUCA | 508 | UGAGCCAG CUGAUGAGGCCGUUAGGCCGAA AAAAAGUA | 1139 |
| 2296 | UCCUGGCU C AUCUCUUU | 509 | AAAGAGAU CUGAUGAGGCCGUUAGGCCGAA AGCCAGGA | 1140 |
| 2299 | UGGCUCAU C UCUUUAUU | 510 | AAUAAAGA CUGAUGAGGCCGUUAGGCCGAA AUGAGCCA | 1141 |
| 2301 | GCUCAUCU C UUUAUUCU | 511 | AGAAUAAA CUGAUGAGGCCGUUAGGCCGAA AGAUGAGC | 1142 |
| 2303 | UCAUCUCU U UAUUCUUU | 512 | AAAGAAUA CUGAUGAGGCCGUUAGGCCGAA AGAGAUGA | 1143 |
| 2304 | CAUCUCUU U AUUCUUUU | 513 | AAAAGAAU CUGAUGAGGCCGUUAGGCCGAA AAGAGAUG | 1144 |
| 2305 | AUCUCUUU A UUCUUUUU | 514 | AAAAAGAA CUGAUGAGGCCGUUAGGCCGAA AAAGAGAU | 1145 |
| 2307 | CUCUUUAU U CUUUUUUU | 515 | AAAAAAAG CUGAUGAGGCCGUUAGGCCGAA AUAAAGAG | 1146 |
| 2308 | UCUUUAUU C UUUUUUUU | 516 | AAAAAAAA CUGAUGAGGCCGUUAGGCCGAA AAUAAAGA | 1147 |
| 2310 | UUUAUCUU U UUUUUUUU | 517 | AAAAAAAA CUGAUGAGGCCGUUAGGCCGAA AGAAUAAA | 1148 |
| 2311 | UUAUCUUU U UUUUUUUU | 518 | AAAAAAAA CUGAUGAGGCCGUUAGGCCGAA AAGAAUAA | 1149 |
| 2312 | UAUUCUUU U UUUUUUUU | 519 | AAAAAAAA CUGAUGAGGCCGUUAGGCCGAA AAAGAAUA | 1150 |
| 2313 | AUUCUUUU U UUUUUUUU | 520 | AAAAAAAA CUGAUGAGGCCGUUAGGCCGAA AAAAGAAU | 1151 |
| 2314 | UUCUUUUU U UUUUUUUU | 521 | AAAAAAAA CUGAUGAGGCCGUUAGGCCGAA AAAAAGAA | 1152 |
| 2315 | UCUUUUUU U UUUUUUUA | 522 | UAAAAAAA CUGAUGAGGCCGUUAGGCCGAA AAAAAAGA | 1153 |
| 2316 | CUUUUUUU U UUUUUUAA | 523 | UUAAAAAA CUGAUGAGGCCGUUAGGCCGAA AAAAAAAG | 1154 |
| 2317 | UUUUUUUU U UUUUUAAA | 524 | UUUAAAAA CUGAUGAGGCCGUUAGGCCGAA AAAAAAAA | 1155 |
| 2318 | UUUUUUUU U UUUUAAAG | 525 | CUUUAAAA CUGAUGAGGCCGUUAGGCCGAA AAAAAAAA | 1156 |
| 2319 | UUUUUUUU U UUUAAAGA | 526 | UCUUUAAA CUGAUGAGGCCGUUAGGCCGAA AAAAAAAA | 1157 |
| 2320 | UUUUUUUU U UUAAAGAC | 527 | GUCUUUAA CUGAUGAGGCCGUUAGGCCGAA AAAAAAAA | 1158 |
| 2321 | UUUUUUUU U UAAAGACA | 528 | UGUCUUUA CUGAUGAGGCCGUUAGGCCGAA AAAAAAAA | 1159 |
| 2322 | UUUUUUUU U AAAGACAG | 529 | CUGUCUUU CUGAUGAGGCCGUUAGGCCGAA AAAAAAAA | 1160 |
| 2323 | UUUUUUUU A AAGACAGA | 530 | UCUGUCUU CUGAUGAGGCCGUUAGGCCGAA AAAAAAAA | 1161 |
| 2334 | GACAGAGU C UCGCUCUG | 531 | CAGAGCGA CUGAUGAGGCCGUUAGGCCGAA ACUCUGUC | 1162 |
| 2336 | CAGAGUCU C GCUCUGUU | 532 | AACAGAGC CUGAUGAGGCCGUUAGGCCGAA AGACUCUG | 1163 |
| 2340 | GUCUCGCU C UGUUGCCC | 533 | GGGCAACA CUGAUGAGGCCGUUAGGCCGAA AGCGAGAC | 1164 |
| 2344 | CGCUCUGU U GCCCAGGC | 534 | GCCUGGGC CUGAUGAGGCCGUUAGGCCGAA ACAGAGCG | 1165 |
| 2372 | GACACAGU C UUGGCUCA | 535 | UGAGCCAA CUGAUGAGGCCGUUAGGCCGAA ACUGUGUC | 1166 |
| 2374 | CACAGUCU U GGCUCACU | 536 | AGUGAGCC CUGAUGAGGCCGUUAGGCCGAA AGACUGUG | 1167 |
| 2379 | UCUUGGCU C ACUGCAAC | 537 | GUUGCAGU CUGAUGAGGCCGUUAGGCCGAA AGCCAAGA | 1168 |
| 2389 | CUGCAACU U CUGCCUCU | 538 | AGAGGCAG CUGAUGAGGCCGUUAGGCCGAA AGUUGCAG | 1169 |
| 2390 | UGCAACUU C UGCCUCUU | 539 | AAGAGGCA CUGAUGAGGCCGUUAGGCCGAA AAGUUGCA | 1170 |
| 2396 | UUCUGCCU C UUGGGUUC | 540 | GAACCCAA CUGAUGAGGCCGUUAGGCCGAA AGGCAGAA | 1171 |
| 2398 | CUGCCUCU U GGGUUCAA | 541 | UUGAACCC CUGAUGAGGCCGUUAGGCCGAA AGAGGCAG | 1172 |
| 2403 | UCUUGGGU U CAAGUGAU | 542 | AUCACUUG CUGAUGAGGCCGUUAGGCCGAA ACCCAAGA | 1173 |
| 2404 | CUUGGGUU C AAGUGAUU | 543 | AAUCACUU CUGAUGAGGCCGUUAGGCCGAA AACCCAAG | 1174 |
| 2412 | CAAGUGAU U CUCCUGCC | 544 | GGCAGGAG CUGAUGAGGCCGUUAGGCCGAA AUCACUUG | 1175 |
| 2413 | AAGUGAUU C UCCUGCCU | 545 | AGGCAGGA CUGAUGAGGCCGUUAGGCCGAA AAUCACUU | 1176 |
| 2415 | GUGAUUCU C CUGCCUCA | 546 | UGAGGCAG CUGAUGAGGCCGUUAGGCCGAA AGAAUCAC | 1177 |
| 2422 | UCCUGCCU C AGCCUCCU | 547 | AGGAGGCU CUGAUGAGGCCGUUAGGCCGAA AGGCAGGA | 1178 |
| 2428 | CUCAGCCU C CUGAGUAG | 548 | CUACUCAG CUGAUGAGGCCGUUAGGCCGAA AGGCUGAG | 1179 |
| 2435 | UCCUGAGU A GCUGGAUU | 549 | AAUCCAGC CUGAUGAGGCCGUUAGGCCGAA ACUCAGGA | 1180 |
| 2443 | AGCUGGAU U ACAGGCAU | 550 | AUGCCUGU CUGAUGAGGCCGUUAGGCCGAA AUCCAGCU | 1181 |
| 2444 | GCUGGAUU A CAGGCAUG | 551 | CAUGCCUG CUGAUGAGGCCGUUAGGCCGAA AAUCCAGC | 1182 |
| 2469 | ACCCAACU A AUUUUUGU | 552 | ACAAAAAU CUGAUGAGGCCGUUAGGCCGAA AGUUGGGU | 1183 |
| 2472 | CAACUAAU U UUUGUGUU | 553 | AACACAAA CUGAUGAGGCCGUUAGGCCGAA AUUAGUUG | 1184 |
| 2473 | AACUAAUU U UUGUGUUU | 554 | AAACACAA CUGAUGAGGCCGUUAGGCCGAA AAUUAGUU | 1185 |
| 2474 | ACUAAUUU U UGUGUUUU | 555 | AAAACACA CUGAUGAGGCCGUUAGGCCGAA AAAUUAGU | 1186 |
| 2475 | CUAAUUUU U GUGUUUUU | 556 | AAAAACAC CUGAUGAGGCCGUUAGGCCGAA AAAAUUAG | 1187 |
| 2480 | UUUUGUGU U UUUAAUAA | 557 | UUAAUUAA CUGAUGAGGCCGUUAGGCCGAA ACACAAAA | 1188 |
| 2481 | UUUGUGUU U UUAAUAAA | 558 | UUUAUUAA CUGAUGAGGCCGUUAGGCCGAA AACACAAA | 1189 |
| 2482 | UUGUGUUU U UAAUAAAG | 559 | CUUUAUUA CUGAUGAGGCCGUUAGGCCGAA AAACACAA | 1190 |
| 2483 | UGUGUUUU U AAUAAAGA | 560 | UCUUUAUU CUGAUGAGGCCGUUAGGCCGAA AAAACACA | 1191 |
| 2484 | GUGUUUUU A AUAAAGAC | 561 | GUCUUUAU CUGAUGAGGCCGUUAGGCCGAA AAAAACAC | 1192 |
| 2487 | UUUUUAAU A AGACAGG | 562 | CCUGUCUU CUGAUGAGGCCGUUAGGCCGAA AUUAAAAA | 1193 |
| 2498 | GACAGGGU U UCACCAUG | 563 | CAUGGUGA CUGAUGAGGCCGUUAGGCCGAA ACCCUGUC | 1194 |
| 2499 | ACAGGGUU U CACCAUGU | 564 | ACAUGGUG CUGAUGAGGCCGUUAGGCCGAA AACCCUGU | 1195 |
| 2500 | CAGGGUUU C ACCAUGUU | 565 | AACAUGGU CUGAUGAGGCCGUUAGGCCGAA AAACCCUG | 1196 |
| 2508 | CACCAUGU U GGCCAGGC | 566 | GCCUGGCC CUGAUGAGGCCGUUAGGCCGAA ACAUGGUG | 1197 |
| 2521 | AGGCUGGU C UCAAACUC | 567 | GAGUUUGA CUGAUGAGGCCGUUAGGCCGAA ACCAGCCU | 1198 |
| 2523 | GCUGGUCU C AAACUCCU | 568 | AGGAGUUU CUGAUGAGGCCGUUAGGCCGAA AGACCAGC | 1199 |
| 2529 | CUCAAACU C CUGACCUC | 569 | GAGGUCAG CUGAUGAGGCCGUUAGGCCGAA AGUUUGAG | 1200 |
| 2537 | CCUGACCU C AAGUAAUC | 570 | GAUUACUU CUGAUGAGGCCGUUAGGCCGAA AGGUCAGG | 1201 |
| 2542 | CCUCAAGU A AUCCACCU | 571 | AGGUGGAU CUGAUGAGGCCGUUAGGCCGAA ACUUGAGG | 1202 |
| 2545 | CAAGUAAU C CACCUGCC | 572 | GGCAGGUG CUGAUGAGGCCGUUAGGCCGAA AUUACUUG | 1203 |
| 2555 | ACCUGCCU C GGCCUCCC | 573 | GGGAGGCC CUGAUGAGGCCGUUAGGCCGAA AGGCAGGU | 1204 |
| 2561 | CUCGGCCU C CCAAAGUG | 574 | CACUUUGG CUGAUGAGGCCGUUAGGCCGAA AGGCCGAG | 1205 |
| 2577 | GCUGGGAU U ACAGGGAU | 575 | AUCCCUGU CUGAUGAGGCCGUUAGGCCGAA AUCCCAGC | 1206 |
| 2578 | CUGGGAUU A CAGGGAUG | 576 | CAUCCCUG CUGAUGAGGCCGUUAGGCCGAA AAUCCCAG | 1207 |
| 2605 | CCCAGCCU C AUCUCUUU | 577 | AAAGAGAU CUGAUGAGGCCGUUAGGCCGAA AGGCUGGG | 1208 |
| 2608 | AGCCUCAU C UCUUUGUU | 578 | AACAAAGA CUGAUGAGGCCGUUAGGCCGAA AUGAGGCU | 1209 |
| 2610 | CCUCAUCU C UUUGUUCU | 579 | AGAACAAA CUGAUGAGGCCGUUAGGCCGAA AGAUGAGG | 1210 |
| 2612 | UCAUCUCU U UGUUCUAA | 580 | UUAGAACA CUGAUGAGGCCGUUAGGCCGAA AGAGAUGA | 1211 |
| 2613 | CAUCUCUU U GUUCUAAA | 581 | UUUAGAAC CUGAUGAGGCCGUUAGGCCGAA AAGAGAUG | 1212 |
| 2616 | CUCUUUGU U CUAAAGAU | 582 | AUCUUUAG CUGAUGAGGCCGUUAGGCCGAA ACAAAGAG | 1213 |

TABLE VIII-continued

Human PKR Hammerhead and Substrate Sequence

| Pos | Substrate | Seq ID | Hammerhead | Seq ID |
|---|---|---|---|---|
| 2617 | UCUUUGUU C UAAAGAUG | 583 | CAUCUUUA CUGAUGAG<u>GCCGUUAGGC</u>CGAA AACAAAGA | 1214 |
| 2619 | UUUGUUCU A AAGAUGGA | 584 | UCCAUCUU CUGAUGAG<u>GCCGUUAGGC</u>CGAA AGAACAAA | 1215 |
| 2644 | CCCCAAAU U UUCUUUUU | 585 | AAAAAGAA CUGAUGAG<u>GCCGUUAGGC</u>CGAA AUUUGGGG | 1216 |
| 2645 | CCCAAAUU U UCUUUUUA | 586 | UAAAAAGA CUGAUGAG<u>GCCGUUAGGC</u>CGAA AAUUUGGG | 1217 |
| 2646 | CCAAAUUU U CUUUUUAU | 587 | AUAAAAAG CUGAUGAG<u>GCCGUUAGGC</u>CGAA AAAUUUGG | 1218 |
| 2647 | CAAAUUUU C UUUUUAUA | 588 | UAUAAAAA CUGAUGAG<u>GCCGUUAGGC</u>CGAA AAAAUUUG | 1219 |
| 2649 | AAUUUUCU U UUUAUACU | 589 | AGUAUAAA CUGAUGAG<u>GCCGUUAGGC</u>CGAA AGAAAAUU | 1220 |
| 2650 | AUUUUCUU U UUAUACUA | 590 | UAGUAUAA CUGAUGAG<u>GCCGUUAGGC</u>CGAA AAGAAAAU | 1221 |
| 2651 | UUUUCUUU U UAUACUAU | 591 | AUAGUAUA CUGAUGAG<u>GCCGUUAGGC</u>CGAA AAAGAAAA | 1222 |
| 2652 | UUUCUUUU U AUACUAUU | 592 | AAUAGUAU CUGAUGAG<u>GCCGUUAGGC</u>CGAA AAAAGAAA | 1223 |
| 2653 | UUCUUUUU A UACUAUUA | 593 | UAAUAGUA CUGAUGAG<u>GCCGUUAGGC</u>CGAA AAAAAGAA | 1224 |
| 2655 | CUUUUUAU A CUAUUAAU | 594 | AUUAAUAG CUGAUGAG<u>GCCGUUAGGC</u>CGAA AUAAAAAG | 1225 |
| 2658 | UUUAUACU A UUAAUGAA | 595 | UUCAUUAA CUGAUGAG<u>GCCGUUAGGC</u>CGAA AGUAUAAA | 1226 |
| 2660 | UAUACUAU U AAUGAAUC | 596 | GAUUCAUU CUGAUGAG<u>GCCGUUAGGC</u>CGAA AUAGUAUA | 1227 |
| 2661 | AUACUAUU A AUGAAUCA | 597 | UGAUUCAU CUGAUGAG<u>GCCGUUAGGC</u>CGAA AAUAGUAU | 1228 |
| 2668 | UAAUGAAU C AAUCAAUU | 598 | AAUUGAUU CUGAUGAG<u>GCCGUUAGGC</u>CGAA AUUCAUUA | 1229 |
| 2672 | GAAUCAAU C AAUUCAUA | 599 | UAUGAAUU CUGAUGAG<u>GCCGUUAGGC</u>CGAA AUUGAUUC | 1230 |
| 2676 | CAAUCAAU U CAUUCUA | 600 | UAGAUAUG CUGAUGAG<u>GCCGUUAGGC</u>CGAA AUUGAUUG | 1231 |
| 2677 | AAUCAAUU C AUAUCUAU | 601 | AUAGAUAU CUGAUGAG<u>GCCGUUAGGC</u>CGAA AAUUGAUU | 1232 |
| 2680 | CAAUUCAU A UCUAUUUA | 602 | UAAAUAGA CUGAUGAG<u>GCCGUUAGGC</u>CGAA AUGAAUUG | 1233 |
| 2682 | AUUCAUAU C UAUUUAUU | 603 | AAUAAAUA CUGAUGAG<u>GCCGUUAGGC</u>CGAA AUAUGAAU | 1234 |
| 2684 | UCAUAUCU A UUUAUUAA | 604 | UUAAUAAA CUGAUGAG<u>GCCGUUAGGC</u>CGAA AGAUAUGA | 1235 |
| 2686 | AUAUCUAU U UAUUAAAU | 605 | AUUUAAUA CUGAUGAG<u>GCCGUUAGGC</u>CGAA AUAGAUAU | 1236 |
| 2687 | UAUCUAUU U AUUAAAUU | 606 | AAUUUAAU CUGAUGAG<u>GCCGUUAGGC</u>CGAA AAUAGAUA | 1237 |
| 2688 | AUCUAUUU A UUAAAUUU | 607 | AAAUUUAA CUGAUGAG<u>GCCGUUAGGC</u>CGAA AAAUAGAU | 1238 |
| 2690 | CUAUUUAU U AAAUUUCU | 608 | AGAAAUUU CUGAUGAG<u>GCCGUUAGGC</u>CGAA AUAAAUAG | 1239 |
| 2691 | UAUUUAUU A AAUUUCUA | 609 | UAGAAAUU CUGAUGAG<u>GCCGUUAGGC</u>CGAA AAUAAAUA | 1240 |
| 2695 | UAUUAAAU U UCUACCGC | 610 | GCGGUAGA CUGAUGAG<u>GCCGUUAGGC</u>CGAA AUUUAAUA | 1241 |
| 2696 | AUUAAAUU U CUACCGCU | 611 | AGCGGUAG CUGAUGAG<u>GCCGUUAGGC</u>CGAA AAUUUAAU | 1242 |
| 2697 | UUAAAUUU C UACCGCUU | 612 | AAGCGGUA CUGAUGAG<u>GCCGUUAGGC</u>CGAA AAAUUUAA | 1243 |
| 2699 | AAAUUUCU A CCGCUUUU | 613 | AAAAGCGG CUGAUGAG<u>GCCGUUAGGC</u>CGAA AGAAAUUU | 1244 |
| 2705 | CUACCGCU U UUAGGCCA | 614 | UGGCCUAA CUGAUGAG<u>GCCGUUAGGC</u>CGAA AGCGGUAG | 1245 |
| 2706 | UACCGCUU U UAGGCCAA | 615 | UUGGCCUA CUGAUGAG<u>GCCGUUAGGC</u>CGAA AAGCGGUA | 1246 |
| 2707 | ACCGCUUU U AGGCCAAA | 616 | UUUGGCCU CUGAUGAG<u>GCCGUUAGGC</u>CGAA AAAGCGGU | 1247 |
| 2708 | CCGCUUUU A GGCCAAAA | 617 | UUUUGGCC CUGAUGAG<u>GCCGUUAGGC</u>CGAA AAAAGCGG | 1248 |
| 2723 | AAAAAUGU A AGAUCGUU | 618 | AACGAUCU CUGAUGAG<u>GCCGUUAGGC</u>CGAA ACAUUUUU | 1249 |
| 2728 | UGUAAGAU C GUUCUCUG | 619 | CAGAGAAC CUGAUGAG<u>GCCGUUAGGC</u>CGAA AUCUUACA | 1250 |
| 2731 | AAGAUCGU U CUCUGCCU | 620 | AGGCAGAG CUGAUGAG<u>GCCGUUAGGC</u>CGAA ACGAUCUU | 1251 |
| 2732 | AGAUCGUU C UCUGCCUC | 621 | GAGGCAGA CUGAUGAG<u>GCCGUUAGGC</u>CGAA AACGAUCU | 1252 |
| 2734 | AUCGUUCU C UGCCUCAC | 622 | GUGAGGCA CUGAUGAG<u>GCCGUUAGGC</u>CGAA AGAACGAU | 1253 |
| 2740 | CUCUGCCU C ACAUAGCU | 623 | AGCUAUGU CUGAUGAG<u>GCCGUUAGGC</u>CGAA AGGCAGAG | 1254 |
| 2745 | CCUCACAU A GCUUACAA | 624 | UUGUAAGC CUGAUGAG<u>GCCGUUAGGC</u>CGAA AUGUGAGG | 1255 |
| 2749 | ACAUAGCU U ACAAGCCA | 625 | UGGCUUGU CUGAUGAG<u>GCCGUUAGGC</u>CGAA AGCUAUGU | 1256 |
| 2750 | CAUAGCUU A CAAGCCAG | 626 | CUGGCUUG CUGAUGAG<u>GCCGUUAGGC</u>CGAA AAGCUAUG | 1257 |
| 2769 | GGAGAAAU A UGGUACUC | 627 | GAGUACCA CUGAUGAG<u>GCCGUUAGGC</u>CGAA AUUUCUCC | 1258 |
| 2774 | AAUAUGGU A CUCAUUAA | 628 | UUAAUGAG CUGAUGAG<u>GCCGUUAGGC</u>CGAA ACCAUAUU | 1259 |
| 2777 | AUGGUACU C AUUAAAAA | 629 | UUUUUAAU CUGAUGAG<u>GCCGUUAGGC</u>CGAA AGUACCAU | 1260 |
| 2780 | GUACUCAU U AAAAAAAA | 630 | UUUUUUUU CUGAUGAG<u>GCCGUUAGGC</u>CGAA AUGAGUAC | 1261 |
| 2781 | UACUCAUU A AAAAAAA | 631 | UUUUUUUU CUGAUGAG<u>GCCGUUAGGC</u>CGAA AAUGAGUA | 1262 |

Input Sequence = NM_002759. Cut Site = UH/.
Arm Length = 8. Core Sequence = CUGAUGAG <u>GCCGUUAGGC</u> CGAA NM_002759 (*Homo sapiens* protein kinase, interferon-inducible double stranded RNA dependent (PRKR), mRNA.; 2808 bp)

50

Underlined region can be any X sequence or linker, as described herein.

TABLE IX

Human PKR Inozyme and Substrate Sequence

| Pos | Substrate | Seq ID | Inozyme | Seq ID |
|---|---|---|---|---|
| 17 | GGCGGCGC A GUUUGCUC | 1263 | GAGCAAAC CUGAUGAG<u>GCCGUUAGGC</u>CGAA ICGCCGCC | 1762 |
| 24 | CAGUUUGC U CAUACUUU | 1264 | AAAGUAUG CUGAUGAG<u>GCCGUUAGGC</u>CGAA ICAAACUG | 1763 |
| 26 | GUUUGCUC A UACUUUGU | 1265 | ACAAAGUA CUGAUGAG<u>GCCGUUAGGC</u>CGAA IAGCAAAC | 1764 |
| 30 | GCUCAUAC U UUGUGACU | 1266 | AGUCACAA CUGAUGAG<u>GCCGUUAGGC</u>CGAA IUAUGAGC | 1765 |
| 38 | UUUGUGAC U UGCGGUCA | 1267 | UGACCGCA CUGAUGAG<u>GCCGUUAGGC</u>CGAA IUCACAAA | 1766 |
| 46 | UUGCGGUC A CAGUGGCA | 1268 | UGCCACUG CUGAUGAG<u>GCCGUUAGGC</u>CGAA IACCGCAA | 1767 |
| 48 | GCGGUCAC A GUGGCAUU | 1269 | AAUGCCAC CUGAUGAG<u>GCCGUUAGGC</u>CGAA IUGACCGC | 1768 |
| 54 | ACAGUGGC A UUCAGCUC | 1270 | GAGCUGAA CUGAUGAG<u>GCCGUUAGGC</u>CGAA ICCACUGU | 1769 |

TABLE IX-continued

Human PKR Inozyme and Substrate Sequence

| Pos | Substrate | Seq ID | Inozyme | Seq ID |
|---|---|---|---|---|
| 58 | UGGCAUUC A GCUCCACA | 1271 | UGUGGAGC CUGAUGAGGCCGUUAGGCCGAA IAAUGCCA | 1770 |
| 61 | CAUUCAGC U CCACACUU | 1272 | AAGUGUGG CUGAUGAGGCCGUUAGGCCGAA ICUGAAUG | 1771 |
| 63 | UUCAGCUC C ACACUUGG | 1273 | CCAAGUGU CUGAUGAGGCCGUUAGGCCGAA IAGCUGAA | 1772 |
| 64 | UCAGCUCC A CACUUGGU | 1274 | ACCAAGUG CUGAUGAGGCCGUUAGGCCGAA IGAGCUGA | 1773 |
| 66 | AGCUCCAC A CUUGGUAG | 1275 | CUACCAAG CUGAUGAGGCCGUUAGGCCGAA IUGGAGCU | 1774 |
| 68 | CUCCACAC U UGGUAGAA | 1276 | UUCUACCA CUGAUGAGGCCGUUAGGCCGAA IUGUGGAG | 1775 |
| 78 | GGUAGAAC C ACAGGCAC | 1277 | GUGCCUGU CUGAUGAGGCCGUUAGGCCGAA IUUCUACC | 1776 |
| 79 | GUAGAACC A CAGGCACG | 1278 | CGUGCCUG CUGAUGAGGCCGUUAGGCCGAA IGUUCUAC | 1777 |
| 81 | AGAACCAC A GGCACGAC | 1279 | GUCGUGCC CUGAUGAGGCCGUUAGGCCGAA IUGGUUCU | 1778 |
| 85 | CCACAGGC A CGACAAGC | 1280 | GCUUGUCG CUGAUGAGGCCGUUAGGCCGAA ICCUGUGG | 1779 |
| 90 | GGCACGAC A AGCAUAGA | 1281 | UCUAUGCU CUGAUGAGGCCGUUAGGCCGAA IUCGUGCC | 1780 |
| 94 | CGACAAGC A UAGAAACA | 1282 | UGUUUCUA CUGAUGAGGCCGUUAGGCCGAA ICUUGUCG | 1781 |
| 102 | AUAGAAAC A UCCUAAAC | 1283 | GUUUAGGA CUGAUGAGGCCGUUAGGCCGAA IUUUCUAU | 1782 |
| 105 | GAAACAUC C UAAACAAU | 1284 | AUUGUUUA CUGAUGAGGCCGUUAGGCCGAA IAUGUUUC | 1783 |
| 106 | AAACAUCC U AAACAAUC | 1285 | GAUUGUUU CUGAUGAGGCCGUUAGGCCGAA IGAUGUUU | 1784 |
| 111 | UCCUAAAC A AUCUUCAU | 1286 | AUGAAGAU CUGAUGAGGCCGUUAGGCCGAA IUUUAGGA | 1785 |
| 115 | AAACAUC U UCAUCGAG | 1287 | CUCGAUGA CUGAUGAGGCCGUUAGGCCGAA IAUUGUUU | 1786 |
| 118 | CAAUCUUC A UCGAGGCA | 1288 | UGCCUCGA CUGAUGAGGCCGUUAGGCCGAA IAAGAUUG | 1787 |
| 126 | AUCGAGGC A UCGAGGUC | 1289 | GACCUCGA CUGAUGAGGCCGUUAGGCCGAA ICCUCGAU | 1788 |
| 135 | UCGAGGUC C AUCCCAAU | 1290 | AUUGGGAU CUGAUGAGGCCGUUAGGCCGAA IACCUCGA | 1789 |
| 136 | CGAGGUCC A UCCCAUA | 1291 | UAUUGGGA CUGAUGAGGCCGUUAGGCCGAA IGACCUCG | 1790 |
| 139 | GGUCCAUC C CAAUAAAA | 1292 | UUUUAUUG CUGAUGAGGCCGUUAGGCCGAA IAUGGACC | 1791 |
| 140 | GUCCAUCC C AAUAAAAA | 1293 | UUUUUAUU CUGAUGAGGCCGUUAGGCCGAA IGAUGGAC | 1792 |
| 141 | UCCAUCCC A AUAAAAAU | 1294 | AUUUUUAU CUGAUGAGGCCGUUAGGCCGAA IGGAUGGA | 1793 |
| 151 | UAAAAAUC G GGAGACCC | 1295 | GGGUCUCC CUGAUGAGGCCGUUAGGCCGAA IAUUUUUA | 1794 |
| 158 | CAGGAGAC C CUGGCUAU | 1296 | AUAGCCAG CUGAUGAGGCCGUUAGGCCGAA IUCUCCUG | 1795 |
| 159 | AGGAGACC C UGGCUAUC | 1297 | GAUAGCCA CUGAUGAGGCCGUUAGGCCGAA IGUCUCCU | 1796 |
| 160 | GGAGACCC U GGCUAUCA | 1298 | UGAUAGCC CUGAUGAGGCCGUUAGGCCGAA IGGUCUCC | 1797 |
| 164 | ACCCUGGC U AUCAUAGA | 1299 | UCUAUGAU CUGAUGAGGCCGUUAGGCCGAA ICCAGGGU | 1798 |
| 168 | UGGCUAUC A UAGACCUU | 1300 | AAGGUCUA CUGAUGAGGCCGUUAGGCCGAA IAUAGCCA | 1799 |
| 174 | UCAUAGAC C UUAGUCUU | 1301 | AAGACUAA CUGAUGAGGCCGUUAGGCCGAA IUCUAUGA | 1800 |
| 175 | CAUAGACC U UAGUCUUC | 1302 | GAAGACUA CUGAUGAGGCCGUUAGGCCGAA IGUCUAUG | 1801 |
| 181 | CCUUAGUC U UCGCUGGU | 1303 | ACCAGCGA CUGAUGAGGCCGUUAGGCCGAA IACUAAGG | 1802 |
| 186 | GUCUUCGC U GGUAUACU | 1304 | AGUAUACC CUGAUGAGGCCGUUAGGCCGAA ICGAAGAC | 1803 |
| 194 | UGGUAUAC U CGCUGUCU | 1305 | AGACAGCG CUGAUGAGGCCGUUAGGCCGAA IUAUACCA | 1804 |
| 198 | AUACUCGC U GUCUGUCA | 1306 | UGACAGAC CUGAUGAGGCCGUUAGGCCGAA ICGAGUAU | 1805 |
| 202 | UCGCUGUC U GUCAACCA | 1307 | UGGUUGAC CUGAUGAGGCCGUUAGGCCGAA IACAGCGA | 1806 |
| 206 | UGUCUGUC A ACCAGCGG | 1308 | CCGCUGGU CUGAUGAGGCCGUUAGGCCGAA IACAGACA | 1807 |
| 209 | CUGUCAAC C AGCGGUUG | 1309 | CAACCGCU CUGAUGAGGCCGUUAGGCCGAA IUUGACAG | 1808 |
| 210 | UGUCAACC A GCGGUUGA | 1310 | UCAACCGC CUGAUGAGGCCGUUAGGCCGAA IGUUGACA | 1809 |
| 220 | CGGUUGAC U UUUUUUAA | 1311 | UUAAAAAA CUGAUGAGGCCGUUAGGCCGAA IUCAACCG | 1810 |
| 231 | UUUUAAGC U UUCUUUUU | 1312 | AAAAAGAA CUGAUGAGGCCGUUAGGCCGAA ICUUAAAA | 1811 |
| 232 | UUUAAGCC U UCUUUUUC | 1313 | AAAAAAGA CUGAUGAGGCCGUUAGGCCGAA IGCUUAAA | 1812 |
| 235 | AAGCCUUC U UUUUCUC | 1314 | GAGAAAAA CUGAUGAGGCCGUUAGGCCGAA IAAGGCUU | 1813 |
| 242 | CUUUUUUC U CUUUUACC | 1315 | GGUAAAAG CUGAUGAGGCCGUUAGGCCGAA IAAAAAAG | 1814 |
| 244 | UUUUUCUC U UUUACCAG | 1316 | CUGGUAAA CUGAUGAGGCCGUUAGGCCGAA IAGAAAAA | 1815 |
| 250 | UCUUUUAC C AGUUUCUG | 1317 | CAGAAACU CUGAUGAGGCCGUUAGGCCGAA IUAAAAGA | 1816 |
| 251 | CUUUUACC A GUUUCUGG | 1318 | CCAGAAAC CUGAUGAGGCCGUUAGGCCGAA IGUAAAAG | 1817 |
| 257 | CCAGUUUC U GGAGCAAA | 1319 | UUUGCUCC CUGAUGAGGCCGUUAGGCCGAA IAAACUGG | 1818 |
| 263 | UCUGGAGC A AAUUCAGU | 1320 | ACUGAAUU CUGAUGAGGCCGUUAGGCCGAA ICUCCAGA | 1819 |
| 269 | GCAAAUUC A GUUGCCU | 1321 | AGGCAAAC CUGAUGAGGCCGUUAGGCCGAA IAAUUUGC | 1820 |
| 276 | CAGUUUGC C UUCCUGGA | 1322 | UCCAGGAA CUGAUGAGGCCGUUAGGCCGAA ICAAACUG | 1821 |
| 277 | AGUUUGCC U UCCUGGAU | 1323 | AUCCAGGA CUGAUGAGGCCGUUAGGCCGAA IGCAAACU | 1822 |
| 280 | UUGCCUUC C UGGAUUUG | 1324 | CAAAUCCA CUGAUGAGGCCGUUAGGCCGAA IAAGGCAA | 1823 |
| 281 | UGCCUUCC U GGAUUUGU | 1325 | ACAAAUCC CUGAUGAGGCCGUUAGGCCGAA IGAAGGCA | 1824 |
| 303 | GUAAUGAC C UCAAAACU | 1326 | AGUUUUGA CUGAUGAGGCCGUUAGGCCGAA IUCAUUAC | 1825 |
| 304 | UAAUGACC U CAAAACUU | 1327 | AAGUUUUG CUGAUGAGGCCGUUAGGCCGAA IGUCAUUA | 1826 |
| 306 | AUGACCUC A AAACUUUA | 1328 | UAAAGUUU CUGAUGAGGCCGUUAGGCCGAA IAGGUCAU | 1827 |
| 311 | CUCAAAAC U UUAGCAGU | 1329 | ACUGCUAA CUGAUGAGGCCGUUAGGCCGAA IUUUUGAG | 1828 |
| 317 | ACUUUAGC A GUUCUUCC | 1330 | GGAAGAAC CUGAUGAGGCCGUUAGGCCGAA ICUAAAGU | 1829 |
| 322 | AGCAGUUC U UCCAUCUG | 1331 | CAGAUGGA CUGAUGAGGCCGUUAGGCCGAA IAACUGCU | 1830 |
| 325 | AGUUCUUC C AUCUGACU | 1332 | AGUCAGAU CUGAUGAGGCCGUUAGGCCGAA IAAGAACU | 1831 |
| 326 | GUUCUUCC A UCUGACUC | 1333 | GAGUCAGA CUGAUGAGGCCGUUAGGCCGAA IGAAGAAC | 1832 |
| 329 | CUUCCAUC U GACUCAGG | 1334 | CCUGAGUC CUGAUGAGGCCGUUAGGCCGAA IAUGGAAG | 1833 |
| 333 | CAUCUGAC U CAGGUUUG | 1335 | CAAACCUG CUGAUGAGGCCGUUAGGCCGAA IUCAGAUG | 1834 |
| 335 | UCUGACUC A GGUUUGCU | 1336 | AGCAAACC CUGAUGAGGCCGUUAGGCCGAA IAGUCAGA | 1835 |
| 343 | AGGUUUGC U UCUCUGGC | 1337 | GCCAGAGA CUGAUGAGGCCGUUAGGCCGAA ICAAACCU | 1836 |
| 346 | UUUGCUUC U CUGGCGGU | 1338 | ACCGCCAG CUGAUGAGGCCGUUAGGCCGAA IAAGCAAA | 1837 |
| 348 | UGCUUCUC U GGCGGUCU | 1339 | AGACCGCC CUGAUGAGGCCGUUAGGCCGAA IAGAAGCA | 1838 |
| 356 | UGGCGGUC U UCAGAAUC | 1340 | GAUUCUGA CUGAUGAGGCCGUUAGGCCGAA IACCGCCA | 1839 |
| 359 | CGGUCUUC U GAAUCAC | 1341 | GUUGAUUC CUGAUGAGGCCGUUAGGCCGAA IAAGACCG | 1840 |
| 365 | UCAGAAUC A ACAUCCAC | 1342 | GUGGAUGU CUGAUGAGGCCGUUAGGCCGAA IAUUCUGA | 1841 |
| 368 | GAAUCAAC A UCCACACU | 1343 | AGUGUGGA CUGAUGAGGCCGUUAGGCCGAA IUUGAUUC | 1842 |
| 371 | UCAACAUC C ACACUUCC | 1344 | GGAAGUGU CUGAUGAGGCCGUUAGGCCGAA IAUGUUGA | 1843 |
| 372 | CAACAUCC A CACUUCCG | 1345 | CGGAAGUG CUGAUGAGGCCGUUAGGCCGAA IGAUGUUG | 1844 |

TABLE IX-continued

Human PKR Inozyme and Substrate Sequence

| Pos | Substrate | Seq ID | Inozyme | Seq ID |
|---|---|---|---|---|
| 374 | ACAUCCAC A CUUCCGUG | 1346 | CACGGAAG CUGAUGAGGCCGUUAGGCCGAA IUGGAUGU | 1845 |
| 376 | AUCCACAC U UCCGUGAU | 1347 | AUCACGGA CUGAUGAGGCCGUUAGGCCGAA IUGUGGAU | 1846 |
| 379 | CACACUUC C GUGAUUAU | 1348 | AUAAUCAC CUGAUGAGGCCGUUAGGCCGAA IAAGUGUG | 1847 |
| 389 | UGAUUAUC U GCGUGCAU | 1349 | AUGCACGC CUGAUGAGGCCGUUAGGCCGAA IAUAAUCA | 1848 |
| 396 | CUGCGUGC A UUUUGGAC | 1350 | GUCCAAAA CUGAUGAGGCCGUUAGGCCGAA ICACGCAG | 1849 |
| 405 | UUUUGGAC A AAGCUUCC | 1351 | GGAAGCUU CUGAUGAGGCCGUUAGGCCGAA IUCCAAAA | 1850 |
| 410 | GACAAAGC U UCCAACCA | 1352 | UGGUUGGA CUGAUGAGGCCGUUAGGCCGAA ICUUUGUC | 1851 |
| 413 | AAAGCUUC C AACCAGGA | 1353 | UCCUGGUU CUGAUGAGGCCGUUAGGCCGAA IAAGCUUU | 1852 |
| 414 | AAGCUUCC A ACCAGGAU | 1354 | AUCCUGGU CUGAUGAGGCCGUUAGGCCGAA IGAAGCUU | 1853 |
| 417 | CUUCCAAC C AGGAUACG | 1355 | CGUAUCCU CUGAUGAGGCCGUUAGGCCGAA IUUGGAAG | 1854 |
| 418 | UUCCAACC A GGAUACGG | 1356 | CCGUAUCC CUGAUGAGGCCGUUAGGCCGAA IGUUGGAA | 1855 |
| 441 | GAAAUGGC U GGUGAUCU | 1357 | AGAUCACC CUGAUGAGGCCGUUAGGCCGAA ICCAUUUC | 1856 |
| 449 | UGGUGAUC U UUCAGCAG | 1358 | CUGCUGAA CUGAUGAGGCCGUUAGGCCGAA IAUCACCA | 1857 |
| 453 | GAUCUUUC A GCAGGUUU | 1359 | AAACCUGC CUGAUGAGGCCGUUAGGCCGAA IAAAGAUC | 1858 |
| 456 | CUUUCAGC A GGUUUCUU | 1360 | AAGAAACC CUGAUGAGGCCGUUAGGCCGAA ICUGAAAG | 1859 |
| 463 | CAGGUUUC U UCAUGGAG | 1361 | CUCCAUGA CUGAUGAGGCCGUUAGGCCGAA IAAACCUG | 1860 |
| 466 | GUUUCUUC A UGGAGGAA | 1362 | UUCCUCCA CUGAUGAGGCCGUUAGGCCGAA IAAGAAAC | 1861 |
| 476 | GGAGGAAC U UAAUACAU | 1363 | AUGUAUUA CUGAUGAGGCCGUUAGGCCGAA IUUCCUCC | 1862 |
| 483 | CUUAAUAC A UACCGUCA | 1364 | UGACGGUA CUGAUGAGGCCGUUAGGCCGAA IUAUUAAG | 1863 |
| 487 | AUACAUAC C GUCAGAAG | 1365 | CUUCUGAC CUGAUGAGGCCGUUAGGCCGAA IUAUGUAU | 1864 |
| 491 | AUACCGUC A GAAGCAGG | 1366 | CCUGCUUC CUGAUGAGGCCGUUAGGCCGAA IACGGUAU | 1865 |
| 497 | UCAGAAGC A GGGAGUAG | 1367 | CUACUCCC CUGAUGAGGCCGUUAGGCCGAA ICUUCUGA | 1866 |
| 509 | AGUAGUAC U UAAAUAUC | 1368 | GAUAUUUA CUGAUGAGGCCGUUAGGCCGAA IUACUACU | 1867 |
| 518 | UAAAUAUC A AGAACUGC | 1369 | GCAGUUCU CUGAUGAGGCCGUUAGGCCGAA IAUAUUUA | 1868 |
| 524 | UCAAGAAC U GCCUAAUU | 1370 | AAUUAGGC CUGAUGAGGCCGUUAGGCCGAA IUUCUUGA | 1869 |
| 527 | AGAACUGC C UAAUUCAG | 1371 | CUGAAUUA CUGAUGAGGCCGUUAGGCCGAA ICAGUUCU | 1870 |
| 528 | GAACUGCC U AAUUCAGG | 1372 | CCUGAAUU CUGAUGAGGCCGUUAGGCCGAA IGCAGUUC | 1871 |
| 534 | CCUAAUUC A GGACCUCC | 1373 | GGAGGUCC CUGAUGAGGCCGUUAGGCCGAA IAAUUAGG | 1872 |
| 539 | UUCAGGAC C UCCACAUG | 1374 | CAUGUGGA CUGAUGAGGCCGUUAGGCCGAA IUCCUGAA | 1873 |
| 540 | UCAGGACC U CCACAUGA | 1375 | UCAUGUGG CUGAUGAGGCCGUUAGGCCGAA IGUCCUGA | 1874 |
| 542 | AGGACCUC C ACAUGAUA | 1376 | UAUCAUGU CUGAUGAGGCCGUUAGGCCGAA IAGGUCCU | 1875 |
| 543 | GGACCUCC A CAUGAUAG | 1377 | CUAUCAUG CUGAUGAGGCCGUUAGGCCGAA IGAGGUCC | 1876 |
| 545 | ACCUCCAC A UGAUAGGA | 1378 | UCCUAUCA CUGAUGAGGCCGUUAGGCCGAA IUGGAGGU | 1877 |
| 561 | AGGUUUAC A UUUCAAGU | 1379 | ACUUGAAA CUGAUGAGGCCGUUAGGCCGAA IUAAACCU | 1878 |
| 566 | UACAUUUC A AGUUAUAA | 1380 | UUAUAACU CUGAUGAGGCCGUUAGGCCGAA IAAAUGUA | 1879 |
| 593 | AGAAUUUC C AGAAGGUG | 1381 | CACCUUCU CUGAUGAGGCCGUUAGGCCGAA IAAAUUCU | 1880 |
| 594 | GAAUUUCC A GAAGGUGA | 1382 | UCACCUUC CUGAUGAGGCCGUUAGGCCGAA IGAAAUUC | 1881 |
| 612 | GGUAGAUC A AAGAAGGA | 1383 | UCCUUCUU CUGAUGAGGCCGUUAGGCCGAA IAUCUACC | 1882 |
| 624 | AAGGAAGC A AAAAAUGC | 1384 | GCAUUUUU CUGAUGAGGCCGUUAGGCCGAA ICUUCCUU | 1883 |
| 633 | AAAAAUGC C GCAGCCAA | 1385 | UUGGCUGC CUGAUGAGGCCGUUAGGCCGAA ICAUUUUU | 1884 |
| 636 | AAUGCCGC A GCCAAAUU | 1386 | AAUUUGGC CUGAUGAGGCCGUUAGGCCGAA ICGGCAUU | 1885 |
| 639 | GCCGCAGC C AAAUUAGC | 1387 | GCUAAUUU CUGAUGAGGCCGUUAGGCCGAA ICUGCGGC | 1886 |
| 640 | CCGCAGCC A AAUUAGCU | 1388 | AGCUAAUU CUGAUGAGGCCGUUAGGCCGAA IGCUGCGG | 1887 |
| 648 | AAAUUAGC U GUUGAGAU | 1389 | AUCUCAAC CUGAUGAGGCCGUUAGGCCGAA ICUAAUUU | 1888 |
| 659 | UGAGAUAC U UAAUAAGG | 1390 | CCUUAUUA CUGAUGAGGCCGUUAGGCCGAA IUAUCUCA | 1889 |
| 678 | AAGAAGGC A GUUAGUCC | 1391 | GGACUAAC CUGAUGAGGCCGUUAGGCCGAA ICCUUCUU | 1890 |
| 686 | AGUUAGUC C UUUAUUAU | 1392 | AUAAUAAA CUGAUGAGGCCGUUAGGCCGAA IACUAACU | 1891 |
| 687 | GUUAGUCC U UUAUUAUU | 1393 | AAUAAUAA CUGAUGAGGCCGUUAGGCCGAA IGACUAAC | 1892 |
| 699 | UUAUUGAC A ACAACGAA | 1394 | UUCGUUGU CUGAUGAGGCCGUUAGGCCGAA IUCAAUAA | 1893 |
| 702 | UUGACAAC A ACGAAUUC | 1395 | GAAUUCGU CUGAUGAGGCCGUUAGGCCGAA IUUGUCAA | 1894 |
| 711 | ACGAAUUC U UCAGAAGG | 1396 | CCUUCUGA CUGAUGAGGCCGUUAGGCCGAA IAAUUCGU | 1895 |
| 714 | AAUUCUUC A GAAGGAUU | 1397 | AAUCCUUC CUGAUGAGGCCGUUAGGCCGAA IAAGAAUU | 1896 |
| 726 | GGAUUAUC C AUGGGAAA | 1398 | UUCCCAUU CUGAUGAGGCCGUUAGGCCGAA IAUAAUCC | 1897 |
| 727 | GAUUAUCC A UGGGGAAU | 1399 | AUUCCCCA CUGAUGAGGCCGUUAGGCCGAA IGAUAAUC | 1898 |
| 739 | GGAUUAC A UAGGCCUU | 1400 | AAGGCCUA CUGAUGAGGCCGUUAGGCCGAA IUAAUUCC | 1899 |
| 745 | ACAUAGGC C UUAUCAUU | 1401 | AUUGAUAA CUGAUGAGGCCGUUAGGCCGAA ICCUAUGU | 1900 |
| 746 | CAUAGGCC U UAUCAUAA | 1402 | UAUUGAUA CUGAUGAGGCCGUUAGGCCGAA IGCCUAUG | 1901 |
| 751 | GCCUUAUC A UAGAAUU | 1403 | AAUUCUAU CUGAUGAGGCCGUUAGGCCGAA IAUAAGGC | 1902 |
| 762 | AGAAUUGC C CAGAAGAA | 1404 | UUCUUCUG CUGAUGAGGCCGUUAGGCCGAA ICAAUUCU | 1903 |
| 763 | GAAUUGCC C AGAAGAAA | 1405 | UUUCUUCU CUGAUGAGGCCGUUAGGCCGAA IGCAAUUC | 1904 |
| 764 | AAUUGCCC A GAAGAAAA | 1406 | UUUUCUUC CUGAUGAGGCCGUUAGGCCGAA IGGCAAUU | 1905 |
| 776 | GAAAAGAC U AACUGUAA | 1407 | UUACAGUU CUGAUGAGGCCGUUAGGCCGAA IUCUUUUC | 1906 |
| 780 | AGACUAAC U GUAAAUUA | 1408 | UAAUUUAC CUGAUGAGGCCGUUAGGCCGAA IUUAGUCU | 1907 |
| 794 | UUAUGAAC A GUGUGCAU | 1409 | AUGCACAC CUGAUGAGGCCGUUAGGCCGAA IUUCAUAA | 1908 |
| 801 | CAGUGUGC A UCGGGGGU | 1410 | ACCCCCGA CUGAUGAGGCCGUUAGGCCGAA ICACACUG | 1909 |
| 812 | GGGGGUGC A UGGGCCAG | 1411 | CUGGCCCA CUGAUGAGGCCGUUAGGCCGAA ICACCCCC | 1910 |
| 818 | GCAUGGGC C AGAAGGAU | 1412 | AUCCUUCU CUGAUGAGGCCGUUAGGCCGAA ICCCAUGC | 1911 |
| 819 | CAUGGGCC A GAAGGAUU | 1413 | AAUCCUUC CUGAUGAGGCCGUUAGGCCGAA IGCCCAUG | 1912 |
| 830 | AGGAUUUC A UUAUAAAU | 1414 | AUUUAUAA CUGAUGAGGCCGUUAGGCCGAA IAAAUCCU | 1913 |
| 841 | AUAAAUGC A AAAUGGGA | 1415 | UCCCAUUU CUGAUGAGGCCGUUAGGCCGAA ICAUUUAU | 1914 |
| 851 | AAUGGGAC A GAAAGAAU | 1416 | AUUCUUUC CUGAUGAGGCCGUUAGGCCGAA IUCCCAUU | 1915 |
| 873 | AUUGGUAC A GGUUCUAC | 1417 | GUAGAACC CUGAUGAGGCCGUUAGGCCGAA IACCAAU | 1916 |
| 879 | ACAGGUUC U ACAAACA | 1418 | UGUUUAGU CUGAUGAGGCCGUUAGGCCGAA IAACCUGU | 1917 |
| 882 | GGUUCUAC U AAACAGGA | 1419 | UCCUGUUU CUGAUGAGGCCGUUAGGCCGAA IUAGAACC | 1918 |
| 887 | UACUAAAC A GGAAGCAA | 1420 | UUGCUUCC CUGAUGAGGCCGUUAGGCCGAA IUUUAGUA | 1919 |

TABLE IX-continued

Human PKR Inozyme and Substrate Sequence

| Pos | Substrate | Seq ID | Inozyme | Seq ID |
|---|---|---|---|---|
| 894 | CAGGAAGC A AAACAAUU | 1421 | AAUUGUUU CUGAUGAGGCCGUUAGGCCGAA ICUUCCUG | 1920 |
| 899 | AGCAAAAC A AUUGGCCG | 1422 | CGGCCAAU CUGAUGAGGCCGUUAGGCCGAA IUUUUGCU | 1921 |
| 906 | CAAUUGGC C GCUAAACU | 1423 | AGUUUAGC CUGAUGAGGCCGUUAGGCCGAA ICCAAUUG | 1922 |
| 909 | UUGGCCGC U AAACUUGC | 1424 | GCAAGUUU CUGAUGAGGCCGUUAGGCCGAA ICGGCCAA | 1923 |
| 914 | CGCUAAAC U UGCAUAUC | 1425 | GAUAUGCA CUGAUGAGGCCGUUAGGCCGAA IUUUAGCG | 1924 |
| 918 | AAACUUGC A UAUCUUCA | 1426 | UGAAGAUA CUGAUGAGGCCGUUAGGCCGAA ICAAGUUU | 1925 |
| 923 | UGCAUAUC U UCAGAUAU | 1427 | AUAUCUGA CUGAUGAGGCCGUUAGGCCGAA IAUAUGCA | 1926 |
| 926 | AUAUCUUC A GAUAUUAU | 1428 | AUAAUAUC CUGAUGAGGCCGUUAGGCCGAA IAAGAUAU | 1927 |
| 936 | AUAUUAUC A GAAGAAAC | 1429 | GUUUCUUC CUGAUGAGGCCGUUAGGCCGAA IAUAAUAU | 1928 |
| 945 | GAAGAAAC C UCAGUGAA | 1430 | UUCACUGA CUGAUGAGGCCGUUAGGCCGAA IUUUCUUC | 1929 |
| 946 | AAGAAACC U CAGUGAAA | 1431 | UUUCACUG CUGAUGAGGCCGUUAGGCCGAA IGUUUCUU | 1930 |
| 948 | GAAACCUC A GUGAAAUC | 1432 | GAUUUCAC CUGAUGAGGCCGUUAGGCCGAA IAGGUUUC | 1931 |
| 957 | GUGAAAUC U GACUACCU | 1433 | AGGUAGUC CUGAUGAGGCCGUUAGGCCGAA IAUUUCAC | 1932 |
| 961 | AAUCUGAC U ACCUGUCC | 1434 | GGACAGGU CUGAUGAGGCCGUUAGGCCGAA IUCAGAUU | 1933 |
| 964 | CUGACUAC C UGUCCUCU | 1435 | AGAGGACA CUGAUGAGGCCGUUAGGCCGAA IUAGUCAG | 1934 |
| 965 | UGACUACC U GUCCUCUG | 1436 | CAGAGGAC CUGAUGAGGCCGUUAGGCCGAA IGUAGUCA | 1935 |
| 969 | UACCUGUC C UCGGUUCU | 1437 | GAACCAGA CUGAUGAGGCCGUUAGGCCGAA IACAGGUA | 1936 |
| 970 | ACCUGUCC U CGGUUCUU | 1438 | AGAACCAG CUGAUGAGGCCGUUAGGCCGAA IGACAGGU | 1937 |
| 972 | CUGUCCUC U GGUUCUUU | 1439 | AAAGAACC CUGAUGAGGCCGUUAGGCCGAA IAGGACAG | 1938 |
| 978 | UCGGUUCU U UUUGCUAC | 1440 | GUAGCAAA CUGAUGAGGCCGUUAGGCCGAA IAACCAGA | 1939 |
| 984 | UCUUUUGC U ACUACGUG | 1441 | CACGUAGU CUGAUGAGGCCGUUAGGCCGAA ICAAAAGA | 1940 |
| 987 | UUUGCUAC U ACGUGUGA | 1442 | UCACACGU CUGAUGAGGCCGUUAGGCCGAA IUAGCAAA | 1941 |
| 999 | UGUGAGUC C AAAGCAAC | 1443 | UUGCUUUG CUGAUGAGGCCGUUAGGCCGAA IACUCACA | 1942 |
| 1000 | GUGAGUCC C AAAGCAAC | 1444 | GUUGCUUU CUGAUGAGGCCGUUAGGCCGAA IGACUCAC | 1943 |
| 1001 | UGAGUCCC A AAGCAACU | 1445 | AGUUGCUU CUGAUGAGGCCGUUAGGCCGAA IGGACUCA | 1944 |
| 1006 | CCCAAAGC A ACUCUUUA | 1446 | UAAAGAGU CUGAUGAGGCCGUUAGGCCGAA ICUUUGGG | 1945 |
| 1009 | AAAGCAAC U CUUUAGUG | 1447 | CACUAAAG CUGAUGAGGCCGUUAGGCCGAA IUUGCUUU | 1946 |
| 1011 | AGCAACUC U UUAGUGAC | 1448 | GUCACUAA CUGAUGAGGCCGUUAGGCCGAA IAGUUGCU | 1947 |
| 1020 | UUAGUGAC A AGCACACU | 1449 | AGUGUGCU CUGAUGAGGCCGUUAGGCCGAA IUCACUAA | 1948 |
| 1021 | UAGUGACC A GCACACUC | 1450 | GAGUGUGC CUGAUGAGGCCGUUAGGCCGAA IGUCACUA | 1949 |
| 1024 | UGACCAGC A CACUCGCU | 1451 | AGCGAGUG CUGAUGAGGCCGUUAGGCCGAA ICUGGUCA | 1950 |
| 1026 | ACCAGCAC A CUCGCUUC | 1452 | GAAGCGAG CUGAUGAGGCCGUUAGGCCGAA IUGCUGGU | 1951 |
| 1028 | CAGCACAC U CGCUUCUG | 1453 | CAGAAGCG CUGAUGAGGCCGUUAGGCCGAA IUGUGCUG | 1952 |
| 1032 | ACACUCGC U UCUGAAUC | 1454 | GAUUCAGA CUGAUGAGGCCGUUAGGCCGAA ICGAGUGU | 1953 |
| 1035 | CUCGCUUC U GAAUCAUC | 1455 | GAUGAUUC CUGAUGAGGCCGUUAGGCCGAA IAAGCGAG | 1954 |
| 1041 | UCUGAAUC A UCAUCUGA | 1456 | UCAGAUGA CUGAUGAGGCCGUUAGGCCGAA IAUUCAGA | 1955 |
| 1044 | GAAUCAUC A UCUGAAGG | 1457 | CCUUCAGA CUGAUGAGGCCGUUAGGCCGAA IAUGAUUC | 1956 |
| 1047 | UCAUCAUC U GAAGGUGA | 1458 | UCACCUUC CUGAUGAGGCCGUUAGGCCGAA IAUGAUGA | 1957 |
| 1057 | AAGGUGAC U UCUCAGCA | 1459 | UGCUGAGA CUGAUGAGGCCGUUAGGCCGAA IUCACCUU | 1958 |
| 1060 | GUGACUUC U CAGCAGAU | 1460 | AUCUGCUG CUGAUGAGGCCGUUAGGCCGAA IAAGUCAC | 1959 |
| 1062 | GACUUCUC A GCAGAUAC | 1461 | GUAUCUGC CUGAUGAGGCCGUUAGGCCGAA IAGAAGUC | 1960 |
| 1065 | UUCUCAGC A GAUACAUC | 1462 | GAUGUAUC CUGAUGAGGCCGUUAGGCCGAA ICUGAGAA | 1961 |
| 1071 | GCAGAUAC A UCAGAGAU | 1463 | AUCUCUGA CUGAUGAGGCCGUUAGGCCGAA IUAUCUGC | 1962 |
| 1074 | GAUACAUC A GAGAUAAA | 1464 | UUUAUCUC CUGAUGAGGCCGUUAGGCCGAA IAUGUAUC | 1963 |
| 1086 | AUAAAUUC A AACAGUGA | 1465 | UCACUGUU CUGAUGAGGCCGUUAGGCCGAA IAAUUUAU | 1964 |
| 1090 | AUUCUAAC A GUGACAGU | 1466 | ACUGUCAC CUGAUGAGGCCGUUAGGCCGAA IUUAGAAU | 1965 |
| 1096 | ACAGUGAC A GUUUAAAC | 1467 | GUUUAAAC CUGAUGAGGCCGUUAGGCCGAA IUCACUGU | 1966 |
| 1105 | GUUUAAAC A GUUCUUCG | 1468 | CGAAGAAC CUGAUGAGGCCGUUAGGCCGAA IUUUAAAC | 1967 |
| 1110 | AACAGUUC U UCGUUGCU | 1469 | AGCAACGA CUGAUGAGGCCGUUAGGCCGAA IAACUGUU | 1968 |
| 1118 | UUCGUUGC U UAUGAAUA | 1470 | CAUUCAUA CUGAUGAGGCCGUUAGGCCGAA ICAACGAA | 1969 |
| 1130 | GAAUGGUC U CAGAAAUA | 1471 | UAUUUCUG CUGAUGAGGCCGUUAGGCCGAA IACCAUUC | 1970 |
| 1132 | AUGGUCUC U GAAAUAAU | 1472 | AUUAUUUC CUGAUGAGGCCGUUAGGCCGAA IAGACCAU | 1971 |
| 1142 | AAAUAAUC A AAGGAAGG | 1473 | CCUUCCUU CUGAUGAGGCCGUUAGGCCGAA IAUUAUUU | 1972 |
| 1152 | AGGAAGGC A AAAAGAUC | 1474 | GAUCUUUU CUGAUGAGGCCGUUAGGCCGAA ICCUUCCU | 1973 |
| 1161 | AAAAGAUC U UGGCACC | 1475 | GGUGCCAA CUGAUGAGGCCGUUAGGCCGAA IAUCUUUU | 1974 |
| 1167 | UCUUUGGC A CCCAGAUU | 1476 | AAUCUGGG CUGAUGAGGCCGUUAGGCCGAA ICCAAAGA | 1975 |
| 1169 | UUUGGCAC C CAGAUUUG | 1477 | CAAAUCUG CUGAUGAGGCCGUUAGGCCGAA IUGCCAAA | 1976 |
| 1170 | UUGGCACC C AGAUUUGA | 1478 | UCAAAUCU CUGAUGAGGCCGUUAGGCCGAA IGUGCCAA | 1977 |
| 1171 | UGGCACCC A GAUUUGAC | 1479 | GUCAAAUC CUGAUGAGGCCGUUAGGCCGAA IGGUGCCA | 1978 |
| 1180 | GAUUUGAC C UUCCUGAC | 1480 | GUCAGGAA CUGAUGAGGCCGUUAGGCCGAA ICAAAUC | 1979 |
| 1181 | AUUUGACC U UCCUGACA | 1481 | UGUCAGGA CUGAUGAGGCCGUUAGGCCGAA IGUCAAAU | 1980 |
| 1184 | UGACCUUC C UGACAUGA | 1482 | UCAUGUCA CUGAUGAGGCCGUUAGGCCGAA IAAGGUCA | 1981 |
| 1185 | GACCUUCC U GACAUGAA | 1483 | UUCAUGUC CUGAUGAGGCCGUUAGGCCGAA IGAAGGUC | 1982 |
| 1189 | UUCCUGAC A UGAAAGAA | 1484 | UUCUUUCA CUGAUGAGGCCGUUAGGCCGAA ICAGGAA | 1983 |
| 1200 | AAAGAAAC A AGUAUAC | 1485 | GUAUACUU CUGAUGAGGCCGUUAGGCCGAA IUUUCUUU | 1984 |
| 1209 | AAGUAUAC U GGGACAA | 1486 | UUGUCCAC CUGAUGAGGCCGUUAGGCCGAA IUAUACUU | 1985 |
| 1216 | CUGUGGAC A AGAGGUUU | 1487 | AAACCUCU CUGAUGAGGCCGUUAGGCCGAA IUCCACAG | 1986 |
| 1228 | GGUUUGGC U UGGAUUUU | 1488 | AAAAUCCA CUGAUGAGGCCGUUAGGCCGAA ICCAAACC | 1987 |
| 1258 | UAAUUGGC U CAGGUGGA | 1489 | UCCACCUG CUGAUGAGGCCGUUAGGCCGAA ICCAAUUA | 1988 |
| 1260 | AUUGGCUC A GGUGGAUU | 1490 | AAUCCACC CUGAUGAGGCCGUUAGGCCGAA IAGCCAAU | 1989 |
| 1273 | GAUUUGGC C AAGUUUC | 1491 | GAAACUUU CUGAUGAGGCCGUUAGGCCGAA ICCAAAUC | 1990 |
| 1274 | AUUUGGCC A AGUUUCA | 1492 | UGAAACUU CUGAUGAGGCCGUUAGGCCGAA IGCCAAAU | 1991 |
| 1282 | AAGUUUC A AAGCAAA | 1493 | UUUUGCUU CUGAUGAGGCCGUUAGGCCGAA IAAAACUU | 1992 |
| 1287 | UUCAAAGC A AAACACAG | 1494 | CUGUGUUU CUGAUGAGGCCGUUAGGCCGAA ICUUUGAA | 1993 |
| 1292 | AGCAAAAC A CAGAAUUG | 1495 | CAAUUCUG CUGAUGAGGCCGUUAGGCCGAA IUUUUGCU | 1994 |

TABLE IX-continued

Human PKR Inozyme and Substrate Sequence

| Pos | Substrate | Seq ID | Inozyme | Seq ID |
|---|---|---|---|---|
| 1294 | CAAAACAC A GAAUUGAC | 1496 | GUCAAUUC CUGAUGAGGCCGUUAGGCCGAA IGUUUUG | 1995 |
| 1311 | GGAAAGAC U UACGUUAU | 1497 | AUAACGUA CUGAUGAGGCCGUUAGGCCGAA IUCUUUCC | 1996 |
| 1368 | GUAAAAGC A UUGGCAAA | 1498 | UUUGCCAA CUGAUGAGGCCGUUAGGCCGAA ICUUUUAC | 1997 |
| 1374 | GCAUUGGC A AAACUUGA | 1499 | UCAAGUUU CUGAUGAGGCCGUUAGGCCGAA ICCAAUGC | 1998 |
| 1379 | GGCAAAAC U UGAUCAUG | 1500 | CAUGAUCA CUGAUGAGGCCGUUAGGCCGAA IUUUUGCC | 1999 |
| 1385 | ACUUGAUC A UGUAAAUA | 1501 | UAUUUACA CUGAUGAGGCCGUUAGGCCGAA IAUCAAGU | 2000 |
| 1400 | UAUUGUUC A CUACAAUG | 1502 | CAUUGUAG CUGAUGAGGCCGUUAGGCCGAA IAACAAUA | 2001 |
| 1402 | UUGUUCAC U ACAAUGGC | 1503 | GCCAUUGU CUGAUGAGGCCGUUAGGCCGAA IUGAACAA | 2002 |
| 1405 | UUCACUAC A AUGGCUGU | 1504 | ACAGCCAU CUGAUGAGGCCGUUAGGCCGAA IUAGUGAA | 2003 |
| 1411 | ACAAUGGC U GUUGGGAU | 1505 | AUCCCAAC CUGAUGAGGCCGUUAGGCCGAA ICCAUUGU | 2004 |
| 1436 | UUAUGAUC C UGAGACCA | 1506 | UGGUCUCA CUGAUGAGGCCGUUAGGCCGAA IAUCAUAA | 2005 |
| 1437 | UAUGAUCC U GAGACCAG | 1507 | CUGGUCUC CUGAUGAGGCCGUUAGGCCGAA IGAUCAUA | 2006 |
| 1443 | CCUGAGAC C AGUGAUGA | 1508 | UCAUCACU CUGAUGAGGCCGUUAGGCCGAA IUCUCAGG | 2007 |
| 1444 | CUGAGACC A GUGAUGAU | 1509 | AUCAUCAC CUGAUGAGGCCGUUAGGCCGAA IGUCUCAG | 2008 |
| 1455 | GAUGAUUC U CUUGAGAG | 1510 | CUCUCAAG CUGAUGAGGCCGUUAGGCCGAA IAAUCAUC | 2009 |
| 1457 | UGAUUCUC U UGAGAGCA | 1511 | UGCUCUCA CUGAUGAGGCCGUUAGGCCGAA IAGAAUCA | 2010 |
| 1465 | UUGAGAGC A GUGAUUAU | 1512 | AUAAUCAC CUGAUGAGGCCGUUAGGCCGAA ICUCUCAA | 2011 |
| 1478 | UUAUGAUC C UGAGAACA | 1513 | UGUUCUCA CUGAUGAGGCCGUUAGGCCGAA IAUCAUAA | 2012 |
| 1479 | UAUGAUCC U GAGAACAG | 1514 | CUGUCCUC CUGAUGAGGCCGUUAGGCCGAA IGAUCAUA | 2013 |
| 1486 | CUGAGAAC A GCAAAAAU | 1515 | AUUUUUGC CUGAUGAGGCCGUUAGGCCGAA IUUCUCAG | 2014 |
| 1489 | AGAACAGC A AAAUAGU | 1516 | ACUAUUUU CUGAUGAGGCCGUUAGGCCGAA ICUGUUCU | 2015 |
| 1500 | AAUAGUUC A AGGUCAAA | 1517 | UUUGACCU CUGAUGAGGCCGUUAGGCCGAA IAACUAUU | 2016 |
| 1506 | UCAAGGUC A AAGACUAA | 1518 | UUAGUCUU CUGAUGAGGCCGUUAGGCCGAA IACCUUGA | 2017 |
| 1512 | UCAAAGAC U AAGUGCCU | 1519 | AGGCACUU CUGAUGAGGCCGUUAGGCCGAA IUCUUUGA | 2018 |
| 1519 | CUAAGUGC C UUUUCAUC | 1520 | GAUGAAAA CUGAUGAGGCCGUUAGGCCGAA ICACUUAG | 2019 |
| 1520 | UAAGUGCC U UUUCAUCC | 1521 | GGAUGAAA CUGAUGAGGCCGUUAGGCCGAA IGCACUUA | 2020 |
| 1525 | GCCUUUUC A UCCAAAUG | 1522 | CAUUUGGA CUGAUGAGGCCGUUAGGCCGAA IAAAAGGC | 2021 |
| 1528 | UUUUCAUC C AAAUGAA | 1523 | UUCCAUUU CUGAUGAGGCCGUUAGGCCGAA IAUGAAAA | 2022 |
| 1529 | UUUCAUCC A AAUGGAAU | 1524 | AUUCCAUU CUGAUGAGGCCGUUAGGCCGAA IGAUGAAA | 2023 |
| 1540 | UGGAAUUC U GUGAUAAA | 1525 | UUUAUCAC CUGAUGAGGCCGUUAGGCCGAA IAAUUCCA | 2024 |
| 1554 | AAAGGGAC C UUGGAACA | 1526 | UGUUCCAA CUGAUGAGGCCGUUAGGCCGAA IUCCCUUU | 2025 |
| 1555 | AAGGGACC U UGGAACAA | 1527 | UUGUUCCA CUGAUGAGGCCGUUAGGCCGAA IGUCCCUU | 2026 |
| 1562 | CUUGGAAC A AUGGAUUG | 1528 | CAAUCCAU CUGAUGAGGCCGUUAGGCCGAA IUUCCAAG | 2027 |
| 1592 | CGAGAAAC U AGACAAAG | 1529 | CUUUGUCU CUGAUGAGGCCGUUAGGCCGAA IUUUCUCG | 2028 |
| 1597 | AACUAGAC A AAGUUUUG | 1530 | CAAAACUU CUGAUGAGGCCGUUAGGCCGAA IUCUAGUU | 2029 |
| 1608 | GUUUUGGC U UUGGAACU | 1531 | AGUUCCAA CUGAUGAGGCCGUUAGGCCGAA ICCAAAAC | 2030 |
| 1616 | UUUGGAAC U CUUGAAC | 1532 | GUUCAAAG CUGAUGAGGCCGUUAGGCCGAA IUUCCAAA | 2031 |
| 1618 | UGGAACUC U UUGAACAA | 1533 | UUGUUCAA CUGAUGAGGCCGUUAGGCCGAA IAGUUCCA | 2032 |
| 1625 | CUUUGAAC A AAUAACAA | 1534 | UUGUUAUU CUGAUGAGGCCGUUAGGCCGAA IUUCAAAG | 2033 |
| 1632 | CAAAUAAC A AAAGGGGU | 1535 | ACCCCUUU CUGAUGAGGCCGUUAGGCCGAA IUUAUUUG | 2034 |
| 1652 | UAUAUAC A UUCAAAAA | 1536 | UUUUUGAA CUGAUGAGGCCGUUAGGCCGAA IUAUAUAA | 2035 |
| 1656 | AUACAUUC A AAAAAUU | 1537 | AAUUUUUU CUGAUGAGGCCGUUAGGCCGAA IAAUGUAU | 2036 |
| 1670 | AUUAAUUC A UAGAGAUC | 1538 | GAUCUCUA CUGAUGAGGCCGUUAGGCCGAA IAAUUAUU | 2037 |
| 1679 | UAGAGAUC U UAAGCCAA | 1539 | UUGGCUUA CUGAUGAGGCCGUUAGGCCGAA IAUCUCUA | 2038 |
| 1685 | UCUUAAGC C AAGUAAUA | 1540 | UAUUACUU CUGAUGAGGCCGUUAGGCCGAA ICUUAAGA | 2039 |
| 1686 | CUUAAGCC A AGUAAUAU | 1541 | AUAUUACU CUGAUGAGGCCGUUAGGCCGAA IGCUUAAG | 2040 |
| 1699 | AUAUAUUC U UAGUAGAU | 1542 | AUCUACUA CUGAUGAGGCCGUUAGGCCGAA IAAUAUAU | 2041 |
| 1710 | GUAGAUAC A AAACAAGU | 1543 | ACUUGUUU CUGAUGAGGCCGUUAGGCCGAA IUAUCUAC | 2042 |
| 1715 | UACAAAAC A AGUAAAGA | 1544 | UCUUUACU CUGAUGAGGCCGUUAGGCCGAA IUUUUGUA | 2043 |
| 1732 | UUGGAGAC U UUGGACUU | 1545 | AAGUCCAA CUGAUGAGGCCGUUAGGCCGAA IUCUCCAA | 2044 |
| 1739 | CUUUGGAC U UGUAACAU | 1546 | AUGUUACA CUGAUGAGGCCGUUAGGCCGAA IUCCAAAG | 2045 |
| 1746 | CUUGUAAC A UCUCUGAA | 1547 | UUCAGAGA CUGAUGAGGCCGUUAGGCCGAA IUUACAAG | 2046 |
| 1749 | GUAACAUC U CUGAAAAA | 1548 | UUUUUCAG CUGAUGAGGCCGUUAGGCCGAA IAUGUUAC | 2047 |
| 1751 | AACAUCUC U GAAAAAUG | 1549 | CAUUUUUC CUGAUGAGGCCGUUAGGCCGAA IAGAUGUU | 2048 |
| 1773 | AAGCGAAC A AGGAGUAA | 1550 | UUACUCCU CUGAUGAGGCCGUUAGGCCGAA IUUCGCUU | 2049 |
| 1788 | AAGGGAAC U UUGCGAUA | 1551 | UAUCGCAA CUGAUGAGGCCGUUAGGCCGAA IUUCCCUU | 2050 |
| 1798 | UGCGAUAC A UGAGCCCA | 1552 | UGGGCUCA CUGAUGAGGCCGUUAGGCCGAA IUAUCGCA | 2051 |
| 1804 | ACAUGAGC C CAGAACAG | 1553 | CUGUUCUG CUGAUGAGGCCGUUAGGCCGAA ICUCAUGU | 2052 |
| 1805 | CAUGAGCC C AGAACAGA | 1554 | UCUGUUCU CUGAUGAGGCCGUUAGGCCGAA IGCUCAUG | 2053 |
| 1806 | AUGAGCCC A GAACAGAU | 1555 | AUCUGUUC CUGAUGAGGCCGUUAGGCCGAA IGGCUCAU | 2054 |
| 1811 | CCCAGAAC A GAUUCUU | 1556 | AAGAAAUC CUGAUGAGGCCGUUAGGCCGAA IUUCUGGG | 2055 |
| 1818 | CAGAUUUC U UCGCAAGA | 1557 | UCUUGCGA CUGAUGAGGCCGUUAGGCCGAA IAAAUCUG | 2056 |
| 1823 | UUCUUCGC A AGACUAUG | 1558 | CAUAGUCU CUGAUGAGGCCGUUAGGCCGAA ICGAAGAA | 2057 |
| 1828 | CGCAAGAC U AUGGAAAG | 1559 | CUUUCCAU CUGAUGAGGCCGUUAGGCCGAA IUCUUGCG | 2058 |
| 1846 | AAGUGGAC C UCUACGCU | 1560 | AGCGUAGA CUGAUGAGGCCGUUAGGCCGAA IUCCACUU | 2059 |
| 1847 | AGUGGACC U CUACGCUU | 1561 | AAGCGUAG CUGAUGAGGCCGUUAGGCCGAA IGUCCACU | 2060 |
| 1849 | UGGACCUC U ACGCUUUG | 1562 | CAAAGCGU CUGAUGAGGCCGUUAGGCCGAA IAGGUCCA | 2061 |
| 1854 | CUCUACGC U UUGGGCU | 1563 | AGCCCCAA CUGAUGAGGCCGUUAGGCCGAA ICGUAGAG | 2062 |
| 1862 | UUUGGGGC U AAUUCUUG | 1564 | CAAGAAUU CUGAUGAGGCCGUUAGGCCGAA ICCCCAAA | 2063 |
| 1868 | GCUAAUUC U UGCGAAC | 1565 | GUUCAGCA CUGAUGAGGCCGUUAGGCCGAA IAAUUAGC | 2064 |
| 1872 | AUUCUUGC U GAACUUCU | 1566 | AGAAGUUC CUGAUGAGGCCGUUAGGCCGAA ICAAGAAU | 2065 |
| 1877 | UGCUGAAC U UCUUCAUG | 1567 | CAUGAAGA CUGAUGAGGCCGUUAGGCCGAA IUUCAGCA | 2066 |
| 1880 | UGAACUUC U UCAUGUAU | 1568 | AUACAUGA CUGAUGAGGCCGUUAGGCCGAA IAAGUUCA | 2067 |
| 1883 | ACUUCUUC A UGUAUGUG | 1569 | CACAUACA CUGAUGAGGCCGUUAGGCCGAA IAAGAAGU | 2068 |
| 1894 | UAUGUGAC A CUGCUUUU | 1570 | AAAAGCAG CUGAUGAGGCCGUUAGGCCGAA IUCACAUA | 2069 |

TABLE IX-continued

Human PKR Inozyme and Substrate Sequence

| Pos | Substrate | Seq ID | Inozyme | Seq ID |
|---|---|---|---|---|
| 1896 | UGUGACAC U GCUUUUGA | 1571 | UCAAAAGC CUGAUGAGGCCGUUAGGCCGAA IUGUCACA | 2070 |
| 1899 | GACACUGC U UUUGAAAC | 1572 | GUUUCAAA CUGAUGAGGCCGUUAGGCCGAA ICAGUGUC | 2071 |
| 1908 | UUUGAAAC A UCAAAGUU | 1573 | AACUUUGA CUGAUGAGGCCGUUAGGCCGAA IUUUCAAA | 2072 |
| 1911 | GAAACAUC A AAGUUUUU | 1574 | AAAAACUU CUGAUGAGGCCGUUAGGCCGAA IAUGUUUC | 2073 |
| 1921 | AGUUUUUC A CAGACCUA | 1575 | UAGGUCUG CUGAUGAGGCCGUUAGGCCGAA IAAAAACU | 2074 |
| 1923 | UUUUUCAC A GACCUACG | 1576 | CGUAGGUC CUGAUGAGGCCGUUAGGCCGAA IUGAAAAA | 2075 |
| 1927 | UCACAGAC C UACGGAUU | 1577 | AUCCCGUA CUGAUGAGGCCGUUAGGCCGAA IUCUGUGA | 2076 |
| 1928 | CACAGACC U ACGGAUG | 1578 | CAUCCCGU CUGAUGAGGCCGUUAGGCCGAA IGUCUGUG | 2077 |
| 1939 | GGGAUGGC A UCAUCUCA | 1579 | UGAGAUGA CUGAUGAGGCCGUUAGGCCGAA ICCAUCCC | 2078 |
| 1942 | AUGGCAUC A UCUCAGAU | 1580 | AUCUGAGA CUGAUGAGGCCGUUAGGCCGAA IAUGCCAU | 2079 |
| 1945 | GCAUCAUC U CAGAUAUA | 1581 | UAUAUCUG CUGAUGAGGCCGUUAGGCCGAA IAUGAUGC | 2080 |
| 1947 | AUCAUCUC A GAUAUAUU | 1582 | AAUAUAUC CUGAUGAGGCCGUUAGGCCGAA IAGAUGAU | 2081 |
| 1974 | GAAAAAAC U CUUCUACA | 1583 | UGUAGAAG CUGAUGAGGCCGUUAGGCCGAA IUUUUUUC | 2082 |
| 1976 | AAAAACUC U UCUACAGA | 1584 | UCUGUAGA CUGAUGAGGCCGUUAGGCCGAA IAGUUUUU | 2083 |
| 1979 | AACUCUUC U ACAGAAAU | 1585 | AUUUCUGU CUGAUGAGGCCGUUAGGCCGAA IAAGAGUU | 2084 |
| 1982 | UCUUCUAC A GAAAUUAC | 1586 | GUAAUUUC CUGAUGAGGCCGUUAGGCCGAA IUAGAAGA | 2085 |
| 1991 | GAAAUUAC U CUCAAAGA | 1587 | UCUUUGAG CUGAUGAGGCCGUUAGGCCGAA IUAAUUUC | 2086 |
| 1993 | AAUUACUC U CAAAGAAA | 1588 | UUUCUUUG CUGAUGAGGCCGUUAGGCCGAA IAGUAAUU | 2087 |
| 1995 | UUACUCUC A AAGAAACC | 1589 | GGUUUCUU CUGAUGAGGCCGUUAGGCCGAA IAGAGUAA | 2088 |
| 2003 | AAAGAAAC C UGAGGAUC | 1590 | GAUCCUCA CUGAUGAGGCCGUUAGGCCGAA IUUUCUUU | 2089 |
| 2004 | AAGAAACC U GAGGAUCG | 1591 | CGAUCCUC CUGAUGAGGCCGUUAGGCCGAA IGUUUCUU | 2090 |
| 2015 | GGAUCGAC C UAACACAU | 1592 | AUGUGUUA CUGAUGAGGCCGUUAGGCCGAA IUCGAUCC | 2091 |
| 2016 | GAUCGACC U AACACAUC | 1593 | GAUGUGUU CUGAUGAGGCCGUUAGGCCGAA IGUCGAUC | 2092 |
| 2020 | GACCUAAC A CAUCUGAA | 1594 | UUCAGAUG CUGAUGAGGCCGUUAGGCCGAA IUUAGGUC | 2093 |
| 2022 | CCUAACAC A UCUGAAAU | 1595 | AUUUCAGA CUGAUGAGGCCGUUAGGCCGAA IUGUUAGG | 2094 |
| 2025 | AACACAUC U GAAAUACU | 1596 | AGUAUUUC CUGAUGAGGCCGUUAGGCCGAA IAUGUGUU | 2095 |
| 2033 | UGAAAUAC U AAGGACCU | 1597 | AGGUCCUU CUGAUGAGGCCGUUAGGCCGAA IUAUCUCA | 2096 |
| 2040 | CUAAGGAC C UUGACUGU | 1598 | ACAGUCAA CUGAUGAGGCCGUUAGGCCGAA IUCCUUAG | 2097 |
| 2041 | UAAGGACC U UGACUGUG | 1599 | CACAGUCA CUGAUGAGGCCGUUAGGCCGAA IGUCCUUA | 2098 |
| 2046 | ACCUUGAC U GUGGGAA | 1600 | UUCCACAC CUGAUGAGGCCGUUAGGCCGAA IUCAAGGU | 2099 |
| 2062 | AGAAAAGC C CAGAGAAA | 1601 | UUUCUCUG CUGAUGAGGCCGUUAGGCCGAA ICUUUUCU | 2100 |
| 2063 | GAAAAGCC C AGAGAAAA | 1602 | UUUUCUCU CUGAUGAGGCCGUUAGGCCGAA IGCUUUUC | 2101 |
| 2064 | AAAAGCCC C AGAAAAA | 1603 | UUUUUCUC CUGAUGAGGCCGUUAGGCCGAA IGGCUUUU | 2102 |
| 2081 | UGAACGAC A CACAUGUU | 1604 | AACAUGUG CUGAUGAGGCCGUUAGGCCGAA IUCGUUCA | 2103 |
| 2083 | AACGACAC A CAUGUUAG | 1605 | CUAACAUG CUGAUGAGGCCGUUAGGCCGAA IUGUCGUU | 2104 |
| 2085 | CGACACAC A UGUUAGAG | 1606 | CUCUAACA CUGAUGAGGCCGUUAGGCCGAA IUGUGUCG | 2105 |
| 2095 | GUUAGAGC C CUUCUGAA | 1607 | UUCAGAAG CUGAUGAGGCCGUUAGGCCGAA ICUCUAAC | 2106 |
| 2096 | UUAGAGCC C UUCUGAAA | 1608 | UUUCAGAA CUGAUGAGGCCGUUAGGCCGAA IGCUCUAA | 2107 |
| 2097 | UAGAGCCC U UCUGAAAA | 1609 | UUUUCAGA CUGAUGAGGCCGUUAGGCCGAA IGGCUCUA | 2108 |
| 2100 | AGCCCUUC U GAAAAGU | 1610 | ACUUUUUC CUGAUGAGGCCGUUAGGCCGAA IAAGGGCU | 2109 |
| 2112 | AAAGUAUC U UGCUUCUG | 1611 | CAGAAGCA CUGAUGAGGCCGUUAGGCCGAA IAUACUUU | 2110 |
| 2113 | AAGUAUCC U GCUUCUGA | 1612 | UCAGAAGC CUGAUGAGGCCGUUAGGCCGAA IGAUACUU | 2111 |
| 2116 | UAUCCUGC U UCUGAUAU | 1613 | AUAUCAGA CUGAUGAGGCCGUUAGGCCGAA ICAGGAUA | 2112 |
| 2119 | CCUGCUUC U GAUAUGCA | 1614 | UGCAUAUC CUGAUGAGGCCGUUAGGCCGAA IAAGCAGG | 2113 |
| 2127 | UGAUAUGC A GUUUCCU | 1615 | AGGAAAAC CUGAUGAGGCCGUUAGGCCGAA ICAUAUCA | 2114 |
| 2134 | CAGUUUUC C UUAAAUUA | 1616 | UAAUUUAA CUGAUGAGGCCGUUAGGCCGAA IAAAACUG | 2115 |
| 2135 | AGUUUUCC U UAAAUUAU | 1617 | AUAAUUUA CUGAUGAGGCCGUUAGGCCGAA IGAAAACU | 2116 |
| 2145 | AAAUUAUC U AAAACUG | 1618 | CAGAUUUU CUGAUGAGGCCGUUAGGCCGAA IAUAAUUU | 2117 |
| 2152 | CUAAAAUC U GCUAGGGA | 1619 | UCCCUAGC CUGAUGAGGCCGUUAGGCCGAA IAUUUUAG | 2118 |
| 2155 | AAAUCUGC U AGGGAAUA | 1620 | UAUUCCCU CUGAUGAGGCCGUUAGGCCGAA ICAGAUUU | 2119 |
| 2166 | GGAAUAUC A AUAGAUU | 1621 | AUAUCUAU CUGAUGAGGCCGUUAGGCCGAA IAUAUUCC | 2120 |
| 2179 | AUAUUUAC C UUUUAUUU | 1622 | AAAUAAAA CUGAUGAGGCCGUUAGGCCGAA IUAAAUAU | 2121 |
| 2180 | UAUUUACC U UUUAUUUU | 1623 | AAAAUAAA CUGAUGAGGCCGUUAGGCCGAA IGUAAAUA | 2122 |
| 2197 | AAGUUUUC C UUUAAUUUU | 1624 | AAAAUUAA CUGAUGAGGCCGUUAGGCCGAA IAAACAUU | 2123 |
| 2198 | AUGUUUCC U UUAAUUUU | 1625 | AAAAUUAA CUGAUGAGGCCGUUAGGCCGAA IGAAACAU | 2124 |
| 2211 | UUUUUUAC U AUUUUAC | 1626 | GUAAAAAU CUGAUGAGGCCGUUAGGCCGAA IUAAAAAA | 2125 |
| 2220 | AUUUUUAC U AAUCUUUC | 1627 | GAAAGAUU CUGAUGAGGCCGUUAGGCCGAA IUAAAAAU | 2126 |
| 2225 | UACUAAUC U UCUGCAG | 1628 | CUGCAGAA CUGAUGAGGCCGUUAGGCCGAA IAUUAGUA | 2127 |
| 2229 | AAUCUUUC U GCAGAAAC | 1629 | GUUUCUGC CUGAUGAGGCCGUUAGGCCGAA IAAAGAUU | 2128 |
| 2232 | CUUUCUGC A GAAACAGA | 1630 | UCUGUUUC CUGAUGAGGCCGUUAGGCCGAA ICAGAAAG | 2129 |
| 2238 | GCAGAAAC A GAAAGGUU | 1631 | AACCUUUC CUGAUGAGGCCGUUAGGCCGAA IUUUCUGC | 2130 |
| 2250 | AGGUUUUC U UCUUUUG | 1632 | CAAAAAGA CUGAUGAGGCCGUUAGGCCGAA IAAAACCU | 2131 |
| 2253 | UUUUCUUC U UUUUGCUU | 1633 | AAGCAAAA CUGAUGAGGCCGUUAGGCCGAA IAAGAAAA | 2132 |
| 2260 | CUUUUUGC U UCAAAAC | 1634 | GUUUUGA CUGAUGAGGCCGUUAGGCCGAA ICAAAAAG | 2133 |
| 2263 | UUUGCUUC A AAAACAUU | 1635 | AAUGUUUU CUGAUGAGGCCGUUAGGCCGAA IAAGCAAA | 2134 |
| 2269 | UCAAAAAC A UUCUUACA | 1636 | UGUAAGAA CUGAUGAGGCCGUUAGGCCGAA IUUUUUGA | 2135 |
| 2273 | AAACAUUC U UACAUUUU | 1637 | AAAAUGUA CUGAUGAGGCCGUUAGGCCGAA IAAUGUUU | 2136 |
| 2277 | AUUCUUAC A UUUUACUU | 1638 | AAGUAAAA CUGAUGAGGCCGUUAGGCCGAA IUAAGAAU | 2137 |
| 2284 | CAUUUUAC U UUUCCUG | 1639 | CAGGAAAA CUGAUGAGGCCGUUAGGCCGAA IUAAAAUG | 2138 |
| 2290 | ACUUUUUC C UGGCUCAU | 1640 | AUGAGCCA CUGAUGAGGCCGUUAGGCCGAA IAAAAAGU | 2139 |
| 2291 | CUUUUUCC U GGCUCAUC | 1641 | GAUGAGCC CUGAUGAGGCCGUUAGGCCGAA IGAAAAAG | 2140 |
| 2295 | UUCCUGGC U CAUCUCUU | 1642 | AAGAGAUG CUGAUGAGGCCGUUAGGCCGAA ICCAGGAA | 2141 |
| 2297 | CCUGGCUC A UCUCUUA | 1643 | UAAGAGA CUGAUGAGGCCGUUAGGCCGAA IAGCCAGG | 2142 |
| 2300 | GGCUCAUC U CUUUAUUC | 1644 | GAAUAAAG CUGAUGAGGCCGUUAGGCCGAA IAUGAGCC | 2143 |
| 2302 | CUCAUCUC U UUAUUCUU | 1645 | AAGAAUAA CUGAUGAGGCCGUUAGGCCGAA IAGAUGAG | 2144 |

TABLE IX-continued

Human PKR Inozyme and Substrate Sequence

| Pos | Substrate | Seq ID | Inozyme | Seq ID |
|---|---|---|---|---|
| 2309 | CUUUAUUC U UUUUUUUU | 1646 | AAAAAAAA CUGAUGAGGCCGUUAGGCCGAA IAAUAAAG | 2145 |
| 2329 | UUAAAGAC A GAGUCUCG | 1647 | CGAGACUC CUGAUGAGGCCGUUAGGCCGAA IUCUUUAA | 2146 |
| 2335 | ACAGAGUC U CGCUCUGU | 1648 | ACAGAGCG CUGAUGAGGCCGUUAGGCCGAA IACUCUGU | 2147 |
| 2339 | AGUCUCGC U CUGUUGCC | 1649 | GGCAACAG CUGAUGAGGCCGUUAGGCCGAA ICGAGACU | 2148 |
| 2341 | UCUCGCUC U GUUGCCCA | 1650 | UGGGCAAC CUGAUGAGGCCGUUAGGCCGAA IAGCGAGA | 2149 |
| 2347 | UCUGUUGC C CAGGCUGG | 1651 | CCAGCCUG CUGAUGAGGCCGUUAGGCCGAA ICAACAGA | 2150 |
| 2348 | CUGUUGCC C AGGCUGGA | 1652 | UCCAGCCU CUGAUGAGGCCGUUAGGCCGAA IGCAACAG | 2151 |
| 2349 | UGUUGCCC A GGCUGGAG | 1653 | CUCCAGCC CUGAUGAGGCCGUUAGGCCGAA IGGCAACA | 2152 |
| 2353 | GCCCAGGC U GGAGUGCA | 1654 | UGCACUCC CUGAUGAGGCCGUUAGGCCGAA ICCUGGGC | 2153 |
| 2361 | UGGAGUGC A AUGACACA | 1655 | UGUGUCAU CUGAUGAGGCCGUUAGGCCGAA ICACUCCA | 2154 |
| 2367 | GCAAUGAC A CAGUCUUG | 1656 | CAAGACUG CUGAUGAGGCCGUUAGGCCGAA IUCAUUGC | 2155 |
| 2369 | AAUGACAC A GUCUUGGC | 1657 | GCCAAGAC CUGAUGAGGCCGUUAGGCCGAA IUGUCAUU | 2156 |
| 2373 | ACACAGUC U UGGCUCAC | 1658 | GUGAGCCA CUGAUGAGGCCGUUAGGCCGAA IACUGUGU | 2157 |
| 2378 | GUCUUGGC U CACUGCAA | 1659 | UUGCAGUG CUGAUGAGGCCGUUAGGCCGAA ICCAAGAC | 2158 |
| 2380 | CUUGGCUC A CUGCAACU | 1660 | AGUUGCAG CUGAUGAGGCCGUUAGGCCGAA IAGCCAAG | 2159 |
| 2382 | UGGCUCAC U GCAACUUC | 1661 | GAAGUUGC CUGAUGAGGCCGUUAGGCCGAA IUGAGCCA | 2160 |
| 2385 | CUCACUGC A ACUUCUGC | 1662 | GCAGAAGU CUGAUGAGGCCGUUAGGCCGAA ICAGUGAG | 2161 |
| 2388 | ACUGCAAC U UCUGCCUC | 1663 | GAGGCAGA CUGAUGAGGCCGUUAGGCCGAA IUUGCAGU | 2162 |
| 2391 | GCAACUUC U GCCUCUUG | 1664 | CAAGAGGC CUGAUGAGGCCGUUAGGCCGAA IAAGUUGC | 2163 |
| 2394 | ACUUCUGC C UCUUGGGU | 1665 | ACCCAAGA CUGAUGAGGCCGUUAGGCCGAA ICAGAAGU | 2164 |
| 2395 | CUUCUGCC U CUUGGGUU | 1666 | AACCCAAG CUGAUGAGGCCGUUAGGCCGAA IGCAGAAG | 2165 |
| 2397 | UCUGCCUC U UGGGUUCA | 1667 | UGAACCCA CUGAUGAGGCCGUUAGGCCGAA IAGGCAGA | 2166 |
| 2405 | UUGGGUUC A AGUGAUUC | 1668 | GAAUCACU CUGAUGAGGCCGUUAGGCCGAA IAACCCAA | 2167 |
| 2414 | AGUGAUUC U CCUGCCUC | 1669 | GAGGCAGG CUGAUGAGGCCGUUAGGCCGAA IAAUCACU | 2168 |
| 2416 | UGAUUCUC C UGCCUCAG | 1670 | CUGAGGCA CUGAUGAGGCCGUUAGGCCGAA IAGAAUCA | 2169 |
| 2417 | GAUUCUCC U GCCUCAGC | 1671 | GCUGAGGC CUGAUGAGGCCGUUAGGCCGAA IGAGAAUC | 2170 |
| 2420 | UCUCCUGC C UCAGCCUC | 1672 | GAGGCUGA CUGAUGAGGCCGUUAGGCCGAA ICAGGAGA | 2171 |
| 2421 | CUCCUGCC U CAGCCUCC | 1673 | GGAGGCUG CUGAUGAGGCCGUUAGGCCGAA IGCAGGAG | 2172 |
| 2423 | CCUGCCUC A GCCUCCUG | 1674 | CAGGAGGC CUGAUGAGGCCGUUAGGCCGAA IAGGCAGG | 2173 |
| 2426 | GCCUCAGC C UCCUGAGU | 1675 | ACUCAGGA CUGAUGAGGCCGUUAGGCCGAA ICUGAGGC | 2174 |
| 2427 | CCUCAGCC U CCUGAGUA | 1676 | UACUCAGG CUGAUGAGGCCGUUAGGCCGAA IGCUGAGG | 2175 |
| 2429 | UCAGCCUC C UGAGUAGC | 1677 | GCUACUCA CUGAUGAGGCCGUUAGGCCGAA IAGGCUGA | 2176 |
| 2430 | CAGCCUCC U GAGUAGCU | 1678 | AGCUACUC CUGAUGAGGCCGUUAGGCCGAA IGAGGCUG | 2177 |
| 2438 | UGAGUAGC U GGAUUACA | 1679 | UGUAAUCC CUGAUGAGGCCGUUAGGCCGAA ICUACUCA | 2178 |
| 2446 | UGGAUUAC A GGCAUGUG | 1680 | CACAUGCC CUGAUGAGGCCGUUAGGCCGAA IUAAUCCA | 2179 |
| 2450 | UUACAGGC A UGUGCCAC | 1681 | GUGGCACA CUGAUGAGGCCGUUAGGCCGAA ICCUGUAA | 2180 |
| 2456 | GCAUGUGC C ACCCACCC | 1682 | GGGUGGGU CUGAUGAGGCCGUUAGGCCGAA ICACAUGC | 2181 |
| 2457 | CAUGUGCC A CCCACCCA | 1683 | UGGGUGGG CUGAUGAGGCCGUUAGGCCGAA IGCACAUG | 2182 |
| 2459 | UGUGCCAC C CACCCAAC | 1684 | GUUGGGUG CUGAUGAGGCCGUUAGGCCGAA IUGGCACA | 2183 |
| 2460 | GUGCCACC C ACCCAACU | 1685 | AGUUGGGU CUGAUGAGGCCGUUAGGCCGAA IGUGGCAC | 2184 |
| 2461 | UGCCACCC A CCCAACUA | 1686 | UAGUUGGG CUGAUGAGGCCGUUAGGCCGAA IGGUGGCA | 2185 |
| 2463 | CCACCCAC C CAACUAAU | 1687 | AUUAGUUG CUGAUGAGGCCGUUAGGCCGAA IUGGGUGG | 2186 |
| 2464 | CACCCACC C AACUAAUU | 1688 | AAUUAGUU CUGAUGAGGCCGUUAGGCCGAA IGUGGGUG | 2187 |
| 2465 | ACCCACCC A ACUAAUUU | 1689 | AAAUUAGU CUGAUGAGGCCGUUAGGCCGAA IGGUGGGU | 2188 |
| 2468 | CACCCAAC U AAUUUUUG | 1690 | CAAAAAUU CUGAUGAGGCCGUUAGGCCGAA IUUGGGUG | 2189 |
| 2493 | AUAAAGAC A GGGUUUCA | 1691 | UGAAACCC CUGAUGAGGCCGUUAGGCCGAA IUCUUUAU | 2190 |
| 2501 | AGGGUUUC A CCAUGUUG | 1692 | CAACAUGG CUGAUGAGGCCGUUAGGCCGAA IAAACCCU | 2191 |
| 2503 | GGUUUCAC C AUGUUGGC | 1693 | GCCAACAU CUGAUGAGGCCGUUAGGCCGAA IUGAAACC | 2192 |
| 2504 | GUUUCACC A UGUUGGCC | 1694 | GGCCAACA CUGAUGAGGCCGUUAGGCCGAA IGUGAAAC | 2193 |
| 2512 | AUGUUGGC C AGGCUGGU | 1695 | ACCAGCCU CUGAUGAGGCCGUUAGGCCGAA ICCAACAU | 2194 |
| 2513 | UGUUGGCC A GGCUGGUC | 1696 | GACCAGCC CUGAUGAGGCCGUUAGGCCGAA IGCCAACA | 2195 |
| 2517 | GGCCAGGC U GGUCUCAA | 1697 | UUGAGACC CUGAUGAGGCCGUUAGGCCGAA ICCUGGCC | 2196 |
| 2522 | GGCUGGUC U CAAACUCC | 1698 | GGAGUUUG CUGAUGAGGCCGUUAGGCCGAA IACCAGCC | 2197 |
| 2524 | CUGGUCUC A AACUCCUG | 1699 | CAGGAGUU CUGAUGAGGCCGUUAGGCCGAA IAGACCAG | 2198 |
| 2528 | UCUCAAAC U CCUGACCU | 1700 | AGGUCAGG CUGAUGAGGCCGUUAGGCCGAA IUUUGAGA | 2199 |
| 2530 | UCAAACUC C UGACCUCA | 1701 | UGAGGUCA CUGAUGAGGCCGUUAGGCCGAA IAGUUUGA | 2200 |
| 2531 | CAAACUCC U GACCUCAA | 1702 | UUGAGGUC CUGAUGAGGCCGUUAGGCCGAA IGAGUUUG | 2201 |
| 2535 | CUCCUGAC C UCAAGUAA | 1703 | UUACUUGA CUGAUGAGGCCGUUAGGCCGAA IUCAGGAG | 2202 |
| 2536 | UCCUGACC U CAAGUAAU | 1704 | AUUACUUG CUGAUGAGGCCGUUAGGCCGAA IGUCAGGA | 2203 |
| 2538 | CUGACCUC A AGUAAUCC | 1705 | GGAUUACU CUGAUGAGGCCGUUAGGCCGAA IAGGUCAG | 2204 |
| 2546 | AAGUAAUC C ACCUGCCU | 1706 | AGGCAGGU CUGAUGAGGCCGUUAGGCCGAA IAUUACUU | 2205 |
| 2547 | AGUAAUCC A CCUGCCUC | 1707 | GAGGCAGG CUGAUGAGGCCGUUAGGCCGAA IGAUUACU | 2206 |
| 2549 | UAAUCCAC C UGCCUCGG | 1708 | CCGAGGCA CUGAUGAGGCCGUUAGGCCGAA IUGGAUUA | 2207 |
| 2550 | AAUCCACC U GCCUCGGC | 1709 | GCCGAGGC CUGAUGAGGCCGUUAGGCCGAA IGUGGAUU | 2208 |
| 2553 | CCACCUGC C UCGGCCUC | 1710 | GAGGCCGA CUGAUGAGGCCGUUAGGCCGAA ICAGGUGG | 2209 |
| 2554 | CACCUGCC U CGGCCUCC | 1711 | GGAGGCCG CUGAUGAGGCCGUUAGGCCGAA IGCAGGUG | 2210 |
| 2559 | GCCUCGGC C UCCCAAAG | 1712 | CUUUGGGA CUGAUGAGGCCGUUAGGCCGAA ICCGAGGC | 2211 |
| 2560 | CCUCGGCC U CCCAAAGU | 1713 | ACUUUGGG CUGAUGAGGCCGUUAGGCCGAA IGCCGAGG | 2212 |
| 2562 | UCGGCCUC C CAAAGUGC | 1714 | GCACUUUG CUGAUGAGGCCGUUAGGCCGAA IAGGCCGA | 2213 |
| 2563 | CGGCCUCC C AAAGUGCU | 1715 | AGCACUUU CUGAUGAGGCCGUUAGGCCGAA IGAGGCCG | 2214 |
| 2564 | GGCCUCCC A AAGUGCUG | 1716 | CAGCACUU CUGAUGAGGCCGUUAGGCCGAA IGGAGGCC | 2215 |
| 2571 | CAAAGUGC U GGGAUUAC | 1717 | GUAAUCCC CUGAUGAGGCCGUUAGGCCGAA IACUUUG | 2216 |
| 2580 | GGGAUUAC A GGGAUGAG | 1718 | CUCAUCCC CUGAUGAGGCCGUUAGGCCGAA IUAAUCCC | 2217 |
| 2590 | GGAUGAGC C ACCGCGCC | 1719 | GGCGCGGU CUGAUGAGGCCGUUAGGCCGAA ICUCAUCC | 2218 |
| 2591 | GAUGAGCC A CCGCGCCC | 1720 | GGGCGCGG CUGAUGAGGCCGUUAGGCCGAA IGCUCAUC | 2219 |

TABLE IX-continued

Human PKR Inozyme and Substrate Sequence

| Pos | Substrate | Seq ID | Inozyme | Seq ID |
|---|---|---|---|---|
| 2593 | UGAGCCAC C GCGCCCAG | 1721 | CUGGGCGC CUGAUGAGGCCGUUAGGCCGAA IUGGCUCA | 2220 |
| 2598 | CACCGCGC C CAGCCUCA | 1722 | UGAGGCUG CUGAUGAGGCCGUUAGGCCGAA ICGCGGUU | 2221 |
| 2599 | ACCGCGCC C AGCCUCAU | 1723 | AUGAGGCU CUGAUGAGGCCGUUAGGCCGAA IGCGCGGU | 2222 |
| 2600 | CCGCGCCC A GCCUCAUC | 1724 | GAUGAGGC CUGAUGAGGCCGUUAGGCCGAA IGGCGCGG | 2223 |
| 2603 | CGCCCAGC C UCAUCUCU | 1725 | AGAGAUGA CUGAUGAGGCCGUUAGGCCGAA ICUGGGCG | 2224 |
| 2604 | GCCCAGCC U CAUCUCUU | 1726 | AAGAGAUG CUGAUGAGGCCGUUAGGCCGAA IGCUGGGC | 2225 |
| 2606 | CCAGCCUC A UCUCUUUG | 1727 | CAAAGAGA CUGAUGAGGCCGUUAGGCCGAA IAGGCUGG | 2226 |
| 2609 | GCCUCAUC U CUUUGUUC | 1728 | GAACAAAG CUGAUGAGGCCGUUAGGCCGAA IAUGAGGC | 2227 |
| 2611 | CUCAUCUC U UUGUUCUA | 1729 | UAGAACAA CUGAUGAGGCCGUUAGGCCGAA IAGAUGAG | 2228 |
| 2618 | CUUUGUUC U AAAGAUGG | 1730 | CCAUCUUU CUGAUGAGGCCGUUAGGCCGAA IAACAAAG | 2229 |
| 2633 | GGAAAAAC C ACCCCAA | 1731 | UUGGGGGU CUGAUGAGGCCGUUAGGCCGAA IUUUUUCC | 2230 |
| 2634 | GAAAAACC C CCCCAAA | 1732 | UUUGGGGG CUGAUGAGGCCGUUAGGCCGAA IGUUUUUC | 2231 |
| 2636 | AAAACCAC C CCCAAAUU | 1733 | AAUUUGGG CUGAUGAGGCCGUUAGGCCGAA IUGGUUUU | 2232 |
| 2637 | AAACCACC C CCAAAUUU | 1734 | AAAUUUGG CUGAUGAGGCCGUUAGGCCGAA IGUGGUUU | 2233 |
| 2638 | AACCACCC C CAAAUUUU | 1735 | AAAAUUUG CUGAUGAGGCCGUUAGGCCGAA IGGUGGUU | 2234 |
| 2639 | ACCACCCC C AAAUUUUC | 1736 | GAAAAUUU CUGAUGAGGCCGUUAGGCCGAA IGGGUGGU | 2235 |
| 2640 | CCACCCCC A AAUUUUCU | 1737 | AGAAAAUU CUGAUGAGGCCGUUAGGCCGAA IGGGGUGG | 2236 |
| 2648 | AAAUUUUC U UUUUAUAC | 1738 | GUAUAAAA CUGAUGAGGCCGUUAGGCCGAA IAAAAUUU | 2237 |
| 2657 | UUUUAUAC U AUUAAUGA | 1739 | UCAUUAAU CUGAUGAGGCCGUUAGGCCGAA IUAUAAAA | 2238 |
| 2669 | AAUGAAUC A AUCAAUUC | 1740 | GAAUUGAU CUGAUGAGGCCGUUAGGCCGAA IAUUCAUU | 2239 |
| 2673 | AAUCAAUC A AUUCAUAU | 1741 | AUAUGAAU CUGAUGAGGCCGUUAGGCCGAA IAUUGAUU | 2240 |
| 2678 | AUCAAUUC A UAUCUAUU | 1742 | AAUAGAUA CUGAUGAGGCCGUUAGGCCGAA IAAUUGAU | 2241 |
| 2683 | UUCAUAUC U AUUUAUUA | 1743 | UAAUAAAU CUGAUGAGGCCGUUAGGCCGAA IAUAUGAA | 2242 |
| 2698 | UAAAUUUC U ACCGCUUU | 1744 | AAAGCGGU CUGAUGAGGCCGUUAGGCCGAA IAAAUUUA | 2243 |
| 2701 | AUUUCUAC C GCUUUUAG | 1745 | CUAAAAGC CUGAUGAGGCCGUUAGGCCGAA IUAGAAAU | 2244 |
| 2704 | UCUACCGC U UUUAGGCC | 1746 | GGCCUAAA CUGAUGAGGCCGUUAGGCCGAA ICGGUAGA | 2245 |
| 2712 | UUUUAGGC C AAAAAAU | 1747 | AUUUUUUU CUGAUGAGGCCGUUAGGCCGAA ICCUAAAA | 2246 |
| 2713 | UUUAGGCC A AAAAAUG | 1748 | CAUUUUUU CUGAUGAGGCCGUUAGGCCGAA IGCCUAAA | 2247 |
| 2733 | GAUCGUUC U CUGCCUCA | 1749 | UGAGGCAG CUGAUGAGGCCGUUAGGCCGAA IAACGAUC | 2248 |
| 2735 | UCGUUCUC U GCCUCACA | 1750 | UGUGAGGC CUGAUGAGGCCGUUAGGCCGAA IAGAACGA | 2249 |
| 2738 | UUCUCUGC C UCACAUAG | 1751 | CUAUGUGA CUGAUGAGGCCGUUAGGCCGAA ICAGAGAA | 2250 |
| 2739 | UCUCUGCC U CACAUAGC | 1752 | GCUAUGUG CUGAUGAGGCCGUUAGGCCGAA IGCAGAGA | 2251 |
| 2741 | UCUGCCUC A CAUAGCUU | 1753 | AAGCUAUG CUGAUGAGGCCGUUAGGCCGAA IAGGCAGA | 2252 |
| 2743 | UGCCUCAC A UAGCUUAC | 1754 | GUAAGCUA CUGAUGAGGCCGUUAGGCCGAA IUGAGGCA | 2253 |
| 2748 | CACAUAGC U UACAAGCC | 1755 | GGCUUGUA CUGAUGAGGCCGUUAGGCCGAA ICUAUGUG | 2254 |
| 2752 | UAGCUUAC A AGCCAGCU | 1756 | AGCUGGCU CUGAUGAGGCCGUUAGGCCGAA IUAAGCUA | 2255 |
| 2756 | UUACAAGC C AGCUGGAG | 1757 | CUCCAGCU CUGAUGAGGCCGUUAGGCCGAA ICUUGUAA | 2256 |
| 2757 | UACAAGCC A GCUGGAGA | 1758 | UCUCCAGC CUGAUGAGGCCGUUAGGCCGAA IGCUUGUA | 2257 |
| 2760 | AAGCCAGC U GGAGAAAU | 1759 | AUUUCUCC CUGAUGAGGCCGUUAGGCCGAA ICUGGCUU | 2258 |
| 2776 | UAUGGUAC U CAUUAAAA | 1760 | UUUUAAUG CUGAUGAGGCCGUUAGGCCGAA IUACCAUA | 2259 |
| 2778 | UGGUACUC A UUAAAAAA | 1761 | UUUUUUAA CUGAUGAGGCCGUUAGGCCGAA IAGUACCA | 2260 |

Input Sequence = NM_002759. Cut Site = CH/.
Arm Length = 8. Core Sequence = CUGAUGAG X CGAA (X = GCCGUUAGGC or other stem II)
NM_002759 (*Homo sapiens* protein kinase, interferon-inducible double stranded RNA dependent (PRKR), mRNA.; 2808 bp)

Underlined region can be any X sequence or linker, as described herein. "I" stands for Inosine.

TABLE X

Human PKR Zinzyme and Substrate Sequence

| Pos | Substrate | Seq ID | Zinzyme | Seq ID |
|---|---|---|---|---|
| 10 | CGGCGGCG G CGGCGCAG | 2261 | CUGCGCCG GCCGAAAGGCGAGUGAGGUCU CGCCGCCG | 2480 |
| 13 | CGGCGGCG G CGCAGUUU | 2433 | AAACUGCG GCCGAAAGGCGAGUGAGGUCU CGCCGCCG | 2652 |
| 15 | GCGGCGGC G CAGUUUGC | 2434 | GCAAACUG GCCGAAAGGCGAGUGAGGUCU GCCGCCGC | 2653 |
| 18 | GCGGCGCA G UUUGCUCA | 2435 | UGAGCAAA GCCGAAAGGCGAGUGAGGUCU UGCGCCGC | 2654 |
| 22 | CGCAGUUU G CUCAUACU | 2436 | AGUAUGAG GCCGAAAGGCGAGUGAGGUCU AAACUGCG | 2655 |
| 33 | CAUACUUU G UGACUUGC | 2437 | GCAAGUCA GCCGAAAGGCGAGUGAGGUCU AAAGUAUG | 2656 |
| 40 | UGUGACUU G CGGUCACA | 2438 | UGUGACCG GCCGAAAGGCGAGUGAGGUCU AAGUCACA | 2657 |
| 43 | GACUUGCG G UCACAGUG | 2439 | CACUGUGA GCCGAAAGGCGAGUGAGGUCU CGCAAGUC | 2658 |
| 49 | CGGUCACA G UGGCAUUC | 2440 | GAAUGCCA GCCGAAAGGCGAGUGAGGUCU UGUGACCG | 2659 |
| 52 | UCACAGUG G CAUUCAGC | 2441 | GCUGAAUG GCCGAAAGGCGAGUGAGGUCU CACUGUGA | 2660 |
| 59 | GGCAUUCA G CUCCACAC | 2442 | GUGUGGAG GCCGAAAGGCGAGUGAGGUCU UGAAUGCC | 2661 |
| 71 | CACACUUG G UAGAACCA | 2443 | UGGUUCUA GCCGAAAGGCGAGUGAGGUCU CAAGUGUG | 2662 |
| 83 | AACCACAG G CACGACAA | 2444 | UUGUCGUG GCCGAAAGGCGAGUGAGGUCU CUGUGGUU | 2663 |
| 92 | CACGACAA G CAUAGAAA | 2445 | UUUCUAUG GCCGAAAGGCGAGUGAGGUCU UUGUCGUG | 2664 |
| 124 | UCAUCGAG G CAUCGAGG | 2446 | CCUCGAUG GCCGAAAGGCGAGUGAGGUCU CUCGAUGA | 2665 |
| 132 | GCAUCGAG G UCCAUCCC | 2447 | GGGAUGGA GCCGAAAGGCGAGUGAGGUCU CUCGAUGC | 2666 |

TABLE X-continued

Human PKR Zinzyme and Substrate Sequence

| Pos | Substrate | | | Seq ID | Zinzyme | | | Seq ID |
|---|---|---|---|---|---|---|---|---|
| 162 | AGACCCUG | G | CUAUCAUA | 2448 | UAUGAUAG | GCCGAAAGGCGAGUGAGGUCU | CAGGGUCU | 2667 |
| 178 | AGACCUUA | G | UCUUCGCU | 2449 | AGCGAAGA | GCCGAAAGGCGAGUGAGGUCU | UAAGGUCU | 2668 |
| 184 | UAGUCUUC | G | CUGGUAUA | 2450 | UAUACCAG | GCCGAAAGGCGAGUGAGGUCU | GAAGACUA | 2669 |
| 188 | CUUCGCUG | G | UAUACUCG | 2451 | CGAGUAUA | GCCGAAAGGCGAGUGAGGUCU | CAGCGAAG | 2670 |
| 196 | GUAUACUC | G | CUGUCUGU | 2452 | ACAGACAG | GCCGAAAGGCGAGUGAGGUCU | GAGUAUAC | 2671 |
| 199 | UACUCGCU | G | UCUGUCAA | 2453 | UUGACAGA | GCCGAAAGGCGAGUGAGGUCU | AGCGAGUA | 2672 |
| 203 | CGCUGUCU | G | UCAACCAG | 2454 | CUGGUUGA | GCCGAAAGGCGAGUGAGGUCU | AGACAGCG | 2673 |
| 211 | GUCAACCA | G | CGGUUGAC | 2455 | GUCAACCG | GCCGAAAGGCGAGUGAGGUCU | UGGUUGAC | 2674 |
| 214 | AACCAGCG | G | UUGACUUU | 2456 | AAAGUCAA | GCCGAAAGGCGAGUGAGGUCU | CGCUGGUU | 2675 |
| 229 | UUUUUUAA | G | CCUUCUUU | 2457 | AAAGAAGG | GCCGAAAGGCGAGUGAGGUCU | UUAAAAAA | 2676 |
| 252 | UUUUACCA | G | UUUCUGGA | 2458 | UCCAGAAA | GCCGAAAGGCGAGUGAGGUCU | UGGUAAAA | 2677 |
| 261 | UUUCUGGA | G | CAAAUUCA | 2459 | UGAAUUUG | GCCGAAAGGCGAGUGAGGUCU | UCCAGAAA | 2678 |
| 270 | CAAAUUCA | G | UUUGCCUU | 2460 | AAGGCAAA | GCCGAAAGGCGAGUGAGGUCU | UGAAUUUG | 2679 |
| 274 | UUCAGUUU | G | CCUUCCUG | 2461 | CAGGAAGG | GCCGAAAGGCGAGUGAGGUCU | AAACUGAA | 2680 |
| 288 | CUGGAUUU | G | UAAAUUGU | 2462 | ACAAUUUA | GCCGAAAGGCGAGUGAGGUCU | AAAUCCAG | 2681 |
| 295 | UGUAAAUU | G | UAAUGACC | 2463 | GGUCAUUA | GCCGAAAGGCGAGUGAGGUCU | AAUUUACA | 2682 |
| 315 | AAACUUUA | G | CAGUUCUU | 2464 | AAGAACUG | GCCGAAAGGCGAGUGAGGUCU | UAAAGUUU | 2683 |
| 318 | CUUUAGCA | G | UUCUUCCA | 2465 | UGGAAGAA | GCCGAAAGGCGAGUGAGGUCU | UGCUAAAG | 2684 |
| 337 | UGACUCAG | G | UUUGCUUC | 2466 | GAAGCAAA | GCCGAAAGGCGAGUGAGGUCU | CUGAGUCA | 2685 |
| 341 | UCAGGUUU | G | CUUCUCUG | 2467 | CAGAGAAG | GCCGAAAGGCGAGUGAGGUCU | AAACCUGA | 2686 |
| 350 | CUUCUCUG | G | CGGUCUUC | 2468 | GAAGACCG | GCCGAAAGGCGAGUGAGGUCU | CAGAGAAG | 2687 |
| 353 | CUCUGGCG | G | UCUUCAGA | 2469 | UCUGAAGA | GCCGAAAGGCGAGUGAGGUCU | CGCCAGAG | 2688 |
| 380 | ACACUUCC | G | UGAUUAUC | 2470 | GAUAAUCA | GCCGAAAGGCGAGUGAGGUCU | GGAAGUGU | 2689 |
| 390 | GAUUAUCU | G | CGUGCAUU | 2471 | AAUGCACG | GCCGAAAGGCGAGUGAGGUCU | AGAUAAUC | 2690 |
| 392 | UUAUCUGC | G | UGCAUUUU | 2472 | AAAAUGCA | GCCGAAAGGCGAGUGAGGUCU | GCAGAUAA | 2691 |
| 394 | AUCUGCGU | G | CAUUUUGG | 2473 | CCAAAAUG | GCCGAAAGGCGAGUGAGGUCU | ACGCAGAU | 2692 |
| 408 | UGGACAAA | G | CUUCCAAC | 2474 | GUUGGAAG | GCCGAAAGGCGAGUGAGGUCU | UUUGUCCA | 2693 |
| 439 | AAGAAAUG | G | CUGGUGAU | 2475 | AUCACCAG | GCCGAAAGGCGAGUGAGGUCU | CAUUUCUU | 2694 |
| 443 | AAUGGCUG | G | UGAUCUUU | 2476 | AAAGAUCA | GCCGAAAGGCGAGUGAGGUCU | CAGCCAUU | 2695 |
| 454 | AUCUUUCA | G | CAGGUUUC | 2477 | GAAACCUG | GCCGAAAGGCGAGUGAGGUCU | UGAAAGAU | 2696 |
| 458 | UUCAGCAG | G | UUUCUUCA | 2478 | UGAAGAAA | GCCGAAAGGCGAGUGAGGUCU | CUGCUGAA | 2697 |
| 488 | UACAUACC | G | UCAGAAGC | 2479 | GCUUCUGA | GCCGAAAGGCGAGUGAGGUCU | GGUAUGUA | 2698 |
| 495 | CGUCAGAA | G | CAGGGAGU | 2262 | ACUCCCUG | GCCGAAAGGCGAGUGAGGUCU | UUCUGACG | 2481 |
| 502 | AGCAGGGA | G | UAGUACUU | 2263 | AAGUACUA | GCCGAAAGGCGAGUGAGGUCU | UCCCUGCU | 2482 |
| 505 | AGGGAGUA | G | UACUUAAA | 2264 | UUUAAGUA | GCCGAAAGGCGAGUGAGGUCU | UACUCCCU | 2483 |
| 525 | CAAGAACU | G | CCUAAUUC | 2265 | GAAUUAGG | GCCGAAAGGCGAGUGAGGUCU | AGUUCUUG | 2484 |
| 555 | GAUAGGAG | G | UUUACAUU | 2266 | AAUGUAAA | GCCGAAAGGCGAGUGAGGUCU | CUCCUAUC | 2485 |
| 568 | CAUUUCAA | G | UUUAUAUA | 2267 | UAUUAUAA | GCCGAAAGGCGAGUGAGGUCU | UUGAAAUG | 2486 |
| 599 | UCCAGAAG | G | UGAAGGUA | 2268 | UACCUUCA | GCCGAAAGGCGAGUGAGGUCU | CUUCUGGA | 2487 |
| 605 | AGGUGAAG | G | UAGAUCAA | 2269 | UUGAUCUA | GCCGAAAGGCGAGUGAGGUCU | CUUCACCU | 2488 |
| 622 | AGAAGGAA | G | CAAAAAAU | 2270 | AUUUUUUG | GCCGAAAGGCGAGUGAGGUCU | UUCCUUCU | 2489 |
| 631 | CAAAAAAU | G | CCGCAGCC | 2271 | GGCUGCGG | GCCGAAAGGCGAGUGAGGUCU | AUUUUUUG | 2490 |
| 634 | AAAAUGCC | G | CAGCCAAA | 2272 | UUUGGCUG | GCCGAAAGGCGAGUGAGGUCU | GGCAUUUU | 2491 |
| 637 | AUGCCGCA | G | CCAAAUUA | 2273 | UAAUUUGG | GCCGAAAGGCGAGUGAGGUCU | UGCGGCAU | 2492 |
| 646 | CCAAAUUA | G | CUGUUGAG | 2274 | CUCAACAG | GCCGAAAGGCGAGUGAGGUCU | UAAUUUGG | 2493 |
| 649 | AAUUAGCU | G | UUGAGAUA | 2275 | UAUCUCAA | GCCGAAAGGCGAGUGAGGUCU | AGCUAAUU | 2494 |
| 676 | AAAAGAAG | G | CAGUUAGU | 2276 | ACUAACUG | GCCGAAAGGCGAGUGAGGUCU | CUUCUUUU | 2495 |
| 679 | AGAAGGCA | G | UUAGUCCU | 2277 | AGGACUAA | GCCGAAAGGCGAGUGAGGUCU | UGCCUUCU | 2496 |
| 683 | GGCAGUUA | G | UCCUUUAU | 2278 | AUAAAGGA | GCCGAAAGGCGAGUGAGGUCU | UAACUGCC | 2497 |
| 743 | UUUACAUA | G | CCUUAUCA | 2279 | UGAUAAGG | GCCGAAAGGCGAGUGAGGUCU | CUAUGUAA | 2498 |
| 760 | AUAGAAUU | G | CCCAGAAG | 2280 | CUUCUGGG | GCCGAAAGGCGAGUGAGGUCU | AAUUCUAU | 2499 |
| 781 | GACUAACU | G | UAAAUUAU | 2281 | AUAAUUUA | GCCGAAAGGCGAGUGAGGUCU | AGUUAGUC | 2500 |
| 795 | UAUGAACA | G | UGUGCAUC | 2282 | GAUGCACA | GCCGAAAGGCGAGUGAGGUCU | UGUUCAUA | 2501 |
| 797 | UGAACAGU | G | UGCAUCGG | 2283 | CCGAUGCA | GCCGAAAGGCGAGUGAGGUCU | ACUGUUCA | 2502 |
| 799 | AACAGUGU | G | CAUCGGGG | 2284 | CCCCGAUG | GCCGAAAGGCGAGUGAGGUCU | ACACUGUU | 2503 |
| 808 | CAUCGGGG | G | UGCAUGGG | 2285 | CCCAUGCA | GCCGAAAGGCGAGUGAGGUCU | CCCCGAUG | 2504 |
| 810 | UCGGGGGU | G | CAUGGGCC | 2286 | GGCCCAUG | GCCGAAAGGCGAGUGAGGUCU | ACCCCCGA | 2505 |
| 816 | GUGCAUGG | G | CCAGAAGG | 2287 | CCUUCUGG | GCCGAAAGGCGAGUGAGGUCU | CCAUGCAC | 2506 |
| 839 | UUAUAAAU | G | CAAAAUGG | 2288 | CCAUUUUG | GCCGAAAGGCGAGUGAGGUCU | AUUUAUAA | 2507 |
| 863 | AGAAUAUA | G | UAUUGGUA | 2289 | UACCAAUA | GCCGAAAGGCGAGUGAGGUCU | UAUAUUCU | 2508 |
| 869 | UAGUAUUG | G | UACAGGUU | 2290 | AACCUGUA | GCCGAAAGGCGAGUGAGGUCU | CAAUACUA | 2509 |
| 875 | UGGUACAG | G | UUCUACUA | 2291 | UAGUAGAA | GCCGAAAGGCGAGUGAGGUCU | CUGUACCA | 2510 |
| 892 | AACAGGAA | G | CAAAACAA | 2292 | UUGUUUUG | GCCGAAAGGCGAGUGAGGUCU | UUCCUGUU | 2511 |
| 904 | AACAAUUG | G | CCGCUAAA | 2293 | UUUAGCGG | GCCGAAAGGCGAGUGAGGUCU | CAAUUGUU | 2512 |
| 907 | AAUUGGCC | G | CUAAACUU | 2294 | AAGUUUAG | GCCGAAAGGCGAGUGAGGUCU | GGCCAAUU | 2513 |
| 916 | CUAAACUU | G | CAUAUCUU | 2295 | AAGAUAUG | GCCGAAAGGCGAGUGAGGUCU | AAGUUUAG | 2514 |
| 949 | AAACCUCA | G | UGAAAUCU | 2296 | AGAUUUCA | GCCGAAAGGCGAGUGAGGUCU | UGAGGUUU | 2515 |
| 966 | GACUACCU | G | UCCUCUGG | 2297 | CCAGAGGA | GCCGAAAGGCGAGUGAGGUCU | AGGUAGUC | 2516 |
| 974 | GUCCUCUG | G | UUCUUUUG | 2298 | CAAAAGAA | GCCGAAAGGCGAGUGAGGUCU | CAGAGGAC | 2517 |
| 982 | GUUCUUUU | G | CUACUACG | 2299 | CGUAGUAG | GCCGAAAGGCGAGUGAGGUCU | AAAAGAAC | 2518 |
| 990 | GCUACUAC | G | UGUGAGUC | 2300 | GACUCACA | GCCGAAAGGCGAGUGAGGUCU | GUAGUAGC | 2519 |
| 992 | UACUACGU | G | UGAGUCCC | 2301 | GGGACUCA | GCCGAAAGGCGAGUGAGGUCU | ACGUAGUA | 2520 |
| 996 | ACGUGUGA | G | UCCCAAAG | 2302 | CUUUGGGA | GCCGAAAGGCGAGUGAGGUCU | UCACACGU | 2521 |
| 1004 | GUCCCAAA | G | CAACUCUU | 2303 | AAGAGUUG | GCCGAAAGGCGAGUGAGGUCU | UUUGGGAC | 2522 |
| 1015 | ACUCUUUA | G | UGACCAGC | 2304 | GCUGGUCA | GCCGAAAGGCGAGUGAGGUCU | UAAAGAGU | 2523 |

TABLE X-continued

Human PKR Zinzyme and Substrate Sequence

| Pos | Substrate | Seq ID | Zinzyme | Seq ID |
|---|---|---|---|---|
| 1022 | AGUGACCA G CACACUCG | 2305 | CGAGUGUG GCCGAAAGGCGAGUGAGGUCU UGGUCACU | 2524 |
| 1030 | GCACACUC G CUUCUGAA | 2306 | UUCAGAAG GCCGAAAGGCGAGUGAGGUCU GAGUGUGC | 2525 |
| 1052 | AUCUGAAG G UGACUUCU | 2307 | AGAAGUCA GCCGAAAGGCGAGUGAGGUCU CUUCAGAU | 2526 |
| 1063 | ACUUCUCA G CAGAUACA | 2308 | UGUAUCUG GCCGAAAGGCGAGUGAGGUCU UGAGAAGU | 2527 |
| 1091 | UUCUAACA G UGACAGUU | 2309 | AACUGUCA GCCGAAAGGCGAGUGAGGUCU UGUUAGAA | 2528 |
| 1097 | CAGUGACA G UUUAAACA | 2310 | UGUUUAAA GCCGAAAGGCGAGUGAGGUCU UGUCACUG | 2529 |
| 1106 | UUUAAACA G UUCUUCGU | 2311 | ACGAAGAA GCCGAAAGGCGAGUGAGGUCU UGUUUAAA | 2530 |
| 1113 | AGUUCUUC G UUGCUUAU | 2312 | AUAAGCAA GCCGAAAGGCGAGUGAGGUCU GAAGAACU | 2531 |
| 1116 | UCUUCGUU G CUUAUGAA | 2313 | UUCAUAAG GCCGAAAGGCGAGUGAGGUCU AACGAAGA | 2532 |
| 1127 | UAUGAAUG G UCUCAGAA | 2314 | UUCUGAGA GCCGAAAGGCGAGUGAGGUCU CAUUCAUA | 2533 |
| 1150 | AAAGGAAG G CAAAAGA | 2315 | UCUUUUUG GCCGAAAGGCGAGUGAGGUCU CUUCCUUU | 2534 |
| 1165 | GAUCUUUG G CACCCAGA | 2316 | UCUGGGUG GCCGAAAGGCGAGUGAGGUCU CAAAGAUC | 2535 |
| 1203 | GAAACAAA G UAUACUGU | 2317 | ACAGUAUA GCCGAAAGGCGAGUGAGGUCU UUUGUUUC | 2536 |
| 1210 | AGUAUACU G UGGACAAG | 2318 | CUUGUCCA GCCGAAAGGCGAGUGAGGUCU AGUAUACU | 2537 |
| 1221 | GACAAGAG G UUUGGCAU | 2319 | AUGCCAAA GCCGAAAGGCGAGUGAGGUCU CUCUUGUC | 2538 |
| 1226 | GAGGUUUG G CAUGGAUU | 2320 | AAUCCAUG GCCGAAAGGCGAGUGAGGUCU CAAACCUC | 2539 |
| 1256 | AUUAAUUG G CUCAGGUG | 2321 | CACCUGAG GCCGAAAGGCGAGUGAGGUCU CAAUUAAU | 2540 |
| 1262 | UGGCUCAG G UGGAUUUG | 2322 | CAAAUCCA GCCGAAAGGCGAGUGAGGUCU CUGAGCCA | 2541 |
| 1271 | UGGAUUUG G CCAAGUUU | 2323 | AAACUUGG GCCGAAAGGCGAGUGAGGUCU CAAAUCCA | 2542 |
| 1276 | UUGGCCAA G UUUUCAAA | 2324 | UUUGAAAA GCCGAAAGGCGAGUGAGGUCU UUGGCCAA | 2543 |
| 1285 | UUUUCAAA G CAAAACAC | 2325 | GUGUUUUG GCCGAAAGGCGAGUGAGGUCU UUUGAAAA | 2544 |
| 1315 | AGACUUAC G UUAUUAAA | 2326 | UUUAAUAA GCCGAAAGGCGAGUGAGGUCU GUAAGUCU | 2545 |
| 1325 | UAUUAAAC G UGUUAAAU | 2327 | AUUUAACA GCCGAAAGGCGAGUGAGGUCU GUUUAAUA | 2546 |
| 1327 | UUAAACGU G UUAAAUAU | 2328 | AUAUUUAA GCCGAAAGGCGAGUGAGGUCU ACGUUUAA | 2547 |
| 1348 | ACGAGAAG G CGGAGCGU | 2329 | ACGCUCCG GCCGAAAGGCGAGUGAGGUCU CUUCUCGU | 2548 |
| 1353 | AAGGCGGA G CGUGAAGU | 2330 | ACUUCACG GCCGAAAGGCGAGUGAGGUCU UCCGCCUU | 2549 |
| 1355 | GGCGGAGC G UGAAGUAA | 2331 | UUACUUCA GCCGAAAGGCGAGUGAGGUCU GCUCCGCC | 2550 |
| 1360 | AGCGUGAA G UAAAAGCA | 2332 | UGCUUUUA GCCGAAAGGCGAGUGAGGUCU UUCACGCU | 2551 |
| 1366 | AAGUAAAA G CAUUGGCA | 2333 | UGCCAAUG GCCGAAAGGCGAGUGAGGUCU UUUUACUU | 2552 |
| 1372 | AAGCAUUG G CAAAACUU | 2334 | AAGUUUUG GCCGAAAGGCGAGUGAGGUCU CAAUGCUU | 2553 |
| 1387 | UUGAUCAU G UAAAUAUU | 2335 | AAUAUUUA GCCGAAAGGCGAGUGAGGUCU AUGAUCAA | 2554 |
| 1396 | UAAAUAUU G UUCACUAC | 2336 | GUAGUGAA GCCGAAAGGCGAGUGAGGUCU AAUAUUUA | 2555 |
| 1409 | CUACAAUG G CUGUUGGG | 2337 | CCCAACAG GCCGAAAGGCGAGUGAGGUCU CAUUGUAG | 2556 |
| 1412 | CAAUGGCU G UUGGGAUG | 2338 | CAUCCCAA GCCGAAAGGCGAGUGAGGUCU AGCCAUUG | 2557 |
| 1445 | UGAGACCA G UGAUGAUU | 2339 | AAUCAUCA GCCGAAAGGCGAGUGAGGUCU UGGUCUCA | 2558 |
| 1463 | UCUUGAGA G CAGUGAUU | 2340 | AAUCACUG GCCGAAAGGCGAGUGAGGUCU UCUCAAGA | 2559 |
| 1466 | UGAGAGCA G UGAUUAUG | 2341 | CAUAAUCA GCCGAAAGGCGAGUGAGGUCU UGCUCUCA | 2560 |
| 1487 | UGAGAACA G CAAAAAUA | 2342 | UAUUUUUG GCCGAAAGGCGAGUGAGGUCU UGUUCUCA | 2561 |
| 1496 | CAAAAAUA G UUCAAGGU | 2343 | ACCUUGAA GCCGAAAGGCGAGUGAGGUCU UAUUUUUG | 2562 |
| 1503 | AGUUCAAG G UCAAAGAC | 2344 | GUCUUUGA GCCGAAAGGCGAGUGAGGUCU CUUGAACU | 2563 |
| 1515 | AAGACUAA G UGCCUUUU | 2345 | AAAAGGCA GCCGAAAGGCGAGUGAGGUCU UUAGUCUU | 2564 |
| 1517 | GACUAAGU G CCUUUUCA | 2346 | UGAAAAGG GCCGAAAGGCGAGUGAGGUCU ACUUAGUC | 2565 |
| 1541 | GGAAUUCU G UGAUAAAG | 2347 | CUUUAUCA GCCGAAAGGCGAGUGAGGUCU AGAAUUCC | 2566 |
| 1583 | AAGAAGAG G CGAGAAAC | 2348 | GUUUCUCG GCCGAAAGGCGAGUGAGGUCU CUCUUCUU | 2567 |
| 1600 | UAGACAAA G UUUUGGCU | 2349 | AGCCAAAA GCCGAAAGGCGAGUGAGGUCU UUUGUCUA | 2568 |
| 1606 | AAGUUUUG G CUUUGGAA | 2350 | UUCCAAAG GCCGAAAGGCGAGUGAGGUCU CAAAACUU | 2569 |
| 1639 | CAAAAGGG G UGGAUUAU | 2351 | AUAAUCCA GCCGAAAGGCGAGUGAGGUCU CCCUUUUG | 2570 |
| 1683 | GAUCUUAA G CCAAGUAA | 2352 | UUACUUGG GCCGAAAGGCGAGUGAGGUCU UUAAGAUC | 2571 |
| 1688 | UAAGCCAA G UAAUAUAU | 2353 | AUAUAUUA GCCGAAAGGCGAGUGAGGUCU UUGGCUUA | 2572 |
| 1702 | UAUUCUUA G UAGAUACA | 2354 | UGUAUCUA GCCGAAAGGCGAGUGAGGUCU UAAGAAUA | 2573 |
| 1717 | CAAAACAA G UAAAGAUU | 2355 | AAUCUUUA GCCGAAAGGCGAGUGAGGUCU UUGUUUUG | 2574 |
| 1741 | UUGGACUU G UAACAUCU | 2356 | AGAUGUUA GCCGAAAGGCGAGUGAGGUCU AAGUCCAA | 2575 |
| 1767 | GAUGGAAA G CGAACAAG | 2357 | CUUGUUCG GCCGAAAGGCGAGUGAGGUCU UUUCCAUC | 2576 |
| 1778 | AACAAGGA G UAAGGGAA | 2358 | UUCCCUUA GCCGAAAGGCGAGUGAGGUCU UCCUUGUU | 2577 |
| 1791 | GGAACUUU G CGAUACAU | 2359 | AUGUAUCG GCCGAAAGGCGAGUGAGGUCU AAAGUUCC | 2578 |
| 1802 | AUACAUGA G CCCAGAAC | 2360 | GUUCUGGG GCCGAAAGGCGAGUGAGGUCU UCAUGUAU | 2579 |
| 1821 | AUUUCUUC G CAAGACUA | 2361 | UAGUCUUG GCCGAAAGGCGAGUGAGGUCU GAAGAAAU | 2580 |
| 1840 | GAAAGGAA G UGGACCUC | 2362 | GAGGUCCA GCCGAAAGGCGAGUGAGGUCU UUCCUUUC | 2581 |
| 1852 | ACCUCUAC G CUUUGGGG | 2363 | CCCCAAAG GCCGAAAGGCGAGUGAGGUCU GUAGAGGU | 2582 |
| 1860 | GCUUUGGG G CUAAUUCU | 2364 | AGAAUUAG GCCGAAAGGCGAGUGAGGUCU CCCAAAGC | 2583 |
| 1870 | UAAUUCUU G CUGAACUU | 2365 | AAGUUCAG GCCGAAAGGCGAGUGAGGUCU AAGAAUUA | 2584 |
| 1885 | UUCUUCAU G UAUGUGAC | 2366 | GUCACAUA GCCGAAAGGCGAGUGAGGUCU AUGAAGAA | 2585 |
| 1889 | UCAUGUAU G UGACACUG | 2367 | CAGUGUCA GCCGAAAGGCGAGUGAGGUCU AUACAUGA | 2586 |
| 1897 | GUGACACU G CUUUUGAA | 2368 | UUCAAAAG GCCGAAAGGCGAGUGAGGUCU AGUGUCAC | 2587 |
| 1914 | ACAUCAAA G UUUUUCAC | 2369 | GUGAAAAA GCCGAAAGGCGAGUGAGGUCU UUUGAUGU | 2588 |
| 1937 | ACGGGAUG G CAUCAUCU | 2370 | AGAUGAUG GCCGAAAGGCGAGUGAGGUCU CAUCCCGU | 2589 |
| 2047 | CCUUGACU G UGUGGAAG | 2371 | CUUCCACA GCCGAAAGGCGAGUGAGGUCU AGUCAAGG | 2590 |
| 2049 | UUGACUGU G UGGAAGAA | 2372 | UUCUUCCA GCCGAAAGGCGAGUGAGGUCU ACAGUCAA | 2591 |
| 2060 | GAAGAAAA G CCCAGAGA | 2373 | UCUCUGGG GCCGAAAGGCGAGUGAGGUCU UUUCUUC | 2592 |
| 2087 | ACACACAU G UUAGAGCC | 2374 | GGCUCUAA GCCGAAAGGCGAGUGAGGUCU AUGUGUGU | 2593 |
| 2093 | AUGUUAGA G CCCUUCUG | 2375 | CAGAAGGG GCCGAAAGGCGAGUGAGGUCU UCUAACAU | 2594 |
| 2107 | CUGAAAAA G UAUCCUGC | 2376 | GCAGGAUA GCCGAAAGGCGAGUGAGGUCU UUUUUCAG | 2595 |
| 2114 | AGUAUCCU G CUUCUGAU | 2377 | AUCAGAAG GCCGAAAGGCGAGUGAGGUCU AGGAUACU | 2596 |
| 2125 | UCUGAUAU G CAGUUUUC | 2378 | GAAAACUG GCCGAAAGGCGAGUGAGGUCU AUAUCAGA | 2597 |
| 2128 | GAUAUGCA G UUUUCCUU | 2379 | AAGGAAAA GCCGAAAGGCGAGUGAGGUCU UGCAUAUC | 2598 |

TABLE X-continued

Human PKR Zinzyme and Substrate Sequence

| Pos | Substrate | Seq ID | Zinzyme | Seq ID |
|---|---|---|---|---|
| 2153 | UAAAAUCU G CUAGGGAA | 2380 | UUCCCUAG GCCGAAAGGCGAGUGAGGUCU AGAUUUUA | 2599 |
| 2192 | AUUUUAAU G UUUCCUUU | 2381 | AAAGGAAA GCCGAAAGGCGAGUGAGGUCU AUUAAAAU | 2600 |
| 2230 | AUCUUUCU G CAGAAACA | 2382 | UGUUUCUG GCCGAAAGGCGAGUGAGGUCU AGAAAGAU | 2601 |
| 2244 | ACAGAAAG G UUUUCUUC | 2383 | GAAGAAAA GCCGAAAGGCGAGUGAGGUCU CUUUCUGU | 2602 |
| 2258 | UUCUUUUU G CUUCAAAA | 2384 | UUUUGAAG GCCGAAAGGCGAGUGAGGUCU AAAAAGAA | 2603 |
| 2293 | UUUUCCUG G CUCAUCUC | 2385 | GAGAUGAG GCCGAAAGGCGAGUGAGGUCU CAGGAAAA | 2604 |
| 2332 | AAGACAGA G UCUCGCUC | 2386 | GAGCGAGA GCCGAAAGGCGAGUGAGGUCU UCUGUCUU | 2605 |
| 2337 | AGAGUCUC G CUCUGUUG | 2387 | CAACAGAG GCCGAAAGGCGAGUGAGGUCU GAGACUCU | 2606 |
| 2342 | CUCGCUCU G UUGCCAAG | 2388 | CUGGGCAA GCCGAAAGGCGAGUGAGGUCU AGAGCGAG | 2607 |
| 2345 | GCUCUGUU G CCCAGGCU | 2389 | AGCCUGGG GCCGAAAGGCGAGUGAGGUCU AACAGAGC | 2608 |
| 2351 | UUGCCCAG G CUGGAGUG | 2390 | CACUCCAG GCCGAAAGGCGAGUGAGGUCU CUGGGCAA | 2609 |
| 2357 | AGGCUGGA G UGCAAUGA | 2391 | UCAUUGCA GCCGAAAGGCGAGUGAGGUCU UCCAGCCU | 2610 |
| 2359 | GCUGGAGU G CAAUGACA | 2392 | UGUCAUUG GCCGAAAGGCGAGUGAGGUCU ACUCCAGC | 2611 |
| 2370 | AUGACACA G UCUUGGCU | 2393 | AGCCAAGA GCCGAAAGGCGAGUGAGGUCU UGUGUCAU | 2612 |
| 2376 | CAGUCUUG G CUCACUGC | 2394 | GCAGUGAG GCCGAAAGGCGAGUGAGGUCU CAAGACUG | 2613 |
| 2383 | GGCUCACU G CAACUUCU | 2395 | AGAAGUUG GCCGAAAGGCGAGUGAGGUCU AGUGAGCC | 2614 |
| 2392 | CAACUUCU G CCUCUUGG | 2396 | CCAAGAGG GCCGAAAGGCGAGUGAGGUCU AGAAGUUG | 2615 |
| 2401 | CCUCUUGG G UUCAAGUG | 2397 | CACUUGAA GCCGAAAGGCGAGUGAGGUCU CCAAGAGG | 2616 |
| 2407 | GGGUUCAA G UGAUUCUC | 2398 | GAGAAUCA GCCGAAAGGCGAGUGAGGUCU UUGAACCC | 2617 |
| 2418 | AUUCUCCU G CCUCAGCC | 2399 | GGCUGAGG GCCGAAAGGCGAGUGAGGUCU AGGAGAAU | 2618 |
| 2424 | CUGCCUCA G CCUCCUGA | 2400 | UCAGGAGG GCCGAAAGGCGAGUGAGGUCU UGAGGCAG | 2619 |
| 2433 | CCUCCUGA G UAGCUGGA | 2401 | UCCAGCUA GCCGAAAGGCGAGUGAGGUCU UCAGGAGG | 2620 |
| 2436 | CCUGAGUA G CUGGAUUA | 2402 | UAAUCCAG GCCGAAAGGCGAGUGAGGUCU UACUCAGG | 2621 |
| 2448 | GAUUACAG G CAUGUGCC | 2403 | GGCACAUG GCCGAAAGGCGAGUGAGGUCU CUGUAAUC | 2622 |
| 2452 | ACAGGCAU G UGCCACCC | 2404 | GGGUGGCA GCCGAAAGGCGAGUGAGGUCU AUGCCUGU | 2623 |
| 2454 | AGGCAUGU G CCACCCAC | 2405 | GUGGGUGG GCCGAAAGGCGAGUGAGGUCU ACAUGCCU | 2624 |
| 2476 | UAAUUUUU G UGUUUUUA | 2406 | UAAAAACA GCCGAAAGGCGAGUGAGGUCU AAAAAUUA | 2625 |
| 2478 | AUUUUUGU G UUUUUAAU | 2407 | AUUAAAAA GCCGAAAGGCGAGUGAGGUCU ACAAAAAU | 2626 |
| 2496 | AAGACAGG G UUUACCA | 2408 | UGGUGAAA GCCGAAAGGCGAGUGAGGUCU CCUGUCUU | 2627 |
| 2506 | UUCACCAU G UUGGCCAA | 2409 | CUGGCCAA GCCGAAAGGCGAGUGAGGUCU AUGGUGAA | 2628 |
| 2510 | CCAUGUUG G CCAGGCUG | 2410 | CAGCCUGG GCCGAAAGGCGAGUGAGGUCU CAACAUGG | 2629 |
| 2515 | UUGGCCAG G CUGGUCUC | 2411 | GAGACCAG GCCGAAAGGCGAGUGAGGUCU CUGGCCAA | 2630 |
| 2519 | CCAGGCUG G UCUCAAAC | 2412 | GUUUGAGA GCCGAAAGGCGAGUGAGGUCU CAGCCUGG | 2631 |
| 2540 | GACCUCAA G UAAUCCAC | 2413 | GUGGAUUA GCCGAAAGGCGAGUGAGGUCU UUGAGGUC | 2632 |
| 2551 | AUCCACCU G CCUCGGCC | 2414 | GGCCGAGG GCCGAAAGGCGAGUGAGGUCU AGGUGGAU | 2633 |
| 2557 | CUGCCUCG G CCUCCCAA | 2415 | UUGGGAGG GCCGAAAGGCGAGUGAGGUCU CGAGGCAG | 2634 |
| 2567 | CUCCCAAA G UGCUGGGA | 2416 | UCCCAGCA GCCGAAAGGCGAGUGAGGUCU UUUGGGAG | 2635 |
| 2569 | CCCAAAGU G CUGGGAUU | 2417 | AAUCCCAG GCCGAAAGGCGAGUGAGGUCU ACUUUGGG | 2636 |
| 2588 | AGGGAUGA G CCACCGCG | 2418 | CGCGCUGG GCCGAAAGGCGAGUGAGGUCU UCAUCCCU | 2637 |
| 2594 | GAGCCACC G CGCCCAGC | 2419 | GCUGGGCG GCCGAAAGGCGAGUGAGGUCU GGUGGCUC | 2638 |
| 2596 | GCCACCGC G CCCAGCCU | 2420 | AGGCUGGG GCCGAAAGGCGAGUGAGGUCU GCGGUGGC | 2639 |
| 2601 | CGCGCCCA G CCUCAUCU | 2421 | AGAUGAGG GCCGAAAGGCGAGUGAGGUCU UGGGCGCG | 2640 |
| 2614 | AUCUCUUU G UUCUAAAG | 2422 | CUUUAGAA GCCGAAAGGCGAGUGAGGUCU AAAGAGAU | 2641 |
| 2702 | UUUCUACC G CUUUUAGG | 2423 | CCUAAAAG GCCGAAAGGCGAGUGAGGUCU GGUAGAAA | 2642 |
| 2710 | GCUUUUAG G CCAAAAAA | 2424 | UUUUUUGG GCCGAAAGGCGAGUGAGGUCU CUAAAAGC | 2643 |
| 2721 | AAAAAAAU G UAAGAUCG | 2425 | CGAUCUUA GCCGAAAGGCGAGUGAGGUCU AUUUUUUU | 2644 |
| 2729 | GUAAGAUC G UUCUCUGC | 2426 | GCAGAGAA GCCGAAAGGCGAGUGAGGUCU GAUCUUAC | 2645 |
| 2736 | CGUUCUCU G CCUCACAU | 2427 | AUGUGAGG GCCGAAAGGCGAGUGAGGUCU AGAGAACG | 2646 |
| 2746 | CUCACAUA G CUUACAAG | 2428 | CUUGUAAG GCCGAAAGGCGAGUGAGGUCU UAUGUGAG | 2647 |
| 2754 | GCUUACAA G CCAGCUGG | 2429 | CCAGCUGG GCCGAAAGGCGAGUGAGGUCU UUGUAAGC | 2648 |
| 2758 | ACAAGCCA G CUGGAGAA | 2430 | UUCUCCAG GCCGAAAGGCGAGUGAGGUCU UGGCUUGU | 2649 |
| 2772 | GAAAUAUG G UACUCAUU | 2431 | AAUGAGUA GCCGAAAGGCGAGUGAGGUCU CAUAUUUC | 2650 |
| 2796 | AAAAAAAA G UGAUGUAC | 2432 | GUACAUCA GCCGAAAGGCGAGUGAGGUCU UUUUUUUU | 2651 |

Input Sequence = NM_002759. Cut Site = G/Y
Arm Length = 8. Core Sequence = GCcgaaagGCGaGuCaaGGuCu NM_002759 (*Homo sapiens* protein kinase, interferon-inducible double stranded RNA dependent (PRKR), mRNA.; 2808 bp)

TABLE XI

Human PKR DNAzyme and Substrate Sequence

| Pos | Substrate | Seq ID | DNAzyme | Seq ID |
|---|---|---|---|---|
| 10 | CGGCGGCG G CGGCGCAG | 2261 | CTGCGCCG GGCTAGCTACAACGA CGCCGCCG | 2904 |
| 13 | CGGCGGCG G CGCAGUUU | 2433 | AAACTGCG GGCTAGCTACAACGA CGCCGCCG | 2905 |
| 15 | GCGGCGGC G CAGUUUGC | 2434 | GCAAACTG GGCTAGCTACAACGA GCCGCCGC | 2906 |
| 18 | GCGGCGCA G UUUGCUCA | 2435 | TGAGCAAA GGCTAGCTACAACGA TGCGCCGC | 2907 |
| 22 | CGCAGUUU G CUCAUACU | 2436 | AGTATGAG GGCTAGCTACAACGA AAACTGCG | 2908 |
| 26 | GUUUGCUC A UACUUUGU | 1265 | ACAAAGTA GGCTAGCTACAACGA GAGCAAAC | 2909 |
| 28 | UUGCUCAU A CUUUGUGA | 4 | TCACAAAG GGCTAGCTACAACGA ATGAGCAA | 2910 |
| 33 | CAUACUUU G UGACUUGC | 2437 | GCAAGTCA GGCTAGCTACAACGA AAAGTATG | 2911 |

TABLE XI-continued

Human PKR DNAzyme and Substrate Sequence

| Pos | Substrate | Seq ID | DNAzyme | Seq ID |
|---|---|---|---|---|
| 36 | ACUUUGUG A CUUGCGGU | 2699 | ACCGCAAG GGCTAGCTACAACGA CACAAAGT | 2912 |
| 40 | UGUGACUU G CGGUCACA | 2438 | TGTGACCG GGCTAGCTACAACGA AAGTCACA | 2913 |
| 43 | GACUUGCG G UCACAGUG | 2439 | CACTGTGA GGCTAGCTACAACGA CGCAAGTC | 2914 |
| 46 | UUGCGGUC A CAGUGGCA | 1268 | TGCCACTG GGCTAGCTACAACGA GACCGCAA | 2915 |
| 49 | CGGUCACA G UGGCAUUC | 2440 | GAATGCCA GGCTAGCTACAACGA TGTGACCG | 2916 |
| 52 | UCACAGUG G CAUUCAGC | 2441 | GCTGAATG GGCTAGCTACAACGA CACTGTGA | 2917 |
| 54 | ACAGUGGC A UUCAGCUC | 1270 | GAGCTGAA GGCTAGCTACAACGA GCCACTGT | 2918 |
| 59 | GGCAUUCA G CUCCACAC | 2442 | GTGTGGAG GGCTAGCTACAACGA TGAATGCC | 2919 |
| 64 | UCAGCUCC A CACUUGGU | 1274 | ACCAAGTG GGCTAGCTACAACGA GGAGCTGA | 2920 |
| 66 | AGCUCCAC A CUUGGUAG | 1275 | CTACCAAG GGCTAGCTACAACGA GTGGAGCT | 2921 |
| 71 | CACACUUG G UAGAACCA | 2443 | TGGTTCTA GGCTAGCTACAACGA CAAGTGTG | 2922 |
| 76 | UUGGUAGA A CCACAGGC | 2700 | GCCTGTGG GGCTAGCTACAACGA TCTACCAA | 2923 |
| 79 | GUAGAACC A CAGGCACG | 1278 | GCTGCCTG GGCTAGCTACAACGA GGTTCTAC | 2924 |
| 83 | AACCACAG G CACGACAA | 2444 | TTGTCGTG GGCTAGCTACAACGA CTGTGGTT | 2925 |
| 85 | CCACAGGC A CGACAAGC | 1280 | GCTTGTCG GGCTAGCTACAACGA GCCTGTGG | 2926 |
| 88 | CAGGCACG A CAAGCAUA | 2701 | TATGCTTG GGCTAGCTACAACGA CGTGCCTG | 2927 |
| 92 | CACGACAA G CAUAGAAA | 2445 | TTTCTATG GGCTAGCTACAACGA TTGTCGTG | 2928 |
| 94 | CGACAAGC A UAGAAACA | 1282 | TGTTTCTA GGCTAGCTACAACGA GCTTGTCG | 2929 |
| 100 | GCAUAGAA A CAUCCUAA | 2702 | TTAGGATG GGCTAGCTACAACGA TTCTATGC | 2930 |
| 102 | AUAGAAAC A UCCUAAAC | 1283 | GTTTAGGA GGCTAGCTACAACGA GTTTCTAT | 2931 |
| 109 | CAUCCUAA C CAAUCUUC | 2703 | GAAGATTG GGCTAGCTACAACGA TTAGGATG | 2932 |
| 112 | CCUAAACA A UCUUCAUC | 2704 | GATGAAGA GGCTAGCTACAACGA TGTTTAGG | 2933 |
| 118 | CAAUCUUC A UCGAGGCA | 1288 | TGCCTCGA GGCTAGCTACAACGA GAAGATTG | 2934 |
| 124 | UCAUCGAG G CAUCGAGG | 2446 | CCTCGATG GGCTAGCTACAACGA CTCGATGA | 2935 |
| 126 | AUCGAGGC A UCGAGGCC | 1289 | GACCTCGA GGCTAGCTACAACGA GCCTCGAT | 2936 |
| 132 | GCAUCGAG G UCCAUCCC | 2447 | GGGATGGA GGCTAGCTACAACGA CTCGATGC | 2937 |
| 136 | CGAGGUCC A UCCCAAUA | 1291 | TATTGGGA GGCTAGCTACAACGA GGACCTCG | 2938 |
| 142 | CCAUCCCA A UAAAAAUC | 2705 | GATTTTTA GGCTAGCTACAACGA TGGGATGG | 2939 |
| 148 | CAAUAAAA A UCAGGAGA | 2706 | TCTCCTGA GGCTAGCTACAACGA TTTTATTG | 2940 |
| 156 | AUCAGGAG A CCCUGGCU | 2707 | AGCCAGGG GGCTAGCTACAACGA CTCCTGAT | 2941 |
| 162 | AGACCCUG G CUAUCAUA | 2448 | TATGATAG GGCTAGCTACAACGA CAGGGTCT | 2942 |
| 165 | CCCUGGCU A UCAUAGAC | 26 | GTCTATGA GGCTAGCTACAACGA AGCCAGGG | 2943 |
| 168 | UGGCUAUC A UAGACCUU | 1300 | AAGGTCTA GGCTAGCTACAACGA GATAGCCA | 2944 |
| 172 | UAUCAUAG A CCUUAGUC | 2708 | GACTAAGG GGCTAGCTACAACGA CTATGATA | 2945 |
| 178 | AGACCUUA G UCUUCGCU | 2449 | AGCGAAGA GGCTAGCTACAACGA TAAGGTCT | 2946 |
| 184 | UAGUCUUC G CUGGUAUA | 2450 | TATACCAG GGCTAGCTACAACGA GAAGACTA | 2947 |
| 188 | CUUCGCUG G UAUACUCG | 2451 | CGAGTATA GGCTAGCTACAACGA CAGCGAAG | 2948 |
| 190 | UCGCUGGU A UACUCGCU | 34 | AGCGAGTA GGCTAGCTACAACGA ACCAGCGA | 2949 |
| 192 | GCUGGUAU A CUCGCUGU | 35 | ACAGCGAG GGCTAGCTACAACGA ATACCAGC | 2950 |
| 196 | GUAUACUC G CUGUCUGU | 2452 | ACAGACAG GGCTAGCTACAACGA GAGTATAC | 2951 |
| 199 | UACUCGCU G UCAACCAG | 2453 | TTGACAGA GGCTAGCTACAACGA AGCGAGTA | 2952 |
| 203 | CGCUGUCU G UCAACCAG | 2454 | CTGGTTGA GGCTAGCTACAACGA AGACAGCG | 2953 |
| 207 | GUCUGUCA A CCAGCGGU | 2709 | ACCGCTGG GGCTAGCTACAACGA TGACAGAC | 2954 |
| 211 | GUCAACCA G CGGUUGAC | 2455 | GTCAACCG GGCTAGCTACAACGA TGGTTGAC | 2955 |
| 214 | AACCAGCG G UUGACUUU | 2456 | AAAGTCAA GGCTAGCTACAACGA CGCTGGTT | 2956 |
| 218 | AGCGGUUG A CUUUUUUU | 2710 | AAAAAAAG GGCTAGCTACAACGA CAACCGCT | 2957 |
| 229 | UUUUUUAA G CCUUCUUU | 2457 | AAAGAAGG GGCTAGCTACAACGA TTAAAAAA | 2958 |
| 248 | UCUCUUUU A CCAGUUUC | 59 | GAAACTGG GGCTAGCTACAACGA AAAAGAGA | 2959 |
| 252 | UUUUACCA G UUUCUGGA | 2458 | TCCAGAAA GGCTAGCTACAACGA TGGTAAAA | 2960 |
| 261 | UUUCUGGA G CAAAUUCA | 2459 | TGAATTTG GGCTAGCTACAACGA TCCAGAAA | 2961 |
| 265 | UGGAGCAA A UUCAGUUU | 2711 | AAACTGAA GGCTAGCTACAACGA TTGCTCCA | 2962 |
| 270 | CAAAUUCA G UUUGCCUU | 2460 | AAGGCAAA GGCTAGCTACAACGA TGAATTTG | 2963 |
| 274 | UUCAGUUU G CCUUCCUG | 2461 | CAGGAAGG GGCTAGCTACAACGA AAACTGAA | 2964 |
| 284 | CUUCCUGG A UUUGUAAA | 2712 | TTTACAAA GGCTAGCTACAACGA CCAGGAAG | 2965 |
| 288 | CUGGAUUU G UAAAUUGU | 2462 | ACAATTTA GGCTAGCTACAACGA AAATCCAG | 2966 |
| 292 | AUUUGUAA A UUGUAAUG | 2713 | CATTACAA GGCTAGCTACAACGA TTACAAAT | 2967 |
| 295 | UGUAAAUU G UAAUGACC | 2463 | GGTCATTA GGCTAGCTACAACGA AATTTACA | 2968 |
| 298 | AAAUUGUA A UGACCUCA | 2714 | TGAGGTCA GGCTAGCTACAACGA TACAATTT | 2969 |
| 301 | UUGUAAUG A CCUCAAAA | 2715 | TTTTGAGG GGCTAGCTACAACGA CATTACAA | 2970 |
| 309 | ACCUCAAA A CUUUAGCA | 2716 | TGCTAAAG GGCTAGCTACAACGA TTTGAGGT | 2971 |
| 315 | AAACUUUA G CAGUUCUU | 2464 | AAGAACTG GGCTAGCTACAACGA TAAAGTTT | 2972 |
| 318 | CUUUAGCA G UUCUUCCA | 2465 | TGGAAGAA GGCTAGCTACAACGA TGCTAAAG | 2973 |
| 326 | GUUCUUCC A UCUGACUC | 1333 | GAGTCAGA GGCTAGCTACAACGA GGAAGAAC | 2974 |
| 331 | UCCAUCUG A CUCAGGUU | 2717 | AACCTGAG GGCTAGCTACAACGA CAGATGGA | 2975 |
| 337 | UGACUCAG G UUUGCUUC | 2466 | GAAGCAAA GGCTAGCTACAACGA CTGAGTCA | 2976 |
| 341 | UCAGGUUU G CUUCUCUG | 2467 | CAGAGAAG GGCTAGCTACAACGA AAACCTGA | 2977 |
| 350 | CUUCUCUG G CGGUCUUC | 2468 | GAAGACCG GGCTAGCTACAACGA CAGAGAAG | 2978 |
| 353 | CUCUGGCG G UCUUCAGA | 2469 | TCTGAAGA GGCTAGCTACAACGA CGCCAGAG | 2979 |
| 362 | UCUUCAGA A UCAACAUC | 2718 | GATGTTGA GGCTAGCTACAACGA TCTGAAGA | 2980 |
| 366 | CAGAAUCA A CAUCCACA | 2719 | TGTGGATG GGCTAGCTACAACGA TGATTCTG | 2981 |
| 368 | GAAUCAAC A UCCACACU | 1343 | AGTGTGGA GGCTAGCTACAACGA GTTGATTC | 2982 |
| 372 | CAACAUCC A CACUUCCG | 1345 | CGGAAGTG GGCTAGCTACAACGA GGATGTTG | 2983 |
| 374 | ACAUCCAC A CUUCCGUG | 1346 | CACGGAAG GGCTAGCTACAACGA GTGGATGT | 2984 |
| 380 | ACACUUCC G UGAUUAUC | 2470 | GATAATCA GGCTAGCTACAACGA GGAAGTGT | 2985 |
| 383 | CUUCCGUG A UUAUCUGC | 2720 | GCAGATAA GGCTAGCTACAACGA CACGGAAG | 2986 |

TABLE XI-continued

Human PKR DNAzyme and Substrate Sequence

| Pos | Substrate | Seq ID | DNAzyme | Seq ID |
|---|---|---|---|---|
| 386 | CCGUGAUU A UCUGCGUG | 97 | CACGCAGA GGCTAGCTACAACGA AATCACGG | 2987 |
| 390 | GAUUAUCU G CGUGCAUU | 2471 | AATGCACG GGCTAGCTACAACGA AGATAATC | 2988 |
| 392 | UUAUCGCG G UGCAUUUU | 2472 | AAAATGCA GGCTAGCTACAACGA GCAGATAA | 2989 |
| 394 | AUCUGCGU G CAUUUUGG | 2473 | CCAAAATG GGCTAGCTACAACGA ACGCAGAT | 2990 |
| 396 | CUGCGUGC A UUUUGGAC | 1350 | GTCCAAAA GGCTAGCTACAACGA GCACGCAG | 2991 |
| 403 | CAUUUUGG A CAAAGCUU | 2721 | AAGCTTTG GGCTAGCTACAACGA CCAAAATG | 2992 |
| 408 | UGGACAAA G CUUCCAAC | 2474 | GTTGGAAG GGCTAGCTACAACGA TTTGTCCA | 2993 |
| 415 | AGCUUCCA A CCAGGAUA | 2722 | TATCCTGG GGCTAGCTACAACGA TGGAAGCT | 2994 |
| 421 | CAACCAGG A UACGGGAA | 2723 | TTCCCGTA GGCTAGCTACAACGA CCTGGTTG | 2995 |
| 423 | ACCAGGAU A CGGGAAGA | 104 | TCTTCCCG GGCTAGCTACAACGA ATCCTGGT | 2996 |
| 436 | AAGAAGAA A UGGCUGGU | 2724 | ACCAGCCA GGCTAGCTACAACGA TTCTTCTT | 2997 |
| 439 | AAGAAAUG G CUGGUGAU | 2475 | ATCACCAG GGCTAGCTACAACGA CATTTCTT | 2998 |
| 443 | AAUGGCUG G UGAUCUUU | 2476 | AAAGATCA GGCTAGCTACAACGA CAGCCATT | 2999 |
| 446 | GGCUGGUG A UCUUUCAG | 2725 | CTGAAAGA GGCTAGCTACAACGA CACCAGCC | 3000 |
| 454 | AUCUUUCA G CAGGUUUC | 2477 | GAAACCTG GGCTAGCTACAACGA TGAAAGAT | 3001 |
| 458 | UUCAGCAG G UUUCUUCA | 2478 | TGAAGAAA GGCTAGCTACAACGA CTGCTGAA | 3002 |
| 466 | GUUUCUUC A UGGAGGAA | 1362 | TTCCTCCA GGCTAGCTACAACGA GAAGAAAC | 3003 |
| 474 | AUGGAGGA A CUUAAUAC | 2726 | GTATTAAG GGCTAGCTACAACGA TCCTCCAT | 3004 |
| 479 | GGAACUUA A UACAUACC | 2727 | GGTATGTA GGCTAGCTACAACGA TAAGTTCC | 3005 |
| 481 | AACUUAAU A CAUACCGU | 116 | ACGGTATG GGCTAGCTACAACGA ATTAAGTT | 3006 |
| 483 | CUUAAUAC A UACCGUCA | 1364 | TGACGGTA GGCTAGCTACAACGA GTATTAAG | 3007 |
| 485 | UAAUACAU A CCGUCAGA | 117 | TCTGACGG GGCTAGCTACAACGA ATGTATTA | 3008 |
| 488 | UACAUACC G UCAGAAGC | 2479 | GCTTCTGA GGCTAGCTACAACGA GGTATGTA | 3009 |
| 495 | CGUCAGAA G CAGGGAGU | 2262 | ACTCCCTG GGCTAGCTACAACGA TTCTGACG | 3010 |
| 502 | AGCAGGGA G UAGACUUU | 2263 | AAGTACTA GGCTAGCTACAACGA TCCCTGCT | 3011 |
| 505 | AGGGAGUA G UACUUAAA | 2264 | TTTAAGTA GGCTAGCTACAACGA TACTCCCT | 3012 |
| 507 | GGAGUAGU A CUUAAAUA | 120 | TATTTAAG GGCTAGCTACAACGA ACTACTCC | 3013 |
| 513 | GUACUUAA A UAUCAAGA | 2728 | TCTTGATA GGCTAGCTACAACGA TTAAGTAC | 3014 |
| 515 | ACUUAAAU A UCAAGAAC | 123 | GTTCTTGA GGCTAGCTACAACGA ATTTAAGT | 3015 |
| 522 | UAUCAAGA A CUGCCUAA | 2729 | TTAGGCAG GGCTAGCTACAACGA TCTTGATA | 3016 |
| 525 | CAAGAACU G CCUAAUUC | 2265 | GAATTAGG GGCTAGCTACAACGA AGTTCTTG | 3017 |
| 530 | ACUGCCUA A UUCAGGAC | 2730 | GTCCTGAA GGCTAGCTACAACGA TAGGCAGT | 3018 |
| 537 | AAUUCAGG A CCUCCACA | 2731 | TGTGGAGG GGCTAGCTACAACGA CCTGAATT | 3019 |
| 543 | GGACCUCC A CAUGAUAG | 1377 | CTATCATG GGCTAGCTACAACGA GGAGGTCC | 3020 |
| 545 | ACCUCCAC A UGAUAGGA | 1378 | TCCTATCA GGCTAGCTACAACGA GTGGAGGT | 3021 |
| 548 | UCCACAUG A UAGGAGGU | 2732 | ACCTCCTA GGCTAGCTACAACGA CATGTGGA | 3022 |
| 555 | GAUAGGAG G UUUACAUU | 2266 | AATGTAAA GGCTAGCTACAACGA CTCCTATC | 3023 |
| 559 | GGAGGUUU A CAUUUCAA | 132 | TTGAAATG GGCTAGCTACAACGA AAACCTCC | 3024 |
| 561 | AGGUUUAC A UUUCAAGU | 1379 | ACTTGAAA GGCTAGCTACAACGA GTAAACCT | 3025 |
| 568 | CAUUUCAA G UUAUAAUA | 2267 | TATTATAA GGCTAGCTACAACGA TTGAAATG | 3026 |
| 571 | UUCAAGUU A UAAUAGAU | 137 | ATCTATTA GGCTAGCTACAACGA AACTTGAA | 3027 |
| 574 | AAGUUAUA A UAGAUGGA | 2733 | TCCATCTA GGCTAGCTACAACGA TATAACTT | 3028 |
| 578 | UAUAAUAG A UGGAAGAG | 2734 | CTCTTCCA GGCTAGCTACAACGA CTATTATA | 3029 |
| 588 | GGAAGAGA A UUCCAGAA | 2735 | TCTGGAAA GGCTAGCTACAACGA TCTCTTCC | 3030 |
| 599 | UCCAGAAG G UGAAGGUA | 2268 | TACCTTCA GGCTAGCTACAACGA CTTCTGGA | 3031 |
| 605 | AGGUGAAG G UAGAUCAA | 2269 | TTGATCTA GGCTAGCTACAACGA CTTCACCT | 3032 |
| 609 | GAAGGUAG A UCAAAGAA | 2736 | TTCTTTGA GGCTAGCTACAACGA CTACCTTC | 3033 |
| 622 | AGAAGGAA G CAAAAAAU | 2270 | ATTTTTTG GGCTAGCTACAACGA TTCCTTCT | 3034 |
| 629 | AGCAAAAA A UGCCGCAG | 2737 | CTGCGGCA GGCTAGCTACAACGA TTTTTGCT | 3035 |
| 631 | CAAAAAAU G CCGCAGCC | 2271 | GGCTGCGG GGCTAGCTACAACGA ATTTTTTG | 3036 |
| 634 | AAAAUGCC G CAGCCAAA | 2272 | TTTGGCTG GGCTAGCTACAACGA GGCATTTT | 3037 |
| 637 | AUGCCGCA G CCAAAUUA | 2273 | TAATTTGG GGCTAGCTACAACGA TGCGGCAT | 3038 |
| 642 | GCAGCCAA A UUAGCUGU | 2738 | ACAGCTAA GGCTAGCTACAACGA TTGGCTGC | 3039 |
| 646 | CCAAAUUA G CUGUUGAG | 2274 | CTCAACAG GGCTAGCTACAACGA TAATTTGG | 3040 |
| 649 | AAUUAGCU G UUGAGAUA | 2275 | TATCTCAA GGCTAGCTACAACGA AGCTAATT | 3041 |
| 655 | CUGUUGAG A UACUUAAU | 2739 | ATTAAGTA GGCTAGCTACAACGA CTCAACAG | 3042 |
| 657 | GUUGAGAU A CUUAAUAA | 148 | TTATTAAG GGCTAGCTACAACGA ATCTCAAC | 3043 |
| 662 | GAUACUUA A UAAGGAAA | 2740 | TTTCCTTA GGCTAGCTACAACGA TAAGTATC | 3044 |
| 676 | AAAAGAAG G CAGUUAGU | 2276 | ACTAACTG GGCTAGCTACAACGA CTTCTTTT | 3045 |
| 679 | AGAAGGCA G UUAGUCCU | 2277 | AGGACTAA GGCTAGCTACAACGA TGCCTTCT | 3046 |
| 683 | GGCAGUUA G UCCUUUAU | 2278 | ATAAAGGA GGCTAGCTACAACGA TAACTGCC | 3047 |
| 690 | AGUCCUUU A UUAUUGAC | 157 | GTCAATAA GGCTAGCTACAACGA AAAGGACT | 3048 |
| 693 | CCUUUAUU A UUGACAAC | 159 | GTTGTCAA GGCTAGCTACAACGA AATAAAGG | 3049 |
| 697 | UAUUAUUG A CAACAACG | 2741 | CGTTGTTG GGCTAGCTACAACGA CAATAATA | 3050 |
| 700 | UAUUGACA A CAACGAAU | 2742 | ATTCGTTG GGCTAGCTACAACGA TGTCAATA | 3051 |
| 703 | UGACAACA A CGAAUUCU | 2743 | AGAATTCG GGCTAGCTACAACGA TGTTGTCA | 3052 |
| 707 | AACAACGA A UUCUUCAG | 2744 | CTGAAGAA GGCTAGCTACAACGA TCGTTGTT | 3053 |
| 720 | UCAGAAGG A UUACCAU | 2745 | ATGGATAA GGCTAGCTACAACGA CCTTCTGA | 3054 |
| 723 | GAAGGAUU A UCCAUGGG | 166 | CCCATGGA GGCTAGCTACAACGA AATCCTTC | 3055 |
| 727 | GAUUAUCC A UGGGAAU | 1399 | ATTCCCCA GGCTAGCTACAACGA GGATAATC | 3056 |
| 734 | CAUGGGGA A UUACAUAG | 2746 | CTATGTAA GGCTAGCTACAACGA TCCCCATG | 3057 |
| 737 | GGGGAAUU A CAUAGGCC | 169 | GGCCTATG GGCTAGCTACAACGA AATTCCCC | 3058 |
| 739 | GGAAUUAC A UAGGCCUU | 1400 | AAGGCCTA GGCTAGCTACAACGA GTAATTCC | 3059 |
| 743 | UUACAUAG G CCUUAUCA | 2279 | TGATAAGG GGCTAGCTACAACGA CTATGTAA | 3060 |
| 748 | UAGGCCUU A UCAAUAGA | 172 | TCTATTGA GGCTAGCTACAACGA AAGGCCTA | 3061 |

TABLE XI-continued

Human PKR DNAzyme and Substrate Sequence

| Pos | Substrate | Seq ID | DNAzyme | Seq ID |
|---|---|---|---|---|
| 752 | CCUUAUCA A UAGAAUUG | 2747 | CAATTCTA GGCTAGCTACAACGA TGATAAGG | 3062 |
| 757 | UCAAUAGA A UUGCCCAG | 2748 | CTGGGCAA GGCTAGCTACAACGA TCTATTGA | 3063 |
| 760 | AUAGAAUU G CCCAGAAG | 2280 | CTTCTGGG GGCTAGCTACAACGA AATTCTAT | 3064 |
| 774 | AAGAAAAG C CUAACUGU | 2749 | ACAGTTAG GGCTAGCTACAACGA CTTTTCTT | 3065 |
| 778 | AAAGACUA A CUGUAAAU | 2750 | ATTTACAG GGCTAGCTACAACGA TAGTCTTT | 3066 |
| 781 | GACUAACU G UAAAUUAU | 2281 | ATAATTTA GGCTAGCTACAACGA AGTTAGTC | 3067 |
| 785 | AACUGUAA A UUAUGAAC | 2751 | GTTCATAA GGCTAGCTACAACGA TTACAGTT | 3068 |
| 788 | UGUAAAUU A UGAACAGU | 179 | ACTGTTCA GGCTAGCTACAACGA AATTTACA | 3069 |
| 792 | AAUUAUGA A CAGUGUGC | 2752 | GCACACTG GGCTAGCTACAACGA TCATAATT | 3070 |
| 795 | UAUGAACA G UGUGCAUC | 2282 | GATGCACA GGCTAGCTACAACGA TGTTCATA | 3071 |
| 797 | UGAACAGU G UGCAUCGG | 2283 | CCGATGCA GGCTAGCTACAACGA ACTGTTCA | 3072 |
| 799 | AACAGUGU G CAUCGGGG | 2284 | CCCCGATG GGCTAGCTACAACGA ACACTGTT | 3073 |
| 801 | CAGUGUGC A UCGGGGU | 1410 | ACCCCCGA GGCTAGCTACAACGA GCACACTG | 3074 |
| 808 | CAUCGGGG G UGCAUGGG | 2285 | CCCATGCA GGCTAGCTACAACGA CCCCGATG | 3075 |
| 810 | UCGGGGU G CAUGGGCC | 2286 | GGCCCATG GGCTAGCTACAACGA ACCCCGA | 3076 |
| 812 | GGGGUGC A UGGGCCAG | 1411 | CTGGCCCA GGCTAGCTACAACGA GCACCCCC | 3077 |
| 816 | GUGCAUGG G CCAGAAGG | 2287 | CCTTCTGG GGCTAGCTACAACGA CCATGCAC | 3078 |
| 825 | CCAGAAGG A UUUCAUUA | 2753 | TAATGAAA GGCTAGCTACAACGA CCTTCTGG | 3079 |
| 830 | AGGAUUUC A UUAUAAAU | 1414 | ATTTATAA GGCTAGCTACAACGA GAAATCCT | 3080 |
| 833 | AUUUCAUU A UAAAUGCA | 185 | TGCATTTA GGCTAGCTACAACGA AATGAAAT | 3081 |
| 837 | CAUUAUAA A UGCAAAAU | 2754 | ATTTTGCA GGCTAGCTACAACGA TTATAATG | 3082 |
| 839 | UUAUAAAU G CAAAAUGG | 2288 | CCATTTTG GGCTAGCTACAACGA ATTTATAA | 3083 |
| 844 | AAUGCAAA A UGGGACAG | 2755 | CTGTCCCA GGCTAGCTACAACGA TTTGCATT | 3084 |
| 849 | AAAAUGGG A CAGAAAGA | 2756 | TCTTTCTG GGCTAGCTACAACGA CCCATTTT | 3085 |
| 858 | CAGAAAGA A UAUAGUAU | 2757 | ATACTATA GGCTAGCTACAACGA TCTTTCTG | 3086 |
| 860 | GAAAGAAU A UAGUAUUG | 187 | CAATACTA GGCTAGCTACAACGA ATTCTTTC | 3087 |
| 863 | AGAAUAUA G UAUUGGUA | 2289 | TACCAATA GGCTAGCTACAACGA TATATTCT | 3088 |
| 865 | AAUAUAGU A UUGGUACA | 189 | TGTACCAA GGCTAGCTACAACGA ACTATATT | 3089 |
| 869 | UAGUAUUG G UACAGGUU | 2290 | AACCTGTA GGCTAGCTACAACGA CAATACTA | 3090 |
| 871 | GUAUUGGU A CAGGUUCU | 191 | AGAACCTG GGCTAGCTACAACGA ACCAATAC | 3091 |
| 875 | UGGUACAG G UUCUACUA | 2291 | TAGTAGAA GGCTAGCTACAACGA CTGTACCA | 3092 |
| 880 | CAGGUUCU A CUAAACAG | 194 | CTGTTTAG GGCTAGCTACAACGA AGAACCTG | 3093 |
| 885 | UCUACUAA A CAGGAAGC | 2758 | GCTTCCTG GGCTAGCTACAACGA TTAGTAGA | 3094 |
| 892 | AACAGGAA G CAAAACAA | 2292 | TTGTTTTG GGCTAGCTACAACGA TTCCTGTT | 3095 |
| 897 | GAAGCAAA A CAAUUGGC | 2759 | GCCAATTG GGCTAGCTACAACGA TTTGCTTC | 3096 |
| 900 | GCAAAACA A UUGGCCGC | 2760 | GCGGCCAA GGCTAGCTACAACGA TGTTTTGC | 3097 |
| 904 | AACAAUUG G CCGCUAAA | 2293 | TTTAGCGG GGCTAGCTACAACGA CAATTGTT | 3098 |
| 907 | AAUUGGCC G CUAAACUU | 2294 | AAGTTTAG GGCTAGCTACAACGA GGCCAATT | 3099 |
| 912 | GCCGCUAA A CUUGCAUA | 2761 | TATGCAAG GGCTAGCTACAACGA TTAGCGGC | 3100 |
| 916 | CUAAACUU G CAUAUCUU | 2295 | AAGATATG GGCTAGCTACAACGA AAGTTTAG | 3101 |
| 918 | AAACUUGC A UAUCUUCA | 1426 | TGAAGATA GGCTAGCTACAACGA GCAAGTTT | 3102 |
| 920 | ACUUGCAU A UCUUCAGA | 199 | TCTGAAGA GGCTAGCTACAACGA ATGCAAGT | 3103 |
| 928 | AUCUUCAG A UAUUAUCA | 2762 | TGATAATA GGCTAGCTACAACGA CTGAAGAT | 3104 |
| 930 | CUUCAGAU A UUAUCAGA | 203 | TCTGATAA GGCTAGCTACAACGA ATCTGAAG | 3105 |
| 933 | CAGAUAUU A UCAGAAGA | 205 | TCTTCTGA GGCTAGCTACAACGA AATATCTG | 3106 |
| 943 | CAGAAGAA A CCUCAGUG | 2763 | CACTGAGG GGCTAGCTACAACGA TTCCTTCTG | 3107 |
| 949 | AAACCUCA G UGAAAUCU | 2296 | AGATTTCA GGCTAGCTACAACGA TGAGGTTT | 3108 |
| 954 | UCAGUGAA A UCUGACUA | 2764 | TAGTCAGA GGCTAGCTACAACGA TTCACTGA | 3109 |
| 959 | GAAAUCUG A CUACCUGU | 2765 | ACAGGTAG GGCTAGCTACAACGA CAGATTTC | 3110 |
| 962 | AUCUGACU A CCUGUCCU | 209 | AGGACAGG GGCTAGCTACAACGA AGTCAGAT | 3111 |
| 966 | GACUACCU G UCCUCUGG | 2297 | CCAGAGGA GGCTAGCTACAACGA AGGTAGTC | 3112 |
| 974 | GUCCUCUG G UUCUUUUG | 2298 | CAAAAGAA GGCTAGCTACAACGA CAGAGGAC | 3113 |
| 982 | GUUCUUUU G CUACUACG | 2299 | CGTAGTAG GGCTAGCTACAACGA AAAAGAAC | 3114 |
| 985 | CUUUUGCU A CUACGUGU | 217 | ACACGTAG GGCTAGCTACAACGA AGCAAAAG | 3115 |
| 988 | UUGCUACU A CGUGUGAG | 218 | CTCACACG GGCTAGCTACAACGA AGTAGCAA | 3116 |
| 990 | GCUACUAC G UGUGAGUC | 2300 | GACTCACA GGCTAGCTACAACGA GTAGTAGC | 3117 |
| 992 | UACUACGU G UGAGUCCC | 2301 | GGGACTCA GGCTAGCTACAACGA ACGTAGTA | 3118 |
| 996 | ACGUGUGA G UCCCAAAG | 2302 | CTTTGGGA GGCTAGCTACAACGA TCACACGT | 3119 |
| 1004 | GUCCCAAA G CAACUCUU | 2303 | AAGAGTTG GGCTAGCTACAACGA TTTGGGAC | 3120 |
| 1007 | CCAAAGCA A CUCUUUAG | 2766 | CTAAAGAG GGCTAGCTACAACGA TGCTTTGG | 3121 |
| 1015 | ACUCUUUA G UGACCAGC | 2304 | GCTGGTCA GGCTAGCTACAACGA TAAAGAGT | 3122 |
| 1018 | CUUUAGUG A CCAGCACA | 2767 | TGTGCTGG GGCTAGCTACAACGA CACTAAAG | 3123 |
| 1022 | AGUGACCA G CACACUCG | 2305 | CGAGTGTG GGCTAGCTACAACGA TGGTCACT | 3124 |
| 1024 | UGACCAGC A CACUCGCU | 1451 | AGCGAGTG GGCTAGCTACAACGA GCTGGTCA | 3125 |
| 1026 | ACCAGCAC A CUCGCUUC | 1452 | GAAGCGAG GGCTAGCTACAACGA GTGCTGGT | 3126 |
| 1030 | GCACACUC G CUUCUGAA | 2306 | TTCAGAAG GGCTAGCTACAACGA GAGTGTGC | 3127 |
| 1038 | GCUUCUGA A UCAUCAUC | 2768 | GATGATGA GGCTAGCTACAACGA TCAGAAGC | 3128 |
| 1041 | UCUGAAUC A UCAUCUGA | 1456 | TCAGATGA GGCTAGCTACAACGA GATTCAGA | 3129 |
| 1044 | GAAUCAUC A UCUGAAGG | 1457 | CCTTCAGA GGCTAGCTACAACGA GATGATTC | 3130 |
| 1052 | AUCUGAAG G UGACUUCU | 2307 | AGAAGTCA GGCTAGCTACAACGA CTTCAGAT | 3131 |
| 1055 | UGAAGGUG A CUUCUCAG | 2769 | CTGAGAAG GGCTAGCTACAACGA CACCTTCA | 3132 |
| 1063 | ACUUCUCA G CAGAUACA | 2308 | TGTATCTG GGCTAGCTACAACGA TGAGAAGT | 3133 |
| 1067 | CUCAGCAG A UACAUCAG | 2770 | CTGATGTA GGCTAGCTACAACGA CTGCTGAG | 3134 |
| 1069 | CAGCAGAU A CAUCAGAG | 233 | CTCTGATG GGCTAGCTACAACGA ATCTGCTG | 3135 |
| 1071 | GCAGAUAC A UCAGAGAU | 1463 | ATCTCTGA GGCTAGCTACAACGA GTATCTGC | 3136 |

TABLE XI-continued

Human PKR DNAzyme and Substrate Sequence

| Pos | Substrate | Seq ID | DNAzyme | Seq ID |
|---|---|---|---|---|
| 1078 | CAUCAGAG A UAAAUUCU | 2771 | AGAATTTA GGCTAGCTACAACGA CTCTGATG | 3137 |
| 1082 | AGAGAUAA A UUCUAACA | 2772 | TGTTAGAA GGCTAGCTACAACGA TTATCTCT | 3138 |
| 1088 | AAAUUCUA A CAGUGACA | 2773 | TGTCACTG GGCTAGCTACAACGA TAGAATTT | 3139 |
| 1091 | UUCUAACA G UGACAGUU | 2309 | AACTGTCA GGCTAGCTACAACGA TGTTAGAA | 3140 |
| 1094 | UAACAGUG A CAGUUUAA | 2774 | TTAAACTG GGCTAGCTACAACGA CACTGTTA | 3141 |
| 1097 | CAGUGACA G UUUAAACA | 2310 | TGTTTAAA GGCTAGCTACAACGA TGTCACTG | 3142 |
| 1103 | CAGUUUAA A CAGUUCUU | 2775 | AAGAACTG GGCTAGCTACAACGA TTAAACTG | 3143 |
| 1106 | UUUAAACA G UUCUUCGU | 2311 | ACGAAGAA GGCTAGCTACAACGA TGTTTAAA | 3144 |
| 1113 | AGUUCUUC G UUGCUUAU | 2312 | ATAAGCAA GGCTAGCTACAACGA GAAGAACT | 3145 |
| 1116 | UCUUCGUU G CUUAUGAA | 2313 | TTCATAAG GGCTAGCTACAACGA AACGAAGA | 3146 |
| 1120 | CGUUGCUU A UGAAUGGU | 248 | ACCATTCA GGCTAGCTACAACGA AAGCAACG | 3147 |
| 1124 | GCUUAUGA A UGGUCUCA | 2776 | TGAGACCA GGCTAGCTACAACGA TCATAAGC | 3148 |
| 1127 | UAUGAAUG G UCUCAGAA | 2314 | TTCTGAGA GGCTAGCTACAACGA CATTCATA | 3149 |
| 1136 | UCUCAGAA A UAAUCAAA | 2777 | TTTGATTA GGCTAGCTACAACGA TTCTGAGA | 3150 |
| 1139 | CAGAAAUA A UCAAAGGA | 2778 | TCCTTTGA GGCTAGCTACAACGA TATTTCTG | 3151 |
| 1150 | AAAGGAAG C AAAAAGA | 2315 | TCTTTTTG GGCTAGCTACAACGA CTTCCTTT | 3152 |
| 1158 | GCAAAAAG A UCUUUGGC | 2779 | GCCAAAGA GGCTAGCTACAACGA CTTTTTGC | 3153 |
| 1165 | GAUCUUUG G CACCCAGA | 2316 | TCTGGGTG GGCTAGCTACAACGA CAAAGATC | 3154 |
| 1167 | UCUUUGGC A CCCAGAUU | 1476 | AATCTGGG GGCTAGCTACAACGA GCCAAAGA | 3155 |
| 1173 | GCACCCAG A UUUGACCU | 2780 | AGGTCAAA GGCTAGCTACAACGA CTGGGTGC | 3156 |
| 1178 | CAGAUUUG A CCUUCCUG | 2781 | CAGGAAGG GGCTAGCTACAACGA CAAATCTG | 3157 |
| 1187 | CCUUCCUG A CAUGAAAG | 2782 | CTTTCATG GGCTAGCTACAACGA CAGGAAGG | 3158 |
| 1189 | UUCCUGAC A UGAAAGAA | 1484 | TTCTTTCA GGCTAGCTACAACGA GTCAGGAA | 3159 |
| 1198 | UGAAAGAA A CAAAGUAU | 2783 | ATACTTTG GGCTAGCTACAACGA TTCTTTCA | 3160 |
| 1203 | GAAACAAA G UAUACUGU | 2317 | ACAGTATA GGCTAGCTACAACGA TTTGTTTC | 3161 |
| 1205 | AACAAAGU A UACUGUGG | 260 | CCACAGTA GGCTAGCTACAACGA ACTTTGTT | 3162 |
| 1207 | CAAAGUAU A CUGUGGAC | 261 | GTCCACAG GGCTAGCTACAACGA ATACTTTG | 3163 |
| 1210 | AGUAUACU G UGGACAAG | 2318 | CTTGTCCA GGCTAGCTACAACGA AGTATACT | 3164 |
| 1214 | UACUGUGG A CAAGAGGU | 2784 | ACCTCTTG GGCTAGCTACAACGA CCACAGTA | 3165 |
| 1221 | GACAAGAG G UUUGGCAU | 2319 | ATGCCAAA GGCTAGCTACAACGA CTCTTGTC | 3166 |
| 1226 | GAGGUUUG G CAUGGAUU | 2320 | AATCCATG GGCTAGCTACAACGA CAAACCTC | 3167 |
| 1228 | GGUUUGGC A UGGAUUUU | 1488 | AAAATCCA GGCTAGCTACAACGA GCCAAACC | 3168 |
| 1232 | UGGCAUGG A UUUUAAAG | 2785 | CTTTAAAA GGCTAGCTACAACGA CCATGCCA | 3169 |
| 1243 | UUAAGAA A UAGAAUUA | 2786 | TAATTCTA GGCTAGCTACAACGA TTCTTTAA | 3170 |
| 1248 | GAAAUAGA A UUAAUUGG | 2787 | CCAATTAA GGCTAGCTACAACGA TCTATTTC | 3171 |
| 1252 | UAGAAUUA A UUGGCUCA | 2788 | TGAGCCAA GGCTAGCTACAACGA TAATTCTA | 3172 |
| 1256 | AUUAAUUG G CUCAGGUG | 2321 | CACCTGAG GGCTAGCTACAACGA CAATTAAT | 3173 |
| 1262 | UGGCUCAG G UGGAUUUG | 2322 | CAAATCCA GGCTAGCTACAACGA CTGAGCCA | 3174 |
| 1266 | UCAGGUGG A UUUGGCCA | 2789 | TGGCCAAA GGCTAGCTACAACGA CCACCTGA | 3175 |
| 1271 | UGGAUUUG G CCAAGUUU | 2323 | AAACTTGG GGCTAGCTACAACGA CAAATCCA | 3176 |
| 1276 | UUGGCCAA G UUUCUAAA | 2324 | TTTGAAAA GGCTAGCTACAACGA TTGGCCAA | 3177 |
| 1285 | UUUUCAAA G CAAAACAC | 2325 | GTGTTTTG GGCTAGCTACAACGA TTTGAAAA | 3178 |
| 1290 | AAAGCAAA A CACAGAAU | 2790 | ATTCTGTG GGCTAGCTACAACGA TTTGCTTT | 3179 |
| 1292 | AGCAAAAC A CAGAAUUG | 1495 | CAATTCTG GGCTAGCTACAACGA GTTTTGCT | 3180 |
| 1297 | AACACAGA A UUGACGGU | 2791 | TCCGTCAA GGCTAGCTACAACGA TCTGTGTT | 3181 |
| 1301 | CAGAAUUG A CGGAAGA | 2792 | TCTTTCCG GGCTAGCTACAACGA CAATTCTG | 3182 |
| 1309 | ACGGAAAG A CUUACGUU | 2793 | AACGTAAG GGCTAGCTACAACGA CTTTCCGT | 3183 |
| 1313 | AAAGACUU A CGUUAUUA | 281 | TAATAACG GGCTAGCTACAACGA AAGTCTTT | 3184 |
| 1315 | AGACUUAC G UUAUUAAA | 2326 | TTTAATAA GGCTAGCTACAACGA GTAAGTCT | 3185 |
| 1318 | CUUACGUU A UUAAACGU | 283 | ACGTTTAA GGCTAGCTACAACGA AACGTAAG | 3186 |
| 1323 | GUUAUUAA A CGUGUUAA | 2794 | TTAACACG GGCTAGCTACAACGA TTAATAAC | 3187 |
| 1325 | UAUUAAAC G UGUUAAUA | 2327 | ATTTAACA GGCTAGCTACAACGA GTTTAATA | 3188 |
| 1327 | UUAAACGU G UUAAAUAU | 2328 | ATATTTAA GGCTAGCTACAACGA ACGTTTAA | 3189 |
| 1332 | CGUGUUAA A UAUAAUA | 2795 | TTATTATA GGCTAGCTACAACGA TTAACACG | 3190 |
| 1334 | UGUUAAAU A UAAUAACG | 288 | CGTTATTA GGCTAGCTACAACGA ATTTAACA | 3191 |
| 1337 | UAAAUAUA A UAACGAGA | 2796 | TCTCGTTA GGCTAGCTACAACGA TATATTTA | 3192 |
| 1340 | AUAUAAUA A CGAGAAGG | 2797 | CCTTCTCG GGCTAGCTACAACGA TATTATAT | 3193 |
| 1348 | ACGAGAAG G CGGACGCGU | 2329 | ACGCTCCG GGCTAGCTACAACGA CTTCTCGT | 3194 |
| 1353 | AAGGCGGA G CGUGAAGU | 2330 | ACTTCACG GGCTAGCTACAACGA TCCGCCTT | 3195 |
| 1355 | GGCGGAGC G UGAAGUAA | 2331 | TTACTTCA GGCTAGCTACAACGA GCTCCGCC | 3196 |
| 1360 | AGCGUGAA G UAAAAGCA | 2332 | TGCTTTTA GGCTAGCTACAACGA TTCACGCT | 3197 |
| 1366 | AAGUAAAA G CAUUGGCA | 2333 | TGCCAATG GGCTAGCTACAACGA TTTTACTT | 3198 |
| 1368 | GUAAAAGC A UUGGCAAA | 1498 | TTTGCCAA GGCTAGCTACAACGA GCTTTTAC | 3199 |
| 1372 | AAGCAUUG G CAAACUU | 2334 | AAGTTTTG GGCTAGCTACAACGA CAATGCTT | 3200 |
| 1377 | UUGGCAAA A CUUGAUCA | 2798 | TGATCAAG GGCTAGCTACAACGA TTTGCCAA | 3201 |
| 1382 | AAAACUUG A UCAUGUAA | 2799 | TTACATGA GGCTAGCTACAACGA CAAGTTTT | 3202 |
| 1385 | ACUUGAUC A UGUAAAUA | 1501 | TATTTACA GGCTAGCTACAACGA GATCAAGT | 3203 |
| 1387 | UUGAUCAU G UAAAUAUU | 2335 | AATATTTA GGCTAGCTACAACGA ATGATCAA | 3204 |
| 1391 | UCAUGUAA A UAUUGUUC | 2800 | GAACAATA GGCTAGCTACAACGA TTACATGA | 3205 |
| 1393 | AUGUAAAU A UUGUUCAC | 296 | GTGAACAA GGCTAGCTACAACGA ATTTACAT | 3206 |
| 1396 | UAAAUAUU G UUCACUAC | 2336 | GTAGTGAA GGCTAGCTACAACGA AATATTTA | 3207 |
| 1400 | UAUUGUUC A CUACAAUG | 1502 | CATTGTAG GGCTAGCTACAACGA GAACAATA | 3208 |
| 1403 | UGUUCACU A CAAUGGCU | 300 | AGCCATTG GGCTAGCTACAACGA AGTGAACA | 3209 |
| 1406 | UCACUACA A UGGCUGUU | 2801 | AACAGCCA GGCTAGCTACAACGA TGTAGTGA | 3210 |
| 1409 | CUACAAUG G CUGUUGGG | 2337 | CCCAACAG GGCTAGCTACAACGA CATTGTAG | 3211 |

TABLE XI-continued

Human PKR DNAzyme and Substrate Sequence

| Pos | Substrate | Seq ID | DNAzyme | Seq ID |
|---|---|---|---|---|
| 1412 | CAAUGGCU G UUGGGAUG | 2338 | CATCCCAA GGCTAGCTACAACGA AGCCATTG | 3212 |
| 1418 | CUGUUGGG A UGGAUUUG | 2802 | CAAATCCA GGCTAGCTACAACGA CCCAACAG | 3213 |
| 1422 | UGGGAUGG A UUUGAUUA | 2803 | TAATCAAA GGCTAGCTACAACGA CCATCCCA | 3214 |
| 1427 | UGGAUUUG A UUAUGAUC | 2804 | GATCATAA GGCTAGCTACAACGA CAAATCCA | 3215 |
| 1430 | AUUUGAUU A UGAUCCUG | 305 | CAGGATCA GGCTAGCTACAACGA AATCAAAT | 3216 |
| 1433 | UGAUUAUG A UCCUGAGA | 2805 | TCTCAGGA GGCTAGCTACAACGA CATAATCA | 3217 |
| 1441 | AUCCUGAG A CCAGUGAU | 2806 | ATCACTGG GGCTAGCTACAACGA CTCAGGAT | 3218 |
| 1445 | UGAGACCA G UGAUGAUU | 2339 | AATCATCA GGCTAGCTACAACGA TGGTCTCA | 3219 |
| 1448 | GACCAGUG A UGAUUCUC | 2807 | GAGAATCA GGCTAGCTACAACGA CACTGGTC | 3220 |
| 1451 | CAGUGAUG A UUCUCUUG | 2808 | CAAGAGAA GGCTAGCTACAACGA CATCACTG | 3221 |
| 1463 | UCUUGAGA G CAGUGAUU | 2340 | AATCACTG GGCTAGCTACAACGA TCTCAAGA | 3222 |
| 1466 | UGAGCA G UGAUUAUG | 2341 | CATAATCA GGCTAGCTACAACGA TGCTCTCA | 3223 |
| 1469 | GAGCAGUG A UUAUGAUC | 2809 | GATCATAA GGCTAGCTACAACGA CACTGCTC | 3224 |
| 1472 | CAGUGAUU A UGAUCCUG | 312 | CAGGATCA GGCTAGCTACAACGA AATCACTG | 3225 |
| 1475 | UGAUUAUG A UCCUGAGA | 2805 | TCTCAGGA GGCTAGCTACAACGA CATAATCA | 3217 |
| 1484 | UCCUGAGA A CAGCAAAA | 2810 | TTTTGCTG GGCTAGCTACAACGA TCTCAGGA | 3226 |
| 1487 | UGAGAACA G CAAAAAUA | 2342 | TATTTTTG GGCTAGCTACAACGA TGTTCTCA | 3227 |
| 1493 | CAGCAAAA A UAGUUCAA | 2811 | TTGAACTA GGCTAGCTACAACGA TTTTGCTG | 3228 |
| 1496 | CAAAAAUA G UUCAAGGU | 2343 | ACCTTGAA GGCTAGCTACAACGA TATTTTTG | 3229 |
| 1503 | AGUUCAAG G UCAAAGAC | 2344 | GTCTTTGA GGCTAGCTACAACGA CTTGAACT | 3230 |
| 1510 | GGUCAAAG A CUAAGUGC | 2812 | GCACTTAG GGCTAGCTACAACGA CTTTGACC | 3231 |
| 1515 | AAGACUAA G UGCCUUUU | 2345 | AAAAGGCA GGCTAGCTACAACGA TTAGTCTT | 3232 |
| 1517 | GACUAAGU G CCUUUUCA | 2346 | TGAAAAGG GGCTAGCTACAACGA ACTTAGTC | 3233 |
| 1525 | GCCUUUUC A UCCAAAUG | 1522 | CATTTGGA GGCTAGCTACAACGA GAAAAGGC | 3234 |
| 1531 | UCAUCCAA A UGGAAUUC | 2813 | GAATTCCA GGCTAGCTACAACGA TTGGATGA | 3235 |
| 1536 | CAAAUGGA A UUCUGUGA | 2814 | TCACAGAA GGCTAGCTACAACGA TCCATTTG | 3236 |
| 1541 | GGAAUUCU G UGAUAAAG | 2347 | CTTTATCA GGCTAGCTACAACGA AGAATTCC | 3237 |
| 1544 | AUUCUGUG A UAAAGGGA | 2815 | TCCCTTTA GGCTAGCTACAACGA CACAGAAT | 3238 |
| 1552 | AUAAAGGG A CCUUGGAA | 2816 | TTCCAAGG GGCTAGCTACAACGA CCCTTTAT | 3239 |
| 1560 | ACCUUGGA A CAAUGGAU | 2817 | ATCCATTG GGCTAGCTACAACGA TCCAAGGT | 3240 |
| 1563 | UUGGAACA A UGGAUUGA | 2818 | TCAATCCA GGCTAGCTACAACGA TGTTCCAA | 3241 |
| 1567 | AACAAUGG A UUGAAAAA | 2819 | TTTTTCAA GGCTAGCTACAACGA CCATTGTT | 3242 |
| 1583 | AAGAAGAG A CGAGAAAC | 2348 | GTTTCTCG GGCTAGCTACAACGA CTCTTCTT | 3243 |
| 1590 | GGCGAGAA A CUAGACAA | 2820 | TTGTCTAG GGCTAGCTACAACGA TTCTCGCC | 3244 |
| 1595 | GAAACUAG A CAAAGUUU | 2821 | AAACTTTG GGCTAGCTACAACGA CTAGTTTC | 3245 |
| 1600 | UAGACAAA G UUUUGGCU | 2349 | AGCCAAAA GGCTAGCTACAACGA TTTGTCTA | 3246 |
| 1606 | AAGUUUUG G CUUUGGAA | 2350 | TTCCAAAG GGCTAGCTACAACGA CAAAACTT | 3247 |
| 1614 | GCUUUGGA A CUCUUUGA | 2822 | TCAAGAG GGCTAGCTACAACGA TCCAAAGC | 3248 |
| 1623 | CUCUUUGA A CAAAUAAC | 2823 | GTTATTTG GGCTAGCTACAACGA TCAAAGAG | 3249 |
| 1627 | UUGAACAA A UAACAAAA | 2824 | TTTTGTTA GGCTAGCTACAACGA TTGTTCAA | 3250 |
| 1630 | AACAAAUA A CAAAAGGG | 2825 | CCCTTTTG GGCTAGCTACAACGA TATTTGTT | 3251 |
| 1639 | CAAAAGGG G UGGAUUAU | 2351 | ATAATCCA GGCTAGCTACAACGA CCCTTTTG | 3252 |
| 1643 | AGGGUGG A UUAUAUAC | 2826 | GTATATAA GGCTAGCTACAACGA CCACCCCT | 3253 |
| 1646 | GGUGGAUU A UAUACAUU | 340 | AATGTATA GGCTAGCTACAACGA AATCCACC | 3254 |
| 1648 | UGGAUUAU A UACAUUCA | 341 | TGAATGTA GGCTAGCTACAACGA ATAATCCA | 3255 |
| 1650 | GAUUAUAU A CAUUCAAA | 342 | TTTGAATG GGCTAGCTACAACGA ATATAATC | 3256 |
| 1652 | UUAUAUAC A UUCAAAAA | 1536 | TTTTTGAA GGCTAGCTACAACGA GTATATAA | 3257 |
| 1662 | UCAAAAAA A UUAAUUCA | 2827 | TGAATTAA GGCTAGCTACAACGA TTTTTTGA | 3258 |
| 1666 | AAAAUUA A UUCAUAGA | 2828 | TCTATGAA GGCTAGCTACAACGA TAATTTTT | 3259 |
| 1670 | AUUAAUUC A UAGAGAUC | 1538 | GATCTCTA GGCTAGCTACAACGA GAATTAAT | 3260 |
| 1676 | UCAUAGAG A UCUUAAGC | 2829 | GCTTAAGA GGCTAGCTACAACGA CTCTATGA | 3261 |
| 1683 | GAUCUUAA G CCAAGUAA | 2352 | TTACTTGG GGCTAGCTACAACGA TTAAGATC | 3262 |
| 1688 | UAAGCCAA G UAAUAUAU | 2353 | ATATATTA GGCTAGCTACAACGA TTGGCTTA | 3263 |
| 1691 | GCCAAGUA A UAUAUUCU | 2830 | AGAATATA GGCTAGCTACAACGA TACTTGGC | 3264 |
| 1693 | CAAGUAAU A UAUUCUUA | 354 | TAAGAATA GGCTAGCTACAACGA ATTACTTG | 3265 |
| 1695 | AGUAAUAU A UUCUUAGU | 355 | ACTAAGAA GGCTAGCTACAACGA ATATTACT | 3266 |
| 1702 | UAUUCUUA G UAGAUACA | 2354 | TGTATCTA GGCTAGCTACAACGA TAAGAATA | 3267 |
| 1706 | CUUAGUAG A UACAAAAC | 2831 | GTTTTGTA GGCTAGCTACAACGA CTACTAAG | 3268 |
| 1708 | UAGAGAU A CAAAACAA | 361 | TTGTTTTG GGCTAGCTACAACGA ATCTACTA | 3269 |
| 1713 | GAUACAAA A CAAGUAAA | 2832 | TTTACTTG GGCTAGCTACAACGA TTTGTATC | 3270 |
| 1717 | CAAAACAA G UAAAGAUU | 2355 | AATCTTTA GGCTAGCTACAACGA TTGTTTTG | 3271 |
| 1723 | AAGUAAAG A UUGGAGAC | 2833 | GTCTCCAA GGCTAGCTACAACGA CTTTACTT | 3272 |
| 1730 | GAUUGGAG A CUUUGGAC | 2834 | GTCCAAAG GGCTAGCTACAACGA CTCCAATC | 3273 |
| 1737 | GACUUUGG A CUUGUAAC | 2835 | GTTACAAG GGCTAGCTACAACGA CCAAAGTC | 3274 |
| 1741 | UUGGACUU G UAACAUCU | 2356 | AGATGTTA GGCTAGCTACAACGA AAGTCCAA | 3275 |
| 1744 | GACUUGUA A CAUCUCUG | 2836 | CAGAGATG GGCTAGCTACAACGA TACAAGTC | 3276 |
| 1746 | CUUGUAAC A UCUCUGAA | 1547 | TTCAGAGA GGCTAGCTACAACGA GTTACAAG | 3277 |
| 1757 | UCUGAAAA A UGAUGGAA | 2837 | TTCCATCA GGCTAGCTACAACGA TTTTCAGA | 3278 |
| 1760 | GAAAAAUG A UGGAAAGC | 2838 | GCTTTCCA GGCTAGCTACAACGA CATTTTTC | 3279 |
| 1767 | GAUGGAA G CGAACAAG | 2357 | CTTGTTCG GGCTAGCTACAACGA TTTCCATC | 3280 |
| 1771 | GAAAGCGA A CAAGGAGU | 2839 | ACTCCTTG GGCTAGCTACAACGA TCGCTTTC | 3281 |
| 1778 | AACAAGGA G UAAGGAA | 2358 | TTCCCTTA GGCTAGCTACAACGA TCCTTGTT | 3282 |
| 1786 | GUAAGGGA A CUUUGCGA | 2840 | TCGCAAAG GGCTAGCTACAACGA TCCCTTAC | 3283 |
| 1791 | GGAACUUU G CGAUACAU | 2359 | ATGTATCG GGCTAGCTACAACGA AAAGTTCC | 3284 |
| 1794 | ACUUUGCG A UACAUGAG | 2841 | CTCATGTA GGCTAGCTACAACGA CGCAAAGT | 3285 |

TABLE XI-continued

Human PKR DNAzyme and Substrate Sequence

| Pos | Substrate | Seq ID | DNAzyme | Seq ID |
|---|---|---|---|---|
| 1796 | UUUGCGAU A CAUGAGCC | 373 | GGCTCATG GGCTAGCTACAACGA ATCGCAAA | 3286 |
| 1798 | UGCGAUAC A UGAGCCCA | 1552 | TGGGCTCA GGCTAGCTACAACGA GTATCGCA | 3287 |
| 1802 | AUACAUGA G CCCAGAAC | 2360 | GTTCTGGG GGCTAGCTACAACGA TCATGTAT | 3288 |
| 1809 | AGCCCAGA A CAGAUUUC | 2842 | GAAATCTG GGCTAGCTACAACGA TCTGGGCT | 3289 |
| 1813 | CAGAACAG A UUUCUUCG | 2843 | CGAAGAAA GGCTAGCTACAACGA CTGTTCTG | 3290 |
| 1821 | AUUUCUUC G CAAGACUA | 2361 | TAGTCTTG GGCTAGCTACAACGA GAAGAAAT | 3291 |
| 1826 | UUCGCAAG A CUAUGGAA | 2844 | TTCCATAG GGCTAGCTACAACGA CTTGCGAA | 3292 |
| 1829 | GCAAGACU A UGGAAAGG | 379 | CCTTTCCA GGCTAGCTACAACGA AGTCTTGC | 3293 |
| 1840 | GAAAGGAA G UGGACCUC | 2362 | GAGGTCCA GGCTAGCTACAACGA TTCCTTTC | 3294 |
| 1844 | GGAAGUGG A CCUCUACG | 2845 | CGTAGAGG GGCTAGCTACAACGA CCACTTCC | 3295 |
| 1850 | GGACCUCU A CGCUUUGG | 381 | CCAAAGCG GGCTAGCTACAACGA AGAGGTCC | 3296 |
| 1852 | ACCUCUAC G CUUUGGGG | 2363 | CCCCAAAG GGCTAGCTACAACGA GTAGAGGT | 3297 |
| 1860 | GCUUUGGG G CUAAUUCU | 2364 | AGAATTAG GGCTAGCTACAACGA CCCAAAGC | 3298 |
| 1864 | UGGGGCUA A UUCUUGCU | 2846 | AGCAAGAA GGCTAGCTACAACGA TAGCCCCA | 3299 |
| 1870 | UAAUUCUU G CUGAACUU | 2365 | AAGTTCAG GGCTAGCTACAACGA AAGAATTA | 3300 |
| 1875 | CUUGCUGA A CUUCUUCA | 2847 | TGAAGAAG GGCTAGCTACAACGA TCAGCAAG | 3301 |
| 1883 | ACUUCUUC A UGUAUGUG | 1569 | CACATACA GGCTAGCTACAACGA GAAGAAGT | 3302 |
| 1885 | UUCUUCAU G UAUGUGAC | 2366 | GTCACATA GGCTAGCTACAACGA ATGAAGAA | 3303 |
| 1887 | CUUCAUGU A UGUGACAC | 392 | GTGTCACA GGCTAGCTACAACGA ACATGAAG | 3304 |
| 1889 | UCAUGUAU G UGACACUG | 2367 | CAGTGTCA GGCTAGCTACAACGA ATACATGA | 3305 |
| 1892 | UGUAUGUG A CACUGCUU | 2848 | AAGCAGTG GGCTAGCTACAACGA CACATACA | 3306 |
| 1894 | UAUGUGAC A CUGCUUUU | 1570 | AAAAGCAG GGCTAGCTACAACGA GTCACATA | 3307 |
| 1897 | GUGACACU G CUUUUGAA | 2368 | TTCAAAAG GGCTAGCTACAACGA AGTGTCAC | 3308 |
| 1906 | CUUUUGAA A CAUCAAAG | 2849 | CTTTGATG GGCTAGCTACAACGA TTCAAAAG | 3309 |
| 1908 | UUUGAAAC A UCAAAGUU | 1573 | AACTTTGA GGCTAGCTACAACGA GTTTCAAA | 3310 |
| 1914 | ACAUCAAA G UUUUUCAC | 2369 | GTGAAAAA GGCTAGCTACAACGA TTTGATGT | 3311 |
| 1921 | AGUUUUUC A CAGACCUA | 1575 | TAGGTCTG GGCTAGCTACAACGA GAAAAACT | 3312 |
| 1925 | UUUCACAG A CCUACGGG | 2850 | CCCGTAGG GGCTAGCTACAACGA CTGTGAAA | 3313 |
| 1929 | ACAGACCU A CGGGAUGG | 402 | CCATCCCG GGCTAGCTACAACGA AGGTCTGT | 3314 |
| 1934 | CCUACGGG A UGGCAUCA | 2851 | TGATGCCA GGCTAGCTACAACGA CCCGTAGG | 3315 |
| 1937 | ACGGGAUG G CAUCAUCU | 2370 | AGATGATG GGCTAGCTACAACGA CATCCCGT | 3316 |
| 1939 | GGGAUGGC A UCAUCUCA | 1579 | TGAGATGA GGCTAGCTACAACGA GCCATCCC | 3317 |
| 1942 | AUGGCAUC A UCUCAGAU | 1580 | ATCTGAGA GGCTAGCTACAACGA GATGCCAT | 3318 |
| 1949 | CAUCUCAG A UAUAUUUG | 2852 | CAAATATA GGCTAGCTACAACGA CTGAGATG | 3319 |
| 1951 | UCUCAGAU A UAUUUGAU | 406 | ATCAAATA GGCTAGCTACAACGA ATCTGAGA | 3320 |
| 1953 | UCAGAUAU A UUUGAUAA | 407 | TTATCAAA GGCTAGCTACAACGA ATATCTGA | 3321 |
| 1958 | UAUAUUUG A UAAAAAG | 2853 | CTTTTTTA GGCTAGCTACAACGA CAAATATA | 3322 |
| 1972 | AAGAAAAA A CUCUUCUA | 2854 | TAGAAGAG GGCTAGCTACAACGA TTTTTCTT | 3323 |
| 1980 | ACUCUUCU A CAGAAAUU | 414 | AATTTCTG GGCTAGCTACAACGA AGAAGAGT | 3324 |
| 1986 | CUACAGAA A UUACUCUC | 2855 | GAGAGTAA GGCTAGCTACAACGA TTCTGTAG | 3325 |
| 1989 | CAGAAAUU A CUCUCAAA | 416 | TTTGAGAG GGCTAGCTACAACGA AATTTCTG | 3326 |
| 2001 | UCAAAGAA A CCUGAGGA | 2856 | TCCTCAGG GGCTAGCTACAACGA TTCTTTGA | 3327 |
| 2009 | ACCUGAGG A UCGACCUA | 2857 | TAGGTCGA GGCTAGCTACAACGA CCTCAGGT | 3328 |
| 2013 | GAGGAUCG A CCUAACAC | 2858 | GTGTTAGG GGCTAGCTACAACGA CGATCCTC | 3329 |
| 2018 | UCGACCUA A CACAUCUG | 2859 | CAGATGTG GGCTAGCTACAACGA TAGGTCGA | 3330 |
| 2020 | GACCUAAC A CAUCUGAA | 1594 | TTCAGATG GGCTAGCTACAACGA GTTAGGTC | 3331 |
| 2022 | CCUAACAC A UCUGAAAU | 1595 | ATTTCAGA GGCTAGCTACAACGA GTGTTAGG | 3332 |
| 2029 | CAUCUGAA A UACUAAGG | 2860 | CCTTAGTA GGCTAGCTACAACGA TTCAGATG | 3333 |
| 2031 | UCUGAAAU A CUAAGGAC | 422 | GTCCTTAG GGCTAGCTACAACGA ATTTCAGA | 3334 |
| 2038 | UACUAAGG A CCUUGACU | 2861 | AGTCAAGG GGCTAGCTACAACGA CCTTAGTA | 3335 |
| 2044 | GGACCUUG A CUGUGUGG | 2862 | CCACACAG GGCTAGCTACAACGA CAAGGTCC | 3336 |
| 2047 | CCUUGACU G UGGAAG | 2371 | CTTCCACA GGCTAGCTACAACGA AGTCAAGG | 3337 |
| 2049 | UUGACUGU G UGGAAGAA | 2372 | TTCTTCCA GGCTAGCTACAACGA ACAGTCAA | 3338 |
| 2060 | GAAGAAAA G CCCAGAGA | 2373 | TCTCTGGG GGCTAGCTACAACGA TTTTCTTC | 3339 |
| 2072 | AGAGAAAA A UGAACGAC | 2863 | GTCGTTCA GGCTAGCTACAACGA TTTTCTCT | 3340 |
| 2076 | AAAAUGA A CGACACAUG | 2864 | GTGTGTCG GGCTAGCTACAACGA TCATTTTT | 3341 |
| 2079 | AAUGAACG A CACACAUG | 2865 | CATGTGTG GGCTAGCTACAACGA CGTTCATT | 3342 |
| 2081 | UGAACGAC A CACAUGUU | 1604 | AACATGTG GGCTAGCTACAACGA GTCGTTCA | 3343 |
| 2083 | AACGACAC A CAUGUUAG | 1605 | CTAACATG GGCTAGCTACAACGA GTGTCGTT | 3344 |
| 2085 | CGACACAC A UGUUAGAG | 1606 | CTCTAACA GGCTAGCTACAACGA GTGTGTCG | 3345 |
| 2087 | ACACACAU G UUAGAGCC | 2374 | GGCTCTAA GGCTAGCTACAACGA ATGTGTGT | 3346 |
| 2093 | AUGUUAGA G CCCUUCUG | 2375 | CAGAAGGG GGCTAGCTACAACGA TCTAACAT | 3347 |
| 2107 | CUGAAAAA G UAUCCUGC | 2376 | GCAGGATA GGCTAGCTACAACGA TTTTTCAG | 3348 |
| 2109 | GAAAAAGU A UCCUGCUU | 429 | AAGCAGGA GGCTAGCTACAACGA ACTTTTTC | 3349 |
| 2114 | AGUAUCCU G CUUCUGAU | 2377 | ATCAGAAG GGCTAGCTACAACGA AGGATACT | 3350 |
| 2121 | UGCUUCUG A UAUGCAGU | 2866 | ACTGCATA GGCTAGCTACAACGA CAGAAGCA | 3351 |
| 2123 | CUUCUGAU A UGCAGUUU | 433 | AAACTGCA GGCTAGCTACAACGA ATCAGAAG | 3352 |
| 2125 | UCUGAUAU G CAGUUUUC | 2378 | GAAAACTG GGCTAGCTACAACGA ATATCAGA | 3353 |
| 2128 | GAUAUGCA G UUUUCCUU | 2379 | AAGGAAAA GGCTAGCTACAACGA TGCATATC | 3354 |
| 2139 | UUCCUUAA A UUAUCUAA | 2867 | TTAGATAA GGCTAGCTACAACGA TTAAGGAA | 3355 |
| 2142 | CUUAAAUU A UCUAAAAU | 441 | ATTTTAGA GGCTAGCTACAACGA AATTTAAG | 3356 |
| 2149 | UAUCUAAA A UCUGCUAG | 2868 | CTAGCAGA GGCTAGCTACAACGA TTTAGATA | 3357 |
| 2153 | UAAAAUCU G CUAGGGAA | 2380 | TTCCCTAG GGCTAGCTACAACGA AGATTTTA | 3358 |
| 2161 | GCUAGGGA A UAUCAAUA | 2869 | TATTGATA GGCTAGCTACAACGA TCCCTAGC | 3359 |
| 2163 | UAGGGAAU A UCAAUAGA | 446 | TCTATTGA GGCTAGCTACAACGA ATTCCCTA | 3360 |

TABLE XI-continued

Human PKR DNAzyme and Substrate Sequence

| Pos | Substrate | Seq ID | DNAzyme | Seq ID |
|---|---|---|---|---|
| 2167 | GAAUAUCA A UAGAUAUU | 2870 | AATATCTA GGCTAGCTACAACGA TGATATTC | 3361 |
| 2171 | AUCAAUAG A UAUUUACC | 2871 | GGTAAATA GGCTAGCTACAACGA CTATTGAT | 3362 |
| 2173 | CAAUAGAU A UUUACCUU | 449 | AAGGTAAA GGCTAGCTACAACGA ATCTATTG | 3363 |
| 2177 | AGAUAUUA A CCUUUUAU | 452 | ATAAAAGG GGCTAGCTACAACGA AAATATCT | 3364 |
| 2184 | UACCUUUU A UUUUAAUG | 456 | CATTAAAA GGCTAGCTACAACGA AAAAGGTA | 3365 |
| 2190 | UUAUUUUA A UGUUUCCU | 2872 | AGGAAACA GGCTAGCTACAACGA TAAAATAA | 3366 |
| 2192 | AUUUUAAU G UUUCCUUU | 2381 | AAAGGAAA GGCTAGCTACAACGA ATTAAAAT | 3367 |
| 2202 | UUCCUUUA A UUUUUUAC | 2873 | GTAAAAAA GGCTAGCTACAACGA TAAAGGAA | 3368 |
| 2209 | AAUUUUUU A CUAUUUUU | 472 | AAAAATAG GGCTAGCTACAACGA AAAAAATT | 3369 |
| 2212 | UUUUUACU A UUUUACUU | 473 | AGTAAAAA GGCTAGCTACAACGA AGTAAAAA | 3370 |
| 2218 | CUAUUUUU A CUAACUUU | 478 | AAGATTAG GGCTAGCTACAACGA AAAAATAG | 3371 |
| 2222 | UUUUACUA A UCUUUCUG | 2874 | CAGAAAGA GGCTAGCTACAACGA TAGTAAAA | 3372 |
| 2230 | AUCUUUCU G CAGAAACA | 2382 | TGTTTCTG GGCTAGCTACAACGA AGAAAGAT | 3373 |
| 2236 | CUGCAGAA A CAGAAAGG | 2875 | CCTTTCTG GGCTAGCTACAACGA TTCTGCAG | 3374 |
| 2244 | ACAGAAAG G UUUUCUUC | 2383 | GAAGAAAA GGCTAGCTACAACGA CTTTCTGT | 3375 |
| 2258 | UUCUUUUU G CUUCAAAA | 2384 | TTTTGAAG GGCTAGCTACAACGA AAAAAGAA | 3376 |
| 2267 | CUUCAAAA A CAUUCUUA | 2876 | TAAGAATG GGCTAGCTACAACGA TTTTGAAG | 3377 |
| 2269 | UCAAAAAC A UUCUUACA | 1636 | TGTAAGAA GGCTAGCTACAACGA GTTTTTGA | 3378 |
| 2275 | ACAUUCUU A CAUUUUAC | 499 | GTAAAATG GGCTAGCTACAACGA AAGAATGT | 3379 |
| 2277 | AUUCUUAC A UUUUACUU | 1638 | AAGTAAAA GGCTAGCTACAACGA GTAAGAAT | 3380 |
| 2282 | UACAUUUU A CUUUUUCC | 503 | GGAAAAAG GGCTAGCTACAACGA AAAATGTA | 3381 |
| 2293 | UUUUCCUG G CUCAUCUC | 2385 | GAGATGAG GGCTAGCTACAACGA CAGGAAAA | 3382 |
| 2297 | CCUGGCUC A UCUCUUUA | 1643 | TAAAGAGA GGCTAGCTACAACGA GAGCCAGG | 3383 |
| 2305 | AUCUCUUU A UUCUUUUU | 514 | AAAAAGAA GGCTAGCTACAACGA AAAGAGAT | 3384 |
| 2327 | UUUUAAAG A CAGAGUCU | 2877 | AGACTCTG GGCTAGCTACAACGA CTTTAAAA | 3385 |
| 2332 | AAGACAGA G UCUCGCUC | 2386 | GAGCGAGA GGCTAGCTACAACGA TCTGTCTT | 3386 |
| 2337 | AGAGUCUC G CUCUGUUG | 2387 | CAACAGAG GGCTAGCTACAACGA GAGACTCT | 3387 |
| 2342 | CUCGCUCU G UUGCCCAG | 2388 | CTGGGCAA GGCTAGCTACAACGA AGAGCGAG | 3388 |
| 2345 | GCUCUGUU G CCCAGGCU | 2389 | AGCCTGGG GGCTAGCTACAACGA AACAGAGC | 3389 |
| 2351 | UUGCCCAG G CUGGAGUG | 2390 | CACTCCAG GGCTAGCTACAACGA CTGGGCAA | 3390 |
| 2357 | AGGCUGGA G UGCAAUGA | 2391 | TCATTGCA GGCTAGCTACAACGA TCCAGCCT | 3391 |
| 2359 | GCUGGAGU G CAAUGACA | 2392 | TGTCATTG GGCTAGCTACAACGA ACTCCAGC | 3392 |
| 2362 | GGAGUGCA A UGACACAG | 2878 | CTGTGTCA GGCTAGCTACAACGA TGCACTCC | 3393 |
| 2365 | GUGCAAUG A CACAGUCU | 2879 | AGACTGTG GGCTAGCTACAACGA CATTGCAC | 3394 |
| 2367 | GCAAUGAC A CAGUCUUG | 1656 | CAAGACTG GGCTAGCTACAACGA GTCATTGC | 3395 |
| 2370 | AUGACACA G UCUUGGCU | 2393 | AGCCAAGA GGCTAGCTACAACGA TGTGTCAT | 3396 |
| 2376 | CAGUCUUG G CUCACUGC | 2394 | GCAGTGAG GGCTAGCTACAACGA CAAGACTG | 3397 |
| 2380 | CUUGGCUC A CUGCAACU | 1660 | AGTTGCAG GGCTAGCTACAACGA GAGCCAAG | 3398 |
| 2383 | GGCUCACU G CAACUUCU | 2395 | AGAAGTTG GGCTAGCTACAACGA AGTGAGCC | 3399 |
| 2386 | UCACUGCA A CUUCUGCC | 2880 | GGCAGAAG GGCTAGCTACAACGA TGCAGTGA | 3400 |
| 2392 | CAACUUCU G CCUCUUGG | 2396 | CCAAGAGG GGCTAGCTACAACGA AGAAGTTG | 3401 |
| 2401 | CCUCUUGG G UUCAAGUG | 2397 | CACTTGAA GGCTAGCTACAACGA CCAAGAGG | 3402 |
| 2407 | GGGUUCAA G UGAUUCUC | 2398 | GAGAATCA GGCTAGCTACAACGA TTGAACCC | 3403 |
| 2410 | UUCAAGUG A UUCUCCUG | 2881 | CAGGAGAA GGCTAGCTACAACGA CACTTGAA | 3404 |
| 2418 | AUUCUCCU G CCUCAGCC | 2399 | GGCTGAGG GGCTAGCTACAACGA AGGAGAAT | 3405 |
| 2424 | CUGCCUCA G CCUCCUGA | 2400 | TCAGGAGG GGCTAGCTACAACGA TGAGGCAG | 3406 |
| 2433 | CCUCCUGA G UAGCUGGA | 2401 | TCCAGCTA GGCTAGCTACAACGA TCAGGAGG | 3407 |
| 2436 | CCUGAGUA G CUGGAUUA | 2402 | TAATCCAG GGCTAGCTACAACGA TACTCAGG | 3408 |
| 2441 | GUAGCUGG A UUACAGGC | 2882 | GCCTGTAA GGCTAGCTACAACGA CCAGCTAC | 3409 |
| 2444 | GCUGGAUU A CAGGCAUG | 551 | CATGCCTG GGCTAGCTACAACGA AATCCAGC | 3410 |
| 2448 | GAUUACAG G CAUGUGCC | 2403 | GGCACATG GGCTAGCTACAACGA CTGTAATC | 3411 |
| 2450 | UUACAGGC A UGUGCCAC | 1681 | GTGGCACA GGCTAGCTACAACGA GCCTGTAA | 3412 |
| 2452 | ACAGGCAU G UGCCACCC | 2404 | GGGTGGCA GGCTAGCTACAACGA ATGCCTGT | 3413 |
| 2454 | AGGCAUGU G CCACCCAC | 2405 | GTGGGTGG GGCTAGCTACAACGA ACATGCCT | 3414 |
| 2457 | CAUGUGCC A CCCACCCA | 1683 | TGGGTGGG GGCTAGCTACAACGA GGCACATG | 3415 |
| 2461 | UGCCACCC A CCCAACUA | 1686 | TAGTTGGG GGCTAGCTACAACGA GGGTGGCA | 3416 |
| 2466 | CCCACCCA A CUAAUUUU | 2883 | AAAATTAG GGCTAGCTACAACGA TGGGTGGG | 3417 |
| 2470 | CCCAACUA A UUUUUGUU | 2884 | CACAAAAA GGCTAGCTACAACGA TAGTTGGG | 3418 |
| 2476 | UAAUUUUU G UGUUUUUA | 2406 | TAAAAACA GGCTAGCTACAACGA AAAAATTA | 3419 |
| 2478 | AUUUUUGU G UUUUUAAU | 2407 | ATTAAAAA GGCTAGCTACAACGA ACAAAAAT | 3420 |
| 2485 | UGUUUUUA A UAAAGACA | 2885 | TGTCTTTA GGCTAGCTACAACGA TAAAAACA | 3421 |
| 2491 | UAAUAAAG A CAGGGUUU | 2886 | AAACCCTG GGCTAGCTACAACGA CTTTATTA | 3422 |
| 2496 | AAGACAGG G UUUCACCA | 2408 | TGGTGAAA GGCTAGCTACAACGA CCTGTCTT | 3423 |
| 2501 | AGGGUUUC A CCAUGUUG | 1692 | CAACATGG GGCTAGCTACAACGA GAAACCCT | 3424 |
| 2504 | GUUUCACC A UGUUGGCC | 1694 | GGCCAACA GGCTAGCTACAACGA GGTGAAAC | 3425 |
| 2506 | UUCACCAU G UUGGCCAG | 2409 | CTGGCCAA GGCTAGCTACAACGA ATGGTGAA | 3426 |
| 2510 | CCAUGUUG G CCAGGCUG | 2410 | CAGCCTGG GGCTAGCTACAACGA CAACATGG | 3427 |
| 2515 | UUGGCCAG G CUGGUCUC | 2411 | GAGACCAG GGCTAGCTACAACGA CTGGCCAA | 3428 |
| 2519 | CCAGGCUG G UCUCAAAC | 2412 | GTTTGAGA GGCTAGCTACAACGA CAGCCTGG | 3429 |
| 2526 | GGUCUCAA A CUCCUGAC | 2887 | GTCAGGAG GGCTAGCTACAACGA TTGAGACC | 3430 |
| 2533 | AACUCCUG A CCUCAAGU | 2888 | ACTTGAGG GGCTAGCTACAACGA CAGGAGTT | 3431 |
| 2540 | GACCUCAA G UAAUCCAC | 2413 | GTGGATTA GGCTAGCTACAACGA TTGAGGTC | 3432 |
| 2543 | CUCAAGUA A UCCACCUG | 2889 | CAGGTGGA GGCTAGCTACAACGA TACTTGAG | 3433 |
| 2547 | AGUAAUCC A CCUGCCUC | 1707 | GAGGCAGG GGCTAGCTACAACGA GGATTACT | 3434 |
| 2551 | AUCCACCU G CCUCGGCC | 2414 | GGCCGAGG GGCTAGCTACAACGA AGGTGGAT | 3435 |

TABLE XI-continued

Human PKR DNAzyme and Substrate Sequence

| Pos | Substrate | Seq ID | DNAzyme | Seq ID |
|---|---|---|---|---|
| 2557 | CUGCCUCG G CCUCCCAA | 2415 | TTGGGAGG GGCTAGCTACAACGA CGAGGCAG | 3436 |
| 2567 | CUCCCAAA G UGCUGGGA | 2416 | TCCCAGCA GGCTAGCTACAACGA TTTGGGAG | 3437 |
| 2569 | CCCAAAGU G CUGGGAUU | 2417 | AATCCCAG GGCTAGCTACAACGA ACTTTGGG | 3438 |
| 2575 | GUGCUGGG A UUACAGGG | 2890 | CCCTGTAA GGCTAGCTACAACGA CCCAGCAC | 3439 |
| 2578 | CUGGGAUU A CAGGGAUG | 576 | CATCCCTG GGCTAGCTACAACGA AATCCCAG | 3440 |
| 2584 | UUACAGGG A UGAGCCAC | 2891 | GTGGCTCA GGCTAGCTACAACGA CCCTGTAA | 3441 |
| 2588 | AGGGAUGA G CCACCGCG | 2418 | CGCGGTGG GGCTAGCTACAACGA TCATCCCT | 3442 |
| 2591 | GAUGAGCC A CCGCGCCC | 1720 | GGGCGCGG GGCTAGCTACAACGA GGCTCATC | 3443 |
| 2594 | GAGCCACC G CGCCCAGC | 2419 | GCTGGGCG GGCTAGCTACAACGA GGTGGCTC | 3444 |
| 2596 | GCCACCGC G CCCAGCCU | 2420 | AGGCTGGG GGCTAGCTACAACGA GCGGTGGC | 3445 |
| 2601 | CGCGCCCA G CCUCAUCU | 2421 | AGATGAGG GGCTAGCTACAACGA TGGGCGCG | 3446 |
| 2606 | CCAGCCUC G UCUCUUUG | 1727 | CAAAGAGA GGCTAGCTACAACGA GAGGCTGG | 3447 |
| 2614 | AUCUCUUU G UUCUAAAG | 2422 | CTTTAGAA GGCTAGCTACAACGA AAAGAGAT | 3448 |
| 2623 | UUCUAAAG A UGGAAAAA | 2892 | TTTTTCCA GGCTAGCTACAACGA CTTTAGAA | 3449 |
| 2631 | AUGGAAAA A CCACCCCC | 2893 | GGGGGTGG GGCTAGCTACAACGA TTTTCCAT | 3450 |
| 2634 | GAAAAACC A CCCCCAAA | 1732 | TTTGGGGG GGCTAGCTACAACGA GGTTTTTC | 3451 |
| 2642 | ACCCCCAA A UUUUCUUU | 2894 | AAAGAAAA GGCTAGCTACAACGA TTGGGGGT | 3452 |
| 2653 | UUCUUUUU A UACUAUUA | 593 | TAATAGTA GGCTAGCTACAACGA AAAAAGAA | 3453 |
| 2655 | CUUUUUAU A CUAUUAAU | 594 | ATTAATAG GGCTAGCTACAACGA ATAAAAAG | 3454 |
| 2658 | UUUAUACU A UUAAUGAA | 595 | TTCATTAA GGCTAGCTACAACGA AGTATAAA | 3455 |
| 2662 | UACUAUUA A UGAAUCAA | 2895 | TTGATTCA GGCTAGCTACAACGA TAATAGTA | 3456 |
| 2666 | AUUAAUGA A UCAAUCAA | 2896 | TTGATTGA GGCTAGCTACAACGA TCATTAAT | 3457 |
| 2670 | AUGAAUCA A UCAAUUCA | 2897 | TGAATTGA GGCTAGCTACAACGA TGATTCAT | 3458 |
| 2674 | AUCAAUCA A UUCAUAUC | 2898 | GATATGAA GGCTAGCTACAACGA TGATTGAT | 3459 |
| 2678 | AUCAAUUC A UAUCUAUU | 1742 | AATAGATA GGCTAGCTACAACGA GAATTGAT | 3460 |
| 2680 | CAAUUCAU A UCUAUUUA | 602 | TAAATAGA GGCTAGCTACAACGA ATGAATTG | 3461 |
| 2684 | UCAUAUCU A UUUAUUAA | 604 | TTAATAAA GGCTAGCTACAACGA AGATATGA | 3462 |
| 2688 | AUCUAUUU A UUAAAUUU | 607 | AAATTTAA GGCTAGCTACAACGA AAATAGAT | 3463 |
| 2693 | UUUAUUAA A UUUCUACC | 2899 | GGTAGAAA GGCTAGCTACAACGA TTAATAAA | 3464 |
| 2699 | AAAUUUCU A CCGCUUUU | 613 | AAAAGCGG GGCTAGCTACAACGA AGAAATTT | 3465 |
| 2702 | UUUCUACC G CUUUUAGG | 2423 | CCTAAAAG GGCTAGCTACAACGA GGTAGAAA | 3466 |
| 2710 | GCUUUUAG G CCAAAAAA | 2424 | TTTTTTGG GGCTAGCTACAACGA CTAAAAGC | 3467 |
| 2719 | CCAAAAAA G UGUAAGAU | 2900 | ATCTTACA GGCTAGCTACAACGA TTTTTTGG | 3468 |
| 2721 | AAAAAAAU G UAAGAUCG | 2425 | CGATCTTA GGCTAGCTACAACGA ATTTTTTT | 3469 |
| 2726 | AAUGUAAG A UCGUUCUC | 2901 | GAGAACGA GGCTAGCTACAACGA CTTACATT | 3470 |
| 2729 | GUAAGAUC G UUCUCUGC | 2426 | GCAGAGAA GGCTAGCTACAACGA GATCTTAC | 3471 |
| 2736 | CGUUCUCU G CCUCACAU | 2427 | ATGTGAGG GGCTAGCTACAACGA AGAGAACG | 3472 |
| 2741 | UCUGCCUC A CAUAGCUU | 1753 | AAGCTATG GGCTAGCTACAACGA GAGGCAGA | 3473 |
| 2743 | UGCCUCAC A UAGCUUAC | 1754 | GTAAGCTA GGCTAGCTACAACGA GTGAGGCA | 3474 |
| 2746 | CUCACAUA G CUUACAAG | 2428 | CTTGTAAG GGCTAGCTACAACGA TATGTGAG | 3475 |
| 2750 | CAUAGCUU A CAAGCCAG | 626 | CTGGCTTG GGCTAGCTACAACGA AAGCTATG | 3476 |
| 2754 | GCUUACAA G CCAGCUGG | 2429 | CCAGCTGG GGCTAGCTACAACGA TTGTAAGC | 3477 |
| 2758 | ACAAGCCA G CUGGAGAA | 2430 | TTCTCCAG GGCTAGCTACAACGA TGGCTTGT | 3478 |
| 2767 | CUGGAGAA A UAUGGUAC | 2902 | GTACCATA GGCTAGCTACAACGA TTCTCCAG | 3479 |
| 2769 | GGAGAAAU A UGGUACUC | 627 | GAGTACCA GGCTAGCTACAACGA ATTTCTCC | 3480 |
| 2772 | GAAAUAUG G UACUCAUU | 2431 | AATGAGTA GGCTAGCTACAACGA CATATTTC | 3481 |
| 2774 | AAUAUGGU A CUCAUUAA | 628 | TTAATGAG GGCTAGCTACAACGA ACCATATT | 3482 |
| 2778 | UGGUACUC A UUAAAAAA | 1761 | TTTTTTAA GGCTAGCTACAACGA GAGTACCA | 3483 |
| 2796 | AAAAAAAA G UGAUGUAC | 2432 | GTACATCA GGCTAGCTACAACGA TTTTTTTT | 3484 |
| 2799 | AAAAAGUG A UGUACAAC | 2903 | GTTGTACA GGCTAGCTACAACGA CACTTTTT | 3485 |

Input Sequence = NM_002759. Cut Site = R/Y
Arm Length = 8. Core Sequence = GGCTAGCTACAACGA NM_002759 (*Homo sapiens* protein kinase, interferon-inducible double stranded RNA dependent (PRKR), mRNA.; 2808 bp)

TABLE XII

Human PKR Amberzyme and Substrate Sequence

| Pos | Substrate | Seq ID | Amberzyme | Seq ID |
|---|---|---|---|---|
| 9 | GCGGCGGC G GCGGCGCA | 3486 | UGCGCCGC GGAGGAAACUCC CU UCAAGGACAUCGUCCGGG GCCGCCGC | 53814 |
| 10 | CGGCGGCG G CGGCGCAG | 2261 | CUGCGCCG GGAGGAAACUCC CU UCAAGGACAUCGUCCGGG CGCCGCCG | 3815 |
| 12 | GCGGCGGC G GCGCAGUU | 3487 | AACUGCGC GGAGGAAACUCC CU UCAAGGACAUCGUCCGGG GCCGCCGC | 3816 |
| 13 | CGGCGGCG G CGCAGUUU | 2433 | AAACUGCG GGAGGAAACUCC CU UCAAGGACAUCGUCCGGG CGCCGCCG | 3817 |
| 15 | GCGGCGGC G CAGUUUGC | 2434 | GCAAACUG GGAGGAAACUCC CU UCAAGGACAUCGUCCGGG GCCGCCGC | 3818 |
| 18 | GCGGCGCA G UUUGCUCA | 2435 | UGAGCAAA GGAGGAAACUCC CU UCAAGGACAUCGUCCGGG UGCGCCGC | 3819 |
| 22 | CGCAGUUU G CUCAUACU | 2436 | AGUAUGAG GGAGGAAACUCC CU UCAAGGACAUCGUCCGGG AAACUGCG | 3820 |
| 33 | CAUACUUU G UGACUUGC | 2437 | GCAAGUCA GGAGGAAACUCC CU UCAAGGACAUCGUCCGGG AAAGUAUG | 3821 |
| 35 | UACUUUCU G ACUUGCGG | 3488 | CCGCAAGU GGAGGAAACUCC CU UCAAGGACAUCGUCCGGG ACAAAGUA | 3822 |
| 40 | UGUGACUU G CGCUCACA | 2438 | UCUCACCG GGAGGAAACUCC CU UCAAGGACAUCGUCCGGG AAGUCACA | 3823 |
| 42 | UGACUUGC G GUCACAGU | 3489 | ACUGUGAC GGAGGAAACUCC CU UCAAGGACAUCGUCCGGG GCAAGUCA | 3824 |
| 43 | GACUUGCG G UCACAGUG | 2439 | CACUGUGA GGAGGAAACUCC CU UCAAGGACAUCGUCCGGG CGCAAGUC | 3825 |

TABLE XII-continued

Human PKR Amberzyme and Substrate Sequence

| Pos | Substrate | Seq ID | Amberzyme | Seq ID |
|---|---|---|---|---|
| 49 | CGGUCACA G UGGCAUUC | 2440 | GAAUGCCA GGAGGAAACUCC CU UCAAGGACAUCGUCCGGG UGUCACCG | 3826 |
| 51 | GUCACAGU G GCAUUCAG | 3490 | CUGAAUGC GGAGGAAACUCC CU UCAAGGACAUCGUCCGGG ACUGUGAC | 3827 |
| 52 | UCACAGUG G CAUUCAGC | 2441 | GCUGAAUG GGAGGAAACUCC CU UCAAGGACAUCGUCCGGG CACUGUGA | 3828 |
| 59 | GGCAUUCA G CUCCACAC | 2442 | GUGUGGAG GGAGGAAACUCC CU UCAAGGACAUCGUCCGGG UGAAUGCC | 3829 |
| 70 | CCACACUU G GUAGAACC | 3491 | GGUUCUAC GGAGGAAACUCC CU UCAAGGACAUCGUCCGGG AAGUGUGG | 3830 |
| 71 | CACACUUG G UAGAACCA | 2443 | UGGUUCUA CGAGGAAACUCC CU UCAAGGACAUCGUCCGGG CAAGUGUG | 3831 |
| 74 | ACUUGGUA G AACCACAG | 3492 | CUGUGGUU GGAGGAAACUCC CU UCAAGGACAUCGUCCGGG UACCAAGU | 3832 |
| 82 | GAACCACA G GCACGACA | 3493 | UGUCGUGC GGAGGAAACUCC CU UCAAGGACAUCGUCCGGG UGUGGUUC | 3833 |
| 83 | AACCACAG G CACGACAA | 2444 | UUGUCGUG GGAGGAAACUCC CU UCAAGGACAUCGUCCGGG CUGUGGUU | 3834 |
| 87 | ACAGGCAC G ACAAGCAU | 3494 | AUGCUUGU GGAGGAAACUCC CU UCAAGGACAUCGUCCGGG GUGCCUGU | 3835 |
| 92 | CACGACAA G CAUAGAAA | 2445 | UUUCUAUG GGAGGAAACUCC CU UCAAGGACAUCGUCCGGG UUGUCGUG | 3836 |
| 97 | CAACCAUA G AAACAUCC | 3495 | GGAUGUUU GGAGGAAACUCC CU UCAAGGACAUCGUCCGGG UAUGCUUG | 3837 |
| 121 | UCUUCAUC G AGGCAUCG | 3496 | CGAUGCCU GGAGGAAACUCC CU UCAAGGACAUCGUCCGGG GAUGAAGA | 3838 |
| 123 | UUCAUCCA G CAUCGAG | 3497 | CUCGAUGC GGAGGAAACUCC CU UCAAGGACAUCGUCCGGG UCGAUGAA | 3839 |
| 124 | UCAUCCAC G CAUCCAGG | 2446 | CCUCGAUG GGAGGAAACUCC CU UCAAGGACAUCGUCCGGG CUCGAUGA | 3840 |
| 129 | GAGGCAUC G AGGCCAU | 3498 | AUGGACCU GGAGGAAACUCC CU UCAAGGACAUCGUCCGGG GAUGCCUC | 3841 |
| 131 | GGCAUCGA G GUCCAUCC | 3499 | GGAUGGAC GGAGGAAACUCC CU UCAAGGACAUCGUCCGGG UCGAUGCC | 3842 |
| 132 | GCAUCGAC G UCCAUCCC | 2447 | GGGAUGGA GGAGGAAACUCC CU UCAAGGACAUCGUCCGGG CUCGAUGC | 3843 |
| 152 | AAAAAUCA G GAGACCCU | 3500 | AGGGUCUC GGAGGAAACUCC CU UCAAGGACAUCGUCCGGG UCAUUUUU | 3844 |
| 153 | AAAAAUCAG G AGACCUG | 3501 | CAGGGUCU GGAGGAAACUCC CU UCAAGGACAUCGUCCGGG CUGAUUUU | 3845 |
| 155 | AAUCAGGA G ACCCUGGC | 3502 | GCCAGGGU GGAGGAAACUCC CU UCAAGGACAUCGUCCGGG UCCUGAUU | 3846 |
| 161 | GAGACCCU G CUAUCAU | 3503 | AUGAUAGC GGAGGAAACUCC CU UCAAGGACAUCGUCCGGG AGGGUCUC | 3847 |
| 162 | ACACCCUG G CUAUCAUA | 2448 | UAUGAUAG GGAGGAAACUCC CU UCAAGGACAUCGUCCGGG CAGGGUCU | 3848 |
| 171 | CUAUCAUA G ACCUUAGU | 3504 | ACUAAGGU GGAGGAAACUCC CU UCAAGGACAUCGUCCGGG UAUGAUAG | 3849 |
| 178 | AGACCUUA G UCUUCGCU | 2449 | AGCGAAGA GGAGGAAACUCC CU UCAAGGACAUCGUCCGGG UAAGGUCU | 3850 |
| 184 | UAGUCUUC G CUGGUAUA | 2450 | UAUACCAG GGAGGAAACUCC CU UCAAGGACAUCGUCCGGG GAAGACUA | 3851 |
| 187 | UCUUCGCU G GUAUACUC | 3505 | GAGUAUAC GGAGGAAACUCC CU UCAAGGACAUCGUCCGGG AGCGAAGA | 3852 |
| 188 | CUUCGCUG G UAUACUCG | 2451 | CGAGUAUA GGAGGAAACUCC CU UCAAGGACAUCGUCCGGG CAGCGAAG | 3853 |
| 196 | GUAUACUC G CUGUCUGU | 2452 | ACAGACAG GGAGGAAACUCC CU UCAAGGACAUCGUCCGGG GAGUAUAC | 3854 |
| 199 | UACUCGCU G UCUGUCAA | 2453 | UUGACAGA GGAGGAAACUCC CU UCAAGGACAUCGUCCGGG AGCGAGUA | 3855 |
| 203 | CGCUGUCU G UCAACCAG | 2454 | CUGGUUGA GGAGGAAACUCC CU UCAAGGACAUCGUCCGGG AGACAGCG | 3856 |
| 211 | GUCAACCA G CGGUUGAC | 2455 | GUCAACCG GGAGGAAACUCC CU UCAAGGACAUCGUCCGGG UGGUUGAC | 3857 |
| 213 | CAACCAGC G GUUGACUU | 3506 | AAGUCAAC GGAGGAAACUCC CU UCAAGGACAUCGUCCGGG GCUGGUUG | 3858 |
| 214 | AACCAGCG G UUGACUUU | 2456 | AAAGUCAA GGAGGAAACUCC CU UCAAGGACAUCGUCCGGG CGCUGGUU | 3859 |
| 217 | CAGCGGUU G ACUUUUUU | 3507 | AAAAAAGU GGAGGAAACUCC CU UCAAGGACAUCGUCCGGG AACCGCUG | 3860 |
| 229 | UUUUUUAA G CCUUCUUU | 2457 | AAAGAAGG GGAGGAAACUCC CU UCAAGGACAUCGUCCGGG UUAAAAAA | 3861 |
| 252 | UUUUACCA G UUUCUGGA | 2458 | UCCAGAAA GGAGGAAACUCC CU UCAAGGACAUCGUCCGGG UGGUAAAA | 3862 |
| 258 | CAGUUUCU G GAGCAAAU | 3508 | AUUUGCUC GGAGGAAACUCC CU UCAAGGACAUCGUCCGGG AGAAACUG | 3863 |
| 259 | AGUUUCUG G AGCAAAUU | 3509 | AAUUUGCU GGAGGAAACUCC CU UCAAGGACAUCGUCCGGG CAGAAACU | 3864 |
| 261 | UUUCUGGA G CAAAUUCA | 2459 | UGAAUUUG GGAGGAAACUCC CU UCAAGGACAUCGUCCGGG UCCAGAAA | 3865 |
| 270 | CAAAUUCA G UUUGCCUU | 2460 | AAGGCAAA GGAGGAAACUCC CU UCAAGGACAUCGUCCGGG UGAAUUUG | 3866 |
| 274 | UUCAGUUU G CCUUCCUG | 2461 | CAGGAAGG GGAGGAAACUCC CU UCAAGGACAUCGUCCGGG AAACUGAA | 3867 |
| 282 | GCCUUCCU G GAUUGUA | 3510 | UACAAAUC GGAGGAAACUCC CU UCAAGGACAUCGUCCGGG AGGAAGGC | 3868 |
| 283 | CCUUCCUG G AUUUGUAA | 3511 | UUACAAAU GGAGGAAACUCC CU UCAAGGACAUCGUCCGGG CAGGAAGG | 3869 |
| 288 | CUGGAUUU G UAAAUUGU | 2462 | ACAAUUUA GGAGGAAACUCC CU UCAAGGACAUCGUCCGGG AAAUCCAG | 3870 |
| 295 | UCUAAAUU G UAAUGACC | 2463 | GGUCAUUA GGAGGAAACUCC CU UCAAGGACAUCGUCCGGG AAUUUACA | 3871 |
| 300 | AUUGUAAU G ACCUCAAA | 3512 | UUUGAGGU GGAGGAAACUCC CU UCAAGGACAUCGUCCGGG AUUACAAU | 3872 |
| 315 | AAACUUUA G CAGUUCUU | 2464 | AAGAACUG GGAGGAAACUCC CU UCAAGGACAUCGUCCGGG UAAAGUUU | 3873 |
| 318 | CUUUAGCA G UUCUUCCA | 2465 | UGGAAGAA GGAGGAAACUCC CU UCAAGGACAUCGUCCGGG UGCUAAAC | 3874 |
| 330 | UUCCAUCU G ACUCAGGU | 3513 | ACCUGAGU GGAGGAAACUCC CU UCAAGGACAUCGUCCGGG AGAUGGAA | 3875 |
| 336 | CUGACUCA G UUUGCUU | 3514 | AAGCAAAC GGAGGAAACUCC CU UCAAGGACAUCGUCCGGG UGAGUCAG | 3876 |
| 337 | UGACUCAG G UUUGCUUC | 2466 | GAAGCAAA GGAGGAAACUCC CU UCAAGGACAUCGUCCGGG CUGAGUCA | 3877 |
| 341 | UCAGGUUU G CUUCUCUG | 2467 | CAGAGAAG GGAGGAAACUCC CU UCAAGGACAUCGUCCGGG AAACCUGA | 3878 |
| 349 | GCUUCUCU G CGGUCUUC | 3515 | AAGACCGC GGAGGAAACUCC CU UCAAGGACAUCGUCCGGG AGAGAAGC | 3879 |
| 350 | CUUCUCUG G CGGUCUUC | 2468 | GAAGACCG GGAGGAAACUCC CU UCAAGGACAUCGUCCGGG CAGAGAAG | 3880 |
| 352 | UCUCUGGC G GUCUUCAG | 3516 | CUGAAGAC GGAGGAAACUCC CU UCAAGGACAUCGUCCGGG GCCAGAGA | 3881 |
| 353 | CUCUGGCG G UCUUCAGA | 2469 | UCUGAAGA GGAGGAAACUCC CU UCAAGGACAUCGUCCGGG CGCCAGAC | 3882 |
| 360 | CGUCUUCA G AAUCAACA | 3517 | UGUUGAUU GGAGGAAACUCC CU UCAAGGACAUCGUCCGGG UGAAGACC | 3883 |
| 380 | ACACUUCC G UGAUUAUC | 2470 | GAUAAUCA GGAGGAAACUCC CU UCAAGGACAUCGUCCGGG GGAAGUGU | 3884 |
| 382 | ACUUCCGU G AUUAUCUG | 3518 | CAGAUAAU GGAGGAAACUCC CU UCAAGGACAUCGUCCGGG ACGGAAGU | 3885 |
| 390 | GAUUAUCU G CGUGCAUU | 2471 | AAUGCACG GGAGGAAACUCC CU UCAAGGACAUCGUCCGGG AGAUAAUC | 3886 |
| 392 | UUAUCUGC G UGCAUUU | 2472 | AAAAUGCA GGAGGAAACUCC CU UCAAGGACAUCGUCCGGG GCAGAUAA | 3887 |
| 394 | AUCUGCGU G CAUUUUGG | 2473 | CCAAAAUG GGAGGAAACUCC CU UCAAGGACAUCGUCCGGG ACGCAGAU | 3888 |
| 401 | UGCAUUUU G GACAAAGC | 3519 | GCUUUGUC GGAGGAAACUCC CU UCAAGGACAUCGUCCGGG AAAAUGCA | 3889 |
| 402 | GCAUUUUG G ACAAAGCU | 3520 | AGCUUUGU GGAGGAAACUCC CU UCAAGGACAUCGUCCGGG CAAAAUGC | 3890 |
| 408 | UGGACAAA G CUUCCAAC | 2474 | GUUGGAAG GGAGGAAACUCC CU UCAAGGACAUCGUCCGGG UUUGUCCA | 3891 |
| 419 | UCCAACCA G AUACGGGA | 3521 | CCCGUAUC GGAGGAAACUCC CU UCAAGGACAUCGUCCGGG UGGUUGGA | 3892 |
| 420 | CCAACCAG G AUACGGGA | 3522 | UCCCGUAU GGAGGAAACUCC CU UCAAGGACAUCGUCCGGG CUGGUUGG | 3893 |
| 425 | CAGGAUAC G GAAGAAG | 3523 | CUUCUUCC GGAGGAAACUCC CU UCAAGGACAUCGUCCGGG GUAUCCUG | 3894 |
| 426 | AGGAUACG G AAGAAGAA | 3524 | UCUUCUUC GGAGGAAACUCC CU UCAAGGACAUCGUCCGGG CGUAUCCU | 3895 |
| 427 | GGAUACGG A AGAAGAA | 3525 | UUCUUCUU GGAGGAAACUCC CU UCAAGGACAUCGUCCGGG CCGUAUCC | 3896 |
| 430 | UACGGGAA G AAGAAAUG | 3526 | CAUUUCUU GGAGGAAACUCC CU UCAAGGACAUCGUCCGGG UUCCCGUA | 3897 |
| 433 | GGGAAGAA G AAAUGGCU | 3527 | AGCCAUUU GGAGGAAACUCC CU UCAAGGACAUCGUCCGGG UUCUUCCC | 3898 |
| 438 | GAAGAAAU G GCUGGUGA | 3528 | UCACCAGC GGAGGAAACUCC CU UCAAGGACAUCGUCCGGG AUUUCUUC | 3899 |
| 439 | AAGAAAUG G CUGGUGAU | 2475 | AUCACCAG GGAGGAAACUCC CU UCAAGGACAUCGUCCGGG CAUUUCUU | 3900 |

TABLE XII-continued

Human PKR Amberzyme and Substrate Sequence

| Pos | Substrate | | | Seq ID | Amberzyme | | | Seq ID |
|---|---|---|---|---|---|---|---|---|
| 442 | AAAUGGCU | G | GUGAUCUU | 3529 | AAGAUCAC GGAGGAAACUCC CU UCAAGGACAUCGUCCGGG AGCCAUUU | | | 3901 |
| 443 | AAUGGCUG | G | UGAUCUUU | 2476 | AAAGAUCA GGAGGAAACUCC CU UCAAGGACAUCGUCCGGG CAGCCAUU | | | 3902 |
| 445 | UGGCUGGU | G | AUCUUUCA | 3530 | UGAAAGAU GGAGGAAACUCC CU UCAAGGACAUCGUCCGGG ACCAGCCA | | | 3903 |
| 454 | AUCUUUCA | G | CAGGUUUC | 2477 | GAAACCUG GGAGGAAACUCC CU UCAAGGACAUCGUCCGGG UGAAAGAU | | | 3904 |
| 457 | UUUCAGCA | G | GUUUCUUC | 3531 | GAAGAAAC GGAGGAAACUCC CU UCAAGGACAUCGUCCGGG UGCUGAAA | | | 3905 |
| 458 | UUCAGCAG | G | UUUCUUCA | 2478 | UGAAGAAA GGAGGAAACUCC CU UCAAGGACAUCGUCCGGG CUGCUGAA | | | 3906 |
| 468 | UUCUUCAU | G | GAGGAACU | 3532 | AGUUCCUC GGAGGAAACUCC CU UCAAGGACAUCGUCCGGG AUGAAGAA | | | 3907 |
| 469 | UCUUCAUG | G | AGGAACUU | 3533 | AAGUUCCU GGAGGAAACUCC CU UCAAGGACAUCGUCCGGG CAUGAAGA | | | 3908 |
| 471 | UUCAUGGA | G | GAACUUAA | 3534 | UUAAGUUC GGAGGAAACUCC CU UCAAGGACAUCGUCCGGG UCCAUGAA | | | 3909 |
| 472 | UCAUGGAG | G | AACUUAAU | 3535 | AUUAAGUU GGAGGAAACUCC CU UCAAGGACAUCGUCCGGG CUCCAUGA | | | 3910 |
| 488 | UACAUACC | G | UCAGAAGC | 2479 | GCUUCUGA GGAGGAAACUCC CU UCAAGGACAUCGUCCGGG GGUAUGUA | | | 3911 |
| 492 | UACCGUCA | G | AAGCAGGG | 3536 | CCCUGCUU GGAGGAAACUCC CU UCAAGGACAUCGUCCGGG UGACGGUA | | | 3912 |
| 495 | CGUCAGAA | G | CAGGGAGU | 2262 | ACUCCCUG GGAGGAAACUCC CU UCAAGGACAUCGUCCGGG UUCUGACG | | | 3913 |
| 498 | CAGAAGCA | G | GGAGUAGU | 3537 | ACUACUCC GGAGGAAACUCC CU UCAAGGACAUCGUCCGGG UGCUUCUG | | | 3914 |
| 499 | AGAAGCAG | G | GAGUAGUA | 3538 | UACUACUC GGAGGAAACUCC CU UCAAGGACAUCGUCCGGG CUGCUUCU | | | 3915 |
| 500 | GAAGCAGG | G | AGUAGUAC | 3539 | GUACUACU GGAGGAAACUCC CU UCAAGGACAUCGUCCGGG CCUGCUUC | | | 3916 |
| 502 | AGCAGGGA | G | UAGUACUU | 2263 | AAGUACUA GGAGGAAACUCC CU UCAAGGACAUCGUCCGGG UCCCUGCU | | | 3917 |
| 505 | AGGGAGUA | G | UACUUAAA | 2264 | UUUAAGUA GGAGGAAACUCC CU UCAAGGACAUCGUCCGGG UACUCCCU | | | 3918 |
| 520 | AAUAUCAA | G | AACUGCCU | 3540 | AGGCAGUU GGAGGAAACUCC CU UCAAGGACAUCGUCCGGG UUGAUAUU | | | 3919 |
| 525 | CAAGAACU | G | CCUAAUUC | 2265 | GAAUUAGG GGAGGAAACUCC CU UCAAGGACAUCGUCCGGG AGUUCUUG | | | 3920 |
| 535 | CUAAUUCA | G | GACCUCCA | 3541 | UGGAGGUC GGAGGAAACUCC CU UCAAGGACAUCGUCCGGG UGAAUUAG | | | 3921 |
| 536 | UAAUUCAG | G | ACCUCCAC | 3542 | GUGGAGGU GGAGGAAACUCC CU UCAAGGACAUCGUCCGGG CUGAAUUA | | | 3922 |
| 547 | CUCCACAU | G | UAGGAGG | 3543 | CCUCCUAU GGAGGAAACUCC CU UCAAGGACAUCGUCCGGG AUGUGGAG | | | 3923 |
| 551 | ACAUGAUA | G | GAGGUUUA | 3544 | UAAACCUC GGAGGAAACUCC CU UCAAGGACAUCGUCCGGG UAUCAUGU | | | 3924 |
| 552 | CAUGAUAG | G | AGGUUUAA | 3545 | GUAAACCU GGAGGAAACUCC CU UCAAGGACAUCGUCCGGG CUAUCAUG | | | 3925 |
| 554 | UGAUAGGA | G | GUUUACAU | 3546 | AUGUAAAC GGAGGAAACUCC CU UCAAGGACAUCGUCCGGG UCCUAUCA | | | 3926 |
| 555 | GAUAGGAG | G | UUUACAUU | 2266 | AAUGUAAA GGAGGAAACUCC CU UCAAGGACAUCGUCCGGG CUCCUAUC | | | 3927 |
| 568 | CAUUUCAA | G | UUAUAAUA | 2267 | UAUUAUAA GGAGGAAACUCC CU UCAAGGACAUCGUCCGGG UUGAAAUG | | | 3928 |
| 577 | UUAUAAUA | G | AUGGAACA | 3547 | UCUUCCAU GGAGGAAACUCC CU UCAAGGACAUCGUCCGGG UAUUAUAA | | | 3929 |
| 580 | UAAUAGAU | G | GAAGAGAA | 3548 | UUCUCUUC GGAGGAAACUCC CU UCAAGGACAUCGUCCGGG AUCUAUUA | | | 3930 |
| 581 | AAUAGAUG | G | AAGAGAAU | 3549 | AUUCUCUU GGAGGAAACUCC CU UCAAGGACAUCGUCCGGG CAUCUAUU | | | 3931 |
| 584 | AGAUGGAA | G | AGAAUUUC | 3550 | GAAAUUCU GGAGGAAACUCC CU UCAAGGACAUCGUCCGGG UUCCAUCU | | | 3932 |
| 586 | AUGGAAGA | G | AAUUUCCA | 3551 | UGGAAAUU GGAGGAAACUCC CU UCAAGGACAUCGUCCGGG UCUUCCAU | | | 3933 |
| 595 | AAUUUCCA | G | AAGGUGAA | 3552 | UUCACCUU GGAGGAAACUCC CU UCAAGGACAUCGUCCGGG UGGAAAUU | | | 3934 |
| 598 | UUCCAGAA | G | GUGAAGGU | 3553 | ACCUUCAC GGAGGAAACUCC CU UCAAGGACAUCGUCCGGG UUCUGGAA | | | 3935 |
| 599 | UCCAGAAG | G | UGAAGGUA | 2268 | UACCUUCA GGAGGAAACUCC CU UCAAGGACAUCGUCCGGG CUUCUGGA | | | 3936 |
| 601 | CAGAAGGU | G | AAGGUAGA | 3554 | UCUACCUU GGAGGAAACUCC CU UCAAGGACAUCGUCCGGG ACCUUCUG | | | 3937 |
| 604 | AAGGUGAA | G | GUAGAUCA | 3555 | UGAUCUAC GGAGGAAACUCC CU UCAAGGACAUCGUCCGGG UUCACCUU | | | 3938 |
| 605 | AGGUGAAG | G | UAGAUCAA | 2269 | UUGAUCUA GGAGGAAACUCC CU UCAAGGACAUCGUCCGGG CUUCACCU | | | 3939 |
| 608 | UGAAGGUA | G | AUCAAAGA | 3556 | UCUUUGAU GGAGGAAACUCC CU UCAAGGACAUCGUCCGGG UACCUUCA | | | 3940 |
| 615 | AGAUCAAA | G | AAGGAAGC | 3557 | GCUUCCUU GGAGGAAACUCC CU UCAAGGACAUCGUCCGGG UUUGAUCU | | | 3941 |
| 618 | UCAAAGAA | G | GAAGCAAA | 3558 | UUUGCUUC GGAGGAAACUCC CU UCAAGGACAUCGUCCGGG UUCUUUGA | | | 3942 |
| 619 | CAAAGAAG | G | AAGCAAAA | 3559 | UUUUGCUU GGAGGAAACUCC CU UCAAGGACAUCGUCCGGG CUUCUUUG | | | 3943 |
| 622 | ACAAGGAA | G | CAAAAAAU | 2270 | AUUUUUUG GGAGGAAACUCC CU UCAAGGACAUCGUCCGGG UUCCUUCU | | | 3944 |
| 631 | CAAAAAAU | G | CCGCAGCC | 2271 | GGCUGCGG GGAGGAAACUCC CU UCAAGGACAUCGUCCGGG AUUUUUUG | | | 3945 |
| 634 | AAAAUGCC | G | CAGCCAAA | 2272 | UUUGGCUC GGAGGAAACUCC CU UCAAGGACAUCGUCCGGG GGCAUUUU | | | 3946 |
| 637 | AUGCCGCA | G | CCAAAUUA | 2273 | UAAUUUGG GGAGGAAACUCC CU UCAAGGACAUCGUCCGGG UGCGGCAU | | | 3947 |
| 646 | CCAAAUUA | G | CUGUUGAG | 2274 | CUCAACAG GGAGGAAACUCC CU UCAAGGACAUCGUCCGGG UAAUUUGG | | | 3948 |
| 649 | AAUUAGCU | G | UUGAGAUA | 2275 | UAUCUCAA GGAGGAAACUCC CU UCAAGGACAUCGUCCGGG AGCUAAUU | | | 3949 |
| 652 | UAGCUGUU | G | AGAUACUU | 3560 | AAGUAUCU GGAGGAAACUCC CU UCAAGGACAUCGUCCGGG AACAGCUA | | | 3950 |
| 654 | GCUGUUCA | G | AUACUUAA | 3561 | UUAAGUAU GGAGGAAACUCC CU UCAAGGACAUCGUCCGGG UCAACAGC | | | 3951 |
| 666 | CUUAAUAA | G | GAAAACAA | 3562 | UUGUUUUC GGAGGAAACUCC CU UCAAGGACAUCGUCCGGG UUAUUAAG | | | 3952 |
| 667 | UUAAUAAG | G | AAAAGAAG | 3563 | CUUCUUUU GGAGGAAACUCC CU UCAAGGACAUCGUCCGGG CUUAUUAA | | | 3953 |
| 672 | AAGGAAAA | G | AAGGCAGU | 3564 | ACUGCCUU GGAGGAAACUCC CU UCAAGGACAUCGUCCGGG UUUUCCUU | | | 3954 |
| 675 | GAAAACAA | G | GCAGUUAG | 3565 | CUAACUGC GGAGGAAACUCC CU UCAAGGACAUCGUCCGGG UUCUUUUC | | | 3955 |
| 676 | AAAAGAAG | G | CAGUUAGU | 2276 | ACUAACUG GGAGGAAACUCC CU UCAAGGACAUCGUCCGGG CUUCUUUU | | | 3956 |
| 679 | AGAAGGCA | G | UUAGUCCU | 2277 | AGGACUAA GGAGGAAACUCC CU UCAAGGACAUCGUCCGGG UGCCUUCU | | | 3957 |
| 683 | GGCAGUUA | G | UCCUUGAU | 2278 | AUAAAGGA GGAGGAAACUCC CU UCAAGGACAUCGUCCGGG UAACUGCC | | | 3958 |
| 696 | UUAUUAUU | G | ACAACAAC | 3566 | GUUGUUGU GGAGGAAACUCC CU UCAAGGACAUCGUCCGGG AAUAAUAA | | | 3959 |
| 705 | ACAACAAC | G | AAUUCUUC | 3567 | GAAGAAUU GGAGGAAACUCC CU UCAAGGACAUCGUCCGGG GUUGUUGU | | | 3960 |
| 715 | AUUCUUCA | G | AAGGAUUA | 3568 | UAACCUU GGAGGAAACUCC CU UCAAGGACAUCGUCCGGG UGAAGAAU | | | 3961 |
| 718 | CUUCAGAA | G | GAUUAUCC | 3569 | GGAUAAUC GGAGGAAACUCC CU UCAAGGACAUCGUCCGGG UUCUGAAG | | | 3962 |
| 719 | UUCAGAAG | G | AUUAUCCA | 3570 | UGGAUAAU GGAGGAAACUCC CU UCAAGGACAUCGUCCGGG CUUCUGAA | | | 3963 |
| 729 | UUAUCCAU | G | GGAAUUAC | 3571 | UAAUUCCC GGAGGAAACUCC CU UCAAGGACAUCGUCCGGG AUGGAUAA | | | 3964 |
| 730 | UAUCCAUG | G | GAAUUACU | 3572 | GUAAUUCC GGAGGAAACUCC CU UCAAGGACAUCGUCCGGG CAUGGAUA | | | 3965 |
| 731 | AUCCAUGG | G | AAUUACAC | 3573 | UGUAAUUC GGAGGAAACUCC CU UCAAGGACAUCGUCCGGG CCAUGGAU | | | 3966 |
| 732 | UCCAUGGG | G | AAUUACAU | 3574 | AUGUAAUU GGAGGAAACUCC CU UCAAGGACAUCGUCCGGG CCCAUGGA | | | 3967 |
| 742 | AUUACAUA | G | CCUUAUCA | 3575 | GAUAAGGC GGAGGAAACUCC CU UCAAGGACAUCGUCCGGG UAUGUAAU | | | 3968 |
| 743 | UUACAUAG | G | CCUUAUCA | 2279 | UGAUAAGG GGAGGAAACUCC CU UCAAGGACAUCGUCCGGG CUAUGUAA | | | 3969 |
| 755 | UACACAUA | G | AAUUGCCC | 3576 | GGGCAAUU GGAGGAAACUCC CU UCAAGGACAUCGUCCGGG UAUUGUAA | | | 3970 |
| 760 | AUAGAAUU | G | CCCAGAAG | 2280 | CUUCUGGG GGAGGAAACUCC CU UCAAGGACAUCGUCCGGG AAUUCUAU | | | 3971 |
| 765 | AUUGCCCA | G | AAGAAAAG | 3577 | CUUUUCUU GGAGGAAACUCC CU UCAAGGACAUCGUCCGGG UGGGCAAU | | | 3972 |
| 768 | GCCCAGAA | G | AAAAGACU | 3578 | AGUCUUUU GGAGGAAACUCC CU UCAAGGACAUCGUCCGGG UUCUGGGC | | | 3973 |
| 773 | GAAGAAAA | G | ACUAACUG | 3579 | CAGUUAGU GGAGGAAACUCC CU UCAAGGACAUCGUCCGGG UUUUCUUC | | | 3974 |
| 781 | GACUAACU | G | UAAAUUAU | 2281 | AUAAUUUA GGAGGAAACUCC CU UCAAGGACAUCGUCCGGG AGUUAGUC | | | 3975 |

TABLE XII-continued

Human PKR Amberzyme and Substrate Sequence

| Pos | Substrate | Seq ID | Amberzyme | Seq ID |
|---|---|---|---|---|
| 790 | UAAAUUAU G AACAGUGU | 3580 | ACACUGUU GGAGGAAACUCC CU UCAAGGACAUCGUCCGGG AUAAUUUA | 3976 |
| 795 | UAUGAACA G UGUGCAUC | 2282 | GAUGCACA GGAGGAAACUCC CU UCAAGGACAUCGUCCGGG UGUUCAUA | 3977 |
| 797 | UGAACAGU G UGCAUCGG | 2283 | CCGAUGCA GGAGGAAACUCC CU UCAAGGACAUCGUCCGGG ACUGUUCA | 3978 |
| 799 | AACAGUGU G CAUCGGGG | 2284 | CCCCGAUG GGAGGAAACUCC CU UCAAGGACAUCGUCCGGG ACACUGUU | 3979 |
| 804 | UGUGCAUC G GGGUGCA | 3581 | UGCACCCC GGAGGAAACUCC CU UCAAGGACAUCGUCCGGG GAUGCACA | 3980 |
| 805 | GUGCAUCG G GGUGCAU | 3582 | AUGCACCC GGAGGAAACUCC CU UCAAGGACAUCGUCCGGG CGAUGCAC | 3981 |
| 806 | UGCAUCGG G GGUGCAUG | 3583 | CAUGCACC GGAGGAAACUCC CU UCAAGGACAUCGUCCGGG CCGAUGCA | 3982 |
| 807 | GCAUCGGG G GUGCAUGG | 3584 | CCAUGCAC GGAGGAAACUCC CU UCAAGGACAUCGUCCGGG CCCGAUGC | 3983 |
| 808 | CAUCGGGG G UGCAUGGG | 2285 | CCCAUGCA GGAGGAAACUCC CU UCAAGGACAUCGUCCGGG CCCCGAUG | 3984 |
| 810 | UCGGGGGU G CAUGGGCC | 2286 | GGCCCAUG GGAGGAAACUCC CU UCAAGGACAUCGUCCGGG ACCCCCGA | 3985 |
| 814 | GGGUGCAU G GGCCAGAA | 3585 | UUCUGGCC GGAGGAAACUCC CU UCAAGGACAUCGUCCGGG AUGCACCC | 3986 |
| 815 | GGUGCAUG G CCCAGAAG | 3586 | CUUCUGGC GGAGGAAACUCC CU UCAAGGACAUCGUCCGGG CAUGCACC | 3987 |
| 816 | GUGCAUGG G CCAGAAGG | 2287 | CCUUCUGG GGAGGAAACUCC CU UCAAGGACAUCGUCCGGG CCAUGCAC | 3988 |
| 820 | AUGGGCCA G AAGGAUUU | 3587 | AAAUCCUU GGAGGAAACUCC CU UCAAGGACAUCGUCCGGG UGGCCCAU | 3989 |
| 823 | GGCCAGAA G GAUUUCAU | 3588 | AUGAAAUC GGAGGAAACUCC CU UCAAGGACAUCGUCCGGG UUCUGGCC | 3990 |
| 824 | GCCAGAAC G AUUUCAUU | 3589 | AAUGAAAU GGAGGAAACUCC CU UCAAGGACAUCGUCCGGG CUUCUGGC | 3991 |
| 839 | UUAUAAAU G CAAAAUGG | 2288 | CCAUUUUG GGAGGAAACUCC CU UCAAGGACAUCGUCCGGG AUUUAUAA | 3992 |
| 846 | UGCAAAAU G GACAGAA | 3590 | UUCUGUCC GGAGGAAACUCC CU UCAAGGACAUCGUCCGGG AUUUUGCA | 3993 |
| 847 | GCAAAAUG G GACAGAAA | 3591 | UUUCUGUC GGAGGAAACUCC CU UCAAGGACAUCGUCCGGG CAUUUUGC | 3994 |
| 848 | CAAAAUGG G ACAGAAAG | 3592 | CUUUCUGU GGAGGAAACUCC CU UCAAGGACAUCGUCCGGG CCAUUUUG | 3995 |
| 852 | AUGGGACA G AAAGAAUA | 3593 | UAUUCUUU GGAGGAAACUCC CU UCAAGGACAUCGUCCGGG UGUCCCAU | 3996 |
| 856 | GACAGAAA G AAUAUAGU | 3594 | ACUAUAUU GGAGGAAACUCC CU UCAAGGACAUCGUCCGGG UUUCUGUC | 3997 |
| 863 | AGAAUAUA G UAUUGGUA | 2289 | UACCAAUA GGAGGAAACUCC CU UCAAGGACAUCGUCCGGG UAUAUUCU | 3998 |
| 868 | AUAGUAUU G GUACAGGU | 3595 | ACCUGUAC GGAGGAAACUCC CU UCAAGGACAUCGUCCGGG AAUACUAU | 3999 |
| 869 | UAGUAUUG G UACAGGUU | 2290 | AACCUGUA GGAGGAAACUCC CU UCAAGGACAUCGUCCGGG CAAUACUA | 4000 |
| 874 | UUGGUACA G GUUCUACU | 3596 | AGUAGAAC GGAGGAAACUCC CU UCAAGGACAUCGUCCGGG UGUACCAA | 4001 |
| 875 | UGGUACAG G UUCUACUA | 2291 | UAGUAGAA GGAGGAAACUCC CU UCAAGGACAUCGUCCGGG CUGUACCA | 4002 |
| 888 | ACUAAACA G GAAGCAAA | 3597 | UUUGCUUC GGAGGAAACUCC CU UCAAGGACAUCGUCCGGG UGUUUAGU | 4003 |
| 889 | CUAAACAG G AAGCAAAC | 3598 | UUUUGCUU GGAGGAAACUCC CU UCAAGGACAUCGUCCGGG CUGUUUAG | 4004 |
| 892 | AACAGGAA G CAAACAA | 2292 | UUGUUUUG GGAGGAAACUCC CU UCAAGGACAUCGUCCGGG UUCCUGUU | 4005 |
| 903 | AAACAAUU G GCCGCUAA | 3599 | UUAGCGGC GGAGGAAACUCC CU UCAAGGACAUCGUCCGGG AAUUGUUU | 4006 |
| 904 | AACAAUUG G CCGCUAAA | 2293 | UUUAGCGG GGAGGAAACUCC CU UCAAGGACAUCGUCCGGG CAAUUGUU | 4007 |
| 907 | AAUUGGCC G CUAAACUU | 2294 | AAGUUUAG GGAGGAAACUCC CU UCAAGGACAUCGUCCGGG GGCCAAUU | 4008 |
| 916 | CUAAACUU G CAUAUCUU | 2295 | AAGAUAUG GGAGGAAACUCC CU UCAAGGACAUCGUCCGGG AAGUUUAG | 4009 |
| 927 | UAUCUUCA G AUAUUAUC | 3600 | GAUAAUAU GGAGGAAACUCC CU UCAAGGACAUCGUCCGGG UGAAGAUA | 4010 |
| 937 | UAUUAUCA G AAGAAACC | 3601 | GGUUUCUU GGAGGAAACUCC CU UCAAGGACAUCGUCCGGG UGAUAAUA | 4011 |
| 940 | UAUCAGAA G AAACCUCA | 3602 | UGAGGUUU GGAGGAAACUCC CU UCAAGGACAUCGUCCGGG UUCUGAUA | 4012 |
| 949 | AAACCUCA G UGAAAUCU | 2296 | AGAUUUCA GGAGGAAACUCC CU UCAAGGACAUCGUCCGGG UGAGGUUU | 4013 |
| 951 | ACCUCAGU G AAAUCUGA | 3603 | UCAGAUUU GGAGGAAACUCC CU UCAAGGACAUCGUCCGGG ACUGAGGU | 4014 |
| 958 | UGAAAUCU G ACUACCUG | 3604 | CAGGUAGU GGAGGAAACUCC CU UCAAGGACAUCGUCCGGG AGAUUUCA | 4015 |
| 966 | GACUACCU G UCCCUCUG | 2297 | CCAGAGGA GGAGGAAACUCC CU UCAAGGACAUCGUCCGGG AGGUAGUC | 4016 |
| 973 | UGUCCCUCU G GUUCUUUU | 3605 | AAAAGAAC GGAGGAAACUCC CU UCAAGGACAUCGUCCGGG AGAGGACA | 4017 |
| 974 | GUCCUCUG G UUCUUUUG | 2298 | CAAAAGAA GGAGGAAACUCC CU UCAAGGACAUCGUCCGGG CAGAGGAC | 4018 |
| 982 | GUUCUUUU G CUACUACG | 2299 | CGUAGUAG GGAGGAAACUCC CU UCAAGGACAUCGUCCGGG AAAAGAAC | 4019 |
| 990 | GCUACUAC G UGUGACUC | 2300 | GACUCACA GGAGGAAACUCC CU UCAAGGACAUCGUCCGGG GUAGUAGC | 4020 |
| 992 | UACUACGU G UGAGUCCC | 2301 | GGGACUCA GGAGGAAACUCC CU UCAAGGACAUCGUCCGGG ACGUAGUA | 4021 |
| 994 | CUACUGUGU G AGUCCCAA | 3606 | UUGGGACU GGAGGAAACUCC CU UCAAAGGACUCGUCCGGG ACACGUAG | 4022 |
| 996 | ACGUGUGA G UCCCAAAG | 2302 | CUUUGGGA GGAGGAAACUCC CU UCAAAGGACUCGUCCGGG UCACACGU | 4023 |
| 1004 | GUCCCAAA G CAACUCUU | 2303 | AAGAGUUG GGAGGAAACUCC CU UCAAGGACAUCGUCCGGG UUUGGGAC | 4024 |
| 1015 | ACUCUUUA G UGACCAGC | 2304 | GCUGGUCA GGAGGAAACUCC CU UCAAGGACAUCGUCCGGG UAAAGAGU | 4025 |
| 1017 | UCUUUAGU G ACCAGCAC | 3607 | GUGCUGGU GGAGGAAACUCC CU UCAAGGACAUCGUCCGGG ACUAAAGA | 4026 |
| 1022 | AGUGACCA G CACACUCG | 2305 | CGAGUGUG GGAGGAAACUCC CU UCAAGGACAUCGUCCGGG UGGUCACU | 4027 |
| 1030 | GCACACUC G CUUCUGAA | 2306 | UUCAGAAG GGAGGAAACUCC CU UCAAGGACAUCGUCCGGG GAGUGUGC | 4028 |
| 1036 | UCGCUUCU G AAUCAUCA | 3608 | UGAUGAUU GGAGGAAACUCC CU UCAAGGACAUCGUCCGGG AGAAGCGA | 4029 |
| 1048 | CAUCAUCU G AAGGUGAC | 3609 | GUCACCUU GGAGGAAACUCC CU UCAAGGACAUCGUCCGGG AGAUGAUG | 4030 |
| 1051 | CAUCUGAA G GUGACUUC | 3610 | GAAGUCAC GGAGGAAACUCC CU UCAAGGACAUCGUCCGGG UUCAGAUG | 4031 |
| 1052 | AUCUGAAG G UGACUUCU | 2307 | AGAAGUCA GGAGGAAACUCC CU UCAAGGACAUCGUCCGGG CUUCAGAU | 4032 |
| 1054 | CUGAAGGU G ACUUCUCA | 3611 | UGAGAAGU GGAGGAAACUCC CU UCAAUGACAUCGUCCGGG ACCUUCAG | 4033 |
| 1063 | ACUUCUCA G CAGAUACA | 2308 | UGUAUCUG GGAGGAAACUCC CU UCAAGGACAUCGUCCGGG UGAGAAGU | 4034 |
| 1066 | UCUCAGCA G AUACAUCA | 3612 | UGAUGUAU GGAGGAAACUCC CU UCAAGGACAUCGUCCGGG UGCUGAGA | 4035 |
| 1075 | AUACAUCA G AGAUAAAU | 3613 | AUUUAUCU GGAGGAAACUCC CU UCAAGGACAUCGUCCGGG UGAUGUAU | 4036 |
| 1077 | ACAUCAGA G AUAAAUUC | 3614 | GAAUUUAU GGAGGAAACUCC CU UCAAGGACAUCGUCCGGG UCUGAUGU | 4037 |
| 1091 | UUCUAACA G UUCAGUU | 2309 | AACUGUCA GGAGGAAACUCC CU UCAAGGACAUCGUCCGGG UGUUAGAA | 4038 |
| 1093 | CUAACAGU G ACAGUUUA | 3615 | UAAACUGU GGAGGAAACUCC CU UCAAGGACAUCGUCCGGG ACUGUUAG | 4039 |
| 1097 | CAGUGACA G UUUAAACA | 2310 | UGUUUAAA GGAGGAAACUCC CU UCAAGGACAUCGUCCGGG UGUCACUG | 4040 |
| 1106 | UUUAAACA G UUCUUCGU | 2311 | ACGAAGAA GGAGGAAACUCC CU UCAAGGACAUCGUCCGGG UGUUUAAA | 4041 |
| 1113 | AUUUCUUC G UUGCUUAU | 2312 | AUAAGCAA GGAGGAAACUCC CU UCAAGGACAUCGUCCGGG GAAGAACU | 4042 |
| 1116 | UCUUCCUU G CUUAUGAA | 2313 | UUCAUAAG GGAGGAAACUCC CU UCAAGGACAUCGUCCGGG AACGAAGA | 4043 |
| 1122 | UUGCUUAU G AAUGGCUC | 3616 | AGACCAUU GGAGGAAACUCC CU UCAAGGACAUCGUCCGGG AUAAGCAA | 4044 |
| 1126 | UUAUGAAU G GUCUCAGA | 3617 | UCUGAGAC GGAGGAAACUCC CU UCAAGGACAUCGUCCGGG AUUCAUAA | 4045 |
| 1127 | UAUGAAUG G UCUCAGAA | 2314 | UUCCUGAGA GGAGGAAACUCC CU UCAAGGACAUCGUCCGGG CAUUCAUA | 4046 |
| 1133 | UGGUCUCA G AAAUAAUC | 3618 | GAUUAUUU GGAGGAAACUCC CU UCAAGGACAUCGUCCGGG UGAGACCA | 4047 |
| 1145 | UAAUCAAA G AAGGCAA | 3619 | UUGCCUUC GGAGGAAACUCC CU UCAAGGACAUCGUCCGGG UUUGAUUA | 4048 |
| 1146 | AAUCAAAG G AAGGCAAA | 3620 | UUUGCCUU GGAGGAAACUCC CU UCAAGGACAUCGUCCGGG CUUUGAUU | 4049 |
| 1149 | CAAAGGAA G GCAAAAAG | 3621 | CUUUUUGC GGAGGAAACUCC CU UCAAGGACAUCGUCCGGG UUCCUUUG | 4050 |

TABLE XII-continued

Human PKR Amberzyme and Substrate Sequence

| Pos | Substrate | Seq ID | Amberzyme | Seq ID |
|---|---|---|---|---|
| 1150 | AAAGGAAG G CAAAAAGA | 2315 | UCUUUUUG GGAGGAAACUCC CU UCAAGGACAUCGUCCGGG CUUCCUUU | 4051 |
| 1157 | GGCAAAAA G AUCUUUGG | 3622 | CCAAAGAU GGAGGAAACUCC CU UCAAGGACAUCGUCCGGG UUUUUGCC | 4052 |
| 1164 | AGAUCUUU G CACCCAG | 3623 | CUGGGUGC GGAGGAAACUCC CU UCAAGGACAUCGUCCGGG AAAGAUCU | 4053 |
| 1165 | GAUCUUUG G CACCCAGA | 2316 | UCUGGGUG GGAGGAAACUCC CU UCAAGGACAUCGUCCGGG CAAAGAUC | 4054 |
| 1172 | GGCACCCA G AUUUGACC | 3624 | GGUCAAAU GGAGGAAACUCC CU UCAAGGACAUCGUCCGGG UGGGUGCC | 4055 |
| 1177 | CCAGAUUU G ACCUUCCU | 3625 | AGGAAGGU GGAGGAAACUCC CU UCAAGGACAUCGUCCGGG AAAUCUGG | 4056 |
| 1186 | ACCUUCCU G ACAUGAAA | 3626 | UUUCAUGU GGAGGAAACUCC CU UCAAGGACAUCGUCCGGG AGGAAGGU | 4057 |
| 1191 | CCUGACAU G AAAGAAAC | 3627 | GUUUCUUU GGAGGAAACUCC CU UCAAGGACAUCGUCCGGG AUGUCAGG | 4058 |
| 1195 | ACAUGAAA G AAACAAAG | 3628 | CUUUGUUU GGAGGAAACUCC CU UCAAGGACAUCGUCCGGG UUUCAUGU | 4059 |
| 1203 | GAAACAAA G UAUACUGU | 2317 | ACAGUAUA GGAGGAAACUCC CU UCAAGGACAUCGUCCGGG UUUGUUUC | 4060 |
| 1210 | AGUAUACU G UGGACAAG | 2318 | CUUGUCCA GGAGGAAACUCC CU UCAAGGACAUCGUCCGGG AGUAUACU | 4061 |
| 1212 | UAUACUGU G GACAAGAG | 3629 | CUCUUGUC GGAGGAAACUCC CU UCAAGGACAUCGUCCGGG ACAGUAUA | 4062 |
| 1213 | AUACUGUG G ACAAGAGG | 3630 | CCUCUUGU GGAGGAAACUCC CU UCAAGGACAUCGUCCGGG CACAGUAU | 4063 |
| 1218 | GUGGACAA G AGGUUUGG | 3631 | CCAAACCU GGAGGAAACUCC CU UCAAGGACAUCGUCCGGG UUGUCCAC | 4064 |
| 1220 | GGACAAGA G GUUUGGCA | 3632 | UGCCAAAC GGAGGAAACUCC CU UCAAGGACAUCGUCCGGG UCUUGUCC | 4065 |
| 1221 | GACAAGAG G UUUGGCAU | 2319 | AUGCCAAA GGAGGAAACUCC CU UCAAGGACAUCGUCCGGG CUCUUGUC | 4066 |
| 1225 | AGAGGUUU G GCAUGGAU | 3633 | AUCCAUGC GGAGGAAACUCC CU UCAAGGACAUCGUCCGGG AAACCUCU | 4067 |
| 1226 | GAGGUUUG G CAUGGAUU | 2320 | AAUCCAUG GGAGGAAACUCC CU UCAAGGACAUCGUCCGGG CAAACCUC | 4068 |
| 1230 | UUUGGCAU G GAUUUUAA | 3634 | UUAAAAUC GGAGGAAACUCC CU UCAAGGACAUCGUCCGGG AUGCCAAA | 4069 |
| 1231 | UUCGGAUC G AUUUUAAA | 3635 | UUUAAAAU GGAGGAAACUCC CU UCAAGGACAUCGUCCGGG CAUGCCAA | 4070 |
| 1240 | AUUUUAAA G AAAUACAA | 3636 | UUCUAUUU GGAGGAAACUCC CU UCAAGGACAUCGUCCGGG UUUAAAAU | 4071 |
| 1246 | AAGAAAUA G AAUUAAUU | 3637 | AAUUAAUU GGAGGAAACUCC CU UCAAGGACAUCGUCCGGG UAUUUCUU | 4072 |
| 1255 | AAUUAAUU G CUCAGGU | 3638 | ACCUGAGC GGAGGAAACUCC CU UCAAGGACAUCGUCCGGG AAUUAAUU | 4073 |
| 1256 | AUUAAUUG G CUCAGGUG | 2321 | CACCUGAG GGAGGAAACUCC CU UCAAGGACAUCGUCCGGG CAAUUAAU | 4074 |
| 1261 | UUGGCUCA G UGGAUUUG | 3639 | AAAUCCAC GGAGGAAACUCC CU UCAAGGACAUCGUCCGGG UGAGCCAA | 4075 |
| 1262 | UGGCUCAC G UGGAUUUG | 2322 | CAAAUCCA GGAGGAAACUCC CU UCAAGGACAUCGUCCGGG CUGAGCCA | 4076 |
| 1264 | GCUCAGGU G AUUUGGC | 3640 | GCCAAAUC GGAGGAAACUCC CU UCAAGGACAUCGUCCGGG ACCUGAGC | 4077 |
| 1265 | CUCAGGUG G AUUUGGCC | 3641 | GGCCAAAU GGAGGAAACUCC CU UCAAGGACAUCGUCCGGG CACCUGAG | 4078 |
| 1270 | GUGGAUUU G GCCAAGUU | 3642 | AACUUGGC GGAGGAAACUCC CU UCAAGGACAUCGUCCGGG AAAUCCAC | 4079 |
| 1271 | UGGAUUUG G CCAAGUUU | 2323 | AAACUUGG GGAGGAAACUCC CU UCAAGGACAUCGUCCGGG CAAAUCCA | 4080 |
| 1276 | UUGGCCAA G UUUCAAA | 2324 | UUUGAAAA GGAGGAAACUCC CU UCAAGGACAUCGUCCGGG UUGGCCAA | 4081 |
| 1285 | UUUUCAAA G CAAAACAC | 2325 | GUGUUUUG GGAGGAAACUCC CU UCAAGGACAUCGUCCGGG UUUGAAAA | 4082 |
| 1295 | AAAACACA G AAUUGACG | 3643 | CGUCAAUU GGAGGAAACUCC CU UCAAGGACAUCGUCCGGG UGUGUUUU | 4083 |
| 1300 | ACAGAAUU G ACGGAAAG | 3644 | CUUUCCGU GGAGGAAACUCC CU UCAAGGACAUCGUCCGGG AAUUCUGU | 4084 |
| 1303 | GAAUUGAC G GAAAGACU | 3645 | AGUCUUUC GGAGGAAACUCC CU UCAAGGACAUCGUCCGGG GUCAAUUC | 4085 |
| 1304 | AAUUGACG G AAAGACUU | 3646 | AACUCUUU GGAGGAAACUCC CU UCAAGGACAUCGUCCGGG CGUCAAUU | 4086 |
| 1308 | GACGGAAA G ACUUACGU | 3647 | ACGUAAGU GGAGGAAACUCC CU UCAAGGACAUCGUCCGGG UUUCCGUC | 4087 |
| 1315 | AGACUUAC G UUAUUAAA | 2326 | UUUAAUAA GGAGGAAACUCC CU UCAAGGACAUCGUCCGGG GUAAGUCU | 4088 |
| 1325 | UAUUAAAC G UGUUAAAU | 2327 | AUUUAACA GGAGGAAACUCC CU UCAAGGACAUCGUCCGGG GUUUAAUA | 4089 |
| 1327 | UUAAACGU G UUAAAUAU | 2328 | AUAUUUAA GGAGGAAACUCC CU UCAAGGACAUCGUCCGGG ACGUUUAA | 4090 |
| 1342 | AUAAUAAC G AAGGCGA | 3648 | CGCCUUCU GGAGGAAACUCC CU UCAAGGACAUCGUCCGGG GUUAUUAU | 4091 |
| 1344 | AAUAACGA G AAGGCGGA | 3649 | UCCGCCUU GGAGGAAACUCC CU UCAAGGACAUCGUCCGGG UCGUUAUU | 4092 |
| 1347 | AACGAGAA G GCGGAGCG | 3650 | CGCUCCGC GGAGGAAACUCC CU UCAAGGACAUCGUCCGGG UUCUCGUU | 4093 |
| 1348 | ACGAGAAG G CGGAGCGU | 2329 | ACGCUCCG GGAGGAAACUCC CU UCAAGGACAUCGUCCGGG CUUCUCGU | 4094 |
| 1350 | GAGAAGGC G AGCGUGA | 3651 | UCACGCUC GGAGGAAACUCC CU UCAAGGACAUCGUCCGGG GCCUUCUC | 4095 |
| 1351 | AGAAGGCG G AGCGUGAA | 3652 | UUCACGCU GGAGGAAACUCC CU UCAAGGACAUCGUCCGGG CGCCUUCU | 4096 |
| 1353 | AAGGCGGA G CGUGAAGU | 2330 | ACUUCACG GGAGGAAACUCC CU UCAAGGACAUCGUCCGGG UCCGCCUU | 4097 |
| 1355 | GGCGGAGC G UGAAGUAA | 2331 | UUACUUCA GGAGGAAACUCC CU UCAAGGACAUCGUCCGGG CCUCCGCC | 4098 |
| 1357 | CGGAGCGU G AAGUAAAA | 3653 | UUUUACUU GGAGGAAACUCC CU UCAAGGACAUCGUCCGGG ACGCUCCG | 4099 |
| 1360 | AGCGUGAA G UAAAAGCA | 2332 | UGCUUUUA GGAGGAAACUCC CU UCAAGGACAUCGUCCGGG UUCACGCU | 4100 |
| 1366 | AAGUAAAA G CAUUGGCA | 2333 | UGCCAAUG GGAGGAAACUCC CU UCAAGGACAUCGUCCGGG UUUUACUU | 4101 |
| 1371 | AAAGCAUU G GCAAAACU | 3654 | AGUUUUGC GGAGGAAACUCC CU UCAAGGACAUCGUCCGGG AAUGCUUU | 4102 |
| 1372 | AAGCAUUG G CAAAACUU | 2334 | AAGUUUUG GGAGGAAACUCC CU UCAAGGACAUCGUCCGGG CAAUGCUU | 4103 |
| 1381 | CAAAACUU G AUCAUGUA | 3655 | UACAUGAU GGAGGAAACUCC CU UCAAGGACAUCGUCCGGG AAGUUUUG | 4104 |
| 1387 | UUGAUCAU G UAAAUAUU | 2335 | AAUAUUUA GGAGGAAACUCC CU UCAAGGACAUCGUCCGGG AUGAUCAA | 4105 |
| 1396 | UAAAUAUU G UUCACUAC | 2336 | GUAGUGAA GGAGGAAACUCC CU UCAAGGACAUCGUCCGGG AAUAUUUA | 4106 |
| 1408 | ACUACAAU G CCUGUUGG | 3656 | CCAACAGC GGAGGAAACUCC CU UCAAGGACAUCGUCCGGG AUUGUAGU | 4107 |
| 1409 | CUACAAUG G CCUGUUGGG | 2337 | CCCAACAG GGAGGAAACUCC CU UCAAGGACAUCGUCCGGG CAUUGUAC | 4108 |
| 1412 | CAAUGGCU G UUGGGAUC | 2338 | CAUCCCAA GGAGGAAACUCC CU UCAAGGACAUCGUCCGGG AGCCAUUG | 4109 |
| 1415 | UGGCUGUU G GAUGGAU | 3657 | AUCCAUCC GGAGGAAACUCC CU UCAAGGACAUCGUCCGGG AACAGCCA | 4110 |
| 1416 | GGCUGUUG G AUGGAUU | 3658 | AAUCCAUC GGAGGAAACUCC CU UCAAGGACAUCGUCCGGG CAACAGCC | 4111 |
| 1417 | GCUGUUGG G AUGGAUGG | 3659 | AAAUCCAU GGAGGAAACUCC CU UCAAGGACAUCGUCCGGG CCAACAGC | 4112 |
| 1420 | GUUGGGAU G GAUUUGAU | 3660 | AUCAAAUC GGAGGAAACUCC CU UCAAGGACAUCGUCCGGG AUCCCAAC | 4113 |
| 1421 | UUGGGAUG G AUUUGAUU | 3661 | AAUCAAAU GGAGGAAACUCC CU UCAAGGACAUCGUCCGGG CAUCCCAA | 4114 |
| 1426 | AUCCAUUU G AUUAUGAU | 3662 | AUCAUAAU GGAGGAAACUCC CU UCAAGGACAUCGUCCGGG AAAUCCAU | 4115 |
| 1432 | UUGAUUAU G AUCCUGAG | 3663 | CUCAGGAU GGAGGAAACUCC CU UCAAGGACAUCGUCCGGG AUAAUCAA | 4116 |
| 1438 | AUGAUCCU G AGACCAGU | 3664 | ACUGGUCU GGAGGAAACUCC CU UCAAGGACAUCGUCCGGG AGGAUCAU | 4117 |
| 1440 | GAUCCUGA G ACCAGUGA | 3665 | UCACUGGU GGAGGAAACUCC CU UCAAGGACAUCGUCCGGG UCAGGAUC | 4118 |
| 1445 | UGAGACCA G UGAUGAUU | 2339 | AAUCAUCA GGAGGAAACUCC CU UCAAGGACAUCGUCCGGG UGGUCUCA | 4119 |
| 1447 | AGACCAGU G AUGAUUCU | 3666 | AGAAUCAU GGAGGAAACUCC CU UCAAGGACAUCGUCCGGG ACUGGUCU | 4120 |
| 1450 | CCAGUGAU G AUUCUCUU | 3667 | AAGAGAAU GGAGGAAACUCC CU UCAAGGACAUCGUCCGGG AUCACUGG | 4121 |
| 1459 | AUUCUCUU G AGCAGUGA | 3668 | ACUGCUCU GGAGGAAACUCC CU UCAAGGACAUCGUCCGGG AAGAGAAU | 4122 |
| 1461 | UCUCUUGA G AGCAGUGA | 3669 | UCACUGCU GGAGGAAACUCC CU UCAAGGACAUCGUCCGGG UCAAGAGA | 4123 |
| 1463 | UCUUGAGA G CAGUGAUU | 2340 | AAUCACUG GGAGGAAACUCC CU UCAAGGACAUCGUCCGGG UCUCAAGA | 4124 |
| 1466 | UGAGAUCA G UGAUUAUG | 2341 | CAUAAUCA GGAGGAAACUCC CU UCAAGGACAUCGUCCGGG UGCUCUCA | 4125 |

TABLE XII-continued

Human PKR Amberzyme and Substrate Sequence

| Pos | Substrate | Seq ID | Amberzyme | Seq ID |
|---|---|---|---|---|
| 1468 | AGAGCAGU G AUUAUGAU | 3670 | AUCAUAAU GGAGGAAACUCC CU UCAAGGACAUCGUCCGGG ACUGCUCU | 4126 |
| 1474 | GUGAUUAU G AUCCUGAG | 3671 | CUCAGGAU GGAGGAAACUCC CU UCAAGGACAUCGUCCGGG AUAAUCAC | 4127 |
| 1480 | AUGAUCCU G AGAACAGC | 3672 | GCUGUUCU GGAGGAAACUCC CU UCAAGGACAUCGUCCGGG AGGAUCAU | 4128 |
| 1482 | GAUCCUGA G AACAGCAA | 3673 | UUGCUGUU GGAGGAAACUCC CU UCAAGGACAUCGUCCGGG UCAGGAUC | 4129 |
| 1487 | UGAGAACA G CAAAAAUA | 2342 | UAUUUUUG GGAGGAAACUCC CU UCAAGGACAUCGUCCGGG UGUUCUCA | 4130 |
| 1496 | CAAAAAUA G UUCAAGGU | 2343 | ACCUUGAA GGAGGAAACUCC CU UCAAGGACAUCGUCCGGG UAUUUUUG | 4131 |
| 1502 | UAGUUCAA G GUCAAAGA | 3674 | UCUUUGAC GGAGGAAACUCC CU UCAAGGACAUCGUCCGGG UUGAACUA | 4132 |
| 1503 | AGUUCAAG G UCAAAGAC | 2344 | GUCUUUGA GGAGGAAACUCC CU UCAAGGACAUCGUCCGGG CUUGAACU | 4133 |
| 1509 | AGGUCAAA G ACUAAGUG | 3675 | CACUUAGU GGAGGAAACUCC CU UCAAGGACAUCGUCCGGG UUUGACCU | 4134 |
| 1515 | AAGACUAA G UGCCUUUU | 2345 | AAAAGGCA GGAGGAAACUCC CU UCAAGGACAUCGUCCGGG UUAGUCUU | 4135 |
| 1517 | GACUAAGU G CCUUUUCA | 2346 | UGAAAAGG GGAGGAAACUCC CU UCAAGGACAUCGUCCGGG ACUUAGUC | 4136 |
| 1533 | AUCCAAAU G GAAUUCUG | 3676 | CAGAAUUC GGAGGAAACUCC CU UCAAGGACAUCGUCCGGG AUUUGGAU | 4137 |
| 1534 | UCCAAAUG G AAUUCUGU | 3677 | ACAGAAUU GGAGGAAACUCC CU UCAAGGACAUCGUCCGGG CAUUUGUA | 4138 |
| 1541 | GGAAUUCU G UGAUAAAG | 2347 | CUUUAUCA GGAGGAAACUCC CU UCAAGGACAUCGUCCGGG AGAAUUCC | 4139 |
| 1543 | AAUUCUGU G AUAAAGGG | 3678 | CCCUUUAU GGAGGAAACUCC CU UCAAGGACAUCGUCCGGG ACAGAAUU | 4140 |
| 1549 | GUGAUAAA G GUACCUUG | 3679 | CAAGGUCC GGAGGAAACUCC CU UCAAGGACAUCGUCCGGG UUUAUCAC | 4141 |
| 1550 | UGAUAAAG G UACCUUGG | 3680 | CCAAGGUC GGAGGAAACUCC CU UCAAGGACAUCGUCCGGG CUUUAUCA | 4142 |
| 1551 | GAUAAAGG G UACCUUGA | 3681 | UCCAAGGU GGAGGAAACUCC CU UCAAGGACAUCGUCCGGG CCUUUAUC | 4143 |
| 1557 | GGGACCUU G AACAAUG | 3682 | CAUUGUUC GGAGGAAACUCC CU UCAAGGACAUCGUCCGGG AAGGUCCC | 4144 |
| 1558 | UGACCUUG G AACAAUGG | 3683 | CCAUUGUU GGAGGAAACUCC CU UCAAGGACAUCGUCCGGG CAAGGUCC | 4145 |
| 1565 | GGAACAAU G GAUUGAAA | 3684 | UUUCAAUC GGAGGAAACUCC CU UCAAGGACAUCGUCCGGG AUUGUUCC | 4146 |
| 1566 | GAACAAUG G AUUGAAAA | 3685 | UUUUCAAU GGAGGAAACUCC CU UCAAGGACAUCGUCCGGG CAUUGUUC | 4147 |
| 1570 | AAUGGAUU G AAAAAGA | 3686 | UCUUUUUU GGAGGAAACUCC CU UCAAGGACAUCGUCCGGG AAUCCAUU | 4148 |
| 1577 | UGAAAAAA G AAGAGGCG | 3687 | CGCCUCUU GGAGGAAACUCC CU UCAAGGACAUCGUCCGGG UUUUUUCA | 4149 |
| 1580 | AAAAAGAA G AGGCGAGA | 3688 | UCUCGCCU GGAGGAAACUCC CU UCAAGGACAUCGUCCGGG UUCUUUUU | 4150 |
| 1582 | AAAGAAGA G CGAGAAA | 3689 | UUUCUCGC GGAGGAAACUCC CU UCAAGGACAUCGUCCGGG UCUUCUUU | 4151 |
| 1583 | AAGAAGAG G CGAGAAAC | 2348 | GUUUCUCG GGAGGAAACUCC CU UCAAGGACAUCGUCCGGG CUCUUCUU | 4152 |
| 1585 | GAAGAGGC G AGAAACUA | 3690 | UAGUUUCU GGAGGAAACUCC CU UCAAGGACAUCGUCCGGG GCCUCUUC | 4153 |
| 1587 | AGAGGCGA G AAACUAGA | 3691 | UCUAGUUU GGAGGAAACUCC CU UCAAGGACAUCGUCCGGG UCGCCUCU | 4154 |
| 1594 | AGAAACUA G ACAAAGUU | 3692 | AACUUUGU GGAGGAAACUCC CU UCAAGGACAUCGUCCGGG UAGUUUCU | 4155 |
| 1600 | UAGACAAA G UUUUGGCU | 2349 | AGCCAAAA GGAGGAAACUCC CU UCAAGGACAUCGUCCGGG UUUGUCUA | 4156 |
| 1605 | AAAGUUUU G GCUUUGGA | 3693 | UCCAAAGC GGAGGAAACUCC CU UCAAGGACAUCGUCCGGG AAAACUUU | 4157 |
| 1606 | AAGUUUUG G CUUUGGAA | 2350 | UUCCAAAG GGAGGAAACUCC CU UCAAGGACAUCGUCCGGG CAAAACUU | 4158 |
| 1611 | UUGGCUUU G GAACUCUU | 3694 | AAGAGUUC GGAGGAAACUCC CU UCAAGGACAUCGUCCGGG AAAGCCAA | 4159 |
| 1612 | UGGCUUUG G AACUCUUU | 3695 | AAAGAGUU GGAGGAAACUCC CU UCAAGGACAUCGUCCGGG CAAAGCCA | 4160 |
| 1621 | AACUCUUU G AACAAAUA | 3696 | UAUUUGUU GGAGGAAACUCC CU UCAAGGACAUCGUCCGGG AAAGAGUU | 4161 |
| 1636 | UAACAAAA G GGGUGGAU | 3697 | AUCCACCC GGAGGAAACUCC CU UCAAGGACAUCGUCCGGG UUUUGUUA | 4162 |
| 1637 | AACAAAAC G GUGGAUU | 3698 | AAUCCACC GGAGGAAACUCC CU UCAAGGACAUCGUCCGGG CUUUUGUU | 4163 |
| 1638 | ACAAAAGG G UGGAUUA | 3699 | UAAUCCAC GGAGGAAACUCC CU UCAAGGACAUCGUCCGGG CCUUUUGU | 4164 |
| 1639 | CAAAAGGG G UGGAUUAU | 2351 | AUAAUCCA GGAGGAAACUCC CU UCAAGGACAUCGUCCGGG CCCUUUUG | 4165 |
| 1641 | AAAGGGGU G GAUUAUA | 3700 | AUAUAAUC GGAGGAAACUCC CU UCAAGGACAUCGUCCGGG ACCCCUUU | 4166 |
| 1642 | AAGGGGUG G AUUAUAUA | 3701 | UAUAUAAU GGAGGAAACUCC CU UCAAGGACAUCGUCCGGG CACCCCUU | 4167 |
| 1673 | AAUUCAUA G AGAUCUUA | 3702 | UAAGAUCU GGAGGAAACUCC CU UCAAGGACAUCGUCCGGG UAUGAAUU | 4168 |
| 1675 | UUCAUAGA G AUCUUAAG | 3703 | CUUAAGAU GGAGGAAACUCC CU UCAAGGACAUCGUCCGGG UCUAUGAA | 4169 |
| 1683 | GAUCUUAA G CCAAGUAA | 2352 | UUACUUGG GGAGGAAACUCC CU UCAAGGACAUCGUCCGGG UUAAGAUC | 4170 |
| 1688 | UAAGCCAA G UAAUAUAU | 2353 | AUAUAUUA GGAGGAAACUCC CU UCAAGGACAUCGUCCGGG UUGGCUUA | 4171 |
| 1702 | UAUUCUUA G UAGAUACA | 2354 | UGUAUCUA GGAGGAAACUCC CU UCAAGGACAUCGUCCGGG UAAGAAUA | 4172 |
| 1705 | UCUUAGUA G AUACAAAA | 3704 | UUUUGUAU GGAGGAAACUCC CU UCAAGGACAUCGUCCGGG UACUAAGA | 4173 |
| 1717 | CAAAACAA G UAAAGAUU | 2355 | AAUCUUUA GGAGGAAACUCC CU UCAAGGACAUCGUCCGGG UUGUUUUG | 4174 |
| 1722 | CAAGUAAA G AUUGGAGA | 3705 | UCUCCAAU GGAGGAAACUCC CU UCAAGGACAUCGUCCGGG UUUACUUG | 4175 |
| 1726 | UAAAGAUU G GACACUUU | 3706 | AAAGUCUC GGAGGAAACUCC CU UCAAGGACAUCGUCCGGG AAUCUUUA | 4176 |
| 1727 | AAAGAUUC G AGACUUUG | 3707 | CAAAGUCU GGAGGAAACUCC CU UCAAGGACAUCGUCCGGG CAAUCUUU | 4177 |
| 1729 | AGAUUGGA G ACUUUGGA | 3708 | UCCAAAGU GGAGGAAACUCC CU UCAAGGACAUCGUCCGGG UCCAAUCU | 4178 |
| 1735 | GAGACUUU G ACUUGUAA | 3709 | UACAAGUC GGAGGAAACUCC CU UCAAGGACAUCGUCCGGG AAAGUCUC | 4179 |
| 1736 | AGACUUUG G ACUUGUAA | 3710 | UUACAAGU GGAGGAAACUCC CU UCAAGGACAUCGUCCGGG CAAAGUCU | 4180 |
| 1741 | UUGGACUU G UAACAUCU | 2356 | ACAUGUUA GGAGGAAACUCC CU UCAAGGACAUCGUCCGGG AAGUCCAA | 4181 |
| 1752 | ACAUCUCU G AAAAAUGA | 3711 | UCAUUUUU GGAGGAAACUCC CU UCAAGGACAUCGUCCGGG AGAGAUGU | 4182 |
| 1759 | UGAAAAAU G AUGGAAAG | 3712 | CUUUCCAU GGAGGAAACUCC CU UCAAGGACAUCGUCCGGG AUUUUUCA | 4183 |
| 1762 | AAAAUGAU G GAAAGCGA | 3713 | UCGCUUUC GGAGGAAACUCC CU UCAAGGACAUCGUCCGGG AUCAUUUU | 4184 |
| 1763 | AAAUGAUG G AAAGCGAA | 3714 | UUCGCUUU GGAGGAAACUCC CU UCAAGGACAUCGUCCGGG CAUCAUUU | 4185 |
| 1767 | GAUGGAAA G CGAACAAG | 2357 | CUUGUUCG GGAGGAAACUCC CU UCAAGGACAUCGUCCGGG UUUCCAUC | 4186 |
| 1769 | UGGAAAGC G AACAAGGA | 3715 | UCCUUGUG GGAGGAAACUCC CU UCAAGGACAUCGUCCGGG GCUUUCCA | 4187 |
| 1775 | GCGAACAA G GAGUAAGG | 3716 | CCUUACUC GGAGGAAACUCC CU UCAAGGACAUCGUCCGGG UUGUUCGC | 4188 |
| 1776 | CGAACAAG G ACUAAGGG | 3717 | CCCUUACU GGAGGAAACUCC CU UCAAGGACAUCGUCCGGG CUUGUUCG | 4189 |
| 1778 | AACAAGGA G UAAGGGAA | 2358 | UUCCCUUA GGAGGAAACUCC CU UCAAGGACAUCGUCCGGG UCCUUGUU | 4190 |
| 1782 | AGGAGUAA G GGAACUUU | 3718 | AAAGUUCC GGAGGAAACUCC CU UCAAGGACAUCGUCCGGG UUACUCCU | 4191 |
| 1783 | GGAGUAAG G GAACUUUG | 3719 | CAAAGUUC GGAGGAAACUCC CU UCAAGGACAUCGUCCGGG CUUACUCC | 4192 |
| 1784 | GAGUAAGG G AACUUUGC | 3720 | GCAAAGUU GGAGGAAACUCC CU UCAAGGACAUCGUCCGGG CCUUACUC | 4193 |
| 1791 | GGAACUUU G CGAUACAU | 2359 | AUGUAUCG GGAGGAAACUCC CU UCAAGGACAUCGUCCGGG AAAGUUCC | 4194 |
| 1793 | AACUUUGC G AUACAUGA | 3721 | UCAUGUAU GGAGGAAACUCC CU UCAAGGACAUCGUCCGGG GCAAAGUU | 4195 |
| 1800 | CGAUACAU G AGCCCAGA | 3722 | UCUGGGCU GGAGGAAACUCC CU UCAAGGACAUCGUCCGGG AUGUAUCG | 4196 |
| 1802 | AUACAUGA G CCCAGAAC | 2360 | GUUCUGGG GGAGGAAACUCC CU UCAAGGACAUCGUCCGGG UCAUGUAU | 4197 |
| 1807 | UGAGCCCA G AACAGAUU | 3723 | AAUCUGUU GGAGGAAACUCC CU UCAAGGACAUCGUCCGGG UGGGCUCA | 4198 |
| 1812 | CCAGAACA G AUUUCUUC | 3724 | GAAGAAAU GGAGGAAACUCC CU UCAAGGACAUCGUCCGGG UGUUCUGG | 4199 |
| 1821 | AUUUCUUC G CAAGACUA | 2361 | UAGUCUUG GGAGGAAACUCC CU UCAAGGACAUCGUCCGGG GAAGAAAU | 4200 |

TABLE XII-continued

Human PKR Amberzyme and Substrate Sequence

| Pos | Substrate | Seq ID | Amberzyme | Seq ID |
|---|---|---|---|---|
| 1825 | CUUCGCAA G ACUAUGGA | 3725 | UCCAUAGU GGAGGAAACUCC CU UCAAGGACAUCGUCCGGG UUGCGAAG | 4201 |
| 1831 | AAGACUAU G GAAAGGAA | 3726 | UUCCUUUC GGAGGAAACUCC CU UCAAGGACAUCGUCCGGG AUAGUCUU | 4202 |
| 1832 | AGACUAUG G AAAGGAAG | 3727 | CUUCCUUU GGAGGAAACUCC CU UCAAGGACAUCGUCCGGG CAUAGUCU | 4203 |
| 1836 | UAUGGAAA G AAGUGGA | 3728 | UCCACUUC GGAGGAAACUCC CU UCAAGGACAUCGUCCGGG UUUCCAUA | 4204 |
| 1837 | AUGGAAAC G AAGUGGAC | 3729 | GUCCACUU GGAGGAAACUCC CU UCAAGGACAUCGUCCGGG CUUUCCAU | 4205 |
| 1840 | GAAAGGAA G UGGACCUC | 2362 | GAGGUCCA GGAGGAAACUCC CU UCAAGGACAUCGUCCGGG UUCCUUUC | 4206 |
| 1842 | AAGGAAGU G GACCUCUA | 3730 | UAGAGGUC GGAGGAAACUCC CU UCAAGGACAUCGUCCGGG ACUUCCUU | 4207 |
| 1843 | AGGAAGUG G ACCUCUAC | 3731 | GUAGAGGU GGAGGAAACUCC CU UCAAGGACAUCGUCCGGG CACUUCCU | 4208 |
| 1852 | ACCUCUAC G CUUUGGGG | 2363 | CCCCAAAG GGAGGAAACUCC CU UCAAGGACAUCGUCCGGG GUAGAGGU | 4209 |
| 1857 | UACGCUUU G GGCUAAUU | 3732 | AUUAGCCC GGAGGAAACUCC CU UCAAGGACAUCGUCCGGG AAAGCGUA | 4210 |
| 1858 | ACGCUUUG G GCUAAUUC | 3733 | AAUUAGCC GGAGGAAACUCC CU UCAAGGACAUCGUCCGGG CAAAGCGU | 4211 |
| 1859 | CGCUUUGG G CUAAUUC | 3734 | GAAUUAGC GGAGGAAACUCC CU UCAAGGACAUCGUCCGGG CCAAAGCG | 4212 |
| 1860 | GCUUUGGG G CUAAUUCU | 2364 | AGAAUUAG GGAGGAAACUCC CU UCAAGGACAUCGUCCGGG CCCAAAGC | 4213 |
| 1870 | UAAUUCUU G CUGAACUU | 2365 | AAGUUCAG GGAGGAAACUCC CU UCAAGGACAUCGUCCGGG AAGAAUUA | 4214 |
| 1873 | UUCUUGCU G AACUUCUU | 3735 | AAGAAGUU GGAGGAAACUCC CU UCAAGGACAUCGUCCGGG AGCAACAA | 4215 |
| 1885 | UUCUUCAU G UAUGUGAC | 2366 | GUCACAUA GGAGGAAACUCC CU UCAAGGACAUCGUCCGGG AUGAAGAA | 4216 |
| 1889 | UCAUGUAU G UGACACUG | 2367 | CAGUGUCA GGAGGAAACUCC CU UCAAGGACAUCGUCCGGG AUACAUGA | 4217 |
| 1891 | AUGUAUGU G ACACUGCU | 3736 | AGCAGUGU GGAGGAAACUCC CU UCAAGGACAUCGUCCGGG ACAUACAU | 4218 |
| 1897 | GUGACACU G CUUUUGAA | 2368 | UUCAAAAG GGAGGAAACUCC CU UCAAGGACAUCGUCCGGG AGUGUCAC | 4219 |
| 1903 | CUGCUUUU G AAACAUCA | 3737 | UGAUGUUU GGAGGAAACUCC CU UCAAGGACAUCGUCCGGG AAAAGCAG | 4220 |
| 1914 | ACAUCAAA G UUUUUCAC | 2369 | GUGAAAAA GGAGGAAACUCC CU UCAAGGACAUCGUCCGGG UUUGAUGU | 4221 |
| 1924 | UUUUCACA G ACCUACGG | 3738 | CCGUAGGU GGAGGAAACUCC CU UCAAGGACAUCGUCCGGG UGUGAAAA | 4222 |
| 1931 | AGACCUAC G GAUGGCA | 3739 | UGCCAUCC GGAGGAAACUCC CU UCAAGGACAUCGUCCGGG GUAGGUCU | 4223 |
| 1932 | GACCUACG G AUGGCAU | 3740 | AUGCCAUC GGAGGAAACUCC CU UCAAGGACAUCGUCCGGG CGUAGGUC | 4224 |
| 1933 | ACCUACGG G AUGGCAUC | 3741 | GAUGCCAU GGAGGAAACUCC CU UCAAGGACAUCGUCCGGG CCGUAGGU | 4225 |
| 1936 | UACGGGAU G GCAUCAUC | 3742 | GAUGAUGC GGAGGAAACUCC CU UCAAGGACAUCGUCCGGG AUCCCGUA | 4226 |
| 1937 | ACGGGAUG G CAUCAUCU | 2370 | AGAUGAUG GGAGGAAACUCC CU UCAAGGACAUCGUCCGGG CAUCCCGU | 4227 |
| 1948 | UCAUCUCA G AUAUAUUU | 3743 | AAAUAUAU GGAGGAAACUCC CU UCAAGGACAUCGUCCGGG UGAGAUGA | 4228 |
| 1957 | AUAUAUUU G AUAAAAA | 3744 | UUUUUAU GGAGGAAACUCC CU UCAAGGACAUCGUCCGGG AAAUAUAU | 4229 |
| 1966 | AUAAAAAA G AAAAAACU | 3745 | AGUUUUUU GGAGGAAACUCC CU UCAAGGACAUCGUCCGGG UUUUUUAU | 4230 |
| 1983 | CUUCUACA G AAAUUACU | 3746 | AGUAAUUU GGAGGAAACUCC CU UCAAGGACAUCGUCCGGG UGUAGAAG | 4231 |
| 1998 | CUCUCAAA G AAACCUGA | 3747 | UCAGGUUU GGAGGAAACUCC CU UCAAGGACAUCGUCCGGG UUUGAGAG | 4232 |
| 2005 | AGAAACCU G AGGAUCCA | 3748 | UCGAUCCU GGAGGAAACUCC CU UCAAGGACAUCGUCCGGG AGGUUUCU | 4233 |
| 2007 | AAACCUGA G GAUCGACC | 3749 | GGUCGAUC GGAGGAAACUCC CU UCAAGGACAUCGUCCGGG UCAGGUUU | 4234 |
| 2008 | AACCUGAG G AUCCACCU | 3750 | ACGUCGAU GGAGGAAACUCC CU UCAAGGACAUCGUCCGGG CUCAGGUU | 4235 |
| 2012 | UGAGGAUC G ACCUAACA | 3751 | UGUUAGGU GGAGGAAACUCC CU UCAAGGACAUCGUCCGGG GAUCCUCA | 4236 |
| 2026 | ACACAUCU G AAAUACUA | 3752 | UAGUAUUU GGAGGAAACUCC CU UCAAGGACAUCGUCCGGG AGAUGUGU | 4237 |
| 2036 | AAUACUAA G GACCUUGA | 3753 | UCAAGGUC GGAGGAAACUCC CU UCAAGGACAUCGUCCGGG UUAGUAUU | 4238 |
| 2037 | AUACUAAG G ACCUUGAC | 3754 | GUCAAGGU GGAGGAAACUCC CU UCAAGGACAUCGUCCGGG CUUAGUAU | 4239 |
| 2043 | AGGACCUU G ACUGUGUG | 3755 | CACACAGU GGAGGAAACUCC CU UCAAGGACAUCGUCCGGG AAGGUCCU | 4240 |
| 2047 | CCUUGACU G UGUGGAAG | 2371 | CUUCCACA GGAGGAAACUCC CU UCAAGGACAUCGUCCGGG AGUCAAGG | 4241 |
| 2049 | UUGACUGU G UGGAAGAA | 2372 | UUCUUCCA GGAGGAAACUCC CU UCAAGGACAUCGUCCGGG ACAGUCAA | 4242 |
| 2051 | GACUGUGU G GAAGAAAA | 3756 | UUUUCUUC GGAGGAAACUCC CU UCAAGGACAUCGUCCGGG ACACAGUC | 4243 |
| 2052 | ACUGUGUG G AAGAAAAG | 3757 | CUUUUCUU GGAGGAAACUCC CU UCAAGGACAUCGUCCGGG CACACAGU | 4244 |
| 2055 | GUGUGGAA G AAAAGCCC | 3758 | GGGCUUUU GGAGGAAACUCC CU UCAAGGACAUCGUCCGGG UUCCACAC | 4245 |
| 2060 | GAAGAAAA G CCCAGAGA | 2373 | UCUCUGGG GGAGGAAACUCC CU UCAAGGACAUCGUCCGGG UUUUCUUC | 4246 |
| 2065 | AAAGCCCA G AGAAAAU | 3759 | AUUUUUCU GGAGGAAACUCC CU UCAAGGACAUCGUCCGGG UGGGCUUU | 4247 |
| 2067 | AGCCCAGA G AAAAAUGA | 3760 | UCAUUUUU GGAGGAAACUCC CU UCAAGGACAUCGUCCGGG UCUGGGCU | 4248 |
| 2074 | AGAAAAAU G AACGACAC | 3761 | GUGUCGUU GGAGGAAACUCC CU UCAAGGACAUCGUCCGGG AUUUUUCU | 4249 |
| 2078 | AAAUGAAC G ACACACAU | 3762 | AUGUGUGU GGAGGAAACUCC CU UCAAGGACAUCGUCCGGG GUUCAUUU | 4250 |
| 2087 | ACACACAU G UUAGAGCC | 2374 | GGCUCUAA GGAGGAAACUCC CU UCAAGGACAUCGUCCGGG AUGUGUGU | 4251 |
| 2091 | ACAUGUUA G AGCCCUUC | 3763 | GAAGGGCU GGAGGAAACUCC CU UCAAGGACAUCGUCCGGG UAACAUGU | 4252 |
| 2093 | AUGUUAGA G CCCUUCUG | 2375 | CAGAAGGG GGAGGAAACUCC CU UCAAGGACAUCGUCCGGG UCUAACAU | 4253 |
| 2101 | GCCCUUCU G AAAAGUA | 3764 | UACUUUUU GGAGGAAACUCC CU UCAAGGACAUCGUCCGGG AGAAGGGC | 4254 |
| 2107 | CUGAAAAA G UAUCCGC | 2376 | GCAGGAUA GGAGGAAACUCC CU UCAAGGACAUCGUCCGGG UUUUUCAG | 4255 |
| 2114 | AGUAUCCU G CUUCUGAU | 2377 | AUCAGAAG GGAGGAAACUCC CU UCAAGGACAUCGUCCGGG AGGAUACU | 4256 |
| 2120 | CUGCUUCU G AUAUGCAG | 3765 | CUGCAUAU GGAGGAAACUCC CU UCAAGGACAUCGUCCGGG AGAAGCAG | 4257 |
| 2125 | UCUGAUAU G CAGUUUUC | 2378 | GAAAACUG GGAGGAAACUCC CU UCAAGGACAUCGUCCGGG AUAUCAGA | 4258 |
| 2128 | GAUAUGCA G UUUCCUU | 2379 | AAGGAAAA GGAGGAAACUCC CU UCAAGGACAUCGUCCGGG UGCAUAUC | 4259 |
| 2153 | UAAAAUCU G CUAGGGAA | 2380 | UUCCCUAC GGAGGAAACUCC CU UCAAGGACAUCGUCCGGG AGAUUUUA | 4260 |
| 2157 | AUCUGCUA G GAAUAUC | 3766 | GAUAUUCC GGAGGAAACUCC CU UCAAGGACAUCGUCCGGG UAGCACAU | 4261 |
| 2158 | UCUGCUAC G GAAUAUCA | 3767 | UGAUAUUC GGAGGAAACUCC CU UCAAGGACAUCGUCCGGG CUAGCAGA | 4262 |
| 2159 | CUGCUAGG G AAUAUCAA | 3768 | UUGAUAUU GGAGGAAACUCC CU UCAAGGACAUCGUCCGGG CCUAGCAG | 4263 |
| 2170 | UAUCAUA G AUAUUUAC | 3769 | GUAAAUAU GGAGGAAACUCC CU UCAAGGACAUCGUCCGGG UAUUGAUA | 4264 |
| 2192 | AUUUUAAU G UUUCCUUU | 2381 | AAAGGAAA GGAGGAAACUCC CU UCAAGGACAUCGUCCGGG AUUAAAAU | 4265 |
| 2230 | AUCUUUCU G CAGAAGAU | 2382 | UGUUUCUG GGAGGAAACUCC CU UCAAGGACAUCGUCCGGG AGAAAGAU | 4266 |
| 2233 | UUUCUGCA G AAACAGAA | 3770 | UUCUGUUU GGAGGAAACUCC CU UCAAGGACAUCGUCCGGG UGCAGAAA | 4267 |
| 2239 | CAGAAACA G AAAGGUUU | 3771 | AAACCUUU GGAGGAAACUCC CU UCAAGGACAUCGUCCGGG UGUUUCUG | 4268 |
| 2243 | AAGAGAAA G GUUUCUU | 3772 | AAGAAAAC GGAGGAAACUCC CU UCAAGGACAUCGUCCGGG UUUCUGUU | 4269 |
| 2244 | ACAGAAAC G UUUUCUUC | 2383 | GAAGAAAA GGAGGAAACUCC CU UCAAGGACAUCGUCCGGG CUUUCUGU | 4270 |
| 2258 | UUCUUUUU G CUUCAAAA | 2384 | UUUUGAAG GGAGGAAACUCC CU UCAAGGACAUCGUCCGGG AAAAAGAA | 4271 |
| 2292 | UUUUCCU G GCUCAUCU | 3773 | AGAUGAGC GGAGGAAACUCC CU UCAAGGACAUCGUCCGGG AGGAAAAA | 4272 |
| 2293 | UUUUCCUG G CUCAUCUC | 2385 | GAGAUGAG GGAGGAAACUCC CU UCAAGGACAUCGUCCGGG CAGGAAAA | 4273 |
| 2326 | UUUUUAAA G ACAGAGUC | 3774 | GACUCUGU GGAGGAAACUCC CU UCAAGGACAUCGUCCGGG UUUAAAAA | 4274 |
| 2330 | UAAAGACA G AGUCUCGC | 3775 | CGCAGACU GGAGGAAACUCC CU UCAAGGACAUCGUCCGGG UGUCUUUA | 4275 |

TABLE XII-continued

Human PKR Amberzyme and Substrate Sequence

| Pos | Substrate | | | Seq ID | Amberzyme | | | Seq ID |
|---|---|---|---|---|---|---|---|---|
| 2332 | AAGACAGA | G | UCUCGCUC | 2386 | GAGCGAGA | GGAGGAAACUCC CU UCAAGGACAUCGUCCGGG | UCUGUCUU | 4276 |
| 2337 | ACAGUCUC | G | CUCUGUUG | 2387 | CAACAGAG | GGAGGAAACUCC CU UCAAGGACAUCGUCCGGG | GAGACUCU | 4277 |
| 2342 | CUCGCUCU | G | UUGCCCAG | 2388 | CUGGGCAA | GGAGGAAACUCC CU UCAAGGACAUCGUCCGGG | AGAGCGAG | 4278 |
| 2345 | GCUCUGUU | G | CCCAGGCU | 2389 | AUCCUGGG | GGAGGAAACUCC CU UCAAGGACAUCGUCCGGG | AACAGAGC | 4279 |
| 2350 | GUUGCCCA | G | GCUGGAGU | 3776 | ACUCCAGC | GGAGGAAACUCC CU UCAAGGACAUCGUCCGGG | UGGGCAAC | 4280 |
| 2351 | UUGCCCAG | G | CUGGAGUG | 2390 | CACUCCAG | GGAGGAAACUCC CU UCAAGGACAUCGUCCGGG | CUGGGCAA | 4281 |
| 2354 | CCCAGGCU | G | GAGUGCAA | 3777 | UUGCACUC | GGAGGAAACUCC CU UCAAGGACAUCGUCCGGG | AGCCUGGG | 4282 |
| 2355 | CCAGGCUG | G | AGUGCAAU | 3778 | AUUGCACU | GGAGGAAACUCC CU UCAAGGACAUCGUCCGGG | CAGCCUGG | 4283 |
| 2357 | AGGCUGGA | G | UGCAAUGA | 2391 | UCAUUGCA | GGAGGAAACUCC CU UCAAGGACAUCGUCCGGG | UCCAGCCU | 4284 |
| 2359 | GCUGGAGU | G | CAAUGACA | 2392 | UGUCAUUG | GGAGGAAACUCC CU UCAAGGACAUCGUCCGGG | ACUCCAGC | 4285 |
| 2364 | AGUGCAAU | G | ACACAGUC | 3779 | GACUGUGU | GGAGGAAACUCC CU UCAAGGACAUCGUCCGGG | AUUGCACU | 4286 |
| 2370 | AUGACACA | G | UCUUGGCU | 2393 | AGCCAAGA | GGAGGAAACUCC CU UCAAGGACAUCGUCCGGG | UGUGUCAU | 4287 |
| 2375 | ACAGUCUU | G | GCUCACUG | 3780 | CAGUGAGC | GGAGGAAACUCC CU UCAAGGACAUCGUCCGGG | AAGACUGU | 4288 |
| 2376 | CAGUCUUG | G | CUCACUGC | 2394 | GCAGUGAG | GGAGGAAACUCC CU UCAAGGACAUCGUCCGGG | CAAGACUG | 4289 |
| 2383 | GGCUCACU | G | CAACUUCU | 2395 | AGAAGUUG | GGAGGAAACUCC CU UCAAGGACAUCGUCCGGG | AGUGAGCC | 4290 |
| 2392 | CAACUUCU | G | CCUCUUGG | 2396 | CCAAGAGG | GGAGGAAACUCC CU UCAAGGACAUCGUCCGGG | AGAAGUUG | 4291 |
| 2399 | UGCCUCUU | G | GGUUCAAG | 3781 | CUUGAACC | GGAGGAAACUCC CU UCAAGGACAUCGUCCGGG | AAGAGGCA | 4292 |
| 2400 | GCCUCUUG | G | GUUCAAGU | 3782 | ACUUGAAC | GGAGGAAACUCC CU UCAAGGACAUCGUCCGGG | CAAGAGGC | 4293 |
| 2401 | CCUCUUGG | G | UUCAAGUG | 2397 | CACUUGAA | GGAGGAAACUCC CU UCAAGGACAUCGUCCGGG | CCAAGAGG | 4294 |
| 2407 | GGGUUCAA | G | UGAUUCUC | 2398 | GAGAAUCA | GGAGGAAACUCC CU UCAAGGACAUCGUCCGGG | UUGAACCC | 4295 |
| 2409 | GUUCAAGU | G | AUUCUCCU | 3783 | AGGAGAAU | GGAGGAAACUCC CU UCAAGGACAUCGUCCGGG | ACUUGAAC | 4296 |
| 2418 | AUUCUCCU | G | CCUCAGCC | 2399 | GGCUGAGG | GGAGGAAACUCC CU UCAAGGACAUCGUCCGGG | AGGAGAAU | 4297 |
| 2424 | CUGCCUCA | G | CCUCCUGA | 2400 | UCAGGAGG | GGAGGAAACUCC CU UCAAGGACAUCGUCCGGG | UGAGGCAG | 4298 |
| 2431 | AGCCUCCU | G | AGUAGCUG | 3784 | CAGCUACU | GGAGGAAACUCC CU UCAAGGACAUCGUCCGGG | AGGAGGCU | 4299 |
| 2433 | CCUCCUGA | G | UAGCUGGA | 2401 | UCCAGCUA | GGAGGAAACUCC CU UCAAGGACAUCGUCCGGG | UCAGGAGG | 4300 |
| 2436 | CCUGAGUA | G | CUGGAUUA | 2402 | UAAUCCAG | GGAGGAAACUCC CU UCAAGGACAUCGUCCGGG | UACUCAGG | 4301 |
| 2439 | GAGUAGCU | G | GAUUACAG | 3785 | CUGUAAUC | GGAGGAAACUCC CU UCAAGGACAUCGUCCGGG | AUCUACUC | 4302 |
| 2440 | AGUACCUG | G | AUUACAGG | 3786 | CCUGUAAU | GGAGGAAACUCC CU UCAAGGACAUCGUCCGGG | CAGCUACU | 4303 |
| 2447 | GGAUUACA | G | GCAUGUGC | 3787 | GCACAUGC | GGAGGAAACUCC CU UCAAGGACAUCGUCCGGG | UGUAAUCC | 4304 |
| 2448 | GAUUACAG | G | CAUGUGCC | 2403 | GGCACAUG | GGAGGAAACUCC CU UCAAGGACAUCGUCCGGG | CUGUAAUC | 4305 |
| 2452 | ACAGGCAU | G | UGCCACCC | 2404 | GGGUGGCA | GGAGGAAACUCC CU UCAAGGACAUCGUCCGGG | AUGCCUGU | 4306 |
| 2454 | AGGCAUGU | G | CCACCCAC | 2405 | GUGGGUGG | GGAGGAAACUCC CU UCAAGGACAUCGUCCGGG | ACAUGCCU | 4307 |
| 2476 | UAAUUUUU | G | UGUUUUUA | 2406 | UAAAAACA | GGAGGAAACUCC CU UCAAGGACAUCGUCCGGG | AAAAAUUA | 4308 |
| 2478 | AUUUUUGU | G | UUUUUAAU | 2407 | AUUAAAAA | GGAGGAAACUCC CU UCAAGGACAUCGUCCGGG | ACAAAAAU | 4309 |
| 2490 | UUAAUAAA | G | ACAGGGUU | 3788 | AACCCUGU | GGAGGAAACUCC CU UCAAGGACAUCGUCCGGG | UUUAUUAA | 4310 |
| 2494 | UAAAGACA | G | GGUUUCAC | 3789 | GUGAAACC | GGAGGAAACUCC CU UCAAGGACAUCGUCCGGG | UGUCUUUA | 4311 |
| 2495 | AAAGACAG | G | GUUUCACC | 3790 | GGUGAAAC | GGAGGAAACUCC CU UCAAGGACAUCGUCCGGG | CUGUCUUU | 4312 |
| 2496 | AAGACAGG | G | UUUCACCA | 2408 | UGGUGAAA | GGAGGAAACUCC CU UCAAGGACAUCGUCCGGG | CCUGUCUU | 4313 |
| 2506 | UUCACCAU | G | UUGGCCAG | 2409 | CUGGCCAA | GGAGGAAACUCC CU UCAAGGACAUCGUCCGGG | AUGGUGAA | 4314 |
| 2509 | ACCAUGUU | G | GCCAGGCU | 3791 | AGCCUGGC | GGAGGAAACUCC CU UCAAGGACAUCGUCCGGG | AACAUGGU | 4315 |
| 2510 | CCAUGUUG | G | CCAGGCUC | 2410 | CAGCCUGG | GGAGGAAACUCC CU UCAAGGACAUCGUCCGGG | CAACAUGG | 4316 |
| 2514 | GUUGGCCA | G | GCUGGUCU | 3792 | AGACCAGC | GGAGGAAACUCC CU UCAAGGACAUCGUCCGGG | UGGCCAAC | 4317 |
| 2515 | UUGGCCAG | G | CUGGUCUC | 2411 | GAGACCAG | GGAGGAAACUCC CU UCAAGGACAUCGUCCGGG | CUGGCCAA | 4318 |
| 2518 | GCCAGGCU | G | GUCUCAAA | 3793 | UUUGAGAC | GGAGGAAACUCC CU UCAAGGACAUCGUCCGGG | AGCCUGGC | 4319 |
| 2519 | CCAGGCUG | G | UCUCAAAC | 2412 | GUUUGAGA | GGAGGAAACUCC CU UCAAGGACAUCGUCCGGG | CAGCCUGG | 4320 |
| 2532 | AAACUCCU | G | ACCUCAAG | 2794 | CUUGAGGU | GGAGGAAACUCC CU UCAAGGACAUCGUCCGGG | AGGAGUUU | 4321 |
| 2540 | GACCUCAA | G | UAAUCCAC | 2413 | GUGGAUUA | GGAGGAAACUCC CU UCAAGGACAUCGUCCGGG | UUGAGGUC | 4322 |
| 2551 | AUCCACCU | G | CCUCGGCC | 2414 | GGCCGAGG | GGAGGAAACUCC CU UCAAGGACAUCGUCCGGG | AGGUGGAU | 4323 |
| 2556 | CCUGCCUC | G | GCCUCCCA | 3795 | UGGGAGGC | GGAGGAAACUCC CU UCAAGGACAUCGUCCGGG | GAGGCAGG | 4324 |
| 2557 | CUGCCUCG | G | CCUCCCAA | 2415 | UUGGGAGG | GGAGGAAACUCC CU UCAAGGACAUCGUCCGGG | CGAGGCAG | 4325 |
| 2567 | CUCCCAAA | G | UGCUGGGA | 2416 | UCCCAGCA | GGAGGAAACUCC CU UCAAGGACAUCGUCCGGG | UUUGGGAG | 4326 |
| 2569 | CCCAAGU | G | CUGGGAUU | 2417 | AAUCCCAG | GGAGGAAACUCC CU UCAAGGACAUCGUCCGGG | ACUUGGG | 4327 |
| 2572 | AAAGUGCU | G | GGAUUACA | 3796 | UGUAAUCC | GGAGGAAACUCC CU UCAAGGACAUCGUCCGGG | AGCACUUU | 4328 |
| 2573 | AAGUGCUG | G | GAUUACAG | 3797 | CUGUAAUC | GGAGGAAACUCC CU UCAAGGACAUCGUCCGGG | CAGCACUU | 4329 |
| 2574 | AGUGCUGG | G | AUUACAGG | 3798 | CCUGUAAU | GGAGGAAACUCC CU UCAAGGACAUCGUCCGGG | CCAGCACU | 4330 |
| 2581 | GGAUUACA | G | GAUGAGCC | 3799 | GCUCAUCC | GGAGGAAACUCC CU UCAAGGACAUCGUCCGGG | UGUAAUCC | 4331 |
| 2582 | GAUUACAG | G | GAUGAGCC | 3800 | GGCUCAUC | GGAGGAAACUCC CU UCAAGGACAUCGUCCGGG | CUGUAAUC | 4332 |
| 2583 | AUUACAGG | G | AUGAGCCA | 3801 | UGGCUCAU | GGAGGAAACUCC CU UCAAGGACAUCGUCCGGG | CCUGUAAU | 4333 |
| 2586 | ACAGGGAU | G | AGCCACCG | 3802 | CGGUGGCU | GGAGGAAACUCC CU UCAAGGACAUCGUCCGGG | AUCCCUGU | 4334 |
| 2588 | AGGGAUGA | G | CCACCGCG | 2418 | CGCGGUGG | GGAGGAAACUCC CU UCAAGGACAUCGUCCGGG | UCAUCCCU | 4335 |
| 2594 | GAGCCACC | G | CGCCCACC | 2419 | GCUGGGCG | GGAGGAAACUCC CU UCAAGGACAUCGUCCGGG | GGUGGCUC | 4336 |
| 2596 | GCCACCGC | G | CCCAGCCU | 2420 | AGGCUGGG | GGAGGAAACUCC CU UCAAGGACAUCGUCCGGG | GCGUGGCG | 4337 |
| 2601 | CGCGCCCA | G | CCUCUCU | 2421 | AGAUGAGG | GGAGGAAACUCC CU UCAAGGACAUCGUCCGGG | UGGGCGCG | 4338 |
| 2614 | AUCUCUUU | G | UUCUAAAG | 2422 | CUUUAGAA | GGAGGAAACUCC CU UCAAGGACAUCGUCCGGG | AAAGAGAU | 4339 |
| 2622 | CUUCUAAA | G | AUGCAAAA | 3803 | UUUUCCAU | GGAGGAAACUCC CU UCAAGGACAUCGUCCGGG | UUUAGAAC | 4340 |
| 2625 | CUAAAGAU | G | CAAAAACC | 3804 | GGUUUUUC | GGAGGAAACUCC CU UCAAGGACAUCGUCCGGG | AUCUUUAG | 4341 |
| 2626 | UAAAGAUC | G | AAAAACCA | 3805 | UGGUUUUU | GGAGGAAACUCC CU UCAAGGACAUCGUCCGGG | CAUCUUUA | 4342 |
| 2664 | CUAUUAAU | G | AAUCAAUC | 3806 | GAUUCAUU | GGAGGAAACUCC CU UCAAGGACAUCGUCCGGG | AUUAAUAC | 4343 |
| 2702 | UUUCUACC | G | CUUUUAGG | 2423 | CCUAAAAG | GGAGGAAACUCC CU UCAAGGACAUCGUCCGGG | GGUAGAAA | 4344 |
| 2709 | CGCUUUUA | G | GCCAAAAA | 3807 | UUUUUGGC | GGAGGAAACUCC CU UCAAGGACAUCGUCCGGG | UAAAAGCG | 4345 |
| 2710 | GCUUUUAG | G | CCAAAAAA | 2424 | UUUUUUGG | GGAGGAAACUCC CU UCAAGGACAUCGUCCGGG | CUAAAAGC | 4346 |
| 2721 | AAAAAAAU | G | UAAGAUCG | 2425 | CGAUCUUA | GGAGGAAACUCC CU UCAAGGACAUCGUCCGGG | AUUUUUUU | 4347 |
| 2725 | AAAUGUAA | G | AUCGUUCU | 3808 | AGAACGAU | GGAGGAAACUCC CU UCAAGGACAUCGUCCGGG | UUACAUUU | 4348 |
| 2729 | GUAAGAUC | G | UUCUCGC | 2426 | GCAGAGAA | GGAGGAAACUCC CU UCAAGGACAUCGUCCGGG | GAUCUUAC | 4349 |
| 2736 | CGUUCUCU | G | CCUCACAU | 2427 | AUGUGAGG | GGAGGAAACUCC CU UCAAGGACAUCGUCCGGG | AGAGAACG | 4350 |

TABLE XII-continued

Human PKR Amberzyme and Substrate Sequence

| Pos | Substrate | Seq ID | Amberzyme | Seq ID |
|---|---|---|---|---|
| 2746 | CUCACAUA G CUUACAAG | 2428 | CUUGUAAG GGAGGAAACUCC CU UCAAGGACAUCGUCCGGG UAUGUGAG | 4351 |
| 2754 | GCUUACAA G CCAGCUGG | 2429 | CCAGCUGG GGAGGAAACUCC CU UCAAGGACAUCGUCCGGG UUGUAAGC | 4352 |
| 2758 | ACAAGCCA G CUGGAGAA | 2430 | UUCUCCAG GGAGGAAACUCC CU UCAAGGACAUCGUCCGGG UGGCUUGU | 4353 |
| 2761 | AGCCAGCU G GAGAAAUA | 3809 | UAUUUCU GGAGGAAACUCC CU UCAAGGACAUCGUCCGGG AGCUGGCU | 4354 |
| 2762 | GCCAGCUG G AGAAAUAU | 3810 | AUAUUUCU GGAGGAAACUCC CU UCAAGGACAUCGUCCGGG CAGCUGGC | 4355 |
| 2764 | CAGCUGGA G AAAUAUGG | 3811 | CCAUAUUU GGAGGAAACUCC CU UCAAGGACAUCGUCCGGG UCCAGCUG | 4356 |
| 2771 | AGAAAUAU G UACUCAU | 3812 | AUGAGUAC GGAGGAAACUCC CU UCAAGGACAUCGUCCGGG AUAUUUCU | 4357 |
| 2772 | GAAAUAUG U UACUCAUU | 2431 | AAUGAGUA GGAGGAAACUCC CU UCAAGGACAUCGUCCGGG CAUAUUUC | 4358 |
| 2796 | AAAAAAAA G UGAUGUAC | 2432 | GGACAUCA GGAGGAAACUCC CU UCAAGGACAUCGUCCGGG UUUUUUUU | 4359 |
| 2798 | AAAAAAGU G AUGUACAA | 3813 | UUGUACAU GGAGGAAACUCC CU UCAAGGACAUCGUCCGGG ACUUUUUU | 4360 |

Input Sequence = NM_002759. Cut Site = G/.
Arm Length = 8. Core Sequence = GGAGGAAACUCC CU UCAAGGACAUCGUCCGGG NM_002759 (Homo sapiens protein kinase, interferon-inducible double stranded RNA dependent (PRKR), mRNA.; 2808 bp)

TABLE XIII

Human IKK-gamma and PKR Nucleic Acid and Target molecules

| Gene | Pos | Target | Seq ID | RPI# | Enzymatic Nucleic Acid | Seq ID |
|---|---|---|---|---|---|---|
| PKR | 563 | UUUACAUUUCAAGUU | 7771 | 24072 | $a_s a_s c_s u_s$guacUGauGaggccguuaggccGaaAuguaaaB | 7884 |
| PKR | 571 | UCAAGUUAUAAUAGA | 7772 | 24073 | $u_s c_s u_s a_s$uuacUGAuGaggccguuaggccGaaAacuugaB | 7885 |
| PKR | 644 | GCCAAAUUAGCUGUU | 7773 | 24074 | $a_s a_s c_s a_s$gcucUGAuGaggccguuaggccGaaAuuuggcB | 7886 |
| PKR | 645 | CCAAAUUAGCUGUUG | 7774 | 24075 | $c_s a_s a_s c_s$agccUGAuGaggccguuaggccGaaAauuuggB | 7887 |
| PKR | 1259 | UUGGCUCAGGUGG | 7775 | 24076 | $c_s c_s a_s c_s$cucUGAuGaggccguuaggccGaaAgccaaB | 7888 |
| PKR | 1259 | AUUGGCUCAGGUGGA | 7776 | 24077 | $u_s c_s c_s a_s$cccuUGAuGaggccguuaggccGaaAgccaauB | 7889 |
| PKR | 1538 | UGGAAUUCUGUGA | 7777 | 24078 | $u_s c_s a_s$agcUGAuGaggccguuaggccGaaAuuccaB | 7890 |
| PKR | 1538 | AUGGAAUUCUGUGAU | 7778 | 24079 | $a_s u_s c_s a_s$cagcUGAuGaggccguuaggccGaaAuuccauB | 7891 |
| PKR | 1678 | AGAGAUCUUAAGC | 7779 | 24080 | $g_s c_s u_s$aacUGAuGaggccguuaggccgaaAucucuB | 7892 |
| PKR | control | GACGAUUGCAAUC | 7780 | 24081 | $g_s a_s u_s$gcUGAuGacgccguuaggcgGaaAucgucB | 7893 |
| PKR | control | ACACCGUUGGAUCGC | 7781 | 24082 | $g_s c_s g_s a_s$uccUAGuGacgccguuaggcgGaaAlcguguB | 7894 |
| PKR | 764 | UUGCCCAGAAGAA | 7782 | 24153 | $u_s c_s u_s$uccUGAuGaggccguuaggccGaaAlgcaaB | 7895 |
| PKR | 1540 | GGAAUUCUGUGAUAA | 7783 | 24154 | $u_s u_s a_s u_s$caccUGAuGaggccguuaggccGaaAlaauuccB | 7896 |
| PKR | 1679 | GAGAUCUUAAGCC | 7784 | 24155 | $g_s c_s u_s$acUGAuGaggccguuaggccGaaAlaucucB | 7897 |
| PKR | 1679 | AGAGAUCUUAAGCCA | 7785 | 24156 | $u_s g_s c_s$uuacUGAuGaggccguuaggccGaaAlaucucuB | 7898 |
| PKR | Control | AGUGGCAUACAUG | 7786 | 24157 | $c_s a_s u_s g_s$uacUAGuGacgccguuaggcgGaaAlccaguB | 7899 |
| PKR | Control | CAUUCGCUAAAUGAG | 7787 | 24158 | $c_s u_s c_s a_s$uuucUAGuGacgccguuaggcgGaaAlcgaaugB | 7900 |
| PKR | 1348 | GAGAAGGCGGAGC | 7788 | 24210 | $g_s c_s u_s c_s$cggccgaaaggCgagugaGguCucuucucB | 7901 |
| PKR | Control | CCGUACGUUAAGA | 7789 | 24211 | $u_s c_s u_s u_s$aagccgaaaggCuCugGagugaggguacggB | 7902 |
| PKR | Control | ACGAAGAGUUACCUU | 7790 | 24212 | $a_s a_s g_s g_s$uaagccgaaaggCuCugGagugagucuucguB | 7903 |
| PKR | 1224 | AGAGGUUUGGCAUGG | 7791 | 24416 | ccaugccCUGAUGAggccguuaggccGAAAaccucuB | 7904 |
| PKR | 1556 | GGGACCUUGGAACAA | 7792 | 24417 | uuguuccCUGAUGAggccguuaggccGAAAgguccB | 7905 |
| PKR | 1780 | AAGGAGUAAGGGAAC | 7793 | 24418 | guucccuCUGAUGAggccguuaggccGAAAcuccuuB | 7906 |
| PKR | 2296 | CCUGGCUCAUCUCUU | 7794 | 24419 | aagagauCUGAUGAggccguuaggccGAAAagcaggB | 7907 |
| PKR | 2732 | GAUCGUUCUCUGCCU | 7795 | 24420 | aggcagaCUGAUGAggccguuaggccGAAAacgaucB | 7908 |
| PKR | 198 | UACUCGCUAGUGUCA | 7796 | 24421 | gacagacCUGAUGAggccguuaggccGAAIcgaguaB | 7909 |
| PKR | 322 | GCAGUUCUUCCAUCU | 7797 | 24422 | agaugaCUGAUGAggccguuaggccGAAIaacugcB | 7910 |
| PKR | 1805 | AUGAGCCCAGAACAG | 7798 | 24423 | cuguucuCUGAUGAggccguuaggccGAAIgcucauB | 7911 |
| PKR | 2297 | CUGGCUCAUCUCUUU | 7799 | 24424 | aaagagaCUGAUGAggccguuaggccGAAIagccagB | 7912 |
| PKR | 2733 | AUCGUUCUCUGCCUC | 7800 | 24425 | gaggcagCUGAUGAggccguuaggccGAAIaacgauB | 7913 |
| PKR | 199 | ACUCGCUAGUGUCA | 7801 | 24426 | ugacagagccgaaaggCgagugaGguCuagcgaguB | 7914 |
| PKR | 810 | CGGGGGUGCAUGGGC | 7802 | 24427 | gcccaugccgaaaggCgagugaGGuCuaccccgB | 7915 |
| PKR | 904 | ACAAUUGCCGCUAA | 7803 | 24428 | uuagcgggccgaaaggCgagugaGGuCucaauuguB | 7916 |
| PKR | 966 | ACUACCUGUCCUCUG | 7804 | 24429 | cagaggagccgaaaggCgagugaGGuCuaggguaguB | 7917 |
| PKR | 992 | ACUACGUGAGUCC | 7805 | 24430 | ggacucagccgaaaggCgagugaGGuCuacguaguB | 7918 |
| PKR | 396 | UGCGUGCAUUUUGGA | 7806 | 24431 | uccaaaaGGCUAGCUACAACGAgcacgCaB | 7919 |
| PKR | 966 | ACUACCUGUCCUCUG | 7804 | 24432 | cagaggaGGCUAGCUACAACGAagguaguB | 7920 |
| PKR | 1563 | UGGAACAAUGGAUUG | 7807 | 24433 | caauccuGGCUAGCUACAACGAuguuccaB | 7921 |
| PKR | 2297 | CUGGCUCAUCUCUUU | 7799 | 24434 | aaagagaGGCUAGCUACAACGAgagccagB | 7922 |
| PKR | 2543 | UCAAGUAAUCCACCU | 7808 | 24435 | agguggaGGCUAGCUACAACGAuacuugaB | 7923 |
| PKR | 604 | AGGUGAAGGUAGAUC | 7809 | 24436 | gaucuacGgaggaaacucCCUUCaaggacaucgucCGGGuucaccuB | 7924 |
| PKR | 903 | AACAAUUGGCCGCUA | 7810 | 24437 | uagcggcGgaggaaacucCCUUCaaggacaucgucCGGGaauuguuB | 7925 |
| PKR | 966 | ACUACCUGUCCUCUG | 7804 | 24438 | cagaggaGgaggaaacucCCUUCaaggacaucgucCGGGagguaguB | 7926 |
| PKR | 1186 | CCUUCCUGACAUGAA | 7811 | 24439 | uucauguGgaggaaacucCCUUCaaggacaucgucCGGGagguaaggB | 7927 |
| PKR | 2292 | UUUUCCUGGCUCAUC | 7812 | 24440 | gaugagcGgaggaaacucCCUUCaaggacaucgucCGGGaggaaaaB | 7928 |
| IKKg | 427 | AGUUCCUCAUGUGCA | 7813 | 24083 | $u_s g_s c_s a_s$caucUGAuGaggccguuaggccGaaAggaacuB | 7929 |
| IKKg | 1067 | GCGGAUACUACA | 7814 | 24084 | $u_s g_s u_s a_s$gacUGAuGaggccguuaggccGaaAuccgcB | 7930 |
| IKKg | 1067 | GGCGGAUAUCUACAA | 7815 | 24085 | $u_s u_s g_s u_s$gacUGAuGaggccguuaggccGaaAuccgccB | 7931 |
| IKKg | 1069 | CGGAUAUCUACAAGG | 7816 | 24086 | $c_s c_s u_s u_s$guacUGAuGaggccguuaggccGaaAuauccgB | 7932 |
| IKKg | 1071 | AUAUCUACAAGGC | 7817 | 24087 | $g_s c_s c_s u_s$ugcUGAuGaggccguuaggccGaaAgauauB | 7933 |
| IKKg | 1390 | UACAUGUCAUGGAGU | 7818 | 24088 | $a_s c_s u_s c_s$caucUGAuGaggccguuaggccGaaAcauguaB | 7934 |
| IKKg | 1402 | AGUGCAUUGAGUAGG | 7819 | 24089 | $c_s c_s u_s a_s$cuccUGAuGaggccguuaggccGaaAugcacuB | 7935 |

TABLE XIII-continued

Human IKK-gamma and PKR Nucleic Acid and Target molecules

| Gene | Pos | Target | Seq ID | RPI# | Enzymatic Nucleic Acid | Seq ID |
|---|---|---|---|---|---|---|
| IKKg | control | ACGACUCGGAGCU | 7820 | 24090 | a_sg_sc_su_scccUAGuGacgccguuaggcgGaaAgucguB | 7936 |
| IKKg | control | UCUGAGUCAGGCGAC | 7821 | 24091 | g_su_sc_sg_sccuUAGuGacgccguuaggcgGaaAcucagaB | 7937 |
| IKKg | 195 | UGCAGCCCAGUGG | 7822 | 24159 | c_sc_sa_sc_sugcUGAuGaggccguuaggccGaalcugcaB | 7938 |
| IKKg | 196 | GCAGCCCAGUGGU | 7823 | 24160 | a_sc_sc_sa_scucUGAuGaggccguuaggccGaalgccucB | 7939 |
| IKKg | 303 | CCCUCCAGCGCUG | 7824 | 24161 | c_sa_sg_sc_sgccUGAuGaggccguuaggccGaalgagggB | 7940 |
| IKKg | 324 | AGAAUCAAGAGCU | 7825 | 24162 | a_sg_sc_su_scucUGAuGaggccguuaggccGaalauucuB | 7941 |
| IKKg | 324 | GAGAAUCAAGAGCUC | 7826 | 24163 | g_sa_sg_sc_sucucUGAuGaggccguuaggccGaalauucuB | 7942 |
| IKKg | 556 | GAUGGCUGAGGAC | 7827 | 24164 | g_sg_su_sc_sguccUGAuGaggccguuaggccGaalccaucB | 7943 |
| IKKg | 556 | AGAUGGCUGAGGACA | 7828 | 24165 | u_sg_su_sc_scuccUGAuGaggccguuaggccGaalccaucuB | 7944 |
| IKKg | 568 | ACAAGGCCUCUGUGA | 7829 | 24166 | u_sc_sa_sc_sagacUGAuGaggccguuaggccGaalccuuguB | 7945 |
| IKKg | 571 | GGCCUCUGUGAAA | 7830 | 24167 | u_su_su_sc_saccUGAuGaggccguuaggccGaalaggccB | 7946 |
| IKKg | 580 | UGAAAGCCCAGGUGA | 7831 | 24168 | u_sc_sa_sc_scugcUGAuGaggccguuaggccGaalcuuucaB | 7947 |
| lKKg | 749 | GUGGACCAGCUGC | 7832 | 24169 | g_sc_sa_sg_scucUGAugaggccguuaggccGaaluccacB | 7948 |
| IKKg | 927 | UGCAGCUGGAAGA | 7833 | 24170 | u_sc_su_su_scccUGAuGaggccguuaggccGaalcugcaB | 7949 |
| IKKg | 927 | AUGCAGCUGGAAGAU | 7834 | 24171 | a_su_sc_su_succcUGAuGaggccguuaggccGaalcugcauB | 7950 |
| IKKg | 1012 | GGAGGCCGAGCAG | 7835 | 24172 | c_su_sg_sc_succUGAuGaggccguuaggccGaalccuccB | 7951 |
| IKKg | 1012 | AGGAGGCCGAGCAGC | 7836 | 24173 | g_sc_su_sg_scuccUGAuGaggccguuaggccGaalccuccB | 7952 |
| lKKg | 1020 | AGCAGCACAAGAU | 7837 | 24174 | a_su_sc_su_sugcUGAuGaggccguuaggccGaalcugcuB | 7953 |
| IKKg | 1020 | GAGCAGCACAAGAUU | 7838 | 24175 | a_sa_su_sc_suugcUGAuGaggccguuaggccGaalcugcucB | 7954 |
| IKKg | 1022 | GCAGCACAAGAUUGU | 7839 | 24176 | a_sc_sa_sa_sucucUGAuGaggccguuaggccGaalugcugcB | 7955 |
| IKKg | 1070 | GGAUAUCUACAAGGC | 7840 | 24177 | g_sc_sc_su_succUGAuGaggccguuaggccGaalauauccB | 7956 |
| IKKg | 1143 | AGGAGGAGCUGGA | 7841 | 24178 | u_sc_sc_sa_sgccUGAuGaggccguuaggccGaalcuccuB | 7957 |
| IKKg | 1350 | AAGUGCCAGUAUCAG | 7842 | 24179 | c_su_sg_sa_suaccUGAuGaggccguuaggccGaalgcacuuB | 7958 |
| IKKg | 1391 | CAUGUCAUGGAGU | 7843 | 24180 | a_sc_su_sc_scacUGAuGaggccguuaggccGaalacaugB | 7959 |
| IKKg | 1391 | ACAUGUCAUGGAGUG | 7844 | 24181 | c_sa_sc_su_sccacUGAuGaggccguuaggccGaalacauguB | 7960 |
| IKKg | Control | CACGUCUGCGGAA | 7845 | 24182 | u_su_sc_sc_sgccUAGuGacgccguuaggcgGaalacguguB | 7961 |
| IKKg | Control | UCGGAACCAGGUCUG | 7846 | 24183 | c_sa_sg_sa_sccuUAGuGacgccguuaggcgGaaluuccgaB | 7962 |
| IKKg | 304 | CCCUCCAGCGCUGCC | 7847 | 24213 | g_sg_sc_sa_sgcgccgaaaggCgagugaGguCuuggagggB | 7963 |
| IKKg | 306 | CUCCAGCGCUGCCUG | 7848 | 24214 | c_sa_sg_sg_sca_sgggccgaaaggCgagugaGguCugcuggagB | 7964 |
| IKKg | 309 | AGCGCUGCCUGGA | 7849 | 24215 | u_sc_sc_sa_sgggccgaaaggCgagugaGguCuagcgcuB | 7965 |
| IKKg | 328 | UCAAGAGCUCCGA | 7850 | 24216 | u_sc_sg_sa_saggccgaaaggCgagugaGguCuucuugaB | 7966 |
| IKKg | 328 | AUCAAGAGCUCCGAG | 7851 | 24217 | c_su_sc_sg_sgaggccgaaaggCgagugaGguCuucuugauB | 7967 |
| IKKg | 572 | GCCUCUGUGAAAG | 7852 | 24218 | c_su_su_su_scagccgaaaggCgagugaGguCuagaggcB | 7968 |
| IKKg | 572 | GGCCUCUGUGAAAGC | 7853 | 24219 | g_sc_su_su_sucagccgaaaggCgagugaGguCuagaggccB | 7969 |
| IKKg | 705 | UGGAGAGUGAGCG | 7854 | 24220 | c_sg_sc_su_scagccgaaaggCgagugaGguCuuccucaB | 7970 |
| IKKg | 1028 | CAAGAUUGUGAUGGA | 7855 | 24221 | u_sc_sc_sa_sucagccgaaaggCgagugaGguCuaaucuugB | 7971 |
| IKKg | 1222 | GAGGAAGCGGCAU | 7856 | 24222 | a_su_sg_sc_scggccgaaaggCgagugaGguCuuuccucB | 7972 |
| IKKg | 1222 | UGAGGAAGCGGCAUG | 7857 | 24223 | c_sa_su_sg_sccggccgaaaggCgagugaCguCuuuccucaB | 7973 |
| IKKg | 1351 | AGUGCCAGUAUCAGG | 7858 | 24224 | c_sc_su_sg_sauagccgaaaggCgagugaGguCuuggcacuB | 7974 |
| IKKg | Control | ACUCCGGCUGAGA | 7859 | 24225 | u_sc_su_sa_scggccgaaaggCuCugGagugagcggaguB | 7975 |
| IKKg | Control | GUGACGCGUGUCACA | 7860 | 24226 | u_sg_su_sg_sacagccgaaaggCuCugGagugaggcgucacB | 7976 |
| IKKg | 438 | UGCAAGUUCCAGGAG | 7861 | 24463 | cuccuggCUGAUGAggccguuaggccGAAAcuugcaB | 7977 |
| IKKg | 1167 | AGGGAGUACAGCAAA | 7862 | 24464 | uuugcugCUGAUGAggccguuaggccGAAAcucccuB | 7978 |
| IKKg | 1273 | CCUACCUCUCCUCUC | 7863 | 24465 | gagaggaCUGAUGAggccguuaggccGAAAgguaggB | 7979 |
| IKKg | 1639 | CGCUGCUCUUUUUGU | 7864 | 24466 | acaaaaaCUGAUGAggccguuaggccGAAAgcagcgB | 7980 |
| IKKg | 1781 | GGCAGCUCUUCCUCC | 7865 | 24467 | ggaggaaCUGAUGAggccguuaggccGAAAgcugccB | 7981 |
| IKKg | 741 | AGCGUGCAGGUGGAC | 7866 | 24468 | guccaccCUGAUGAggccguuaggccGAAIcacgcuB | 7982 |
| IKKg | 1158 | CAGCUGCAGAGGGAG | 7867 | 24469 | cucccucCUGAUGAggccguuaggccGAAIcagcugB | 7983 |
| IKKg | 1272 | GCCUACCUCUCCUCU | 7868 | 24470 | agaggagCUGAUGAggccguuaggccGAAIguaggcB | 7984 |
| IKKg | 1650 | UUGUUCCCUUCUGUC | 7869 | 24471 | gacagaaCUGAUGAggccguuaggccGAAIgaacaaB | 7985 |
| IKKg | 1834 | UGCUGCCCUCUUACC | 7870 | 24472 | gguaagaCUGAUGAggccguuaggccGAAIgcagcaB | 7986 |
| IKKg | 52 | CAGAGAAGUGAGGAC | 7871 | 24473 | guccucagccgaaaggCgagugaGGuCuuucucugB | 7987 |
| IKKg | 124 | CAUCGAGGUCCCAUC | 7872 | 24474 | gaugggagccgaaaggCgagugaGGuCucucgaugB | 7988 |
| IKKg | 1338 | UUCUGCUGUCCCAAG | 7873 | 24475 | cuugggagccgaaaggCgagugaGGuCuagcagaaB | 7989 |
| IKKg | 1633 | CUGACUCGCUGCUCU | 7874 | 24476 | agagcaggccgaaaggCgagugaGGuCugagucagB | 7990 |
| IKKg | 1655 | CCCUUCUGUCUGCUC | 7875 | 24477 | gagcagagccgaaaggCgagugaGGuCuagaagggB | 7991 |
| IKKg | 52 | CAGAGAAGUGAGGAC | 7871 | 24478 | guccuca*GGCTAGCTACAACGA*uuucucugB | 7992 |
| IKKg | 216 | GCAGCAGAUCAGGAC | 7876 | 24479 | guccuga*GGCTAGCTACAACGA*cugcugcB | 7993 |
| IKKg | 538 | UGAAGAGAUGCCAGC | 7877 | 24480 | gcugga*GGCTAGCTACAACGA*cucuucaB | 7994 |
| IKKg | 868 | UCCAAGAAUACGACA | 7878 | 24481 | ugucgua*GGCTAGCTACAACGA*ucuuggaB | 7995 |
| IKKg | 940 | AUCUCAAACAGCAGC | 7879 | 24482 | gcugcug*GGCTAGCTACAACGA*uugagauB | 7996 |
| IKKg | 52 | CAGAGAAGUGAGGAC | 7871 | 24483 | guccucaGgaggaaacucCCUUCaaggacaucgucCGGGuucucugB | 7997 |
| IKKg | 215 | GGCAGCAGAUCAGGA | 7880 | 24484 | uccugauGgaggaaacucCCUUCaaggacaucgucCGGGugcugccB | 7998 |
| IKKg | 817 | CGGAGGAAGAGGA | 7881 | 24485 | ucccucuGgaggaaacucCCUUCaaggacaucgucCGGGuccuccgB | 7999 |
| IKKg | 986 | ACAGGAGGUGAUCGA | 7882 | 24486 | ucgaucaGgaggaaacucCCUUCaaggacaucgucCGGGucccuguB | 8000 |
| IKKg | 1826 | CCUGGGAGUGCUGCC | 7883 | 24487 | ggcagcaGgaggaaacucCCUUCaaggacaucgucCGGGucccaggB | 8001 |

A, G, C, U = Ribo
A, G, C, T (*italic*) = deoxy
lower case = 2'-O-methyl
s = phosphorothioate 3'-internucleotide linkage
U = 2'-deoxy-2'-C-allyl uridine
<u>U</u> = 2'-deoxy-2'-Amino uridine
<u>C</u> = 2'-deoxy-2'-Amino cytidine TABLE XIII-continued Human IKK-gamma and PKR Nucleic Acid and Target molecules

| Gene | Pos | Target | Seq ID | RPI# | Enzymatic Nucleic Acid | Seq ID |
|------|-----|--------|--------|------|------------------------|--------|

I = Inosine
B = inverted deoxyabasic derivative

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07022828B2). An electronic copy of the "Sequence Listing" will also be available from the USPTO upon request and payment of the fee set forth in 37 CFR 1.19(b)(3).

What I claim is:

1. A chemically modified double stranded siRNA molecule that down regulates expression of an IKK-gamma gene via RNA interference (RNAi), wherein:
    a) each strand of said siRNA molecule is independently about 18 to about 28 nucleotides in length; and
    b) one strand of said siRNA molecule comprises nucleotide sequence having sufficient complementarity to an RNA of said IKK-gamma gene for the siRNA molecule to direct cleavage of said RNA via RNA interference.

2. The siRNA molecule of claim 1, wherein each strand of the siRNA molecule comprises about 18 to about 28 nucleotides, and wherein each strand comprises at least about 14 to 24 nucleotides that are complementary to the nucleotides of the other strand.

3. The siRNA molecule of claim 1, wherein said siNA molecule is assembled from two separate oligonucleotide fragments wherein a first fragment comprises the sense strand and a second fragment comprises the antisense strand of said siNA molecule.

4. The siRNA molecule of claim 3, wherein said sense strand is connected to the antisense strand via a linker molecule.

5. The siRNA molecule of claim 4, wherein said linker molecule is a polynucleotide linker.

6. The siRNA molecule of claim 4, wherein said linker molecule is a non-nucleotide linker.

7. The siRNA molecule of claim 3, wherein said second fragment comprises a terminal cap moiety at a 5'-end, a 3'-end, or both of the 5' and 3' ends of said second strand.

8. The siRNA molecule of claim 7, wherein said terminal cap moiety is an inverted deoxy abasic moiety.

9. The siRNA molecule of claim 3, wherein said first fragment comprises a phosphorothioate internucleotide linkage at the 3' end of said first strand.

10. The siRNA molecule of claim 1, wherein said siRNA molecule comprises at least one 2'-sugar modification.

11. The siRNA molecule of claim 10, wherein said 2'-sugar modification is a 2'-deoxy-2'-fluoro modification.

12. The siRNA molecule of claim 10, wherein said 2'-sugar modification is a 2'-O-methyl modification.

13. The siRNA molecule of claim 10, wherein said 2'-sugar modification is a 2'-deoxy modification.

14. The siRNA molecule of claim 1, wherein said siRNA molecule comprises at least one nucleic acid base modification.

15. The siRNA molecule of claim 1, wherein said siRNA molecule comprises at least one phosphate backbone modification.

16. A composition comprising the siRNA molecule of claim 1 in a pharmaceutically acceptable carrier or diluent.

* * * * *

(12) EX PARTE REEXAMINATION CERTIFICATE (7175th)
United States Patent
McSwiggen

(10) Number: US 7,022,828 C1
(45) Certificate Issued: Nov. 17, 2009

(54) SIRNA TREATMENT OF DISEASES OR CONDITIONS RELATED TO LEVELS OF IKK-GAMMA

(75) Inventor: James A. McSwiggen, Boulder, CO (US)

(73) Assignee: Sirna Therapeutics Inc., Boulder, CO (US)

Reexamination Request:
No. 90/008,177, Aug. 22, 2006

Reexamination Certificate for:
Patent No.: 7,022,828
Issued: Apr. 4, 2006
Appl. No.: 10/156,306
Filed: May 28, 2002

Related U.S. Application Data
(60) Provisional application No. 60/294,412, filed on May 29, 2001.

(51) Int. Cl.
*C07H 21/02* (2006.01)

(52) U.S. Cl. .................. 536/23.1; 536/23.5
(58) Field of Classification Search .......... None
See application file for complete search history.

(56) References Cited

U.S. PATENT DOCUMENTS

| | | | |
|---|---|---|---|
| 5,998,203 A | 12/1999 | Matulic-Adamic et al. | 435/325 |
| 6,506,559 B1 * | 1/2003 | Fire et al. | 435/6 |
| 6,824,972 B2 | 11/2004 | Kenwrick et al. | 435/4 |

| | | | |
|---|---|---|---|
| 2002/0086356 A1 | 7/2002 | Tuschi et al. | 435/69.1 |

FOREIGN PATENT DOCUMENTS

| | | |
|---|---|---|
| WO | 94/01550 | 1/1994 |
| WO | 02/44321 | 6/2002 |

OTHER PUBLICATIONS

Elbashir et al (Nature, vol. 411, pp. 494–498, May 24, 2001).*
Bass (Nature, vol. 411, pp. 428–429, May 24, 2001).*
Krappmann et al., "The IκB kinase (IKK) complex is tripartite and contains IKKγ but not IKAP as a regular component." *J. Biol. Chem.* 275:29779–29787 (Sep. 22, 2000).
Levin H.L., "An unusual mechanism of self-primed reverse transcription requires the RNase H domain of reverse transcriptase to cleave an RNA duplex." *Mol. Cell Biol.* 16:5645–54 (Oct. 1996).
Smahi et al., "Genomic rearrangement in NEMO impairs NF–κB activation and is a cause of incontinentia pigmenti." *Nature* 405:466–72 (May 25, 2000).
Yamaoka et al., "Complementation cloning of NEMO, a component of the IκB kinase complex essential for NF–κB activation." *Cell* 93:1231–1240 (Jun. 26, 1998).

* cited by examiner

*Primary Examiner*—Padmashri Ponnaluri

(57) ABSTRACT

The present invention relates to nucleic acid molecules, including antisense and enzymatic nucleic acid molecules, such as hammerhead ribozymes, DNAzymes, allozymes, aptamers, decoys and siRNA (RNAi), which modulate the expression or function of IKK genes, such as IKK-gamma, IKK-alpha, or IKK-beta, and PKR genes.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

Claims 1–16 are cancelled.

* * * * *